United States Patent
Mueller et al.

(10) Patent No.: US 7,696,196 B2
(45) Date of Patent: *Apr. 13, 2010

(54) SELECTED CGRP-ANTAGONISTS, PROCESS FOR PREPARING THEM AND THEIR USE AS PHARMACEUTICAL COMPOSITIONS

(75) Inventors: Stephan Georg Mueller, Warthausen (DE); Klaus Rudolf, Warthausen (DE); Philipp Lustenberger, Warthausen (DE); Dirk Stenkamp, Biberach (DE); Alexander Dreyer, Gutenzell-Huerbel (DE); Kirsten Arndt, Biberach (DE); Gerhard Schaenzle, Biberach-Mettenberg (DE); Henri Doods, Warthausen (DE); Marco Santagostino, Mittelbiberach (DE); Fabio Paleari, Monza (IT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/186,005

(22) Filed: Aug. 5, 2008

(65) Prior Publication Data
US 2009/0111797 A1     Apr. 30, 2009

Related U.S. Application Data

(63) Continuation of application No. 11/277,175, filed on Mar. 22, 2006, now Pat. No. 7,491,717.

(30) Foreign Application Priority Data

| Mar. 23, 2005 | (AR) | .............................. P050101139 |
| Mar. 23, 2005 | (PE) | ..................... 000336-2005/OIN |
| Mar. 25, 2005 | (WO) | ............... PCT/EP2005/003094 |

(51) Int. Cl.
C07D 401/14    (2006.01)
C07D 413/04    (2006.01)
A61K 31/551    (2006.01)
A61P 25/06     (2006.01)

(52) U.S. Cl. ..................................... 514/221; 540/500
(58) Field of Classification Search ................. 514/221; 540/500
See application file for complete search history.

(56) References Cited

U.S. PATENT DOCUMENTS

| 5,442,044 A | 8/1995 | Hoover et al. |
| 6,344,449 B1 | 2/2002 | Rudolf et al. |
| 6,521,609 B1 | 2/2003 | Doods et al. |
| 6,653,478 B2 | 11/2003 | Urbanski et al. |
| 2004/0132716 A1 | 7/2004 | Rudolf et al. |
| 2004/0192729 A1 | 9/2004 | Rudolf et al. |
| 2005/0234067 A1 | 10/2005 | Mueller et al. |
| 2005/0282857 A1 | 12/2005 | Rudolf et al. |
| 2006/0079504 A1 | 4/2006 | Rudolf et al. |
| 2006/0252931 A1 | 11/2006 | Mueller et al. |
| 2007/0049581 A1 | 3/2007 | Mueller et al. |
| 2007/0072847 A1 | 3/2007 | Mueller et al. |
| 2008/0086003 A1 | 4/2008 | Ries et al. |

FOREIGN PATENT DOCUMENTS

| CA | 2378428 | 8/2000 |
| CA | 2361939 | 9/2000 |
| CA | 2503455 | 5/2004 |
| CA | 2503462 | 5/2004 |
| EP | 0438233 | 7/1991 |
| WO | 0018764 | 4/2000 |
| WO | 03104236 | 12/2003 |
| WO | 2004037810 | 5/2004 |
| WO | 2004037811 | 5/2004 |

OTHER PUBLICATIONS

Mallee et al.; Receptor Activity-modifying Protein 1 Determines the Species Selectivity of Non-peptide CGRP Receptor Antagonists; The Journal of Biological Chemistry (Apr. 19, 2002) vol. 277, No. 16, pp. 14294-14928; The American Society for Biochemistry and Molecular Biology, Inc.

Doods et al.; Pharmacological profile of BIBN4096BS, the first selective small molecule CGRP antagonist; British Journal of Pharmacology (2000) vol. 129; pp. 420-423; Macmillan Publishers Ltd.

Halliwell; Cationic Amphiphilic Drug-Induced Phospholipidosis; Toxicologic Pathology; 1997; vol. 25; No. 1; pp. 1-8.

*Primary Examiner*—Bruck Kifle
(74) *Attorney, Agent, or Firm*—Michael P. Morris; Mary-Ellen M. Devlin; Alan R. Stempel

(57) ABSTRACT

The present invention relates to the CGRP antagonists of general formula

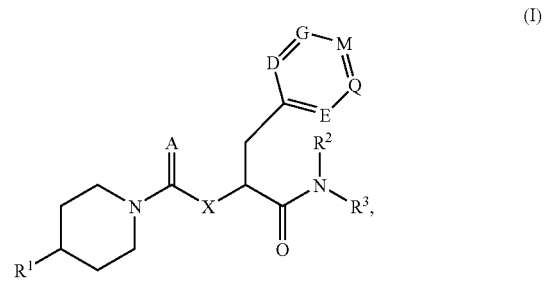

wherein A, X, D, E, G, M, Q and $R^1$ to $R^3$ are defined as in claim 1, the tautomers, the isomers, the diastereomers, the enantiomers, the hydrates thereof, the mixtures thereof and the salts thereof and the hydrates of the salts, particularly the physiologically acceptable salts thereof with inorganic or organic acids, pharmaceutical compositions containing these compounds, the use thereof and processes for the preparation thereof.

6 Claims, No Drawings

SELECTED CGRP-ANTAGONISTS, PROCESS FOR PREPARING THEM AND THEIR USE AS PHARMACEUTICAL COMPOSITIONS

RELATED APPLICATIONS

This application is a continuation of U.S. Ser. No. 11/277,175, filed Mar. 22, 2006, which claims the benefit to PCT/EP2005/003094, filed Mar. 23, 2005, PE000336-2005/OIN, filed Mar. 23, 2005, and ARP050101139, filed Mar. 23, 2005.

FIELD OF THE INVENTION

The present invention relates to the CGRP-antagonists of general formula

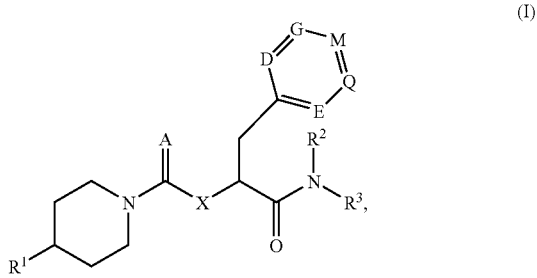

(I)

wherein A, D, E, G, M, Q, X, $R^1$, $R^2$ and $R^3$ are defined as below, the tautomers, the isomers, the diastereomers, the enantiomers, the hydrates thereof, the mixtures thereof and the salts thereof as well as the hydrates of the salts, particularly the physiologically acceptable salts thereof with inorganic or organic acids or bases, pharmaceutical compositions containing these compounds, the use thereof and processes for the preparation thereof.

In the above general formula (I) in a first embodiment
A denotes an oxygen or sulphur atom,
X denotes an oxygen or sulphur atom,
(a) D, E independently of one another in each case denote a methyne group or the nitrogen atom and
  G denotes a methyne group substituted by the group $R^a$,
  M denotes a methyne group substituted by the group $R^b$,
  Q denotes a methyne group substituted by the group $R^c$,
    while one or two of the groups G, M and Q in each case may also represent a nitrogen atom, or (b) D and E in each case denote a methyne group, while one of the groups D and E may also represent a nitrogen atom, and
  G, M and Q in each case denote a nitrogen atom,
while $R^a$, $R^b$ and $R^c$ independently of one another in each case denote a hydrogen or halogen atom, a $C_{1-6}$-alkyl, $C_{2-6}$-alkenyl, $C_{2-6}$-alkynyl, cyclo-$C_{3-7}$-alkyl, cyclo-$C_{3-7}$-alkenyl, cyano, hydroxy, hydroxy-$C_{1-6}$-alkyl, hydroxy-$C_{3-6}$-alkenyl, hydroxy-$C_{3-6}$-alkynyl, $C_{1-6}$-alkoxy, $C_{1-6}$-alkoxy-$C_{1-6}$-alkyl, $C_{1-6}$-alkoxy-$C_{3-6}$-alkenyl, $C_{1-6}$-alkoxy-$C_{3-6}$-alkynyl, $C_{3-6}$-alkenoxy-$C_{1-6}$-alkyl, $C_{3-6}$-alkenoxy-$C_{3-6}$-alkenyl, $C_{3-6}$-alkenoxy-$C_{3-6}$-alkynyl, $C_{3-6}$-alkynoxy-$C_{1-6}$-alkyl, $C_{3-6}$-alkynoxy-$C_{3-6}$-alkenyl, $C_{3-6}$-alkynoxy-$C_{3-6}$-alkynyl, thiohydroxy, $C_{1-6}$-alkylthio, $C_{3-6}$-alkenylthio, $C_{3-6}$-alkynylthio, amino, $C_{1-6}$-alkyl-amino, $C_{3-6}$-alkenyl-amino, $C_{3-6}$-alkynyl-amino, di-($C_{1-6}$-alkyl)-amino, di-($C_{3-6}$-alkenyl)-amino, di-($C_{3-6}$-alkynyl)-amino, amino-$C_{1-6}$-alkyl, $C_{1-3}$-alkyl-amino-$C_{1-6}$-alkyl, di($C_{1-3}$-alkyl)-amino-$C_{1-6}$-alkyl, amino-$C_{3-6}$-alkenyl, $C_{1-3}$-alkyl-amino-$C_{3-6}$-alkenyl, di-($C_{1-3}$-alkyl)-amino-$C_{3-6}$-alkenyl, amino-$C_{3-6}$-alkynyl, $C_{1-3}$-alkyl-amino-$C_{3-6}$-alkynyl, di-($C_{1-3}$-alkyl)-amino-$C_{3-6}$-alkynyl, hydroxycarbonyl, phenylcarbonyl, pyridylcarbonyl, $C_{1-6}$-alkyl-carbonyl, $C_{2-6}$-alkenyl-carbonyl, $C_{2-6}$-alkynyl-carbonyl, formyl, $C_{1-6}$-alkoxy-carbonyl, $C_{3-6}$-alkenoxy-carbonyl, $C_{3-6}$-alkynoxy-carbonyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{2-6}$-alkenyl-carbonylamino, $C_{2-6}$-alkynyl-carbonylamino, formyl-$C_{1-6}$-alkyl-amino, formyl-$C_{3-6}$-alkenyl-amino, formyl-$C_{3-6}$-alkynyl-amino, $C_{1-6}$-alkyl-carbonyl-$C_{1-6}$-alkyl-amino, $C_{2-6}$-alkenyl-carbonyl-$C_{1-6}$-alkyl-amino, $C_{2-6}$-alkynyl-carbonyl-$C_{1-6}$-alkyl-amino, $C_{1-6}$-alkyl-carbonyl-$C_{3-6}$-alkenyl-amino, $C_{2-6}$-alkenyl-carbonyl-$C_{3-6}$-alkenyl-amino, $C_{2-6}$-alkynyl-carbonyl-$C_{3-6}$-alkenyl-amino, $C_{1-6}$-alkyl-carbonyl-$C_{3-6}$-alkynyl-amino, $C_{2-6}$-alkenyl-carbonyl-$C_{3-6}$-alkynyl-amino, $C_{2-6}$-alkynyl-carbonyl-$C_{3-6}$-alkynyl-amino, $C_{1-6}$-alkyl-sulphonyl, $C_{2-6}$-alkenyl-sulphonyl, $C_{2-6}$-alkynyl-sulphonyl, $C_{1-6}$-alkyl-sulphinyl, $C_{2-6}$-alkenyl-sulphinyl, $C_{2-6}$-alkynyl-sulphinyl, $C_{1-6}$-alkyl-sulphonylamino, $C_{2-6}$-alkenyl-sulphonylamino, $C_{2-6}$-alkynyl-sulphonylamino, $C_{1-6}$-alkyl-sulphonyl-$C_{1-6}$-alkylamino, $C_{1-6}$-alkyl-sulphonyl-$C_{3-6}$-alkenylamino, $C_{1-6}$-alkyl-sulphonyl-$C_{3-6}$-alkynylamino, $C_{2-6}$-alkenyl-sulphonyl-$C_{1-6}$-alkylamino, $C_{2-6}$-alkenyl-sulphonyl-$C_{3-6}$-alkenylamino, $C_{2-6}$-alkenyl-sulphonyl-$C_{3-6}$-alkynylamino, $C_{2-6}$-alkynyl-sulphonyl-$C_{1-6}$-alkylamino, $C_{2-6}$-alkynyl-sulphonyl-$C_{3-6}$-alkenylamino, $C_{2-6}$-alkynyl-sulphonyl-$C_{3-6}$-alkynylamino, aminosulphonyl, $C_{1-6}$-alkylaminosulphonyl, di-($C_{1-6}$-alkyl)-aminosulphonyl, $C_{3-6}$-alkenylaminosulphonyl, di-($C_{3-6}$-alkenyl)-aminosulphonyl, $C_{3-6}$-alkynylaminosulphonyl or di-($C_{3-6}$-alkynyl)-aminosulphonyl group
with the provisos that, if none of the groups D, E, G, M and Q denotes a nitrogen atom,
(i) $R^a$ does not denote a hydrogen atom, if both $R^b$ and $R^c$ in each case denote a $C_{1-6}$-alkyl group,
(ii) $R^c$ does not denote a hydrogen atom if both $R^a$ and $R^b$ in each case denote a $C_{1-6}$-alkyl group,
(iii) $R^a$ does not take on the meanings of a hydrogen, fluorine, chlorine, bromine or iodine atom or a difluoro- or trifluoromethyl group if $R^c$ denotes a $C_{1-6}$-alkyl, $C_{2-6}$-alkenyl or $C_{2-6}$-alkynyl group and $R^b$ denotes a chlorine or bromine atom, an amino, methylamino or hydroxy group,
(iv) $R^c$ does not take on the meanings of a hydrogen, fluorine, chlorine, bromine or iodine atom or a difluoro- or trifluoromethyl group if $R^a$ denotes a $C_{1-6}$-alkyl, $C_{2-6}$-alkenyl or $C_{2-6}$-alkynyl group and $R^b$ denotes a chlorine or bromine atom, an amino, methylamino or hydroxy group,
$R^1$ denotes a saturated, mono- or diunsaturated 5- to 7-membered aza, diaza, triaza, oxaza, thiaza, thiadiaza or S,S-dioxido-thiadiaza heterocycle,
  while the above-mentioned heterocycles are linked to the piperidine ring in formula I via a carbon or nitrogen atom
or
  are spirocyclically linked to the piperidine ring in formula I via two carbon atoms, via a carbon and a nitrogen atom, via a carbon and an oxygen atom or via a carbon and a sulphur atom,
  contain one or two carbonyl or thiocarbonyl groups adjacent to a nitrogen atom,
  may be substituted at one of the nitrogen atoms by a $C_{1-6}$-alkyl, $C_{3-6}$-alkenyl or $C_{3-6}$-alkenyl group, may be substituted at one or two carbon atoms by a $C_{1-6}$-alkyl, $C_{2-6}$-alkenyl or $C_{2-6}$-alkynyl group, by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-($C_{1-3}$-alkyl)-pyrazolyl, imidazolyl or 1-($C_{1-3}$-alkyl)-imidazolyl group, while the substituents may be identical or different, and an olefinic double bond of one of the above-mentioned unsaturated heterocycles may be fused to a phenyl, naphthyl, pyridine, diazine, 1,3-oxazole, thienyl, furan, thiazole, pyrrole, N—$C_{1-3}$-alkyl-pyrrole or quinoline ring, to a 1H-quinolin-2-one ring optionally substituted at the nitrogen atom by a $C_{1-6}$-alkyl, $C_{3-6}$-alkenyl or $C_{3-6}$-alkynyl group or to an imidazole or N—$C_{1-3}$-alkyl-imidazole ring or else two olefinic double bonds of one of the above-mentioned unsaturated heterocycles may each be fused to a phenyl or pyridine ring, while the phenyl, pyridinyl, diazinyl, furyl, thienyl, pyrrolyl, 1,3-oxazolyl, 1,3-thiazolyl, isoxazolyl, pyrazolyl, 1-$C_{1-3}$-alkyl-pyrazolyl, imidazolyl or 1-$C_{1-3}$-alkyl-imidazolyl groups contained in $R^1$ and benzo-, thieno-, pyrido- and diazino-fused heterocycles in the carbon skeleton may additionally be mono-, di- or trisubstituted by halogen atoms, $C_{1-6}$-alkyl, $C_{2-6}$-alkenyl, $C_{2-6}$-alkynyl, cyclo-$C_{3-7}$-alkyl, cyclo-$C_{3-7}$-alkenyl, cyano, hydroxy, hydroxy-$C_{1-6}$-alkyl, hydroxy-$C_{3-6}$-alkenyl, hydroxy-$C_{3-6}$-alkynyl, $C_{1-6}$-alkoxy, $C_{1-6}$-alkoxy-$C_{1-6}$-alkyl, $C_{1-6}$-alkoxy-$C_{3-6}$-alkenyl, $C_{1-6}$-alkoxy-$C_{3-6}$-alkynyl, $C_{3-6}$-alkenoxy-$C_{1-6}$-alkyl, $C_{3-6}$-alkenoxy-$C_{3-6}$-alkenyl, $C_{3-6}$-alkenoxy-$C_{3-6}$-alkynyl, $C_{3-6}$-alkynoxy-$C_{1-6}$-alkyl, $C_{3-6}$-alkynoxy-$C_{3-6}$-alkenyl, $C_{3-6}$-alkynoxy-$C_{3-6}$-alkynyl, thiohydroxy, $C_{1-6}$-alkylthio, $C_{3-6}$-alkenylthio, $C_{3-6}$-alkynylthio, amino, $C_{1-6}$-alkyl-amino, $C_{3-6}$-alkenyl-amino, $C_{3-6}$-alkynyl-amino, di-($C_{1-6}$-alkyl)-amino, di-($C_{3-6}$-alkenyl)-amino, di-($C_{3-6}$-alkynyl)-amino, amino-$C_{1-6}$-alkyl, $C_{1-3}$-alkyl-amino-$C_{1-6}$-alkyl, di-($C_{1-3}$-alkyl)-amino-$C_{1-6}$-alkyl, amino-$C_{3-6}$-alkenyl, $C_{1-3}$-alkyl-amino-$C_{3-6}$-alkenyl, di-($C_{1-3}$-alkyl)-amino-$C_{3-6}$-alkenyl, amino-$C_{3-6}$-alkynyl, $C_{1-3}$-alkyl-amino-$C_{3-6}$-alkynyl, di-($C_{1-3}$-alkyl)-amino-$C_{3-6}$-alkynyl, hydroxycarbonyl, phenylcarbonyl, pyridylcarbonyl, $C_{1-6}$-alkyl-carbonyl, $C_{2-6}$-alkenyl-carbonyl, $C_{2-6}$-alkynyl-carbonyl, formyl, $C_{1-6}$-alkoxy-carbonyl, $C_{3-6}$-alkenoxy-carbonyl, $C_{3-6}$-alkynoxy-carbonyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{2-6}$-alkenyl-carbonylamino, $C_{2-6}$-alkynyl-carbonylamino, formyl-$C_{1-6}$-alkyl-amino, formyl-$C_{3-6}$-alkenyl-amino, formyl-$C_{3-6}$-alkynyl-amino, $C_{1-6}$-alkyl-carbonyl-$C_{1-6}$-alkyl-amino, $C_{2-6}$-alkenyl-carbonyl-$C_{1-6}$-alkyl-amino, $C_{2-6}$-alkynyl-carbonyl-$C_{1-6}$-alkyl-amino, $C_{1-6}$-alkyl-carbonyl-$C_{3-6}$-alkenyl-amino, $C_{2-6}$-alkenyl-carbonyl-$C_{3-6}$-alkenyl-amino, $C_{2-6}$-alkynyl-carbonyl-$C_{3-6}$-alkenyl-amino, $C_{1-6}$-alkyl-carbonyl-$C_{3-6}$-alkynyl-amino, $C_{2-6}$-alkenyl-carbonyl-$C_{3-6}$-alkynyl-amino, $C_{2-6}$-alkynyl-carbonyl-$C_{3-6}$-alkynyl-amino, $C_{1-6}$-alkyl-sulphonyl, $C_{2-6}$-alkenyl-sulphonyl, $C_{2-6}$-alkynyl-sulphonyl, $C_{1-6}$-alkyl-sulphinyl, $C_{2-6}$-alkenyl-sulphinyl, $C_{2-6}$-alkynyl-sulphinyl, $C_{1-6}$-alkyl-sulphonylamino, $C_{2-6}$-alkenyl-sulphonylamino, $C_{2-6}$-alkynyl-sulphonylamino, $C_{1-6}$-alkyl-sulphonyl-$C_{1-6}$-alkylamino, $C_{1-6}$-alkyl-sulphonyl-$C_{3-6}$-alkenylamino, $C_{1-6}$-alkyl-sulphonyl-$C_{3-6}$-alkynylamino, $C_{2-6}$-alkenyl-sulphonyl-$C_{1-6}$-alkylamino, $C_{2-6}$-alkenyl-sulphonyl-$C_{3-6}$-alkenylamino, $C_{2-6}$-alkenyl-sulphonyl-$C_{3-6}$-alkynylamino, $C_{2-6}$-alkynyl-sulphonyl-$C_{1-6}$-alkylamino, $C_{2-6}$-alkynyl-sulphonyl-$C_{3-6}$-alkenylamino, $C_{2-6}$-alkynyl-sulphonyl-$C_{3-6}$-alkynylamino, aminosulphonyl, $C_{1-6}$-alkylaminosulphonyl, di-($C_{1-6}$-alkyl)-aminosulphonyl, $C_{3-6}$-alkenylaminosulphonyl, di-($C_{3-6}$-alkenyl)-aminosulphonyl, $C_{3-6}$-alkynylaminosulphonyl, di-($C_{3-6}$-alkynyl)-aminosulphonyl groups, while the substituents may be identical or different and the double and triple bonds of the $C_{3-6}$-alkenyl or $C_{3-6}$-alkynyl groups contained in the groups given as definitions for $R^a$, $R^b$, $R^c$ and $R^1$ hereinbefore may be isolated from any heteroatoms optionally also contained in these groups, $R^2$ denotes the hydrogen atom, a phenylmethyl group or a $C_{2-7}$-alkyl group which may be substituted in the ω position by a cyclo-$C_{3-7}$-alkyl, cyclo-$C_{3-7}$-alkenyl, phenyl, pyridinyl, diazinyl, hydroxy, amino, $C_{1-6}$-alkylamino, di-($C_{1-6}$-alkyl)-amino, $C_{3-6}$-alkenylamino, di-($C_{3-6}$-alkenyl)amino, $C_{3-6}$-alkynylamino, di-($C_{3-6}$-alkynyl)amino, hydroxycarbonyl, $C_{1-6}$-alkoxycarbonyl, aminocarbonyl, aminocarbonylamino, $C_{1-6}$-alkylcarbonylamino, $C_{2-6}$-alkenylcarbonylamino, $C_{2-6}$-alkynylcarbonylamino, 4-morpholinyl, [bis-(2-hydroxyethyl)]amino, 4-($C_{1-6}$-alkyl)-1-piperazinyl or 4-(ω-hydroxy-$C_{2-7}$-alkyl)-1-piperazinyl group, a phenyl or pyridinyl group, while the phenyl, pyridinyl and diazinyl groups mentioned in the groups defined hereinbefore for $R^2$ or contained as substituents may additionally be mono-, di- or trisubstituted in the carbon skeleton by halogen, by $C_{1-3}$-alkyl, $C_{2-3}$-alkenyl, $C_{2-3}$-alkynyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkyl-amino-$C_{1-3}$-alkyl, di-($C_{1-3}$-alkyl)-amino-$C_{1-3}$-alkyl, $C_{1-3}$-alkyl-carbonylamino, $C_{1-3}$-alkylcarbonylamino-$C_{1-3}$-alkyl, aminocarbonyl, $C_{1-3}$-alkyl-aminocarbonyl, di-($C_{1-3}$-alkyl)-aminocarbonyl, cyano, aminosulphonyl, $C_{1-3}$-alkyl-aminosulphonyl, di-($C_{1-3}$-alkyl)-aminosulphonyl, $C_{1-3}$-alkyl-thio, $C_{1-3}$-alkyl-sulphinyl or $C_{1-3}$-alkyl-sulphonyl and the substituents may be identical or different, $R^3$ denotes the hydrogen atom or a $C_{1-3}$-alkyl group substituted by a phenyl or pyridinyl group, while the $C_{1-3}$-alkyl group may be connected to an alkyl group contained in $R^2$ or to a phenyl or pyridyl ring contained in $R^2$ including the nitrogen atom to which $R^2$ and $R^3$ are bound, forming a 4- to 7-membered ring, or $R^2$ and $R^3$ together with the enclosed nitrogen atom denote a group of general formula

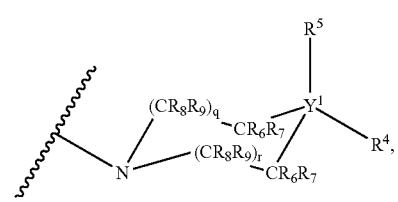

(II)

wherein $Y^1$ denotes the carbon atom or, if $R^5$ denotes a pair of free electrons, it may also denote the nitrogen atom, q and r, if $Y^1$ denotes the carbon atom, denote the numbers 0, 1 or 2, or q and r, if $Y^1$ denotes the nitrogen atom, denote the numbers 1 or 2, $R^4$ denotes the hydrogen atom, an amino, $C_{1-4}$-alkyl-amino, di-($C_{1-4}$-alkyl)-alkylamino, $C_{1-6}$-alkyl, a cyclo-$C_{3-7}$-alkyl or cyclo-$C_{3-7}$-alkenyl group optionally substituted by a hydroxycarbonyl, $C_{1-6}$-alkoxycarbonyl, hydroxycarbonyl-$C_{1-3}$-alkyl or $C_{1-6}$-alkoxycarbonyl-$C_{1-3}$-alkyl group, an amino-$C_{2-7}$-alkyl, $C_{1-4}$-alkyl-amino-$C_{2-7}$-alkyl, di-($C_{1-4}$-alkyl-amino)-$C_{2-7}$-alkyl, aminoiminomethyl, aminocarbonylamino, $C_{1-4}$-alkyl-aminocarbonylamino, di-($C_{1-4}$-alkyl)-aminocarbonylamino, $C_{1-4}$-alkyl-aminocarbonyl-$C_{1-4}$-alkyl-amino, di-($C_{1-4}$-alkyl)-aminocarbonyl-$C_{1-4}$-alkyl-amino, phenylaminocarbonylamino, aminocarbonyl, $C_{1-4}$-alkyl-aminocarbonyl, di-($C_{1-4}$-alkyl)-aminocarbonyl, aminocarbonyl-$C_{1-3}$-alkyl, $C_{1-4}$-alkyl-aminocarbonyl-$C_{1-3}$-alkyl, di-($C_{1-4}$-alkyl)-aminocarbonyl-$C_{1-3}$-alkyl, aminocarbonylamino-$C_{1-3}$-alkyl, $C_{1-6}$-alkoxycarbonyl, $C_{3-6}$-alkenoxycarbonyl, $C_{3-6}$-alkynoxycarbonyl, $C_{1-6}$-alkoxycarbonyl-$C_{1-3}$-alkyl, $C_{1-6}$-alkenoxycarbonyl-$C_{1-3}$-alkyl, $C_{1-6}$-alkynoxycarbonyl-$C_{1-3}$-alkyl or hydroxycarbonyl-$C_{1-3}$-alkyl group, a phenyl, pyridinyl, diazinyl, 1-naphthyl, 2-naphthyl, pyridinylcarbonyl or phenylcarbonyl group which may be mono-, di- or trisubstituted in each case in the carbon skeleton by halogen, by $C_{1-3}$-alkyl, $C_{2-3}$-alkenyl, $C_{2-3}$-alkynyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl, $C_{1-4}$-alkylcarbonylamino, $C_{1-4}$-alkylcarbonylamino-$C_{1-3}$-alkyl, aminocarbonyl, $C_{1-4}$-alkyl-aminocarbonyl, di-($C_{1-4}$-alkyl)-aminocarbonyl, cyano, aminosulphonyl, $C_{1-4}$-alkyl-aminosulphonyl, di-($C_{1-4}$-alkyl)-aminosulphonyl, $C_{1-4}$-alkyl-thio, $C_{1-4}$-alkyl-sulphinyl, or $C_{1-4}$-alkyl-sulphonyl and the substituents may be identical or different, a heterocycle selected from a 4- to 10-membered azacycloalkyl group, a 6- to 10-membered oxaza-, thiaza-, S,S-dioxothiaza- and diazacycloalkyl group and a 6- to 10-membered azabicycloalkyl group, a 1-alkyl-4-piperidinylcarbonyl or 4-alkyl-1-piperazinyl-carbonyl group, while the above-mentioned mono- and bicyclic heterocycles are bound to $Y^1$ in formula (II) via a nitrogen or a carbon atom, in the above-mentioned mono- and bicyclic heterocycles a methyne group not directly linked to a nitrogen, oxygen or sulphur atom may be substituted by a fluorine atom and a methylene group not directly linked to a nitrogen, oxygen or sulphur atom may be substituted by one or two fluorine atoms, the above-mentioned mono- and bicyclic heterocycles and the 1-($C_{1-6}$-alkyl)-4-piperidinylcarbonyl and 4-($C_{1-6}$-alkyl)-1-piperazinylcarbonyl group in the ring may be mono- to tetrasubstituted by hydroxy, $C_{1-6}$-alkyl or hydroxy-$C_{1-3}$-alkyl groups, or, optionally additionally, monosubstituted by a cyclo-$C_{3-7}$-alkyl, hydroxy-$C_{3-7}$-cycloalkyl, cyclo-$C_{3-7}$-alkenyl, cyclo-$C_{3-7}$-alkyl-$C_{1-3}$-alkyl, phenyl-$C_{1-3}$-alkyl, pyridyl-$C_{1-3}$-alkyl, $C_{1-6}$-alkylcarbonyl, $C_{1-6}$-alkylcarbonyl-$C_{1-3}$-alkyl, hydroxy, $C_{1-6}$-alkoxy, amino, $C_{1-4}$-alkylamino, di-($C_{1-4}$-alkyl)amino, phenylcarbonyl, pyridinylcarbonyl, $C_{1-16}$-alkoxycarbonyl, hydroxycarbonyl-carbonyl, $C_{1-6}$-alkoxycarbonyl-carbonyl, hydroxycarbonyl-$C_{1-3}$-alkyl, $C_{1-6}$-alkoxycarbonyl-$C_{1-3}$-alkyl, hydroxycarbonyl-$C_{1-3}$-alkylcarbonyl, $C_{1-6}$-alkoxycarbonyl-$C_{1-3}$-alkylcarbonyl, aminocarbonyl, $C_{1-4}$-alkylaminocarbonyl, di-($C_{1-4}$-alkyl)aminocarbonyl, aminosulphonyl, $C_{1-4}$-alkylaminosulphonyl, di-($C_{1-4}$-alkyl)aminosulphonyl, $C_{1-3}$-alkylsulphonyl, cyclo-$C_{3-7}$-alkylsulphonyl, aminocarbonyl-$C_{1-3}$-alkyl, $C_{1-4}$-alkylaminocarbonyl-$C_{1-3}$-alkyl, di-($C_{1-4}$-alkyl)aminocarbonyl-$C_{1-3}$-alkyl, hydroxyaminocarbonyl-$C_{1-3}$-alkyl, $C_{1-3}$-alkoxyaminocarbonyl-$C_{1-3}$-alkyl or hydroxy-($C_{1-3}$-alkyl)-aminocarbonyl-$C_{1-3}$-alkyl group, by a cyclo-$C_{3-7}$-alkyl-carbonyl, azacyclo-$C_{4-7}$-alkyl-carbonyl, diazacyclo-$C_{5-7}$-alkyl-carbonyl or oxazacyclo-$C_{5-7}$-alkyl-carbonyl group optionally $C_{1-3}$-alkyl-substituted in the ring, while the substituents may be identical or different and may be bound to a cyclic carbon or cyclic nitrogen atom, while the phenyl and pyridinyl groups contained in the groups defined above for $R^4$ may in turn be mono-, di- or trisubstituted by halogen atoms, by $C_{1-3}$-alkyl, $C_{2-3}$-alkenyl, $C_{2-3}$-alkynyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl, $C_{1-4}$-alkylcarbonylamino, $C_{1-4}$-alkylcarbonylamino-$C_{1-3}$-alkyl, aminocarbonyl, $C_{1-3}$-alkyl-aminocarbonyl, di-$C_{1-4}$-alkyl-aminocarbonyl, cyano, aminosulphonyl, $C_{1-4}$-alkyl-aminosulphonyl, di-($C_{1-4}$-alkyl)-aminosulphonyl, $C_{1-3}$-alkyl-thio, $C_{1-3}$-alkyl-sulphinyl, or $C_{1-3}$-alkyl-sulphonyl, while the substituents may be identical or different, or also, if $Y^1$ denotes the carbon atom, the hydroxycarbonyl, aminomethyl, $C_{1-4}$-alkyl-aminomethyl or di-($C_{1-4}$-alkyl)-aminomethyl group, $R^5$ denotes a hydrogen atom or a hydroxy group, a $C_{1-4}$-alkyl group, while an unbranched alkyl group may be substituted in the ω-position by a phenyl, pyridinyl, diazinyl, amino, $C_{1-4}$-alkylamino, di-($C_{1-4}$-alkyl)-amino, 4-$C_{1-4}$-alkyl-1-piperazinyl or 4-morpholinyl group, a $C_{1-6}$-alkoxycarbonyl, cyano or aminocarbonyl group or also, if $Y^1$ denotes a nitrogen atom, a pair of free electrons, or, if $Y^1$ denotes the carbon atom, it may also denote the fluorine atom, or $R^4$ together with $R^5$ and $Y^1$ denote a 4- to 7-membered cycloaliphatic ring wherein a methylene group may be replaced by a group —NH—, —N($C_{1-4}$-alkyl)-, —N($C_{3-4}$-alkenyl)-, —N($C_{3-4}$-alkynyl)-, —N(cyclo-$C_{3-7}$-alkyl)-, —N($C_{3-7}$-cycloalkyl-$C_{1-3}$-alkyl)-, —N(hydroxycarbonyl-$C_{1-3}$-alkyl)- or —N($C_{1-6}$-alkoxycarbonyl-$C_{1-3}$-alkyl)-, while a hydrogen atom bound to a nitrogen atom in one of the groups defined for $R^4$ hereinbefore may be replaced by a protecting group, $R^6$ and $R^7$ which may be identical or different, in each case denote a hydrogen atom, a $C_{1-4}$-alkyl group or also, if $Y^1$ denotes a carbon atom, the fluorine atom, an amino, $C_{1-4}$-alkylamino or di-($C_{1-4}$-alkyl)-amino group, while the two $C_{1-4}$-alkyl groups may be joined together, forming a ring and $R^8$ and $R^9$, which may be identical or different, in each case denote a hydrogen atom or a $C_{1-3}$-alkyl group, while, unless otherwise stated, all the alkyl, alkenyl and alkynyl groups mentioned or contained in the groups defined hereinbefore may be straight-chain or branched, every methyne group contained in the groups defined hereinbefore may be substituted by a fluorine atom, every methylene group may be substituted by up to 2 fluorine atoms and every methyl group may be substituted by up to 3 fluorine atoms and two alkyl and alkenyl groups bound to a nitrogen atom may be joined together forming a 4- to 7-membered, saturated or unsaturated heterocyclic ring, all the aromatic and heteroaromatic groups mentioned or contained in the groups defined hereinbefore may additionally be mono-, di- or trisubstituted by halogen, by cyano or hydroxy groups and the substituents may be identical or different and by the protecting groups mentioned in the definitions above and hereinafter are meant the protective groups familiar from peptide chemistry, particularly a phenylalkoxycarbonyl group with 1 to 3 carbon atoms in the alkoxy moiety, optionally substituted in the phenyl nucleus by a halogen atom, by a nitro or phenyl group or by one or two methoxy groups, for example the benzyloxycarbonyl, 2-nitro-benzyloxycarbonyl, 4-nitrobenzyloxy-carbonyl, 4-methoxy-benzyloxycarbonyl, 2-chloro-benzyloxycarbonyl, 3-chloro-benzyloxycarbonyl, 4-chloro-benzyloxycarbonyl, 4-biphenylyl-α,α-dimethyl-benzyl-oxycarbonyl or 3,5-dimethoxy-α,α-dimethyl-benzyloxycarbonyl group, an alkoxycarbonyl group with a total of 1 to 5 carbon atoms in the alkyl moiety, for example the methoxycarbonyl, ethoxycarbonyl, n-propoxycarbonyl, isopropoxy-carbonyl, n-butoxycarbonyl, 1-methyl propoxycarbonyl, 2-methyl propoxy-carbonyl or tert.butyloxycarbonyl group, the allyloxycarbonyl, 2,2,2-trichloro-(1,1-dimethylethoxy) carbonyl or 9-fluorenylmethoxy-carbonyl group or the formyl, acetyl or trifluoracetyl group.

In the definitions above and hereinafter a group substituted in the ω-position denotes a terminally substituted group, a halogen atom denotes a fluorine, chlorine, bromine or iodine atom and a double or triple bond isolated from a heteroatom denotes a double or triple bond which is linked to a heteroatom via at least one saturated carbon atom.

A second embodiment of the present invention comprises the compounds of the above general formula (I), wherein A, X, D, E, G, M, Q and R' are defined as mentioned above under the first embodiment and $R^2$ denotes the hydrogen atom, a phenylmethyl group or a $C_{2-7}$-alkyl group which may be substituted in the ω-position by a cyclo-$C_{3-7}$-alkyl, cyclo-$C_{3-7}$-alkenyl, phenyl, pyridinyl, diazinyl, hydroxy, amino, $C_{1-6}$-alkylamino, di-($C_{1-6}$-alkyl)-amino, $C_{3-6}$-alkenylamino, di-($C_{3-6}$-alkenyl)amino, $C_{3-6}$-alkynylamino, di-($C_{3-6}$-alkynyl)amino, hydroxycarbonyl, $C_{1-6}$-alkoxycarbonyl, aminocarbonyl, aminocarbonylamino, $C_{1-6}$-alkylcarbonylamino, $C_{2-6}$-alkenylcarbonylamino, $C_{2-6}$-alkynylcarbonylamino, 4-morpholinyl, [bis-(2-hydroxyethyl)]amino, 4-($C_{1-6}$-alkyl)-1-piperazinyl or 4-(ω-hydroxy-$C_{2-7}$-alkyl)-1-piperazinyl group, a phenyl or pyridinyl group, while the phenyl, pyridinyl and diazinyl groups mentioned in the groups defined $R^2$ hereinbefore or contained as substituents therein may additionally be mono-, di- or trisubstituted in the carbon skeleton by halogen, by $C_{1-3}$-alkyl, $C_{2-3}$-alkenyl, $C_{2-3}$-alkynyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkyl-amino-$C_{1-3}$-alkyl, di-($C_{1-3}$-alkyl)-amino-$C_{1-3}$-alkyl, $C_{1-3}$-alkylcarbonylamino, $C_{1-3}$-alkylcarbonylamino-$C_{1-3}$-alkyl, aminocarbonyl, $C_{1-3}$-alkyl-aminocarbonyl, di-($C_{1-3}$-alkyl)-aminocarbonyl, cyano, aminosulphonyl, $C_{1-3}$-alkyl-aminosulphonyl, di-($C_{1-3}$-alkyl)-aminosulphonyl, $C_{1-3}$-alkyl-sulphinyl or $C_{1-3}$-alkyl-sulphonyl and the substituents may be identical or different, $R^3$ denotes the hydrogen atom or a $C_{1-3}$-alkyl group substituted by a phenyl or pyridinyl group, while the $C_{1-3}$-alkyl group may be linked to an alkyl group contained in $R^2$ or a phenyl or pyridyl contained in $R^2$ including the nitrogen atom to which $R^2$ and $R^3$ are bound, forming a 4- to 7-membered ring, or $R^2$ and $R^3$ together with the enclosed nitrogen atom denote a group of general formula

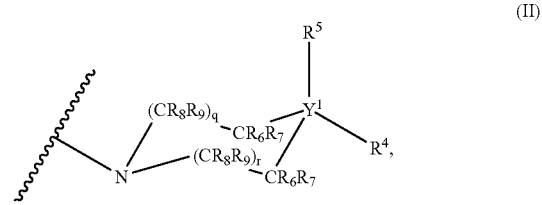

(II)

wherein $Y^1$ denotes the carbon atom or, if $R^5$ denotes a pair of free electrons, may also denote the nitrogen atom, q and r, if $Y^1$ denotes the carbon atom, denote the numbers 0, 1 or 2, or q and r, if $Y^1$ denotes the nitrogen atom, denote the numbers 1 or 2, $R^4$ denotes the hydrogen atom, an amino, $C_{1-4}$-alkylamino, di-($C_{1-4}$-alkyl)-alkylamino, $C_{1-6}$-alkyl, a cyclo-$C_{3-7}$-alkyl, cyclo-$C_{3-7}$-alkenyl, amino-$C_{2-7}$-alkyl, $C_{1-4}$-alkyl-amino-$C_{2-7}$-alkyl, di-($C_{1-4}$-alkyl-amino)-$C_{2-7}$-alkyl, aminoiminomethyl, aminocarbonylamino, $C_{1-4}$-alkyl-aminocarbonylamino, di-($C_{1-4}$-alkyl)-aminocarbonylamino, $C_{1-4}$-alkyl-aminocarbonyl-$C_{1-4}$-alkyl-amino, di-($C_{1-4}$-alkyl)-aminocarbonyl-$C_{1-4}$-alkyl-amino, phenylaminocarbonylamino, aminocarbonyl, $C_{1-4}$-alkyl-aminocarbonyl, di-($C_{1-4}$-alkyl)-aminocarbonyl, aminocarbonyl-$C_{1-3}$-alkyl, $C_{1-4}$-alkyl-aminocarbonyl-$C_{1-3}$-alkyl, di-($C_{1-4}$-alkyl)-aminocarbonyl-$C_{1-3}$-alkyl, aminocarbonylamino-$C_{1-3}$-alkyl, $C_{1-6}$-alkoxycarbonyl, $C_{3-6}$-alkenoxycarbonyl, $C_{3-6}$-alkynoxycarbonyl, $C_{1-6}$-alkoxycarbonyl-$C_{1-3}$-alkyl, $C_{1-6}$-alkenoxycarbonyl-$C_{1-3}$-alkyl, $C_{1-6}$-alkynoxycarbonyl-$C_{1-3}$-alkyl or hydroxycarbonyl-$C_{1-3}$-alkyl group, a phenyl, pyridinyl, diazinyl, 1-naphthyl, 2-naphthyl, pyridinylcarbonyl or phenylcarbonyl group which may be mono-, di- or trisubstituted in each case in the carbon skeleton by halogen, by $C_{1-3}$-alkyl, $C_{2-3}$-alkenyl, $C_{2-3}$-alkynyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl, $C_{1-4}$-alkylcarbonylamino, $C_{1-4}$-alkylcarbonylamino-$C_{1-3}$-alkyl, aminocarbonyl, $C_{1-4}$-alkyl-aminocarbonyl, di-($C_{1-4}$-alkyl)-aminocarbonyl, cyano, aminosulphonyl, $C_{1-4}$-alkyl-aminosulphonyl, di-($C_{1-4}$-alkyl)-aminosulphonyl, $C_{1-4}$-alkyl-thio, $C_{1-4}$-alkyl-sulphinyl or $C_{1-4}$-alkyl-sulphonyl and the substituents may be identical or different, a heterocycle selected from a 4- to 10-membered azacycloalkyl group, a 6- to 10-membered oxaza-, thiaza- and diazacycloalkyl group as well as a 6- to 10-membered azabicycloalkyl group, a 1-alkyl-4-piperidinylcarbonyl or 4-alkyl-1-piperazinylcarbonyl group, while the above-mentioned mono- and bicyclic heterocycles are bound to $Y^1$ in formula (II) via a nitrogen or carbon atom, in the above-mentioned mono- and bicyclic heterocycles a methyne group not directly attached to a nitrogen, oxygen or sulphur atom may be substituted by a fluorine atom and a methylene group not directly attached to a nitrogen, oxygen or sulphur atom may be substituted by one or two fluorine atoms, the above-mentioned mono- and bicyclic heterocycles as well as the 1-($C_{1-6}$-alkyl)-4-piperidinylcarbonyl and 4-($C_{1-6}$-alkyl)-1-piperazinylcarbonyl group may be mono- to tetrasubstituted in the ring by $C_{1-6}$-alkyl groups, or, optionally additionally, monosubstituted by a cyclo-$C_{3-7}$-alkyl, cyclo-$C_{3-7}$-alkenyl, cyclo-$C_{3-7}$-alkyl-$C_{1-3}$-alkyl, phenyl-$C_{1-3}$-alkyl, pyridyl-$C_{1-3}$-alkyl, $C_{1-6}$-alkylcarbonyl, hydroxy, $C_{1-6}$-alkoxy, amino, $C_{1-4}$-alkylamino, di-($C_{1-4}$-alkyl)amino, phenylcarbonyl, pyridinylcarbonyl, hydroxycarbonyl, hydroxycarbonyl-$C_{1-3}$-alkyl, $C_{1-6}$-alkoxycarbonyl, $C_{1-6}$-alkoxycarbonyl-$C_{1-3}$-alkyl, aminocarbonyl, $C_{1-4}$-alkylaminocarbonyl, di-($C_{1-4}$-alkyl)aminocarbonyl, $C_{1-3}$-alkylsulphonyl group, by a cyclo-$C_{3-7}$-alkylcarbonyl, azacyclo-$C_{4-7}$-alkylcarbonyl, diazacyclo-$C_{5-7}$-alkylcarbonyl or oxazacyclo-$C_{5-7}$-alkylcarbonyl group optionally $C_{1-3}$-alkylsubstituted in the ring, while the substituents may be identical or different and may be bound to a cyclic carbon or cyclic nitrogen atom, while the phenyl and pyridinyl groups contained in the groups given as definitions for $R^4$ hereinbefore may in turn be mono-, di- or trisubstituted by halogen atoms, by $C_{1-3}$-alkyl, $C_{2-3}$-alkenyl, $C_{2-3}$-alkynyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl, $C_{1-4}$-alkylcarbonylamino, $C_{1-4}$-alkylcarbonylamino-$C_{1-3}$-alkyl, aminocarbonyl, $C_{1-3}$-alkyl-aminocarbonyl, di-$C_{1-4}$-alkyl-aminocarbonyl, cyano, aminosulphonyl, $C_{1-4}$-alkyl-aminosulphonyl, di-($C_{1-4}$-alkyl)-aminosulphonyl, $C_{1-3}$-alkylthio, $C_{1-3}$-alkyl-sulphinyl or $C_{1-3}$-alkylsulphonyl, while the substituents may be identical or different, or also, if $Y^1$ denotes the carbon atom, the hydroxycarbonyl, aminomethyl, $C_{1-4}$-alkyl-aminomethyl or di-($C_{1-4}$-alkyl)-aminomethyl group, $R^5$ denotes a hydrogen atom, a $C_{1-4}$-alkyl group, while an unbranched alkyl group may be substituted in the ω-position by a phenyl, pyridinyl, diazinyl, amino, $C_{1-4}$-alkylamino, di-($C_{1-4}$-alkyl)-amino, 4-$C_{1-4}$-alkyl-1-piperazinyl or 4-morpholinyl group, a $C_{1-6}$-alkoxycarbonyl, cyano or aminocarbonyl group or, if $Y^1$ denotes a nitrogen atom, a pair of free electrons, or, if $Y^1$ denotes the carbon atom, also the fluorine atom, or $R^4$ together with $R^5$ and $Y^1$ denotes a 4- to 7-membered cycloaliphatic ring wherein a methylene group may be replaced by an —NH—, —N($C_{1-4}$-alkyl)-, —N($C_{3-4}$-alkenyl)-, —N($C_{3-4}$-alkynyl)-, —N(cyclo-$C_{3-7}$-alkyl)- or —N($C_{3-7}$-cycloalkyl-$C_{1-3}$-alkyl)- group, while a hydrogen atom bound to a nitrogen atom in one of the groups defined for $R^4$ hereinbefore may be replaced by a protecting group, $R^6$ and $R^7$ which may be identical or different, in each case denote a hydrogen atom, a $C_{1-4}$-alkyl group or, if $Y^1$ denotes a carbon atom, the fluorine atom, a $C_{1-4}$-alkylamino or di-($C_{1-4}$-alkyl)-amino group, while the two $C_{1-4}$-alkyl groups may be joined together, forming a ring, and $R^8$ and $R^9$, which may be identical or different, in each case denote a hydrogen atom or a $C_{1-3}$-alkyl group, while, unless otherwise stated, all the alkyl, alkenyl and alkynyl groups mentioned or contained in the groups defined hereinbefore may be straight-chain or branched, each methyne group contained in the groups defined hereinbefore may be substituted by a fluorine atom, each methylene group may be substituted by up to 2 fluorine atoms and each methyl group may be substituted by up to 3 fluorine atoms and two alkyl and alkenyl groups bound to a nitrogen atom may be joined together, forming a 4- to 7-membered, saturated or unsaturated heterocyclic ring, all the aromatic and heteroaromatic groups mentioned or contained in the groups defined hereinbefore may additionally be mono-, di- or trisubstituted by halogen, by cyano or hydroxy groups and the substituents may be identical or different, the tautomers, the isomers, the diastereomers, the enantiomers, the hydrates, the mixtures thereof and the salts thereof as well as the hydrates of the salts, particularly the physiologically acceptable salts thereof with inorganic or organic acids or bases.

A third embodiment of the present invention consists of the compounds of the above general formula (I), wherein A, X, D, E, G, M, Q, $R^2$ and $R^3$ are as defined hereinbefore under the first or second embodiment and $R^1$ denotes a mono- or diunsaturated 5- to 7-membered aza, diaza, triaza or thiaza heterocycle, while the above-mentioned heterocycles are linked via a carbon or nitrogen atom or are linked spirocyclically via a carbon and a nitrogen atom, via a carbon and an oxygen atom or via a carbon and a sulphur atom, contain one or two carbonyl groups adjacent to a nitrogen atom, may be substituted at a carbon atom by a phenyl, pyridinyl, diazinyl, thienyl, pyrrolyl, 1,3-thiazolyl, isoxazolyl, pyrazolyl or 1-($C_{1-4}$-alkyl)-pyrazolyl group and an olefinic double bond of one of the above-mentioned unsaturated heterocycles may be fused to a phenyl, naphthyl, pyridine, diazine, thienyl or quinoline ring or to a 1H-quinolin-2-one ring optionally substituted at the nitrogen atom by a methyl group, while the phenyl, pyridinyl, diazinyl, thienyl, pyrrolyl, 1,3-thiazolyl, isoxazolyl, pyrazolyl or 1-($C_{1-4}$-alkyl)-pyrazolyl groups contained in $R^1$ and the benzo-, pyrido- and diazino-fused heterocycles in the carbon skeleton may additionally be mono-, di- or trisubstituted by halogen, by $C_{1-6}$-alkyl, cyclo-$C_{3-7}$-alkyl, cyclo-$C_{3-7}$-alkenyl, $C_{1-6}$-alkoxy, hydroxycarbonyl, $C_{1-6}$-alkoxycarbonyl, cyano, hydroxy, amino, $C_{1-4}$-alkylamino, di-$C_{1-4}$-alkylamino, $C_{1-14}$-alkylcarbonylamino or $C_{1-4}$-alkylcarbonyl groups, while the substituents may be identical or different, and, unless otherwise stated, all the alkyl, alkenyl and alkynyl groups mentioned or contained in the groups defined hereinbefore under $R^1$ may be straight-chain or branched, every methyne group contained in the groups defined hereinbefore may be substituted by a fluorine atom, every methylene group may be substituted by up to 2 fluorine atoms and every methyl group may be substituted by up to 3 fluorine atoms and two alkyl and alkenyl groups bound to a nitrogen atom may be joined together forming a 4- to 7-membered, saturated or unsaturated heterocyclic ring, and all the aromatic and heteroaromatic groups mentioned or contained in the groups defined hereinbefore under $R^1$ may additionally be mono-, di- or trisubstituted by halogen, by cyano or hydroxy groups and the substituents may be identical or different, the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

A fourth embodiment of the present invention consists of the compounds of the above general formula (I), wherein A, X, D, E, G, M, Q, $R^2$ and $R^3$ are defined as mentioned previously under the first or second embodiment and $R^1$ denotes a monounsaturated 5- to 7-membered diaza or triaza heterocycle,
while the above-mentioned heterocycles are linked via a nitrogen atom or
are linked spirocyclically via a carbon and a nitrogen atom or via a carbon and an oxygen atom,
contain a carbonyl group adjacent to a nitrogen atom,
may additionally be substituted by a phenyl group at a carbon atom and
an olefinic double bond of one of the above-mentioned unsaturated heterocycles may be fused to a phenyl, thienyl or quinoline ring,
while the phenyl groups and benzo-fused heterocycles in the carbon skeleton contained in $R^1$ may additionally be mono-, di- or trisubstituted by halogen, by methyl, methoxy, difluoromethyl, trifluoromethyl, hydroxy, amino, $C_{1-14}$-alkylamino, di-($C_{1-4}$-alkyl)-amino, acetylamino, acetyl, hydroxycarbonyl, $C_{1-3}$-alkoxycarbonyl, cyano, difluoromethoxy or trifluoromethoxy groups, while the substituents may be identical or different, but are preferably unsubstituted or monosubstituted by a halogen atom or by a methyl or methoxy group, while, unless otherwise stated, all the alkyl groups mentioned or contained in the groups defined hereinbefore under $R^1$ may be straight-chain or branched, every methyne group contained in the groups defined hereinbefore may be substituted by a fluorine atom, every methylene group may be substituted by up to 2 fluorine atoms and every methyl group may be substituted by up to 3 fluorine atoms, the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

A fifth embodiment of the present invention consists of the compounds of the above general formula (I), wherein A, X, D, E, G, M, Q, $R^2$ and $R^3$ are defined as mentioned hereinbefore under the first or second embodiment and $R^1$ denotes a 1,3,4,5-tetrahydro-1,3-benzodiazepin-2-on-3-yl, 3,4-dihydro-1H-quinazolin-2-on-3-yl, 5-phenyl-2,4-dihydro-1,2,4-triazol-3-on-2-yl, 1,3-dihydro-imidazo[4,5-c]quinolin-2-on-3-yl, 1,3-dihydro-naphth[1,2-d]imidazol-2-on-3-yl, 1,3-dihydro-benzimidazol-2-on-3-yl, 4-phenyl-1,3-dihydro-imidazol-2-on-1-yl, 3,4-dihydro-1H-thieno-[3,2-d]pyrimidin-2-on-3-yl or 3,4-dihydro-1H-thieno[3,4-d]pyrimidin-2-on-3-yl group,
while the heterocycles in the carbon skeleton mentioned under $R^1$ hereinbefore may additionally be monosubstituted by a methoxy group, all the aromatic and heteroaromatic groups mentioned or contained in the groups defined hereinbefore under $R^1$ may additionally be mono-, di- or trisubstituted by halogen atoms, by cyano or hydroxy groups and the substituents may be identical or different, the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

A sixth embodiment of the present invention consists of the compounds of the above general formula (I), wherein A, X, $R^1$, $R^2$ and $R^3$ are defined as mentioned hereinbefore under the first, second, third, fourth or fifth embodiment and (a) D, E independently of one another in each case denote a methyne group or the nitrogen atom and
G denotes a methyne group substituted by the group $R^a$,
M denotes a methyne group substituted by the group $R^b$,
Q denotes a methyne group substituted by the group $R^c$,
while one or two of the groups G, M and Q in each case may also represent a nitrogen atom, or (b) D and E in each case denote a methyne group, while one of the groups D and E may also represent a nitrogen atom, and
G, M and Q in each case denote a nitrogen atom,
while $R^a$, $R^b$ and $R^c$ independently of one another in each case denote a hydrogen or halogen atom, a $C_{1-4}$-alkyl, $C_{2-4}$-alkenyl, $C_{2-4}$-alkynyl, cyclo-$C_{3-6}$-alkyl, cyclo-$C_{3-6}$-alkenyl, cyano, hydroxy, hydroxy-$C_{1-4}$-alkyl, hydroxy-$C_{3-4}$-alkenyl, hydroxy-$C_{3-4}$-alkynyl, $C_{1-4}$-alkoxy, $C_{1-4}$-alkoxy-$C_{1-4}$-alkyl, $C_{1-4}$-alkoxy-$C_{3-4}$-alkenyl, $C_{1-4}$-alkoxy-$C_{3-4}$-alkynyl, thiohydroxy, $C_{1-4}$-alkylthio, amino, $C_{1-4}$-alkylamino, $C_{3-4}$-alkenyl-amino, $C_{3-4}$-alkynyl-amino, di-($C_{1-4}$-alkyl)-amino, di-($C_{3-4}$-alkenyl)-amino, di-($C_{3-4}$-alkynyl)-amino, amino-$C_{1-4}$-alkyl, $C_{1-3}$-alkyl-amino-$C_{1-4}$-alkyl, di-($C_{1-3}$-alkyl)-amino-$C_{1-4}$-alkyl, amino-$C_{3-4}$-alkenyl, $C_{1-3}$-alkyl-amino-$C_{3-4}$-alkenyl, di-($C_{1-3}$-alkyl)-amino-$C_{3-4}$-alkenyl, amino-$C_{3-4}$-alkynyl, $C_{1-3}$-alkyl-amino-$C_{3-4}$-alkynyl, di-($C_{1-3}$-alkyl)-amino-$C_{3-4}$-alkynyl, hydroxycarbonyl, phenylcarbonyl, pyridylcarbonyl, $C_{1-4}$-alkyl-carbonyl, formyl, $C_{1-4}$-alkoxy-carbonyl, $C_{3-4}$-alkenoxy-carbonyl, $C_{3-4}$-alkynoxy-carbonyl, aminocarbonyl, $C_{1-14}$-alkyl-aminocarbonyl, $C_{3-4}$-alkenyl-aminocarbonyl, $C_{3-4}$-alkynyl-aminocarbonyl, di-($C_{1-4}$-alkyl)-aminocarbonyl, di-($C_{3-4}$-alkenyl)-aminocarbonyl, di-$C_{3-4}$-(alkynyl)-aminocarbonyl, formylamino, $C_{1-4}$-alkyl-carbonylamino, formyl-$C_{1-4}$-alkyl-amino, formyl-$C_{3-4}$-alkenyl-amino, formyl-$C_{3-4}$-alkynyl-amino, $C_{1-4}$-alkyl-carbonyl-$C_{1-4}$-alkyl-amino, $C_{1-4}$-alkyl-carbonyl-$C_{3-4}$-alkenyl-amino, $C_{1-4}$-alkyl-carbonyl-$C_{3-4}$-alkynyl-amino, $C_{1-4}$-alkyl-sulphonyl, $C_{2-4}$-alkenyl-sulphonyl, $C_{2-4}$-alkynyl-sulphonyl, $C_{1-4}$-alkyl-sulphinyl, $C_{2-4}$-alkenyl-sulphinyl, $C_{2-4}$-alkynyl-sulphinyl, $C_{1-4}$-alkyl-sulphonylamino, $C_{1-4}$-alkyl-sulphonyl-$C_{1-4}$-alkylamino, $C_{1-4}$-alkyl-sulphonyl-$C_{3-4}$-alkenylamino, $C_{1-4}$-alkyl-sulphonyl-$C_{3-4}$-alkynylamino, aminosulphonyl, $C_{1-4}$-alkylaminosulphonyl, di-($C_{1-4}$-alkyl)-aminosulphonyl, $C_{3-4}$-alkenylaminosulphonyl, di-($C_{3-4}$-alkenyl)-aminosulphonyl, $C_{3-4}$-alkynylaminosulphonyl or di-($C_{3-4}$-alkynyl)-aminosulphonyl group,
with the provisos that, if none of the groups D, E, G, M and Q denotes a nitrogen atom, (i) $R^a$ does not denote a hydrogen atom, if $R^b$ and $R^c$ in each case denote a $C_{1-4}$-alkyl group, (ii) $R^c$ does not denote a hydrogen atom, if $R^a$ and $R^b$ in each case denote a $C_{1-4}$-alkyl group, (iii) $R^a$ does not take on the meanings of a hydrogen, fluorine, chlorine, bromine or iodine atom or a difluoro- or trifluoromethyl group, if $R^c$ denotes a $C_{1-4}$-alkyl, $C_{2-4}$-alkenyl or $C_{2-4}$-alkynyl group and $R^b$ denotes a chlorine or bromine atom or an amino, methylamino or hydroxy group, (iv) $R^c$ does not take on the meanings of a hydrogen, fluorine, chlorine, bromine or iodine atom or a difluoro- or trifluoromethyl group, if $R^a$ denotes a $C_{1-4}$-alkyl, $C_{2-4}$-alkenyl or $C_{2-4}$-alkynyl group and $R^b$ denotes a chlorine or bromine atom, an amino, methylamino or hydroxy group, while, unless otherwise stated, all the alkyl, alkenyl and alkynyl groups mentioned or contained in the groups defined hereinbefore for $R^a$, $R^b$ and $R^c$ may be straight-chain or branched, every methyne group contained in the groups defined hereinbefore may be substituted by a fluorine atom, every methylene group may be substituted by up to 2 fluorine atoms and every methyl group may be substituted by up to 3 fluorine atoms and two alkyl and alkenyl groups bound to a nitrogen atom may be joined together forming a 4- to 7-membered, saturated or unsaturated heterocyclic ring, the double and triple bonds of the $C_{3-4}$-alkenyl or $C_{3-4}$-alkynyl groups contained in the groups given as definitions for $R^a$, $R^b$ and $R^c$ hereinbefore may be isolated from any heteroatoms optionally also contained in these groups, and all the aromatic and heteroaromatic groups mentioned or contained in the groups defined hereinbefore may additionally be mono-, di- or trisubstituted by halogen, by cyano or hydroxy groups and the substituents may be identical or different, the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

A seventh embodiment of the present invention consists of the compounds of the above general formula (I), wherein A, X, $R^1$, $R^2$ and $R^3$ are defined as mentioned hereinbefore under the first, second, third, fourth or fifth embodiment and (a) D, E independently of one another in each case denote a methyne group or the nitrogen atom and G denotes a methyne group substituted by the group $R^a$, M denotes a methyne group substituted by the group $R^b$, Q denotes a methyne group substituted by the group $R^c$, while one or two of the groups G, M and Q in each case may also represent a nitrogen atom, or (b) D and E in each case denote a methyne group, while one of the groups D and E may also represent a nitrogen atom, and G, M and Q in each case denote a nitrogen atom, while $R^a$, $R^b$ and $R^c$ independently of one another in each case denote a hydrogen or halogen atom, a $C_{1-4}$-alkyl, $C_{2-4}$-alkenyl, $C_{2-4}$-alkynyl, cyclo-$C_{3-6}$-alkyl, cyclo-$C_{3-6}$-alkenyl, cyano, hydroxy, hydroxy-$C_{1-2}$-alkyl, hydroxy-$C_3$-alkenyl, hydroxy-$C_3$-alkynyl, $C_{1-4}$-alkoxy, $C_{1-4}$-alkoxy-$C_{1-2}$-alkyl, amino, $C_{1-4}$-alkyl-amino, $C_{3-4}$-alkenyl-amino, $C_{3-4}$-alkynyl-amino, di-($C_{1-4}$-alkyl)-amino, di-($C_{3-4}$-alkenyl)-amino, di-($C_{3-4}$-alkynyl)-amino, amino-$C_{1-2}$-alkyl, $C_{1-3}$-alkyl-amino-$C_{1-2}$-alkyl, di-($C_{1-3}$-alkyl)-amino-$C_{1-2}$-alkyl, amino-$C_3$-alkenyl, $C_{1-3}$-alkyl-amino-$C_3$-alkenyl, di-($C_{1-3}$-alkyl)-amino-$C_3$-alkenyl, amino-$C_3$-alkynyl, $C_{1-3}$-alkyl-amino-$C_3$-alkynyl, di-($C_{1-3}$-alkyl)-amino-$C_3$-alkynyl, hydroxycarbonyl, $C_{1-4}$-alkyl-carbonyl, formyl, $C_{1-4}$-alkoxy-carbonyl, aminocarbonyl, $C_{1-4}$-alkyl-aminocarbonyl, di-($C_{1-4}$-alkyl)-aminocarbonyl, formylamino, $C_{1-4}$-alkyl-carbonylamino, formyl-$C_{1-4}$-alkyl-amino, $C_{1-4}$-alkyl-carbonyl-$C_{1-4}$-alkyl-amino, $C_{1-4}$-alkyl-sulphonyl, $C_{1-4}$-alkyl-sulphinyl, $C_{1-4}$-alkyl-sulphonylamino, $C_{1-4}$-alkyl-sulphonyl-$C_{1-4}$-alkylamino, aminosulphonyl, $C_{1-4}$-alkylaminosulphonyl or di-($C_{1-4}$-alkyl)-aminosulphonyl group, with the provisos that, if none of the groups D, E, G, M and Q denotes a nitrogen atom, (i) $R^a$ does not denote a hydrogen atom if $R^b$ and $R^c$ in each case denote a $C_{1-4}$-alkyl group, (ii) $R^c$ does not denote a hydrogen atom if $R^a$ and $R^b$ in each case denote a $C_{1-4}$-alkyl group, (iii) $R^a$ does not take on the meanings of a hydrogen, fluorine, chlorine, bromine or iodine atom or a difluoro- or trifluoromethyl group if $R^c$ denotes a $C_{1-4}$-alkyl, $C_{2-4}$-alkenyl or $C_{2-4}$-alkynyl group and $R^b$ denotes a chlorine or bromine atom, an amino, methylamino or hydroxy group, (iv) $R^c$ does not take on the meanings of a hydrogen, fluorine, chlorine, bromine or iodine atom or a difluoro- or trifluoromethyl group if $R^a$ denotes a $C_{1-4}$-alkyl, $C_{2-4}$-alkenyl or $C_{2-4}$-alkynyl group and $R^b$ denotes a chlorine or bromine atom, an amino, methylamino or hydroxy group, while, unless otherwise stated, all the alkyl, alkenyl and alkynyl groups mentioned or contained in the groups defined hereinbefore for $R^a$, $R^b$ and $R^c$ may be straight-chain or branched, every methyne group contained in the groups defined hereinbefore may be substituted by a fluorine atom, every methylene group may be substituted by up to 2 fluorine atoms and every methyl group may be substituted by up to 3 fluorine atoms and two alkyl and alkenyl groups bound to a nitrogen atom may be joined together forming a 4- to 7-membered, saturated or unsaturated heterocyclic ring, the double and triple bonds of the $C_{3-4}$-alkenyl or $C_{3-4}$-alkynyl groups contained in the groups given as definitions for $R^a$, $R^b$ and $R^c$ hereinbefore may be isolated from any heteroatoms optionally also contained in these groups, the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

An eighth embodiment of the present invention consists of the compounds of the above general formula (I), wherein A, X, $R^1$, $R^2$ and $R^3$ are defined as mentioned hereinbefore under the first, second, third, fourth or fifth embodiment and (a) D, E independently of one another in each case denote a methyne group or the nitrogen atom and G denotes a methyne group substituted by the group $R^a$, M denotes a methyne group substituted by the group $R^b$, Q denotes a methyne group substituted by the group $R^c$, while one or two of the groups G, M and Q in each case may also represent a nitrogen atom, or (b) D and E in each case denote a methyne group, while one of the groups D and E may also represent a nitrogen atom, and G, M and Q in each case denote a nitrogen atom, while $R^a$, $R^b$ and $R^c$ independently of one another in each case denote a hydrogen or halogen atom, a $C_{1-4}$-alkyl, $C_{2-4}$-alkenyl, $C_{2-4}$-alkynyl, cyclo-$C_{3-6}$-alkyl, cyclo-$C_{3-6}$-alkenyl, cyano, hydroxy, hydroxy-$C_{1-2}$-alkyl, $C_{1-4}$-alkoxy, amino, $C_{1-4}$-alkyl-amino, di-($C_{1-4}$-alkyl)-amino, amino-$C_{1-2}$-alkyl, $C_{1-3}$-alkyl-amino-$C_{1-2}$-alkyl, di-($C_{1-3}$-alkyl)-amino-$C_{1-2}$-alkyl, hydroxycarbonyl, $C_{1-4}$-alkyl-carbonyl, formyl, $C_{1-4}$-alkoxy-carbonyl, aminocarbonyl, $C_{1-4}$-alkyl-aminocarbonyl, di-($C_{1-4}$-alkyl)-aminocarbonyl, formylamino, $C_{1-4}$-alkyl-carbonylamino, formyl-$C_{1-4}$-alkyl-amino or $C_{1-14}$-alkyl-carbonyl-$C_{1-4}$-alkyl-amino group, with the provisos that, if none of the groups D, E, G, M and Q denotes a nitrogen atom, (i) $R^a$ does not denote a hydrogen atom if $R^b$ and $R^c$ in each case denote a $C_{1-4}$-alkyl group, (ii) $R^c$ does not denote a hydrogen atom if $R^a$ and $R^b$ in each case denote a $C_{1-4}$-alkyl group, (iii) $R^a$ does not take on the meanings of a hydrogen, fluorine, chlorine, bromine or iodine atom or a difluoro- or trifluoromethyl group if $R^c$ denotes a $C_{1-4}$-alkyl, $C_{2-4}$-alkenyl or $C_{2-4}$-alkynyl group and $R^b$ denotes a chlorine or bromine atom, an amino, methylamino or hydroxy group, (iv) $R^c$ does not take on the meanings of a hydrogen, fluorine, chlorine, bromine or iodine atom or a difluoro- or trifluoromethyl group if $R^a$ denotes a $C_{1-4}$-alkyl, $C_{2-4}$-alkenyl or $C_{2-4}$-alkynyl group and $R^b$ denotes a chlorine or bromine atom, an amino, methylamino or hydroxy group, while, unless otherwise stated, all the alkyl, alkenyl and alkynyl groups mentioned or contained in the groups defined hereinbefore for $R^a$, $R^b$ and $R^c$ may be straight-chain or branched, every methyne group contained in the groups defined hereinbefore may be substituted by a fluorine atom, every methylene group may be substituted by up to 2 fluorine atoms and every methyl group may be substituted by up to 3 fluorine atoms and two alkyl and alkenyl groups bound to a nitrogen atom may be joined together forming a 4- to 7-membered, saturated or unsaturated heterocyclic ring, the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

A ninth embodiment of the present invention consists of the compounds of the above general formula (I), wherein A, X, $R^1$, $R^2$ and $R^3$ are defined as mentioned hereinbefore under the first, second, third, fourth or fifth embodiment and (a) D, E independently of one another in each case denote a methyne group or the nitrogen atom and G denotes a methyne group substituted by the group $R^a$, M denotes a methyne group substituted by the group $R^b$, Q denotes a methyne group substituted by the group $R^c$, while one or two of the groups G, M and Q in each case may also represent a nitrogen atom, or (b) D and E in each case denote a methyne group, while one of the groups D and E may also represent a nitrogen atom, and G, M and Q in each case denote a nitrogen atom, while $R^a$, $R^b$ and $R^c$ independently of one another in each case denote a hydrogen or -halogen atom, a methyl, difluoromethyl, trifluoromethyl, ethyl, vinyl, ethynyl, cyano, hydroxy, methoxy, difluoromethoxy, trifluoromethoxy, amino, methylamino or dimethylamino group, with the provisos that, if none of the groups D, E, G, M and Q denotes a nitrogen atom, (i) $R^a$ does not denote a hydrogen atom if $R^b$ and $R^c$ in each case denote a methyl or ethyl group, (ii) $R^c$ does not denote a hydrogen atom if $R^a$ and $R^b$ in each case denote a methyl or ethyl group, (iii) $R^a$ does not take on the meanings of a hydrogen, fluorine, chlorine, bromine or iodine atom or a difluoro- or trifluoromethyl group if $R^c$ denotes a methyl, ethyl, vinyl or ethynyl group and $R^b$ denotes a chlorine or bromine atom, an amino, methylamino or hydroxy group, (iv) $R^c$ does not take on the meanings of a hydrogen, fluorine, chlorine, bromine or iodine atom or a difluoro- or trifluoromethyl group if $R^a$ denotes a methyl, ethyl, vinyl or ethynyl group and $R^b$ denotes a chlorine or bromine atom, an amino, methylamino or hydroxy group, the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

A tenth embodiment of the present invention consists of the compounds of the above general formula (I), wherein A, X, D, E, G, M, Q and $R^1$ are defined as mentioned hereinbefore under the first, second, third, fourth, fifth, sixth, seventh, eighth or ninth embodiment and $R^2$ denotes the hydrogen atom or a phenylmethyl group or a $C_{2-7}$-alkyl group which may be substituted in the ω-position by a cyclo-$C_{3-7}$-alkyl, cyclo-$C_{3-7}$-alkenyl, phenyl, pyridinyl, hydroxy, amino, $C_{1-6}$-alkylamino, di-($C_{1-6}$-alkyl)-amino, hydroxycarbonyl, $C_{1-6}$-alkoxycarbonyl, aminocarbonyl, aminocarbonylamino, $C_{1-6}$-alkylamino, 4-morpholinyl group, while the phenyl and pyridinyl groups mentioned in the groups defined for $R^2$ hereinbefore or contained as substituents may additionally be mono-, di- or trisubstituted in the carbon skeleton by halogen, by $C_{1-3}$-alkyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-3}$-alkylcarbonylamino, $C_{1-3}$-alkylcarbonyl-$C_{1-3}$-alkylamino, aminocarbonyl, $C_{1-3}$-alkylaminocarbonyl or di-($C_{1-3}$-alkyl)-aminocarbonyl groups and the substituents may be identical or different, $R^3$ denotes the hydrogen atom or a $C_{1-3}$-alkyl group or $R^2$ and $R^3$ together with the enclosed nitrogen atom denote a group of general formula

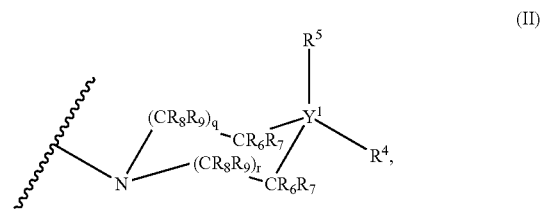

(II)

wherein
- $Y^1$ denotes the carbon atom or, if $R^5$ denotes a pair of free electrons, it may also denote the nitrogen atom,
- q and r, if $Y^1$ denotes the carbon atom, denote the numbers 0 or 1 or
- q and r, if $Y^1$ denotes the nitrogen atom, denote the numbers 1 or 2,
- $R^4$ denotes the hydrogen atom, an amino, $C_{1-4}$-alkyl-amino, di-($C_{1-4}$-alkyl)-alkylamino, $C_{1-6}$-alkyl, a cyclo-$C_{3-7}$-alkyl or cyclo-$C_{3-7}$-alkenyl group optionally substituted by a hydroxycarbonyl, $C_{1-6}$-alkoxycarbonyl, hydroxycarbonyl-$C_{1-3}$-alkyl or $C_{1-6}$-alkoxycarbonyl-$C_{1-3}$-alkyl group, an amino-$C_{2-7}$-alkyl, $C_{1-4}$-alkyl-amino-$C_{2-7}$-alkyl, di-($C_{1-4}$-alkyl-amino)-$C_{2-7}$-alkyl, $C_{1-4}$-alkyl-aminocarbonyl, di-($C_{1-4}$-alkyl)-aminocarbonyl, aminocarbonyl-$C_{1-3}$-alkyl, $C_{1-4}$-alkyl-aminocarbonyl-$C_{1-3}$-alkyl, di-($C_{1-4}$-alkyl)-aminocarbonyl-$C_{1-3}$-alkyl, aminocarbonylamino-$C_{1-3}$-alkyl, $C_{1-6}$-alkoxycarbonyl, $C_{1-6}$-alkoxycarbonyl-$C_{1-3}$-alkyl or hydroxycarbonyl-$C_{1-3}$-alkyl group,
- a phenyl, pyridinyl or diazinyl group which may be substituted in each case by a halogen, a $C_{1-3}$-alkyl, $C_{1-3}$-alkoxy, hydroxy, amino, $C_{1-4}$-alkyl-amino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl group,
- a heterocycle selected from a 4- to 7-membered azacycloalkyl group, a 6- to 7-membered oxaza-, S,S-dioxothiaza- and diazacycloalkyl group and a 7- to 9-membered azabicycloalkyl group,
  - while the above-mentioned mono- and bicyclic heterocycles are bound to $Y^1$ in formula (II) via a nitrogen or a carbon atom,
  - in the above-mentioned mono- and bicyclic heterocycles a methylene group not directly linked to a nitrogen, oxygen or sulphur atom may be substituted by one or two fluorine atoms and
  - the above-mentioned mono- and bicyclic heterocycles may be mono- or disubstituted by hydroxy, $C_{1-3}$-alkyl or hydroxy-$C_{1-3}$-alkyl groups or monosubstituted by a benzyl, cyclo-$C_{3-6}$-alkyl, hydroxycyclo-$C_{3-6}$-alkyl, cyclo-$C_{3-6}$-alkyl-$C_{1-3}$-alkyl, $C_{1-4}$-alkylcarbonyl, $C_{1-4}$-alkylcarbonyl-$C_{1-3}$-alkyl, hydroxy, $C_{1-4}$-alkoxy, amino, $C_{1-4}$-alkylamino, di-($C_{1-4}$-alkyl)-amino, $C_{1-3}$-alkoxycarbonyl, hydroxycarbonyl-carbonyl, $C_{1-3}$-alkoxycarbonyl-carbonyl, hydroxycarbonyl-$C_{1-3}$-alkyl, $C_{1-3}$-alkoxycarbonyl-$C_{1-3}$-alkyl, hydroxycarbonyl-$C_{1-3}$-alkylcarbonyl, $C_{1-3}$-alkoxycarbonyl-$C_{1-3}$-alkylcarbonyl, aminosulphonyl, $C_{1-4}$-alkylaminosulphonyl, di-($C_{1-4}$-alkyl)-aminosulphonyl, $C_{1-3}$-alkylsulphonyl, cyclo-$C_{3-7}$-alkylsulphonyl, aminocarbonyl-$C_{1-3}$-alkyl, $C_{1-4}$-alkylaminocarbonyl-$C_{1-3}$-alkyl, di-($C_{1-4}$-alkyl)-aminocarbonyl-$C_{1-3}$-alkyl, hydroxyaminocarbonyl-$C_{1-3}$-alkyl, $C_{1-3}$-alkoxyaminocarbonyl-$C_{1-3}$-alkyl or hydroxy-($C_{1-3}$-alkyl)-aminocarbonyl-$C_{1-3}$-alkyl group,
  - or also, if $Y^1$ denotes the carbon atom, the hydroxycarbonyl, aminomethyl, $C_{1-4}$-alkyl-aminomethyl or di-($C_{1-4}$-alkyl)-aminomethyl group,
- $R^5$ denotes a hydrogen atom, a $C_{1-3}$-alkyl group or, if $Y^1$ denotes a nitrogen atom, also a pair of free electrons,
- $R^6$ and $R^7$ which may be identical or different, in each case denote a hydrogen atom, a $C_{1-3}$-alkyl group or also, if $Y^1$ denotes a carbon atom, an amino, $C_{1-3}$-alkylamino or di-($C_{1-3}$-alkyl)-amino group, while the two $C_{1-3}$-alkyl groups may be joined together, forming a ring and
- $R^8$ and $R^9$, which may be identical or different, in each case denote a hydrogen atom or a $C_{1-3}$-alkyl group, while, unless otherwise stated, all the alkyl, alkenyl and alkynyl groups mentioned or contained in the groups defined hereinbefore may be straight-chain or branched, every methyne group contained in the groups defined hereinbefore may be substituted by a fluorine atom, every methylene group may be substituted by up to 2 fluorine atoms and every methyl group may be substituted by up to 3 fluorine atoms and two alkyl and alkenyl groups bound to a nitrogen atom may be joined together forming a 4- to 7-membered, saturated or unsaturated heterocyclic ring, all the aromatic and heteroaromatic groups mentioned or contained in the groups defined hereinbefore may additionally be mono-, di- or trisubstituted by halogen, by cyano or hydroxy groups and the substituents may be identical or different, the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

An eleventh embodiment of the present invention comprises the compounds of the above general formula (I), wherein

- A, X, D, E, G, M, Q and $R^1$ are defined as hereinbefore under the first, second, third, fourth, fifth, sixth, seventh, eighth or ninth embodiment and
- $R^2$ denotes the hydrogen atom or
- a phenylmethyl group or a $C_{2-7}$-alkyl group which may be substituted in the ω-position by a cyclo-$C_{3-7}$-alkyl, cyclo-$C_{3-7}$-alkenyl, phenyl, pyridinyl, hydroxy, amino, $C_{1-6}$-alkylamino, di-($C_{1-6}$-alkyl)-amino, hydroxycarbonyl, $C_{1-6}$-alkoxycarbonyl, aminocarbonyl, aminocarbonylamino, $C_{1-6}$-alkylamino, 4-morpholinyl group,
  - while the phenyl and pyridinyl groups mentioned in the groups given as definitions for $R^2$ or contained as substituents therein may additionally be mono-, di- or trisubstituted in the carbon skeleton by halogen, by $C_{1-3}$-alkyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-3}$-alkylcarbonylamino, $C_{1-3}$-alkylcarbonyl-$C_{1-3}$-alkylamino, aminocarbonyl, $C_{1-3}$-alkylaminocarbonyl or di-($C_{1-3}$-alkyl)-aminocarbonyl groups and the substituents may be identical or different,
- $R^3$ denotes the hydrogen atom or a $C_{1-3}$-alkyl group or
- $R^2$ and $R^3$ together with the enclosed nitrogen atom denote a group of general formula

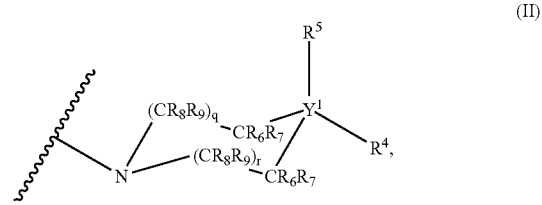

(II)

wherein
- $Y^1$ denotes the carbon atom or, if $R^5$ denotes a pair of free electrons, it may also denote the nitrogen atom,
- q and r, if $Y^1$ denotes the carbon atom, denote the numbers 0 or 1 or
- q and r, if $Y^1$ denotes the nitrogen atom, denote the numbers 1 or 2, R⁴ denotes the hydrogen atom, an amino, $C_{1-4}$-alkyl-amino, di-($C_{1-4}$-alkyl)-alkylamino, $C_{1-6}$-alkyl, cyclo-$C_{3-7}$-alkyl, cyclo-$C_{3-7}$-alkenyl, amino-$C_{2-7}$-alkyl, $C_{1-4}$-alkyl-amino-$C_{2-7}$-alkyl, di-($C_{1-4}$-alkyl-amino)-$C_{2-7}$-alkyl, $C_{1-4}$-alkyl-aminocarbonyl, di-($C_{1-4}$-alkyl)-aminocarbonyl, aminocarbonyl-$C_{1-3}$-alkyl, $C_{1-4}$-alkyl-aminocarbonyl-$C_{1-3}$-alkyl, di-($C_{1-4}$-alkyl)-aminocarbonyl-$C_{1-3}$-alkyl, aminocarbonylamino-$C_{1-3}$-alkyl, $C_{1-6}$-alkoxycarbonyl, $C_{1-16}$-alkoxycarbonyl-$C_{1-3}$-alkyl or hydroxycarbonyl-$C_{1-3}$-alkyl group, a phenyl, pyridinyl or diazinyl group which may be substituted in each case by a halogen, by a $C_{1-3}$-alkyl, $C_{1-3}$-alkoxy, hydroxy, amino, $C_{1-4}$-alkyl-amino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl group, a heterocycle selected from a 4- to 7-membered azacycloalkyl group, a 6- to 7-membered oxaza- and diazacycloalkyl group and a 7- to 9-membered azabicycloalkyl group, while the above-mentioned mono- and bicyclic heterocycles are bound to Y¹ in formula (II) via a nitrogen or carbon atom, in the above-mentioned mono- and bicyclic heterocycles a methylene group not directly attached to a nitrogen, oxygen or sulphur atom may be substituted by one or two fluorine atoms and the above-mentioned mono- and bicyclic heterocycles may be mono- or polysubstituted, for example mono- to trisubstituted, by $C_{1-3}$-alkyl groups or monosubstituted by a benzyl, cyclo-$C_{3-6}$-alkyl, cyclo-$C_{3-6}$-alkyl-$C_{1-3}$-alkyl, $C_{1-4}$-alkylcarbonyl, hydroxy, $C_{1-4}$-alkoxy, amino, $C_{1-4}$-alkylamino, di-($C_{1-4}$-alkyl)-amino, hydroxycarbonyl, $C_{1-3}$-alkoxycarbonyl, hydroxycarbonyl-carbonyl, $C_{1-3}$-alkoxycarbonyl-carbonyl, hydroxycarbonyl-$C_{1-3}$-alkyl, $C_{1-3}$-alkoxycarbonyl-$C_{1-3}$-alkyl or $C_{1-3}$-alkylsulphonyl group, or also, if Y¹ denotes the carbon atom, the hydroxycarbonyl, aminomethyl, $C_{1-4}$-alkyl-aminomethyl or di-($C_{1-4}$-alkyl)-aminomethyl group, R⁵ denotes a hydrogen atom, a $C_{1-3}$-alkyl group or, if Y¹ denotes a nitrogen atom, it may also denote a pair of free electrons, R⁶ and R⁷, which may be identical or different, in each case denote a hydrogen atom, a $C_{1-3}$-alkyl group or also, if Y¹ denotes a carbon atom, a $C_{1-3}$-alkylamino or di-($C_{1-3}$-alkyl)-amino group, while the two $C_{1-3}$-alkyl groups may be joined together forming a ring and R⁸ and R⁹, which may be identical or different, in each case denote a hydrogen atom or a $C_{1-3}$-alkyl group, while, unless otherwise stated, all the alkyl, alkenyl and alkynyl groups mentioned or contained in the groups defined hereinbefore may be straight-chain or branched, each methyne group contained in the groups defined hereinbefore may be substituted by a fluorine atom, each methylene group may be substituted by up to 2 fluorine atoms and each methyl group may be substituted by up to 3 fluorine atoms and two alkyl and alkenyl groups bound to a nitrogen atom may be joined together forming a 4- to 7-membered, saturated or unsaturated heterocyclic ring, all the aromatic and heteroaromatic groups mentioned or contained in the groups defined hereinbefore may additionally be mono-, di- or trisubstituted by halogen or by cyano or hydroxy groups and the substituents may be identical or different, the tautomers, the isomers, the diastereomers, the enantiomers, the hydrates thereof, the mixtures thereof and the salts thereof as well as the hydrates of the salts, particularly the physiologically acceptable salts thereof with inorganic or organic acids or bases.

A twelfth embodiment of the present invention consists of the compounds of the above general formula (I), wherein A, X, D, E, G, M, Q and R¹ are defined as mentioned hereinbefore under the first, second, third, fourth, fifth, sixth, seventh, eighth or ninth embodiment and R² denotes the hydrogen atom or a phenylmethyl group or a $C_{2-7}$-alkyl group which may be substituted in the ω-position by a phenyl, amino, $C_{1-6}$-alkylamino, di-($C_{1-6}$-alkyl)-amino group, while the phenyl and phenylmethyl group mentioned hereinbefore may additionally be mono- or disubstituted at an aromatic carbon atom by halogen, by $C_{1-3}$-alkyl, $C_{1-3}$-alkoxy, amino-$C_{1-3}$-alkyl, $C_{1-3}$-alkylamino-$C_{1-3}$-alkyl or di-($C_{1-3}$-alkyl)-amino-$C_{1-3}$-alkyl groups and the substituents may be identical or different, R³ denotes the hydrogen atom or a $C_{1-3}$-alkyl group or R² and R³ together with the enclosed nitrogen atom denote a group of general formula

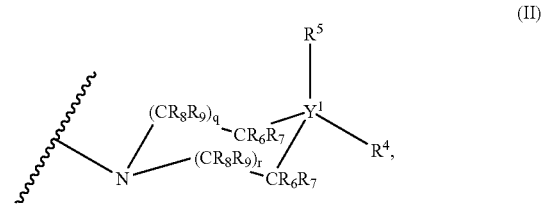

(II)

wherein

Y¹ denotes the carbon atom or, if R⁵ denotes a pair of free electrons, it may also denote the nitrogen atom, q and r, if Y¹ denotes the carbon atom, denote the numbers 0 or 1 or q and r, if Y¹ denotes the nitrogen atom, denote the numbers 1 or 2, R⁴ denotes the hydrogen atom, an amino, $C_{1-4}$-alkyl-amino, di-($C_{1-4}$-alkyl)-alkylamino, $C_{1-6}$-alkyl, a cyclo-$C_{3-7}$-alkyl or cyclo-$C_{3-7}$-alkenyl group optionally substituted by a hydroxycarbonyl, $C_{1-6}$-alkoxycarbonyl, hydroxycarbonyl-$C_{1-3}$-alkyl or $C_{1-6}$-alkoxycarbonyl-$C_{1-3}$-alkyl group, an amino-$C_{2-7}$-alkyl, $C_{1-4}$-alkyl-amino-$C_{2-7}$-alkyl, di-($C_{1-4}$-alkyl-amino)-$C_{2-7}$-alkyl, $C_{1-6}$-alkoxycarbonyl, $C_{1-6}$-alkoxycarbonyl-$C_{1-3}$-alkyl or hydroxycarbonyl-$C_{1-3}$-alkyl group, a phenyl or pyridyl group which may be substituted in each case by a halogen, by a $C_{1-3}$-alkyl, $C_{1-3}$-alkoxy, amino, $C_{1-4}$-alkyl-amino, di-($C_{1-4}$-alkyl)-amino group, a heterocycle selected from a 6- to 7-membered azacycloalkyl group, a 6- to 7-membered S,S-dioxothiaza- and diazacycloalkyl group and a 7- to 9-membered azabicycloalkyl group, while the above-mentioned mono- and bicyclic heterocycles are bound to Y¹ in formula (II) via a nitrogen or a carbon atom, in the above-mentioned mono- and bicyclic heterocycles a methylene group not directly linked to a nitrogen, oxygen or sulphur atom may be substituted by one or two fluorine atoms and the above-mentioned mono- and bicyclic heterocycles may be mono- or disubstituted by a hydroxy, $C_{1-3}$-alkyl or hydroxy-$C_{1-3}$-alkyl group, by a benzyl, cyclo-$C_{3-6}$-alkyl, hydroxy-$C_{3-6}$-cycloalkyl, cyclo-$C_{3-6}$- alkyl-$C_{1-3}$-alkyl, $C_{1-3}$-alkylcarbonyl-$C_{1-3}$-alkyl, amino, $C_{1-4}$-alkylamino or di-($C_{1-4}$-alkyl)-amino, hydroxycarbonyl-carbonyl, $C_{1-6}$-alkoxycarbonyl-carbonyl, hydroxycarbonyl-$C_{1-3}$-alkylcarbonyl, $C_{1-3}$-alkoxycarbonyl-$C_{1-3}$-alkylcarbonyl, aminosulpho-nyl, $C_{1-4}$-alkylaminosulphonyl, di-($C_{1-4}$-alkyl)-aminosulphonyl, cyclo-$C_{3-7}$-alkylsulphonyl, aminocarbonyl-$C_{1-3}$-alkyl, $C_{1-4}$-alkylaminocarbo-nyl-$C_{1-3}$-alkyl, di-($C_{1-4}$-alkyl)-aminocarbonyl-$C_{1-3}$-alkyl, hydroxyaminocarbonyl-$C_{1-3}$-alkyl, $C_{1-3}$-alkoxyaminocarbonyl-$C_{1-3}$-alkyl or hydroxy-($C_{1-3}$-alkyl)-aminocarbonyl-$C_{1-3}$-alkyl groups, or also, if $Y^1$ denotes the carbon atom, the hydroxycarbo-nyl, aminomethyl, $C_{1-4}$-alkyl-aminomethyl or di-($C_{1-4}$-alkyl)-aminomethyl group, $R^5$ denotes a hydrogen atom or, if $Y^1$ denotes a nitrogen atom, may also denote a pair of free electrons, $R^6$ and $R^7$ which may be identical or different, in each case denote a hydrogen atom, a $C_{1-3}$-alkyl group or also, if $Y^1$ denotes a carbon atom, a $C_{1-3}$-alkylamino or di-($C_{1-3}$-alkyl)-amino group, while the two $C_{1-3}$-alkyl groups may be joined together, forming a ring and $R^8$ and $R^9$, which may be identical or different, in each case denote a hydrogen atom or a $C_{1-3}$-alkyl group, the tautomers, the isomers, the diastereomers, the enanti-omers, the hydrates thereof, the mixtures thereof and the salts thereof and the hydrates of the salts, particularly the physiologically acceptable salts thereof with inorganic or organic acids or bases.

A thirteenth embodiment of the present invention consists of the compounds of the above general formula (I), wherein A, X, D, E, G, M, Q and $R^1$ are defined as mentioned herein-before under the first, second, third, fourth, fifth, sixth, seventh, eighth or ninth embodiment and $R^2$ denotes a phenylmethyl group or a $C_{2-7}$-alkyl group which may be substituted in the ω-position by a phenyl, amino, $C_{1-6}$-alkylamino, di-($C_{1-6}$-alkyl)-amino group, while the phenyl and phenylmethyl group mentioned here-inbefore may be substituted at an aromatic carbon atom by an amino-$C_{1-3}$-alkyl, $C_{1-3}$-alkylamino-$C_{1-3}$-alkyl or di-($C_{1-3}$-alkyl)-amino-$C_{1-3}$-alkyl group, $R^3$ denotes the hydrogen atom or a $C_{1-3}$-alkyl group or $R^2$ and $R^3$ together with the enclosed nitrogen atom denote a group of general formula

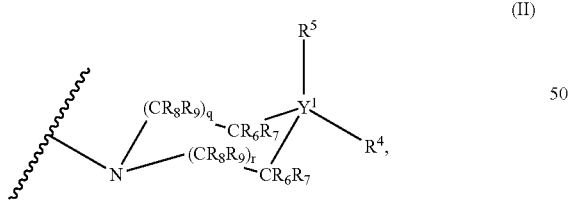

(II)

wherein $R^6$ and $R^7$ in each case denote a hydrogen atom or a dim-ethylamino group, $R^8$ and $R^9$ in each case denote the hydrogen atom and (a) $Y^1$ denotes the carbon atom, q and r denote the numbers 0 or 1, $R^4$ denotes the hydrogen atom, a phenyl, pyridinyl or pyrimidinyl group which may be substituted in each case by a halogen, by an amino, methylamino, dimethylamino, methyl or methoxy group, a hydroxy, 2-diethylamino-ethyl, amino, methy-lamino, dimethylamino, diethylamino, pyrrolidin-1-yl, 3-hydroxy-pyrrolidin-1-yl, 2-hydroxycarbo-nyl-pyrrolidin-1-yl, 2-methoxycarbonyl-pyrrolidin-1-yl, piperidin-1-yl, 4,4-dimethylpiperidin-1-yl, 4-amino-4-methyl-piperidin-1-yl, 2-hydroxycarbonyl-piperidin-1-yl, 2-methoxycarbonyl-piperidin-1-yl, 4-hydroxym-ethyl-piperidin-1-yl, 4-(1-hydroxycyclopropyl)-piperidin-1-yl, 4-amino-piperidin-1-yl, 4-methy-lamino-piperidin-1-yl, 4-dimethylamino-piperidin-1-yl, 4-hydroxy-4-methyl-piperidin-1-yl, 4-hydroxy-4-ethyl-piperidin-1-yl, 4-hydroxy-4-trifluoromethyl-piperidin-1-yl, 4-hydroxy-4-hydroxymethyl-piperidin-1-yl, 3-amino-piperidin-1-yl, 3-methylamino-piperidin-1-yl, 3-dimethylamino-piperidin-1-yl, 3-hydroxy-pip-eridin-1-yl, 4-hydroxy-piperidin-1-yl, 4-hydroxy-carbonylmethyl-piperidin-1-yl, 4-ethoxycarbonyl-methyl-piperidin-1-yl, perhydro-azepin-1-yl, perhydro-1,4-diazepin-1-yl, 4-methyl-perhydro-1,4-diazepin-1-yl, 1-methyl-piperidin-4-yl, piperi-din-4-yl, 1-ethylpiperidin-4-yl, 1-(2-hydroxy-ethyl)-piperidin-4-yl, 1-cyclopropyl-piperidin-4-yl, 1-cyclopropylmethyl-piperidin-4-yl, 1-methylsulphonyl-piperidin-4-yl, 1-ethylsulpho-nyl-piperidin-4-yl, 1-isopropylsulphonyl-piperi-din-4-yl, 1-cyclopropylsulphonyl-piperidin-4-yl, 4-hydroxy-1-methylsulphonyl-piperidin-4-yl, 1-aminosulphonyl-piperidin-4-yl, 1-(methylami-nosulphonyl)-piperidin-4-yl, 1-(dimethylamino-sulphonyl)-piperidin-4-yl, 1-hydroxycarbonylm-ethyl-piperidin-4-yl, 1-ethoxycarbonylmethyl-piperidin-4-yl, 1-(2-hydroxycarbonylethyl)-piperidin-4-yl, 1-(2-ethoxycarbonylethyl)-piperidin-4-yl, 1-(3-hydroxycarbonyl-propionyl)-piperidin-4-yl, 1-(3-ethoxycarbonyl-propionyl)-piperidin-4-yl, 1-(hydroxycarbamoyl-methyl)-piperidin-4-yl, 1-(hydroxy-methyl-carbamoyl-methyl)-piperidin-4-yl, 1-(methoxycarbamoyl-methyl)-piperidin-4-yl, 1-oxalyl-piperidin-4-yl, 1-ethoxyoxalyl-piperidin-4-yl, piperazin-1-yl, 4-methyl-piperazin-1-yl, 4-cyclopropylmethyl-piperazin-1-yl, 4-ethyl-piperazin-1-yl, -(2-hy-droxyethyl)-piperazin-1-yl, 4-cyclopropyl-piper-azin-1-yl, 4-methylsulphonyl-piperazin-1-yl, 4-aminosulphonyl-piperazin-1-yl, 4-(methylami-nosulphonyl)-piperazin-1-yl, 4-(dimethylamino-sulphonyl)-piperazin-1-yl, 4-hydroxycarbonylm-ethyl-piperazin-1-yl, 4-ethoxycarbonylmethyl-piperazin-1-yl, 4-(2-hydroxycarbonylethyl)-piperazin-1-yl, 4-(2-ethoxycarbonylethyl)-piperazin-1-yl, 4-(3-hydroxycarbonyl-propionyl)-piperazin-1-yl, 4-(3-ethoxycarbonyl-propionyl)-piperazin-1-yl, 4-(hydroxycarbamoyl)-methyl-piperazin-1-yl, 4-(hydroxy-methyl-carbamoyl)-methyl-piperazin-1-yl, 4-(methoxycarbamoyl)-methyl-piperazin-1-yl, 1,2-dimethyl-piperazin-1-yl, 3-methyl-piperazin-1-yl, 3,4,5-trimethyl-piperazin-1-yl, 3,5-dimethyl-piperazin-1-yl, 3,3,4-trimethyl-piperazin-1-yl, 3,3-dimethyl-piperazin-1-yl, 3,3,4,5,5-pentamethyl-piperazin-1-yl, 3,3,5,5-tetramethyl-piperazin-1-yl, 3,3,3-trifluoro-2-oxo-propyl)-piperazin-1-yl, morpholin-4-yl, 1,1-dioxo-1$\lambda^6$-thiomorpholin-4-yl, tetrahydropyran-4-yl, 4,4-difluoro-piperidin-1-yl, 8-methyl-8-aza-bicyclo[3.2.1]oct-3-yl, 8-aza-bicyclo[3.2.1]oct-3- yl, azetidin-1-yl, 1-(methoxycarbonylmethyl)-piperidin-4-yl, 1-(ethoxycarbonylmethyl)-piperidin-4-yl, 4-(ethoxycarbonylmethyl)-piperazin-1-yl, 1-hydroxycarbonylmethyl-piperidin-4-yl or 4-hydroxycarbonylmethyl-piperazin-1-yl group, and $R^5$ denotes a hydrogen atom, or (b) $Y^1$ denotes a nitrogen atom, q and r denote the numbers 1 or 2, $R^4$ denotes the hydrogen atom, a phenyl, pyridinyl or pyrimidinyl group which may be substituted in each case by a halogen, by an amino, methylamino, dimethylamino, methyl or methoxy group, a methyl, ethyl, isopropyl, cyclopropyl, cyclopentyl, cyclohexyl, cycloheptyl, 4-hydroxycarbonylmethyl-cylohexyl, 4-ethoxycarbonylmethyl-cyclohexyl, cyclopropylmethyl, 2-diethylamino-propyl, 1-quinuclidin-3-yl, tetrahydropyran-4-yl, 1-piperidin-4-yl, 1-methyl-piperidin-4-yl, 1-ethyl-piperidin-4-yl, 1-(2-hydroxyethyl)-piperidin-4-yl, 1-methylsulphonyl-piperidin-4-yl, 1-aminosulphonyl-piperidin-4-yl, 1-(methylaminosulphonyl)-piperidin-4-yl, 1-(dimethylaminosulphonyl)-piperidin-4-yl, 1-hydroxycarbonylmethyl-piperidin-4-yl, 1-ethoxycarbonylmethyl-piperidin-4-yl, 1-(2-hydroxycarbonylethyl)-piperidin-4-yl, 1-(2-ethoxycarbonylethyl)-piperidin-4-yl, 1-(3-hydroxycarbonyl-propionyl)-piperidin-4-yl, 1-(3-ethoxycarbonyl-propionyl)-piperidin-4-yl, 1-(hydroxycarbamoyl-methyl)-piperidin-4-yl, 1-(hydroxy-methyl-carbamoylmethyl)-piperidin-4-yl, 1-(methoxycarbamoyl-methyl)-piperidin-4-yl, 1-cyclopropyl-piperidin-4-yl, 1-cyclopropylmethyl-piperidin-4-yl, 1-hydroxycarbonylmethyl-piperidin-4-yl or 1-ethoxycarbonylmethyl-piperidin-4-yl group and $R^5$ denotes a pair of free electrons, the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

A fourteenth embodiment of the present invention comprises the compounds of the above general formula (I), wherein A, X, D, E, G, M, Q and $R^1$ are defined as mentioned hereinbefore under the first, second, third, fourth, fifth, sixth, seventh, eighth or ninth embodiment and $R^2$ denotes a phenylmethyl group or a $C_{2-7}$-alkyl group which may be substituted in the ω-position by a phenyl, amino, $C_{1-6}$-alkylamino, di-($C_{1-6}$-alkyl)-amino group, while the above-mentioned phenyl and phenylmethyl group may be substituted at an aromatic carbon atom by an amino-$C_{1-3}$-alkyl, $C_{1-3}$-alkylamino-$C_{1-3}$-alkyl or di-($C_{1-3}$-alkyl)-amino-$C_{1-3}$-alkyl group, $R^3$ denotes the hydrogen atom or a $C_{1-3}$-alkyl group or $R^2$ and $R^3$ together with the enclosed nitrogen atom denote a group of general formula

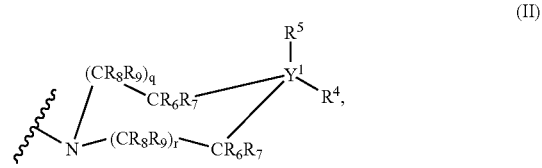

(II)

wherein $R^6$ and $R^7$ in each case denote a hydrogen atom or a dimethylamino group, $R^8$ and $R^9$ in each case denote the hydrogen atom and (a) $Y^1$ denotes the carbon atom, q and r denote the numbers 0 or 1, $R^4$ denotes the hydrogen atom, a phenyl, pyridinyl or pyrimidinyl group which may be substituted in each case by a halogen or by an amino, methylamino, dimethylamino, methyl or methoxy group, a hydroxy, 2-diethylamino-ethyl, amino, methylamino, dimethylamino, diethylamino, pyrrolidin-1-yl, piperidin-1-yl, 4_amino-piperidin-1-yl, 4-methylamino-piperidin-1-yl, 4-dimethylamino-piperidin-1-yl, 3-amino-piperidin-1-yl, 3-methylamino-piperidin-1-yl, 3-dimethylamino-piperidin-1-yl, perhydro-azepin-1-yl, perhydro-1,4-diazepin-1-yl, 4-methyl-perhydro-1,4-diazepin-1-yl, 1-methyl-piperidin-4-yl, piperidin-4-yl, 1-ethylpiperidin-4-yl, 1-cyclopropyl-piperidin-4-yl, 1-cyclopropylmethyl-piperidin-4-yl, piperazin-1-yl, 4-methyl-piperazin-1-yl, 4-cyclopropylmethyl-piperazin-1-yl, 4-ethyl-piperazin-1-yl, 4-cyclopropyl-piperazin-1-yl, 1,2-dimethyl-piperazin-1-yl, 3-methyl-piperazin-1-yl, 3,4,5-trimethyl-piperazin-1-yl, 3,5-dimethyl-piperazin-1-yl, 3,3,4-trimethyl-piperazin-1-yl, 3,3-dimethyl-piperazin-1-yl, 3,3,4,5,5-pentamethyl-piperazin-1-yl, 3,3,5,5-tetramethyl-piperazin-1-yl, morpholin-4-yl, 4,4-difluoro-piperidin-1-yl, 8-methyl-8-aza-bicyclo[3.2.1]oct-3-yl, 8-aza-bicyclo[3.2.1]oct-3-yl, azetidin-1-yl, 1-(methoxycarbonylmethyl)-piperidin-4-yl, 1-(ethoxycarbonylmethyl)-piperidin-4-yl, 4-(ethoxycarbonylmethyl)-piperazin-1-yl, 1-hydroxycarbonylmethyl-piperidin-4-yl or 4-hydroxycarbonylmethyl-piperazin-1-yl group, and $R^5$ denotes a hydrogen atom, or (b) $Y^1$ denotes a nitrogen atom, q and r denote the numbers 1 or 2, $R^4$ denotes the hydrogen atom, a phenyl, pyridinyl or pyrimidinyl group which may be substituted in each case by a halogen or by an amino, methylamino, dimethylamino, methyl or methoxy group, a methyl, ethyl, isopropyl, cyclopropyl, cyclopropylmethyl, 2-diethylamino-propyl, 1-quinuclidin-3-yl, 1-piperidin-4-yl, 1-methyl-piperidin-4-yl, 1-ethyl-piperidin-4-yl, 1-cyclopropyl-piperidin-4-yl, 1-cyclopropylmethyl-piperidin-4-yl, 1-hydroxycarbonylmethyl-piperidin-4-yl or 1-ethoxycarbonylmethyl-piperidin-4-yl group and $R^5$ denotes a pair of free electrons, the tautomers, the diastereomers, the enantiomers, the hydrates, the mixtures thereof and the salts thereof as well as the hydrates of the salts, particularly the physiologically acceptable salts thereof with inorganic or organic acids or bases.

A fifteenth embodiment of the present invention consists of the compounds of the above general formula (I), wherein
D, E, G, M, Q, $R^1$, $R^2$ and $R^3$ are defined as mentioned hereinbefore under the first, second, third, fourth, fifth, sixth, seventh, eighth, ninth, tenth, eleventh, twelfth or thirteenth embodiment and
A and X in each case denote an oxygen atom,
the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

A sixteenth embodiment of the present invention consists of the compounds of the above general formula (I), wherein
A and X in each case denote an oxygen atom,
$R^1$ denotes a 1,3,4,5-tetrahydro-1,3-benzodiazepin-2-on-3-yl, 3,4-dihydro-1H-quinazolin-2-on-3-yl, 5_phenyl-2,4-dihydro-1,2,4-triazol-3-on-2-yl, 1,3-dihydro-imidazo[4,5-c]quinolin-2-on-3-yl, 1,3-dihydro-naphth[1,2-d]imidazol-2-on-3-yl, 1,3-dihydro-benzimidazol-2-on-3-yl, 4-phenyl-1,3-dihydro-imidazol-2-on-1-yl, 3,4-dihydro-1H-thieno-[3,2-d]pyrimidin-2-on-3-yl or 3,4-dihydro-1H-thieno[3,4-d]pyrimidin-2-on-3-yl group,
and $R^2$ and $R^3$ are defined as mentioned hereinbefore under the first or second embodiment,
while the heterocycles in the carbon skeleton mentioned hereinbefore under $R^1$ may additionally be monosubstituted by a methoxy group,
and all the aromatic and heteroaromatic groups and parts of molecules mentioned or contained in the groups defined under $R^1$ may additionally be mono-, di- or trisubstituted by halogen atoms, by cyano or hydroxy groups and the substituents may be identical or different,
and in this and all the preceding embodiments in each case particular importance attaches to the compounds wherein
D and E in each case denote a methyne group,
G denotes a methyne group substituted by the group $R^a$,
M denotes a methyne group substituted by the group $R^b$,
Q denotes a methyne group substituted by the group $R^c$ and
$R^a$, $R^b$ and $R^c$ independently of one another in each case denote a hydrogen or halogen atom, a $C_{1-4}$-alkyl, $C_{2-4}$-alkenyl, $C_{2-4}$-alkynyl, cyclo-$C_{3-6}$-alkyl, cyclo-$C_{3-6}$-alkenyl, cyano, hydroxy, hydroxy-$C_{1-2}$-alkyl, hydroxy-$C_3$-alkenyl, hydroxy-$C_3$-alkynyl, $C_{1-4}$-alkoxy, $C_{1-4}$-alkoxy-$C_{1-2}$-alkyl, amino, $C_{1-4}$-alkyl-amino, $C_{3-4}$-alkenyl-amino, $C_{3-4}$-alkynyl-amino, di-($C_{1-4}$-alkyl)-amino, di-($C_{3-4}$-alkenyl)-amino, di-($C_{3-4}$-alkynyl)-amino, amino-$C_{1-2}$-alkyl, $C_{1-3}$-alkyl-amino-$C_{1-2}$-alkyl, di-($C_{1-3}$-alkyl)-amino-$C_{1-2}$-alkyl, amino-$C_3$-alkenyl, $C_{1-3}$-alkyl-amino-$C_3$-alkenyl, di-($C_{1-3}$-alkyl)-amino-$C_3$-alkenyl, amino-$C_3$-alkynyl, $C_{1-3}$-alkyl-amino-$C_3$-alkynyl, di-($C_{1-3}$-alkyl)-amino-$C_3$-alkynyl, hydroxycarbonyl, $C_{1-4}$-alkyl-carbonyl, formyl, $C_{1-4}$-alkoxy-carbonyl, aminocarbonyl, $C_{1-4}$-alkyl-aminocarbonyl, di-($C_{1-4}$-alkyl)-aminocarbonyl, formylamino, $C_{1-4}$-alkyl-carbonylamino, formyl-$C_{1-4}$-alkyl-amino, $C_{1-4}$-alkyl-carbonyl-$C_{1-4}$-alkyl-amino, $C_{1-4}$-alkyl-sulphonyl, $C_{1-4}$-alkyl-sulphinyl, $C_{1-4}$-alkyl-sulphonylamino, $C_{1-4}$-alkyl-sulphonyl-$C_{1-4}$-alkylamino, aminosulphonyl, $C_{1-4}$-alkylaminosulphonyl or di-($C_{1-4}$-alkyl)-aminosulphonyl group,
while any alkyl, alkenyl and alkynyl groups mentioned or contained in the definitions of the groups $R^a$, $R^b$ and $R^c$ may be straight-chain or branched, every methyne group contained in these groups may be substituted by a fluorine atom, every methylene group may be substituted by up to 2 fluorine atoms and every methyl group may be substituted by up to 3 fluorine atoms and
the double and triple bonds of the $C_{3-4}$-alkenyl or $C_{3-4}$-alkynyl groups contained in the groups defined for $R^a$, $R^b$ and $R^c$ hereinbefore may be isolated from any heteroatoms optionally also contained in these groups,
exceptional importance attaches to the compounds wherein
D and E in each case denote a methyne group,
G denotes a methyne group substituted by the group $R^a$,
M denotes a methyne group substituted by the group $R^b$,
Q denotes a methyne group substituted by the group $R^c$ and
$R^a$, $R^b$ and $R^c$ independently of one another in each case denote a hydrogen or halogen atom, a $C_{1-4}$-alkyl, $C_{2-4}$-alkenyl, $C_{2-4}$-alkynyl, cyclo-$C_{3-6}$-alkyl, cyclo-$C_{3-6}$-alkenyl, cyano, hydroxy, hydroxy-$C_{1-2}$-alkyl, $C_{1-4}$-alkoxy, amino, $C_{1-4}$-alkyl-amino, di-($C_{1-4}$-alkyl)-amino, amino-$C_{1-2}$-alkyl, $C_{1-3}$-alkyl-amino-$C_{1-2}$-alkyl, di-($C_{1-3}$-alkyl)-amino-$C_{1-2}$-alkyl, hydroxycarbonyl, $C_{1-4}$-alkyl-carbonyl, formyl, $C_{1-4}$-alkoxy-carbonyl, aminocarbonyl, $C_{1-4}$-alkyl-aminocarbonyl, di-($C_{1-4}$-alkyl)-aminocarbonyl, formylamino, $C_{1-4}$-alkyl-carbonylamino, formyl-$C_{1-4}$-alkyl-amino or $C_{1-14}$-alkyl-carbonyl-$C_{1-4}$-alkyl-amino group,
while any alkyl, alkenyl and alkynyl groups mentioned or contained in the definitions of the groups $R^a$, $R^b$ and $R^c$ may be straight-chain or branched and every methyne group contained in these groups may be substituted by a fluorine atom, every methylene group may be substituted by up to 2 fluorine atoms and every methyl group may be substituted by up to 3 fluorine atoms, and
most particularly outstanding importance attaches to the compounds wherein
D and E in each case denote a methyne group,
G denotes a methyne group substituted by the group $R^a$,
M denotes a methyne group substituted by the group $R^b$,
Q denotes a methyne group substituted by the group $R^c$ and
$R^a$, $R^b$ and $R^c$ independently of one another in each case denote a hydrogen or halogen atom, a methyl, difluoromethyl, trifluoromethyl, ethyl, vinyl, ethynyl, cyano, hydroxy, methoxy, difluoromethoxy, trifluoromethoxy, amino, methylamino or dimethylamino group,
the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

A seventeenth embodiment of the present invention consists of the compounds of the above general formula (I), wherein
A and X in each case denote an oxygen atom,
$R^1$ is defined as mentioned hereinbefore under the fifth embodiment,
D and E in each case denote a methyne group,
G denotes a methyne group substituted by the group $R^a$,
M denotes a methyne group substituted by the group $R^b$,
Q denotes a methyne group substituted by the group $R^c$ and
$R^a$, $R^b$ and $R^c$ independently of one another in each case denote a hydrogen or halogen atom, a methyl, difluoromethyl, trifluoromethyl, ethyl, vinyl, ethynyl, cyano, hydroxy, methoxy, difluoromethoxy, trifluoromethoxy, amino, methylamino or dimethylamino group,
while in this and all the preceding embodiments in each case outstanding importance attaches to the compounds wherein
$R^2$ and $R^3$ are defined as mentioned hereinbefore under the tenth or eleventh embodiment, particularly exceptional importance attaches to the compounds wherein $R^2$ and $R^3$ are defined as mentioned hereinbefore under the twelfth embodiment, and most particularly outstanding importance attaches to the compounds wherein $R^2$ and $R^3$ are defined as mentioned hereinbefore under the thirteenth embodiment, the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

An eighteenth embodiment of the present invention consists of the compounds of the above general formula (I), wherein A and X in each case denote an oxygen atom, D and E in each case denote a methyne group, G denotes a methyne group substituted by the group $R^a$, M denotes a methyne group substituted by the group $R^b$, Q denotes a methyne group substituted by the group $R^c$, $R^a$, $R^b$ and $R^c$ independently of one another in each case denote a hydrogen or halogen atom, a $C_{1-3}$-alkyl, trifluoromethyl, cyano, hydroxy, methoxy, trifluoromethoxy, amino, methylamino or dimethylamino group, $R^1$ denotes a monounsaturated 5- to 7-membered diaza heterocycle, linked to the piperidine ring in formula (I) via a nitrogen atom, while the heterocycle mentioned hereinbefore contains a carbonyl group adjacent to a nitrogen atom and the carbonyl group is preferably linked to two nitrogen atoms and the olefinic double bond of the heterocycle is fused to a phenyl or thienyl ring and the phenyl and thienyl ring may be mono-, di- or trisubstituted by halogen atoms, by methyl, methoxy, difluoromethyl, trifluoromethyl, hydroxy, amino, $C_{1-3}$-alkylamino, di-($C_{1-3}$-alkyl)-amino, acetylamino, acetyl, cyano, difluoromethoxy or trifluoromethoxy groups, while the substituents may be identical or different, but is preferably unsubstituted or monosubstituted by a halogen atom, by a methyl or methoxy group, and definitions of $R^1$ include for example a 1,3,4,5-tetrahydro-1,3-benzodiazepin-2-on-3-yl, 3,4-dihydro-1H-quinazolin-2-on-3-yl, 5-phenyl-2,4-dihydro-1,2,4-triazol-3-on-2-yl, 1,3-dihydro-imidazo[4,5-c]quinolin-2-on-3-yl, 1,3-dihydro-naphth[1,2-d]imidazol-2-on-3-yl, 1,3-dihydro-benzimidazol-2-on-3-yl, 4-phenyl-1,3-dihydro-imidazol-2-on-1-yl, 3,4-dihydro-1H-thieno[3,2-d]pyrimidin-2-on-3-yl or 3,4-dihydro-1H-thieno[3,4-d]pyrimidin-2-on-3-yl group which is mono-, di- or trisubstituted at an unsaturated carbon atom of the aromatic or heteroaromatic moiety by halogen atoms or by cyano or hydroxy groups and the substituents may be identical or different, but are preferably unsubstituted, $R^2$ and $R^3$ together with the enclosed nitrogen atom denote a group of general formula

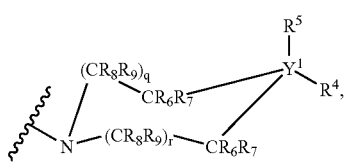

(II)

wherein $Y^1$ denotes the carbon atom or, if $R^5$ denotes a pair of free electrons, it may also denote the nitrogen atom, q and r, if $Y^1$ denotes the carbon atom, denote the numbers 0, 1 or 2, while the total of q and r is 1, 2 or 3, q and r, if $Y^1$ denotes the nitrogen atom, denote the numbers 1 or 2, while the total of q and r is 2 or 3, $R^4$ denotes the hydrogen atom, an amino, $C_{1-4}$-alkylamino, di-($C_{1-4}$-alkyl)-alkylamino, $C_{1-6}$-alkyl, a cyclo-$C_{3-7}$-alkyl, amino-$C_{2-7}$-alkyl, $C_{1-4}$-alkyl-amino-$C_{2-7}$-alkyl, di-($C_{1-4}$-alkyl-amino)-$C_{2-7}$-alkyl, $C_{1-6}$-alkoxycarbonyl, $C_{1-6}$-alkoxycarbonyl-$C_{1-3}$-alkyl or hydroxycarbonyl-$C_{1-3}$-alkyl group optionally substituted by a hydroxycarbonyl, $C_{1-6}$-alkoxycarbonyl, hydroxycarbonyl-$C_{1-3}$-alkyl or $C_{1-6}$-alkoxycarbonyl-$C_{1-3}$-alkyl group, a phenyl or pyridyl group which may be substituted in each case by a halogen atom, by a $C_{1-3}$-alkyl, $C_{1-3}$-alkoxy, amino, $C_{1-4}$-alkyl-amino or di-($C_{1-4}$-alkyl)-amino group, a heterocycle selected from a 5- to 7-membered azacycloalkyl or S,S-dioxothiaza group and a 6- to 7-membered diazacycloalkyl group, while the above-mentioned heterocycles are bound to $Y^1$ in formula (II) via a nitrogen or a carbon atom and may be substituted by one or two hydroxy, $C_{1-3}$-alkyl or hydroxy-$C_{1-3}$-alkyl groups or by a cyclo-$C_{3-6}$-alkyl, hydroxy-$C_{3-6}$-cycloalkyl, cyclo-$C_{3-6}$-alkyl-$C_{1-3}$-alkyl, $C_{1-3}$-alkylcarbonyl-$C_{1-3}$-alkyl, amino, $C_{1-4}$-alkylamino, di-($C_{1-4}$-alkyl)-amino, hydroxycarbonyl-carbonyl, $C_{1-3}$-alkoxycarbonyl-carbonyl, hydroxycarbonyl-$C_{1-3}$-alkylcarbonyl, $C_{1-3}$-alkoxycarbonyl-$C_{1-3}$-alkylcarbonyl, aminosulphonyl, $C_{1-4}$-alkylaminosulphonyl, di-($C_{1-4}$-alkyl)-aminosulphonyl, cyclo-$C_{3-7}$-alkyl-sulphonyl, aminocarbonyl-$C_{1-3}$-alkyl, $C_{1-4}$-alkylaminocarbonyl-$C_{1-3}$-alkyl, di-($C_{1-4}$-alkyl)-aminocarbonyl-$C_{1-3}$-alkyl, hydroxyaminocarbonyl-$C_{1-3}$-alkyl, $C_{1-3}$-alkoxyaminocarbonyl-$C_{1-3}$-alkyl or hydroxy-($C_{1-3}$-alkyl)-aminocarbonyl-$C_{1-3}$-alkyl group, $R^5$ denotes a hydrogen atom or, if $Y^1$ denotes a nitrogen atom, it may also denote a pair of free electrons and $R^6$, $R^7$, $R^8$ and $R^9$, which may be identical or different, in each case denote a hydrogen atom or a $C_{1-3}$-alkyl group, the tautomers, the isomers, the diastereomers, the enantiomers, the hydrates thereof, the mixtures thereof and the salts thereof and the hydrates of the salts, particularly the physiologically acceptable salts thereof with inorganic or organic acids or bases.

A nineteenth embodiment of the present invention consists of the compounds of the above general formula (I), wherein A and X in each case denote an oxygen atom, D and E in each case denote a methyne group, G denotes a methyne group substituted by the group $R^a$, M denotes a methyne group substituted by the group $R^b$, Q denotes a methyne group substituted by the group $R^c$, $R^a$, $R^b$ and $R^c$ independently of one another in each case denote a hydrogen or halogen atom, a $C_{1-3}$-alkyl, trifluoromethyl, cyano, hydroxy, methoxy, trifluoromethoxy, amino, methylamino or dimethylamino group, $R^1$ denotes a monounsaturated 5- to 7-membered diaza heterocycle, linked to the piperidine ring in formula (I) via a nitrogen atom, while the above-mentioned heterocycle contains a carbonyl group adjacent to a nitrogen atom and the carbonyl group is preferably linked to two nitrogen atoms and the olefinic double bond of the heterocycle is fused to a phenyl or thienyl ring and the phenyl and thienyl ring may be mono-, di- or trisubstituted by halogen atoms, by methyl, methoxy, difluoromethyl, trifluoromethyl, hydroxy, amino, $C_{1-3}$-alkylamino, di-($C_{1-3}$-alkyl)-amino, acetylamino, acetyl, cyano, difluoromethoxy or trifluoromethoxy groups, while the substituents may be identical or different, but is preferably unsubstituted or monosubstituted by a halogen atom or by a methyl or methoxy group, and examples of definitions of $R^1$ include a 1,3,4,5-tetrahydro-1,3-benzodiazepin-2-on-3-yl, 3,4-dihydro-1H-quinazolin-2-on-3-yl, 5-phenyl-2,4-dihydro-1,2,4-triazol-3-on-2-yl, 1,3-dihydro-imidazo[4,5-c]quinolin-2-on-3-yl, 1,3-dihydro-naphth[1,2-d]imidazol-2-on-3-yl, 1,3-dihydro-benzimidazol-2-on-3-yl, 4-phenyl-1,3-dihydro-imidazol-2-on-1-yl, 3,4-dihydro-1H-thieno[3,2-d]pyrimidin-2-on-3-yl or 3,4-dihydro-1H-thieno[3,4-d]pyrimidin-2-on-3-yl group, which may be mono-, di- or trisubstituted at an unsaturated carbon atom of the aromatic or heteroaromatic moiety by halogen atoms or by cyano or hydroxy groups and the substituents may be identical or different, but are preferably unsubstituted, $R^2$ and $R^3$ together with the enclosed nitrogen atom denote a group of general formula

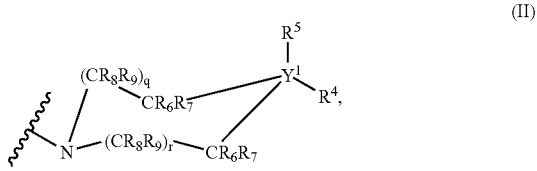

(II)

wherein $Y^1$ denotes the carbon atom or, if $R^5$ denotes a pair of free electrons, it may also denote the nitrogen atom, q and r, if $Y^1$ denotes the carbon atom, denote the numbers 0, 1 or 2, the sum of q and r being 1, 2 or 3, q and r, if $Y^1$ denotes the nitrogen atom, denote the numbers 1 or 2, the sum of q and r being 2 or 3, $R^4$ denotes the hydrogen atom, an amino, $C_{1-4}$-alkylamino, di-($C_{1-4}$-alkyl)-alkylamino, $C_{1-6}$-alkyl, cyclo-$C_{3-7}$-alkyl, amino-$C_{2-7}$-alkyl, $C_{1-4}$-alkyl-amino-$C_{2-7}$-alkyl, di-($C_{1-4}$-alkyl-amino)-$C_{2-7}$-alkyl, $C_{1-6}$-alkoxycarbonyl, $C_{1-6}$-alkoxycarbonyl-$C_{1-3}$-alkyl or hydroxycarbonyl-$C_{1-3}$-alkyl group, a phenyl or pyridyl group which may be substituted in each case by a halogen atom or by a $C_{1-3}$-alkyl, $C_{1-3}$-alkoxy, amino, $C_{1-4}$-alkyl-amino or di-($C_{1-4}$-alkyl)-amino group, a heterocycle selected from a 5- to 7-membered azacycloalkyl group and a 6- to 7-membered diazacycloalkyl group, while the above-mentioned heterocycles are bound to $Y^1$ in formula (II) via a nitrogen or carbon atom and may be substituted by a $C_{1-3}$-alkyl, cyclo-$C_{3-6}$-alkyl, cyclo-$C_{3-6}$-alkyl-$C_{1-3}$-alkyl, amino, $C_{1-4}$-alkylamino or di-($C_{1-4}$-alkyl)-amino group, $R^5$ denotes a hydrogen atom or, if $Y^1$ denotes a nitrogen atom, it may also denote a pair of free electrons and $R^6$, $R^7$, $R^8$ and $R^9$, which may be identical or different, in each case denote a hydrogen atom or a $C_{1-3}$-alkyl group, the tautomers, the diastereomers, the enantiomers, the hydrates, the mixtures thereof and the salts thereof as well as the hydrates of the salts, particularly the physiologically acceptable salts thereof with inorganic or organic acids or bases.

The following compounds are mentioned by way of example as most particularly preferred compounds of the above general formula (I):

| No. | Structure | Name |
|---|---|---|
| (1) | 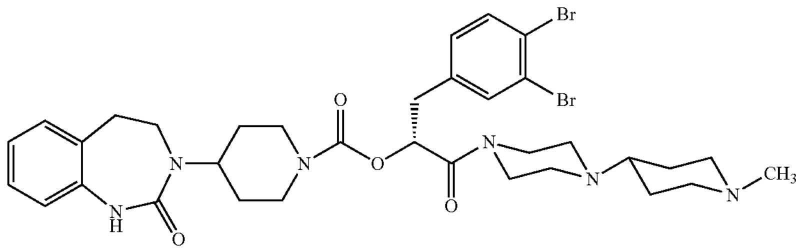 | (R)-1-(3,4-dibromo-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (2) | 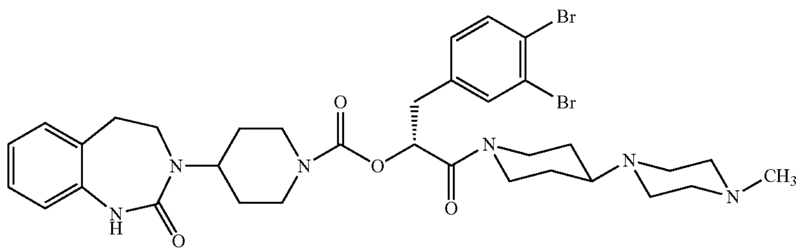 | (R)-1-(3,4-dibromo-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (3) | 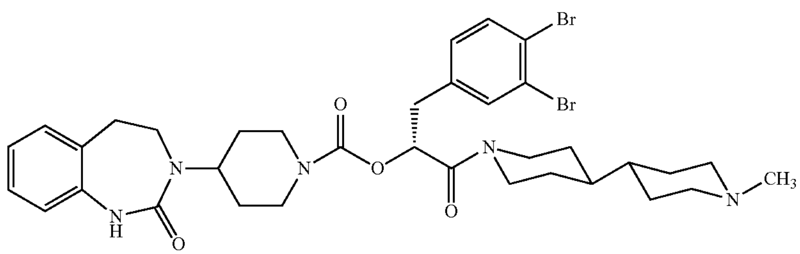 | (R)-1-(3,4-dibromo-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (4) | 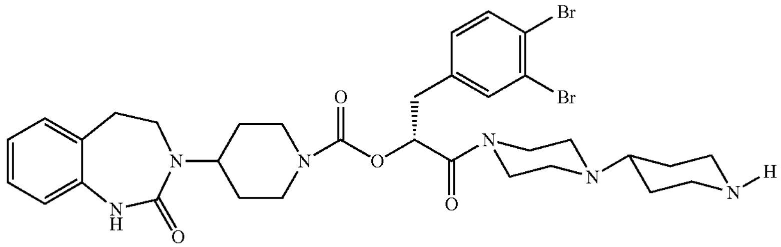 | (R)-1-(3,4-dibromo-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (5) | 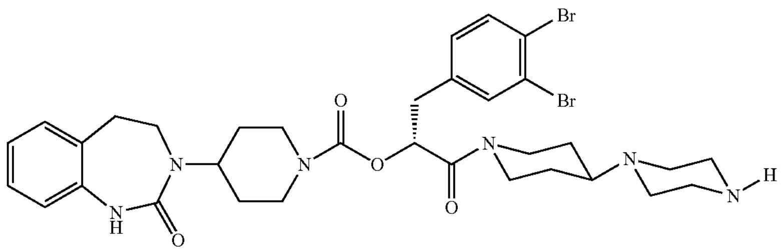 | (R)-1-(3,4-dibromo-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (6) | 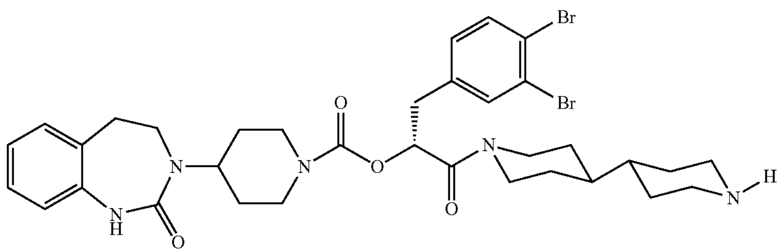 | (R)-2-(4,4'-bipiperidinyl-1-yl)-1-(3,4-dibromo-benzyl)-2-oxo-ethyl 4-(2-oxo-1,2,4,5-tetrahydro-1,3-benzodiazepin-3-yl)-piperidine-1-carboxylate |
| (7) | 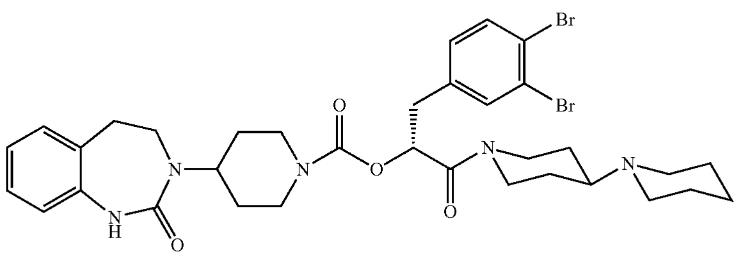 | (R)-2-(1,4'-bipiperidinyl-1'-yl)-1-(3,4-dibromo-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (8) | 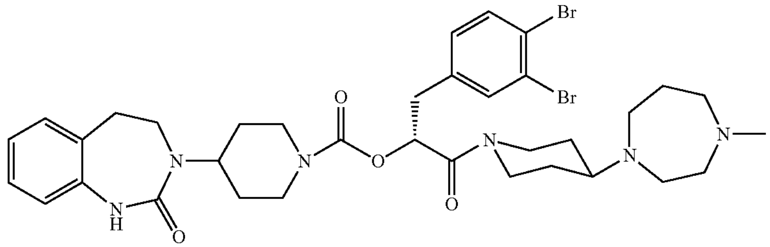 | (R)-1-(3,4-dibromo-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (9) | 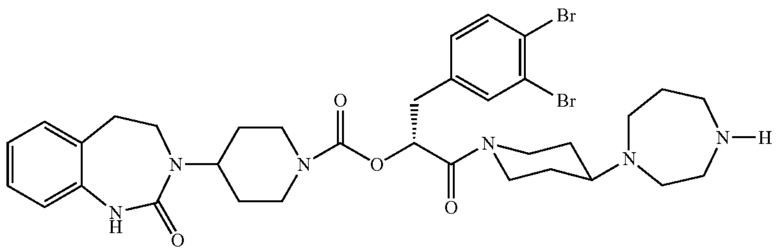 | (R)-1-(3,4-dibromo-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (10) | 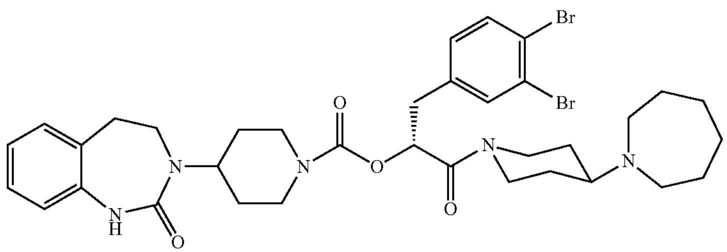 | (R)-1-(3,4-dibromo-benzyl)-2-oxo-2-(4-perhydro-azepin-1-yl-piperidin-1-yl)-ethyl 4-(2-oxo-1,2,4,5-tetrahydro-1,3-benzodiazepin-3-yl)-piperidine-1-carboxylate |
| (11) | 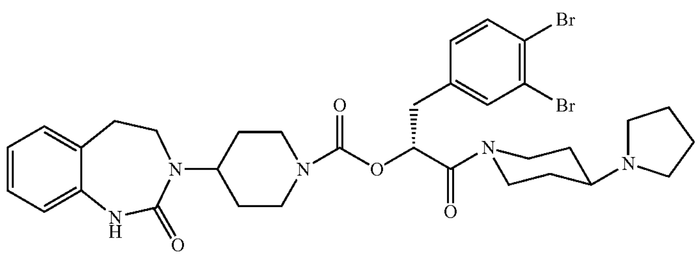 | (R)-1-(3,4-dibromo-benzyl)-2-oxo-2-(4-pyrrolidin-1-yl-piperidin-1-yl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (12) | 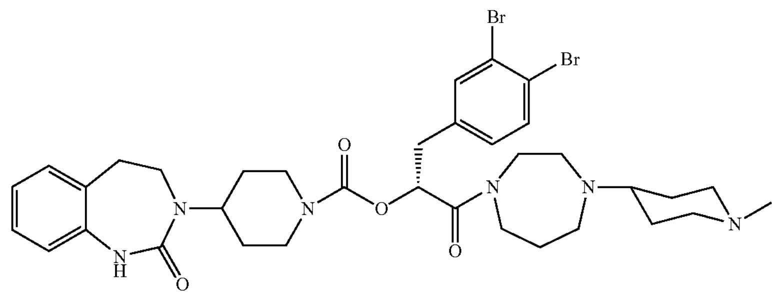 | (R)-1-(3,4-dibromo-benzyl)-2-[4-(1-methyl-piperidin-4-yl)-perhydro-1,4-diazepin-1-yl]-2-oxo-ethyl 4-(2-oxo-1,2,4,5-tetrahydro-1,3-benzodiazepin-3-yl)-piperidine-1-carboxylate |
| (13) | 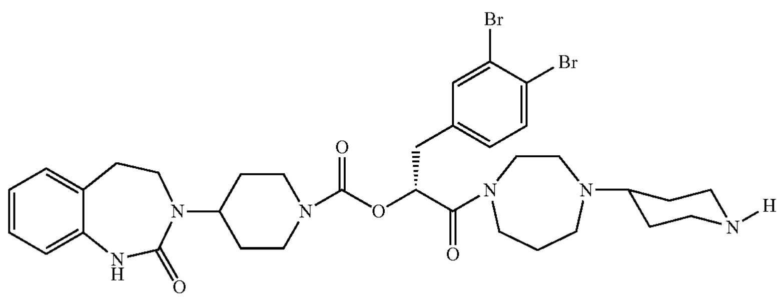 | 4(R)-1-(3,4-dibromo-benzyl)-2-oxo-2-(4-piperidin-4-yl-perhydro-1,4-diazepin-1-yl)-ethyl-1-(2-oxo-1,2,4,5-tetrahydro-1,3-benzo-diazepin-3-yl)-piperidine-1-carboxylate |
| (14) | 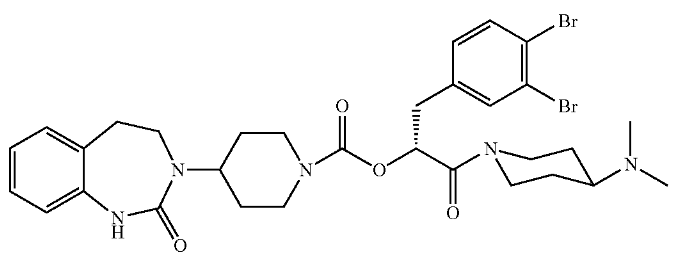 | (R)-1-(3,4-dibromo-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (15) | 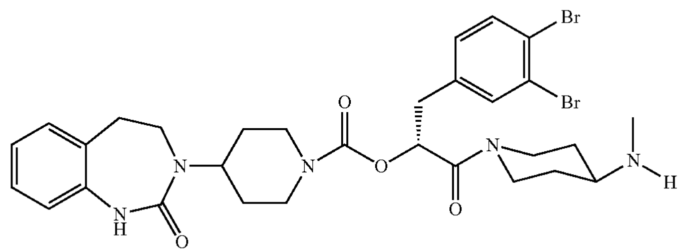 | (R)-1-(3,4-dibromo-benzyl)-2-(4-methyl-amino-piperidin-1-yl)-2-oxo-ethyl 4-(2-oxo-1,2,4,5-tetrahydro-1,3-benzodiazepin-3-yl)-piperidine-1-carboxylate |
| (16) | 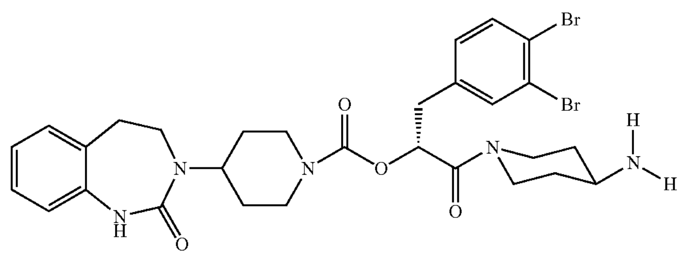 | (R)-1-(3,4-dibromo-benzyl)-2-(4-amino-piperidin-1-yl)-2-oxo-ethyl 4-(2-oxo-1,2,4,5-tetrahydro-1,3-benzodiazepin-3-yl)-piperidine-1-carboxylate |
| (17) | 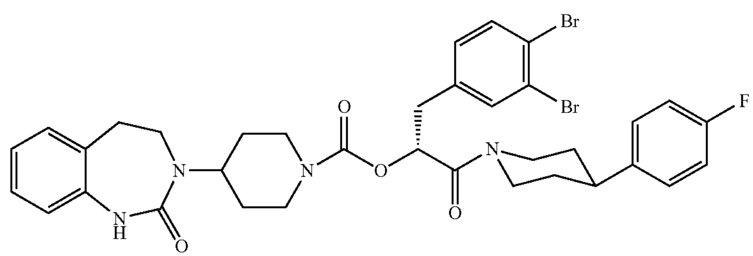 | (R)-1-(3,4-dibromo-benzyl)-2-[4-(4-fluoro-phenyl)-piperidin-1-yl]-2-oxo-ethyl 4-(2-oxo-1,2,4,5-tetrahydro-1,3-benzodiazepin-3-yl)-piperidine-1-carboxylate |
| (18) | 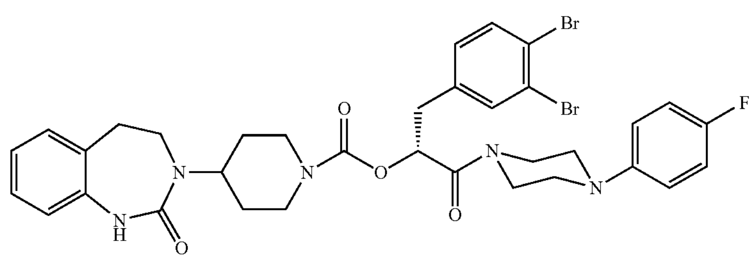 | (R)-1-(3,4-dibromo-benzyl)-2-[4-(4-fluoro-phenyl)-piperazin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (19) | 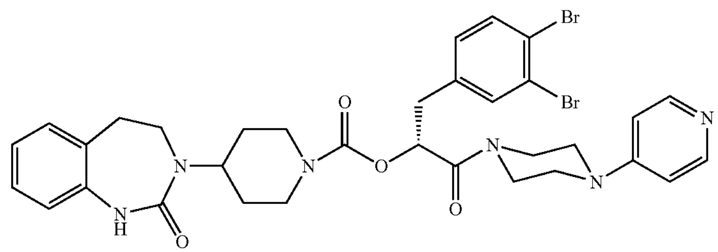 | (R)-1-(3,4-dibromo-benzyl)-2-oxo-2-(4-pyridin-4-yl-piperazin-1-yl)-ethyl 4-(2-oxo-1,2,4,5-tetrahydro-1,3-benzodiazepin-3-yl)-piperidine-1-carboxylate |
| (20) | 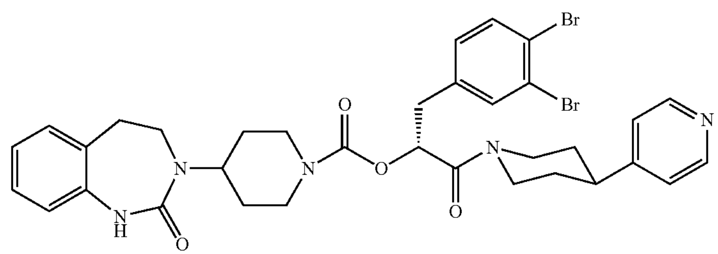 | (R)-1-(3,4-dibromo-benzyl)-2-oxo-2-(3,4,5,6-tetrahydro-2H-4,4'-bipyridinyl-1-yl)-ethyl 4-(2-oxo-1,2,4,5-tetrahydro-1,3-benzodiazepin-3-yl)-piperidine-1-carboxylate |
| (21) | 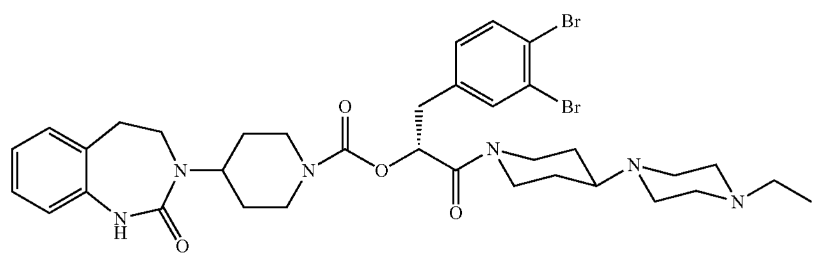 | (R)-1-(3,4-dibromo-benzyl)-2-[4-(4-ethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (22) | 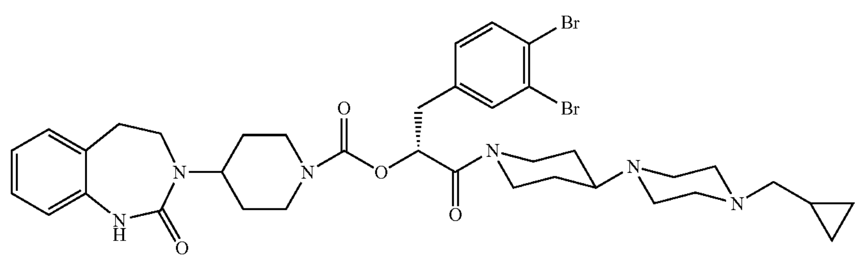 | (R)-2-[4-(4-cyclopropylmethyl-piperazin-1-yl)-piperidin-1-yl]-1-(3,4-dibromo-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (23) | 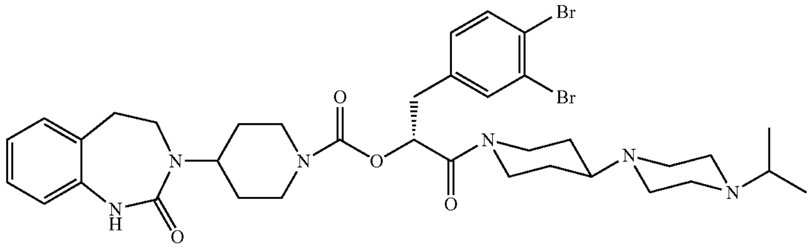 | (R)-1-(3,4-dibromo-benzyl)-2-[4-(4-isopropyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (24) | 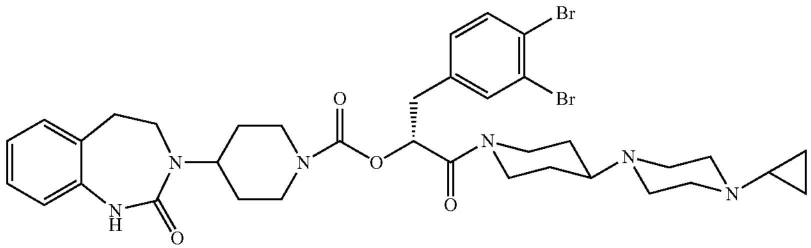 | (R)-2-[4-(4-cyclopropyl-piperazin-1-yl)-piperidin-1-yl]-1-(3,4-dibromo-benzyl)-2-oxo-ethyl 4-(2-oxo-1,2,4,5-tetrahydro-1,3-benzodiazepin-3-yl)-piperidine-1-carboxylate |
| (25) | 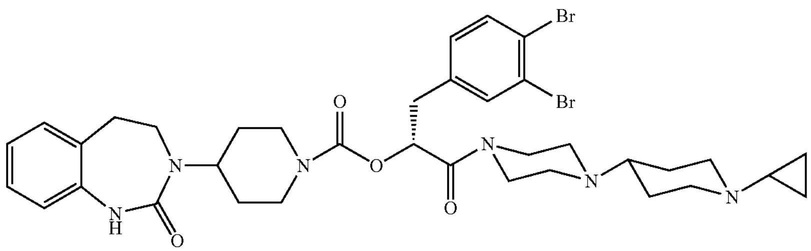 | (R)-2-[4-(1-cyclopropyl-piperidin-4-yl)-piperazin-1-yl]-1-(3,4-dibromo-benzyl)-2-oxo-ethyl 4-(2-oxo-1,2,4,5-tetrahydro-1,3-benzodiazepin-3-yl)-piperidine-1-carboxylate |
| (26) | 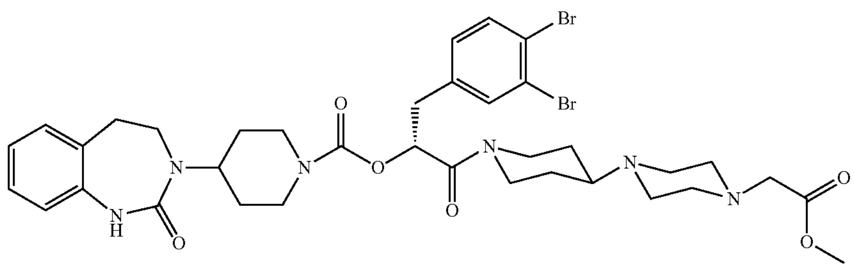 | (R)-1-(3,4-dibromo-benzyl)-2-[4-(4-methoxycarbonylmethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (27) | 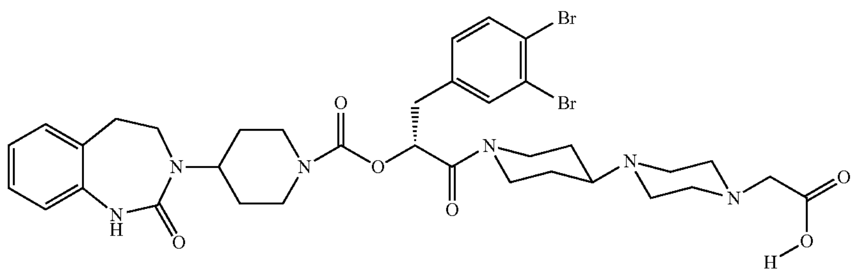 | (R)-2-[4-(4-carboxymethyl-piperazin-1-yl)-piperidin-1-yl]-1-(3,4-dibromo-benzyl)-2-oxo-ethyl 4-(2-oxo-1,2,4,5-tetrahydro-1,3-benzodiazepin-3-yl)-piperidine-1-carboxylate |
| (28) | 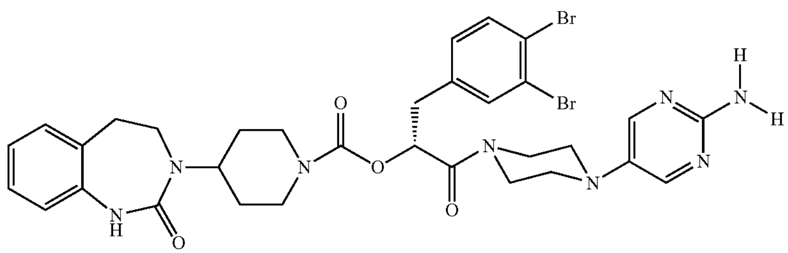 | (R)-2-[4-(2-amino-pyrimidine-5-yl)-piperazin-1-yl]-1-(3,4-dibromo-benzyl)-2-oxo-ethyl 4-(2-oxo-1,2,4,5-tetrahydro-1,3-benzodiazepin-3-yl)-piperidine-1-carboxylate |
| (29) | 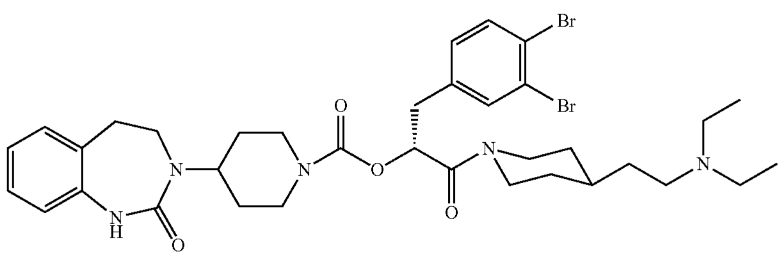 | (R)-1-(3,4-dibromo-benzyl)-2-[4-(2-diethylamino-ethyl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (30) | 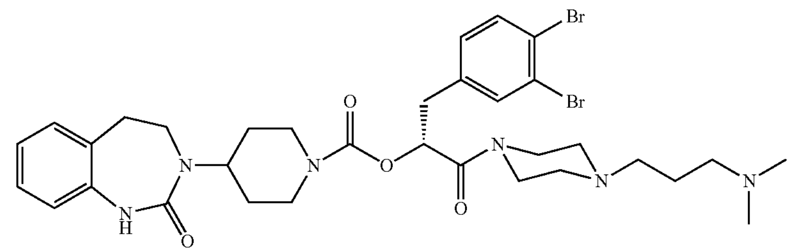 | (R)-1-(3,4-dibromo-benzyl)-2-[4-(3-dimethylamino-propyl)-piperazin-1-yl]-2-oxo-ethyl 4-(2-oxo-1,2,4,5-tetrahydro-1,3-benzodiazepin-3-yl)-piperidine-1-carboxylate |
| (31) | 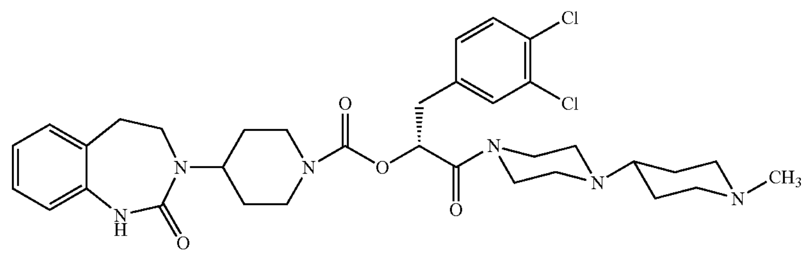 | (R)-1-(3,4-dichloro-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (32) | 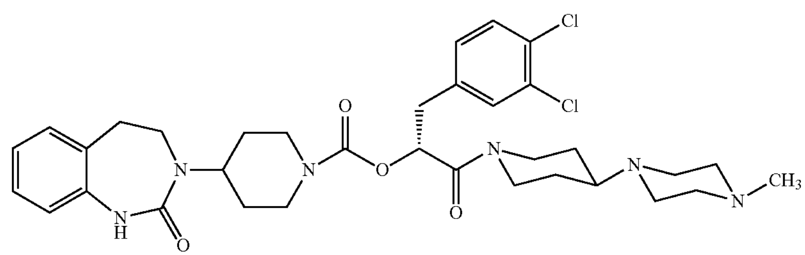 | (R)-1-(3,4-dichloro-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (33) | 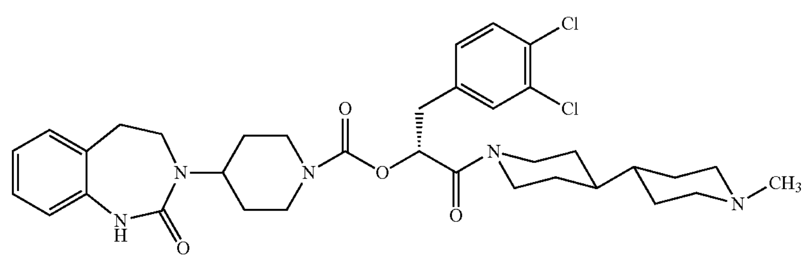 | (R)-1-(3,4-dichloro-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (34) | 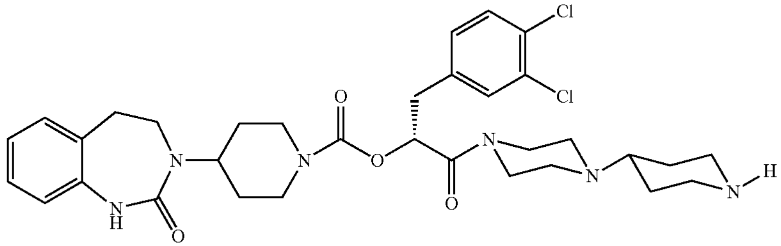 | (R)-1-(3,4-dichloro-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (35) | 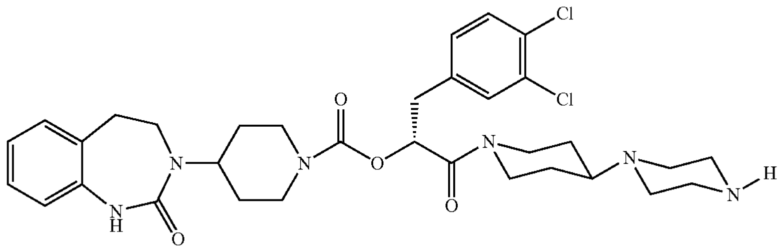 | (R)-1-(3,4-dichloro-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (36) | 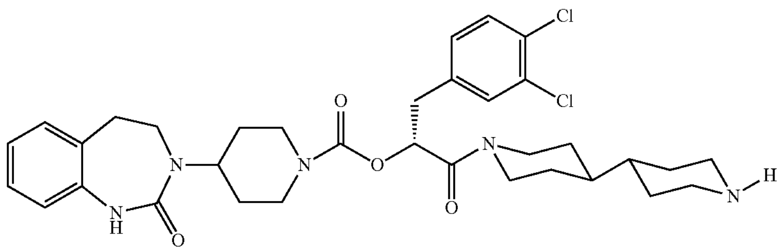 | (R)-2-(4,4'-bipiperidinyl-1'-yl)-1-(3,4-dichloro-benzyl)-2-oxo-ethyl 4-(2-oxo-1,2,4,5-tetrahydro-1,3-benzodiazepin-3-yl)-piperidine-1-carboxylate |
| (37) | 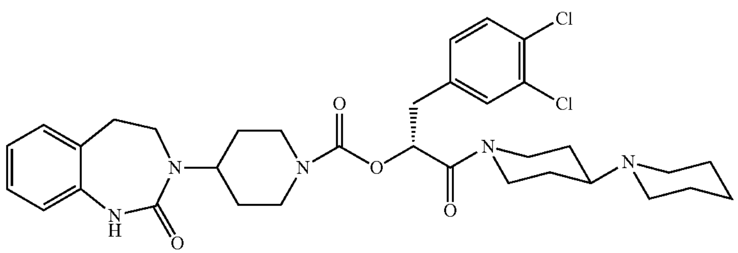 | (R)-2-(1,4'-bipiperidinyl-1'-yl)-1-(3,4-dichloro-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (38) | 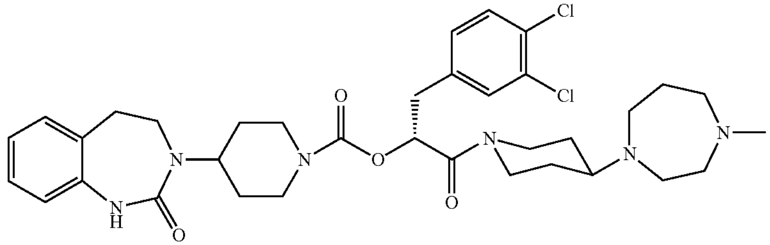 | (R)-1-(3,4-dichloro-benzyl)-2-oxo-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (39) | 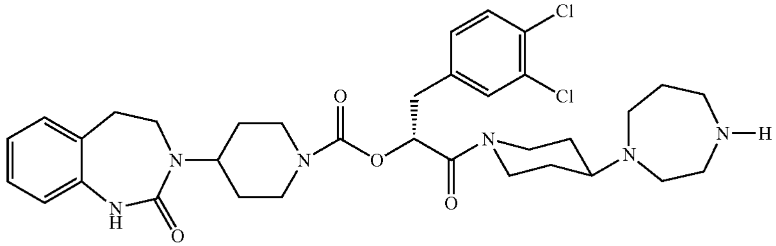 | (R)-1-(3,4-dichloro-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (40) | 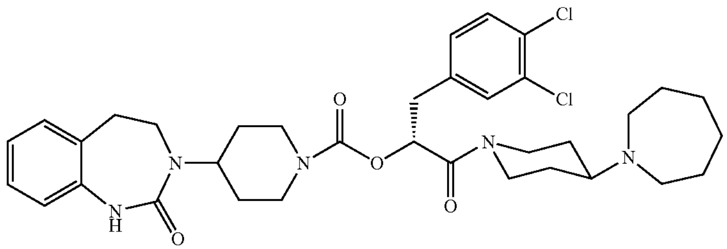 | (R)-1-(3,4-dichloro-benzyl)-2-oxo-2-(4-perhydro-azepin-1-yl-piperidin-1-yl)-ethyl 4-(2-oxo-1,2,4,5-tetrahydro-1,3-benzodiazepin-3-yl)-piperidine-1-carboxylate |
| (41) | 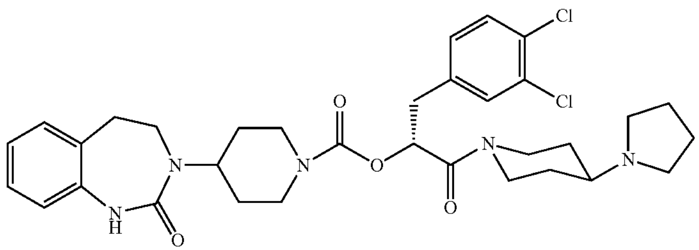 | (R)-1-(3,4-dichloro-benzyl)-2-oxo-2-(4-pyrrolidin-1-yl-piperidin-1-yl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (42) | 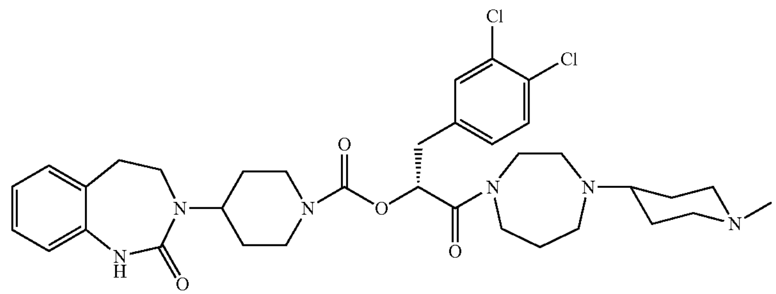 | (R)-1-(3,4-dichloro-benzyl)-2-[4-(1-methyl-piperidin-4-yl)-perhydro-1,4-diazepin-1-yl]-2-oxo-ethyl 4-(2-oxo-1,2,4,5-tetrahydro-1,3-benzodiazepin-3-yl)-piperidine-1-carboxylate |
| (43) | 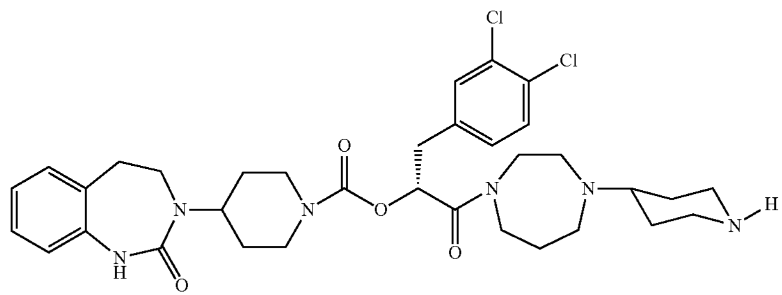 | (R)-1-(3,4-dichloro-benzyl)-2-oxo-2-(4-piperidin-4-yl-perhydro-1,4-diazepin-1-yl)-ethyl 4-(2-oxo-1,2,4,5-tetrahydro-1,3-benzodiazepin-3-yl)-piperidine-1-carboxylate |
| (44) | 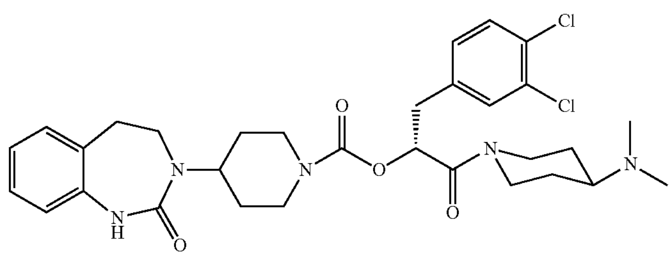 | (R)-1-(3,4-dichloro-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (45) | 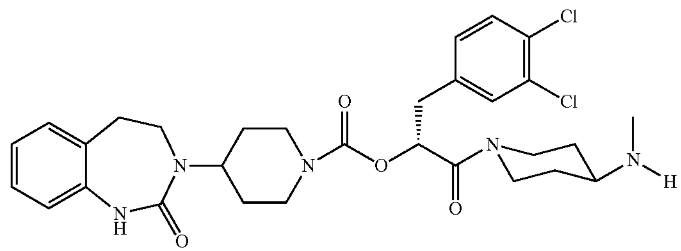 | (R)-1-(3,4-dichloro-benzyl)-2-(4-methylamino-piperidin-1-yl)-2-oxo-ethyl 4-(2-oxo-1,2,4,5-tetrahydro-1,3-benzodiazepin-3-yl)-piperidine-1-carboxylate |
| (46) | 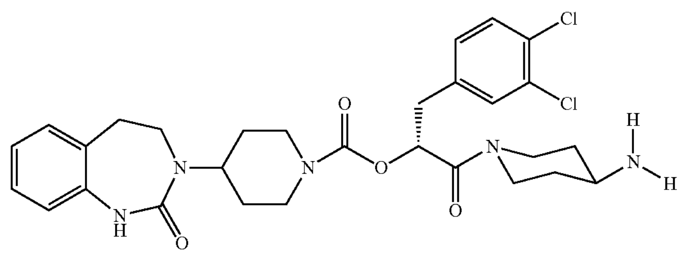 | (R)-1-(3,4-dichloro-benzyl)-2-(4-amino-piperidin-1-yl)-2-oxo-ethyl 4-(2-oxo-1,2,4,5-tetrahydro-1,3-benzodiazepin-3-yl)-piperidine-1-carboxylate |
| (47) | 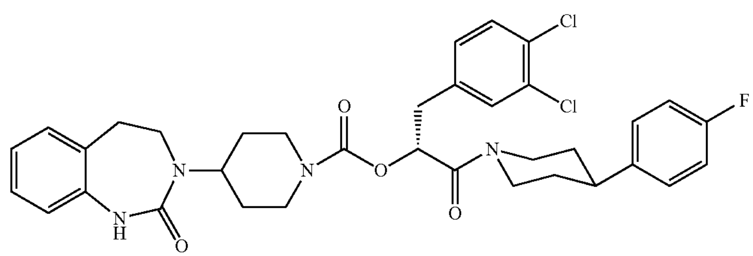 | (R)-1-(3,4-dichloro-benzyl)-2-[4-(4-fluoro-phenyl)-piperidin-1-yl]-2-oxo-ethyl 4-(2-oxo-1,2,4,5-tetrahydro-1,3-benzodiazepin-3-yl)-piperidine-1-carboxylate |
| (48) | 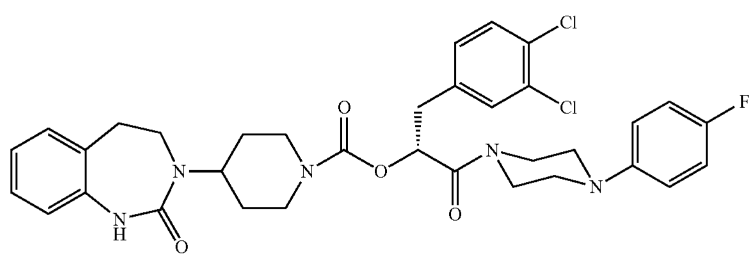 | (R)-1-(3,4-dichloro-benzyl)-2-[4-(4-fluoro-phenyl)-piperazin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (49) | 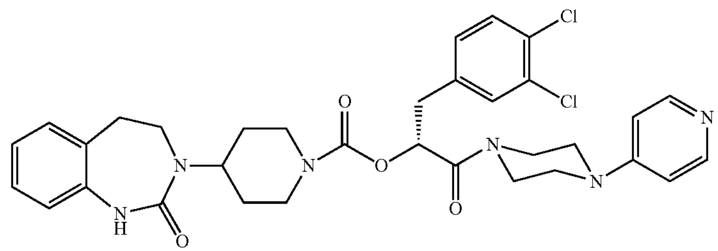 | (R)-1-(3,4-dichloro-benzyl)-2-oxo-2-(4-pyridin-4-yl-piperazin-1-yl)-ethyl 4-(2-oxo-1,2,4,5-tetrahydro-1,3-benzodiazepin-3-yl)-piperidine-1-carboxylate |
| (50) | 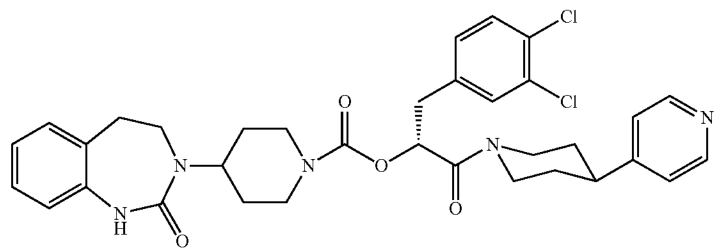 | (R)-1-(3,4-dichloro-benzyl)-2-oxo-2-(3,4,5,6-tetrahydro-2H-4,4'-bipyridinyl-1-yl)-ethyl 4-(2-oxo-1,2,4,5-tetrahydro-1,3-benzodiazepin-3-yl)-piperidine-1-carboxylate |
| (51) | 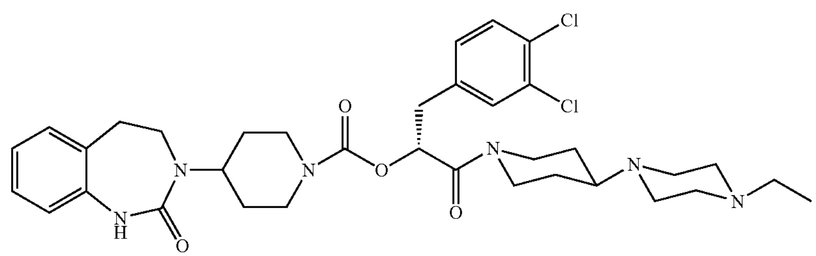 | (R)-1-(3,4-dichloro-benzyl)-2-[4-(4-ethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (52) | 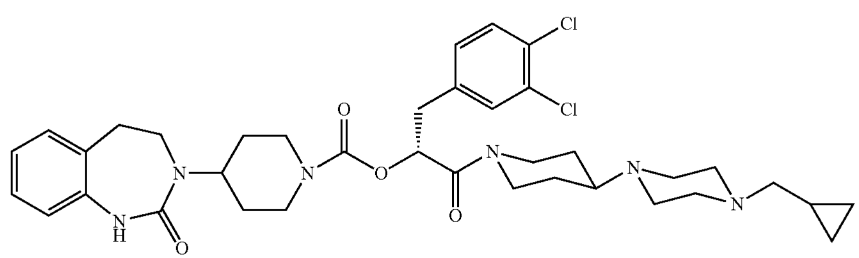 | (R)-2-[4-(4-cyclopropylmethyl-piperazin-1-yl)-piperidin-1-yl]-1-(3,4-dichloro-benzyl)-2-oxo-ethyl 4-(2-oxo-1,2,4,5-tetrahydro-1,3-benzodiazepin-3-yl)-piperidine-1-carboxylate |

-continued

| No. | Name |
|---|---|
| (53) | (R)-1-(3,4-dichloro-benzyl)-2-[4-(4-isopropyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (54) | (R)-2-[4-(4-cyclopropyl-piperazin-1-yl)-piperidin-1-yl]-1-(3,4-dichloro-benzyl)-2-oxo-ethyl 4-(2-oxo-1,2,4,5-tetrahydro-1,3-benzodiazepin-3-yl)-piperidine-1-carboxylate |
| (55) | (R)-2-[4-(1-cyclopropyl-piperidin-4-yl)-piperazin-1-yl]-1-(3,4-dichloro-benzyl)-2-oxo-ethyl 4-(2-oxo-1,2,4,5-tetrahydro-1,3-benzodiazepin-3-yl)-piperidine-1-carboxylate |
| (56) | (R)-1-(3,4-dichloro-benzyl)-2-[4-(4-methoxycarbonylmethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (57) | 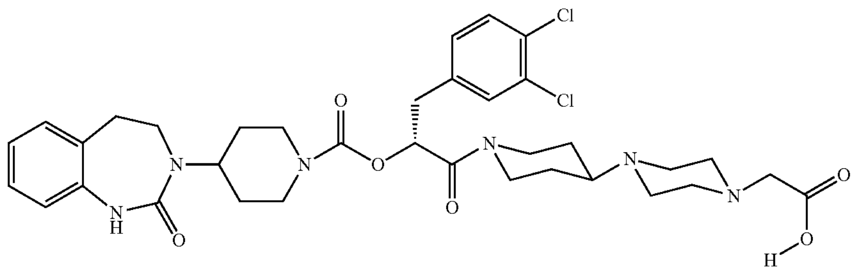 | (R)-2-[4-(4-carboxymethyl-piperazin-1-yl)-piperidin-1-yl]-1-(3,4-dichloro-benzyl)-2-oxo-ethyl 4-(2-oxo-1,2,4,5-tetrahydro-1,3-benzodiazepin-3-yl)-piperidine-1-carboxylate |
| (58) | 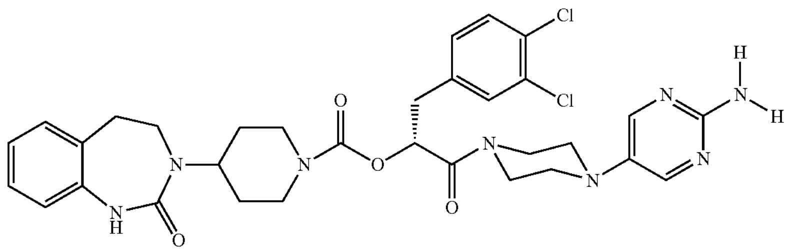 | (R)-2-[4-(2-amino-pyrimidine-5-yl)-piperazin-1-yl]-1-(3,4-dichloro-benzyl)-2-oxo-ethyl 4-(2-oxo-1,2,4,5-tetrahydro-1,3-benzodiazepin-3-yl)-piperidine-1-carboxylate |
| (59) | 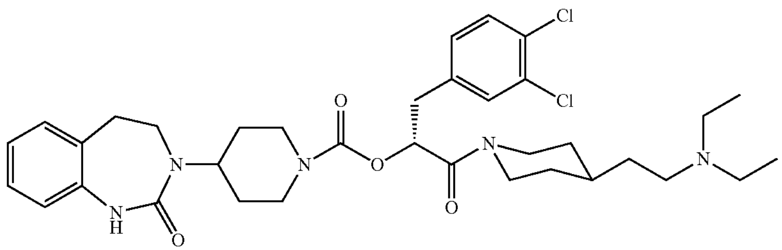 | (R)-1-(3,4-dichloro-benzyl)-2-[4-(2-diethylamino-ethyl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (60) | 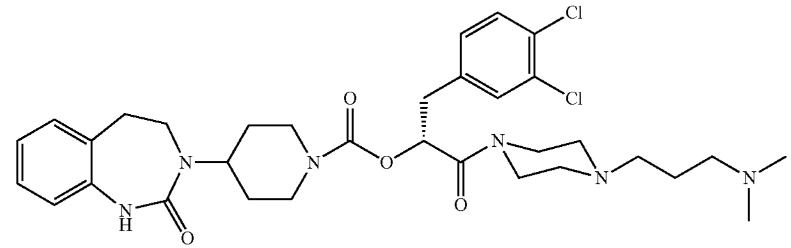 | (R)-1-(3,4-dichloro-benzyl)-2-[4-(3-dimethylamino-propyl)-piperazin-1-yl]-2-oxo-ethyl 4-(2-oxo-1,2,4,5-tetrahydro-1,3-benzodiazepin-3-yl)-piperidine-1-carboxylate |
| (61) | 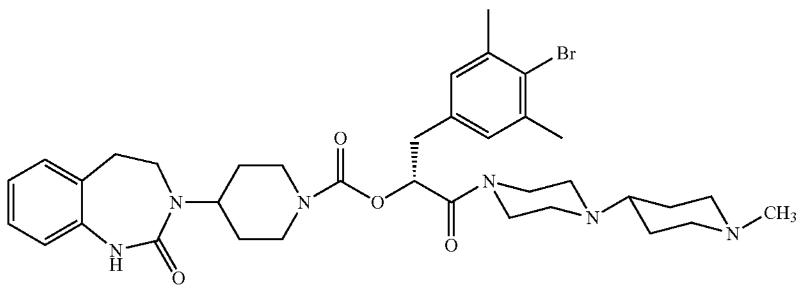 | (R)-1-(4-bromo-3,5-dimethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (62) | 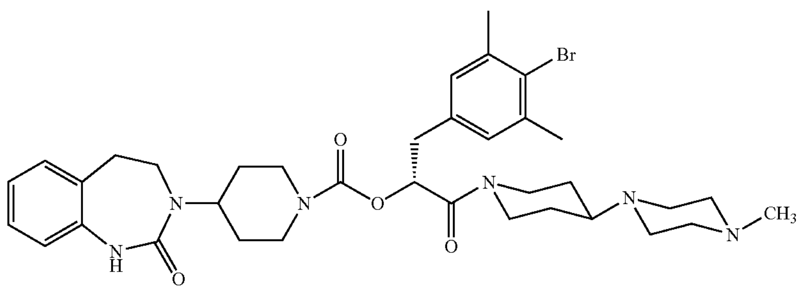 | (R)-1-(4-bromo-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (63) | 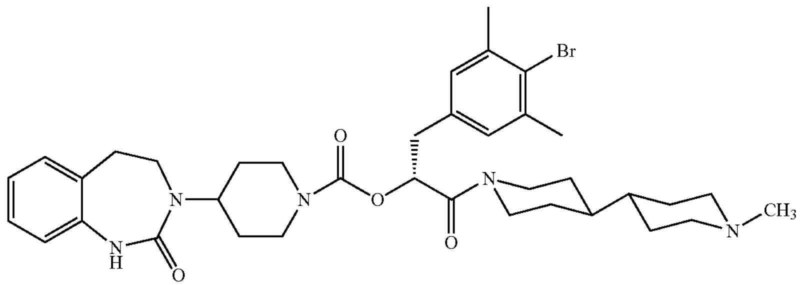 | (R)-1-(4-bromo-3,5-dimethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (64) | 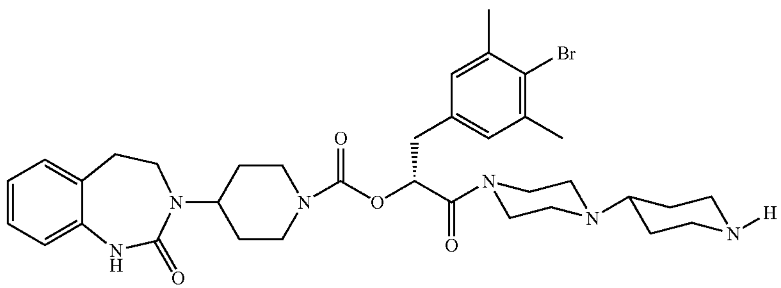 | (R)-1-(4-bromo-3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (65) | 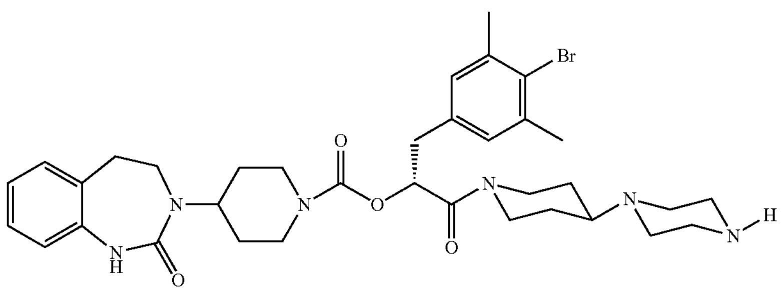 | (R)-1-(4-bromo-3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (66) | 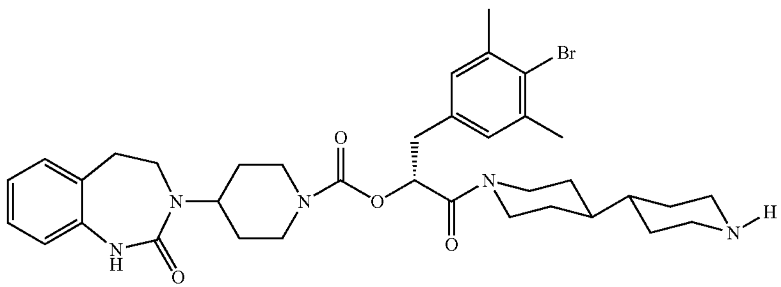 | (R)-2-(4,4'-bipiperidinyl-1-yl)-1-(4-bromo-3,5-dimethyl-benzyl)-2-oxo-ethyl 4-(2-oxo-1,2,4,5-tetrahydro-1,3-benzodiazepin-3-yl)-piperidine-1-carboxylate |
| (67) | 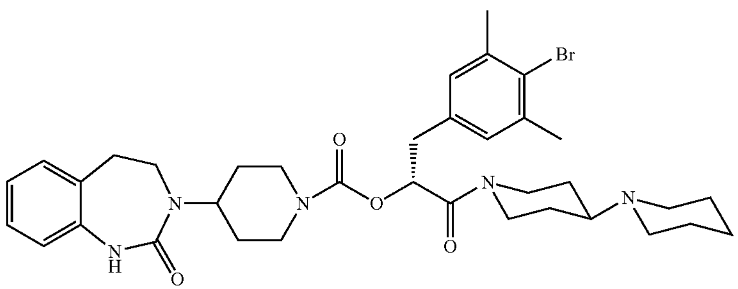 | (R)-2-(1,4'-bipiperidinyl-1'-yl)-1-(4-bromo-3,5-dimethyl-benzyl)-2-oxo-ethyl 4-(2-oxo-1,2,4,5-tetrahydro-1,3-benzodiazepin-3-yl)-piperidine-1-carboxylate |
| (68) | 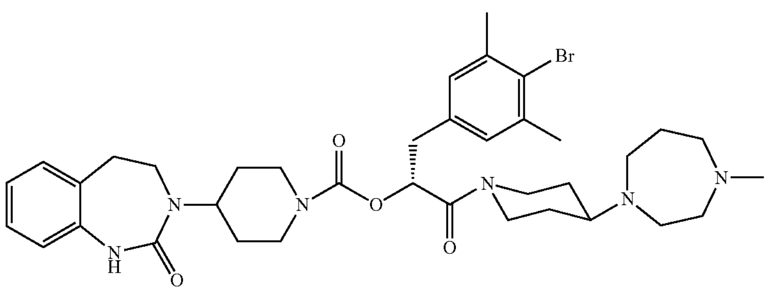 | (R)-1-(4-bromo-3,5-dimethyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (69) | 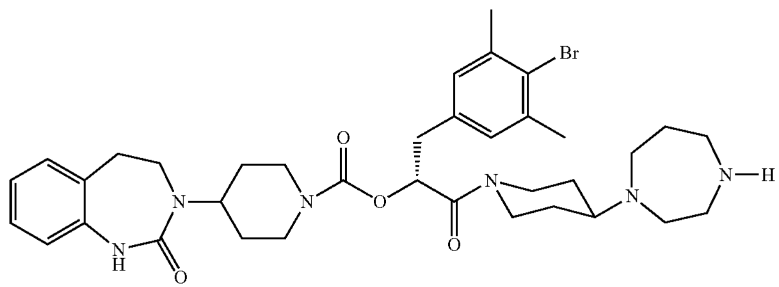 | (R)-1-(4-bromo-3,5-dimethyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (70) | 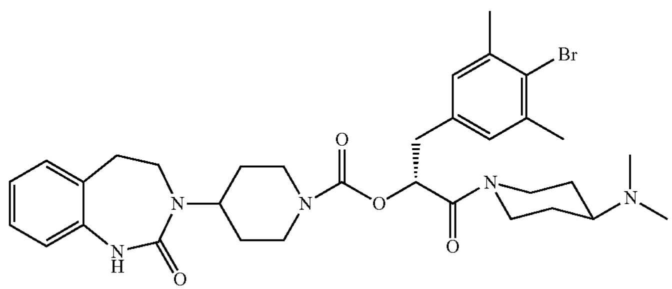 | (R)-1-(4-bromo-3,5-dimethyl-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (71) | 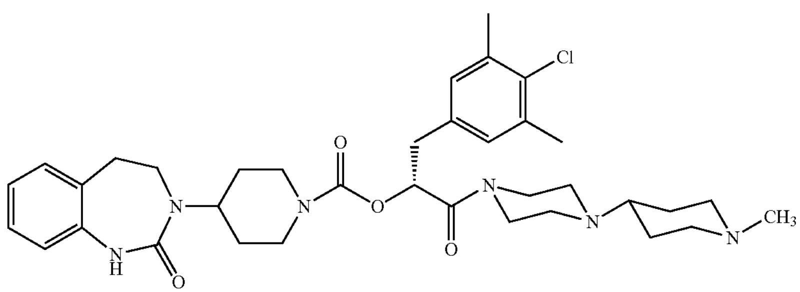 | (R)-1-(4-chloro-3,5-dimethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (72) | 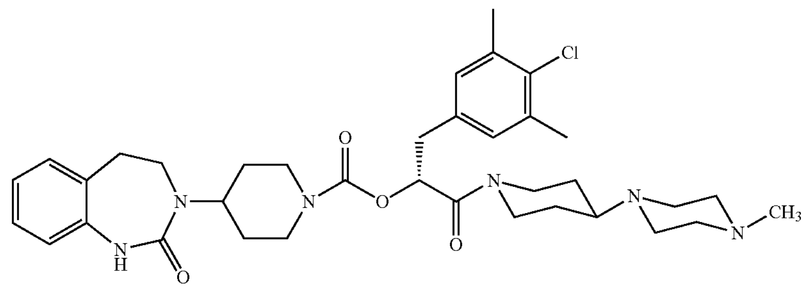 | (R)-1-(4-chloro-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (73) | 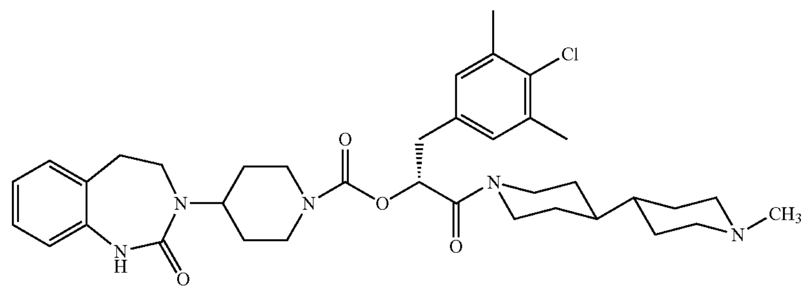 | (R)-1-(4-chloro-3,5-dimethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (74) | 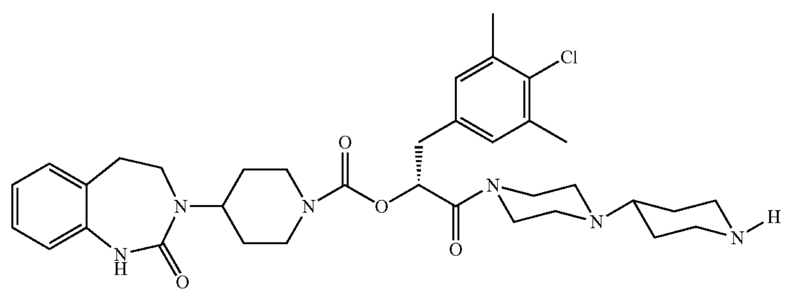 | (R)-1-(4-chloro-3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (75) | 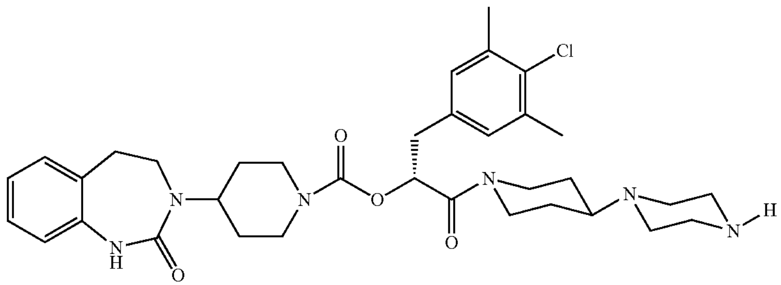 | (R)-1-(4-chloro-3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (76) | 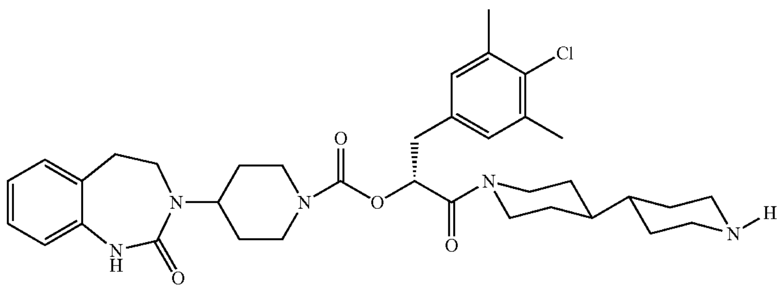 | (R)-2-(4,4'-bipiperidinyl-1-yl)-1-(4-chloro-3,5-dimethyl-benzyl)-2-oxo-ethyl 4-(2-oxo-1,2,4,5-tetrahydro-1,3-benzodiazepin-3-yl)-piperidine-1-carboxylate |
| (77) | 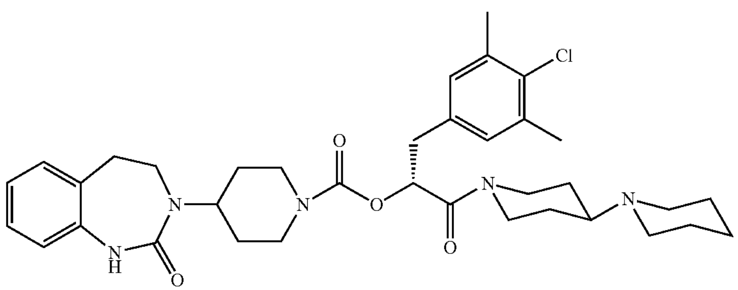 | (R)-2-(1,4'-bipiperidinyl-1'-yl)-1-(4-chloro-3,5-dimethyl-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (78) | 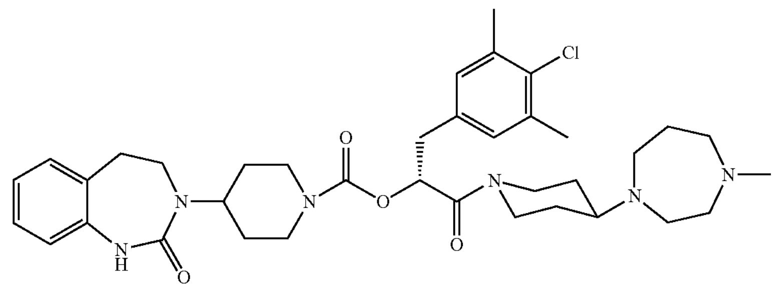 | (R)-1-(4-chloro-3,5-dimethyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (79) | 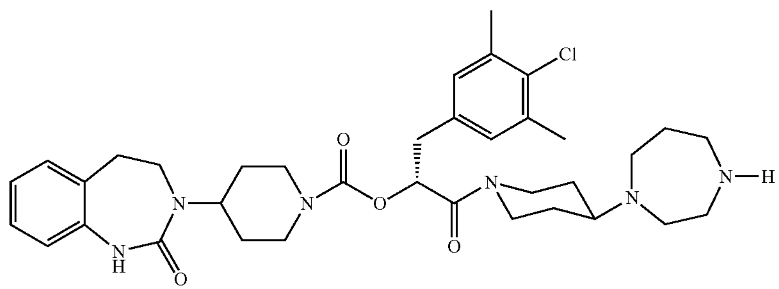 | (R)-1-(4-chloro-3,5-dimethyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (80) | 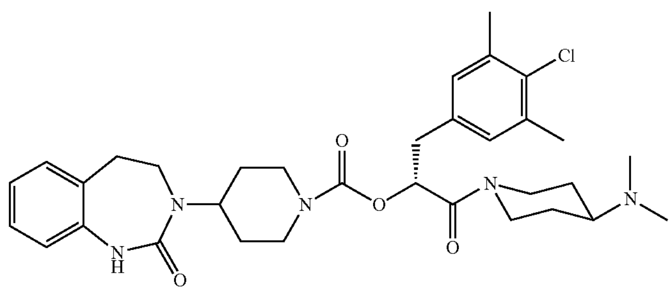 | (R)-1-(4-chloro-3,5-dimethyl-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (81) | 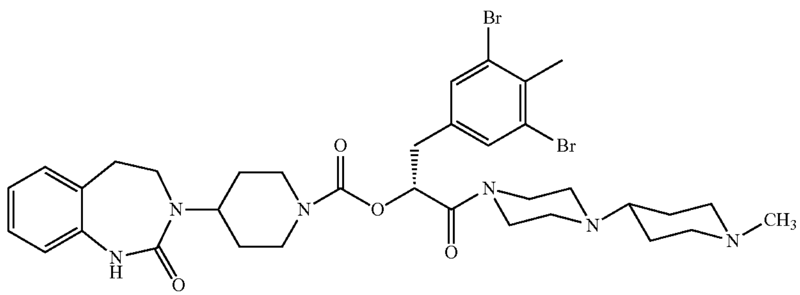 | (R)-1-(3,5-dibromo-4-methyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (82) | 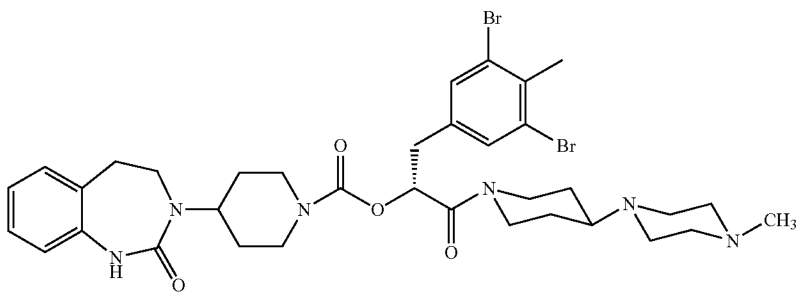 | (R)-1-(3,5-dibromo-4-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (83) | 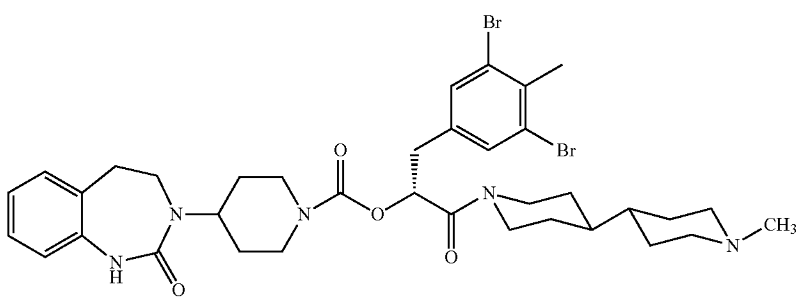 | (R)-1-(3,5-dibromo-4-methyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (84) | 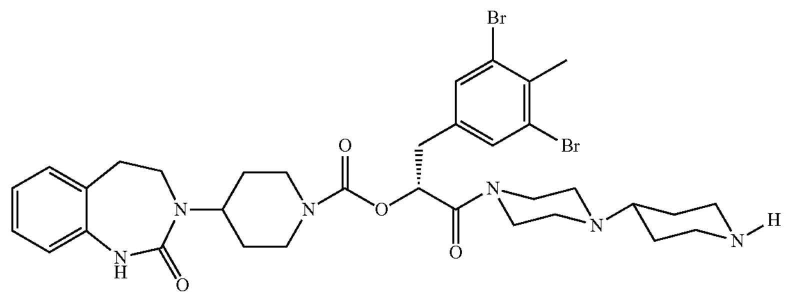 | (R)-1-(3,5-dibromo-4-methyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (85) | 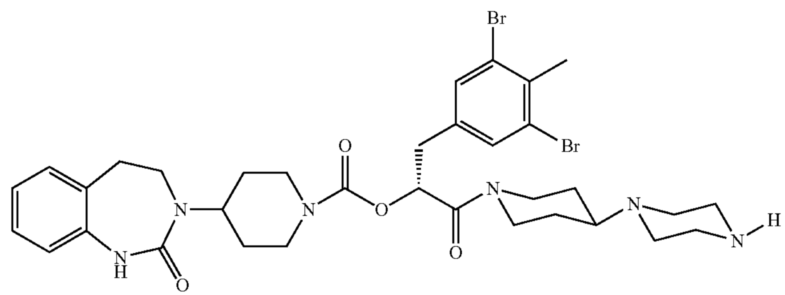 | (R)-1-(3,5-dibromo-4-methyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (86) | 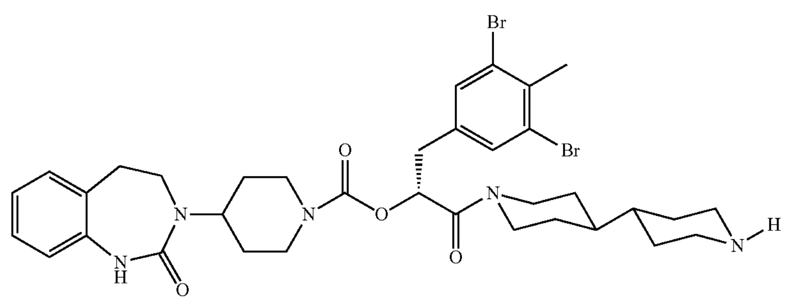 | (R)-2-(4,4'-bipiperidinyl-1-yl)-1-(3,5-dibromo-4-methyl-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (87) | 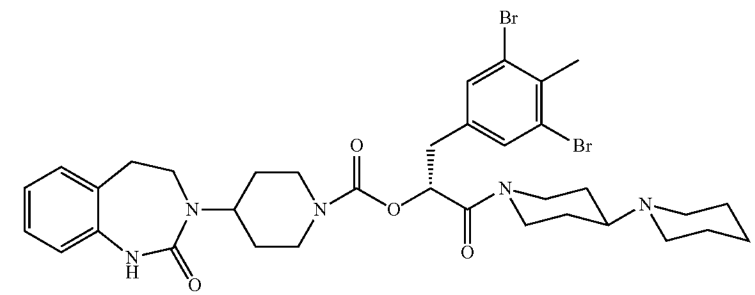 | (R)-2-(1,4'-bipiperidinyl-1'-yl)-1-(3,5-dibromo-4-methyl-benzyl)-2-oxo-ethyl 4-(2-oxo-1,2,4,5-tetrahydro-1,3-benzodiazepin-3-yl)-piperidine-1-carboxylate |
| (88) | 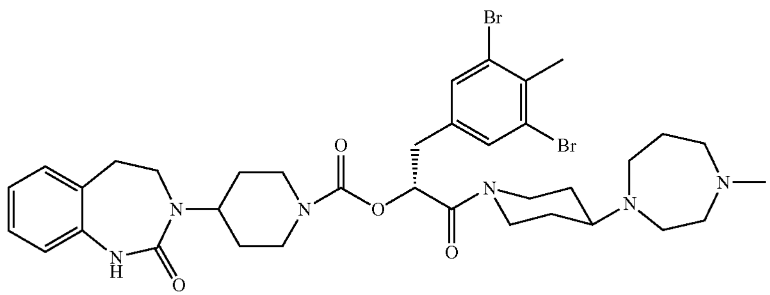 | (R)-1-(3,5-dibromo-4-methyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (89) | 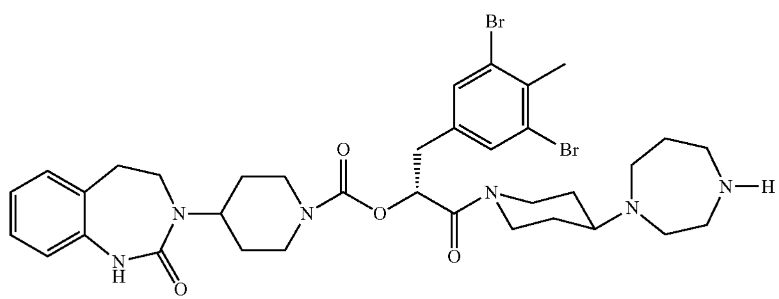 | (R)-1-(3,5-dibromo-4-methyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (90) | 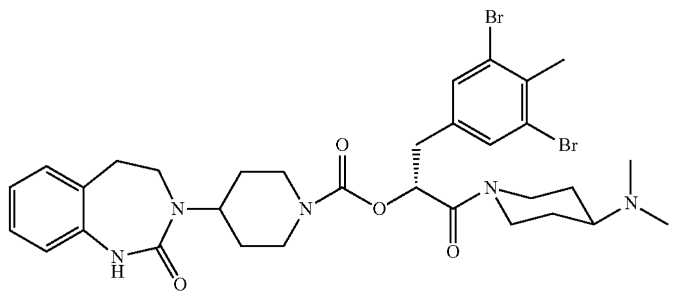 | (R)-1-(3,5-dibromo-4-methyl-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (91) | 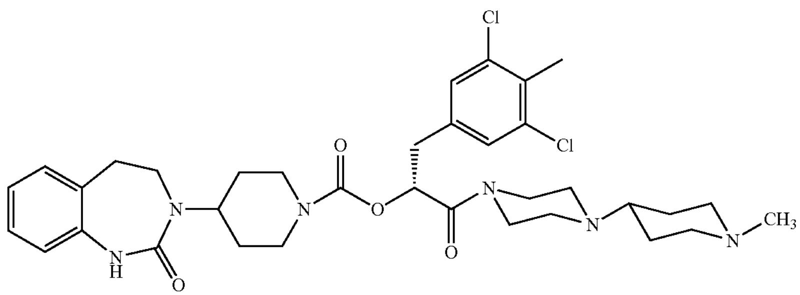 | (R)-1-(3,5-dichloro-4-methyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (92) | 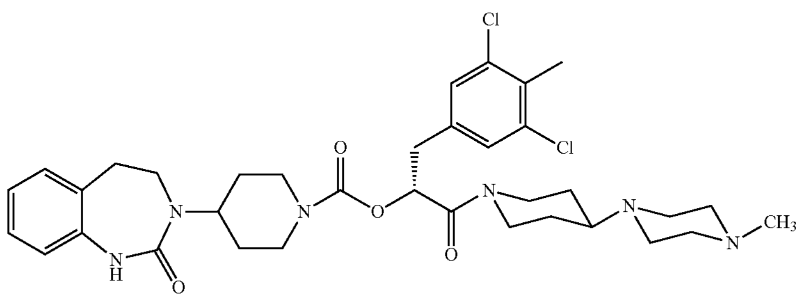 | (R)-1-(3,5-dichloro-4-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (93) | 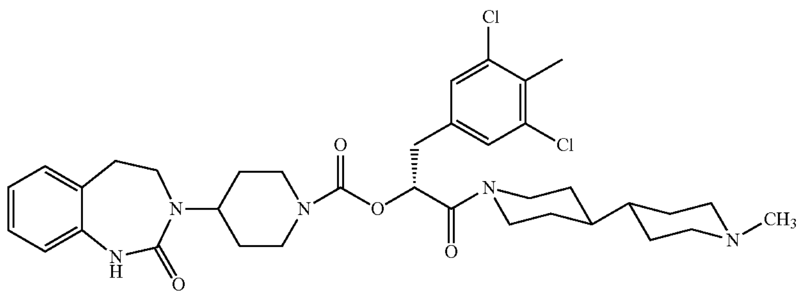 | (R)-1-(3,5-dichloro-4-methyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (94) | 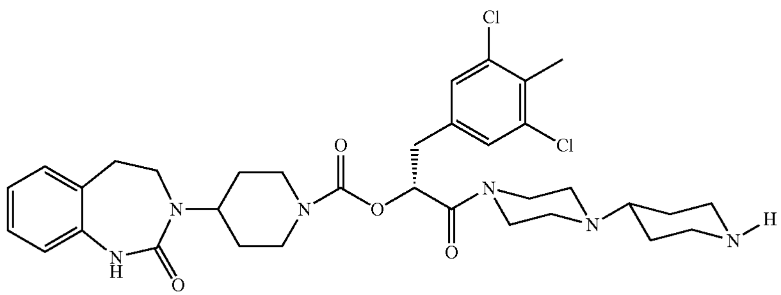 | (R)-1-(3,5-dichloro-4-methyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (95) | 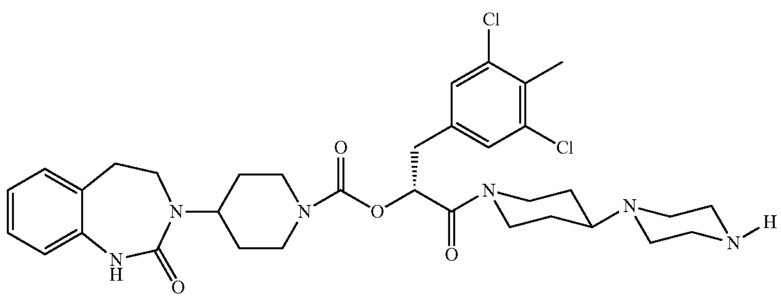 | (R)-1-(3,5-dichloro-4-methyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (96) | 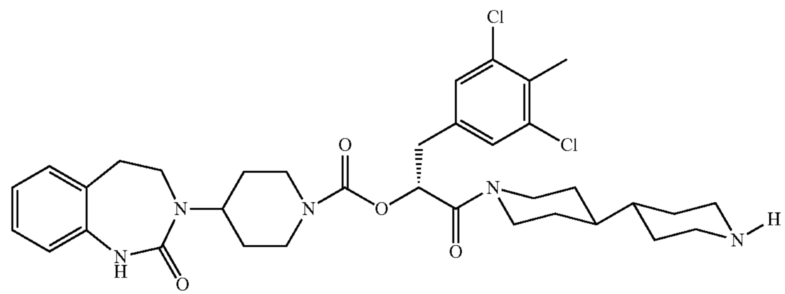 | (R)-2-(4,4'-bipiperidinyl-1-yl)-1-(3,5-dichloro-4-methyl-benzyl)-2-oxo-ethyl 4-(2-oxo-1,2,4,5-tetrahydro-1,3-benzodiazepin-3-yl)-piperidine-1-carboxylate |
| (97) | 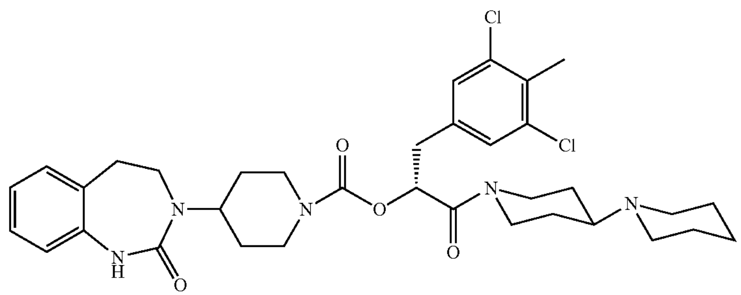 | (R)-2-(1,4'-bipiperidinyl-1'-yl)-1-(3,5-dichloro-4-methyl-benzyl)-2-oxo-ethyl 4-(2-oxo-1,2,4,5-tetrahydro-1,3-benzodiazepin-3-yl)-piperidine-1-carboxylate |
| (98) | 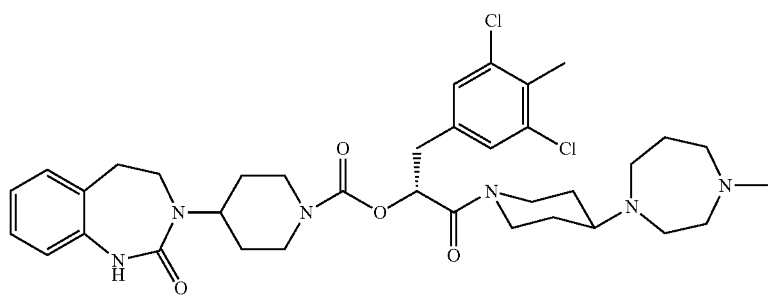 | (R)-1-(3,5-dichloro-4-methyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (99) | 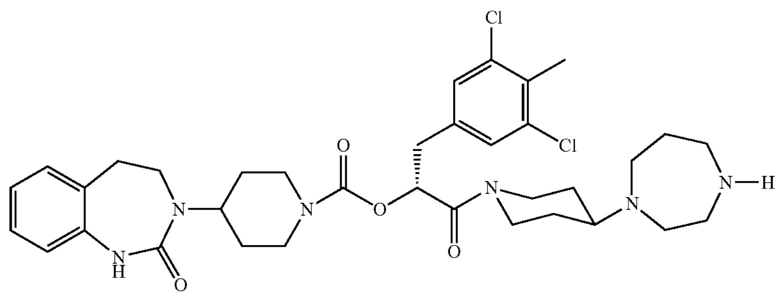 | (R)-1-(3,5-dichloro-4-methyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (100) | 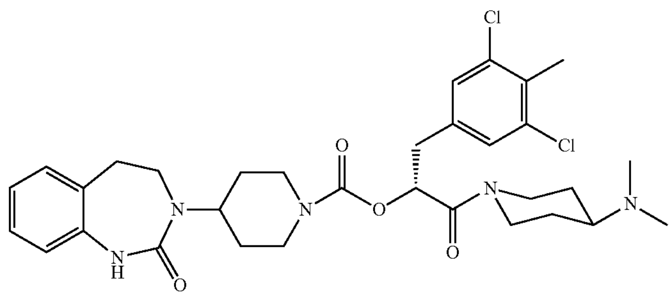 | (R)-1-(3,5-dichloro-4-methyl-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (101) | 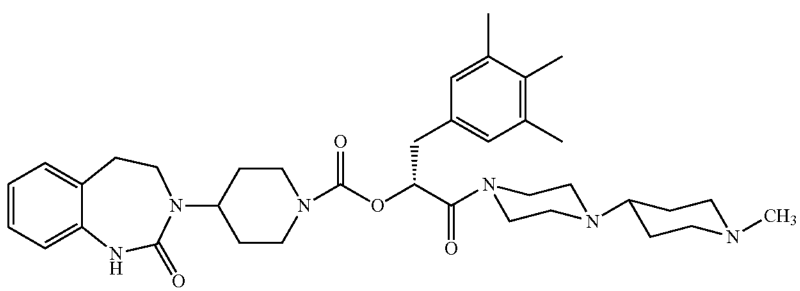 | (R)-2-[4-(1-methyl-piperidin-4-yl)-piperazin-1-yl]-2-oxo-1-(3,4,5-trimethyl-benzyl)-ethyl 4-(2-oxo-1,2,4,5-tetrahydro-1,3-benzodiazepin-3-yl)-piperidine-1-carboxylate |

| No. | Structure | Name |
|---|---|---|
| (102) | 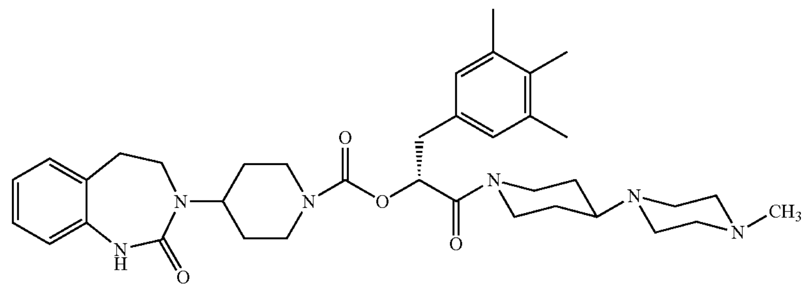 | (R)-2-[4-(4-methyl-piperazin-1-yl)-piperidin-1-yl]-2-oxo-1-(3,4,5-trimethyl-benzyl)-ethyl 4-(2-oxo-1,2,4,5-tetrahydro-1,3-benzodiazepin-3-yl)-piperidine-1-carboxylate |
| (103) | 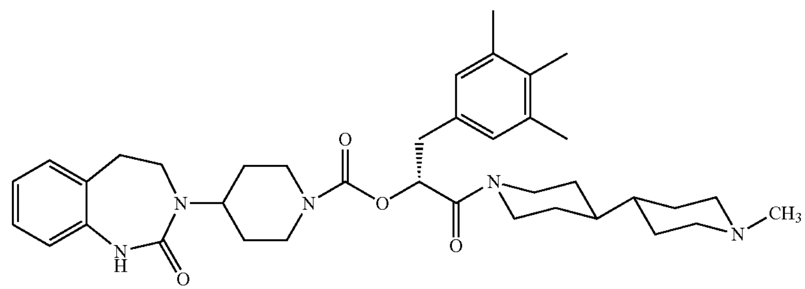 | (R)-2-(1'-methyl-4,4'-bipiperidinyl-1-yl)-2-oxo-1-(3,4,5-trimethyl-benzyl)-ethyl 4-(2-oxo-1,2,4,5-tetrahydro-1,3-benzodiazepin-3-yl)-piperidine-1-carboxylate |
| (104) | 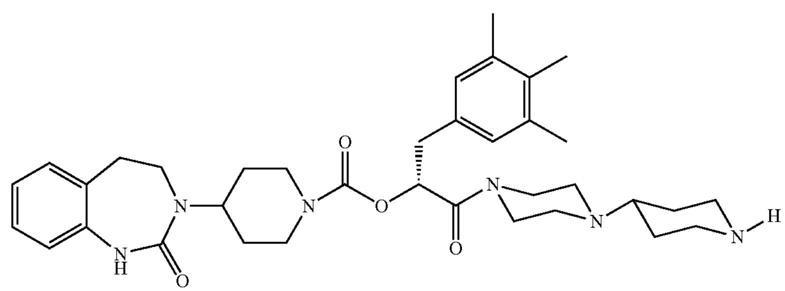 | (R)-2-oxo-2-(4-piperidin-4-yl-piperazin-1-yl)-1-(3,4,5-trimethyl-benzyl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (105) | 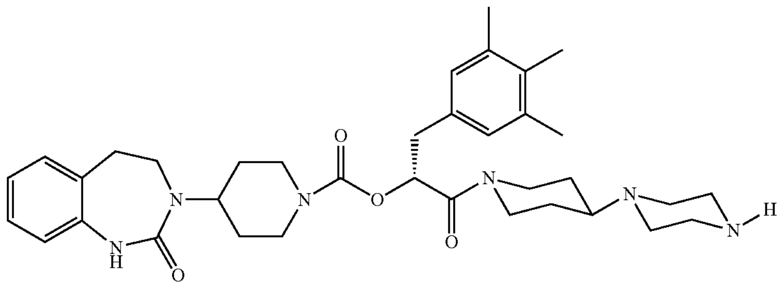 | (R)-2-oxo-2-(4-piperazin-1-yl-piperidin-1-yl)-1-(3,4,5-trimethyl-benzyl)-ethyl 4-(2-oxo-1,2,4,5-tetrahydro-1,3-benzodiazepin-3-yl)-piperidine-1-carboxylate |
| (106) | 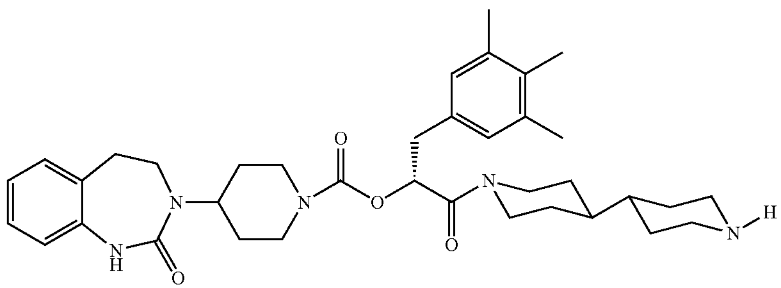 | (R)-2-(4,4'-bipiperidinyl-1-yl)-2-oxo-1-(3,4,5-trimethyl-benzyl)-ethyl 4-(2-oxo-1,2,4,5-tetrahydro-1,3-benzodiazepin-3-yl)-piperidine-1-carboxylate |
| (107) | 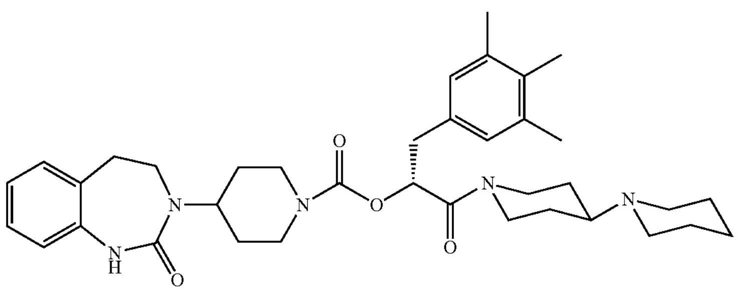 | (R)-2-(1,4'-bipiperidinyl-1'-yl)-2-oxo-1-(3,4,5-trimethyl-benzyl)-ethyl 4-(2-oxo-1,2,4,5-tetrahydro-1,3-benzodiazepin-3-yl)-piperidine-1-carboxylate |

| No. | Structure | Name |
|---|---|---|
| (108) | 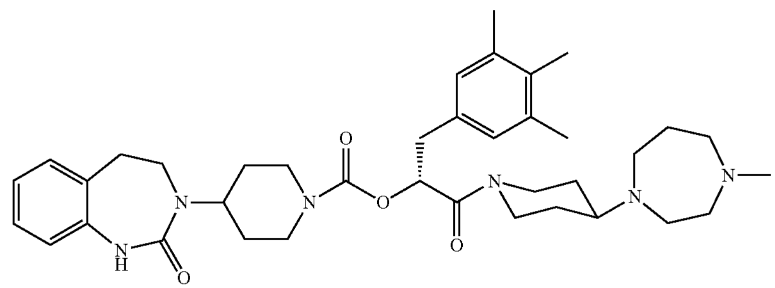 | (R)-2-[4-(4-methyl-perhydro-1,4-diazepin-1-yl)-piperidin-1-yl]-2-oxo-1-(3,4,5-trimethyl-benzyl)-ethyl 4-(2-oxo-1,2,4,5-tetrahydro-1,3-benzodiazepin-3-yl)-piperidine-1-carboxylate |
| (109) | 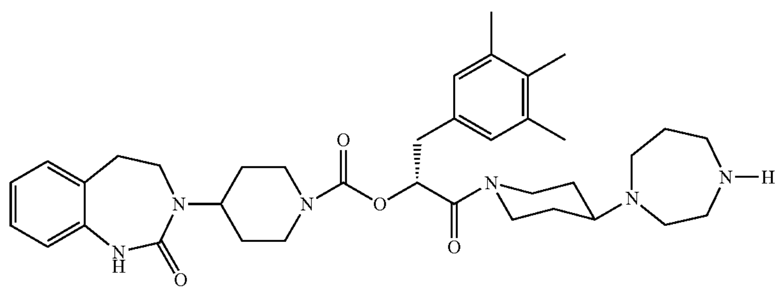 | (R)-2-oxo-2-(4-perhydro-1,4-diazepin-1-yl-piperidin-1-yl)-1-(3,4,5-trimethyl-benzyl)-ethyl 4-(2-oxo-1,2,4,5-tetrahydro-1,3-benzodiazepin-3-yl)-piperidine-1-carboxylate |
| (110) | 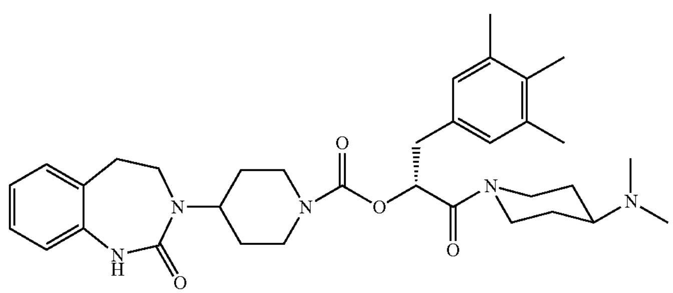 | (R)-2-(4-dimethylamino-piperidin-1-yl)-2-oxo-1-(3,4,5-trimethyl-benzyl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (111) | 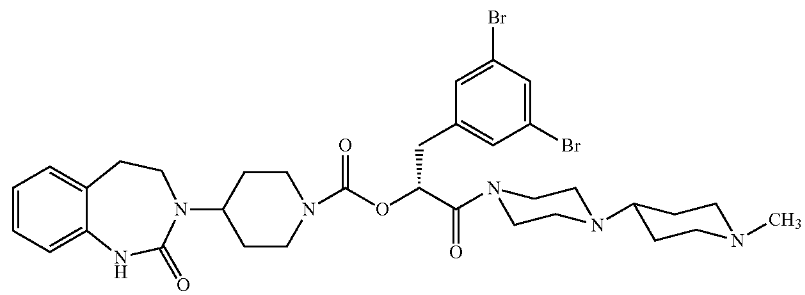 | (R)-1-(3,5-dibromo-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (112) | 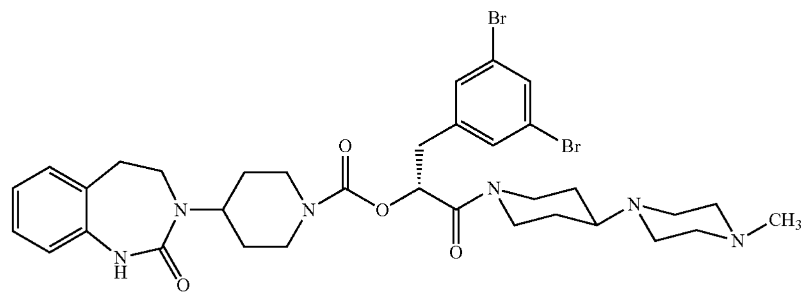 | (R)-1-(3,5-dibromo-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (113) | 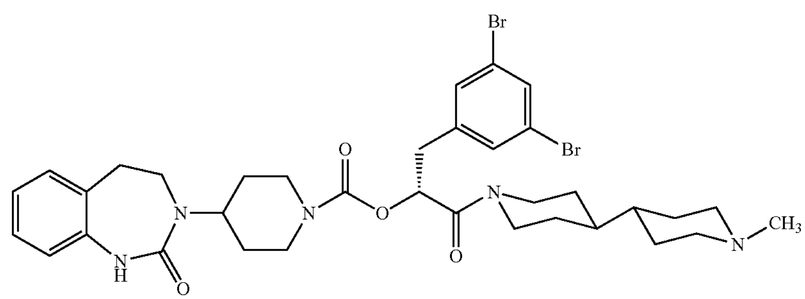 | (R)-1-(3,5-dibromo-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (114) | 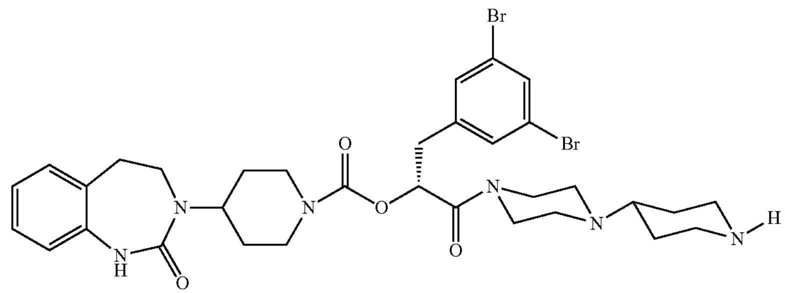 | (R)-1-(3,5-dibromo-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (115) | 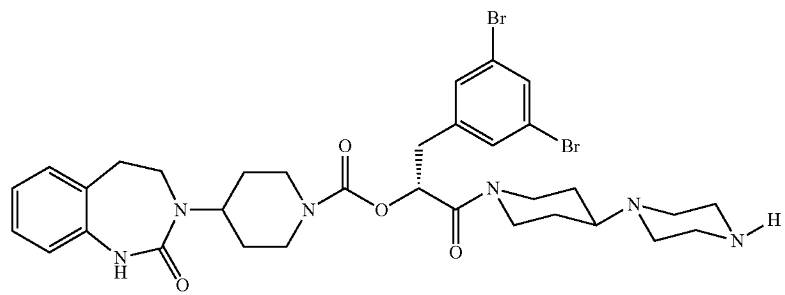 | (R)-1-(3,5-dibromo-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (116) | 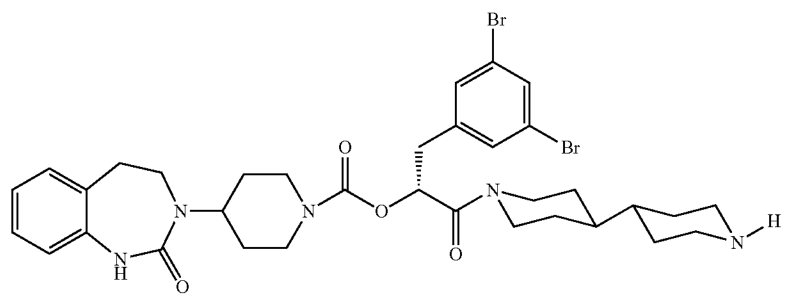 | (R)-2-(4,4'-bipiperidinyl-1-yl)-1-(3,5-dibromo-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (117) | 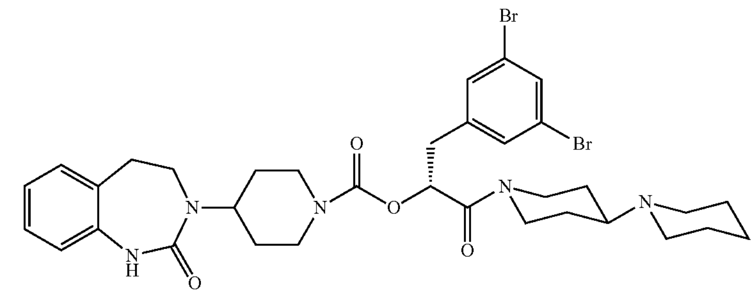 | (R)-2-(1,4'-bipiperidinyl-1'-yl)-1-(3,5-dibromo-benzyl)-2-oxo-ethyl 4-(2-oxo-1,2,4,5-tetrahydro-1,3-benzodiazepin-3-yl)-piperidine-1-carboxylate |
| (118) | 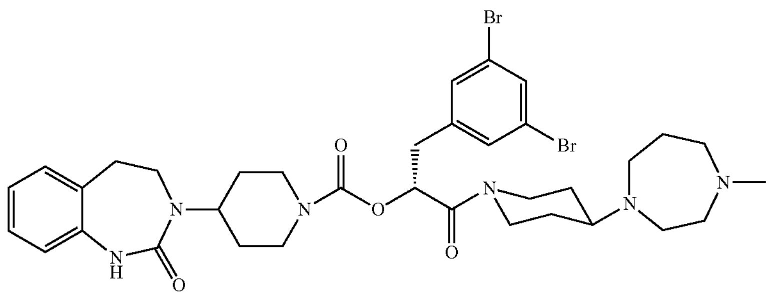 | (R)-1-(3,5-dibromo-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (119) | 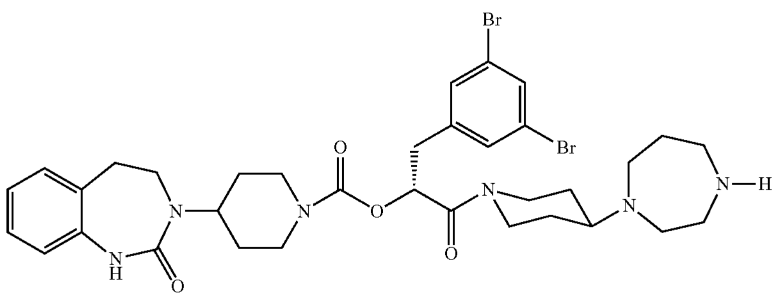 | (R)-1-(3,5-dibromo-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (120) | 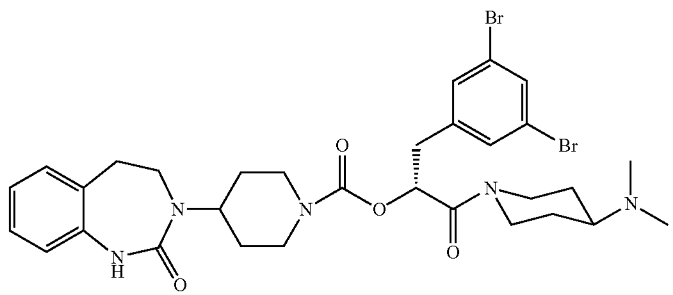 | (R)-1-(3,5-dibromo-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (121) | 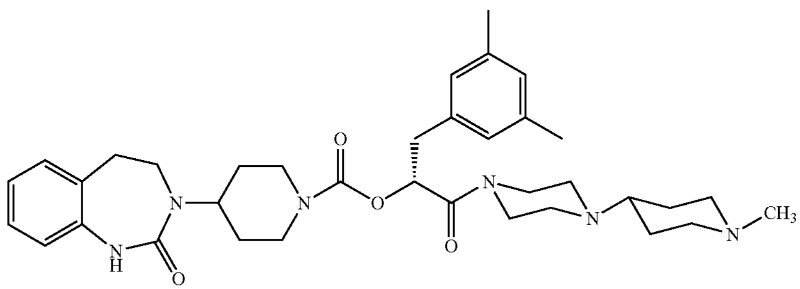 | (R)-1-(3,5-dimethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (122) | 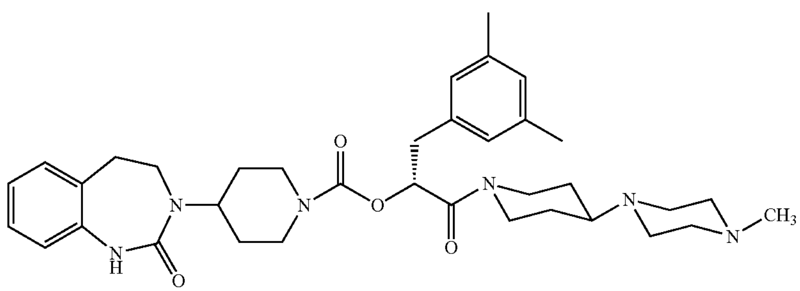 | (R)-1-(3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (123) | 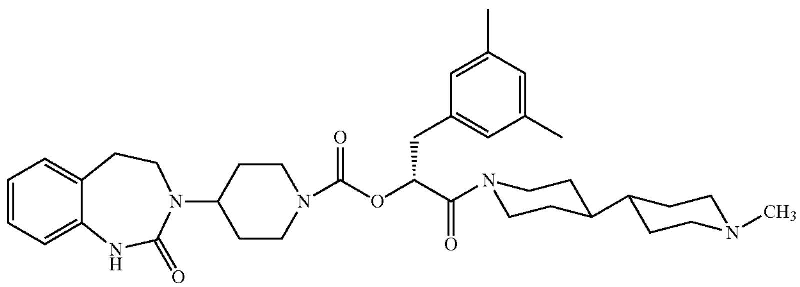 | (R)-1-(3,5-dimethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (124) | 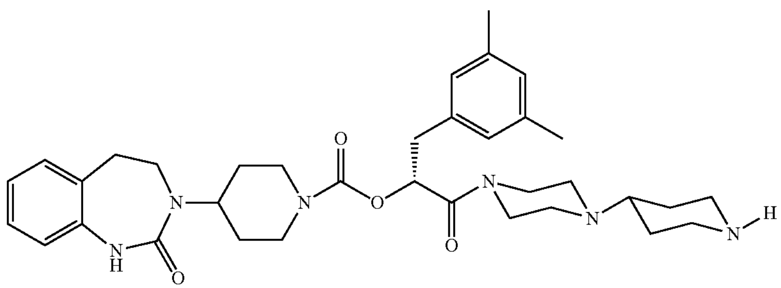 | (R)-1-(3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (125) | 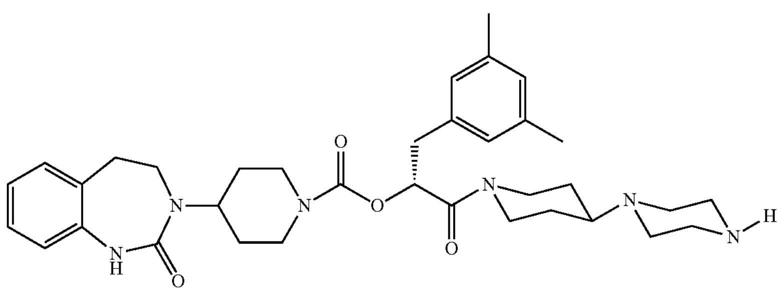 | (R)-1-(3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (126) | 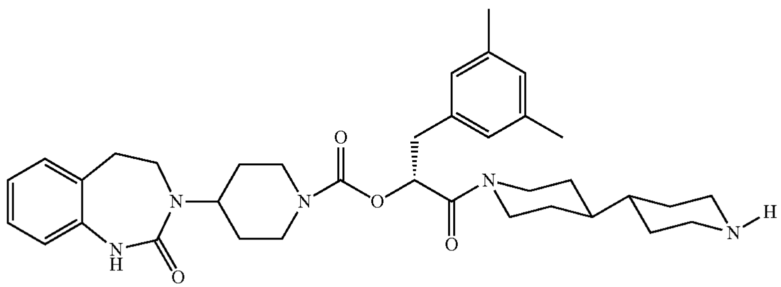 | (R)-2-(4,4'-bipiperidinyl-1-yl)-1-(3,5-dimethyl-benzyl)-2-oxo-ethyl 4-(2-oxo-1,2,4,5-tetrahydro-1,3-benzodiazepin-3-yl)-piperidine-1-carboxylate |
| (127) | 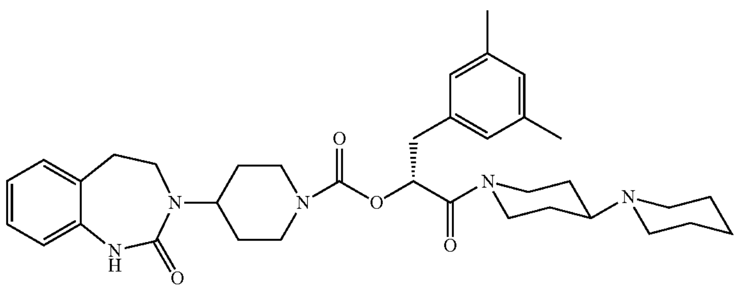 | (R)-2-(1,4'-bipiperidinyl-1'-yl)-1-(3,5-dimethyl-benzyl)-2-oxo-ethyl 4-(2-oxo-1,2,4,5-tetrahydro-1,3-benzodiazepin-3-yl)-piperidine-1-carboxylate |
| (128) | 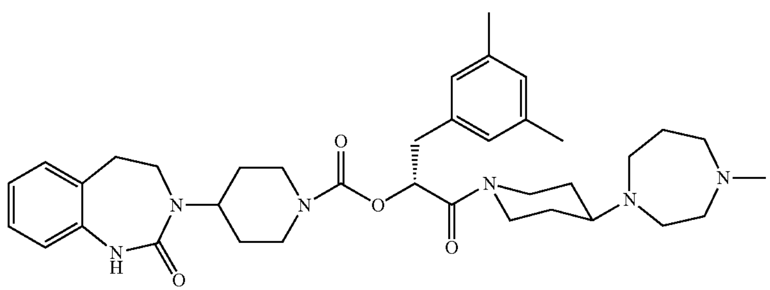 | (R)-1-(3,5-dimethyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (129) | 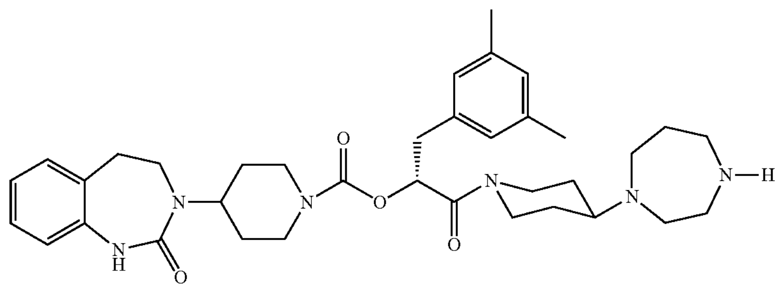 | (R)-1-(3,5-dimethyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (130) | 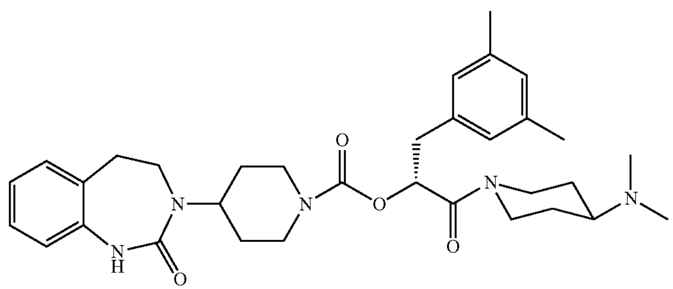 | (R)-2-(4-dimethylamino-piperidin-1-yl)-1-(3,5-dimethyl-benzyl)-2-oxo-ethyl 4-(2-oxo-1,2,4,5-tetrahydro-1,3-benzodiazepin-3-yl)-piperidine-1-carboxylate |
| (131) | 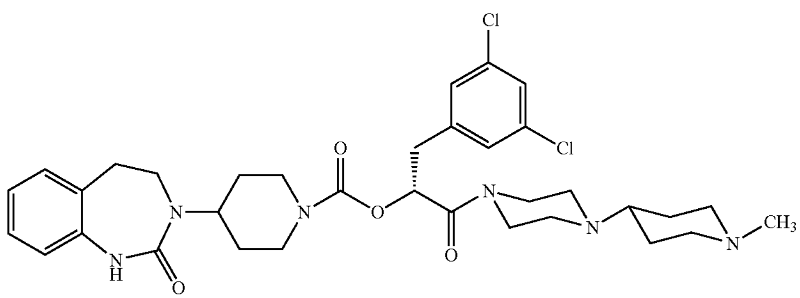 | (R)-1-(3,5-dichloro-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (132) | 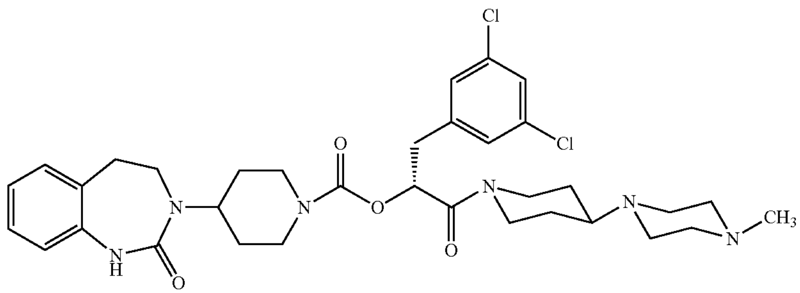 | (R)-1-(3,5-dichloro-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (133) | 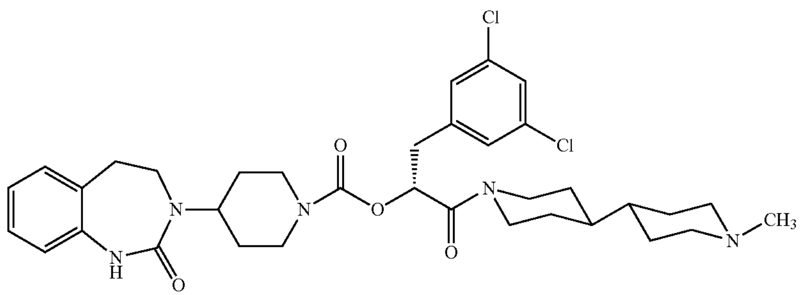 | (R)-1-(3,5-dichloro-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (134) | 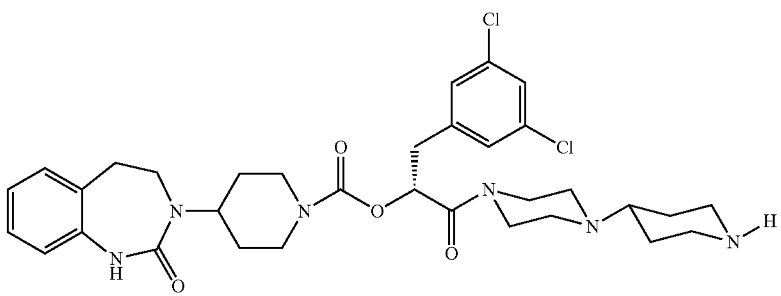 | (R)-1-(3,5-dichloro-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (135) | 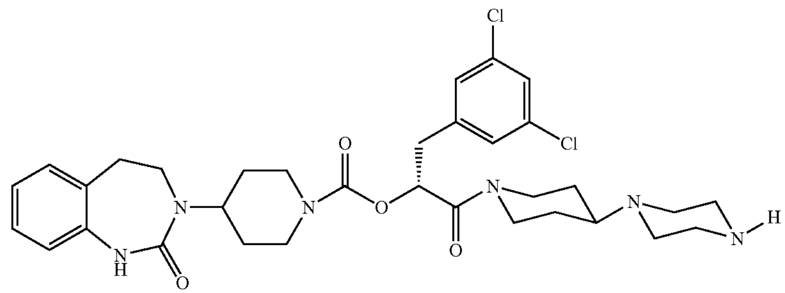 | (R)-1-(3,5-dichloro-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (136) | 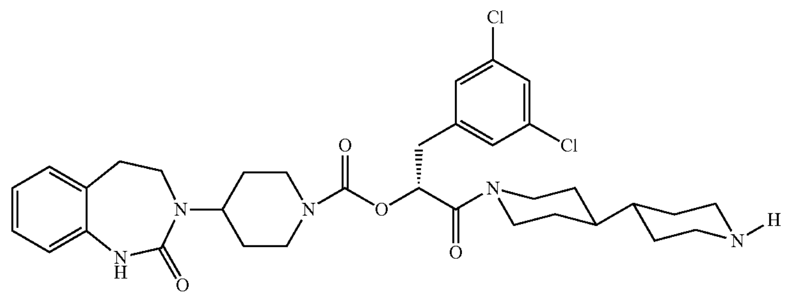 | (R)-2-(4,4'-bipiperidinyl-1-yl)-1-(3,5-dichloro-benzyl)-2-oxo-ethyl 4-(2-oxo-1,2,4,5-tetrahydro-1,3-benzodiazepin-3-yl)-piperidine-1-carboxylate |
| (137) | 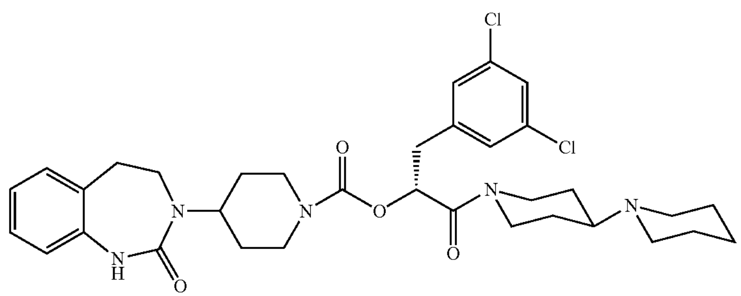 | (R)-2-(1,4'-bipiperidinyl-1'-yl)-1-(3,5-dichloro-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (138) | 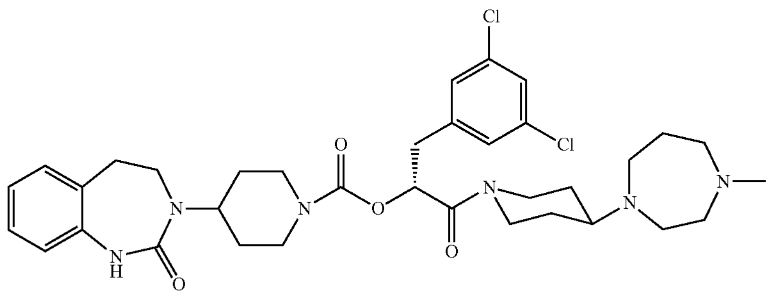 | (R)-1-(3,5-dichloro-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (139) | 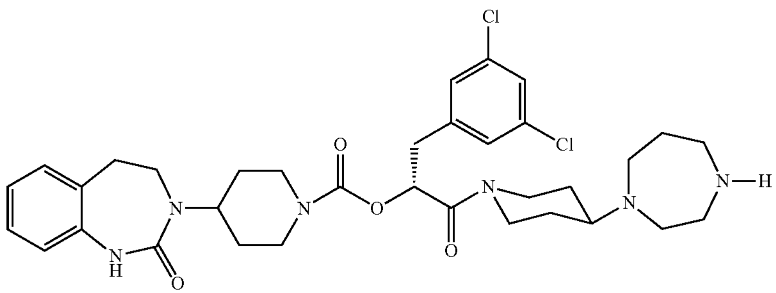 | (R)-1-(3,5-dichloro-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (140) | 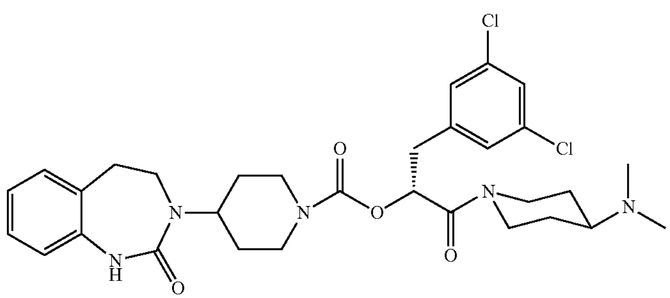 | (R)-1-(3,5-dichloro-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (141) | 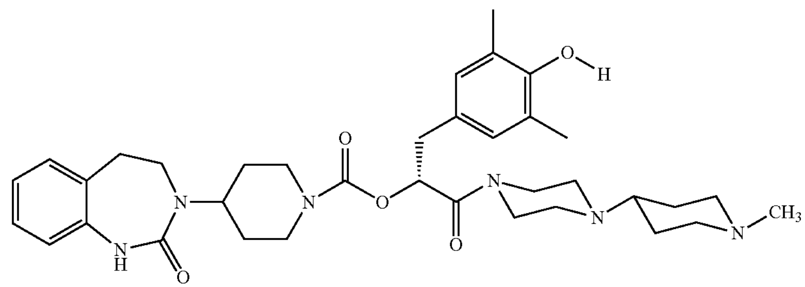 | (R)-1-(4-hydroxy-3,5-dimethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (142) | 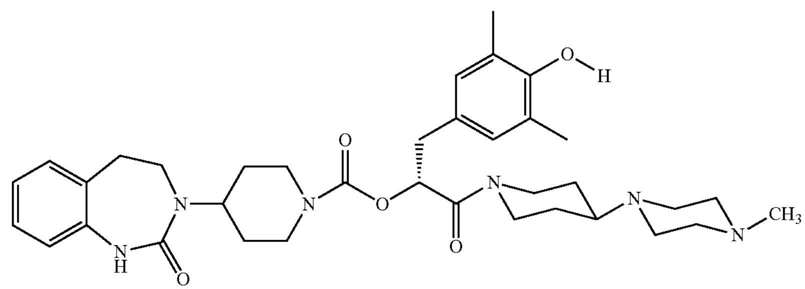 | (R)-1-(4-hydroxy-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (143) | 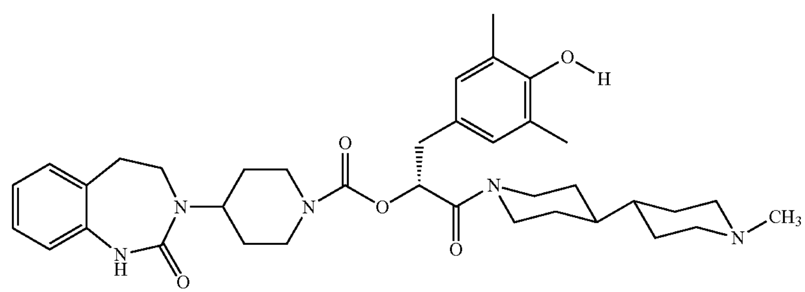 | (R)-1-(4-hydroxy-3,5-dimethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (144) | 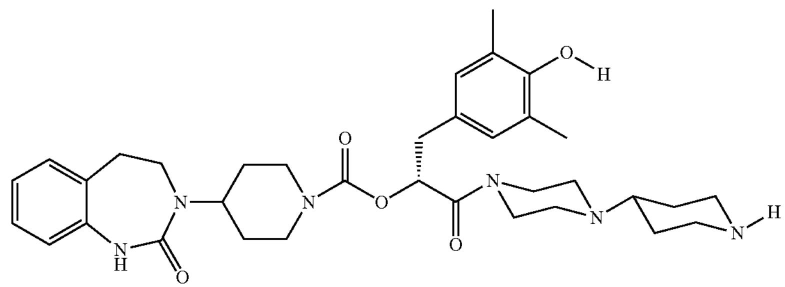 | (R)-1-(4-hydroxy-3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (145) | 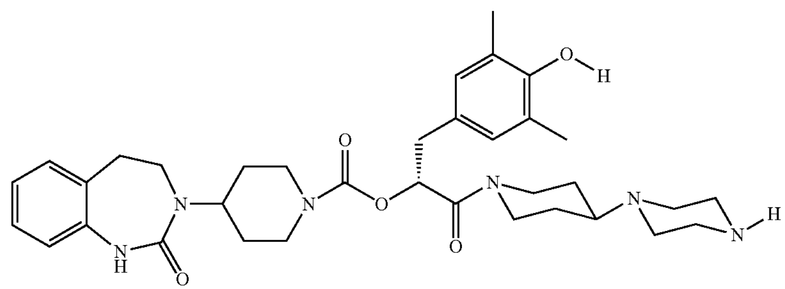 | (R)-1-(4-hydroxy-3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (146) | 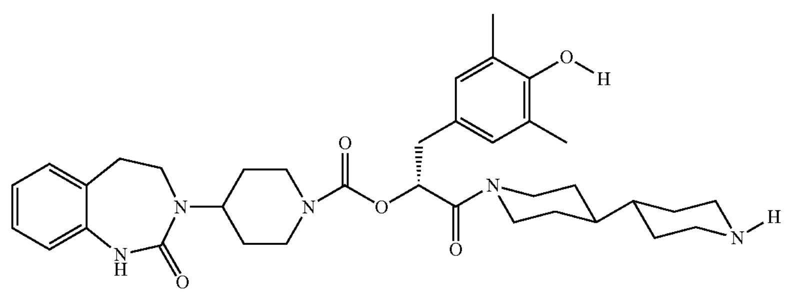 | (R)-2-(4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (147) | 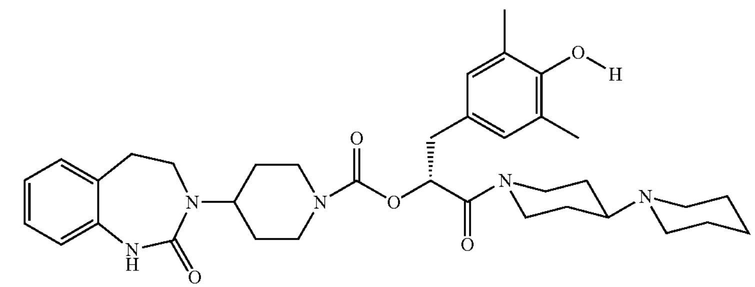 | (R)-2-(1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (148) | 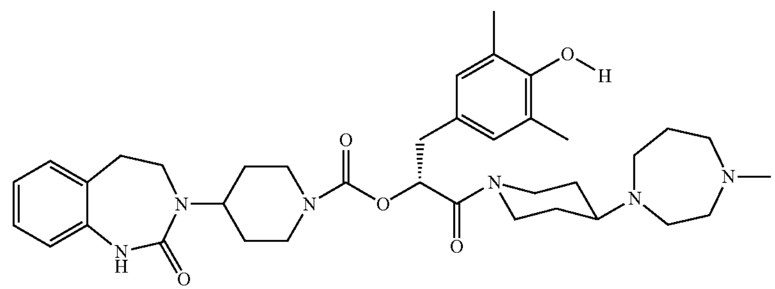 | (R)-1-(4-hydroxy-3,5-dimethyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (149) | 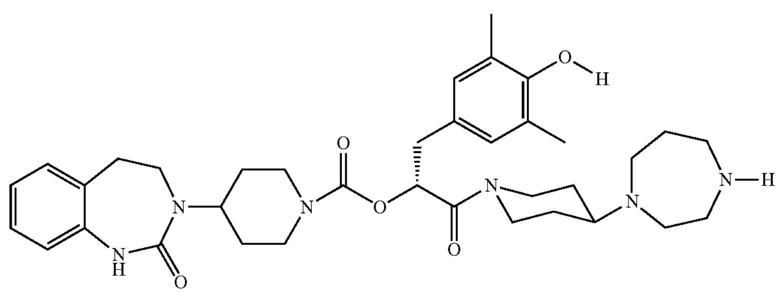 | (R)-1-(4-hydroxy-3,5-dimethyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (150) | 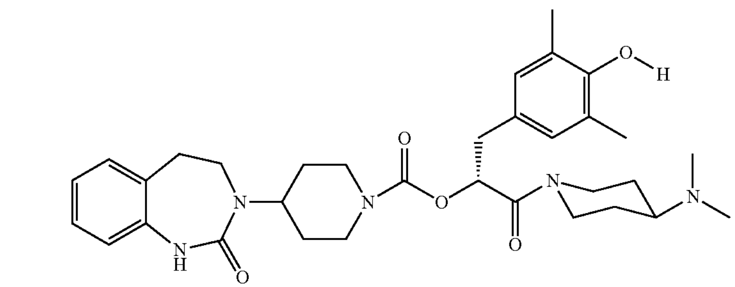 | (R)-2-(4-dimethylamino-piperidin-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (151) | 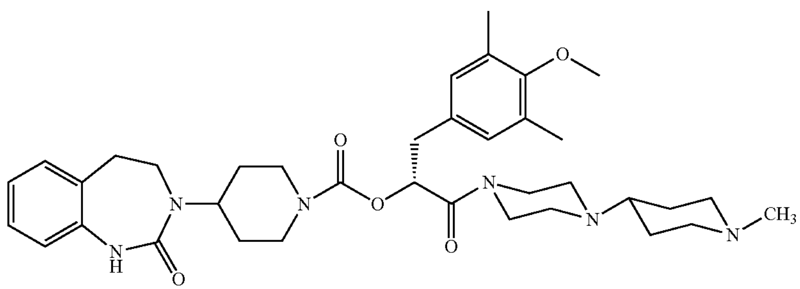 | (R)-1-(4-methoxy-3,5-dimethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (152) | 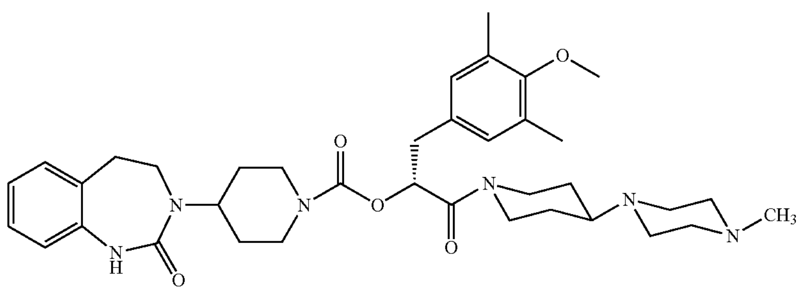 | (R)-1-(4-methoxy-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (153) | 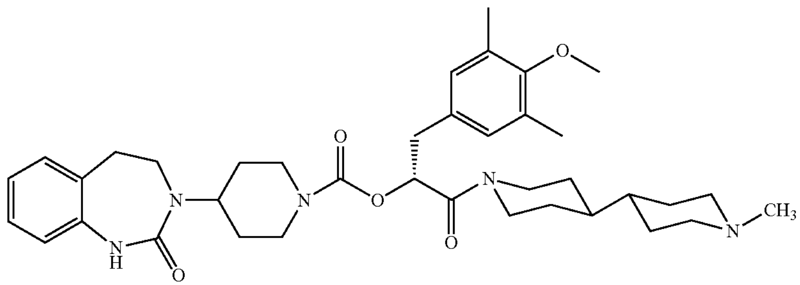 | (R)-1-(4-methoxy-3,5-dimethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (154) | 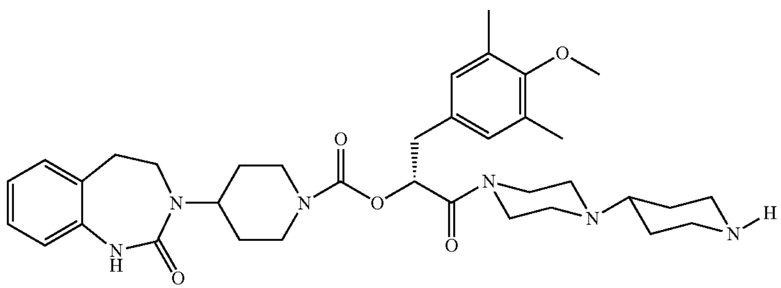 | (R)-1-(4-methoxy-3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (155) | 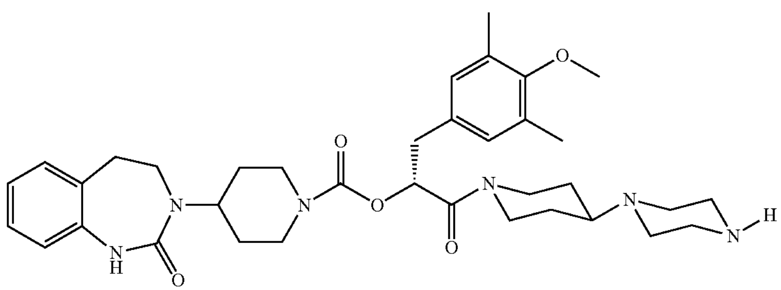 | (R)-1-(4-methoxy-3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (156) | 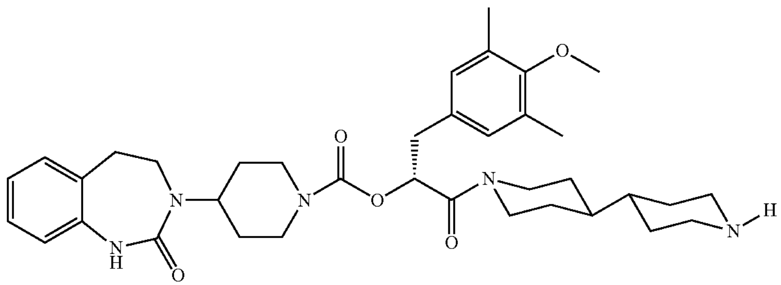 | (R)-2-(4,4'-bipiperidinyl-1-yl)-1-(4-methoxy-3,5-dimethyl-benzyl)-2-oxo-ethyl 4-(2-oxo-1,2,4,5-tetrahydro-1,3-benzodiazepin-3-yl)-piperidine-1-carboxylate |
| (157) | 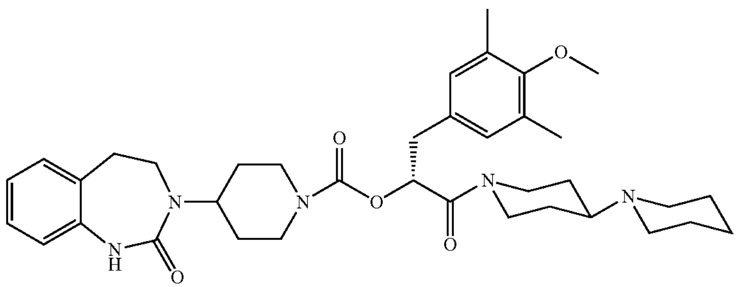 | (R)-2-(1,4'-bipiperidinyl-1'-yl)-1-(4-methoxy-3,5-dimethyl-benzyl)-2-oxo-ethyl 4-(2-oxo-1,2,4,5-tetrahydro-1,3-benzodiazepin-3-yl)-piperidine-1-carboxylate |
| (158) | 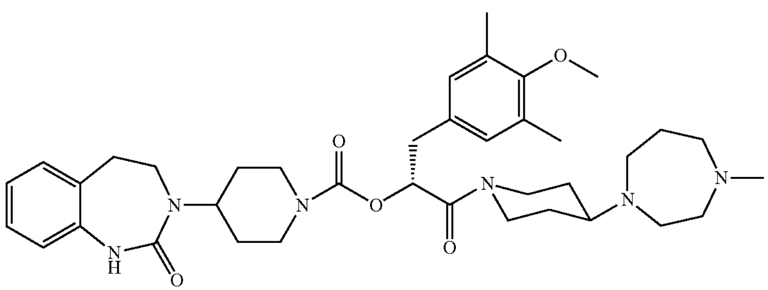 | (R)-1-(4-methoxy-3,5-dimethyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (159) | 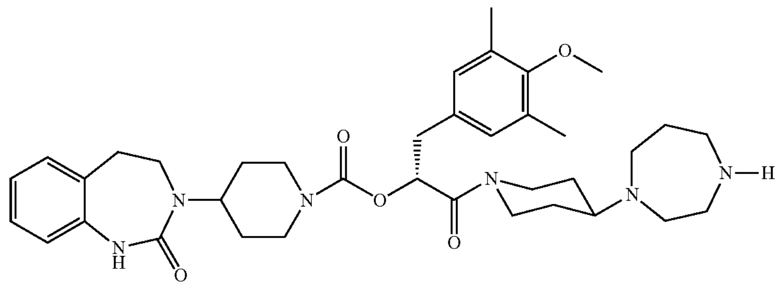 | (R)-1-(4-methoxy-3,5-dimethyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (160) | 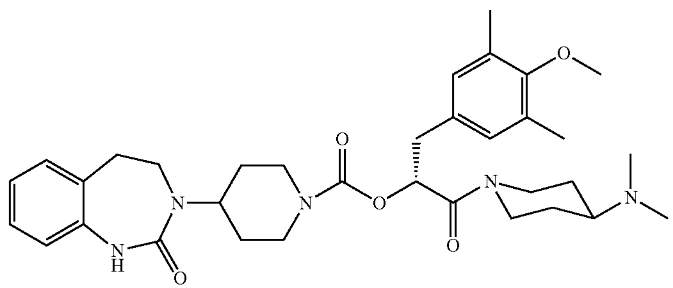 | (R)-2-(4-dimethylamino-piperidin-1-yl)-1-(4-methoxy-3,5-dimethyl-benzyl)-2-oxo-ethyl 4-(2-oxo-1,2,4,5-tetrahydro-1,3-benzodiazepin-3-yl)-piperidine-1-carboxylate |
| (161) | 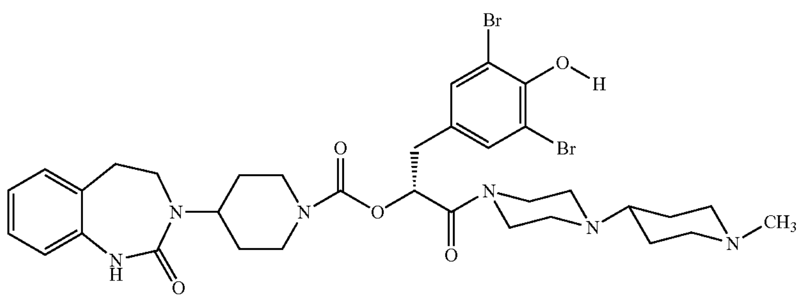 | (R)-1-(3,5-dibromo-4-hydroxy-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (162) | 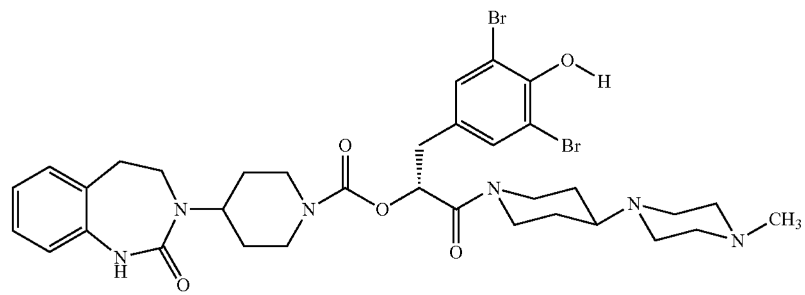 | (R)-1-(3,5-dibromo-4-hydroxy-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (163) | 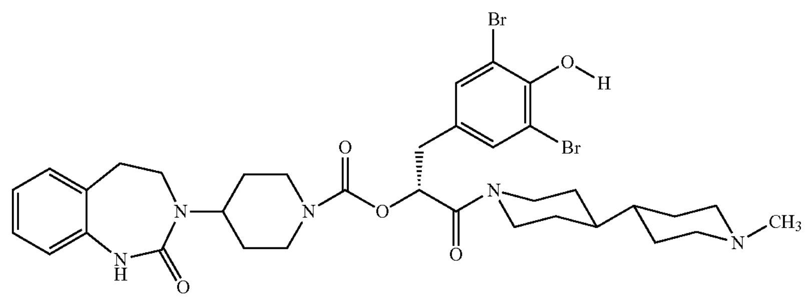 | (R)-1-(3,5-dibromo-4-hydroxy-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (164) | 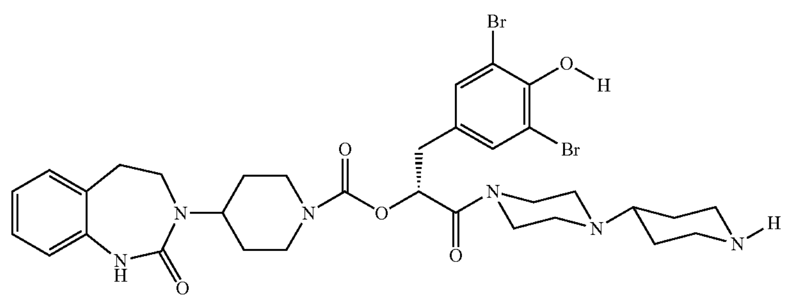 | (R)-1-(3,5-dibromo-4-hydroxy-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (165) | 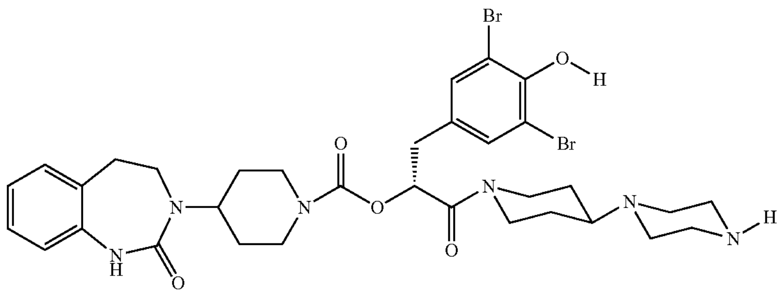 | (R)-1-(3,5-dibromo-4-hydroxy-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (166) | 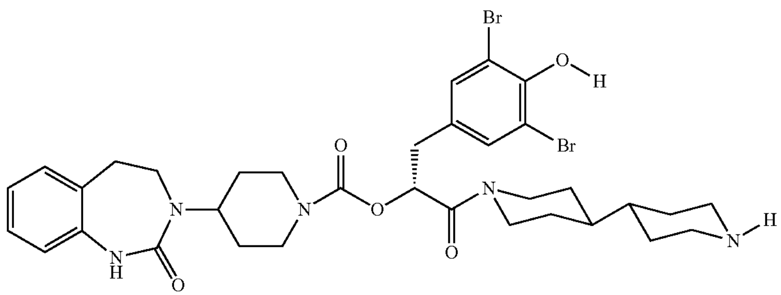 | (R)-2-(4,4'-bipiperidinyl-1-yl)-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (167) | 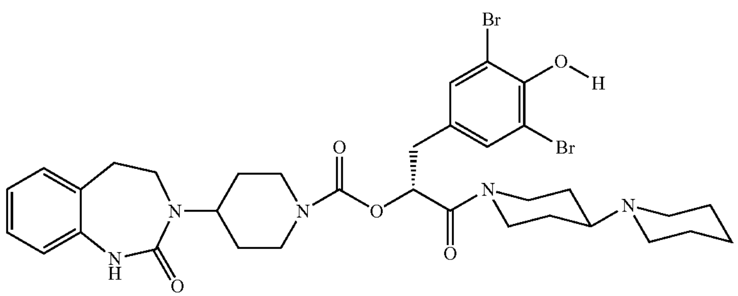 | (R)-2-(1,4'-bipiperidinyl-1'-yl)-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (168) | 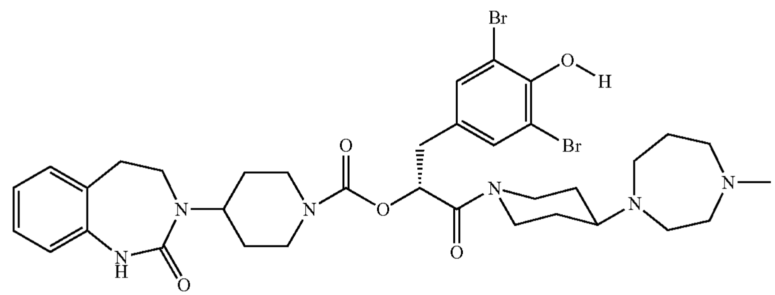 | (R)-1-(3,5-dibromo-4-hydroxy-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (169) | 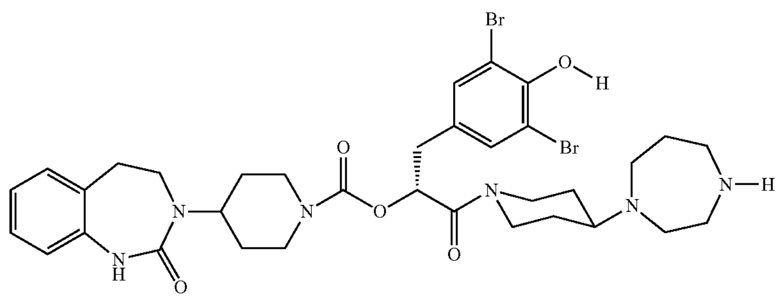 | (R)-1-(3,5-dibromo-4-hydroxy-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (170) | 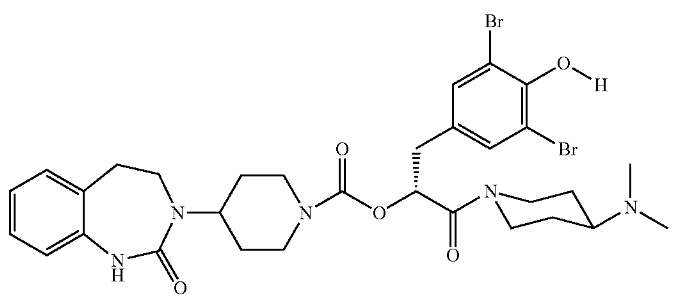 | (R)-1-(3,5-dibromo-4-hydroxy-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (171) | 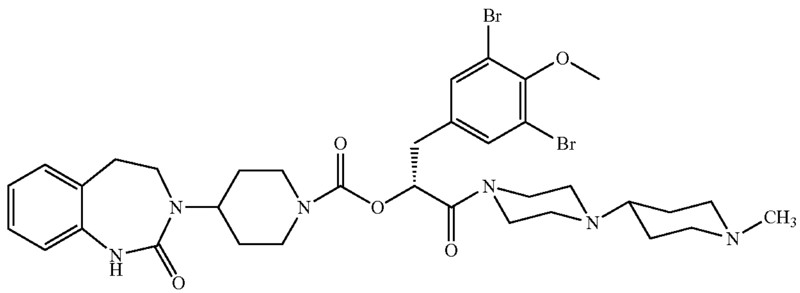 | (R)-1-(3,5-dibromo-4-methoxy-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (172) | 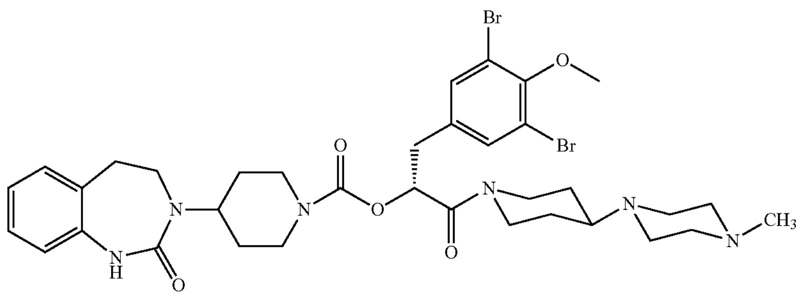 | (R)-1-(3,5-dibromo-4-methoxy-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (173) | 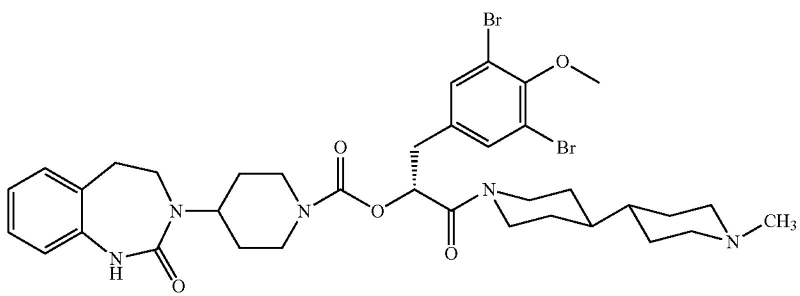 | (R)-1-(3,5-dibromo-4-methoxy-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (174) | 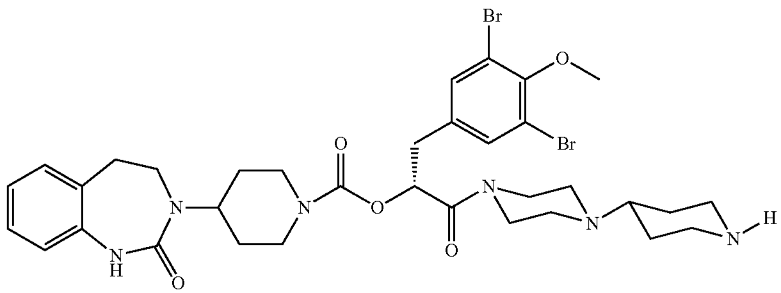 | (R)-1-(3,5-dibromo-4-methoxy-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (175) | 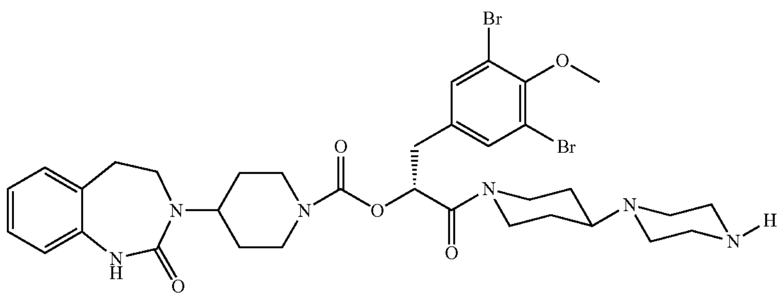 | (R)-1-(3,5-dibromo-4-methoxy-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (176) | 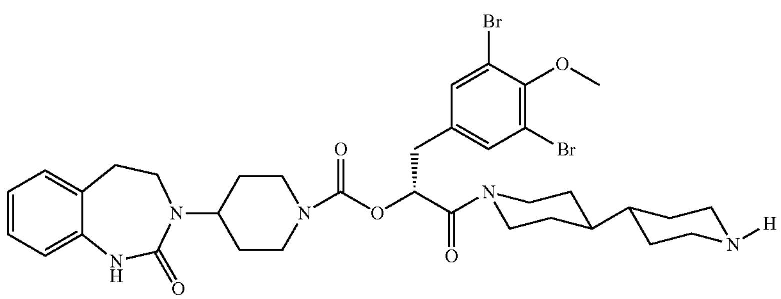 | (R)-2-(4,4'-bipiperidinyl-1-yl)-1-(3,5-dibromo-4-methoxy-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (177) | 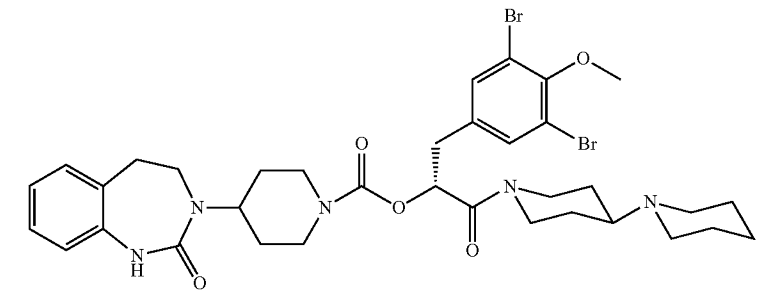 | (R)-2-(1,4-bipiperidinyl-1'-yl)-1-(3,5-dibromo-4-methoxy-benzyl)-2-oxo-ethyl 4-(2-oxo-1,2,4,5-tetrahydro-1,3-benzodiazepin-3-yl)-piperidine-1-carboxylate |
| (178) | 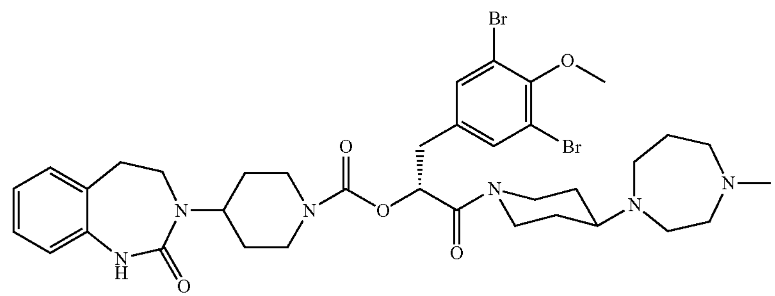 | (R)-1-(3,5-dibromo-4-methoxy-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (179) | 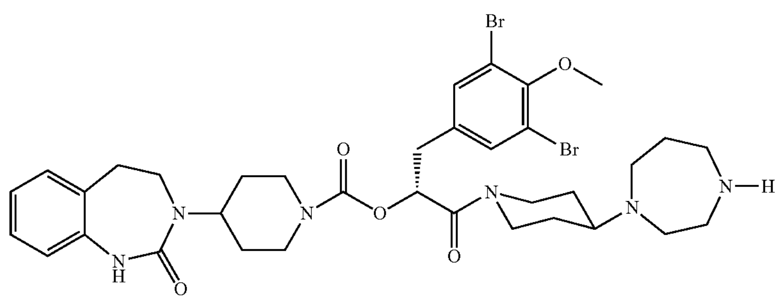 | (R)-1-(3,5-dibromo-4-methoxy-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (180) | 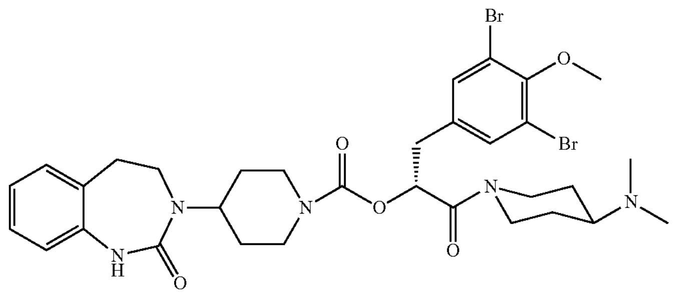 | (R)-1-(3,5-dibromo-4-methoxy-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (181) | 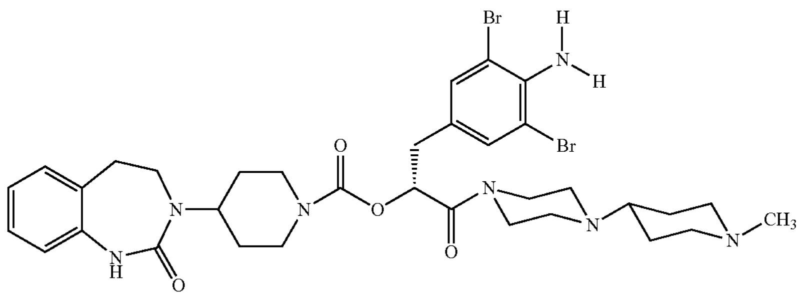 | (R)-1-(4-amino-3,5-dibromo-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (182) | 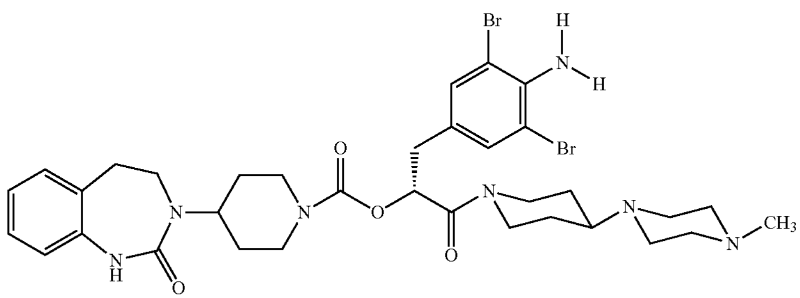 | (R)-1-(4-amino-3,5-dibromo-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (183) | 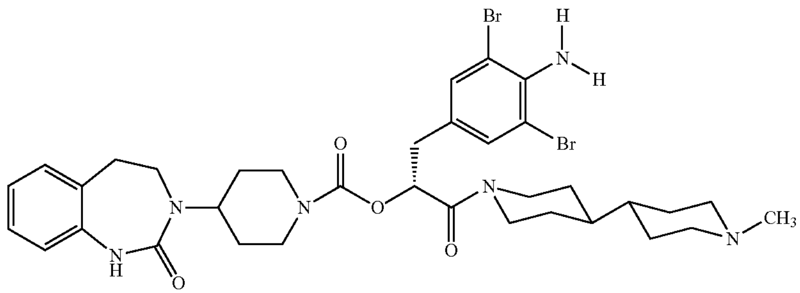 | (R)-1-(4-amino-3,5-dibromo-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (184) | 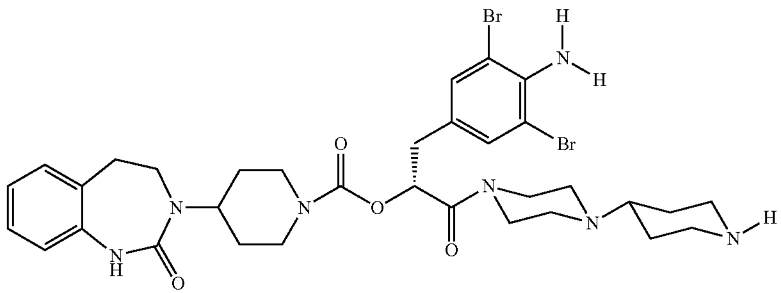 | (R)-1-(4-amino-3,5-dibromo-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (185) | 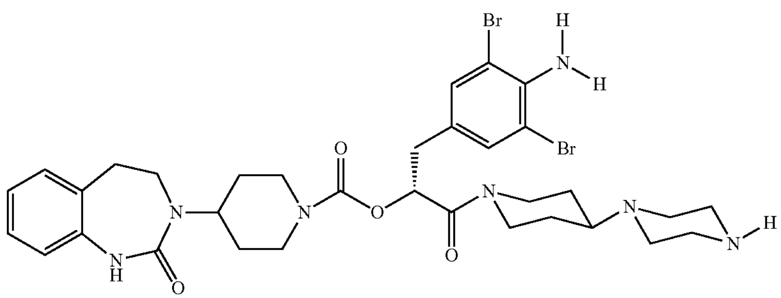 | (R)-1-(4-amino-3,5-dibromo-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (186) | 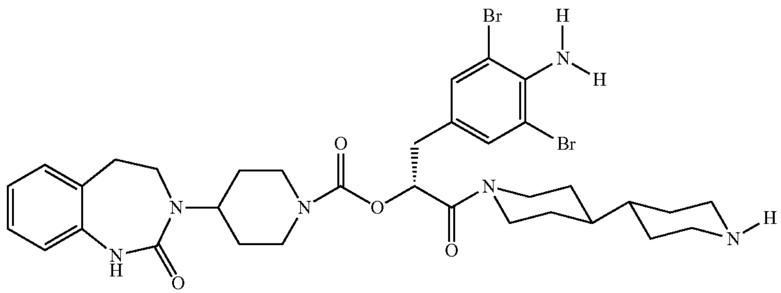 | (R)-1-(4-amino-3,5-dibromo-benzyl)-2-(4,4'-bipiperidinyl-1-yl)-2-oxo-ethyl 4-(2-oxo-1,2,4,5-tetrahydro-1,3-benzodiazepin-3-yl)-piperidine-1-carboxylate |
| (187) | 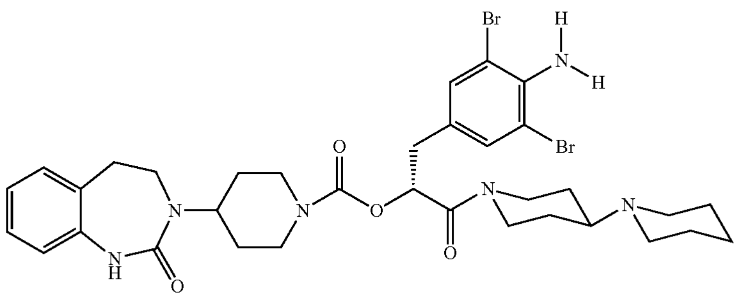 | (R)-1-(4-amino-3,5-dibromo-benzyl)-2-(1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (188) | 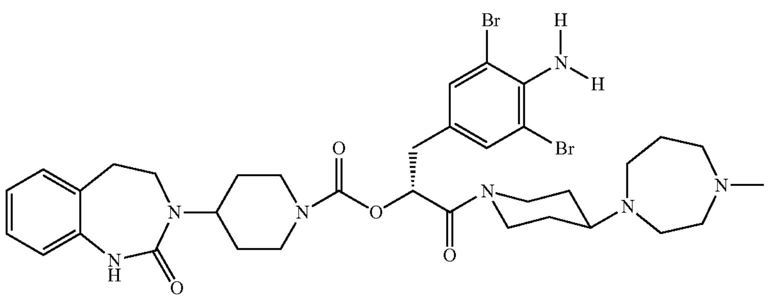 | (R)-1-(4-amino-3,5-dibromo-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (189) | 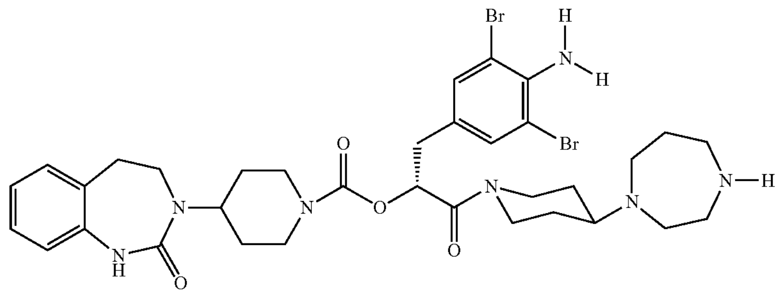 | (R)-1-(4-amino-3,5-dibromo-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (190) | 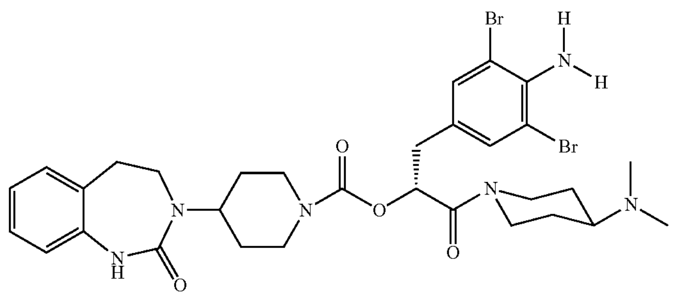 | (R)-1-(4-amino-3,5-dibromo-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (191) | 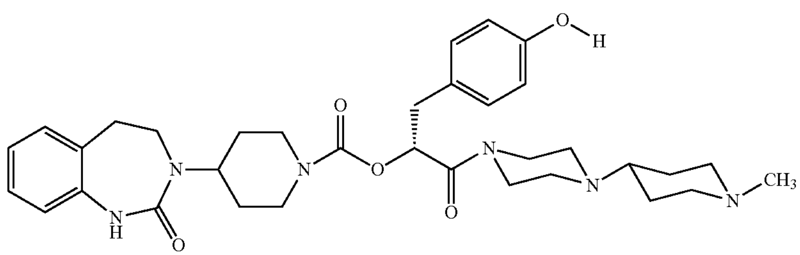 | (R)-1-(4-hydroxy-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (192) | 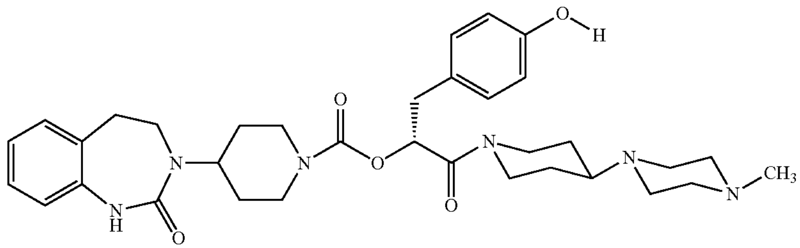 | (R)-1-(4-hydroxy-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (193) | 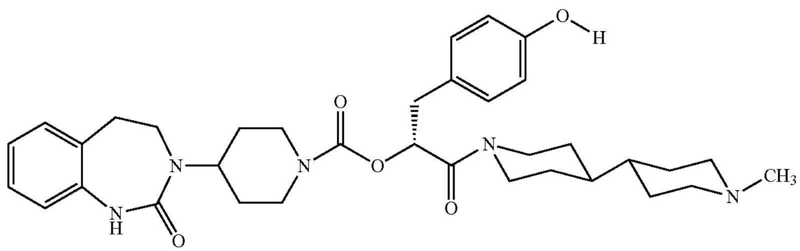 | (R)-1-(4-hydroxy-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (194) | 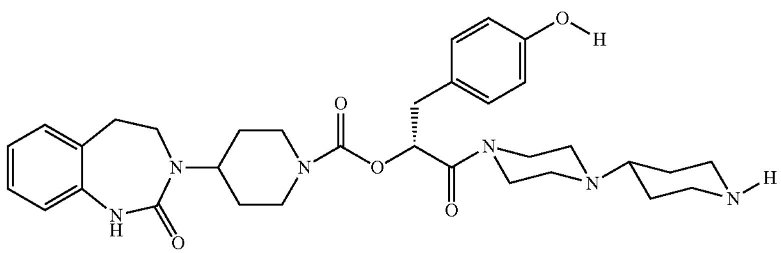 | (R)-1-(4-hydroxy-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (195) | 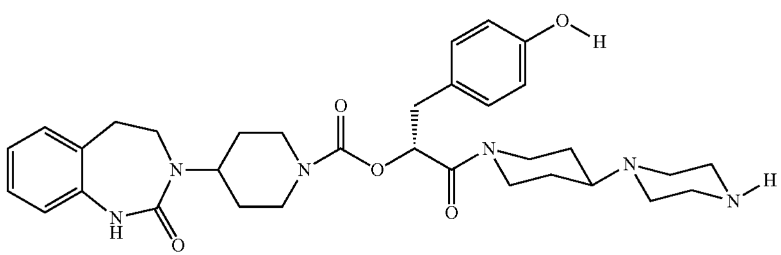 | (R)-1-(4-hydroxy-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (196) | 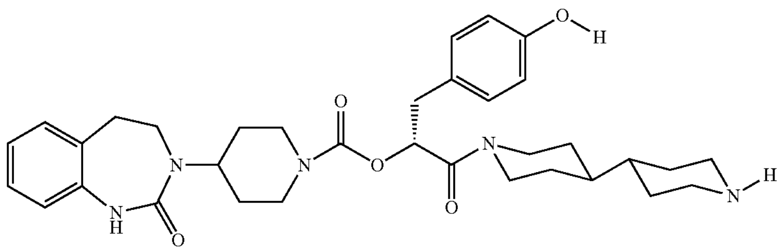 | (R)-2-(4,4'-bipiperidinyl-1-yl)-1-(4-hydroxy-benzyl)-2-oxo-ethyl 4-(2-oxo-1,2,4,5-tetrahydro-1,3-benzodiazepin-3-yl)-piperidine-1-carboxylate |
| (197) | 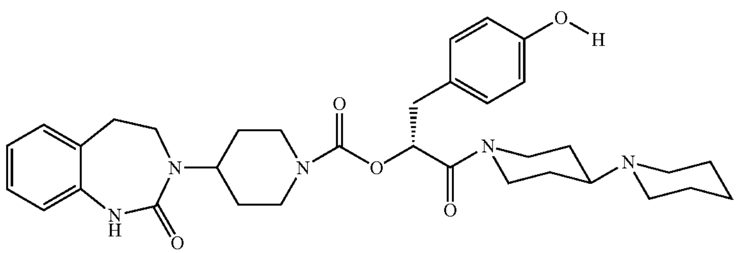 | (R)-2-(1,4'-bipiperidinyl-1'-yl)-1-(4-hydroxy-benzyl)-2-oxo-ethyl 4-(2-oxo-1,2,4,5-tetrahydro-1,3-benzodiazepin-3-yl)-piperidine-1-carboxylate |
| (198) | 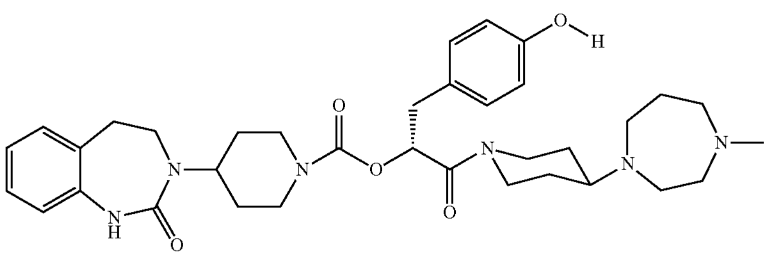 | (R)-1-(4-hydroxy-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (199) | 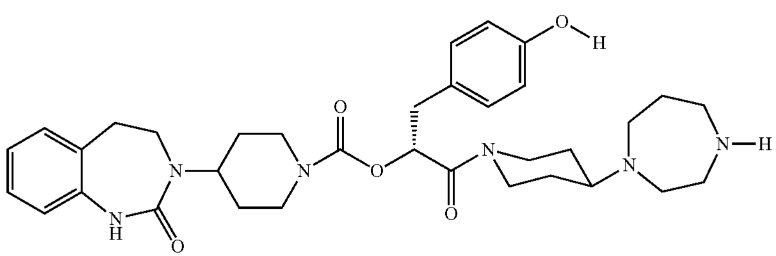 | (R)-1-(4-hydroxy-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (200) | 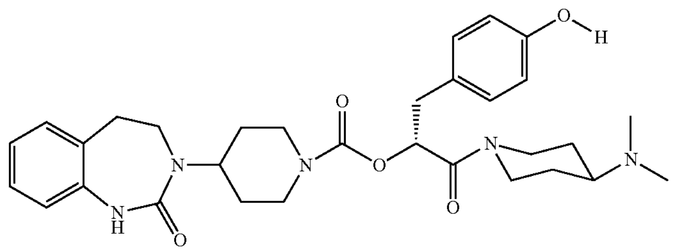 | (R)-2-(4-dimethylamino-piperidin-1-yl)-1-(4-hydroxy-benzyl)-2-oxo-ethyl 4-(2-oxo-1,2,4,5-tetrahydro-1,3-benzodiazepin-3-yl)-piperidine-1-carboxylate |
| (201) | 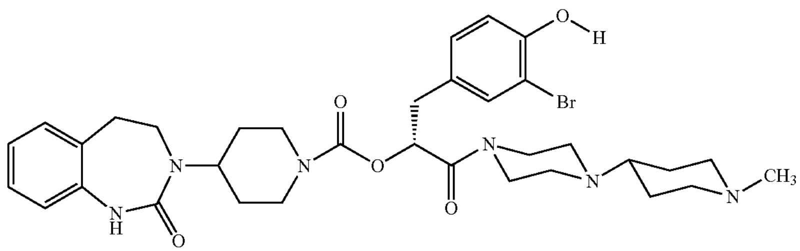 | (R)-1-(3-bromo-4-hydroxy-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (202) | 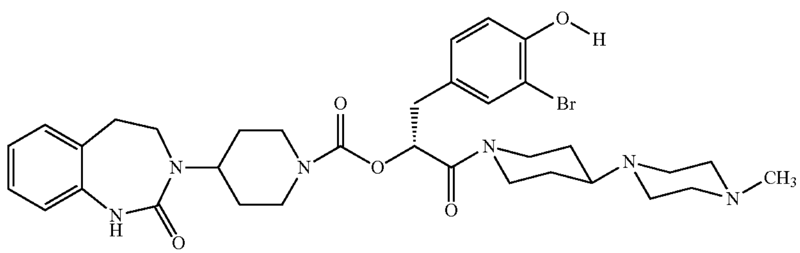 | (R)-1-(3-bromo-4-hydroxy-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (203) | 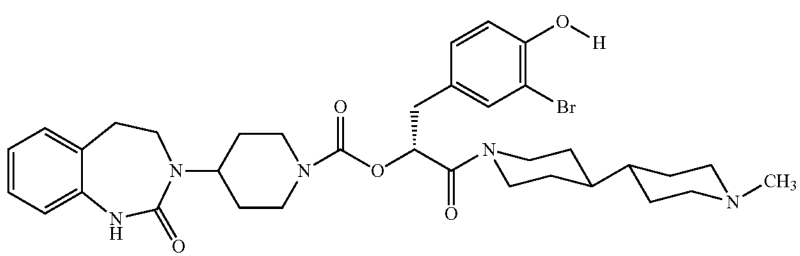 | (R)-1-(3-bromo-4-hydroxy-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (204) | 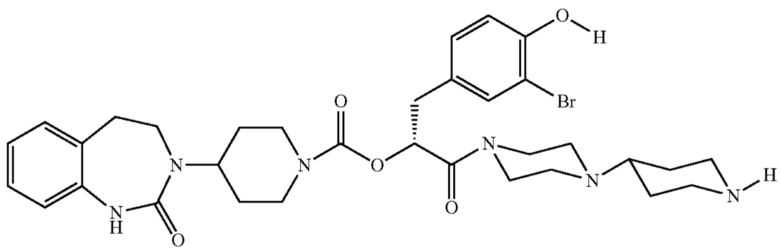 | (R)-1-(3-bromo-4-hydroxy-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (205) | 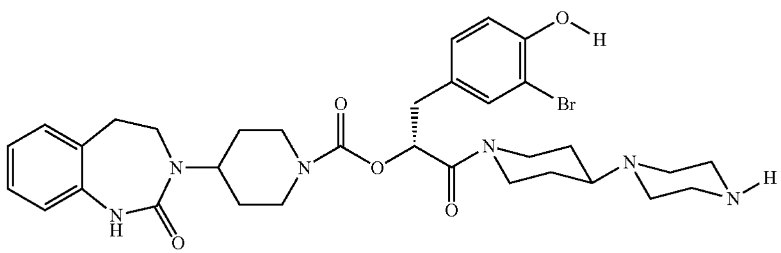 | (R)-1-(3-bromo-4-hydroxy-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (206) | 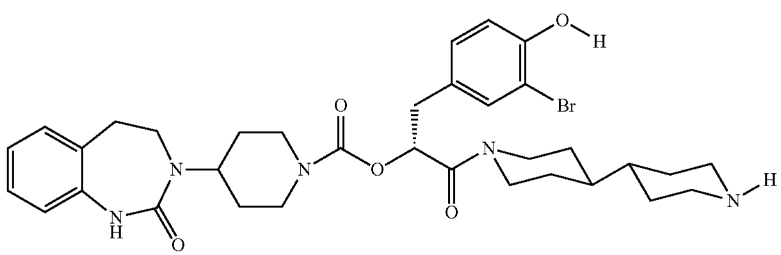 | (R)-2-(4,4'-bipiperidinyl-1-yl)-1-(3-bromo-4-hydroxy-benzyl)-2-oxo-ethyl 4-(2-oxo-1,2,4,5-tetrahydro-1,3-benzodiazepin-3-yl)-piperidine-1-carboxylate |
| (207) | 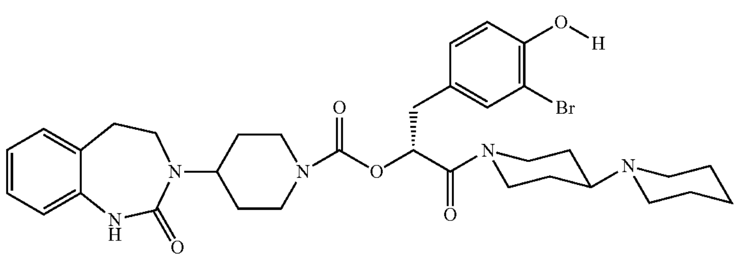 | (R)-2-(1,4'-bipiperidinyl-1'-yl)-1-(3-bromo-4-hydroxy-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (208) | 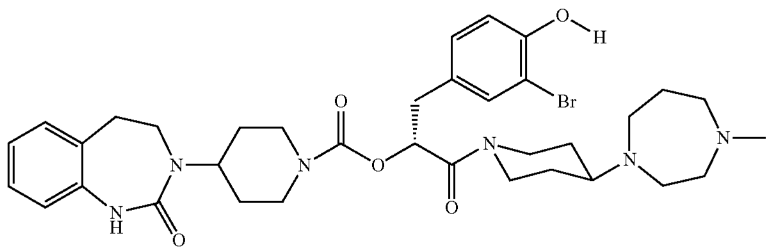 | (R)-1-(3-bromo-4-hydroxy-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (209) | 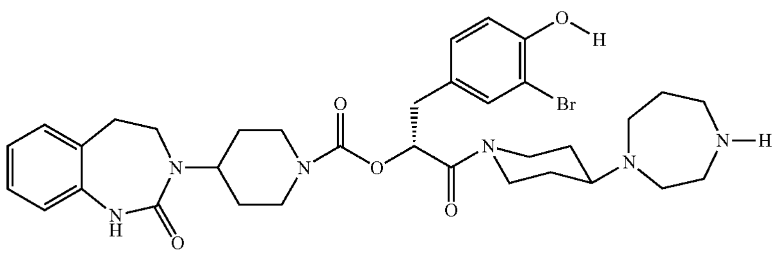 | (R)-1-(3-bromo-4-hydroxy-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (210) | 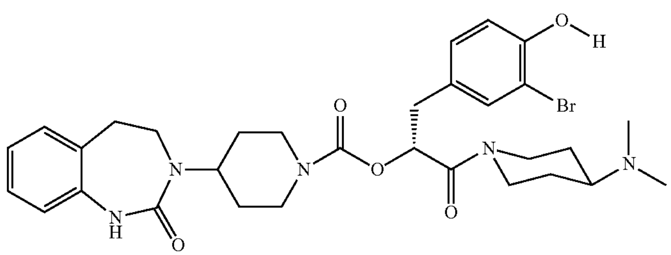 | (R)-1-(3-bromo-4-hydroxy-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (211) | 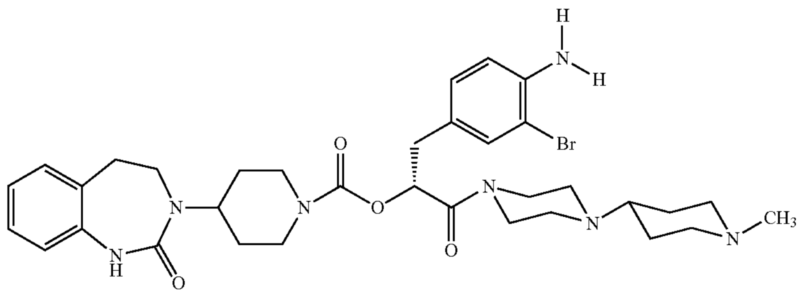 | (R)-1-(4-amino-3-bromo-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (212) | 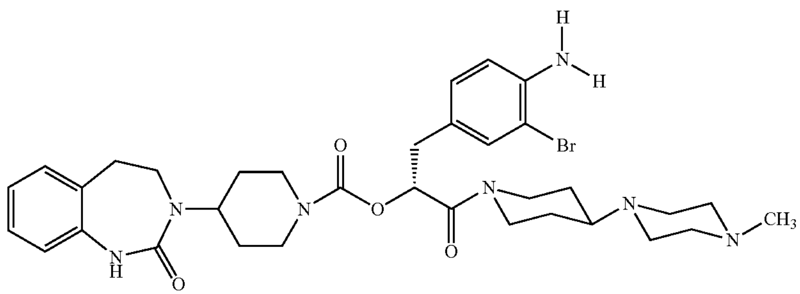 | (R)-1-(4-amino-3-bromo-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (213) | 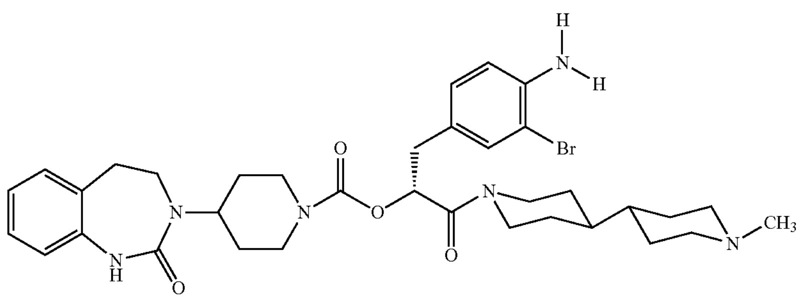 | (R)-1-(4-amino-3-bromo-benzyl)-2-(1′-methyl-4,4′-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (214) | 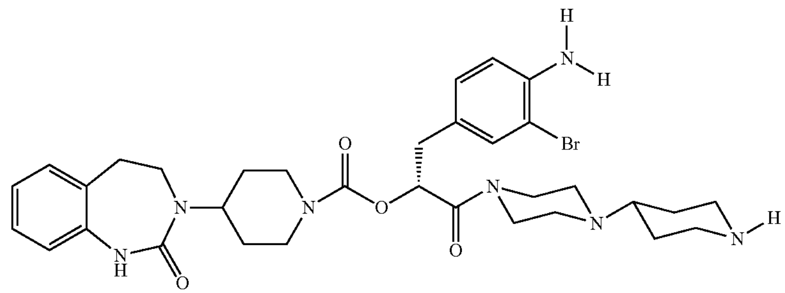 | (R)-1-(4-amino-3-bromo-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (215) | 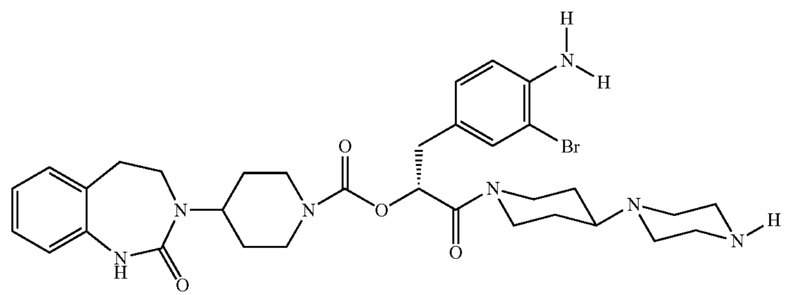 | (R)-1-(4-amino-3-bromo-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (216) | 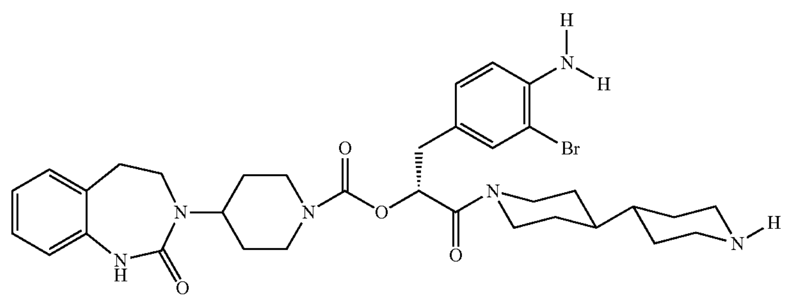 | (R)-1-(4-amino-3-bromo-benzyl)-2-(4,4'-bipiperidinyl-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (217) | 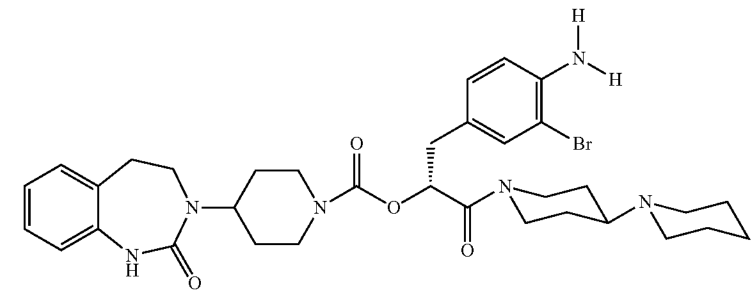 | (R)-1-(4-amino-3-bromo-benzyl)-2-(1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (218) | 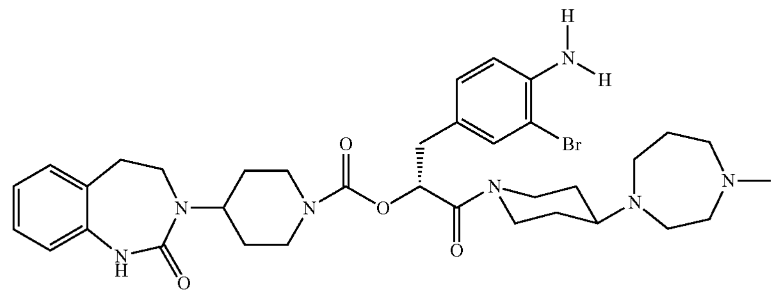 | (R)-1-(4-amino-3-bromo-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (219) | 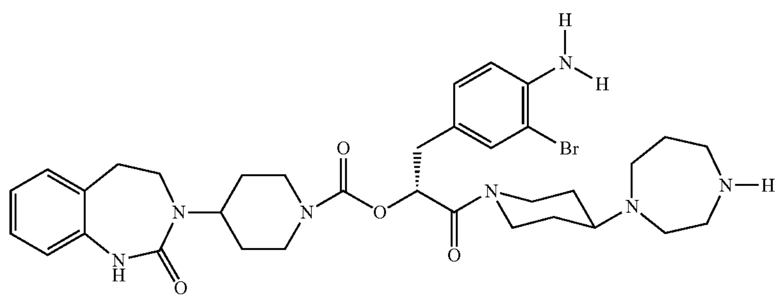 | (R)-1-(4-amino-3-bromo-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (220) | 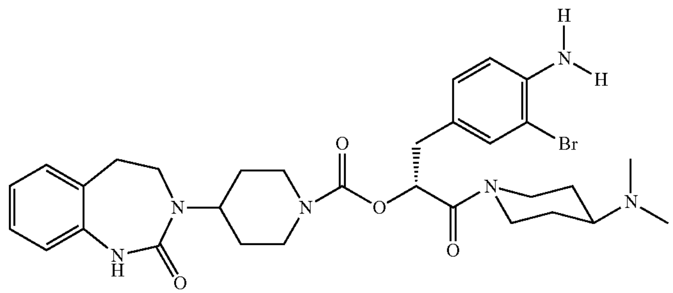 | (R)-1-(4-amino-3-bromo-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (221) | 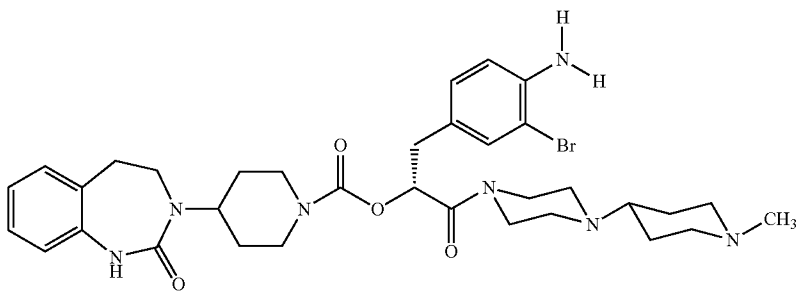 | (R)-1-(4-amino-benzyl)-2-[4-(1-methyl-piperidin-4-yl)piperazin-1-yl]-2-oxo-ethyl 4-(2-oxo-1,2,4,5-tetrahydro-1,3-benzodiazepin-3-yl)-piperidine-1-carboxylate |
| (222) | 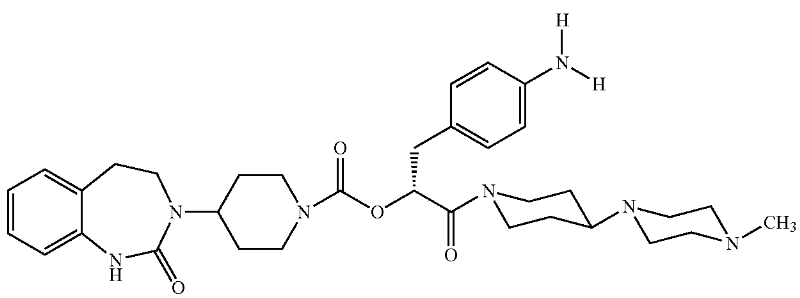 | (R)-1-(4-amino-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (223) | 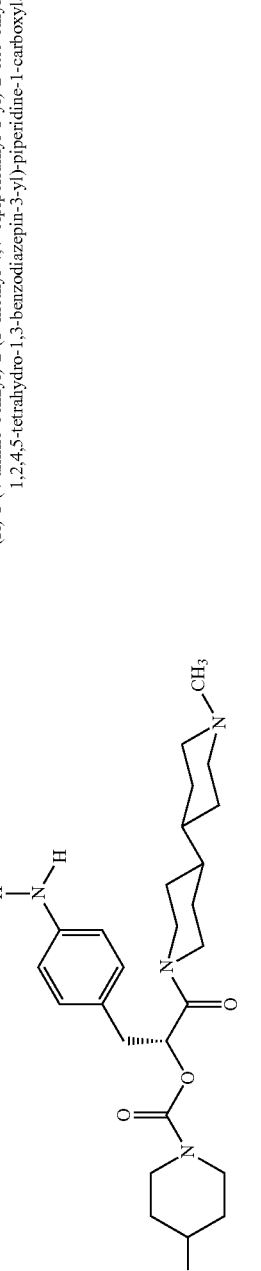 | (R)-1-(4-amino-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (224) | 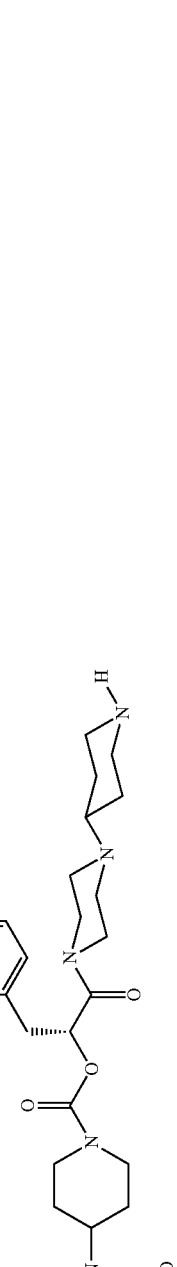 | (R)-1-(4-amino-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (225) | 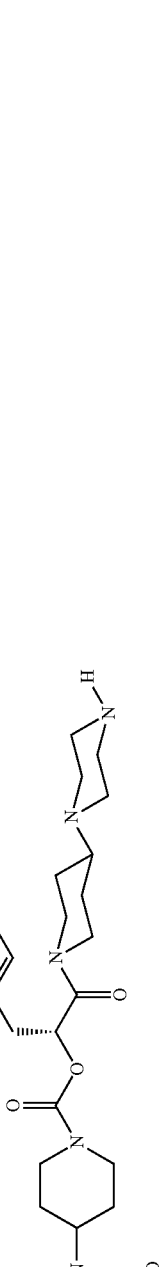 | (R)-1-(4-amino-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (226) | 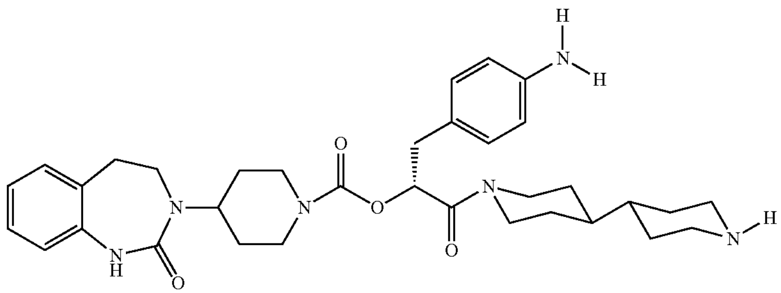 | (R)-1-(4-amino-benzyl)-2-(4,4'-bipiperidinyl-1-yl)-2-oxo-ethyl 4-(2-oxo-1,2,4,5-tetrahydro-1,3-benzodiazepin-3-yl)-piperidine-1-carboxylate |
| (227) | 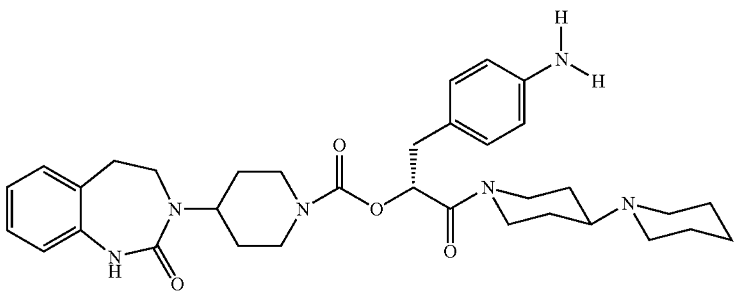 | (R)-1-(4-amino-benzyl)-2-(1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (228) | 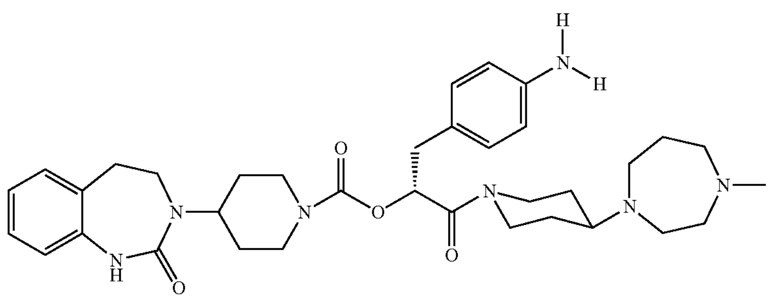 | (R)-1-(4-amino-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (229) | 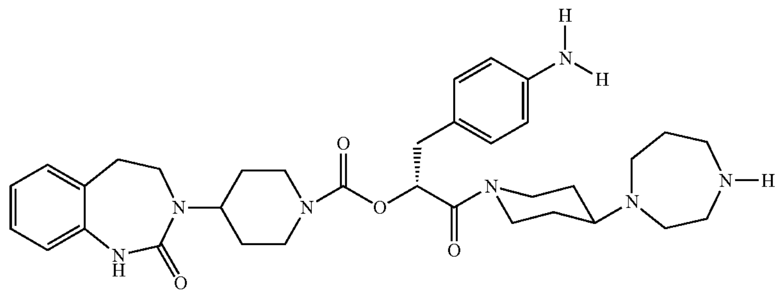 | (R)-1-(4-amino-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (230) | 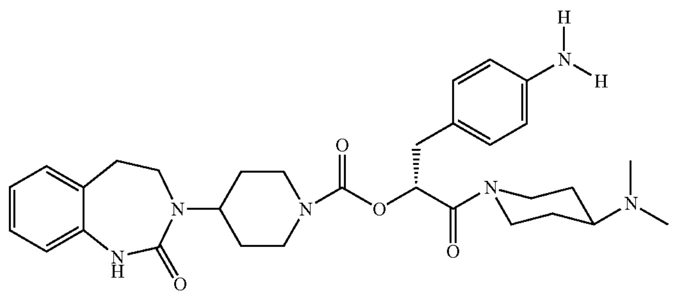 | (R)-1-(4-amino-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (231) | 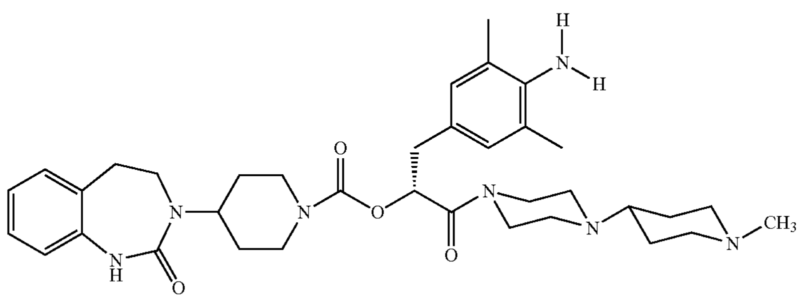 | (R)-1-(4-amino-3,5-dimethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (232) | 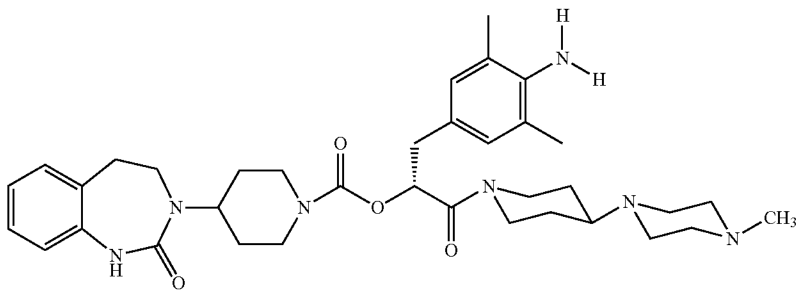 | (R)-1-(4-amino-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (233) | 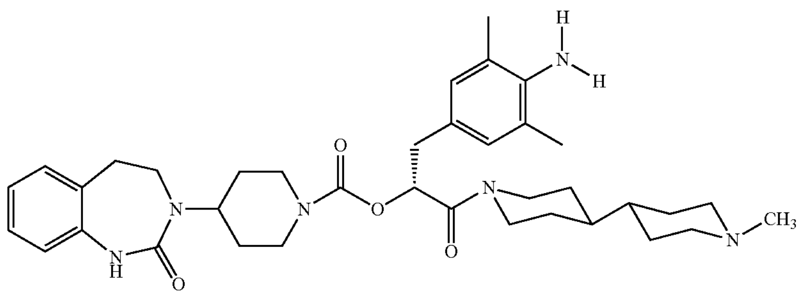 | (R)-1-(4-amino-3,5-dimethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (234) | 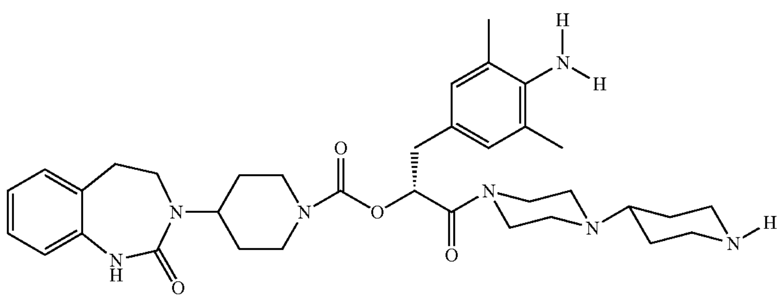 | (R)-1-(4-amino-3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (235) | 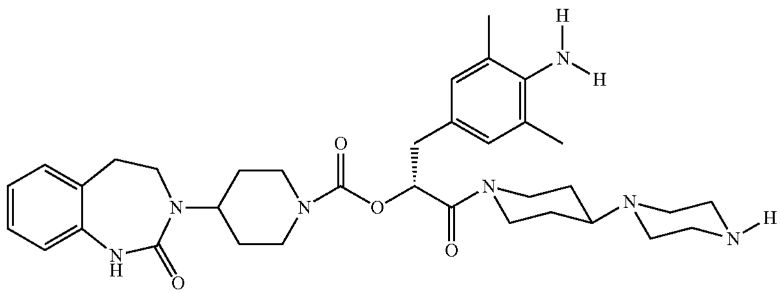 | (R)-1-(4-amino-3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (236) | 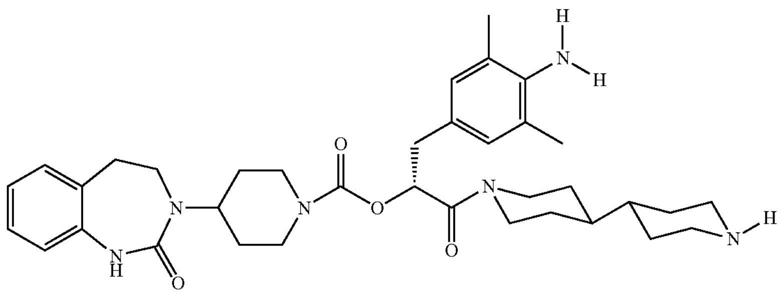 | (R)-1-(4-amino-3,5-dimethyl-benzyl)-2-(4,4'-bipiperidinyl-1-yl)-2-oxo-ethyl 4-(2-oxo-1,2,4,5-tetrahydro-1,3-benzodiazepin-3-yl)-piperidine-1-carboxylate |
| (237) | 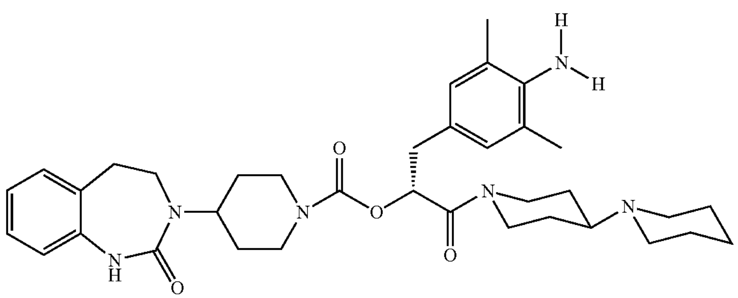 | (R)-1-(4-amino-3,5-dimethyl-benzyl)-2-(1,4'-bipiperidinyl-1'-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (238) | 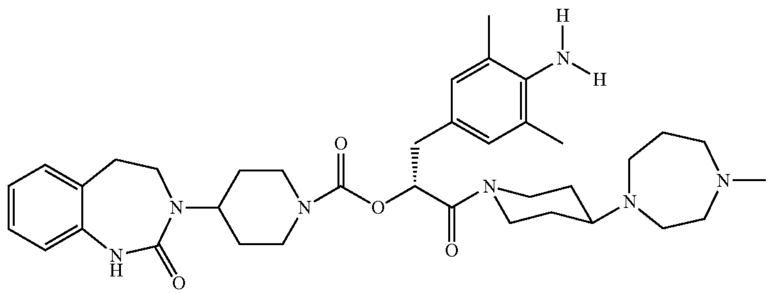 | (R)-1-(4-amino-3,5-dimethyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (239) | 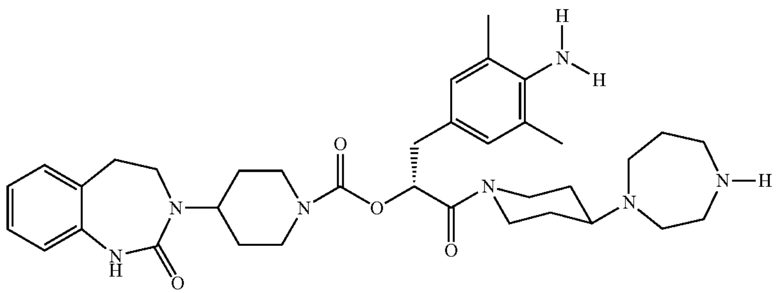 | (R)-1-(4-amino-3,5-dimethyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (240) | 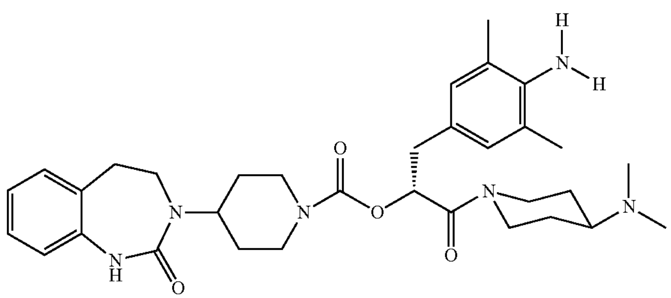 | (R)-1-(4-amino-3,5-dimethyl-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (241) | 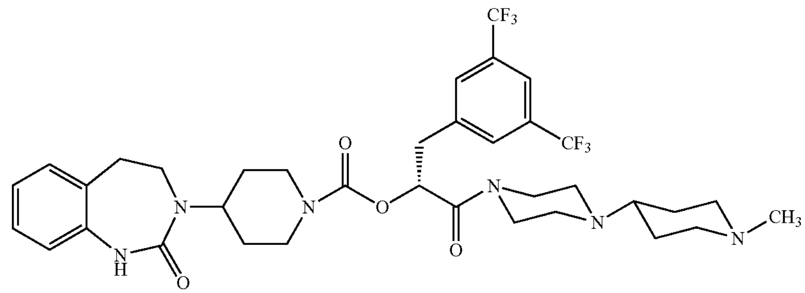 | (R)-1-(3,5-bis-trifluoromethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (242) | 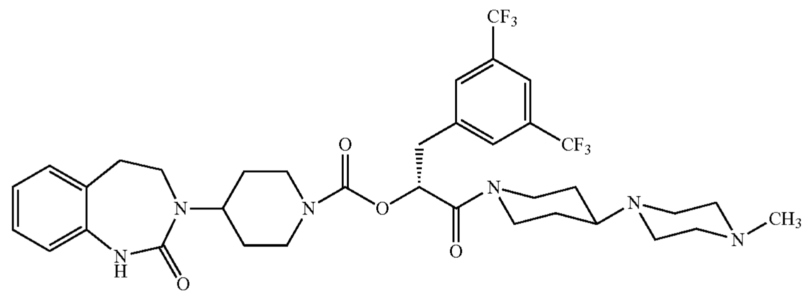 | (R)-1-(3,5-bis-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (243) | 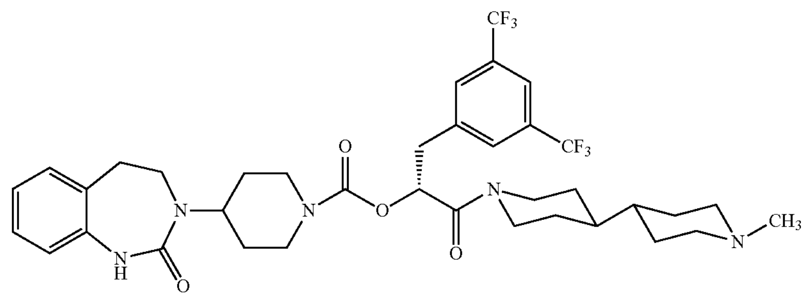 | (R)-1-(3,5-bis-trifluoromethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (244) | 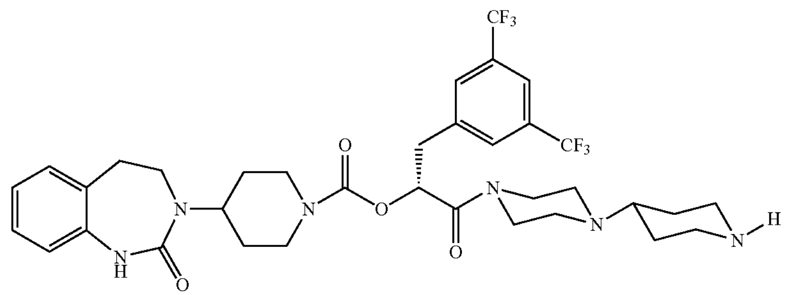 | (R)-1-(3,5-bis-trifluoromethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (245) | 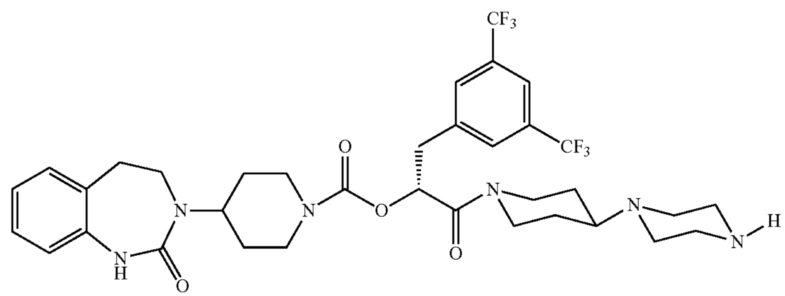 | (R)-1-(3,5-bis-trifluoromethyl-benzyl)-2-oxo-2-(4-piperidin-1-yl-piperazin-1-yl)-ethyl 4-(2-oxo-1,2,4,5-tetrahydro-1,3-benzodiazepin-3-yl)-piperidine-1-carboxylate |
| (246) | 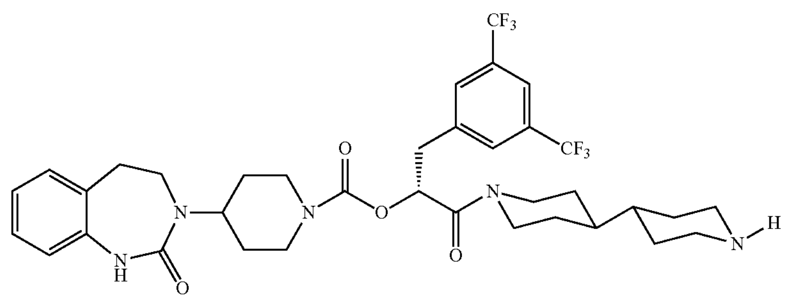 | (R)-2-(4,4'-bipiperidinyl-1-yl)-1-(3,5-bis-trifluoromethyl-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (247) | 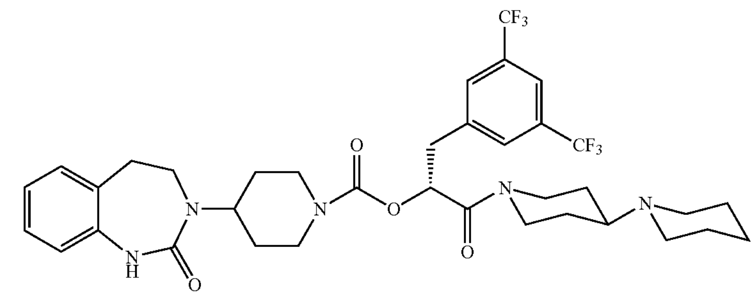 | (R)-2-(1,4'-bipiperidinyl-1'-yl)-1-(3,5-bis-trifluoromethyl-benzyl)-2-oxo-ethyl 4-(2-oxo-1,2,4,5-tetrahydro-1,3-benzodiazepin-3-yl)-piperidine-1-carboxylate |
| (248) | 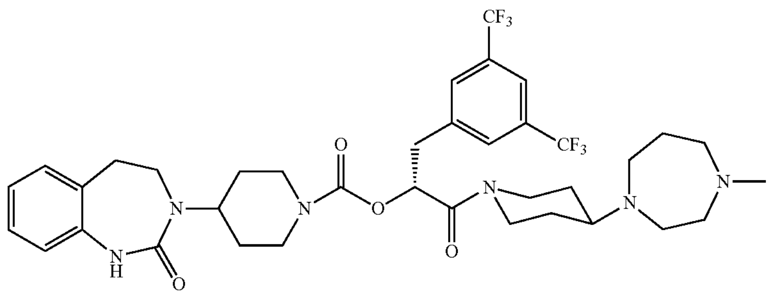 | (R)-1-(3,5-bis-trifluoromethyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (249) | 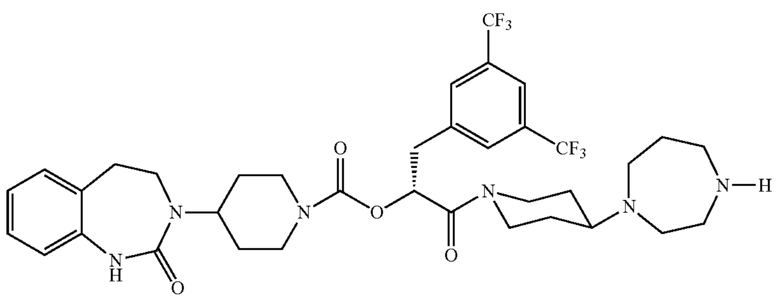 | (R)-1-(3,5-bis-trifluoromethyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (250) | 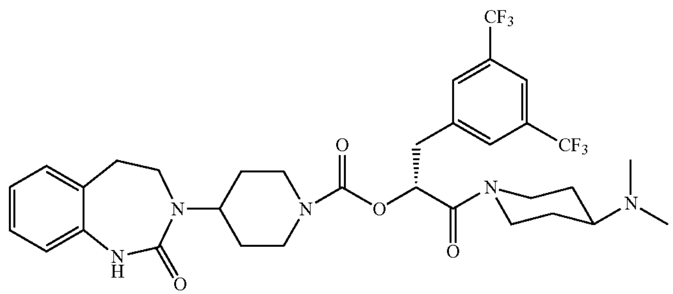 | (R)-1-(3,5-bis-trifluoromethyl-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (251) | 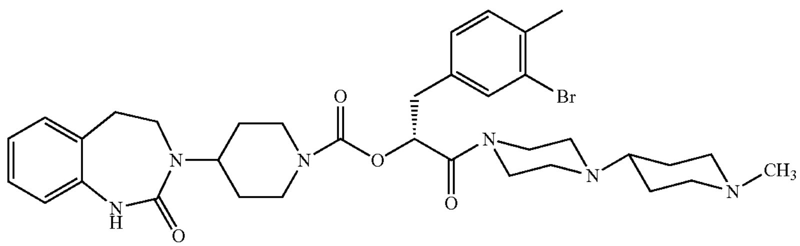 | (R)-1-(3-bromo-4-methyl-benzyl)-2-[4-(1-methyl-piperazin-1-yl)-piperidin-4-yl)-2-oxo-ethyl 4-(2-oxo-1,2,4,5-tetrahydro-1,3-benzodiazepin-3-yl)-piperidine-1-carboxylate |
| (252) | 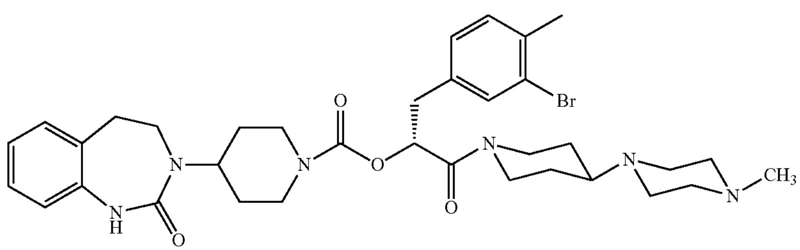 | (R)-1-(3-bromo-4-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (253) | 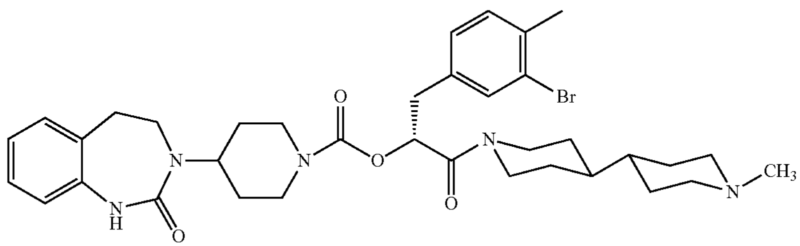 | (R)-1-(3-bromo-4-methyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (254) | 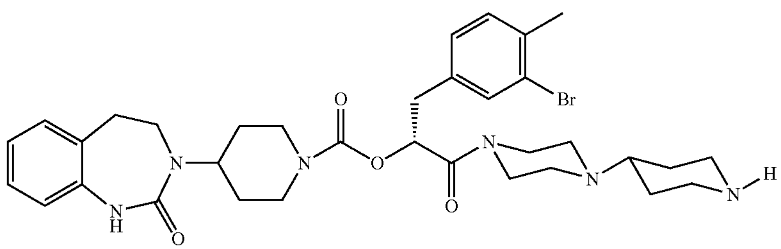 | (R)-1-(3-bromo-4-methyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (255) | 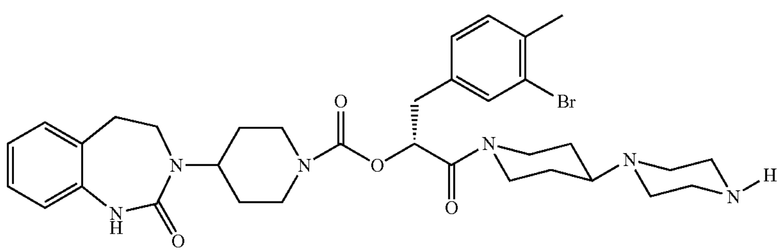 | (R)-1-(3-bromo-4-methyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (256) | 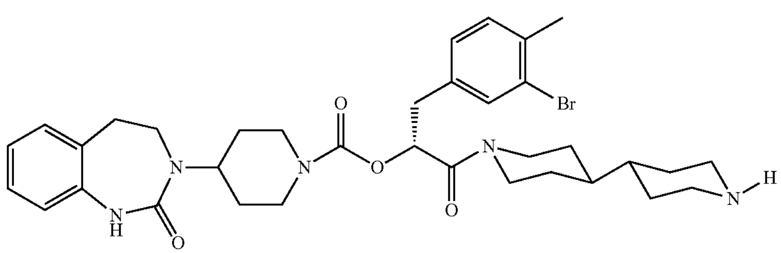 | (R)-2-(4,4'-bipiperidinyl-1-yl)-1-(3-bromo-4-methyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (257) | 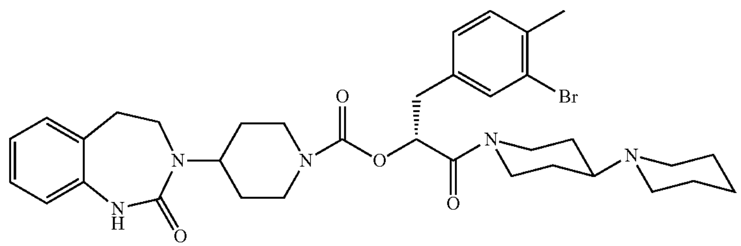 | (R)-2-(1,4'-bipiperidinyl-1'-yl)-1-(3-bromo-4-methyl-benzyl)-2-oxo-ethyl 4-(2-oxo-1,2,4,5-tetrahydro-1,3-benzodiazepin-3-yl)-piperidine-1-carboxylate |
| (258) | 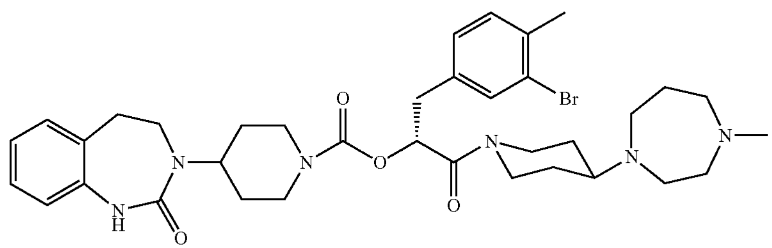 | (R)-1-(3-bromo-4-methyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (259) | 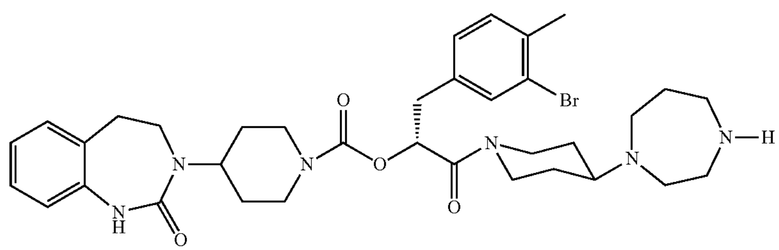 | (R)-1-(3-bromo-4-methyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (260) | 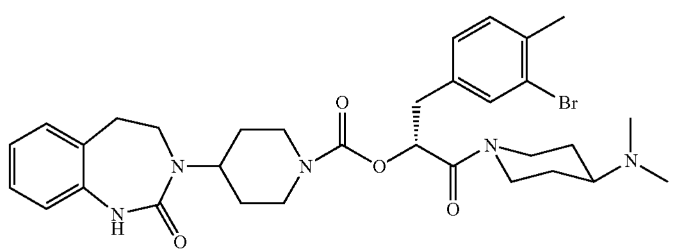 | (R)-1-(3-bromo-4-methyl-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (261) | 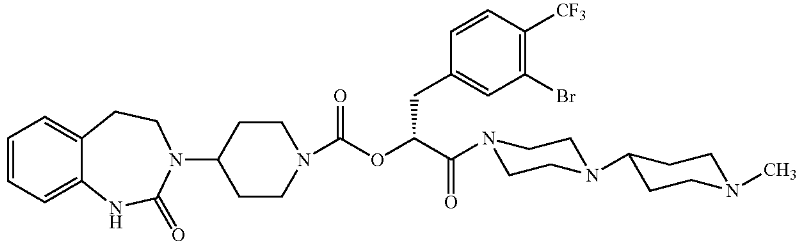 | (R)-1-(3-bromo-4-trifluoromethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (262) | 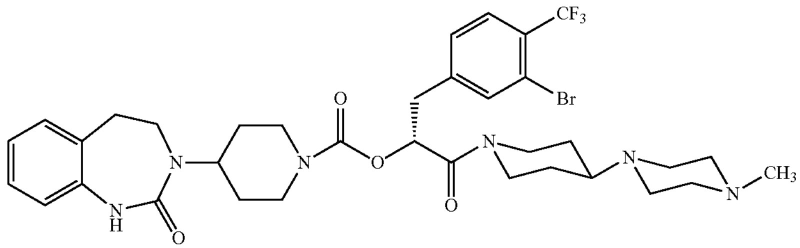 | (R)-1-(3-bromo-4-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (263) | 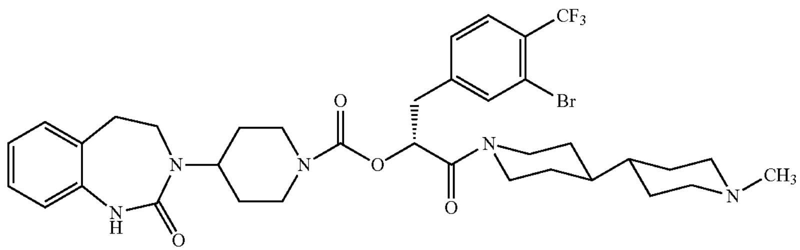 | (R)-1-(3-bromo-4-trifluoromethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (264) | 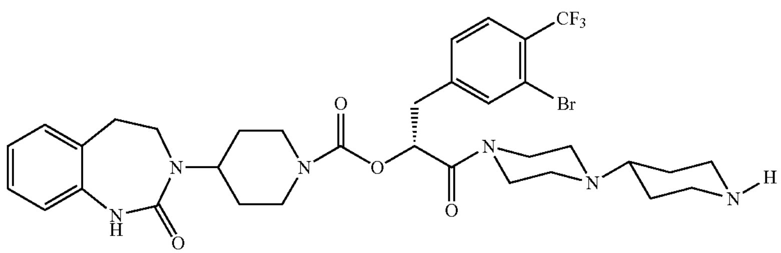 | (R)-1-(3-bromo-4-trifluoromethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (265) | 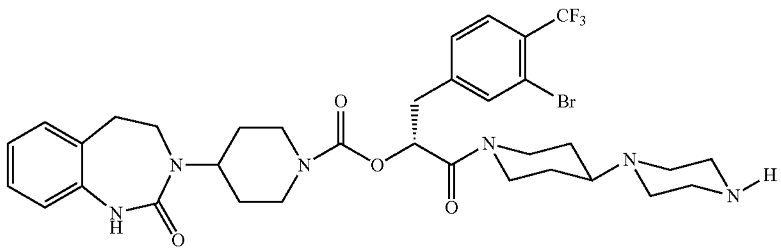 | (R)-1-(3-bromo-4-trifluoromethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (266) | 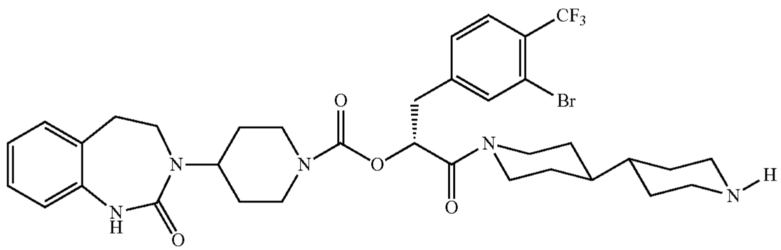 | (R)-2-(4,4'-bipiperidinyl-1'-yl)-1-(3-bromo-4-trifluoromethyl-benzyl)-2-oxo-ethyl 4-(2-oxo-1,2,4,5-tetrahydro-1,3-benzodiazepin-3-yl)-piperidine-1-carboxylate |
| (267) | 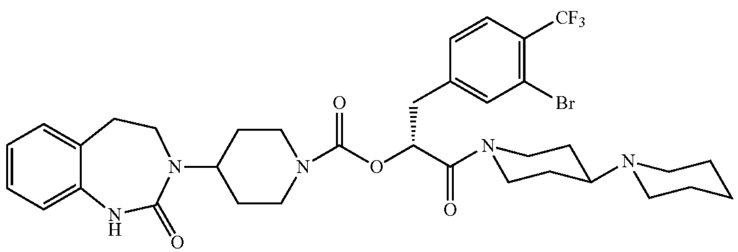 | (R)-2-(1,4'-bipiperidinyl-1'-yl)-1-(3-bromo-4-trifluoromethyl-benzyl)-2-oxo-ethyl 4-(2-oxo-1,2,4,5-tetrahydro-1,3-benzodiazepin-3-yl)-piperidine-1-carboxylate |
| (268) | 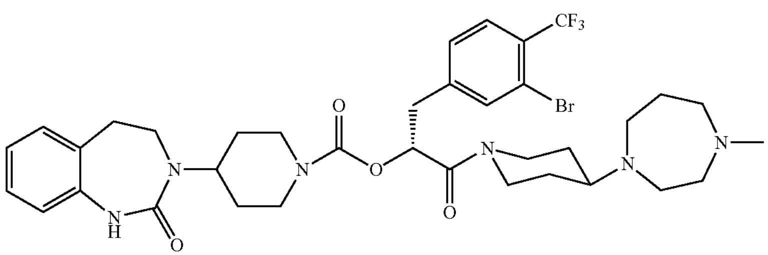 | (R)-1-(3-bromo-4-trifluoromethyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (269) | 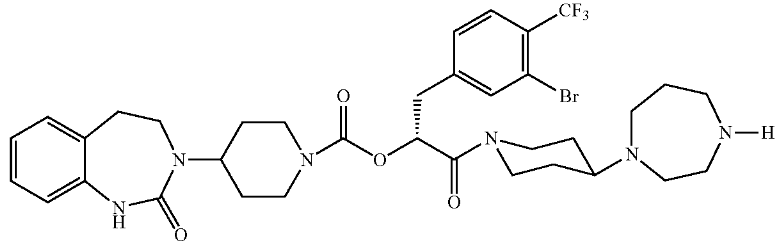 | (R)-1-(3-bromo-4-trifluoromethyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (270) | 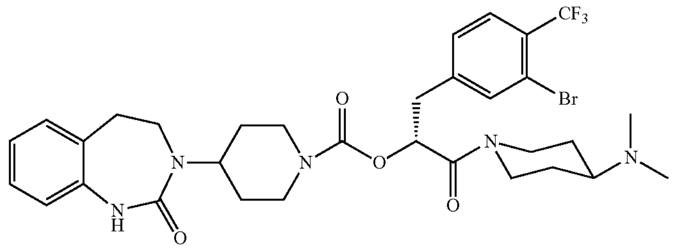 | (R)-1-(3-bromo-4-trifluoromethyl-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (271) | 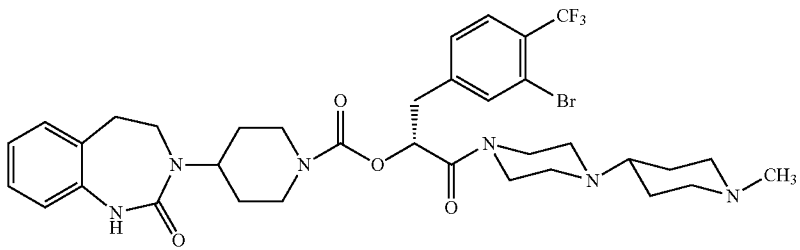 | (R)-1-(3-chloro-4-trifluoromethyl-benzyl)-2-[4-(1-methyl-piperidin-4-yl)piperazin-1-yl]-2-oxo-ethyl 4-(2-oxo-1,2,4,5-tetrahydro-1,3-benzodiazepin-3-yl)-piperidine-1-carboxylate |
| (272) | 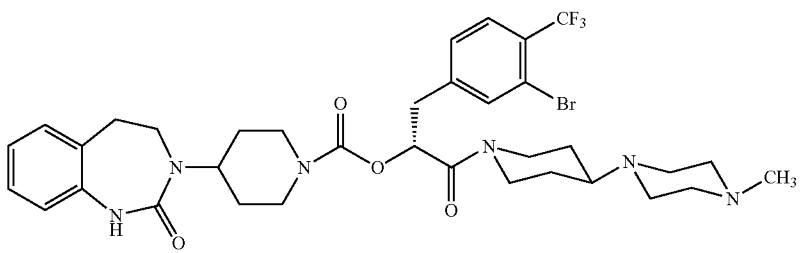 | (R)-1-(3-chloro-4-trifluoromethyl-benzyl)-2-[4-(4-methyl-piperazin-1-yl)piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (273) | 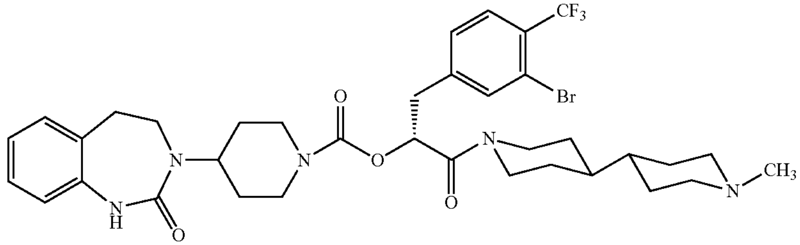 | (R)-1-(3-chloro-4-trifluoromethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (274) | 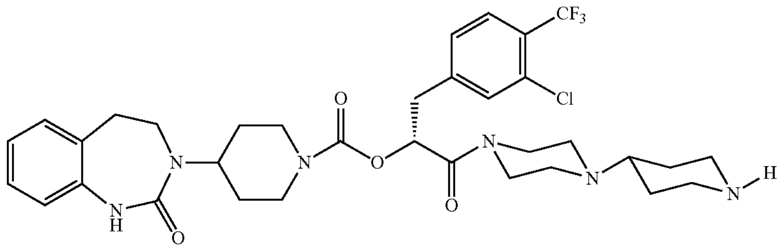 | (R)-1-(3-chloro-4-trifluoromethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (275) | 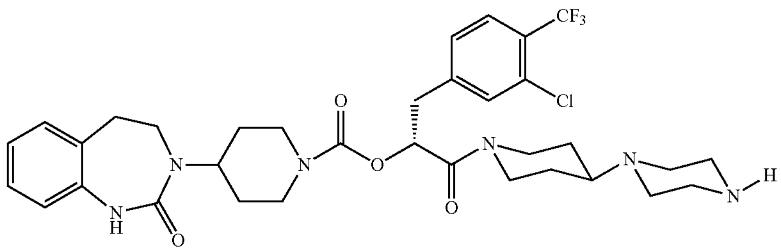 | (R)-1-(3-chloro-4-trifluoromethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (276) | 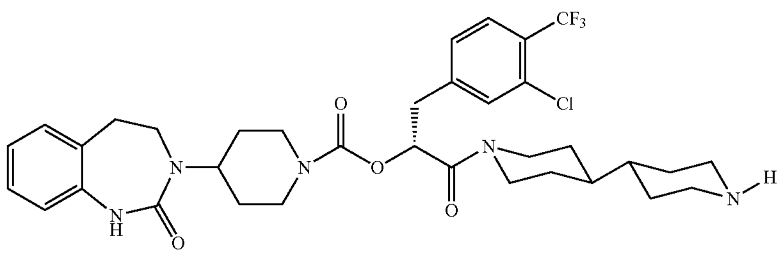 | (R)-2-(4,4'-bipiperidinyl-1-yl)-1-(3-chloro-4-trifluoromethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (277) | 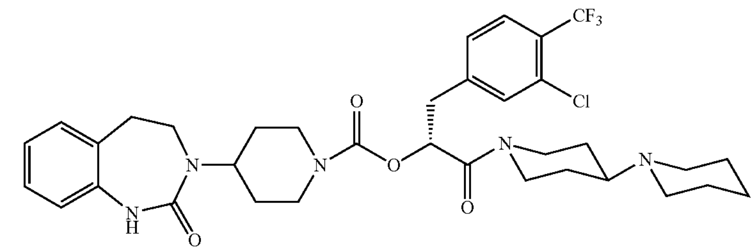 | (R)-2-(1,4'-bipiperidinyl-1'-yl)-1-(3-chloro-4-trifluoromethyl-benzyl)-2-oxo-ethyl 4-(2-oxo-1,2,4,5-tetrahydro-1,3-benzodiazepin-3-yl)-piperidine-1-carboxylate |
| (278) | 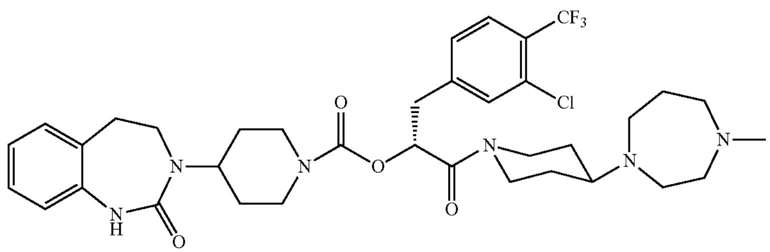 | (R)-1-(3-chloro-4-trifluoromethyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (279) | 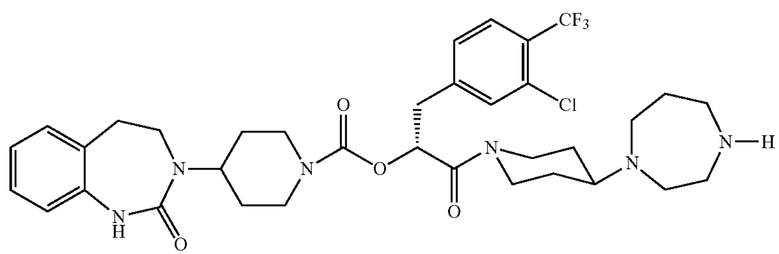 | (R)-1-(3-chloro-4-trifluoromethyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (280) | 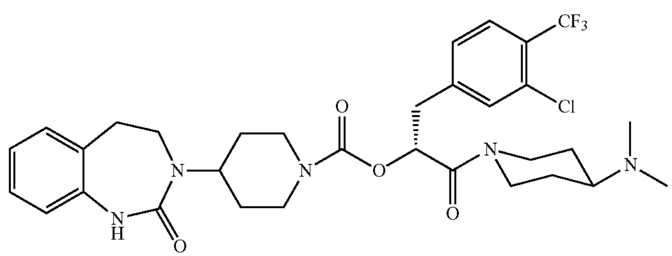 | (R)-1-(3-chloro-4-trifluoromethyl-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (281) | 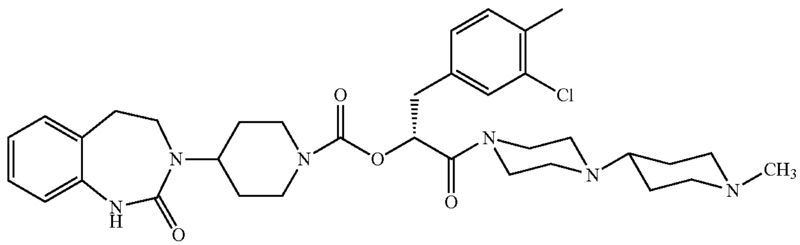 | (R)-1-(3-chloro-4-methyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (282) | 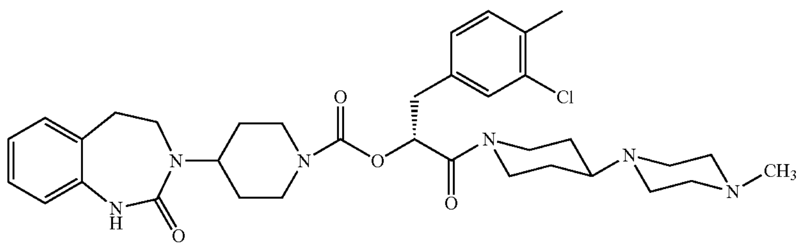 | (R)-1-(3-chloro-4-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (283) | 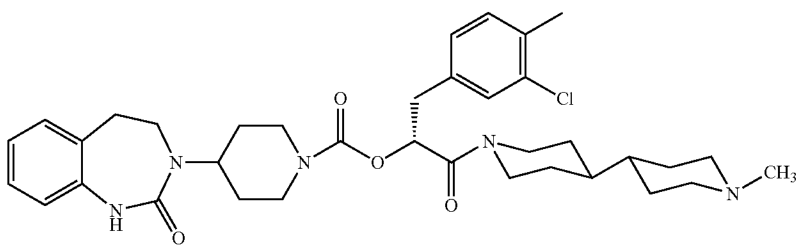 | (R)-1-(3-chloro-4-methyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (284) | 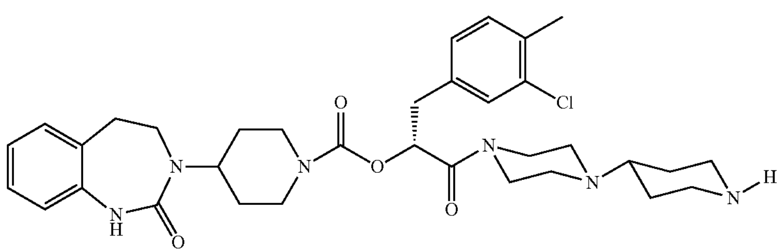 | (R)-1-(3-chloro-4-methyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (285) | 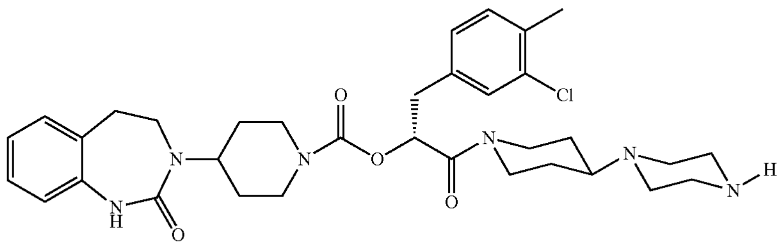 | (R)-1-(3-chloro-4-methyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (286) | 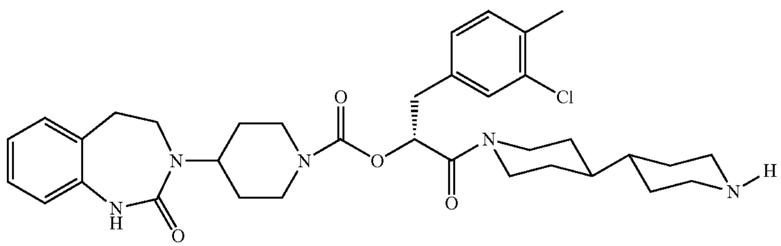 | (R)-2-(4,4'-bipiperidinyl-1-yl)-1-(3-chloro-4-methyl-benzyl)-2-oxo-ethyl 4-(2-oxo-1,2,4,5-tetrahydro-1,3-benzodiazepin-3-yl)-piperidine-1-carboxylate |
| (287) | 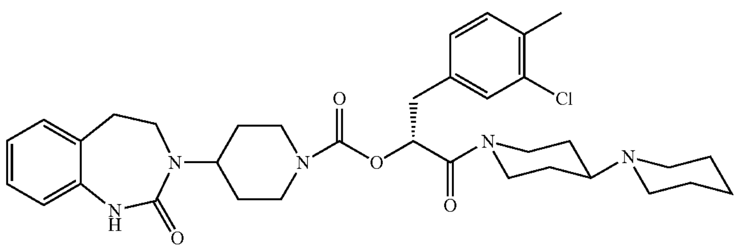 | (R)-2-(1,4'-bipiperidinyl-1'-yl)-1-(3-chloro-4-methyl-benzyl)-2-oxo-ethyl 4-(2-oxo-1,2,4,5-tetrahydro-1,3-benzodiazepin-3-yl)-piperidine-1-carboxylate |
| (288) | 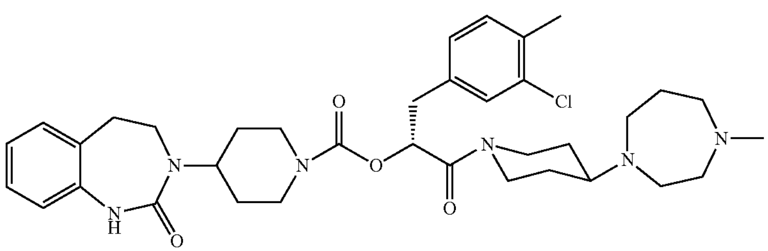 | (R)-1-(3-chloro-4-methyl-benzyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (289) | 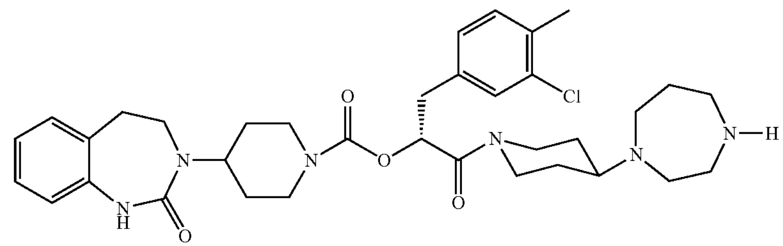 | (R)-1-(3-chloro-4-methyl-benzyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (290) | 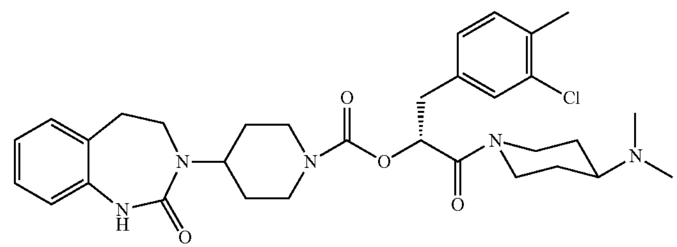 | (R)-1-(3-chloro-4-methyl-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (291) | 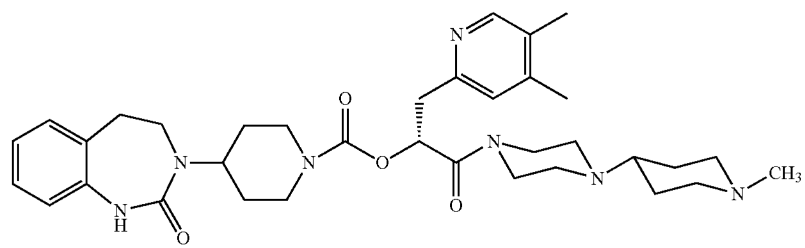 | (R)-1-(4,5-dimethyl-pyridin-2-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (292) | 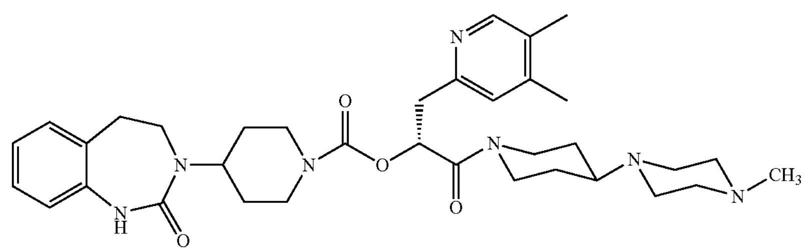 | (R)-1-(4,5-dimethyl-pyridin-2-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (293) | 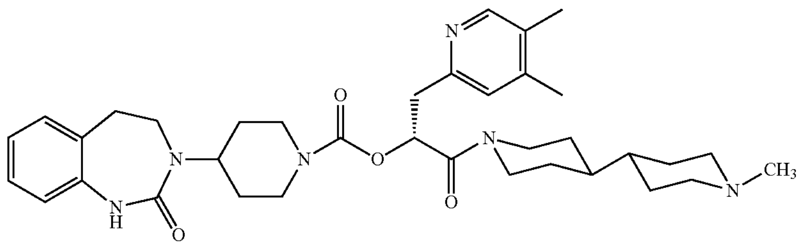 | (R)-1-(4,5-dimethyl-pyridin-2-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (294) | 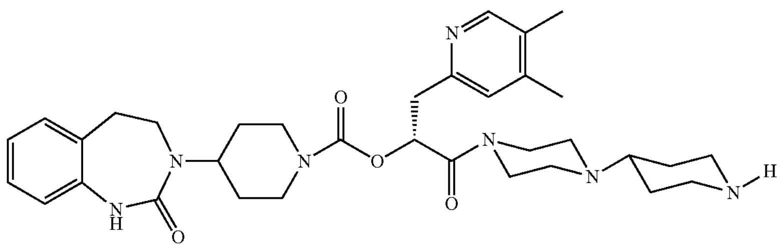 | (R)-1-(4,5-dimethyl-pyridin-2-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (295) | 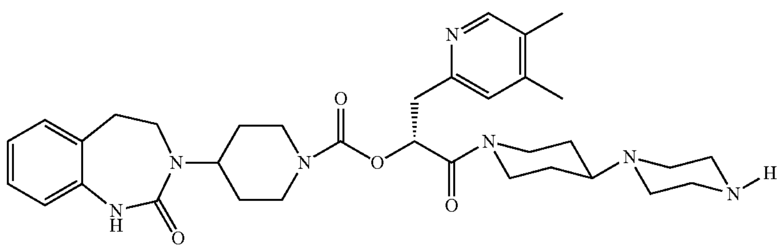 | (R)-1-(4,5-dimethyl-pyridin-2-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (296) | 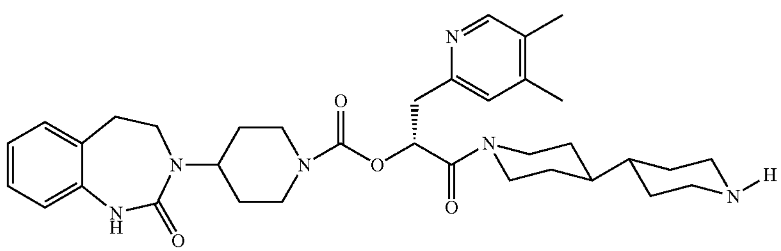 | (R)-2-(4,4'-bipiperidinyl-1-yl)-1-(4,5-dimethyl-pyridin-2-ylmethyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (297) | 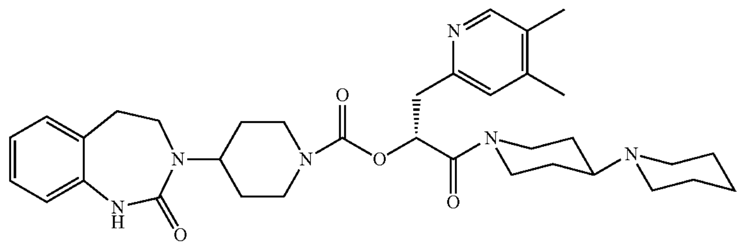 | (R)-2-(1,4'-bipiperidinyl-1'-yl)-1-(4,5-dimethyl-pyridin-2-ylmethyl)-2-oxo-ethyl 4-(2-oxo-1,2,4,5-tetrahydro-1,3-benzodiazepin-3-yl)-piperidine-1-carboxylate |
| (298) | 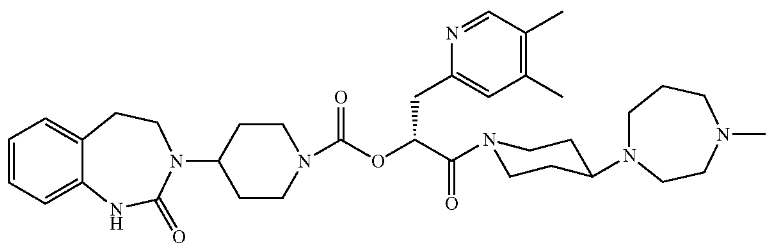 | (R)-1-(4,5-dimethyl-pyridin-2-ylmethyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (299) | 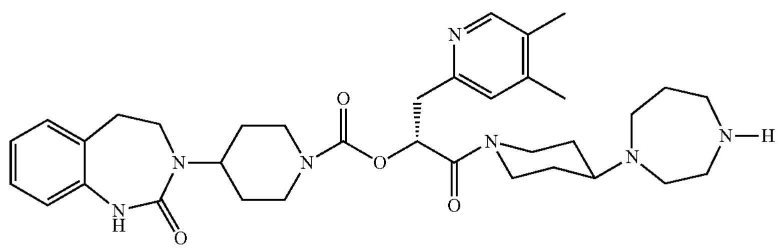 | (R)-1-(4,5-dimethyl-pyridin-2-ylmethyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (300) | 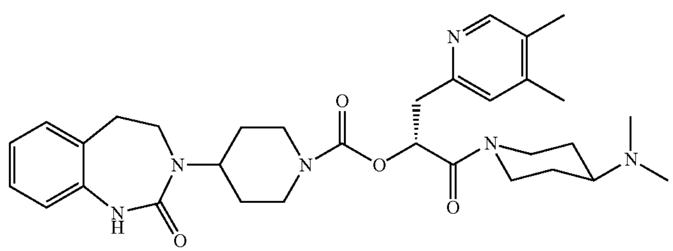 | (R)-2-(4-dimethylamino-piperidin-1-yl)-1-(4,5-dimethyl-pyridin-2-ylmethyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (301) | 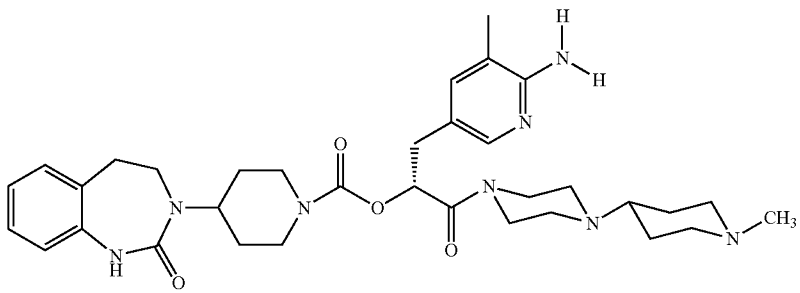 | (R)-1-(6-amino-5-methyl-pyridin-3-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (302) | 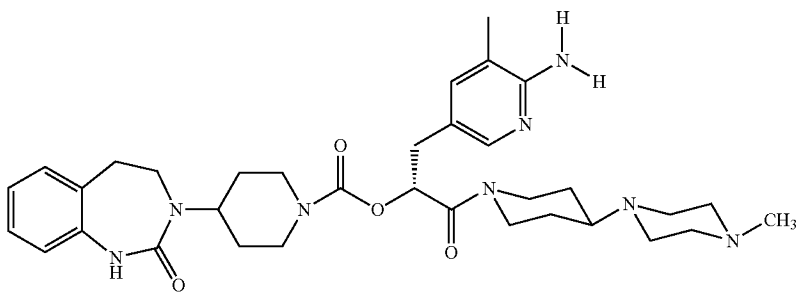 | (R)-1-(6-amino-5-methyl-pyridin-3-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (303) | 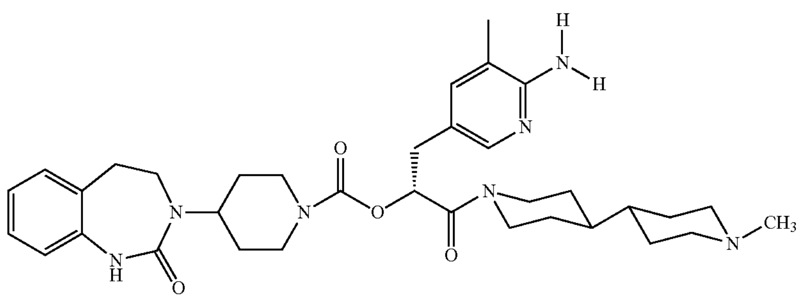 | (R)-1-(6-amino-5-methyl-pyridin-3-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (304) | 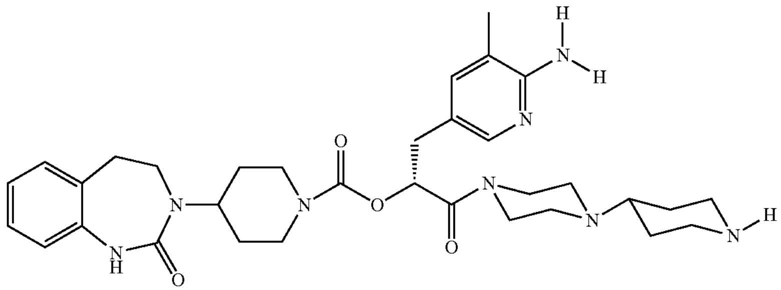 | (R)-1-(6-amino-5-methyl-pyridin-3-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (305) | 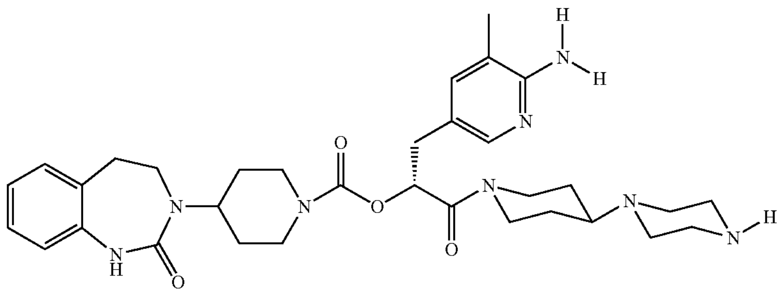 | (R)-1-(6-amino-5-methyl-pyridin-3-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (306) | 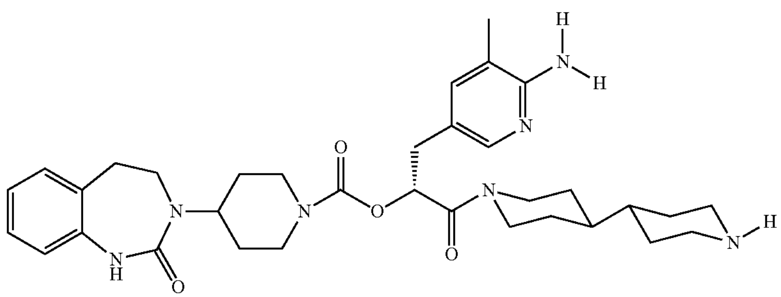 | (R)-1-(6-amino-5-methyl-pyridin-3-ylmethyl)-2-(4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (307) | 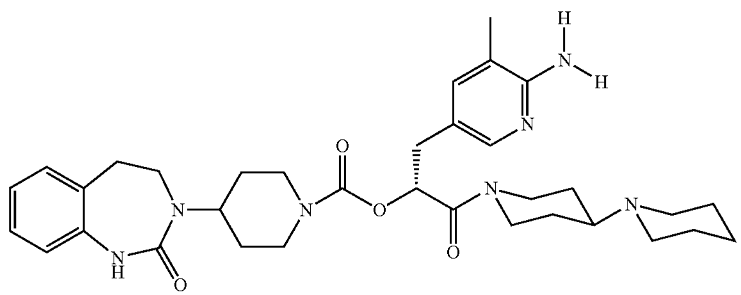 | (R)-1-(6-amino-5-methyl-pyridin-3-ylmethyl)-2-(1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (308) | 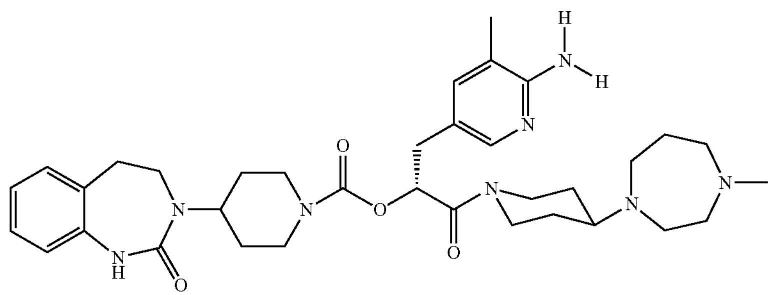 | (R)-1-(6-amino-5-methyl-pyridin-3-ylmethyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (309) | 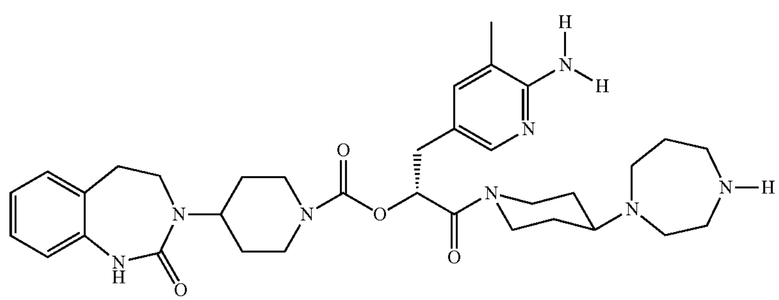 | (R)-1-(6-amino-5-methyl-pyridin-3-ylmethyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (310) | 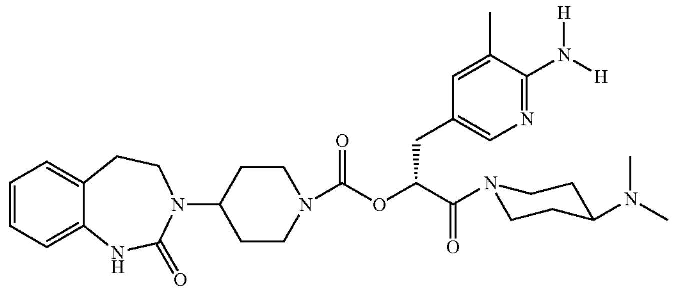 | (R)-1-(6-amino-5-methyl-pyridin-3-ylmethyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (311) | 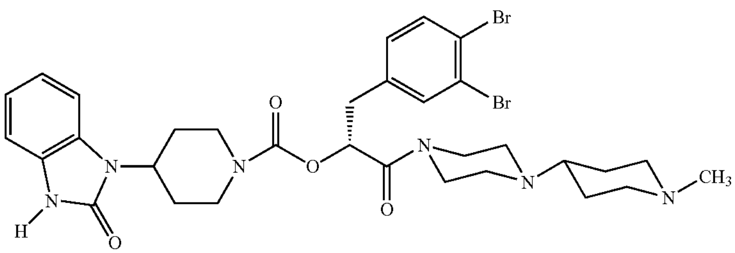 | (R)-1-(3,4-dibromo-benzyl)-2-[4-(1-methyl-piperidin-4-yl)piperazin-1-yl]-2-oxo-ethyl 4-(2-oxo-2,3-dihydro-benzimidazole-1-yl)-piperidine-1-carboxylate |
| (312) | 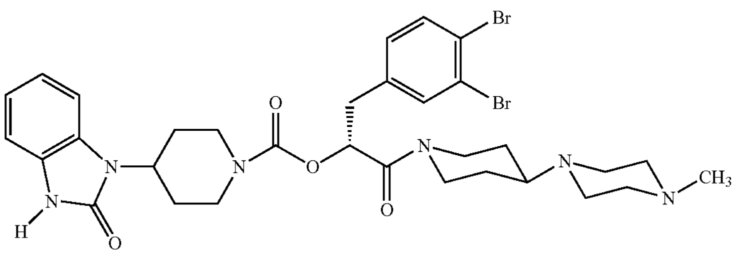 | (R)-1-(3,4-dibromo-benzyl)-2-[4-(4-methyl-piperazin-1-yl)piperidin-1-yl]-2-oxo-ethyl 4-(2-oxo-2,3-dihydro-benzimidazole-1-yl)-piperidine-1-carboxylate |

-continued

| No. | Structure | Name |
|---|---|---|
| (313) | 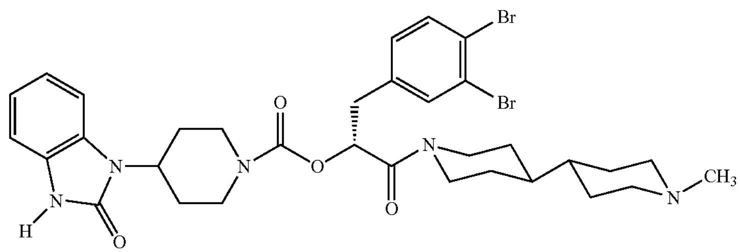 | (R)-1-(3,4-dibromo-benzyl)-2-(1'-methyl-4,4'-bipiperidinyl-1-yl)-2-oxo-ethyl 4-(2-oxo-2,3-dihydro-benzimidazole-1-yl)-piperidine-1-carboxylate |
| (314) | 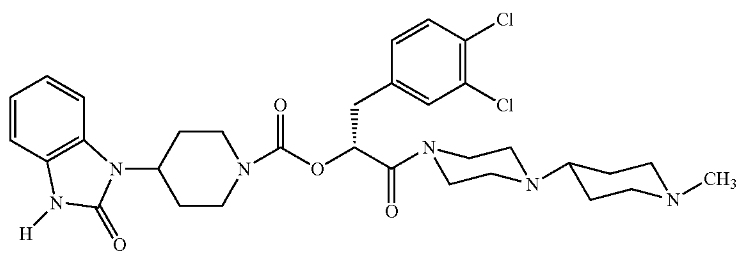 | (R)-1-(3,4-dichloro-benzyl)-2-[4-(1-methyl-piperidin-4-yl)-piperazin-1-yl]-2-oxo-ethyl 4-(2-oxo-2,3-dihydro-benzimidazole-1-yl)-piperidine-1-carboxylate |
| (315) | 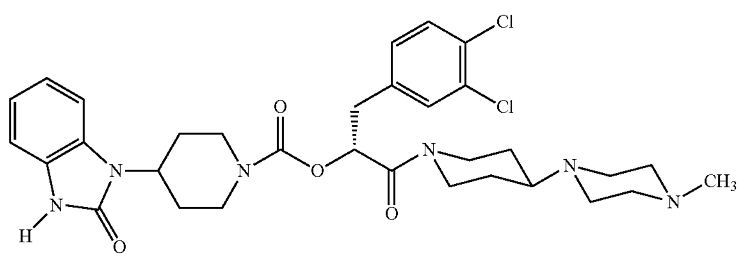 | (R)-1-(3,4-dichloro-benzyl)-2-[4-(4-methyl-piperazin-1-yl)-piperidin-1-yl]-2-oxo-ethyl 4-(2-oxo-2,3-dihydro-benzimidazole-1-yl)-piperidine-1-carboxylate |
| (316) | 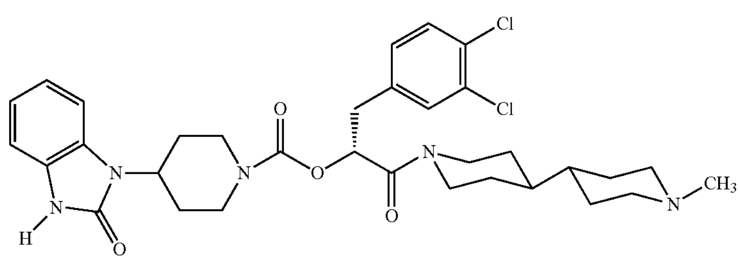 | (R)-1-(3,4-dichloro-benzyl)-2-(1'-methyl-4,4'-bipiperidinyl-1-yl)-2-oxo-ethyl 4-(2-oxo-2,3-dihydro-benzimidazole-1-yl)-piperidine-1-carboxylate |

-continued

| No. | Structure | Name |
|---|---|---|
| (317) | 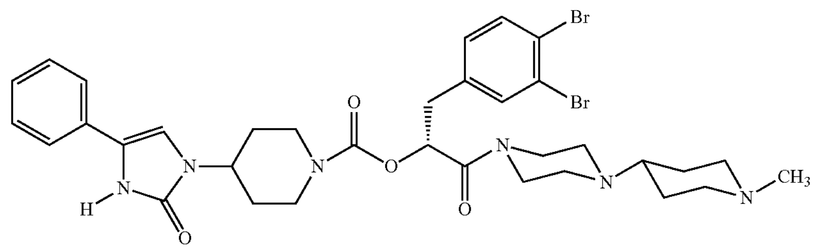 | (R)-1-(3,4-dibromo-benzyl)-2-[4-(1-methyl-piperidin-4-yl)-piperazin-1-yl]-2-oxo-ethyl 4-(2-oxo-4-phenyl-2,3-dihydro-imidazol-1-yl)-piperidine-1-carboxylate |
| (318) | 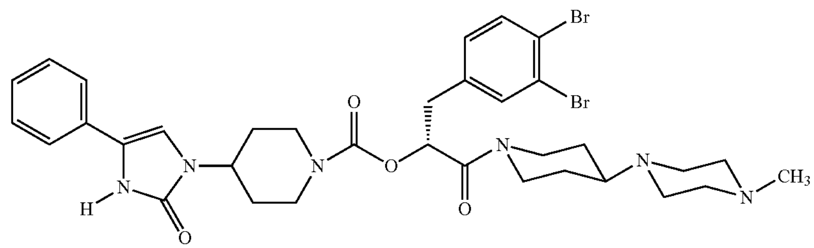 | (R)-1-(3,4-dibromo-benzyl)-2-[4-(4-methyl-piperazin-1-yl)-piperidin-1-yl]-2-oxo-ethyl 4-(2-oxo-4-phenyl-2,3-dihydro-imidazol-1-yl)-piperidine-1-carboxylate |
| (319) | 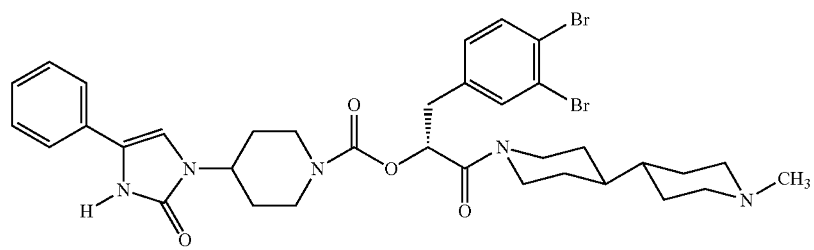 | (R)-1-(3,4-dibromo-benzyl)-2-(1'-methyl-[4,4']bipiperidinyl-1-yl)-2-oxo-ethyl 4-(2-oxo-4-phenyl-2,3-dihydro-imidazol-1-yl)-piperidine-1-carboxylate |
| (320) | 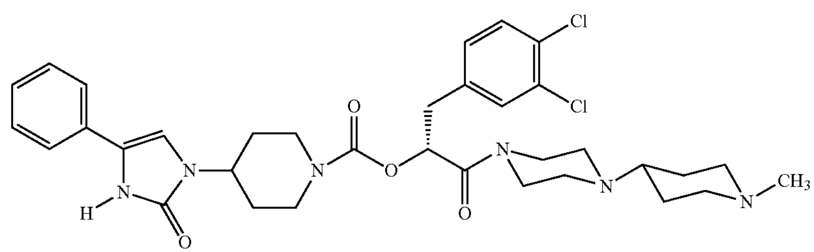 | (R)-1-(3,4-dichloro-benzyl)-2-[4-(1-methyl-piperidin-4-yl)-piperazin-1-yl]-2-oxo-ethyl 4-(2-oxo-4-phenyl-2,3-dihydro-imidazol-1-yl)-piperidine-1-carboxylate |

| No. | Structure | Name |
|---|---|---|
| (321) | 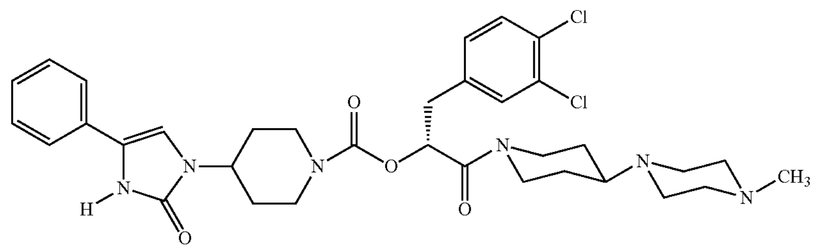 | (R)-1-(3,4-dichloro-benzyl)-2-[4-(4-methyl-piperazin-1-yl)-piperidin-1-yl]-2-oxo-ethyl 4-(2-oxo-4-phenyl-2,3-dihydro-imidazol-1-yl)-piperidine-1-carboxylate |
| (322) | 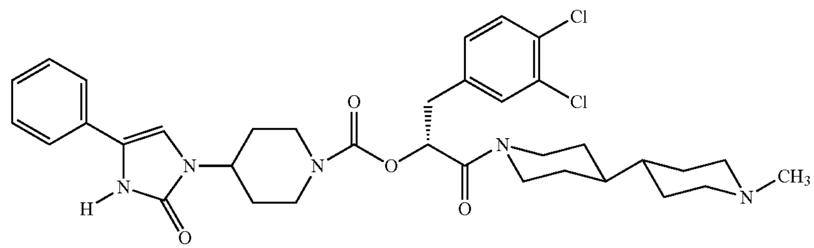 | (R)-1-(3,4-dichloro-benzyl)-2-(1'-methyl-[4,4']bipiperidinyl-1-yl)-2-oxo-ethyl 4-(2-oxo-4-phenyl-2,3-dihydro-imidazol-1-yl)-piperidine-1-carboxylate |
| (323) | 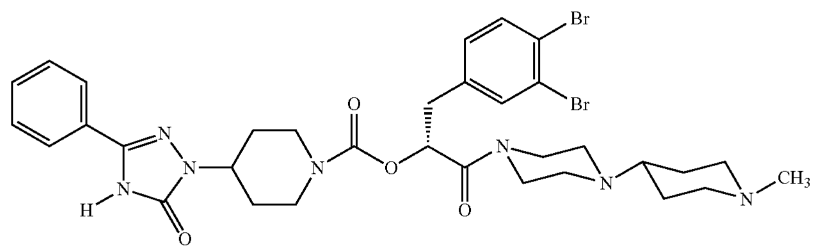 | (R)-1-(3,4-dibromo-benzyl)-2-[4-(1-methyl-piperidin-4-yl)-piperazin-1-yl]-2-oxo-ethyl 4-(5-oxo-3-phenyl-4,5-dihydro-1,2,4-triazol-1-yl)-piperidine-1-carboxylate |
| (324) | 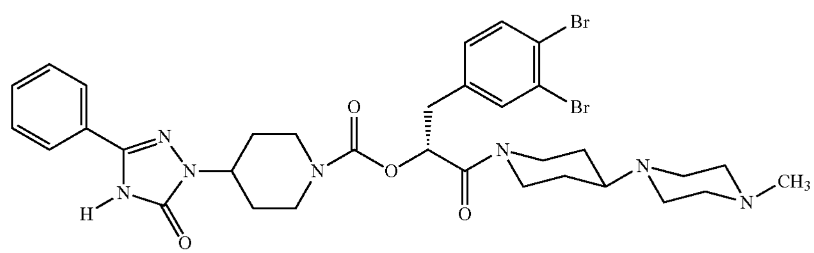 | (R)-1-(3,4-dibromo-benzyl)-2-[4-(4-methyl-piperazin-1-yl)-piperidin-1-yl]-2-oxo-ethyl 4-(5-oxo-3-phenyl-4,5-dihydro-1,2,4-triazol-1-yl)-piperidine-1-carboxylate |

| No. | Structure | Name |
|---|---|---|
| (325) | 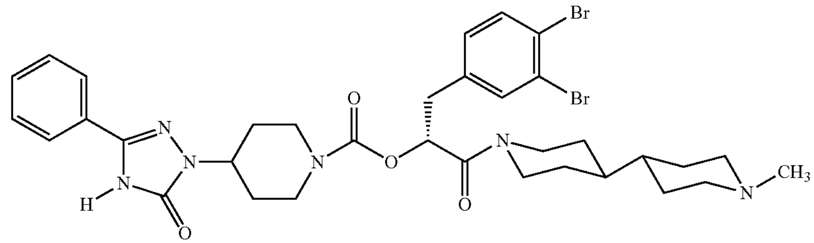 | (R)-1-(3,4-dibromo-benzyl)-2-(1'-methyl-4,4'-bipiperidinyl-1-yl)-2-oxo-ethyl 4-(5-oxo-3-phenyl-4,5-dihydro-1,2,4-triazol-1-yl)-piperidine-1-carboxylate |
| (326) | 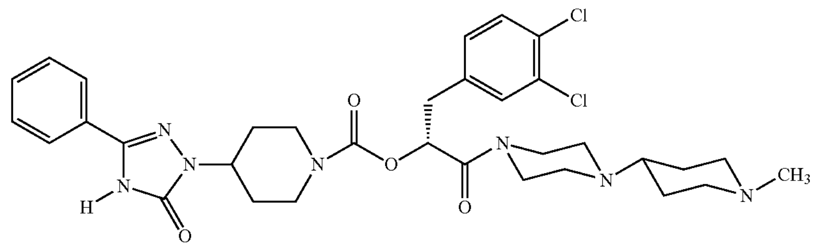 | (R)-1-(3,4-dichloro-benzyl)-2-[4-(1-methyl-piperidin-4-yl)-piperazin-1-yl]-2-oxo-ethyl 4-(5-oxo-3-phenyl-4,5-dihydro-1,2,4-triazol-1-yl)-piperidine-1-carboxylate |
| (327) | 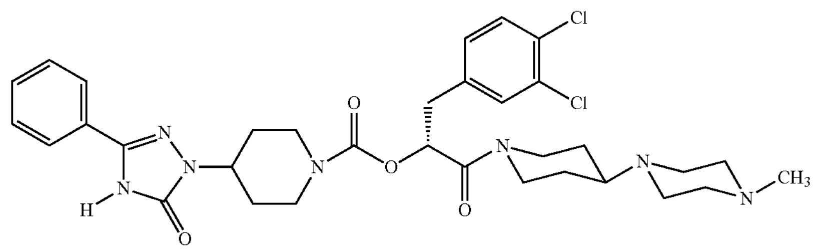 | (R)-1-(3,4-dichloro-benzyl)-2-[4-(4-methyl-piperazin-1-yl)-piperidin-1-yl]-2-oxo-ethyl 4-(5-oxo-3-phenyl-4,5-dihydro-1,2,4-triazol-1-yl)-piperidine-1-carboxylate |
| (328) | 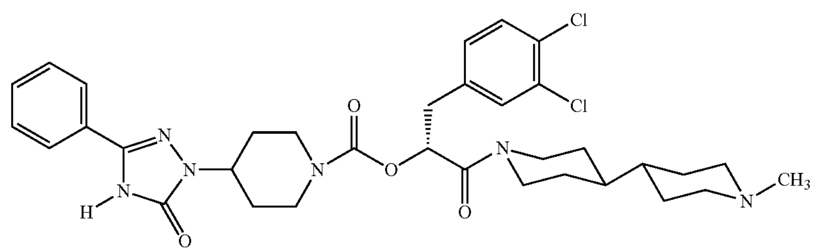 | (R)-1-(3,4-dichloro-benzyl)-2-(1'-methyl-4,4'-bipiperidinyl-1-yl)-2-oxo-ethyl 4-(5-oxo-3-phenyl-4,5-dihydro-1,2,4-triazol-1-yl)-piperidine-1-carboxylate |

-continued

| No. | Structure | Name |
|---|---|---|
| (329) | 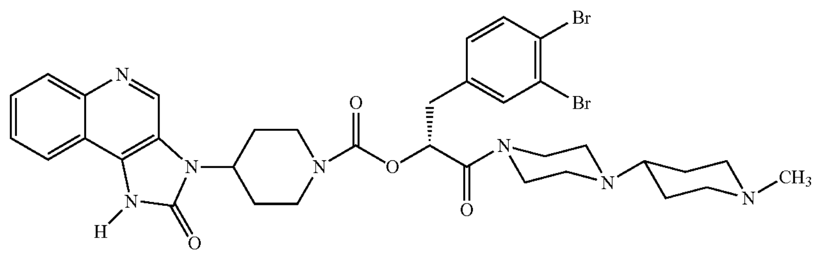 | (R)-1-(3,4-dibromo-benzyl)-2-[4-(1-methyl-piperidin-4-yl)-piperazin-1-yl]-2-oxo-ethyl 4-(2-oxo-1,2-dihydro-imidazo[4,5-c]quinolin-3-yl)-piperidine-1-carboxylate |
| (330) | 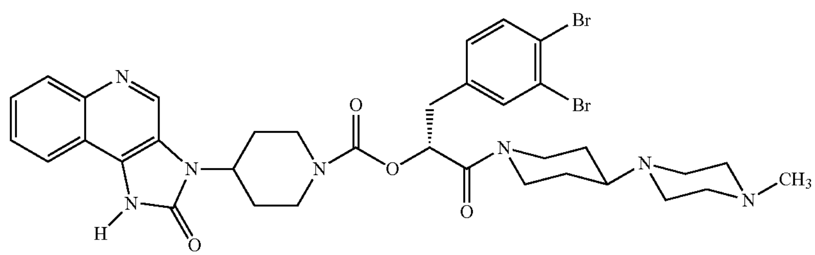 | (R)-1-(3,4-dibromo-benzyl)-2-[4-(4-methyl-piperazin-1-yl)-piperazin-1-yl]-2-oxo-ethyl 4-(2-oxo-1,2-dihydro-imidazo[4,5-c]quinolin-3-yl)-piperidine-1-carboxylate |
| (331) | 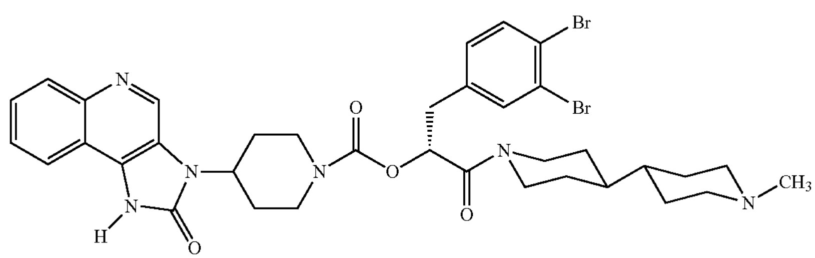 | (R)-1-(3,4-dibromo-benzyl)-2-(1'-methyl-[4,4']bipiperidinyl-1-yl)-2-oxo-ethyl 4-(2-oxo-1,2-dihydro-imidazo[4,5-c]quinolin-3-yl)-piperidine-1-carboxylate |
| (332) | 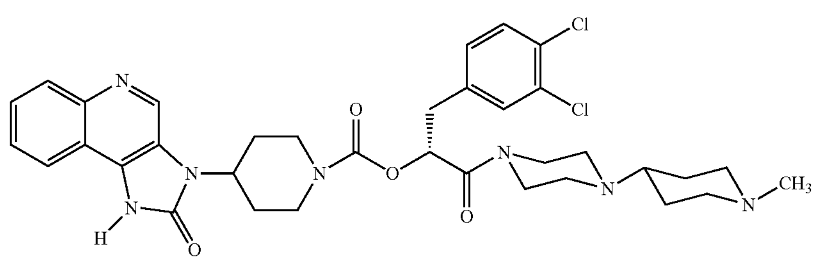 | (R)-1-(3,4-dichloro-benzyl)-2-[4-(1-methyl-piperidin-4-yl)-piperazin-1-yl]-2-oxo-ethyl 4-(2-oxo-1,2-dihydro-imidazo[4,5-c]quinolin-3-yl)-piperidine-1-carboxylate |

| No. | Structure | Name |
|---|---|---|
| (333) | 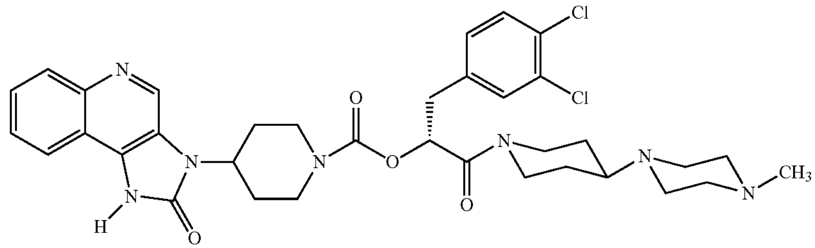 | (R)-1-(3,4-dichloro-benzyl)-2-[4-(4-methyl-piperazin-1-yl)-piperidin-1-yl]-2-oxo-ethyl 4-(2-oxo-1,2-dihydro-imidazo[4,5-c]quinolin-3-yl)-piperidine-1-carboxylate |
| (334) | 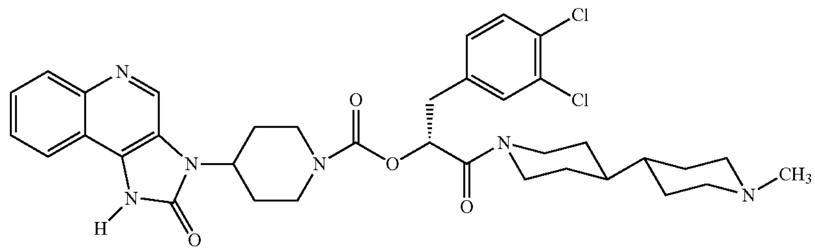 | (R)-1-(3,4-dichloro-benzyl)-2-(1'-methyl-[4,4']bipiperidinyl-1-yl)-2-oxo-ethyl 4-(2-oxo-1,2-dihydro-imidazo[4,5-c]quinolin-3-yl)-piperidine-1-carboxylate |
| (335) | 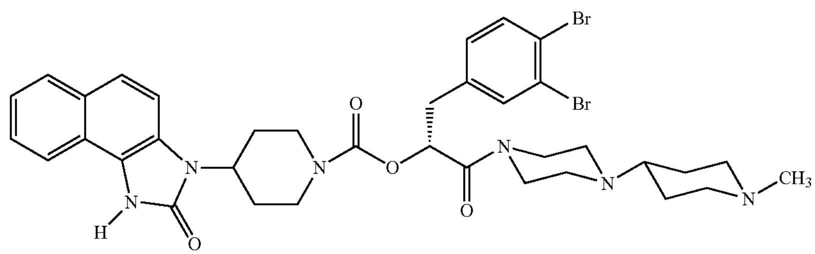 | (R)-1-(3,4-dibromo-benzyl)-2-[4-(1-methyl-piperidin-4-yl)-piperazin-1-yl]-2-oxo-ethyl 4-(2-oxo-1,2-dihydro-naphth[1,2-d]-imidazol-3-yl)-piperidine-1-carboxylate |
| (336) | 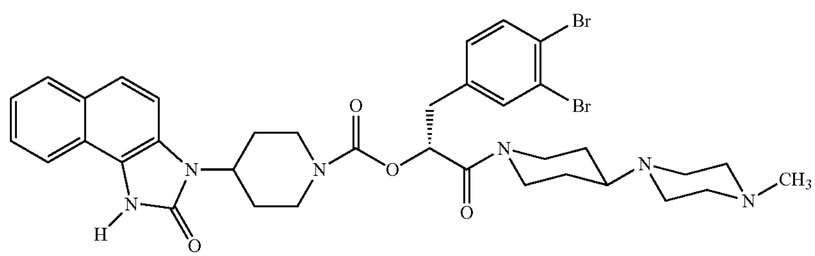 | (R)-1-(3,4-dibromo-benzyl)-2-[4-(4-methyl-piperazin-1-yl)-piperidin-1-yl]-2-oxo-ethyl 4-(2-oxo-1,2-dihydro-naphth[1,2-d]-imidazol-3-yl)-piperidine-1-carboxylate |

| No. | Structure | Name |
|---|---|---|
| (337) | 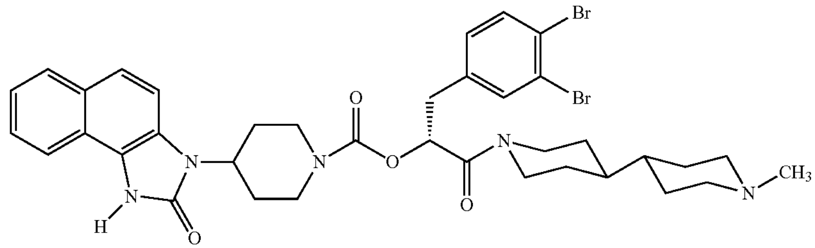 | (R)-1-(3,4-dibromo-benzyl)-2-(1'-methyl-4,4'-bipiperidinyl-1-yl)-2-oxo-ethyl 4-(2-oxo-1,2-dihydro-naphth[1,2-d]imidazol-3-yl)-piperidine-1-carboxylate |
| (338) | 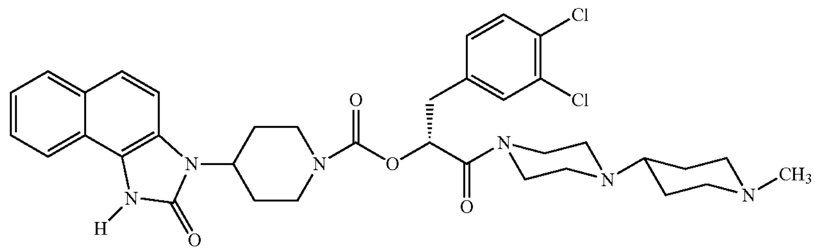 | (R)-1-(3,4-dichloro-benzyl)-2-[4-(1'-methyl-piperidin-4-yl)-piperazin-1-yl]-2-oxo-ethyl 4-(2-oxo-1,2-dihydro-naphth[1,2-d]imidazol-3-yl)-piperidine-1-carboxylate |
| (339) | 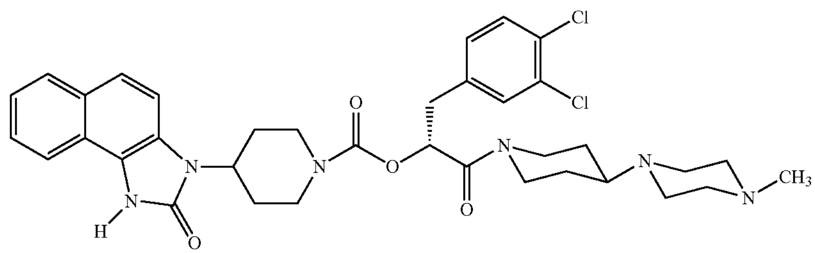 | (R)-1-(3,4-dichloro-benzyl)-2-[4-(4-methyl-piperazin-1-yl)-piperidin-1-yl]-2-oxo-ethyl 4-(2-oxo-1,2-dihydro-naphth[1,2-d]imidazol-3-yl)-piperidine-1-carboxylate |
| (340) | 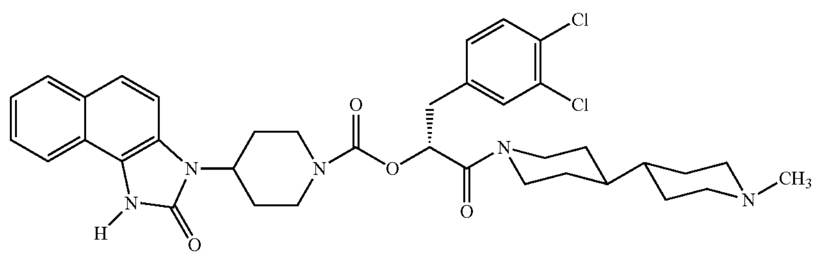 | (R)-1-(3,4-dichloro-benzyl)-2-(1'-methyl-4,4'-bipiperidinyl-1-yl)-2-oxo-ethyl 4-(2-oxo-1,2-dihydro-naphth[1,2-d]imidazol-3-yl)-piperidine-1-carboxylate |

| No. | Structure | Name |
|---|---|---|
| (341) | 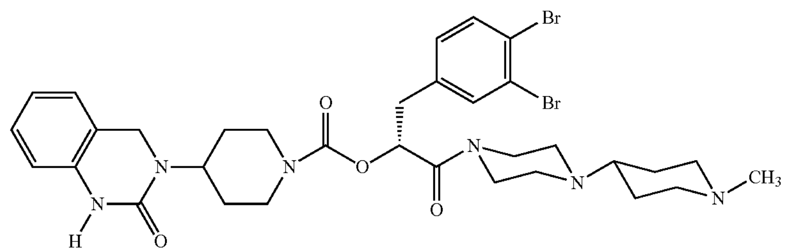 | (R)-1-(3,4-dibromo-benzyl)-2-[4-(1-methyl-piperidin-4-yl)-piperazin-1-yl]-2-oxo-ethyl 4-(2-oxo-1,4-dihydro-2H-quinazolin-3-yl)-piperidine-1-carboxylate |
| (342) | 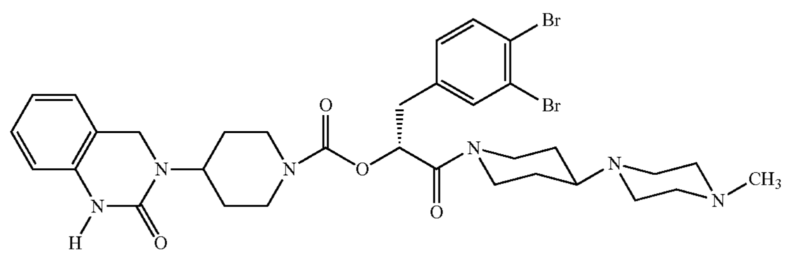 | (R)-1-(3,4-dibromo-benzyl)-2-[4-(4-methyl-piperazin-1-yl)-piperidin-1-yl]-2-oxo-ethyl 4-(2-oxo-1,4-dihydro-2H-quinazolin-3-yl)-piperidine-1-carboxylate |
| (343) | 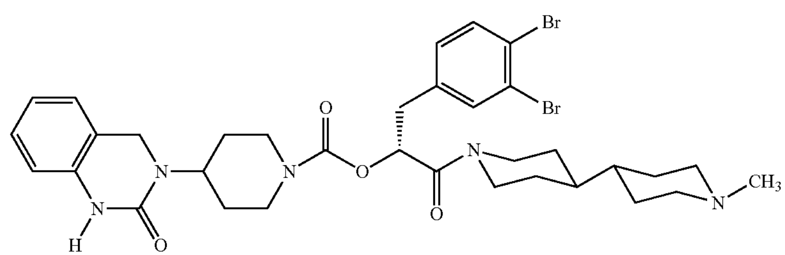 | (R)-1-(3,4-dibromo-benzyl)-2-(1'-methyl-[4,4']bipiperidinyl-1-yl)-2-oxo-ethyl 4-(2-oxo-1,4-dihydro-2H-quinazolin-3-yl)-piperidine-1-carboxylate |
| (344) | 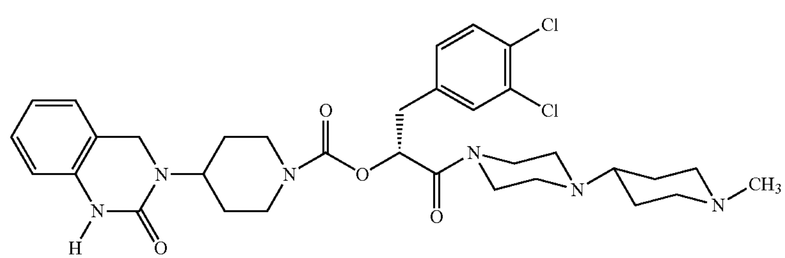 | (R)-1-(3,4-dichloro-benzyl)-2-[4-(1-methyl-piperidin-4-yl)-piperazin-1-yl]-2-oxo-ethyl 4-(2-oxo-1,4-dihydro-2H-quinazolin-3-yl)-piperidine-1-carboxylate |

| No. | Structure | Name |
|---|---|---|
| (345) | 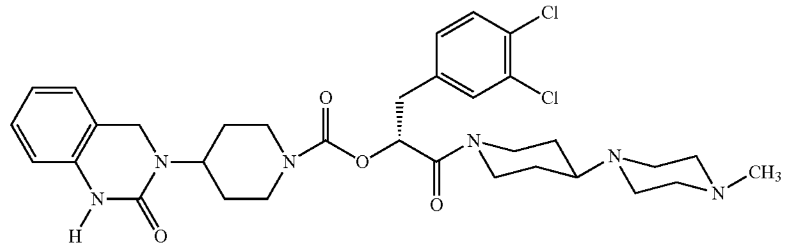 | (R)-1-(3,4-dichloro-benzyl)-2-[4-(4-methyl-piperazin-1-yl)-piperidin-1-yl]-2-oxo-ethyl 4-(2-oxo-1,4-dihydro-2H-quinazolin-3-yl)-piperidine-1-carboxylate |
| (346) | 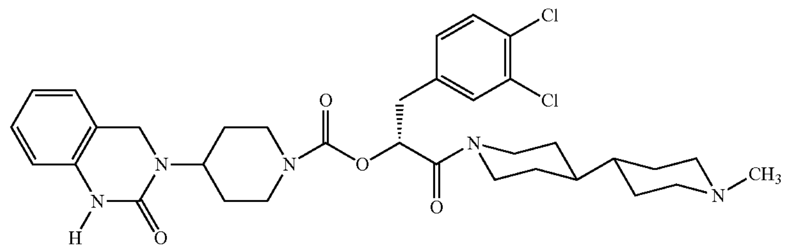 | (R)-1-(3,4-dichloro-benzyl)-2-(1'-methyl-[4,4']bipiperidinyl-1-yl)-2-oxo-ethyl 4-(2-oxo-1,4-dihydro-2H-quinazolin-3-yl)-piperidine-1-carboxylate |
| (347) | 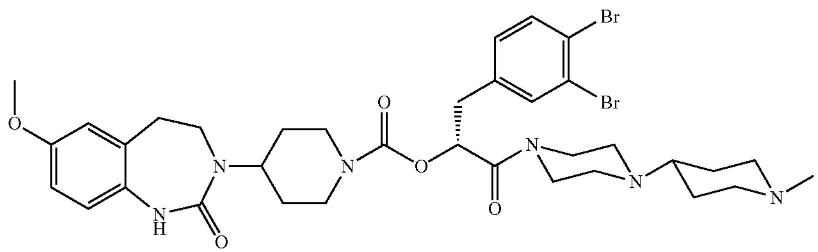 | (R)-1-(3,4-dibromo-benzyl)-2-[4-(1-methyl-piperidin-4-yl)-piperazin-1-yl]-2-oxo-ethyl 4-(7-methoxy-2-oxo-1,2,4,5-tetrahydro-1,3-benzodiazepin-3-yl)-piperidine-1-carboxylate |
| (348) | 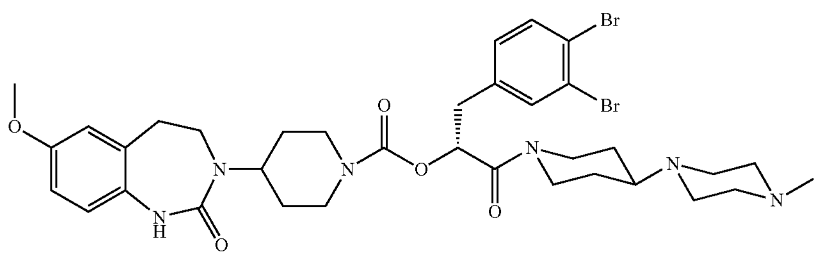 | (R)-1-(3,4-dibromo-benzyl)-2-[4-(4-methyl-piperazin-1-yl)-piperidin-1-yl]-2-oxo-ethyl 4-(7-methoxy-2-oxo-1,2,4,5-tetrahydro-1,3-benzodiazepin-3-yl)-piperidine-1-carboxylate |

| No. | Structure | Name |
|---|---|---|
| (349) | 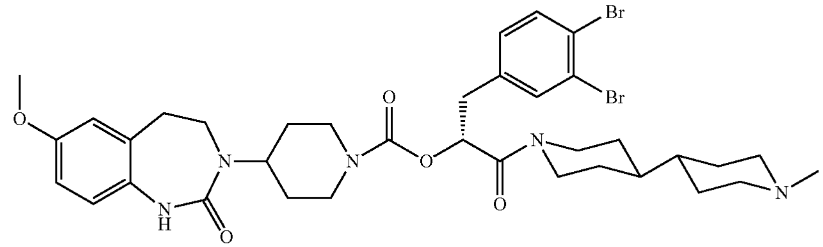 | (R)-1-(3,4-dibromo-benzyl)-2-(1'-methyl-4,4'-bipiperidinyl-1-yl)-2-oxo-ethyl 4-(7-methoxy-2-oxo-1,2,4,5-tetrahydro-1,3-benzodiazepin-3-yl)-piperidine-1-carboxylate |
| (350) | 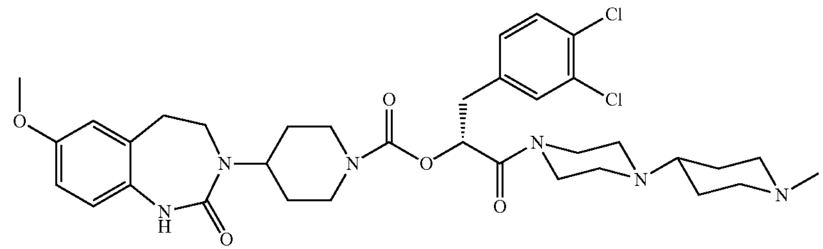 | (R)-1-(3,4-dichloro-benzyl)-2-[4-(1'-methyl-piperidin-4-yl)-piperazin-1-yl]-2-oxo-ethyl 4-(7-methoxy-2-oxo-1,2,4,5-tetrahydro-1,3-benzodiazepin-3-yl)-piperidine-1-carboxylate |
| (351) | 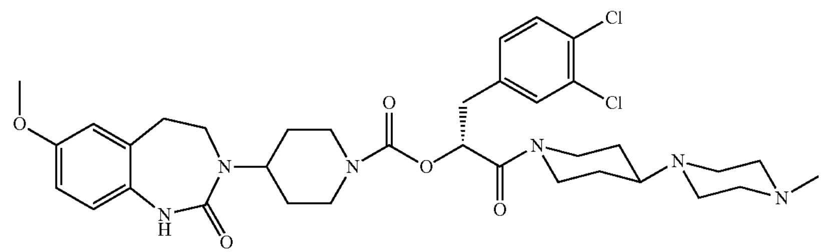 | (R)-1-(3,4-dichloro-benzyl)-2-[4-(4-methyl-piperazin-1-yl)-piperidin-1-yl]-2-oxo-ethyl 4-(7-methoxy-2-oxo-1,2,4,5-tetrahydro-1,3-benzodiazepin-3-yl)-piperidine-1-carboxylate |
| (352) | 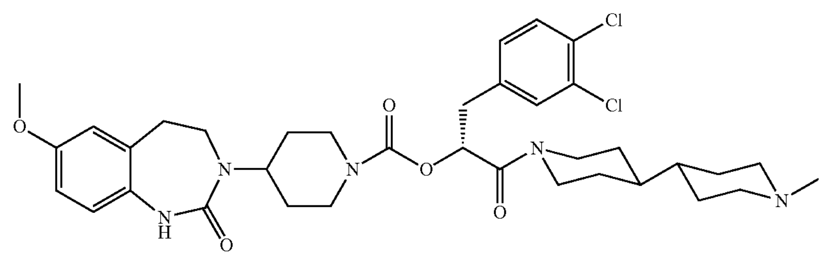 | (R)-1-(3,4-dichloro-benzyl)-2-(1'-methyl-4,4'-bipiperidinyl-1-yl)-2-oxo-ethyl 4-(7-methoxy-2-oxo-1,2,4,5-tetrahydro-1,3-benzodiazepin-3-yl)-piperidine-1-carboxylate |

| No. | Structure | Name |
|---|---|---|
| (353) | 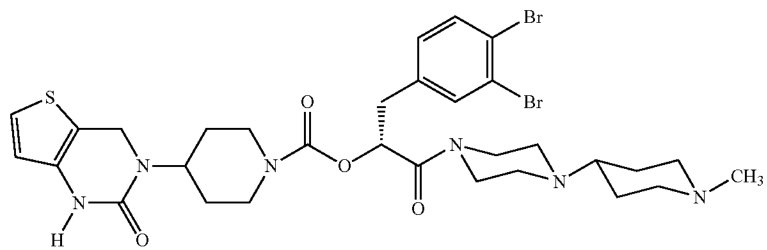 | (R)-1-(3,4-dibromo-benzyl)-2-[4-(1-methyl-piperidin-4-yl)-piperazin-1-yl]-2-oxo-ethyl 4-(2-oxo-1,4-dihydro-2H-thieno[3,2-d]-pyrimidin-3-yl)-piperidine-1-carboxylate |
| (354) | 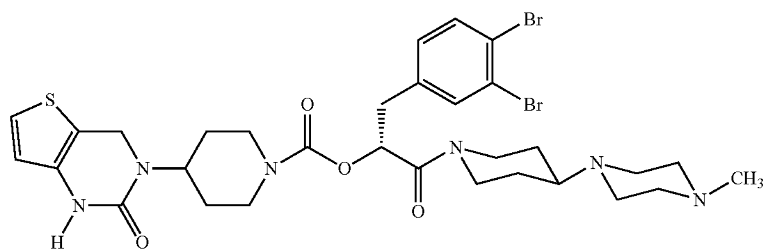 | (R)-1-(3,4-dibromo-benzyl)-2-[4-(4-methyl-piperazin-1-yl)-piperidin-1-yl]-2-oxo-ethyl 4-(2-oxo-1,4-dihydro-2H-thieno[3,2-d]-pyrimidin-3-yl)-piperidine-1-carboxylate |
| (355) | 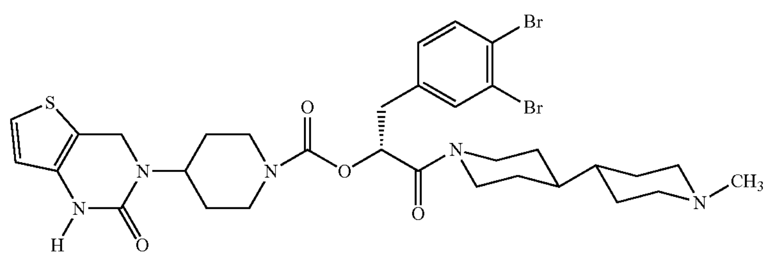 | (R)-1-(3,4-dibromo-benzyl)-2-(1'-methyl-[4,4']bipiperidinyl-1-yl)-2-oxo-ethyl 4-(2-oxo-1,4-dihydro-2H-thieno[3,2-d]-pyrimidin-3-yl)-piperidine-1-carboxylate |
| (356) | 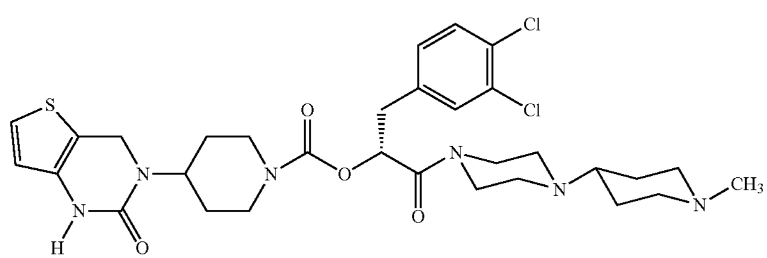 | (R)-1-(3,4-dichloro-benzyl)-2-[4-(1-methyl-piperidin-4-yl)-piperazin-1-yl]-2-oxo-ethyl 4-(2-oxo-1,4-dihydro-2H-thieno[3,2-d]-pyrimidin-3-yl)-piperidine-1-carboxylate |

| No. | Structure | Name |
|---|---|---|
| (357) | 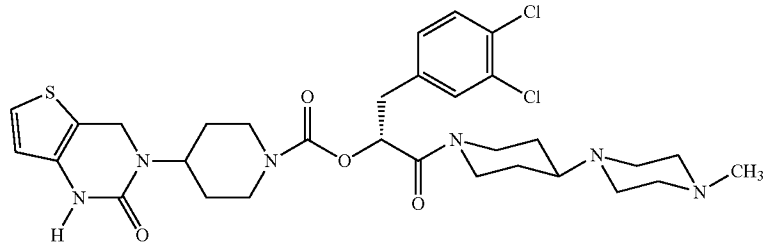 | (R)-1-(3,4-dichloro-benzyl)-2-[4-(4-methyl-piperazin-1-yl)-piperidin-1-yl]-2-oxo-ethyl 4-(2-oxo-1,4-dihydro-2H-thieno[3,2-d]-pyrimidin-3-yl)-piperidine-1-carboxylate |
| (358) | 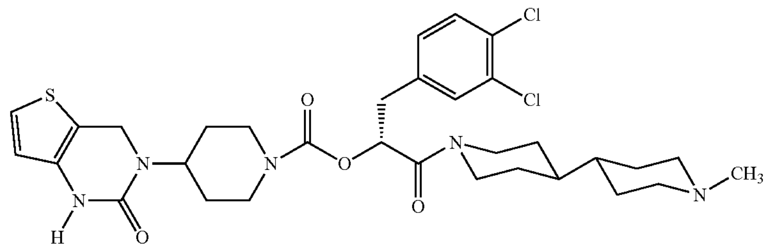 | (R)-1-(3,4-dichloro-benzyl)-2-(1'-methyl-[4,4']bipiperidinyl-1-yl)-2-oxo-ethyl 4-(2-oxo-1,4-dihydro-2H-thieno[3,2-d]pyrimidin-3-yl)-piperidine-1-carboxylate |
| (359) | 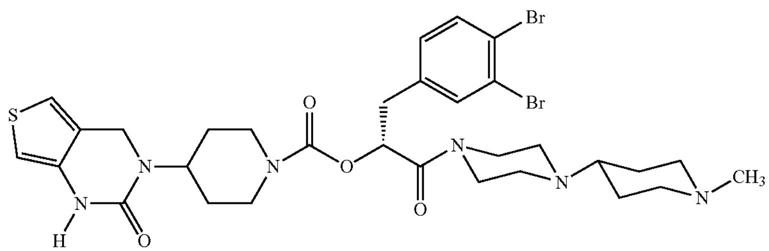 | (R)-1-(3,4-dibromo-benzyl)-2-[4-(1-methyl-piperidin-4-yl)-piperazin-1-yl]-2-oxo-ethyl 4-(2-oxo-1,2-dihydro-4H-thieno[3,4-d]-pyrimidin-3-yl)-piperidine-1-carboxylate |
| (360) | 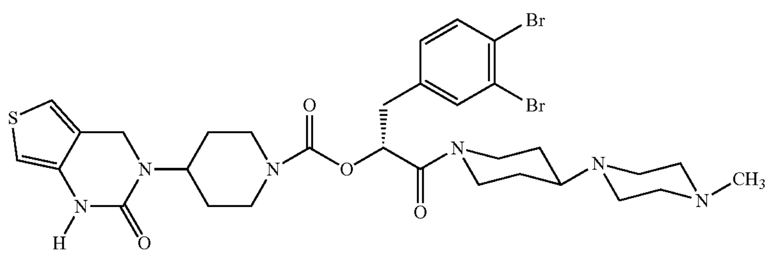 | (R)-1-(3,4-dibromo-benzyl)-2-[4-(4-methyl-piperazin-1-yl)-piperidin-1-yl]-2-oxo-ethyl 4-(2-oxo-1,2-dihydro-4H-thieno[3,4-d]-pyrimidin-3-yl)-piperidine-1-carboxylate |

| No. | Structure | Name |
|---|---|---|
| (361) | 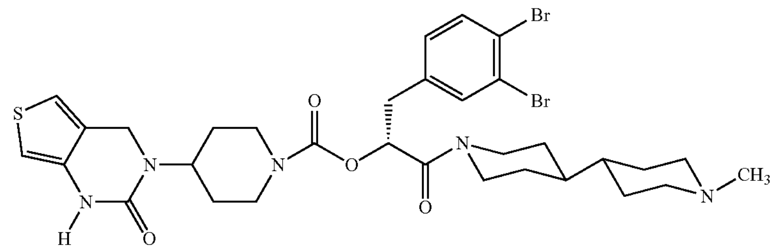 | (R)-1-(3,4-dibromo-benzyl)-2-(1'-methyl-[4,4']bipiperidinyl-1-yl)-2-oxo-ethyl 4-(2-oxo-1,2-dihydro-4H-thieno[3,4-d]pyrimidin-3-yl)-piperidine-1-carboxylate |
| (362) | 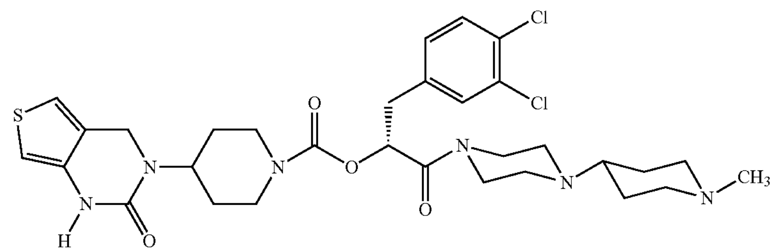 | (R)-1-(3,4-dichloro-benzyl)-2-[4-(1-methyl-piperidin-4-yl)-piperazin-1-yl]-2-oxo-ethyl 4-(2-oxo-1,2-dihydro-4H-thieno[3,4-d]-pyrimidin-3-yl)-piperidine-1-carboxylate |
| (363) | 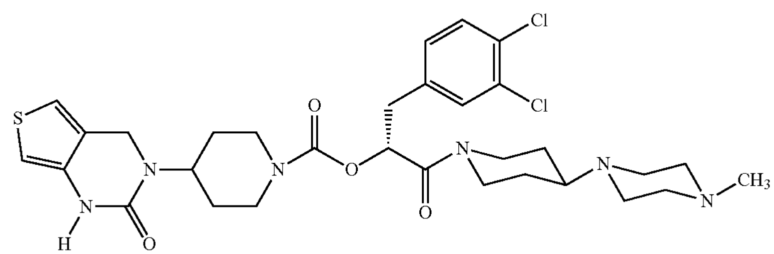 | (R)-1-(3,4-dichloro-benzyl)-2-[4-(4-methyl-piperazin-1-yl)-piperidin-1-yl]-2-oxo-ethyl 4-(2-oxo-1,2-dihydro-4H-thieno[3,4-d]-pyrimidin-3-yl)-piperidine-1-carboxylate |
| (364) | 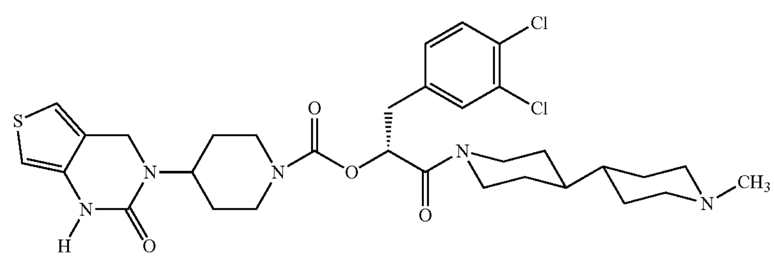 | (R)-1-(3,4-dichloro-benzyl)-2-(1'-methyl-[4,4']bipiperidinyl-1-yl)-2-oxo-ethyl 4-(2-oxo-1,2-dihydro-4H-thieno[3,4-d]pyrimidin-3-yl)-piperidine-1-carboxylate |

| No. | Structure | Name |
|---|---|---|
| (365) | 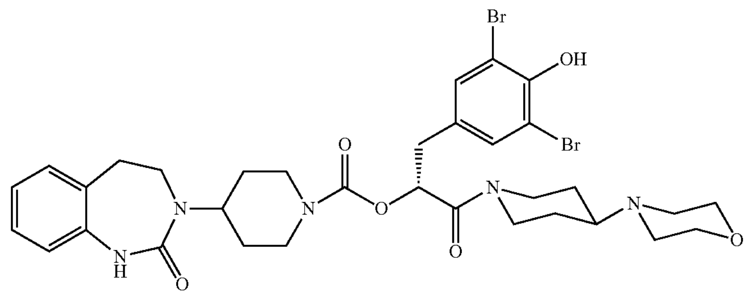 | (R)-1-(3,5-dibromo-4-hydroxy-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (366) | 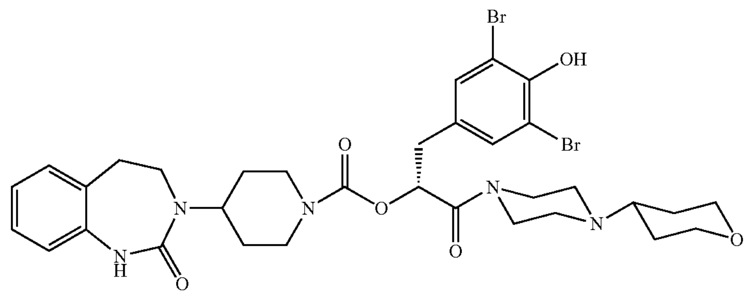 | (R)-1-(3,5-dibromo-4-hydroxy-benzyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (367) | 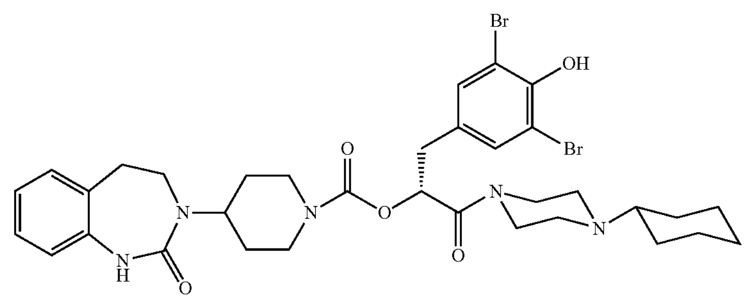 | (R)-2-(4-cyclohexyl-piperazin-1-yl)-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (368) | 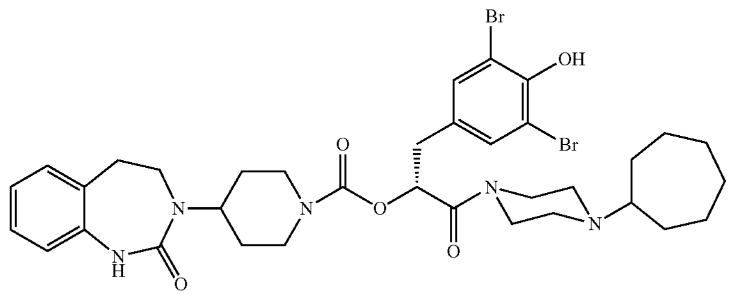 | (R)-2-(4-cycloheptyl-piperazin-1-yl)-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (369) | 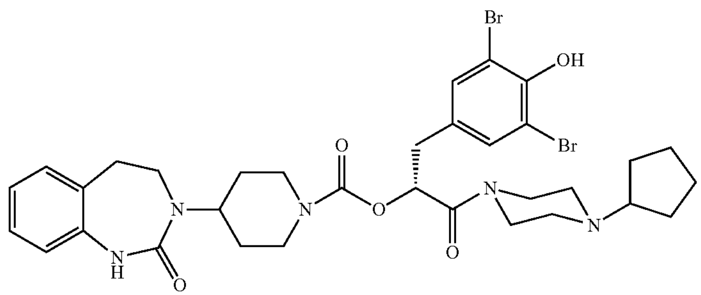 | (R)-2-(4-cyclopentyl-piperazin-1-yl)-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (370) | 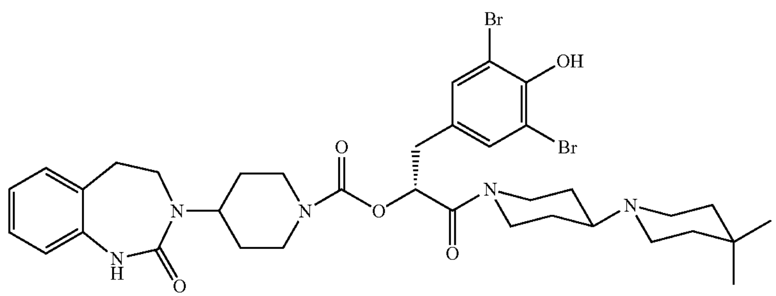 | (R)-1-(3,5-dibromo-4-hydroxy-benzyl)-2-(4,4-dimethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (371) | 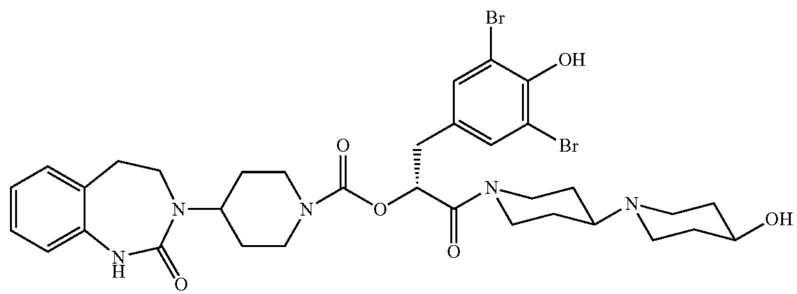 | (R)-1-(3,5-dibromo-4-hydroxy-benzyl)-2-(4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (372) | 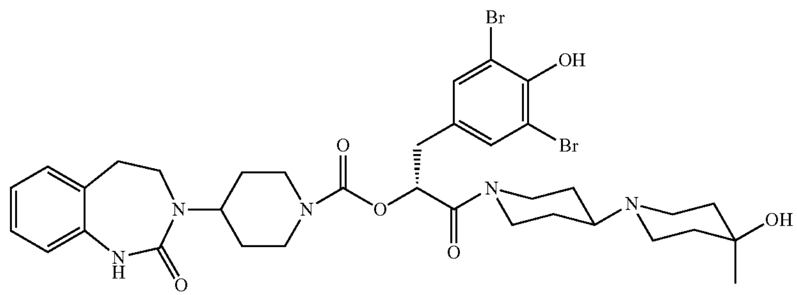 | (R)-1-(3,5-dibromo-4-hydroxy-benzyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (373) | 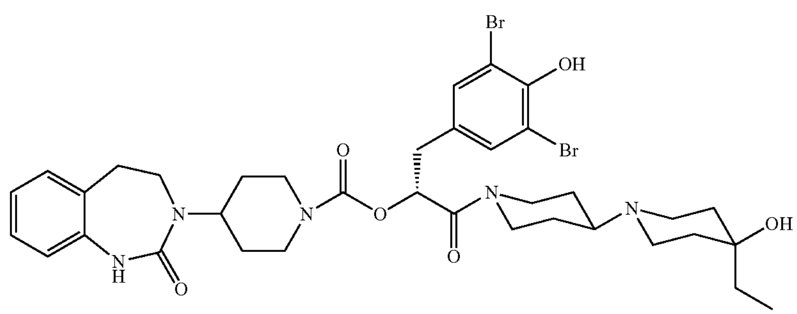 | (R)-1-(3,5-dibromo-4-hydroxy-benzyl)-2-(4-ethyl-4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (374) | 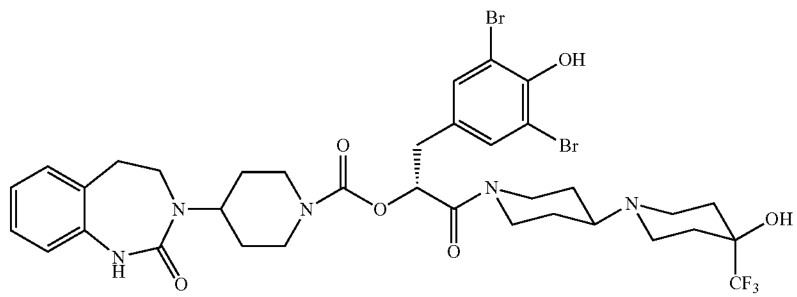 | (R)-1-(3,5-dibromo-4-hydroxy-benzyl)-2-(4-hydroxy-4-trifluormethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (375) | 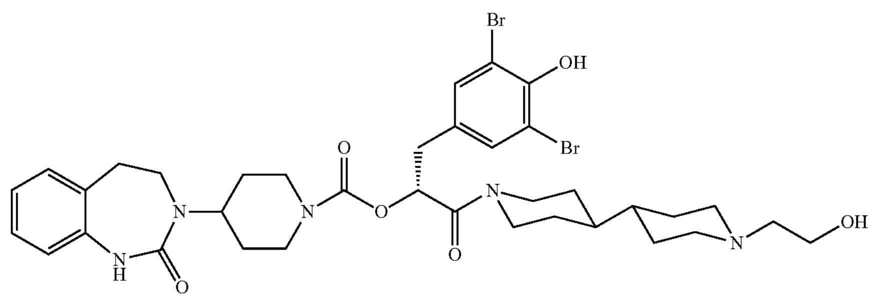 | (R)-1-(3,5-dibromo-4-hydroxy-benzyl)-2-[1'-(2-hydroxy-ethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |
| (376) | 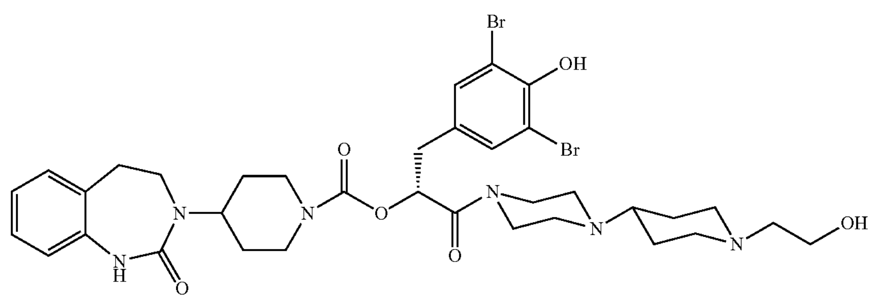 | (R)-1-(3,5-dibromo-4-hydroxy-benzyl)-2-{4-[1-(2-hydroxy-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (377) | 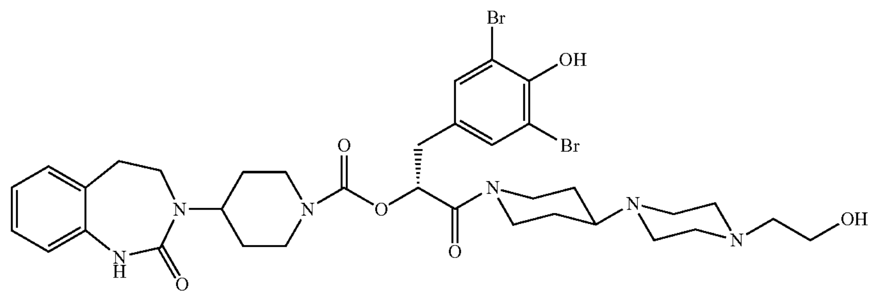 | (R)-1-(3,5-dibromo-4-hydroxy-benzyl)-2-{4-[4-(2-hydroxy-ethyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |
| (378) | 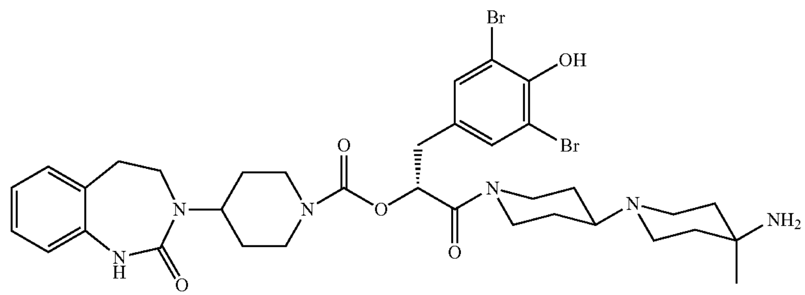 | (R)-2-(4-amino-4-methyl-1,4'-bipiperidinyl-1'-yl)-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (379) | 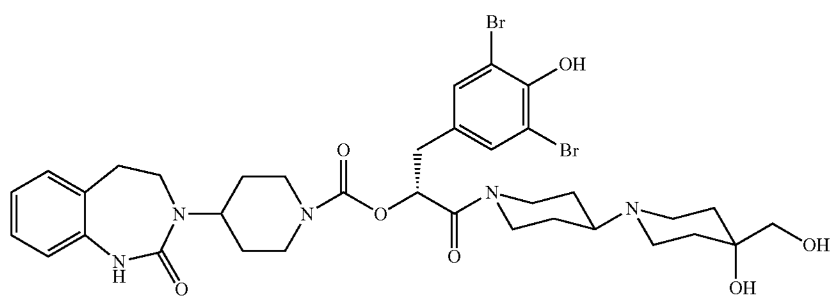 | (R)-1-(3,5-dibromo-4-hydroxy-benzyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (380) | 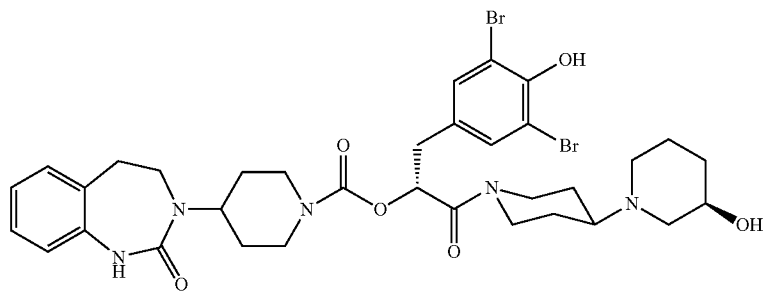 | (R)-1-(3,5-dibromo-4-hydroxy-benzyl)-2-((R)-3-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (381) | 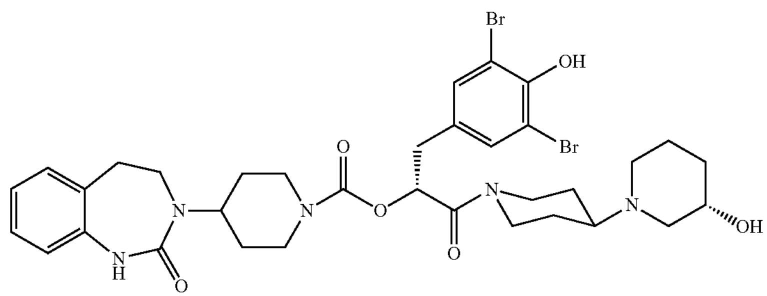 | (R)-1-(3,5-dibromo-4-hydroxy-benzyl)-2-((S)-3-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (382) | 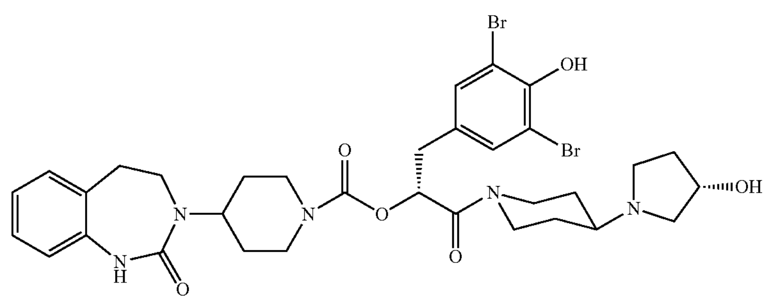 | (R)-1-(3,5-dibromo-4-hydroxy-benzyl)-2-[4-((S)-3-hydroxy-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (383) | 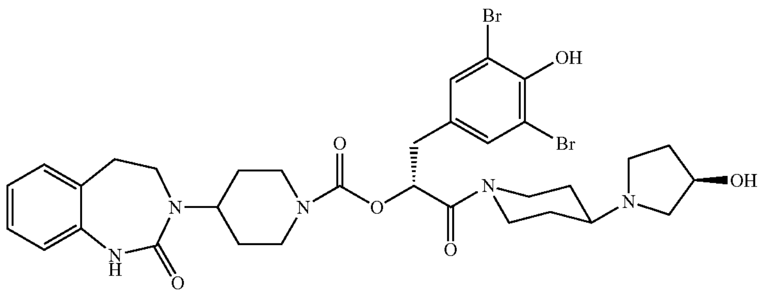 | (R)-1-(3,5-dibromo-4-hydroxy-benzyl)-2-[4-((R)-3-hydroxy-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |
| (384) | 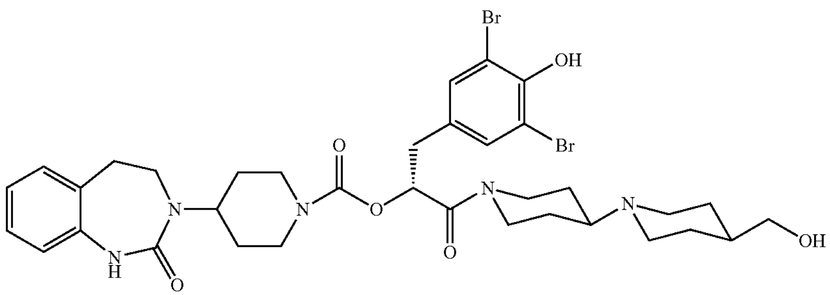 | (R)-1-(3,5-dibromo-4-hydroxy-benzyl)-2-[4-(4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (385) | 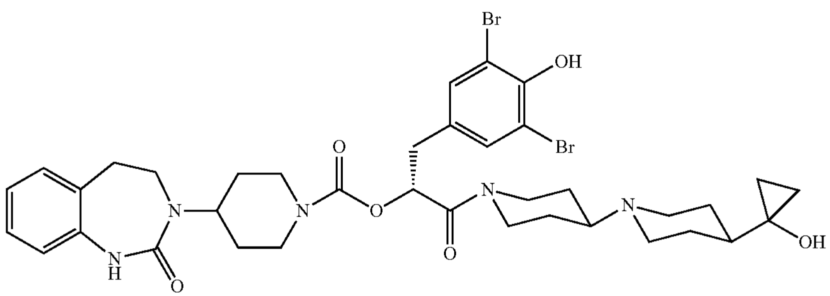 | (R)-1-(3,5-dibromo-4-hydroxy-benzyl)-2-[4-(1-hydroxy-cyclopropyl)-1,4'-bipiperidinyl-1'-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (386) | 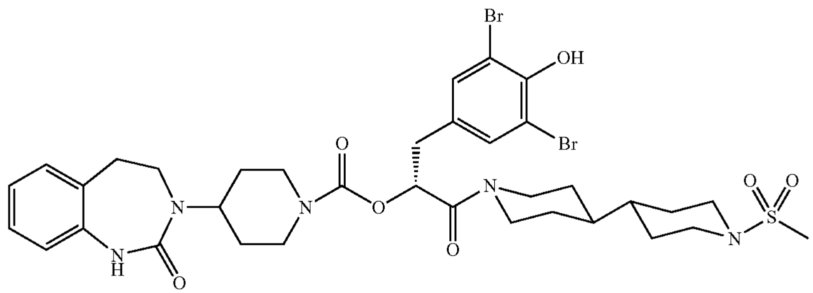 | (R)-1-(3,5-dibromo-4-hydroxy-benzyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (387) | 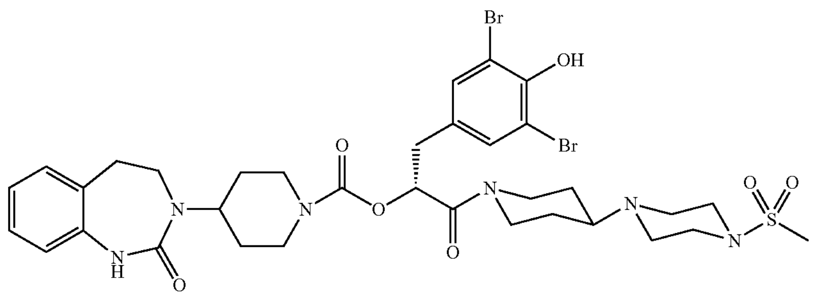 | (R)-1-(3,5-dibromo-4-hydroxy-benzyl)-2-[4-(4-methanesulphonyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (388) | 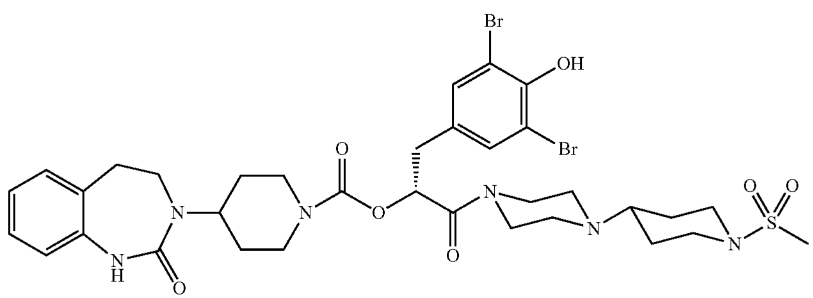 | (R)-1-(3,5-dibromo-4-hydroxy-benzyl)-2-[4-(1-methanesulphonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (389) | 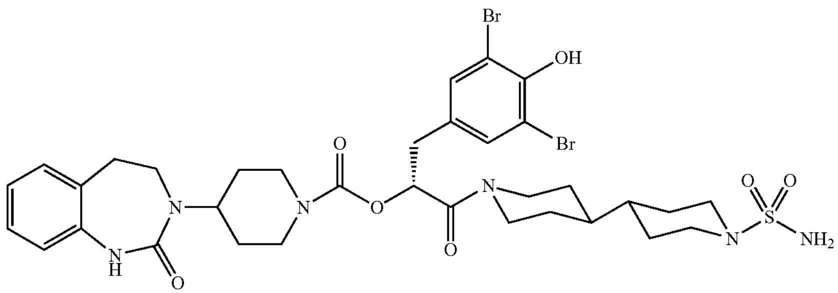 | (R)-1-(3,5-dibromo-4-hydroxy-benzyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (390) | 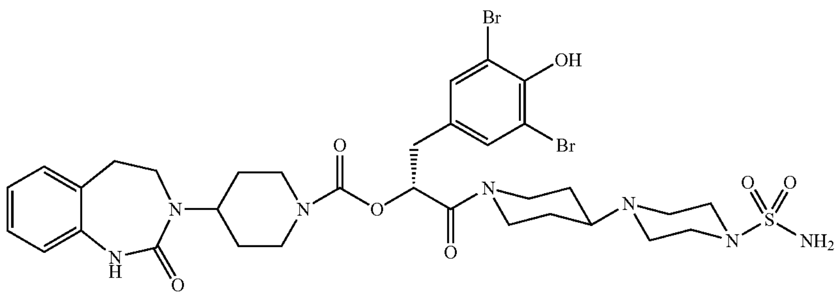 | (R)-1-(3,5-dibromo-4-hydroxy-benzyl)-2-oxo-2-[4-(4-sulphamoyl-piperazin-1-yl)-piperidin-1-yl]-ethyl 4-(2-oxo-1,2,4,5-tetrahydro-1,3-benzodiazepin-3-yl)-piperidine-1-carboxylate |
| (391) | 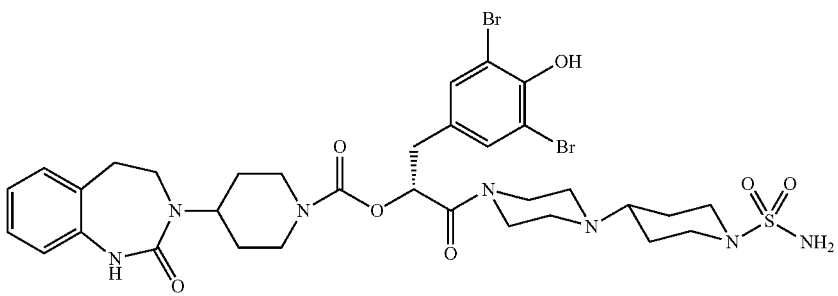 | (R)-1-(3,5-dibromo-4-hydroxy-benzyl)-2-oxo-2-[4-(1-sulphamoyl-piperidin-4-yl)-piperazin-1-yl]-ethyl 4-(2-oxo-1,2,4,5-tetrahydro-1,3-benzodiazepin-3-yl)-piperidine-1-carboxylate |

| No. | Structure | Name |
|---|---|---|
| (392) | 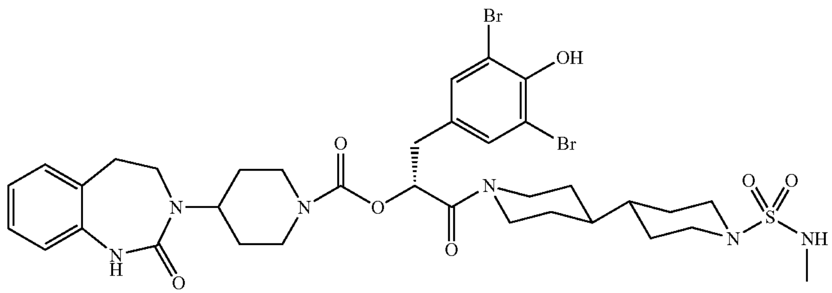 | (R)-1-(3,5-dibromo-4-hydroxy-benzyl)-2-(1'-methylsulphamoyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (393) | 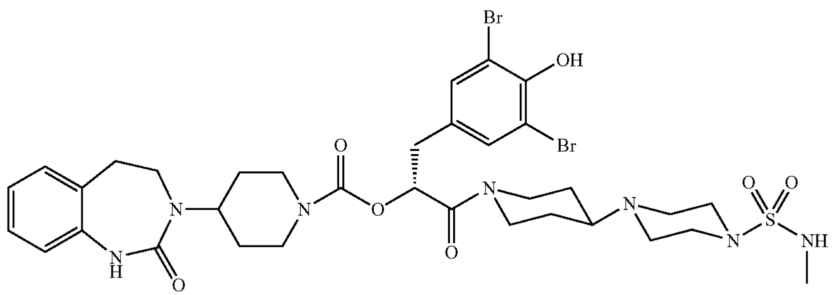 | (R)-1-(3,5-dibromo-4-hydroxy-benzyl)-2-[4-(4-methylsulphamoyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (394) | 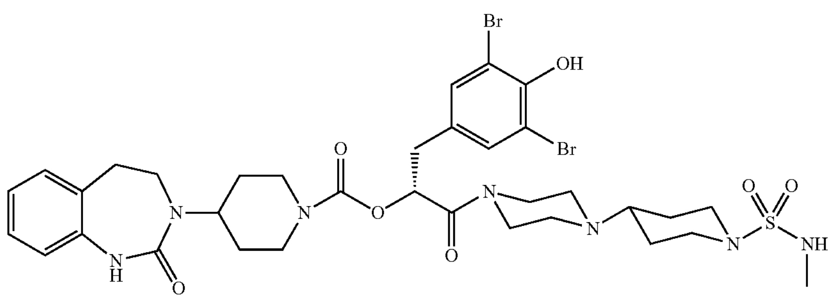 | (R)-1-(3,5-dibromo-4-hydroxy-benzyl)-2-[4-(1-methylsulphamoyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (395) | 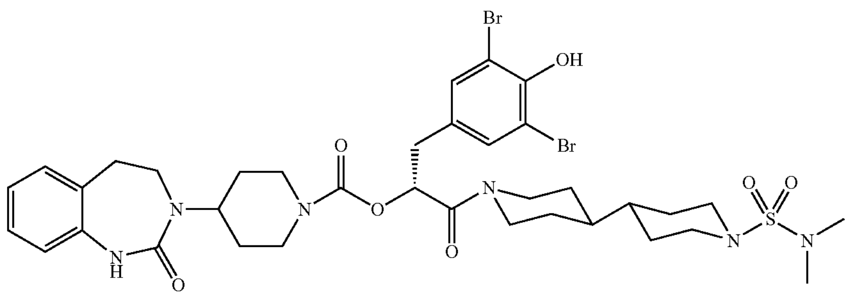 | (R)-1-(3,5-dibromo-4-hydroxy-benzyl)-2-(1'-dimethylsulphamoyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (396) | 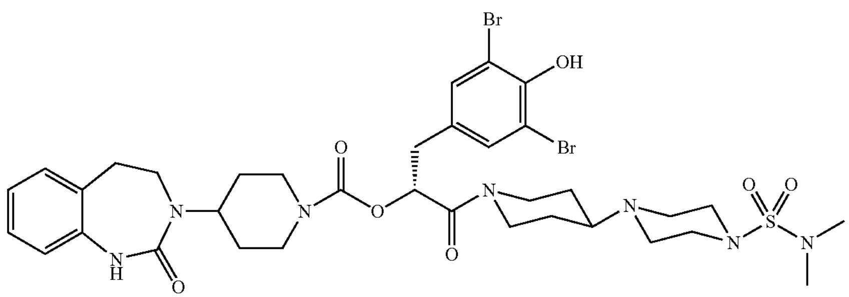 | (R)-1-(3,5-dibromo-4-hydroxy-benzyl)-2-[4-(4-dimethylsulphamoyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (397) | 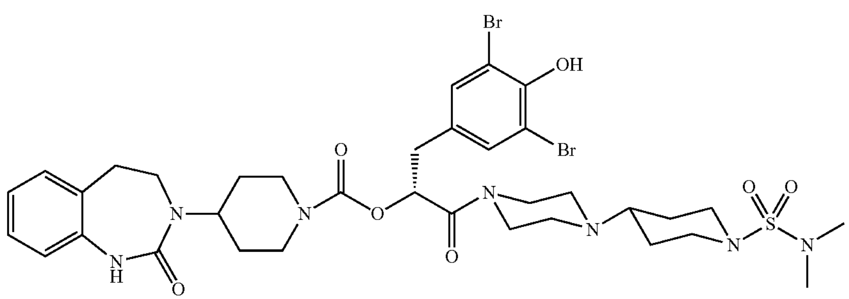 | (R)-1-(3,5-dibromo-4-hydroxy-benzyl)-2-[4-(1-dimethylsulphamoyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (398) | 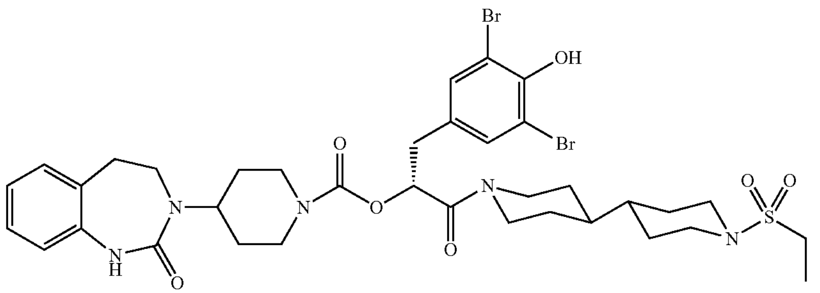 | (R)-1-(3,5-dibromo-4-hydroxy-benzyl)-2-(1'-ethanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (399) | 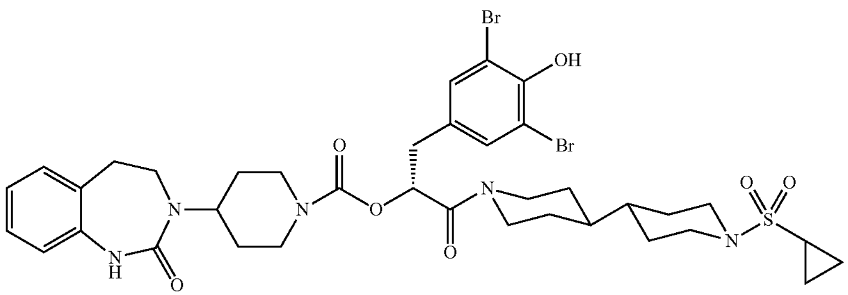 | (R)-2-(1'-cyclopropanesulphonyl-4,4'-bipiperidinyl-1-yl)-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (400) | 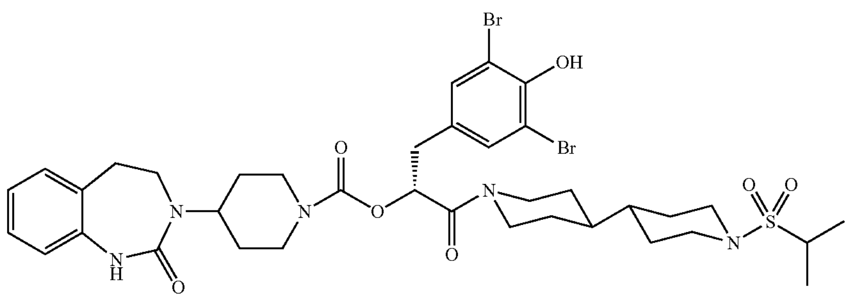 | (R)-1-(3,5-dibromo-4-hydroxy-benzyl)-2-oxo-2-[1'-(propan-2-sulphonyl)-4,4'-bipiperidinyl-1-yl]-ethyl 4-(2-oxo-1,2,4,5-tetrahydro-1,3-benzodiazepin-3-yl)-piperidine-1-carboxylate |

-continued

| No. | Name |
|---|---|
| (401) | (R)-1-(3,5-dibromo-4-hydroxy-benzyl)-2-(4'-hydroxy-1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (402) | (R)-1-(3,5-dibromo-4-hydroxy-benzyl)-2-[4-(1,1-dioxo-1λ⁶-thiomorpholin-4-yl)-piperidin-1-yl]-2-oxo-ethyl 4-(2-oxo-1,2,4,5-tetrahydro-1,3-benzodiazepin-3-yl)-piperidine-1-carboxylate |
| (403) | (R)-1-(3,5-dibromo-4-hydroxy-benzyl)-2-oxo-2-{4-[4-(3,3,3-trifluoro-2-oxo-propyl)-piperazin-1-yl]-piperidin-1-yl}-ethyl 4-(2-oxo-1,2,4,5-tetrahydro-1,3-benzodiazepin-3-yl)-piperidine-1-carboxylate |

-continued

| No. | Structure | Name |
|---|---|---|
| (404) | 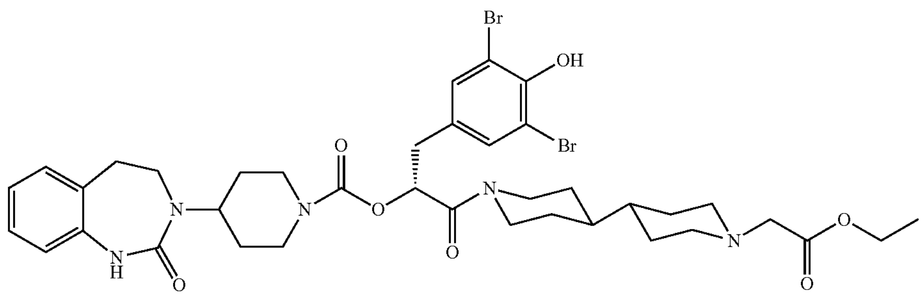 | (R)-1-(3,5-dibromo-4-hydroxy-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (405) | 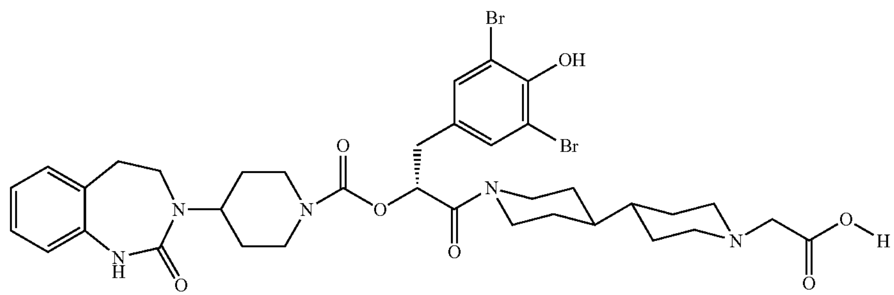 | (R)-2-(1'-carboxymethyl-4,4'-bipiperidinyl-1-yl)-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (406) | 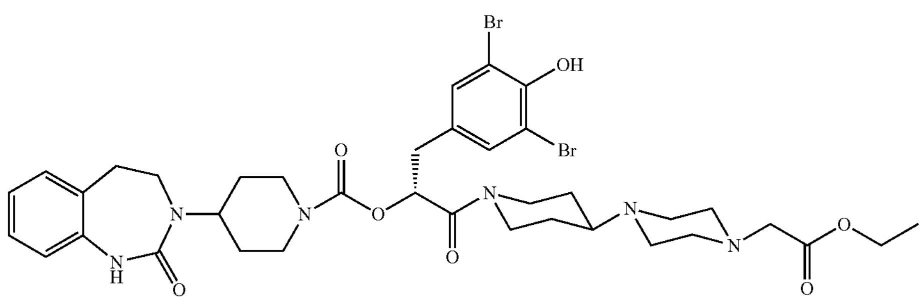 | (R)-1-(3,5-dibromo-4-hydroxy-benzyl)-2-[4-(4-ethoxycarbonylmethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (407) | 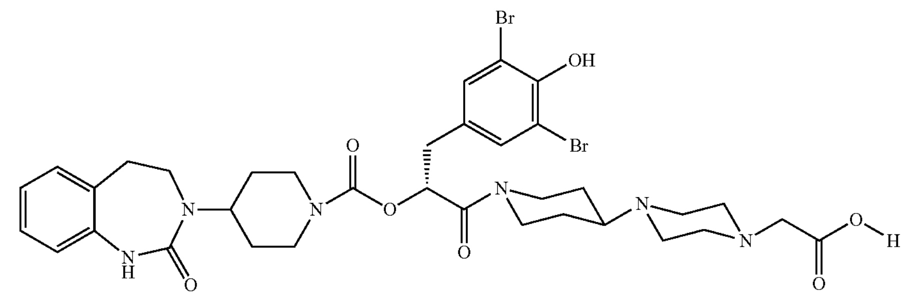 | (R)-2-[4-(4-carboxymethyl-piperazin-1-yl)-piperidin-1-yl]-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (408) | 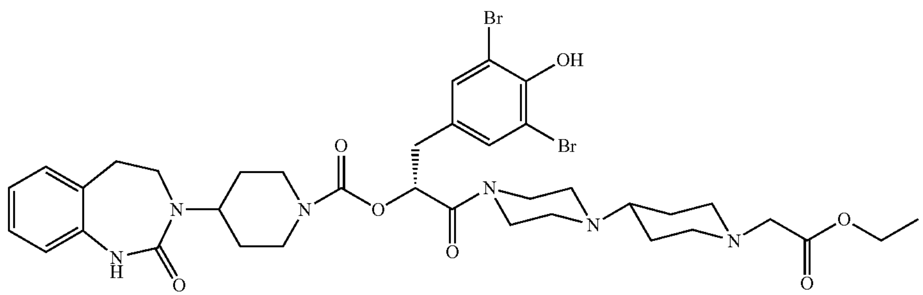 | (R)-1-(3,5-dibromo-4-hydroxy-benzyl)-2-[4-(1-ethoxycarbonylmethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (409) | 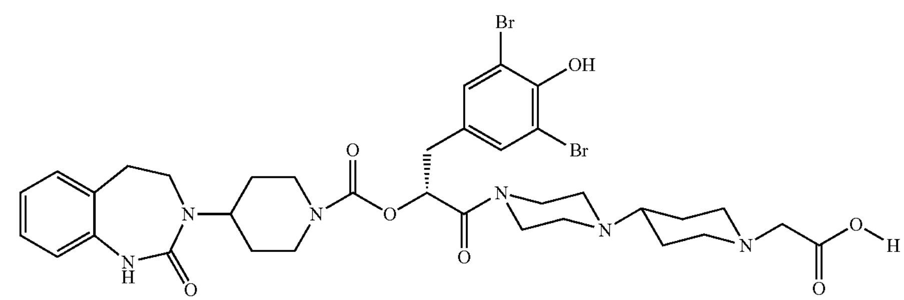 | (R)-2-[4-(1-carboxymethyl-piperidin-4-yl)-piperazin-1-yl]-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (410) | 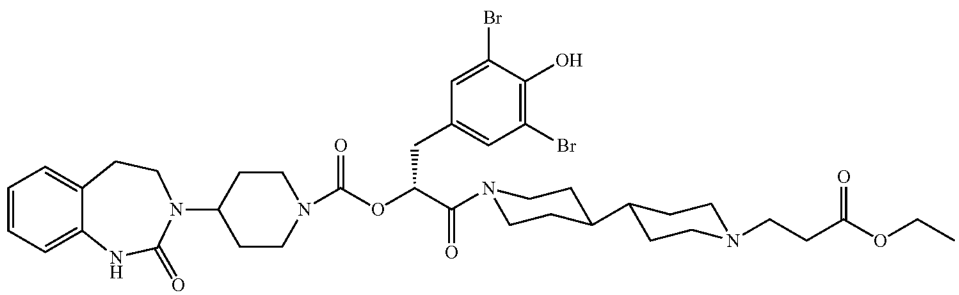 | (R)-1-(3,5-dibromo-4-hydroxy-benzyl)-2-[1'-(2-ethoxycarbonyl-ethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |
| (411) | 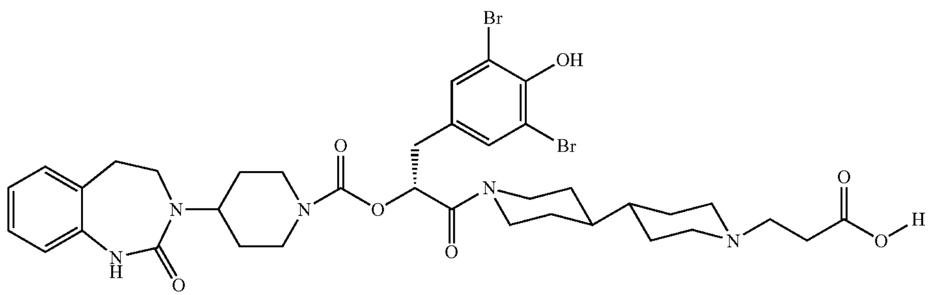 | (R)-2-[1'-(2-carboxy-ethyl)-4,4'-bipiperidinyl-1-yl]-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (412) | 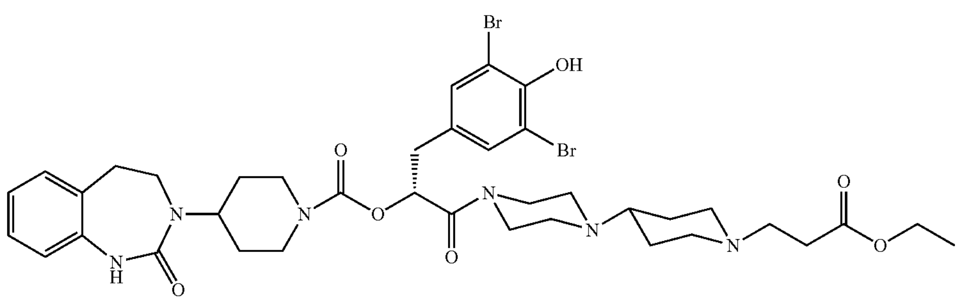 | (R)-1-(3,5-dibromo-4-hydroxy-benzyl)-2-{4-[1-(2-ethoxycarbonyl-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (413) | 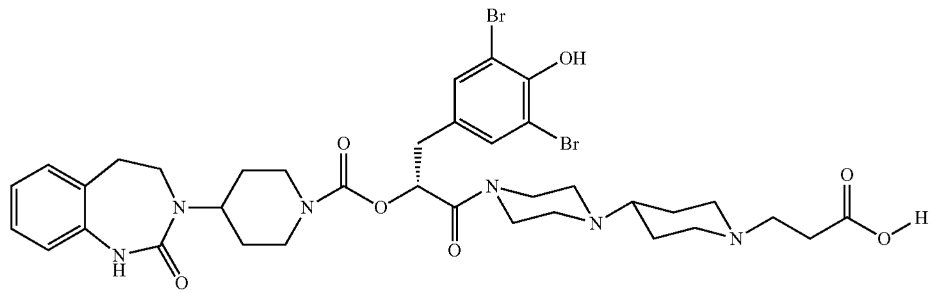 | (R)-2-{4-[1-(2-carboxy-ethyl)-piperidin-4-yl]-piperazin-1-yl}-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (414) | 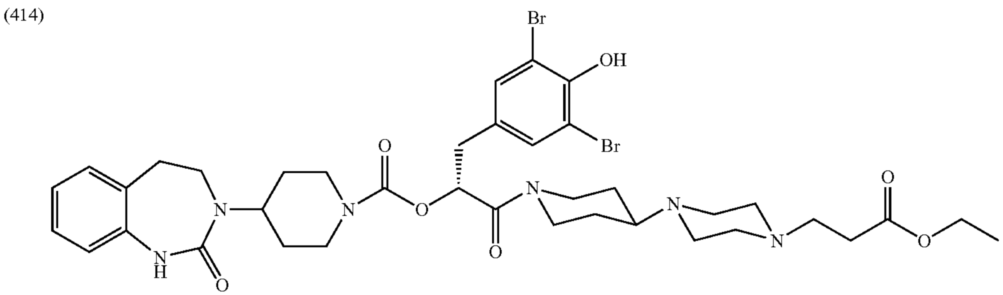 | (R)-1-(3,5-dibromo-4-hydroxy-benzyl)-2-{4-[4-(2-ethoxycarbonyl-ethyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |
| (415) | 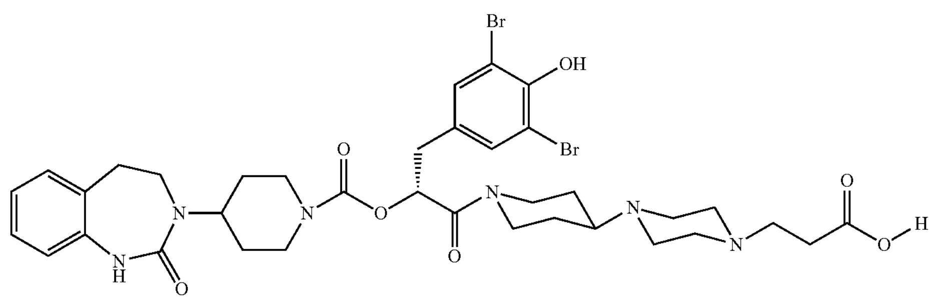 | (R)-2-{4-[4-(2-carboxy-ethyl)-piperazin-1-yl]-piperidin-1-yl}-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (416) | 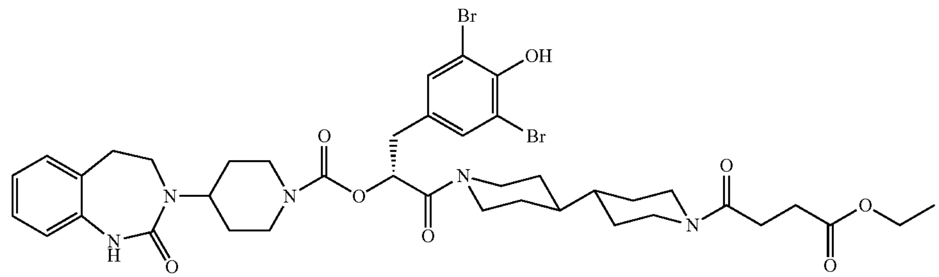 | (R)-1-(3,5-dibromo-4-hydroxy-benzyl)-2-[1'-(3-ethoxycarbonyl-propionyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |
| (417) | 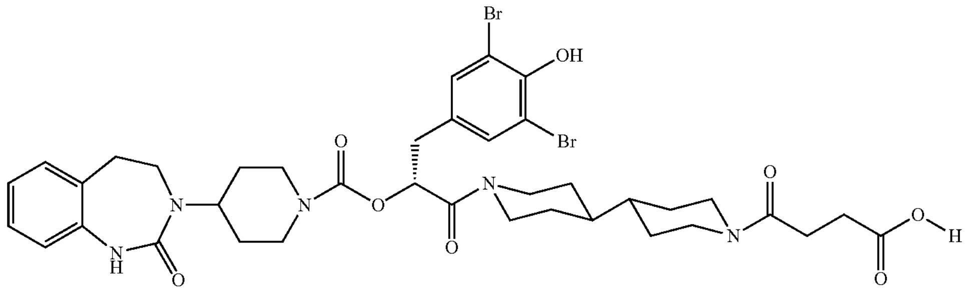 | (R)-2-[1'-(3-carboxy-propionyl)-4,4'-bipiperidinyl-1-yl]-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (418) | 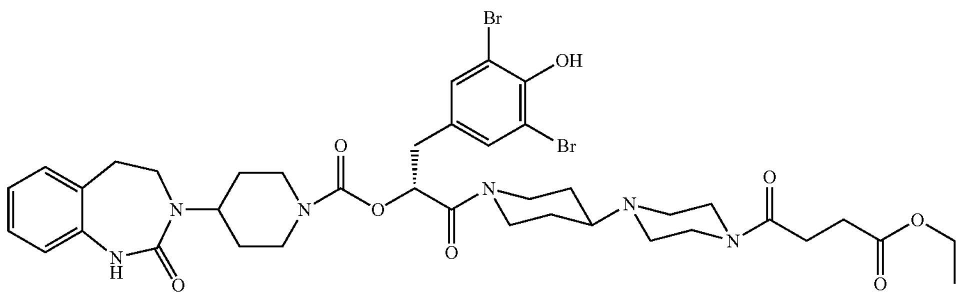 | (R)-1-(3,5-dibromo-4-hydroxy-benzyl)-2-{4-[4-(3-ethoxycarbonyl-propionyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (419) | 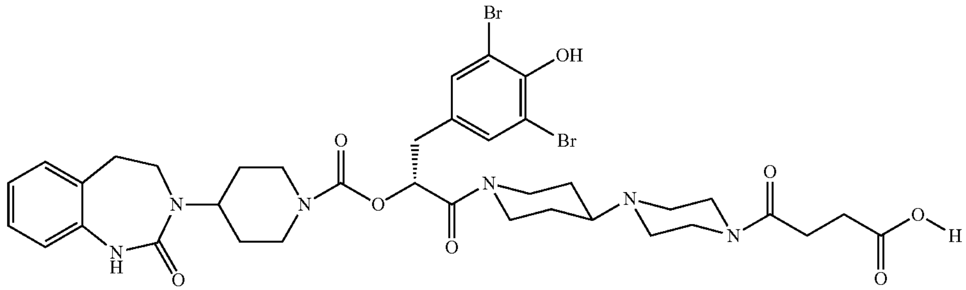 | (R)-2-{4-[4-(3-carboxy-propionyl)-piperazin-1-yl]-piperidin-1-yl}-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (420) | 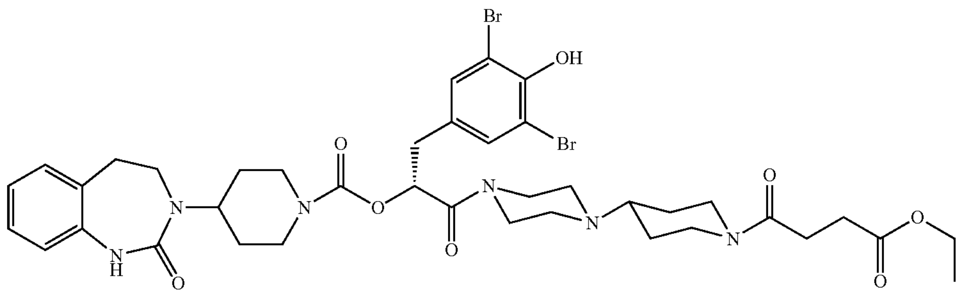 | (R)-1-(3,5-dibromo-4-hydroxy-benzyl)-2-{4-[1-(3-ethoxycarbonyl-propionyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |
| (421) | 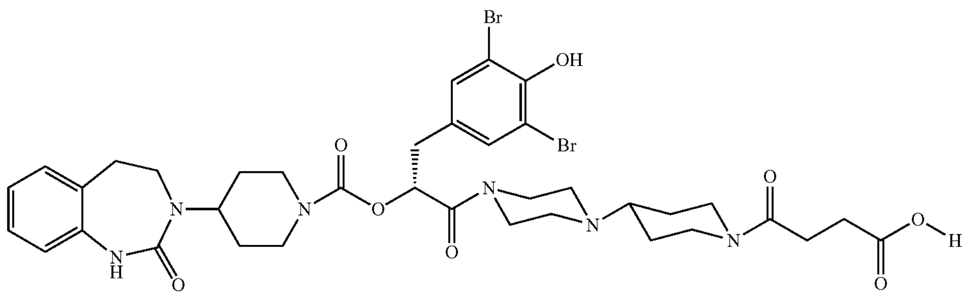 | (R)-2-{4-[1-(3-carboxy-propionyl)-piperidin-4-yl]-piperazin-1-yl}-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (422) | 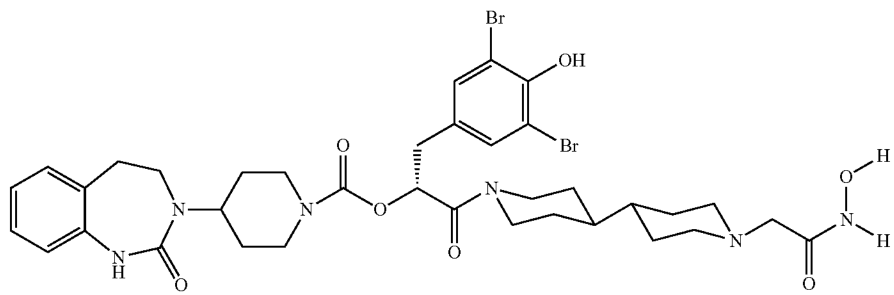 | (R)-1-(3,5-dibromo-4-hydroxy-benzyl)-2-(1'-hydroxycarbamoylmethyl)-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (423) | 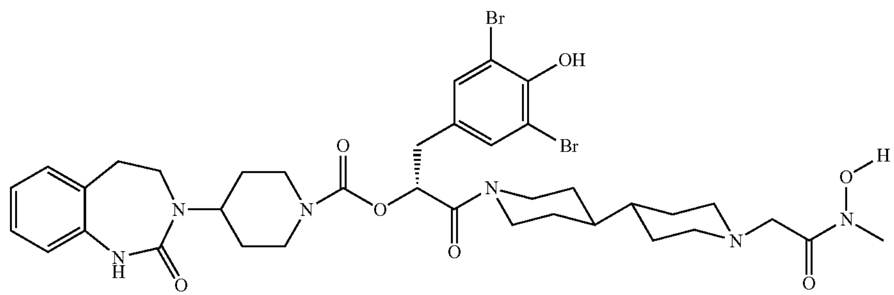 | (R)-1-(3,5-dibromo-4-hydroxy-benzyl)-2-{1'-[(hydroxy-methyl-carbamoyl)-methyl]-4,4'-bipiperidinyl-1-yl}-2-oxo-ethyl 4-(2-oxo-1,2,4,5-tetrahydro-1,3-benzodiazepin-3-yl)-piperidine-1-carboxylate |
| (424) | 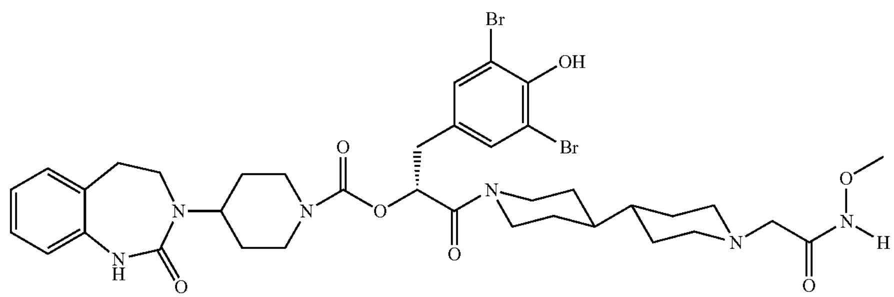 | (R)-1-(3,5-dibromo-4-hydroxy-benzyl)-2-[1'-(methoxycarbamoyl-methyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (425) | 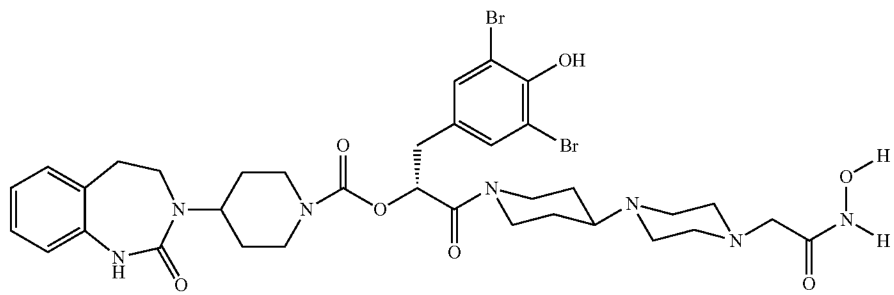 | (R)-1-(3,5-dibromo-4-hydroxy-benzyl)-2-[4-(4-hydroxycarbamoylmethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (426) | 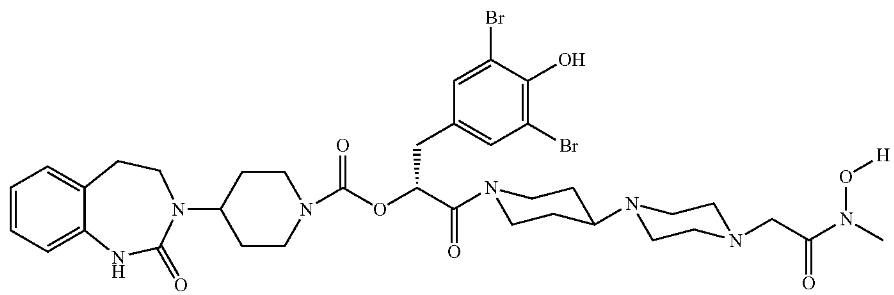 | (R)-1-(3,5-dibromo-4-hydroxy-benzyl)-2-(4-{4-[(hydroxy-methyl-carbamoyl)-methyl]-piperazin-1-yl}-piperidin-1-yl)-2-oxo-ethyl 4-(2-oxo-1,2,4,5-tetrahydro-1,3-benzodiazepin-3-yl)-piperidine-1-carboxylate |
| (427) | 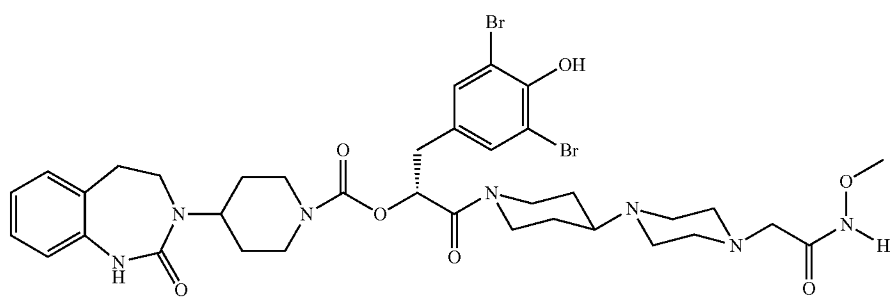 | (R)-1-(3,5-dibromo-4-hydroxy-benzyl)-2-{4-[4-(methoxycarbamoyl-methyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (428) | 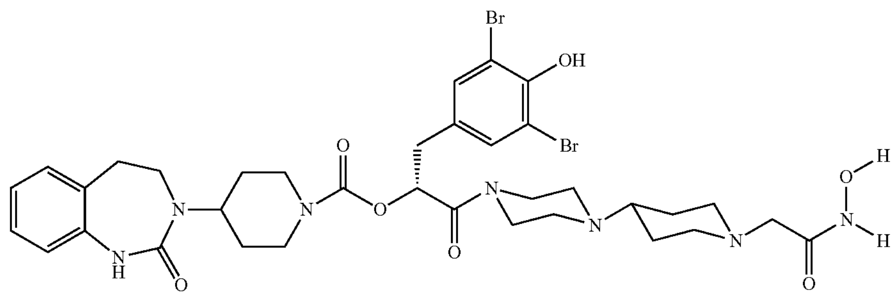 | (R)-1-(3,5-dibromo-4-hydroxy-benzyl)-2-[4-(1-hydroxycarbamoylmethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (429) | 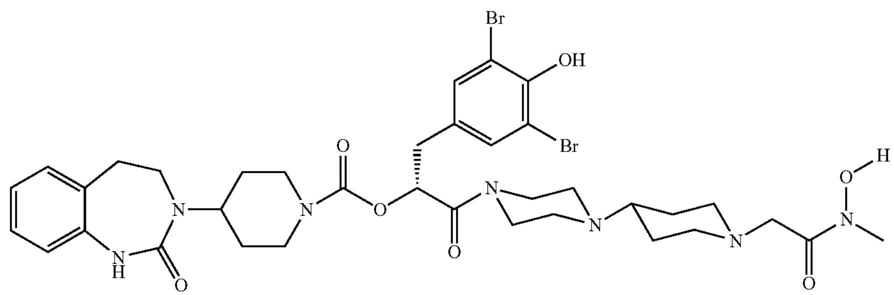 | (R)-1-(3,5-dibromo-4-hydroxy-benzyl)-2-(4-{1-[(hydroxy-methyl-carbamoyl)-methyl]-piperidin-4-yl}-piperazin-1-yl)-2-oxo-ethyl 4-(2-oxo-1,2,4,5-tetrahydro-1,3-benzodiazepin-3-yl)-piperidine-1-carboxylate |
| (430) | 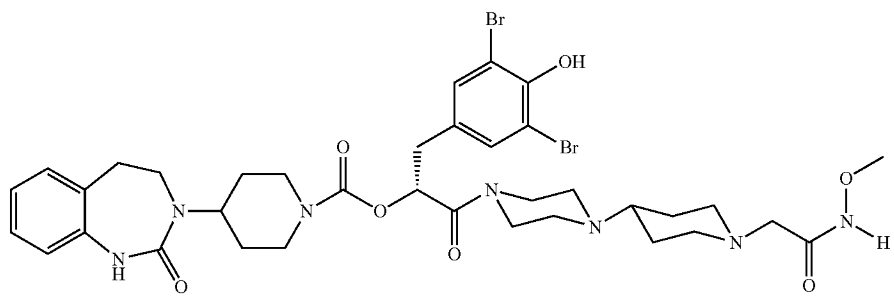 | (R)-1-(3,5-dibromo-4-hydroxy-benzyl)-2-{4-[1-(methoxycarbamoyl-methyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (431) | 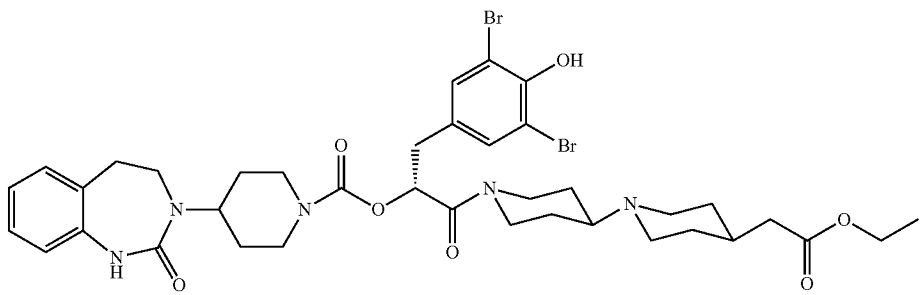 | (R)-1-(3,5-dibromo-4-hydroxy-benzyl)-2-(4-ethoxycarbonylmethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (432) | 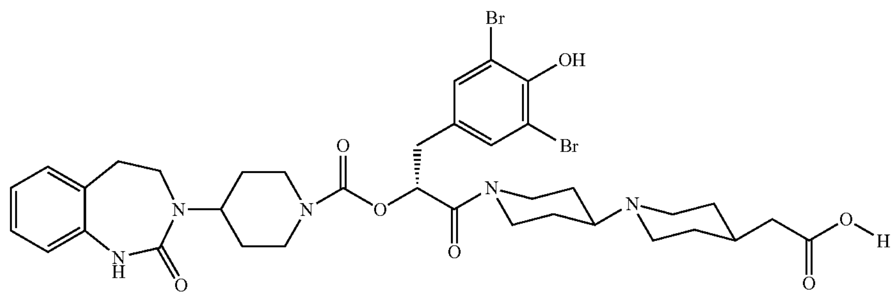 | (R)-2-(4-carboxymethyl-1,4'-bipiperidinyl-1'-yl)-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (433) | 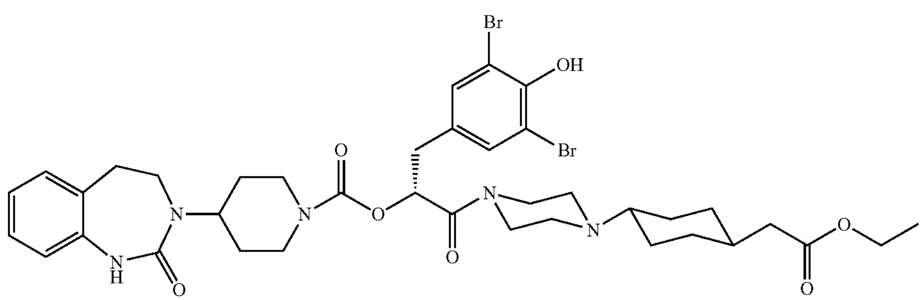 | (R)-1-(3,5-dibromo-4-hydroxy-benzyl)-2-[4-(4-ethoxycarbonylmethyl-cyclohexyl)-piperazin-1-yl]-2-oxo-ethyl cis-4-(2-oxo-1,2,4,5-tetrahydro-1,3-benzodiazepin-3-yl)-piperidine-1-carboxylate |

| No. | Structure | Name |
|---|---|---|
| (434) | 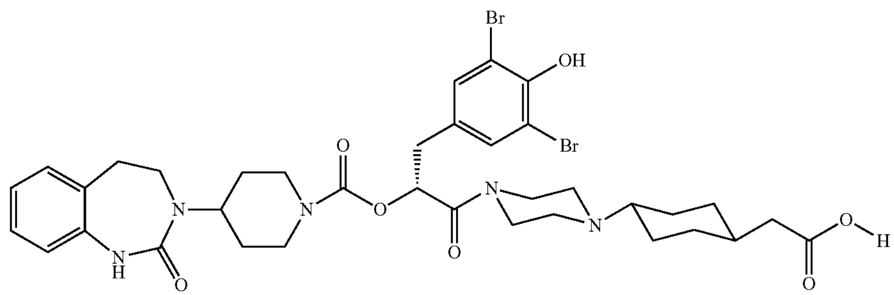 | (R)-2-[4-(4-carboxymethyl-cyclohexyl)-piperazin-1-yl]-1-(3,5-dibromo-4-hydroxy-benzyl)-2-oxo-ethyl cis-4-(2-oxo-1,2,4,5-tetrahydro-1,3-benzodiazepin-3-yl)-piperidine-1-carboxylate |
| (435) | 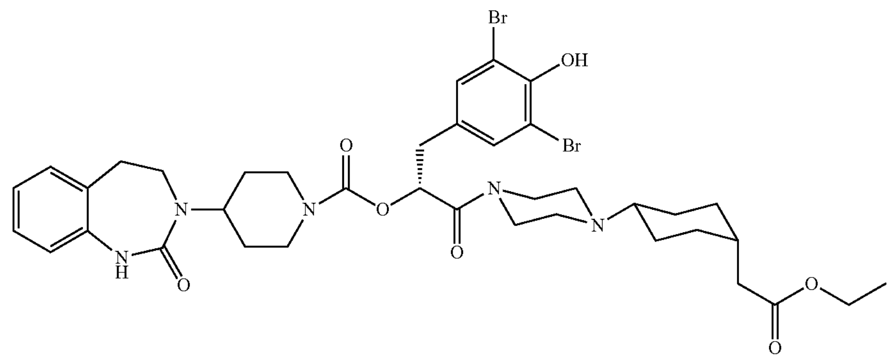 | (R)-1-(3,5-dibromo-4-hydroxy-benzyl)-2-[4-(4-ethoxycarbonylmethyl-cyclohexyl)-piperazin-1-yl]-2-oxo-ethyl trans-4-(2-oxo-1,2,4,5-tetrahydro-1,3-benzodiazepin-3-yl)-piperidine-1-carboxylate |
| (436) | 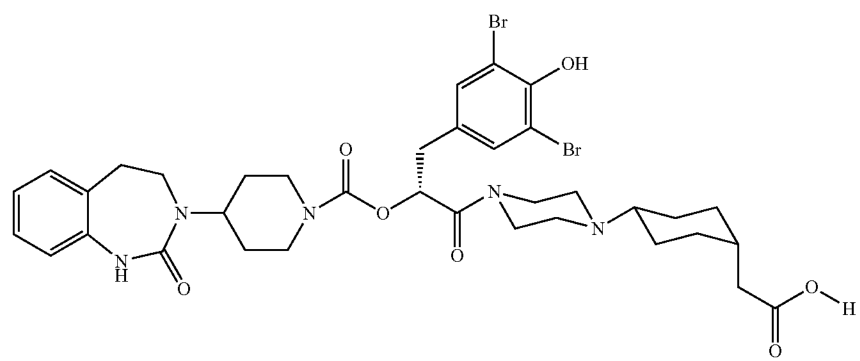 | (R)-2-[4-(4-carboxymethyl-cyclohexyl)-piperazin-1-yl]-1-(3,5-dibromo-4-hydroxy-benzyl)-2-oxo-ethyl trans-4-(2-oxo-1,2,4,5-tetrahydro-1,3-benzodiazepin-3-yl)-piperidine-1-carboxylate |

| No. | Structure | Name |
|---|---|---|
| (437) | 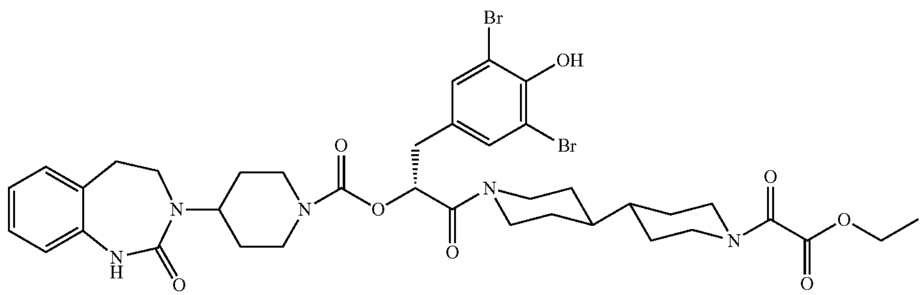 | (R)-1-(3,5-dibromo-4-hydroxy-benzyl)-2-(1'-ethoxyoxalyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (438) | 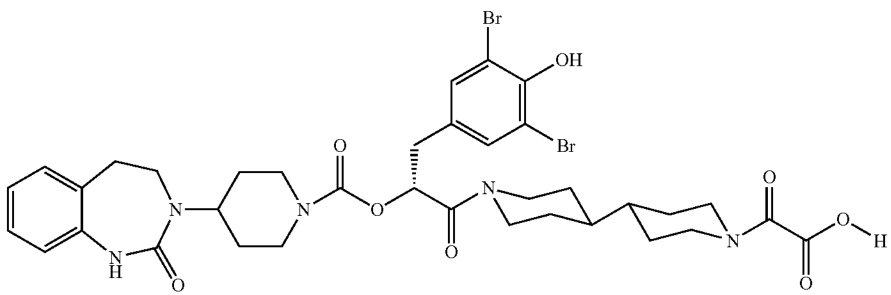 | (R)-1-(3,5-dibromo-4-hydroxy-benzyl)-2-(1'-oxalyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (439) | 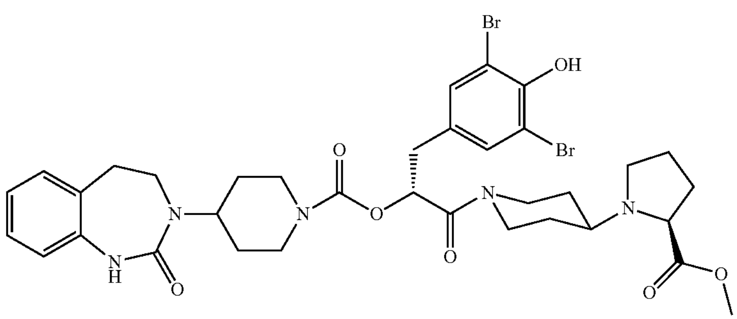 | (R)-1-(3,5-dibromo-4-hydroxy-benzyl)-2-[4-((S)-2-methoxycarbonyl-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (440) | 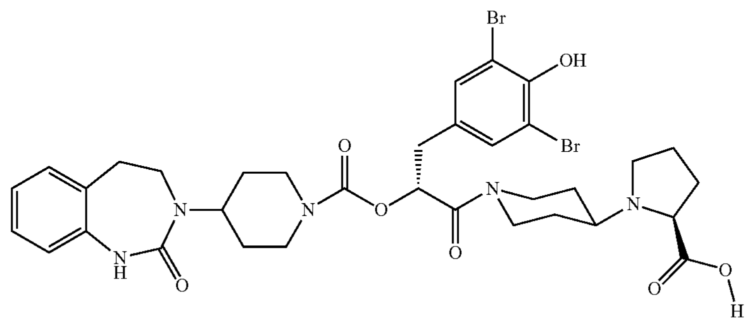 | (R)-2-[4-((S)-2-carboxy-pyrrolidin-1-yl)-piperidin-1-yl]-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |
| (441) | 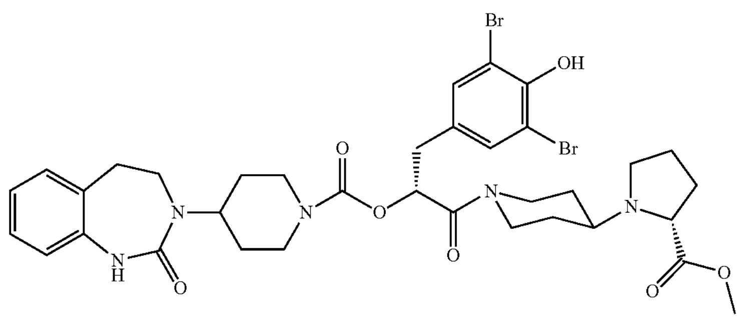 | (R)-1-(3,5-dibromo-4-hydroxy-benzyl)-2-[4-((R)-2-methoxycarbonyl-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |
| (442) | 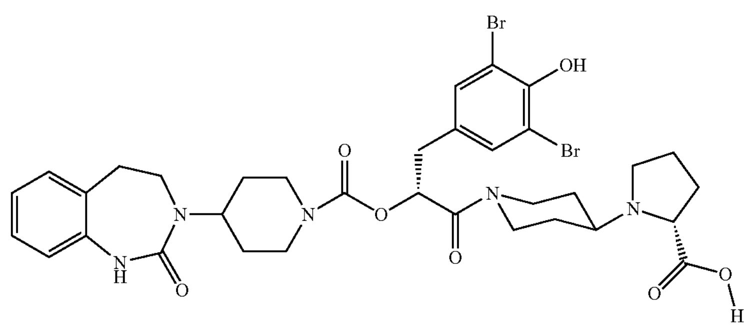 | (R)-2-[4-((R)-2-carboxy-pyrrolidin-1-yl)-piperidin-1-yl]-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (443) | 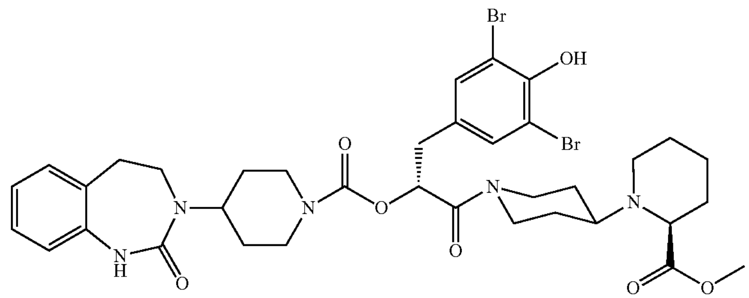 | methyl (S)-1'-{(R)-3-(3,5-dibromo-4-hydroxy-phenyl)-2-[4-(2-oxo-1,2,4,5-tetrahydro-1,3-benzodiazepin-3-yl)-piperidin-1-carbonyloxy]-propionyl}-1,4'-bipiperidinyl-2-carboxylate |
| (444) | 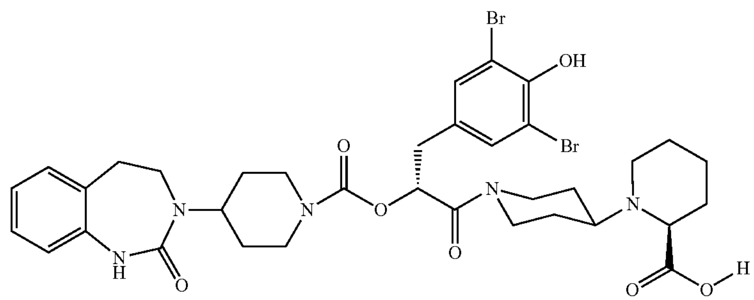 | (S)-1'-{(R)-3-(3,5-dibromo-4-hydroxy-phenyl)-2-[4-(2-oxo-1,2,4,5-tetrahydro-1,3-benzodiazepin-3-yl)-piperidin-1-carbonyloxy]-propionyl}-1,4'-bipiperidinyl-2-carboxylic acid |
| (445) | 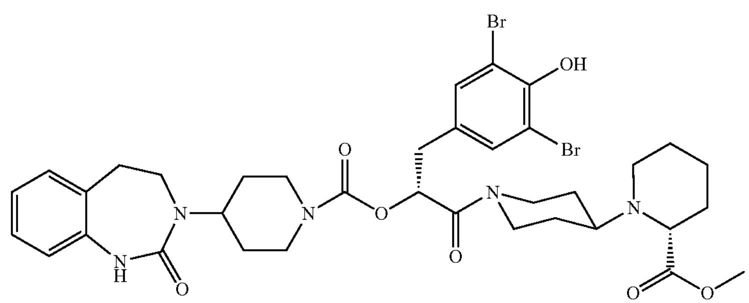 | methyl (R)-1'-{(R)-3-(3,5-dibromo-4-hydroxy-phenyl)-2-[4-(2-oxo-1,2,4,5-tetrahydro-1,3-benzodiazepin-3-yl)-piperidin-1-carbonyloxy]-propionyl}-1,4'-bipiperidinyl-2-carboxylate |

| No. | Structure | Name |
|---|---|---|
| (446) | 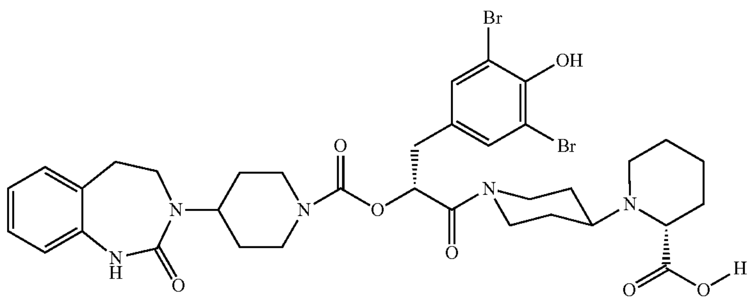 | (R)-1'-[(R)-3-(3,5-dibromo-4-hydroxy-phenyl)-2-[4-(2-oxo-1,2,4,5-tetrahydro-1,3-benzodiazepin-3-yl)-piperidin-1-carbonyloxy]-propionyl]-1,4'-bipiperidinyl-2-carboxylic acid |
| (447) | 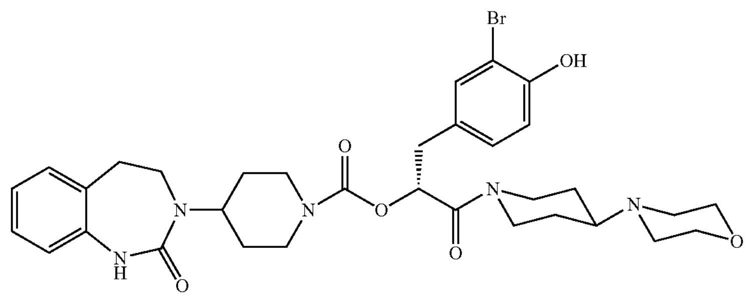 | (R)-1-(3-bromo-4-hydroxy-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (448) | 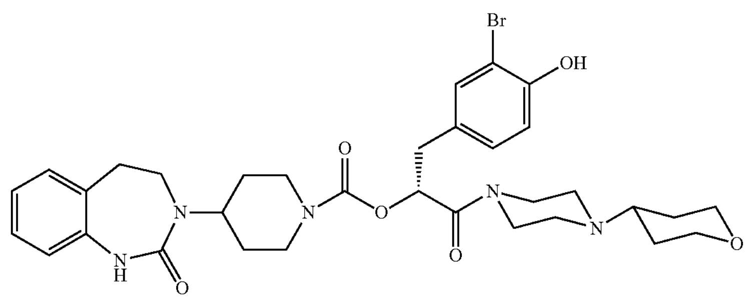 | (R)-1-(3-bromo-4-hydroxy-benzyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |

-continued

| No. | Structure | Name |
|---|---|---|
| (449) | 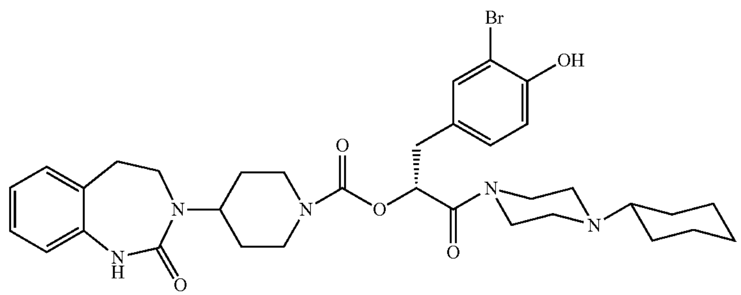 | (R)-1-(3-bromo-4-hydroxy-benzyl)-2-(4-cyclohexyl-piperazin-1-yl)-2-oxo-ethyl 4-(2-oxo-1,2,4,5-tetrahydro-1,3-benzodiazepin-3-yl)-piperidine-1-carboxylate |
| (450) | 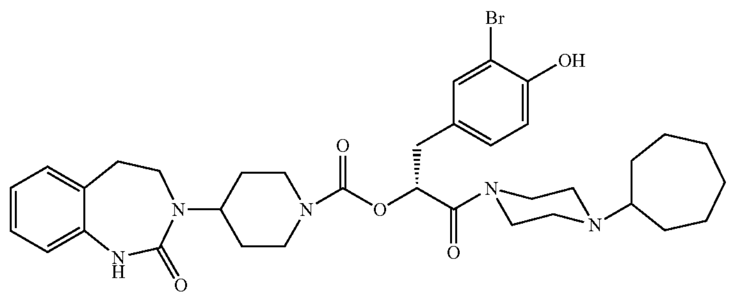 | (R)-1-(3-bromo-4-hydroxy-benzyl)-2-(4-cycloheptyl-piperazin-1-yl)-2-oxo-ethyl 4-(2-oxo-1,2,4,5-tetrahydro-1,3-benzodiazepin-3-yl)-piperidine-1-carboxylate |
| (451) | 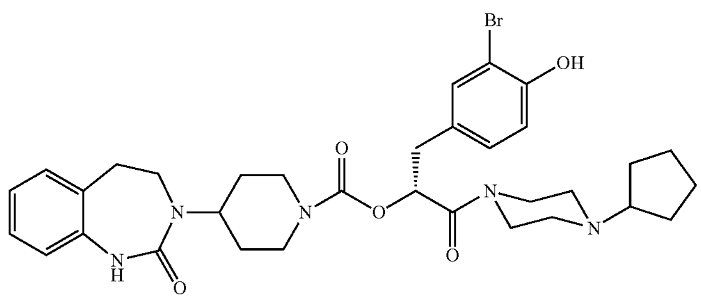 | (R)-1-(3-bromo-4-hydroxy-benzyl)-2-(4-cyclopentyl-piperazin-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (452) | 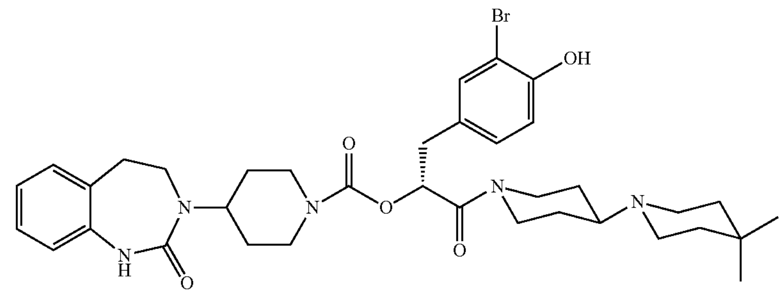 | (R)-1-(3-bromo-4-hydroxy-benzyl)-2-(4,4-dimethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (453) | 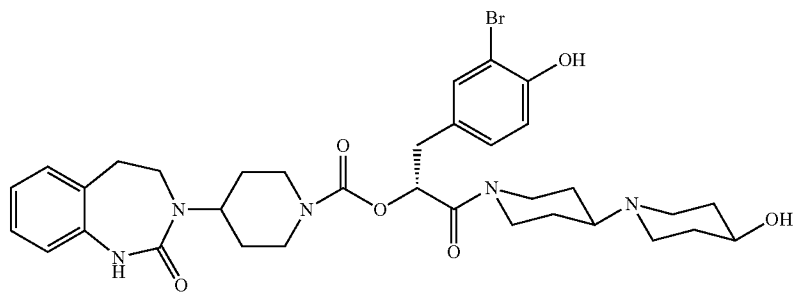 | (R)-1-(3-bromo-4-hydroxy-benzyl)-2-(4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (454) | 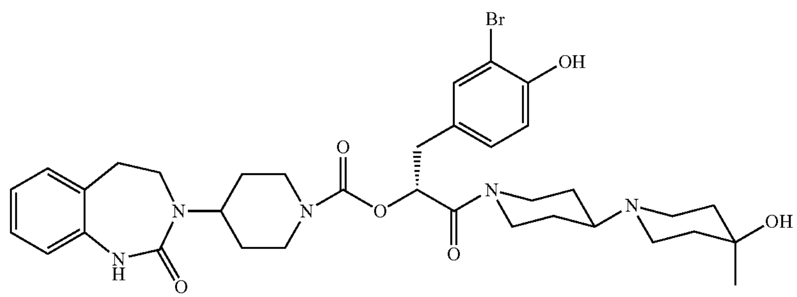 | (R)-1-(3-bromo-4-hydroxy-benzyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (455) | 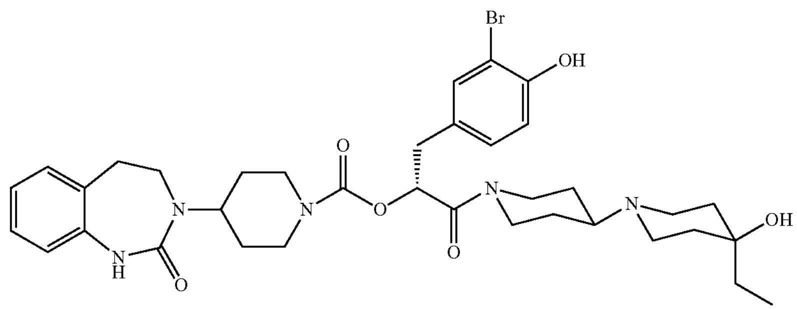 | (R)-1-(3-bromo-4-hydroxy-benzyl)-2-(4-ethyl-4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (456) | 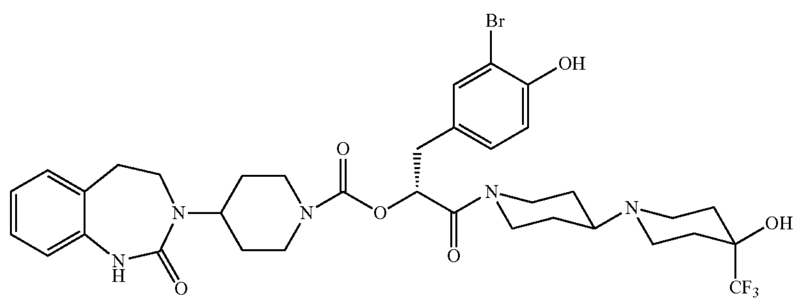 | (R)-1-(3-bromo-4-hydroxy-benzyl)-2-(4-hydroxy-4-trifluormethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (457) | 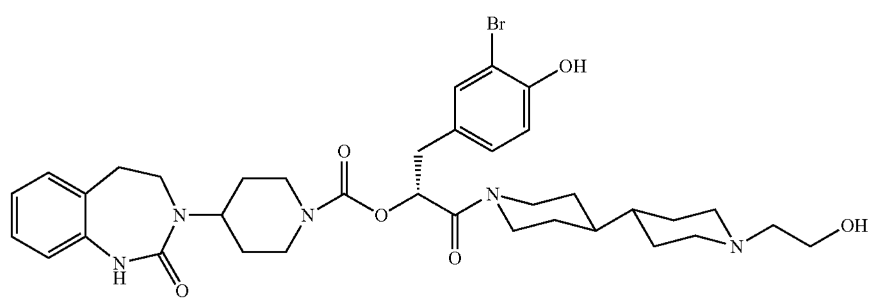 | (R)-1-(3-bromo-4-hydroxy-benzyl)-2-[1'-(2-hydroxy-ethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (458) | 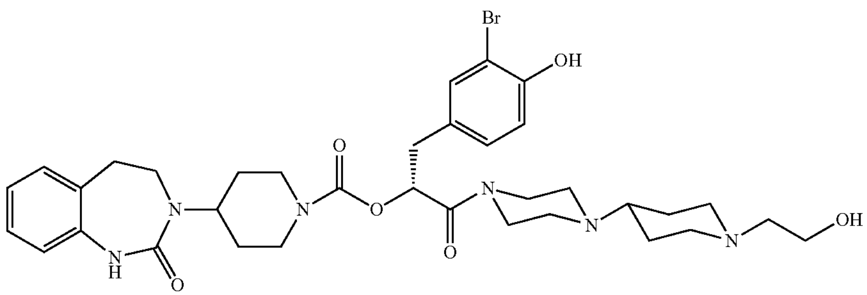 | (R)-1-(3-bromo-4-hydroxy-benzyl)-2-{4-[1-(2-hydroxy-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |
| (459) | 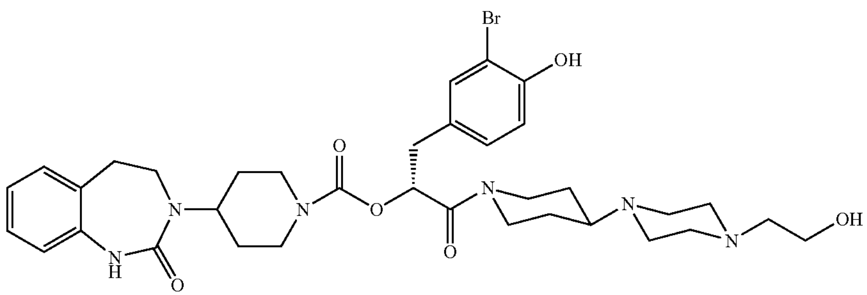 | (R)-1-(3-bromo-4-hydroxy-benzyl)-2-{4-[4-(2-hydroxy-ethyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |
| (460) | 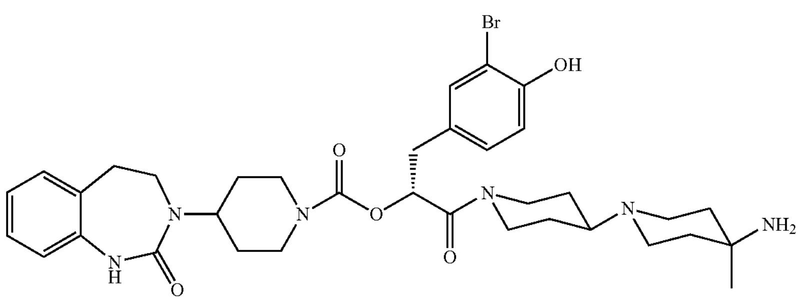 | (R)-2-(4-amino-4-methyl-1,4'-bipiperidinyl-1'-yl)-1-(3-bromo-4-hydroxy-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (461) | 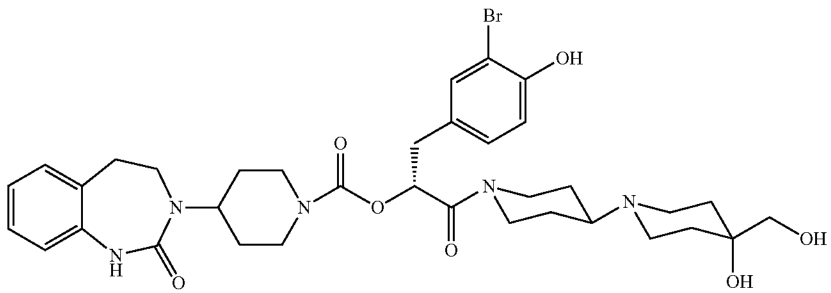 | (R)-1-(3-bromo-4-hydroxy-benzyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (462) | 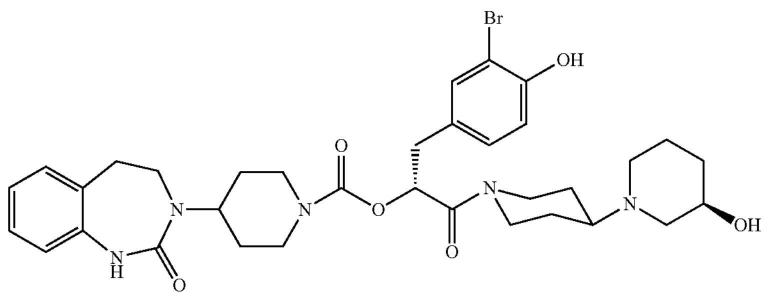 | (R)-1-(3-bromo-4-hydroxy-benzyl)-2-((R)-3-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (463) | 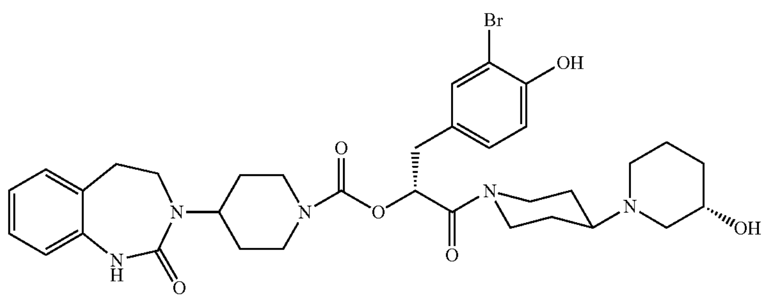 | (R)-1-(3-bromo-4-hydroxy-benzyl)-2-((S)-3-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (464) | 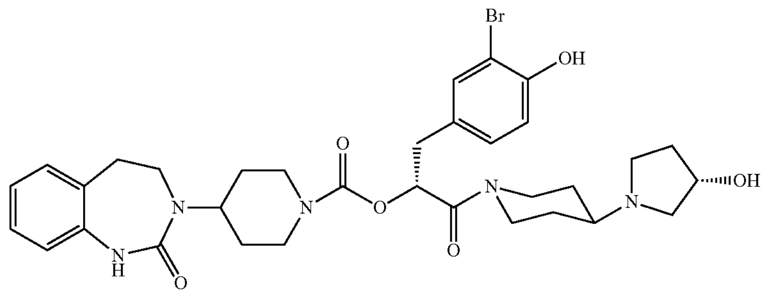 | (R)-1-(3-bromo-4-hydroxy-benzyl)-2-[4-((S)-3-hydroxy-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |
| (465) | 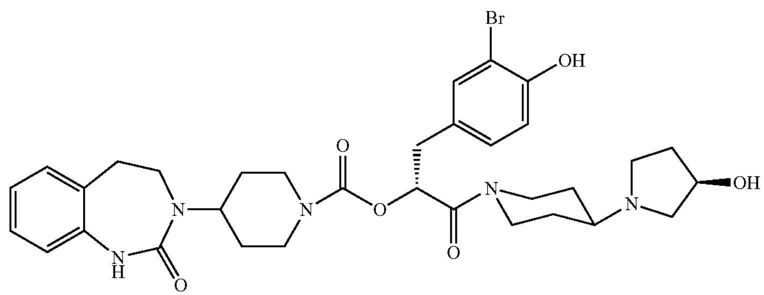 | (R)-1-(3-bromo-4-hydroxy-benzyl)-2-[4-((R)-3-hydroxy-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |
| (466) | 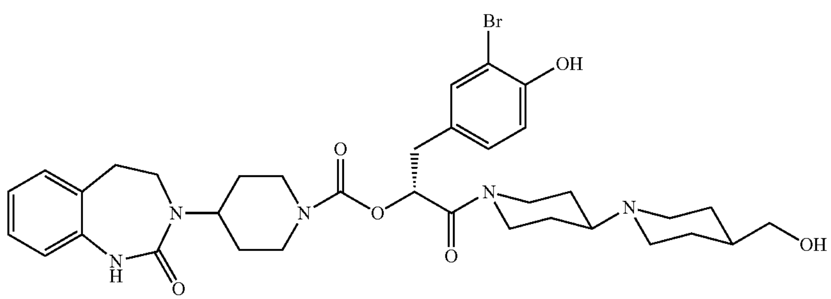 | (R)-1-(3-bromo-4-hydroxy-benzyl)-2-(4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (467) | 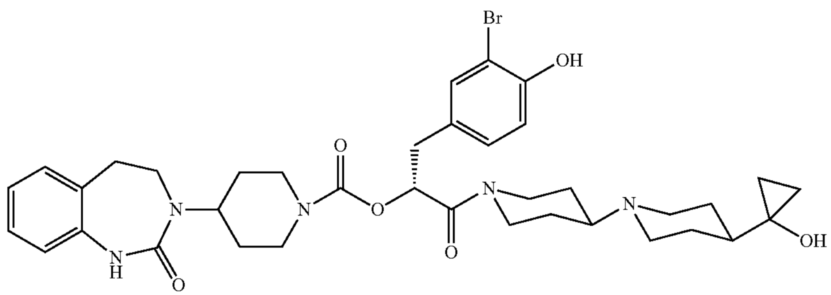 | (R)-1-(3-bromo-4-hydroxy-benzyl)-2-[4-(1-hydroxy-cyclopropyl)-1,4'-bipiperidinyl-1'-yl]-2-oxo-ethyl 4-(2-oxo-1,2,4,5-tetrahydro-1,3-benzodiazepin-3-yl)-piperidine-1-carboxylate |
| (468) | 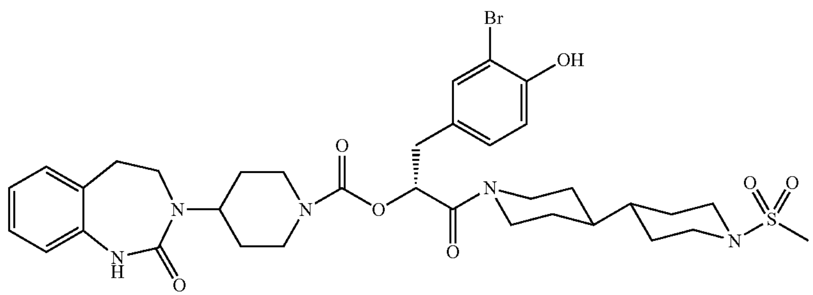 | (R)-1-(3-bromo-4-hydroxy-benzyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (469) | 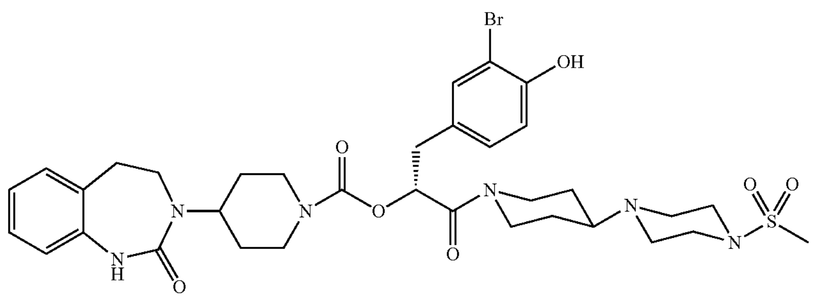 | (R)-1-(3-bromo-4-hydroxy-benzyl)-2-[4-(4-methanesulphonyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (470) | 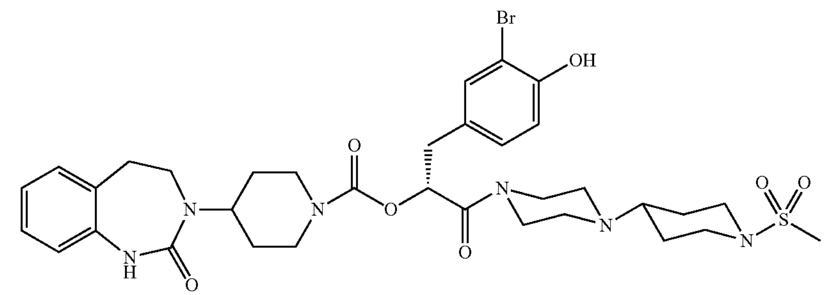 | (R)-1-(3-bromo-4-hydroxy-benzyl)-2-[4-(1-methanesulphonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (471) | 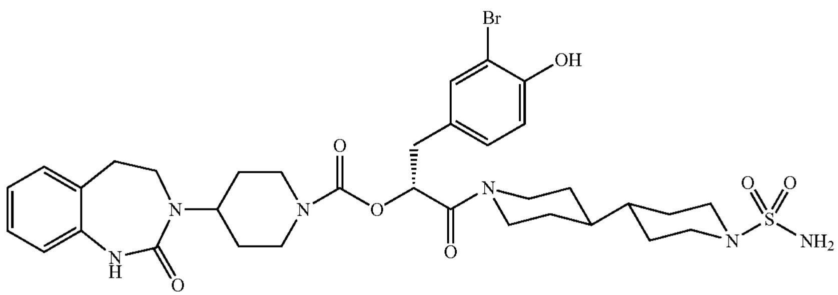 | (R)-1-(3-bromo-4-hydroxy-benzyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (472) | 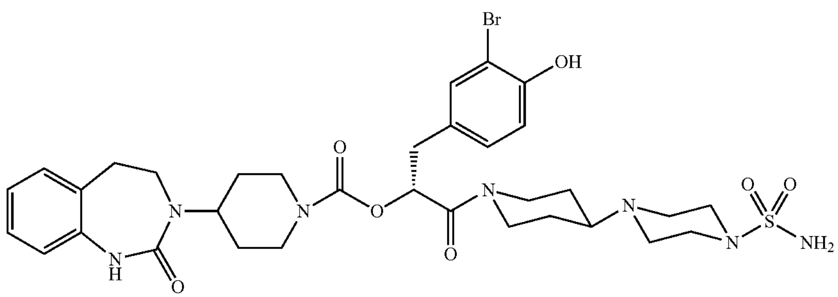 | (R)-1-(3-bromo-4-hydroxy-benzyl)-2-oxo-2-[4-(4-sulphamoyl-piperazin-1-yl)-piperidin-1-yl]-ethyl 4-(2-oxo-1,2,4,5-tetrahydro-1,3-benzodiazepin-3-yl)-piperidine-1-carboxylate |

-continued

| No. | Structure | Name |
|---|---|---|
| (473) | 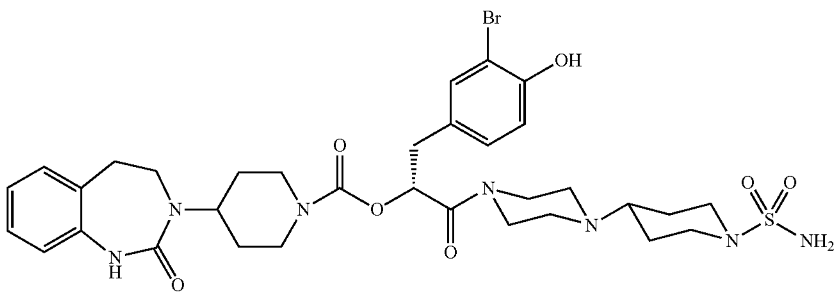 | (R)-1-(3-bromo-4-hydroxy-benzyl)-2-oxo-2-[4-(1-sulphamoyl-piperidin-4-yl)-piperazin-1-yl]-ethyl 4-(2-oxo-1,2,4,5-tetrahydro-1,3-benzodiazepin-3-yl)-piperidine-1-carboxylate |
| (474) | 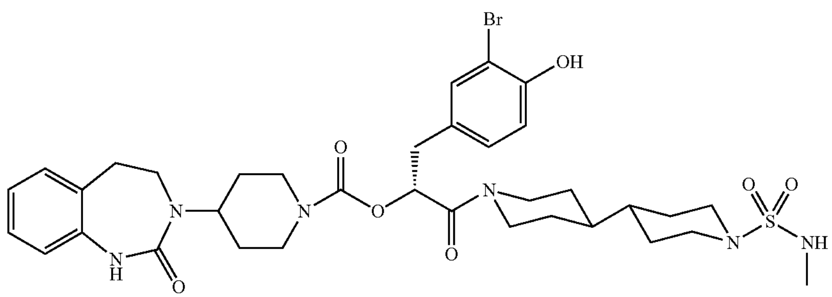 | (R)-1-(3-bromo-4-hydroxy-benzyl)-2-(1'-methylsulphamoyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (475) | 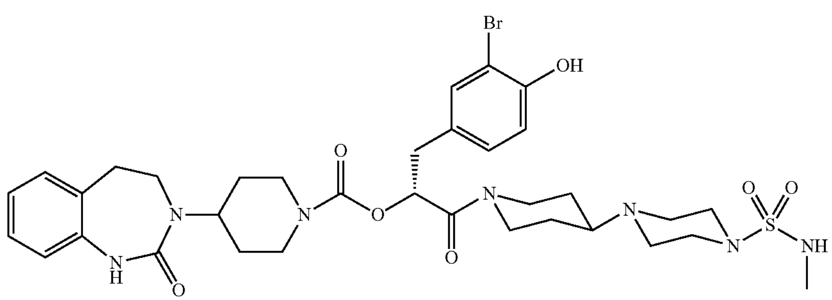 | (R)-1-(3-bromo-4-hydroxy-benzyl)-2-[4-(4-methylsulphamoyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (476) | 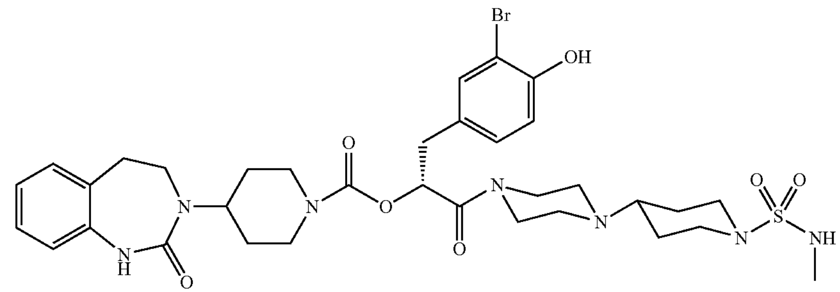 | (R)-1-(3-bromo-4-hydroxy-benzyl)-2-[4-(1-methylsulphamoyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (477) | 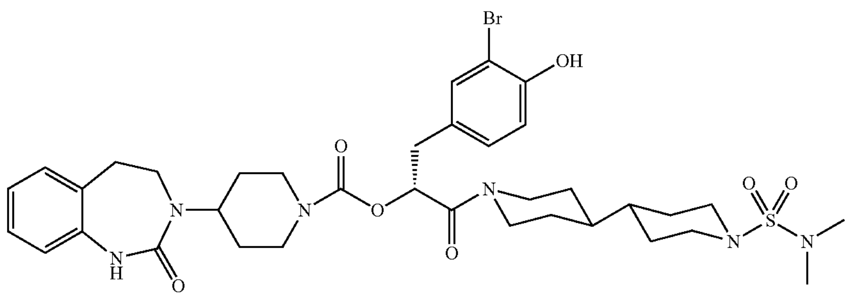 | (R)-1-(3-bromo-4-hydroxy-benzyl)-2-(1'-dimethylsulphamoyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (478) | 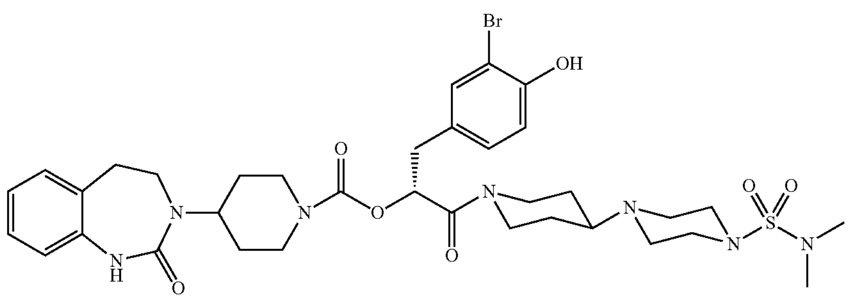 | (R)-1-(3-bromo-4-hydroxy-benzyl)-2-[4-(4-dimethylsulphamoyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (479) | 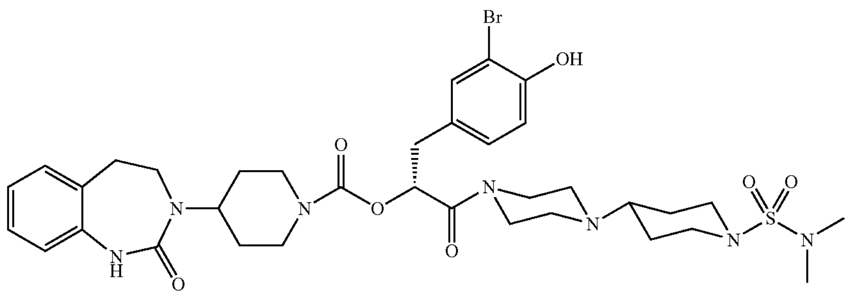 | (R)-1-(3-bromo-4-hydroxy-benzyl)-2-[4-(1-dimethylsulphamoyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (480) | 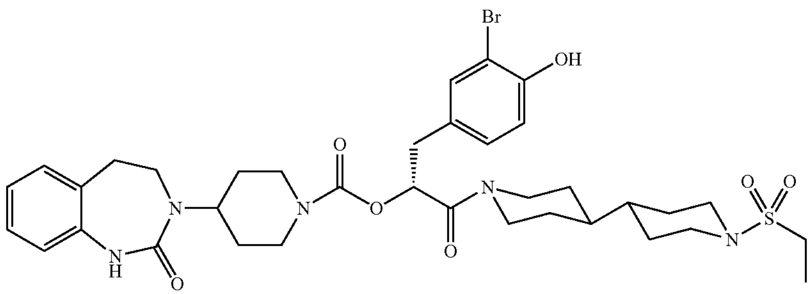 | (R)-1-(3-bromo-4-hydroxy-benzyl)-2-(1'-ethanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (481) | 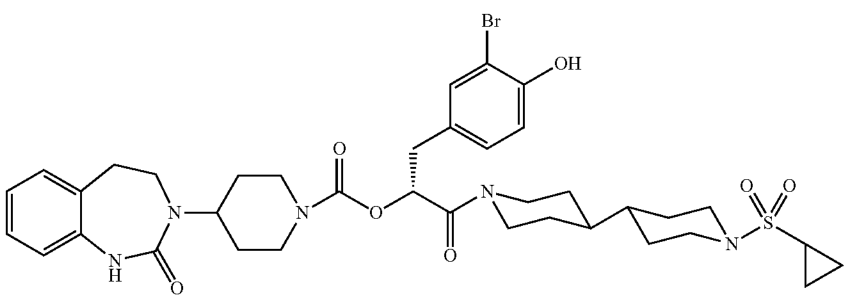 | (R)-1-(3-bromo-4-hydroxy-benzyl)-2-(1'-cyclopropanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (482) | 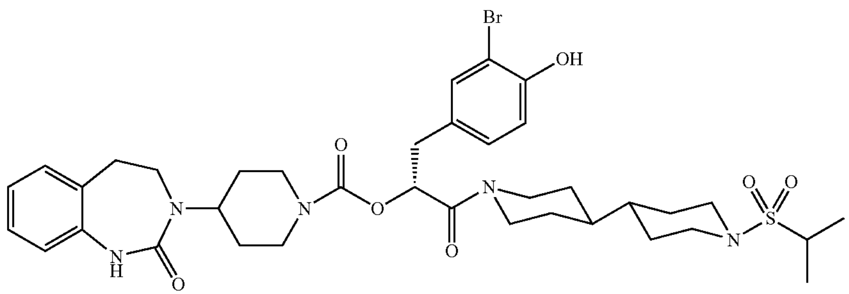 | (R)-1-(3-bromo-4-hydroxy-benzyl)-2-oxo-2-[1'-(propan-2-sulphonyl)-4,4'-bipiperidinyl-1-yl]-ethyl 4-(2-oxo-1,2,4,5-tetrahydro-1,3-benzodiazepin-3-yl)-piperidine-1-carboxylate |
| (483) | 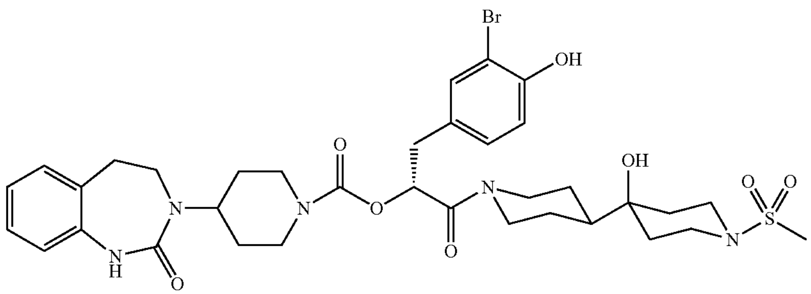 | (R)-1-(3-bromo-4-hydroxy-benzyl)-2-(4'-hydroxy-1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (484) | 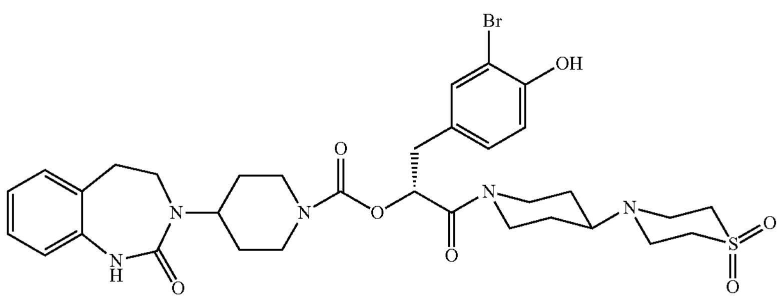 | (R)-1-(3-bromo-4-hydroxy-benzyl)-2-[4-(1,1-dioxo-1$\lambda^6$-thiomorpholin-4-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (485) | 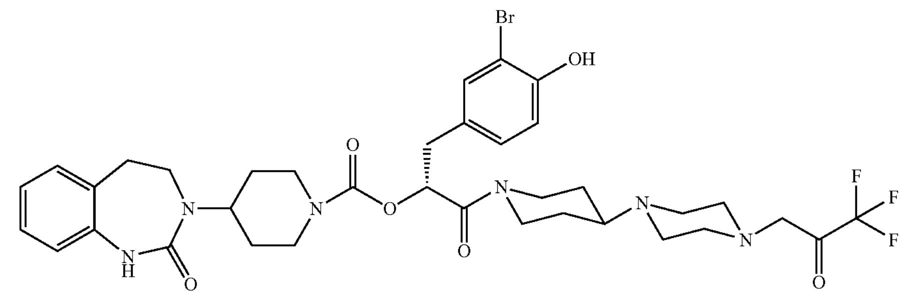 | (R)-1-(3-bromo-4-hydroxy-benzyl)-2-oxo-2-{4-[4-(3,3,3-trifluoro-2-oxo-propyl)-piperazin-1-yl]-piperidin-1-yl}-ethyl 4-(2-oxo-1,2,4,5-tetrahydro-1,3-benzodiazepin-3-yl)-piperidine-1-carboxylate |
| (486) | 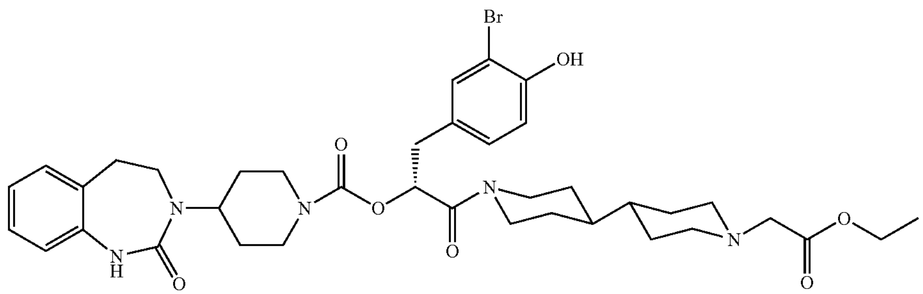 | (R)-1-(3-bromo-4-hydroxy-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (487) | 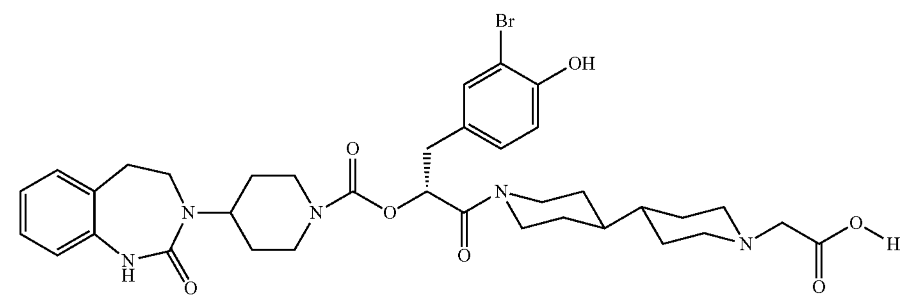 | (R)-1-(3-bromo-4-hydroxy-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (488) | 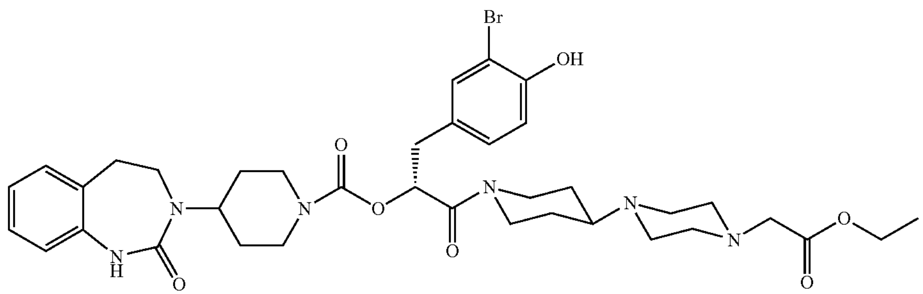 | (R)-1-(3-bromo-4-hydroxy-benzyl)-2-[4-(4-ethoxycarbonylmethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (489) | 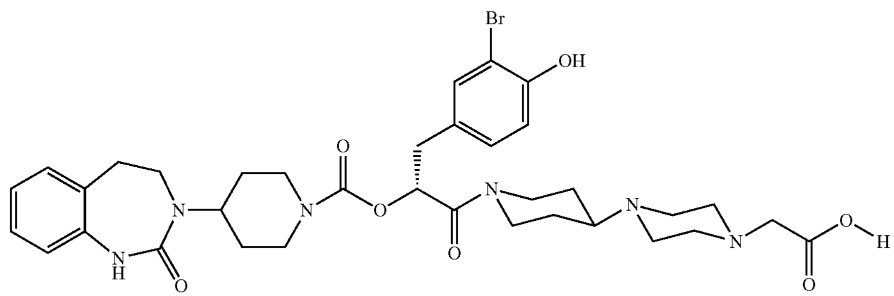 | (R)-1-(3-bromo-4-hydroxy-benzyl)-2-[4-(4-carboxymethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (490) | 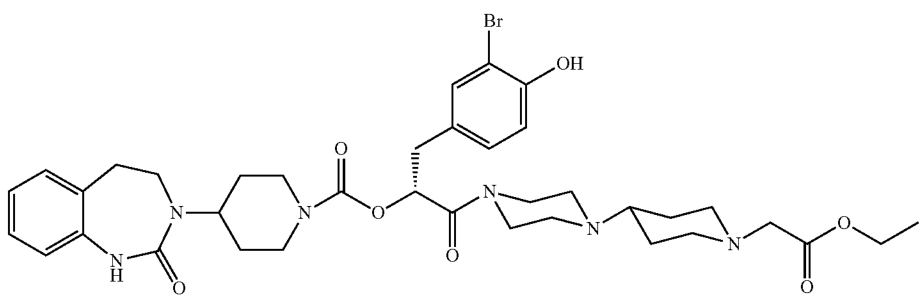 | (R)-1-(3-bromo-4-hydroxy-benzyl)-2-[4-(1-ethoxycarbonylmethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (491) | 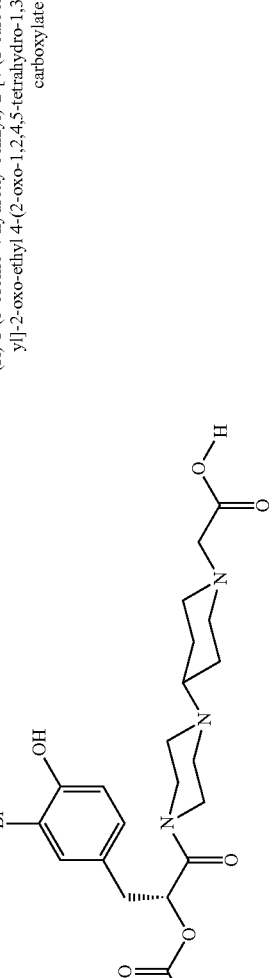 | (R)-1-(3-bromo-4-hydroxy-benzyl)-2-[4-(1-carboxymethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (492) | 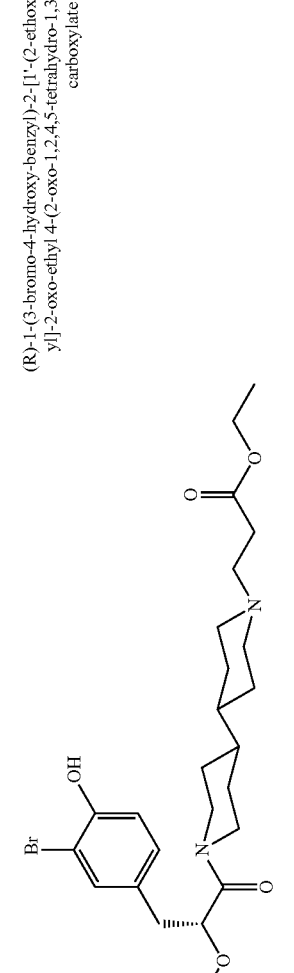 | (R)-1-(3-bromo-4-hydroxy-benzyl)-2-[1'-(2-ethoxycarbonyl-ethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |
| (493) | 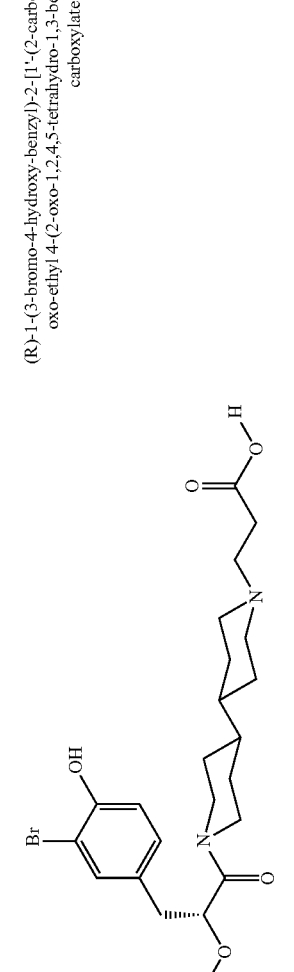 | (R)-1-(3-bromo-4-hydroxy-benzyl)-2-[1'-(2-carboxy-ethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (494) | 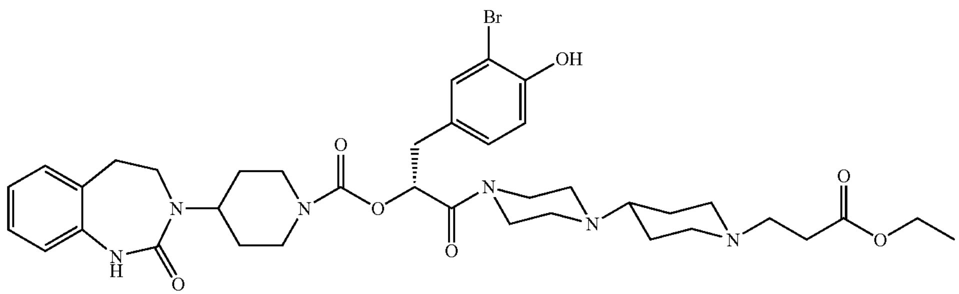 | (R)-1-(3-bromo-4-hydroxy-benzyl)-2-{4-[1-(2-ethoxycarbonyl-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |
| (495) | 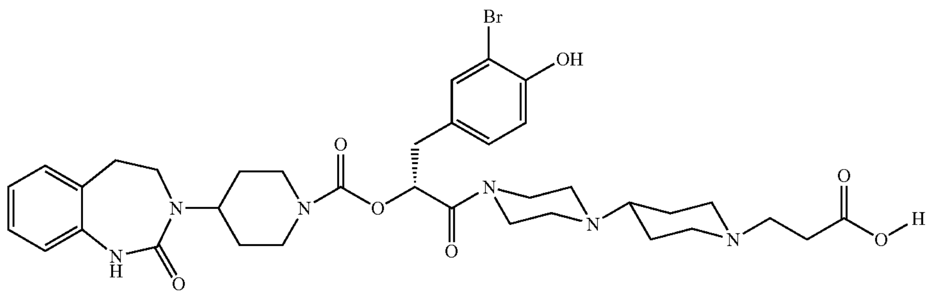 | (R)-1-(3-bromo-4-hydroxy-benzyl)-2-{4-[1-(2-carboxy-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |
| (496) | 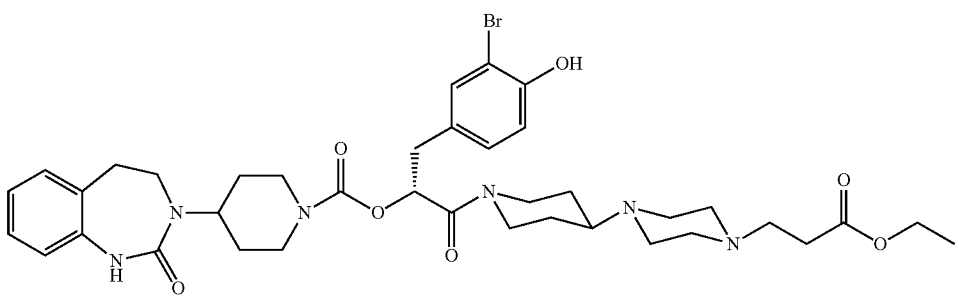 | (R)-1-(3-bromo-4-hydroxy-benzyl)-2-{4-[4-(2-ethoxycarbonyl-ethyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (497) | 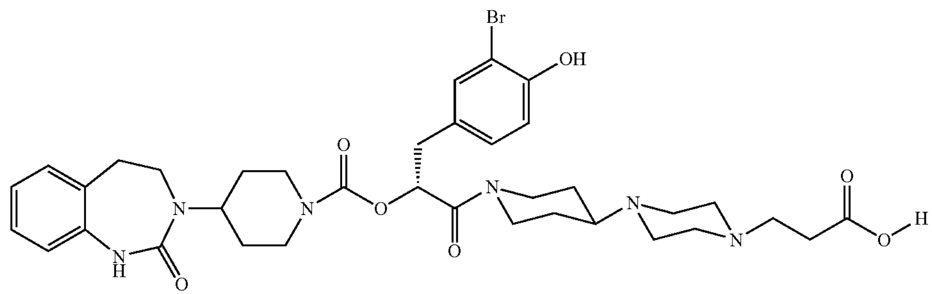 | (R)-1-(3-bromo-4-hydroxy-benzyl)-2-{4-[4-(2-carboxy-ethyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |
| (498) | 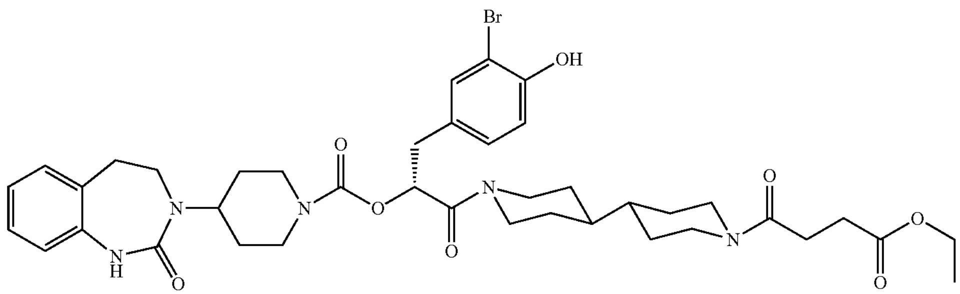 | (R)-1-(3-bromo-4-hydroxy-benzyl)-2-[1'-(3-ethoxycarbonyl-propionyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |
| (499) | 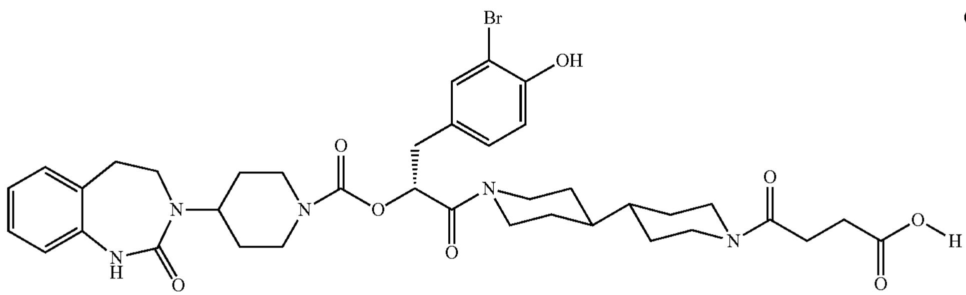 | (R)-1-(3-bromo-4-hydroxy-benzyl)-2-[1'-(3-carboxy-propionyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (500) | 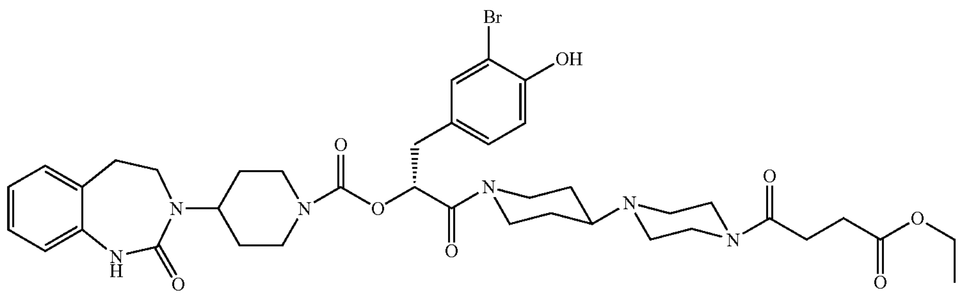 | (R)-1-(3-bromo-4-hydroxy-benzyl)-2-{4-[4-(3-ethoxycarbonyl-propionyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |
| (501) | 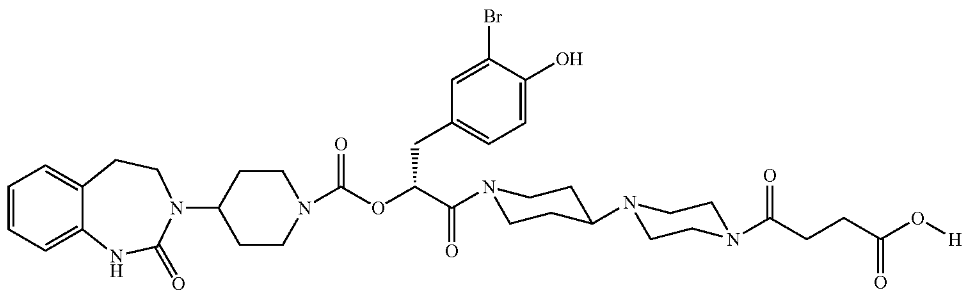 | (R)-1-(3-bromo-4-hydroxy-benzyl)-2-{4-[4-(3-carboxy-propionyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |
| (502) | 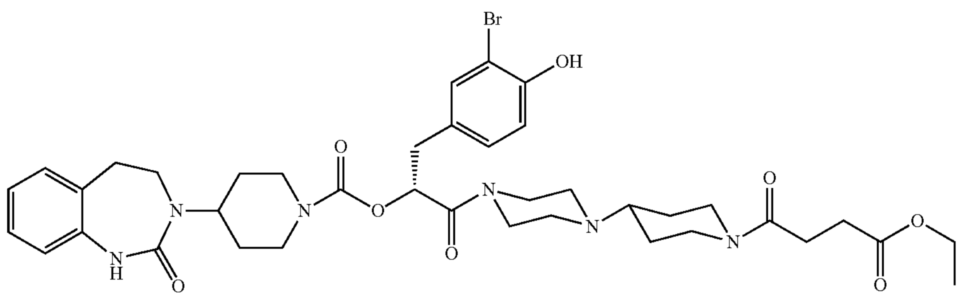 | (R)-1-(3-bromo-4-hydroxy-benzyl)-2-{4-[1-(3-ethoxycarbonyl-propionyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (503) | 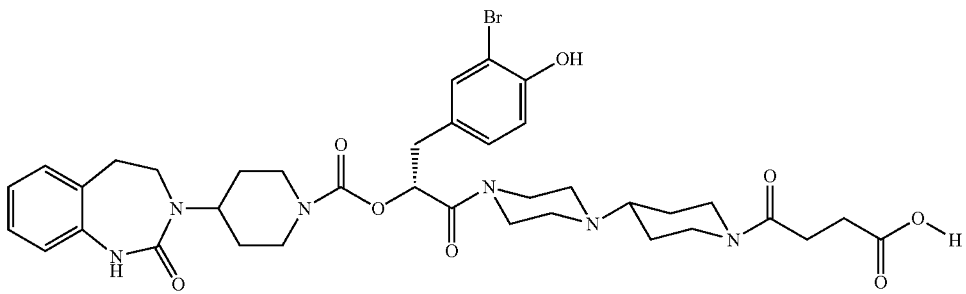 | (R)-1-(3-bromo-4-hydroxy-benzyl)-2-{4-[1-(3-carboxy-propionyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |
| (504) | 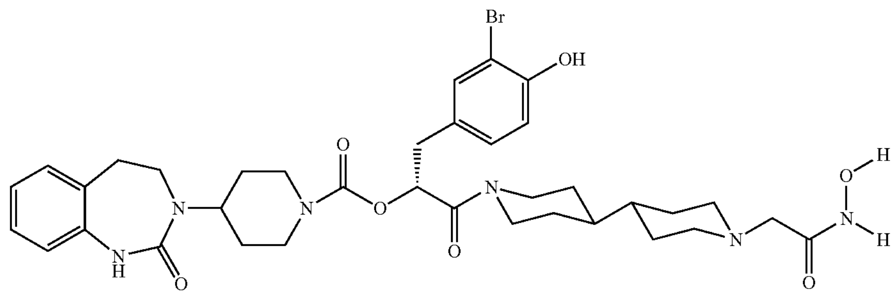 | (R)-1-(3-bromo-4-hydroxy-benzyl)-2-(1'-hydroxycarbamoylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (505) | 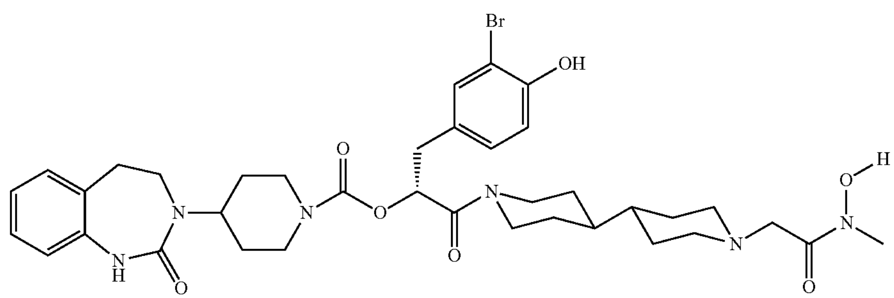 | (R)-1-(3-bromo-4-hydroxy-benzyl)-2-{1'-[(hydroxy-methyl-carbamoyl)-methyl]-4,4'-bipiperidinyl-1-yl}-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (506) | 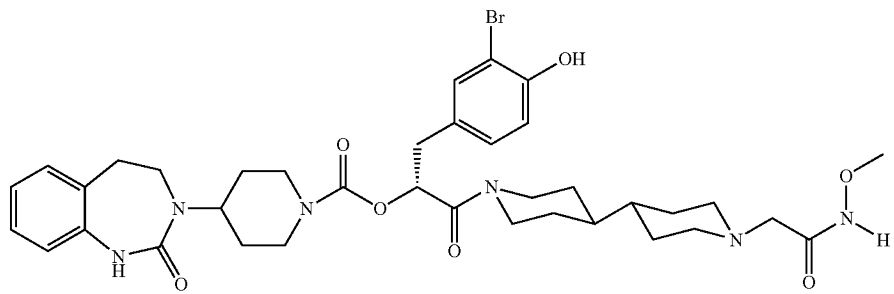 | (R)-1-(3-bromo-4-hydroxy-benzyl)-2-[1'-(methoxycarbamoyl-methyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |
| (507) | 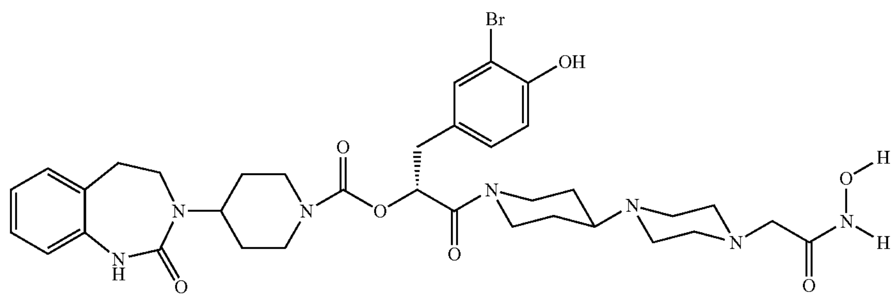 | (R)-1-(3-bromo-4-hydroxy-benzyl)-2-[4-(4-hydroxycarbamoylmethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (508) | 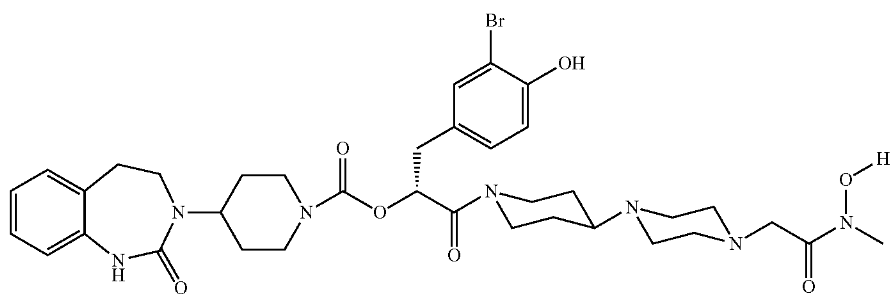 | (R)-1-(3-bromo-4-hydroxy-benzyl)-2-(4-{4-[(hydroxy-methyl-carbamoyl)-methyl]-piperazin-1-yl}-piperidin-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (509) | 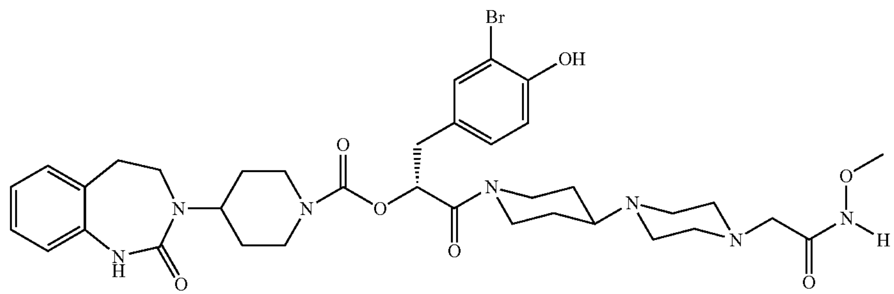 | (R)-1-(3-bromo-4-hydroxy-benzyl)-2-{4-[4-(methoxycarbamoyl-methyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |
| (510) | 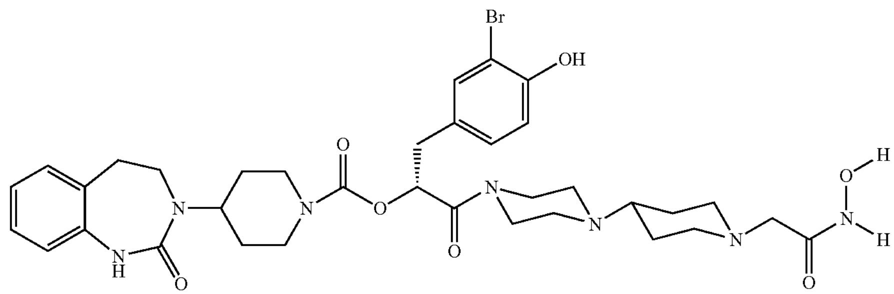 | (R)-1-(3-bromo-4-hydroxy-benzyl)-2-[4-(1-hydroxycarbamoylmethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (511) | 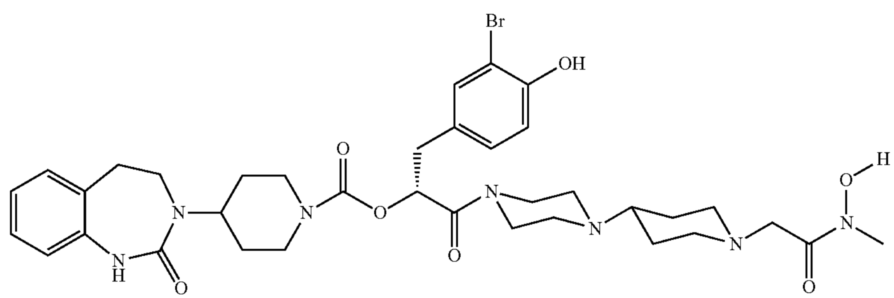 | (R)-1-(3-bromo-4-hydroxy-benzyl)-2-(4-{1-[(hydroxy-methyl-carbamoyl)-methyl]-piperidin-4-yl}-piperazin-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (512) | 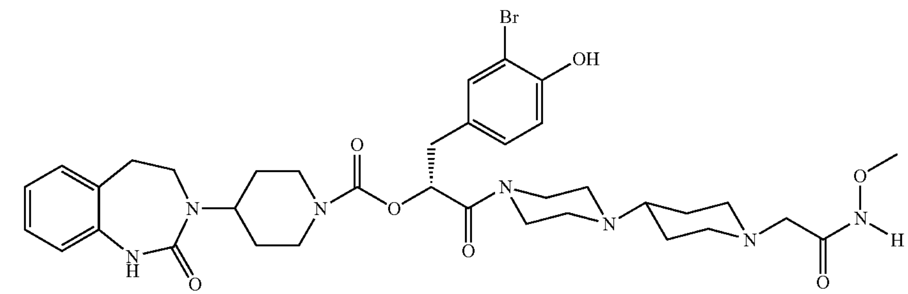 | (R)-1-(3-bromo-4-hydroxy-benzyl)-2-(4-[1-(methoxycarbamoyl-methyl)-piperidin-4-yl]-piperazin-1-yl)-2-oxo-ethyl 4-(2-oxo-1,2,4,5-tetrahydro-1,3-benzodiazepin-3-yl)-piperidine-1-carboxylate |
| (513) | 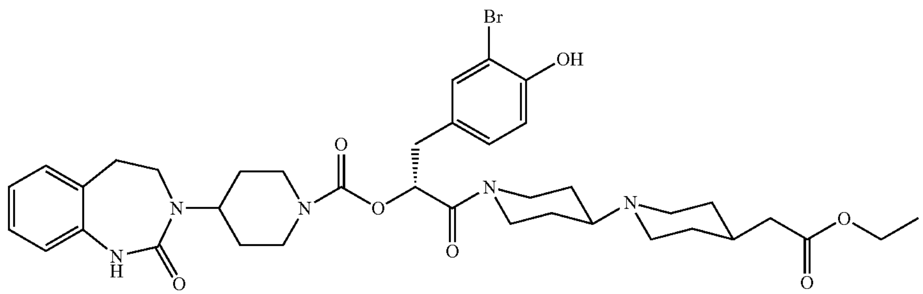 | (R)-1-(3-bromo-4-hydroxy-benzyl)-2-(4-ethoxycarbonylmethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (514) | 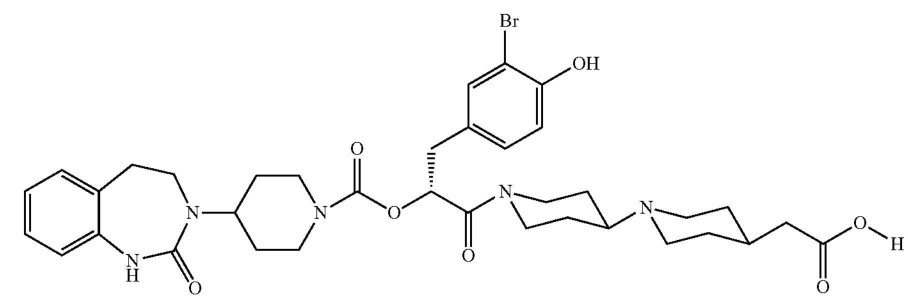 | (R)-1-(3-bromo-4-hydroxy-benzyl)-2-(4-carboxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (515) | 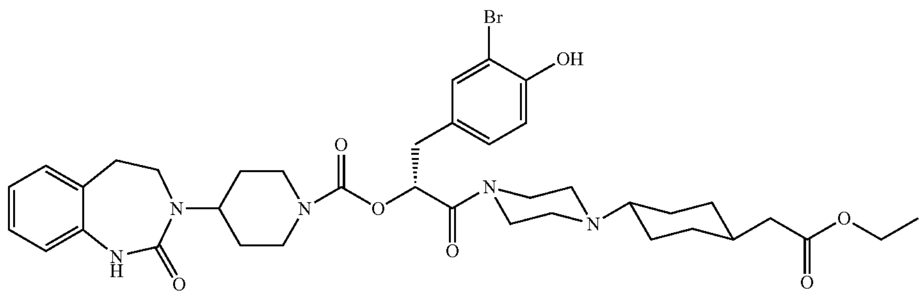 | (R)-1-(3-bromo-4-hydroxy-benzyl)-2-[4-(4-ethoxycarbonylmethyl-cyclohexyl)-piperazin-1-yl]-2-oxo-ethyl trans-4-(2-oxo-1,2,4,5-tetrahydro-1,3-benzodiazepin-3-yl)-piperidine-1-carboxylate |
| (516) | 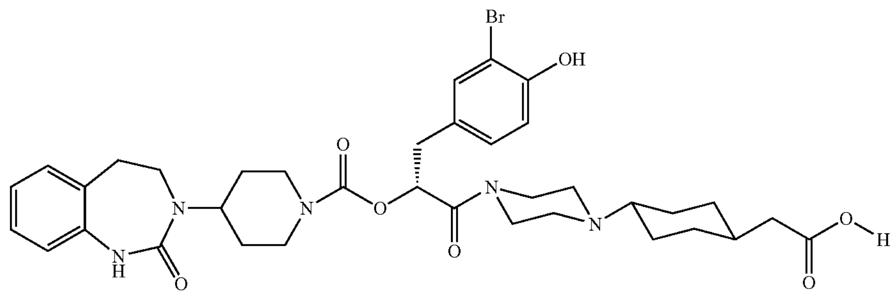 | (R)-1-(3-bromo-4-hydroxy-benzyl)-2-[4-(4-carboxymethyl-cyclohexyl)-piperazin-1-yl]-2-oxo-ethyl trans-4-(2-oxo-1,2,4,5-tetrahydro-1,3-benzodiazepin-3-yl)-piperidine-1-carboxylate |
| (517) | 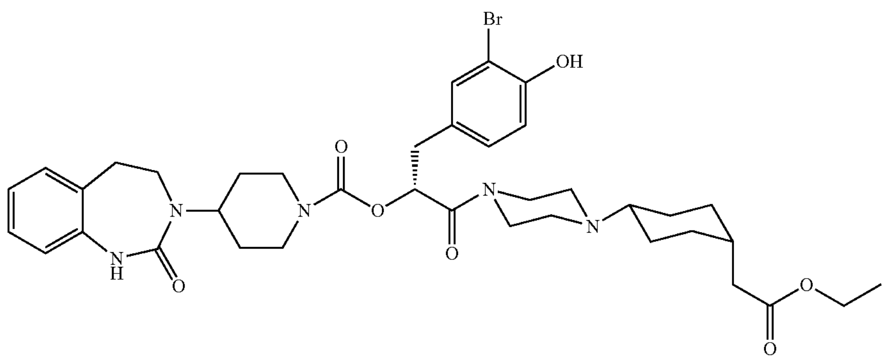 | (R)-1-(3-bromo-4-hydroxy-benzyl)-2-[4-(4-ethoxycarbonylmethyl-cyclohexyl)-piperazin-1-yl]-2-oxo-ethyl cis-4-(2-oxo-1,2,4,5-tetrahydro-1,3-benzodiazepin-3-yl)-piperidine-1-carboxylate |

| No. | Structure | Name |
|---|---|---|
| (518) | 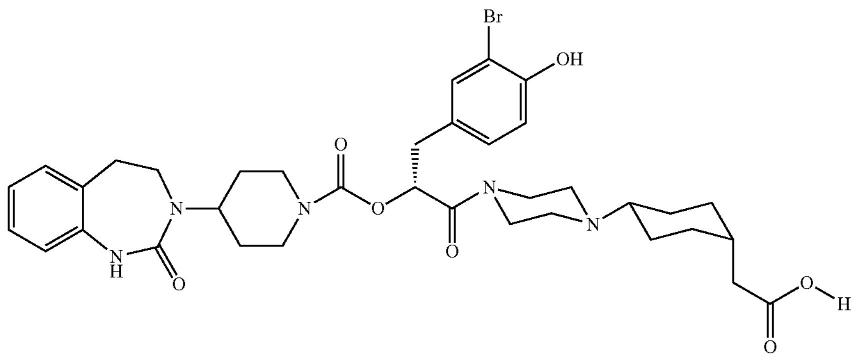 | (R)-1-(3-bromo-4-hydroxy-benzyl)-2-[4-(4-carboxymethyl-cyclohexyl)-piperazin-1-yl]-2-oxo-ethyl cis-4-(2-oxo-1,2,4,5-tetrahydro-1,3-benzodiazepin-3-yl)-piperidine-1-carboxylate |
| (519) | 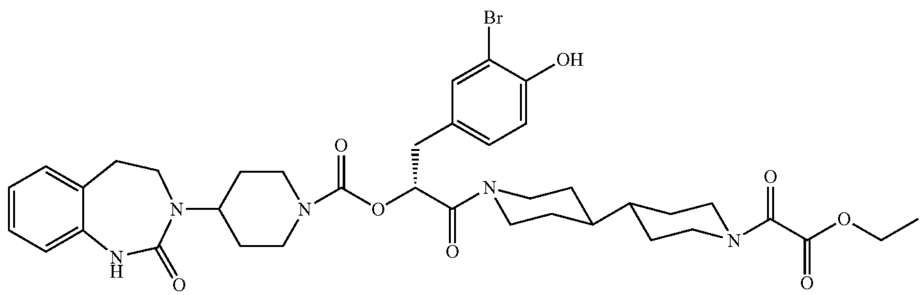 | (R)-1-(3-bromo-4-hydroxy-benzyl)-2-(1'-ethoxyoxalyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (520) | 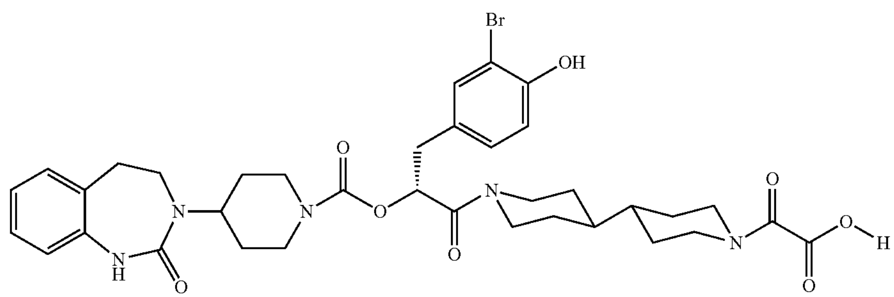 | (R)-1-(3-bromo-4-hydroxy-benzyl)-2-(1'-oxalyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (521) | 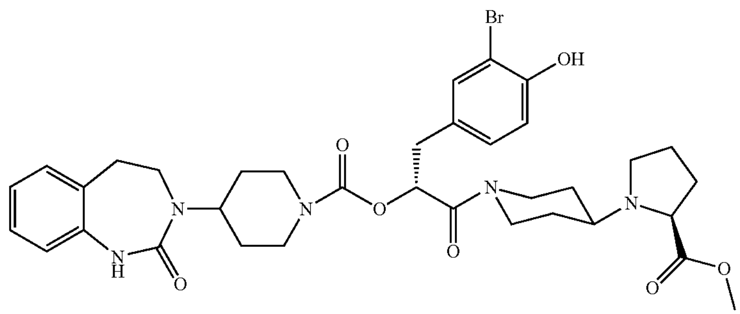 | (R)-1-(3-bromo-4-hydroxy-benzyl)-2-[4-((S)-2-methoxycarbonyl-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |
| (522) | 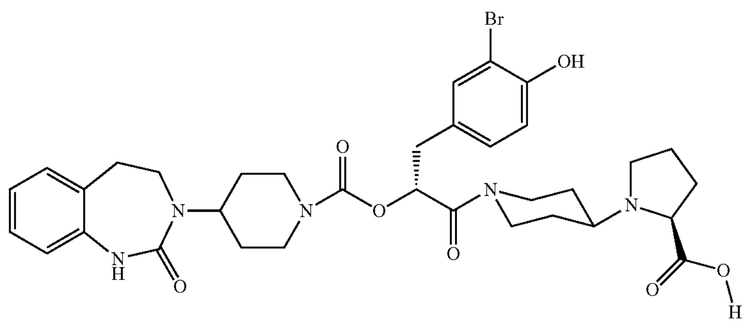 | (R)-1-(3-bromo-4-hydroxy-benzyl)-2-[4-((S)-2-carboxy-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |
| (523) | 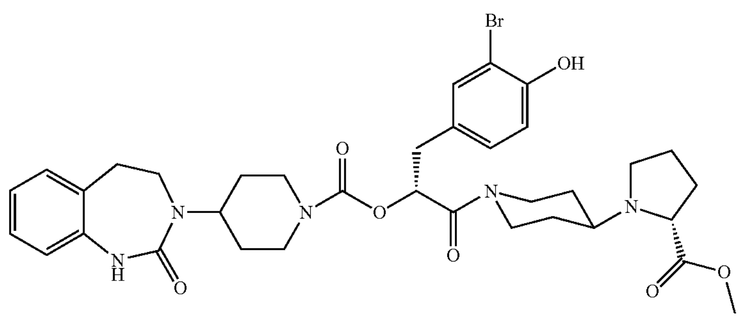 | (R)-1-(3-bromo-4-hydroxy-benzyl)-2-[4-((R)-2-methoxycarbonyl-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (524) | 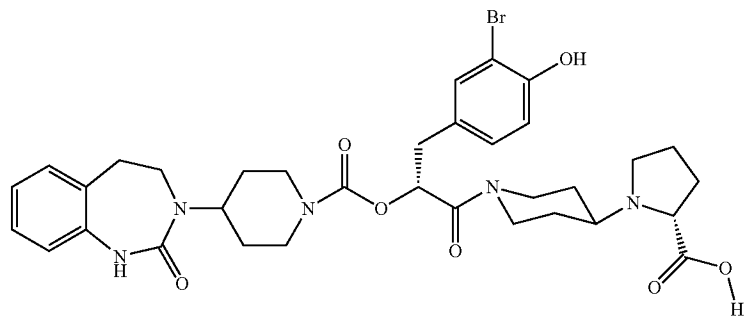 | (R)-1-(3-bromo-4-hydroxy-benzyl)-2-[4-((R)-2-carboxy-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |
| (525) | 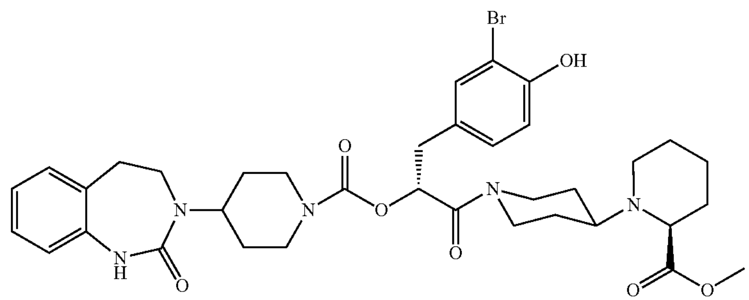 | methyl (S)-1'-{(R)-3-(3-bromo-4-hydroxy-phenyl)-2-[4-(2-oxo-1,2,4,5-tetrahydro-1,3-benzodiazepin-3-yl)-piperidin-1-carbonyloxy]-propionyl}-1,4'-bipiperidinyl-2-carboxylate |
| (526) | 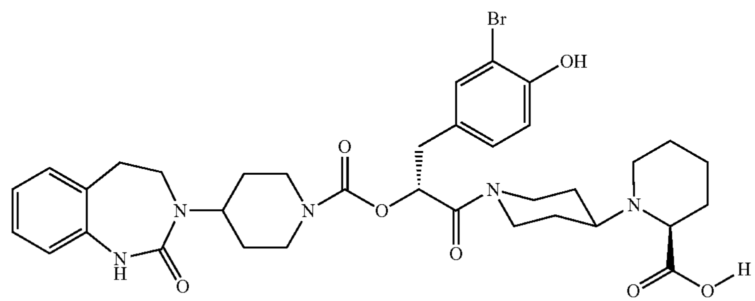 | S)-1'-{(R)-3-(3-bromo-4-hydroxy-phenyl)-2-[4-(2-oxo-1,2,4,5-tetrahydro-1,3-benzodiazepin-3-yl)-piperidin-1-carbonyloxy]-propionyl}-1,4'-bipiperidinyl-2-carboxylic acid |

-continued

| No. | Structure | Name |
|---|---|---|
| (527) | 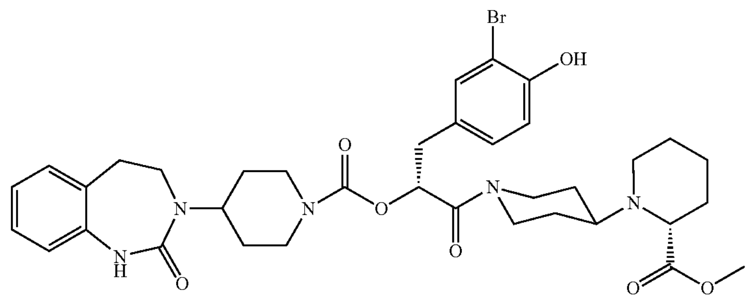 | methyl (R)-1'-{(R)-3-(3-bromo-4-hydroxy-phenyl)-2-[4-(2-oxo-1,2,4,5-tetrahydro-1,3-benzodiazepin-3-yl)-piperidin-1-carbonyloxy]-propionyl}-1,4'-bipiperidinyl-2-carboxylate |
| (528) | 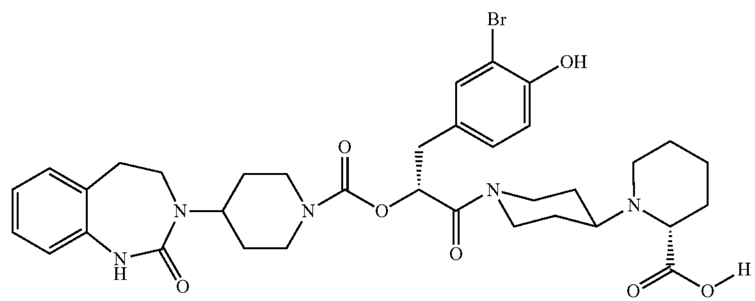 | (R)-1'-{(R)-3-(3-bromo-4-hydroxy-phenyl)-2-[4-(2-oxo-1,2,4,5-tetrahydro-1,3-benzodiazepin-3-yl)-piperidin-1-carbonyloxy]-propionyl}-1,4'-bipiperidinyl-2-carboxylic acid |
| (529) | 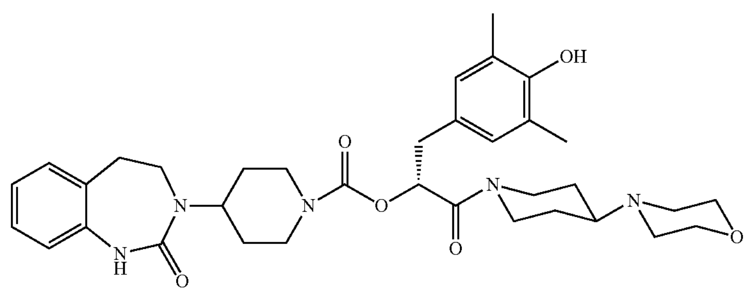 | (R)-1-(4-hydroxy-3,5-dimethyl-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (530) | 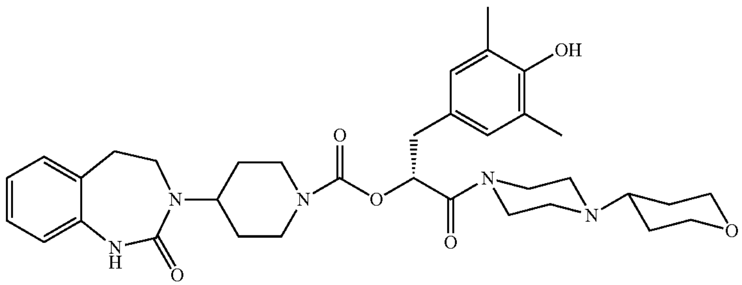 | (R)-1-(4-hydroxy-3,5-dimethyl-benzyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (531) | 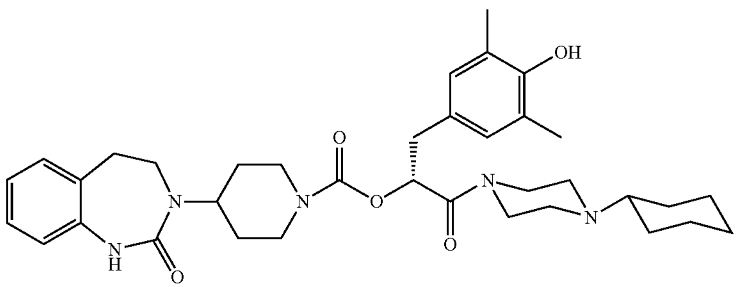 | (R)-2-(4-cyclohexyl-piperazin-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (532) | 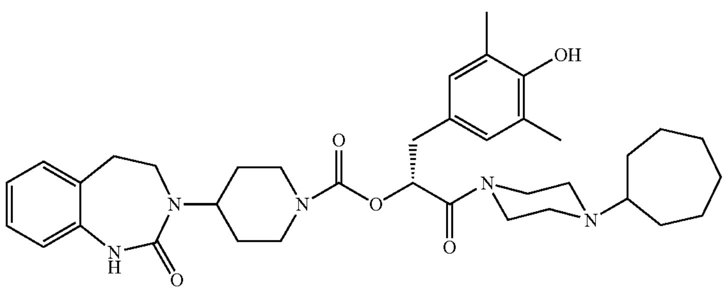 | (R)-2-(4-cycloheptyl-piperazin-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (533) | 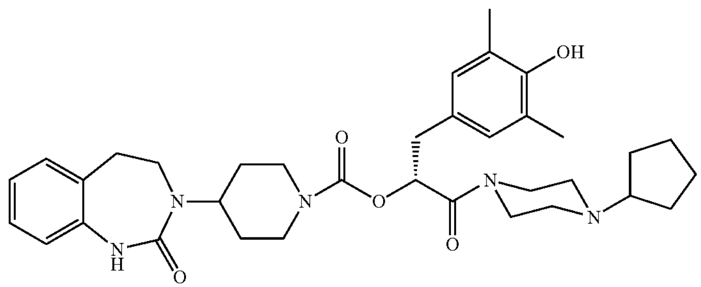 | (R)-2-(4-cyclopentyl-piperazin-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (534) | 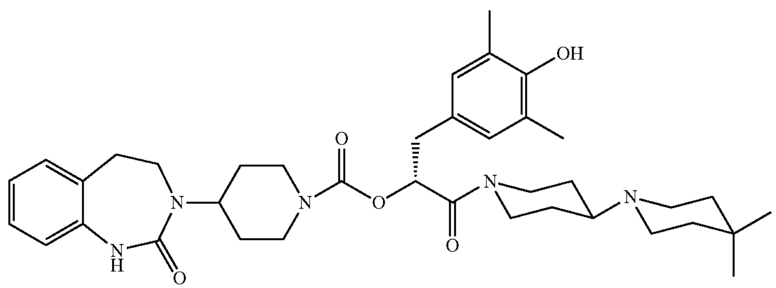 | (R)-2-(4,4-dimethyl-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (535) | 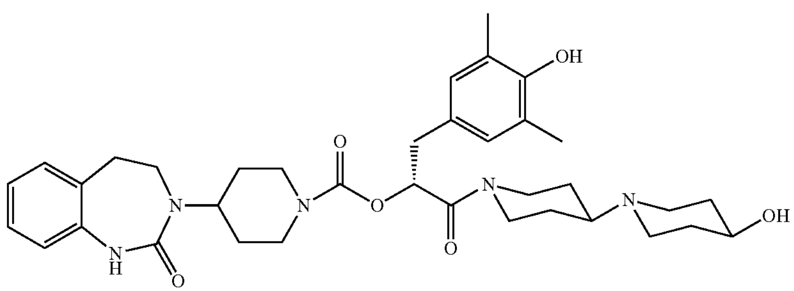 | (R)-2-(4-hydroxy-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (536) | 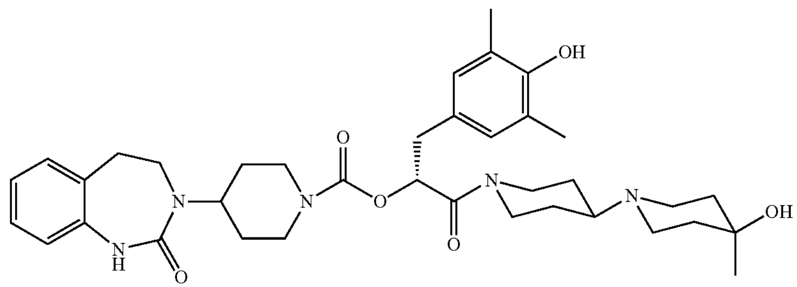 | (R)-1-(4-hydroxy-3,5-dimethyl-benzyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (537) | 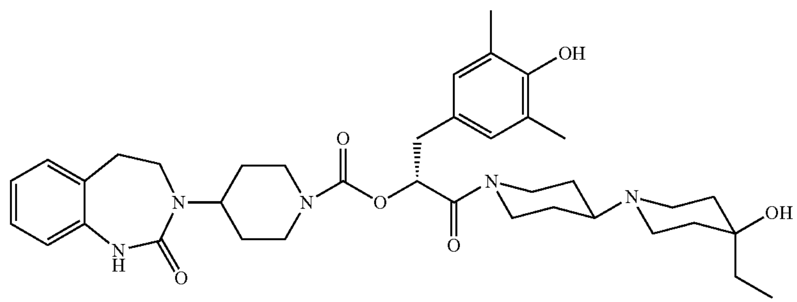 | (R)-2-(4-ethyl-4-hydroxy-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (538) | 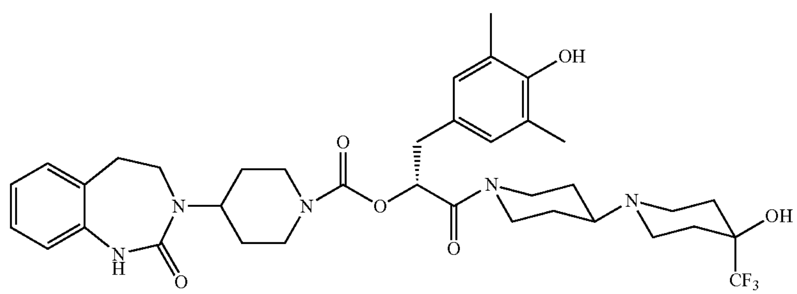 | (R)-1-(4-hydroxy-3,5-dimethyl-benzyl)-2-(4-hydroxy-4-trifluormethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (539) | 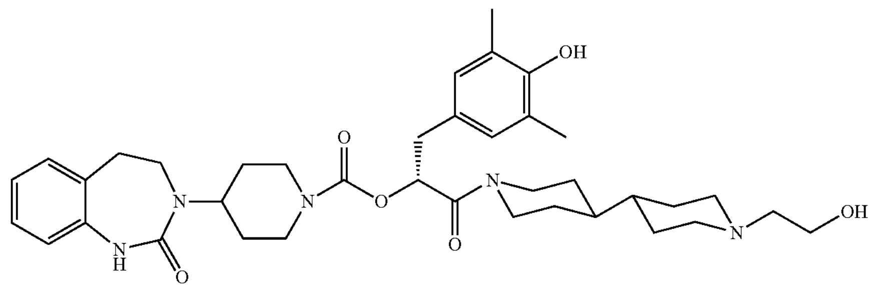 | (R)-1-(4-hydroxy-3,5-dimethyl-benzyl)-2-[1'-(2-hydroxy-ethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |
| (540) | 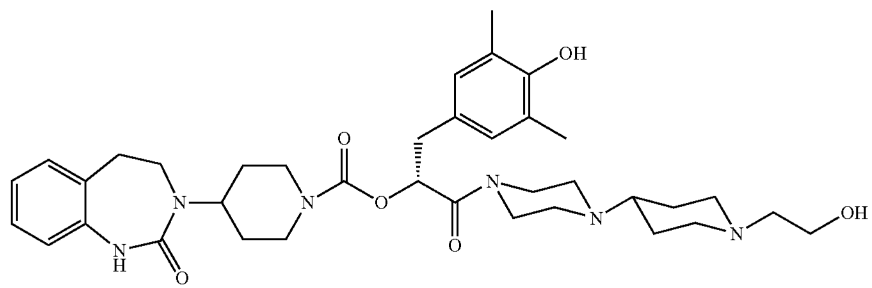 | (R)-1-(4-hydroxy-3,5-dimethyl-benzyl)-2-{4-[1-(2-hydroxy-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |
| (541) | 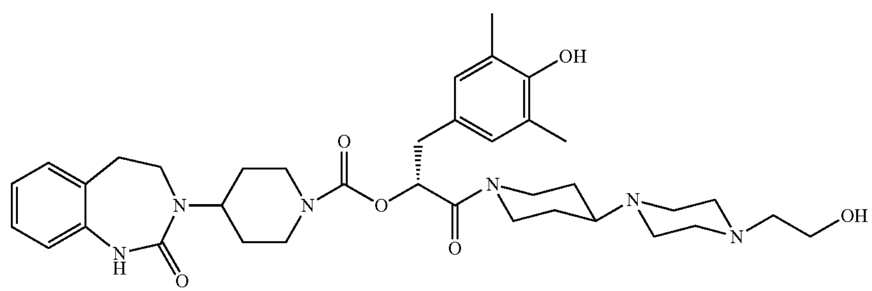 | (R)-1-(4-hydroxy-3,5-dimethyl-benzyl)-2-{4-[4-(2-hydroxy-ethyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (542) | 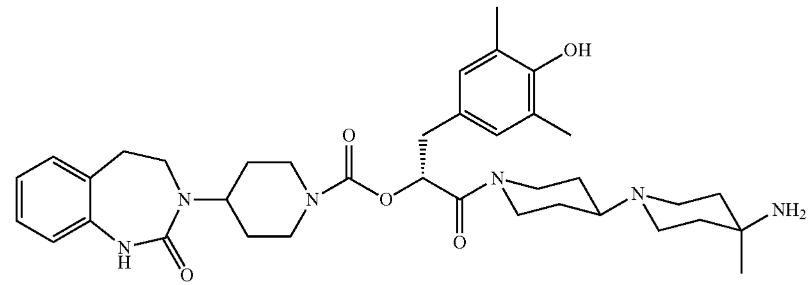 | (R)-2-(4-amino-4-methyl-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (543) | 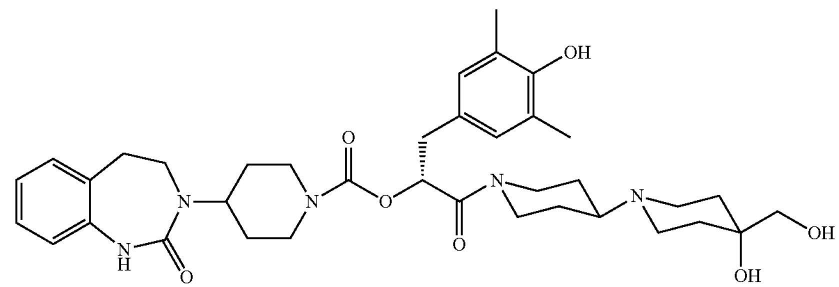 | (R)-1-(4-hydroxy-3,5-dimethyl-benzyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (544) | 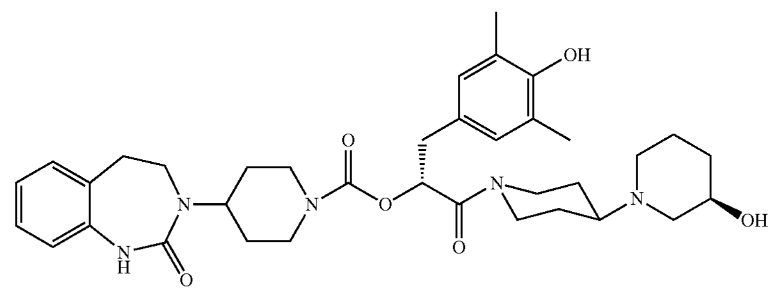 | (R)-2-((R)-3-hydroxy-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (545) | 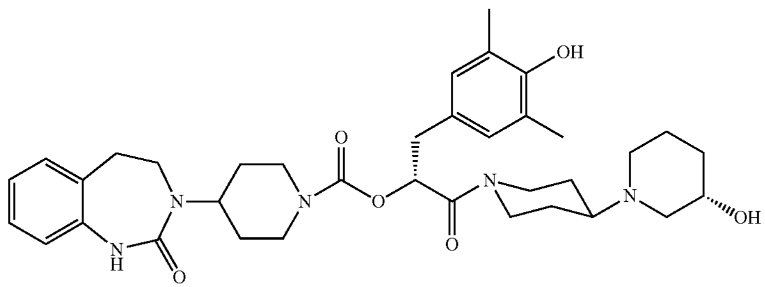 | (R)-2-((S)-3-hydroxy-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (546) | 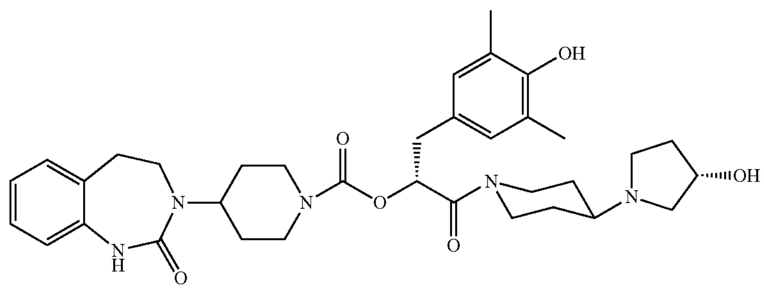 | (R)-1-(4-hydroxy-3,5-dimethyl-benzyl)-2-[4-((S)-3-hydroxy-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |
| (547) | 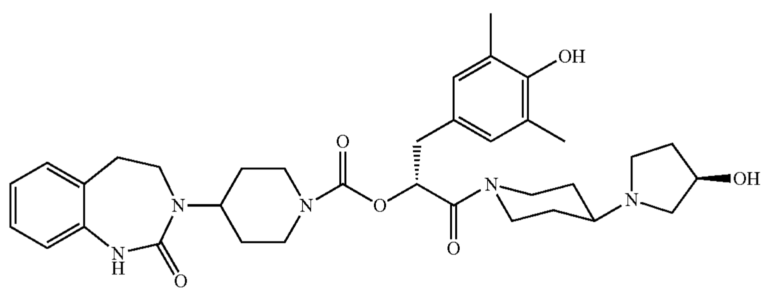 | (R)-1-(4-hydroxy-3,5-dimethyl-benzyl)-2-[4-((R)-3-hydroxy-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (548) | 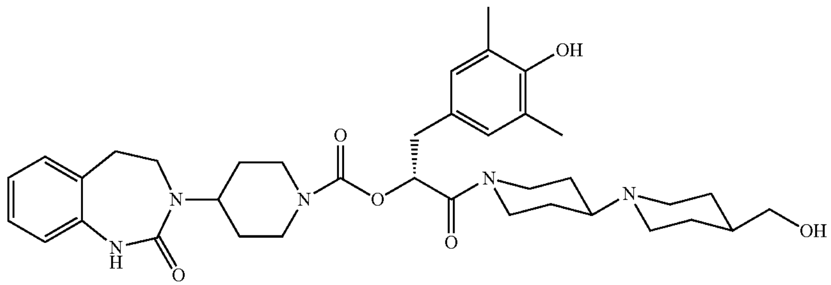 | (R)-1-(4-hydroxy-3,5-dimethyl-benzyl)-2-(4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (549) | 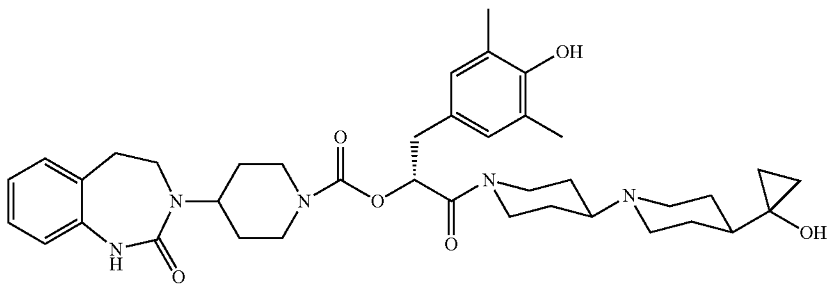 | (R)-2-[4-(1-hydroxy-cyclopropyl)-1,4'-bipiperidinyl-1'-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (550) | 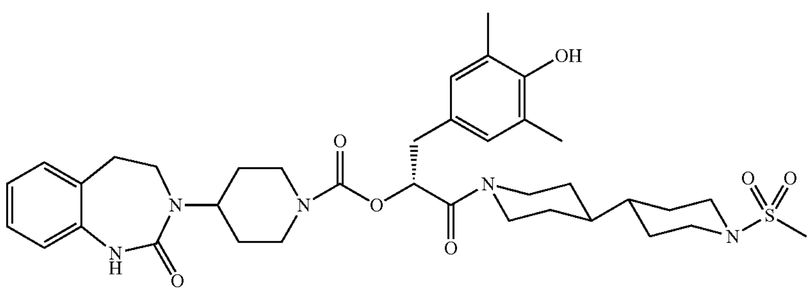 | (R)-1-(4-hydroxy-3,5-dimethyl-benzyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (551) | 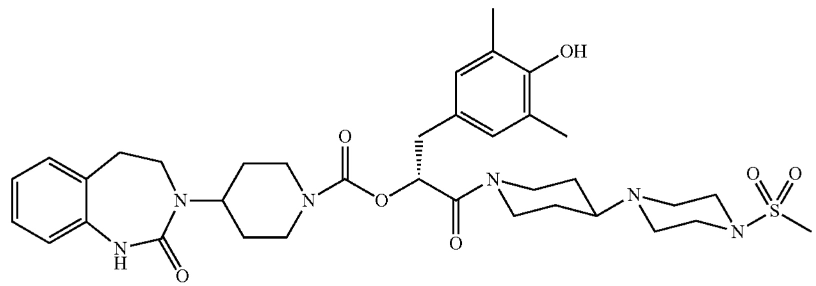 | (R)-1-(4-hydroxy-3,5-dimethyl-benzyl)-2-[4-(4-methanesulphonyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (552) | 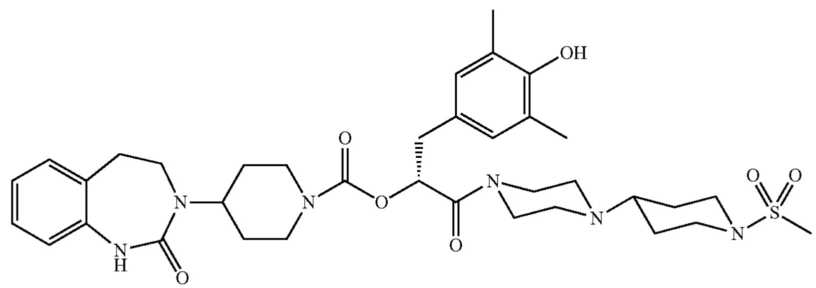 | (R)-1-(4-hydroxy-3,5-dimethyl-benzyl)-2-[4-(1-methanesulphonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (553) | 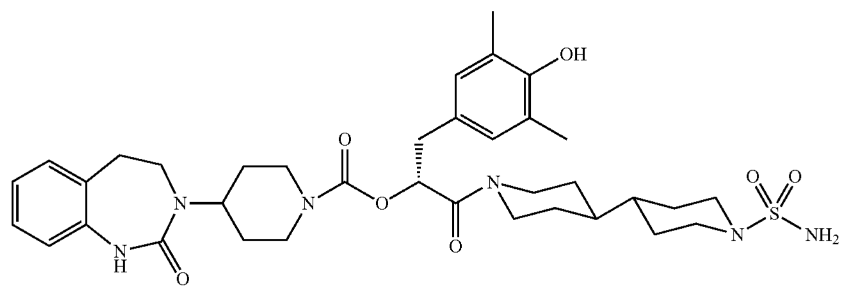 | (R)-1-(4-hydroxy-3,5-dimethyl-benzyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (554) | 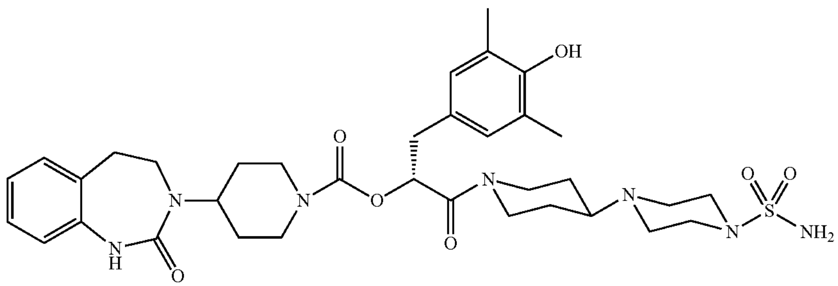 | (R)-1-(4-hydroxy-3,5-dimethyl-benzyl)-2-oxo-2-[4-(4-sulphamoyl-piperazin-1-yl)-piperidin-1-yl]-ethyl 4-(2-oxo-1,2,4,5-tetrahydro-1,3-benzodiazepin-3-yl)-piperidine-1-carboxylate |
| (555) | 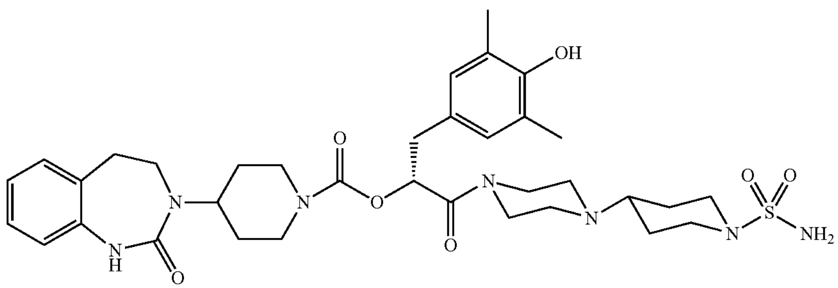 | (R)-1-(4-hydroxy-3,5-dimethyl-benzyl)-2-oxo-2-[4-(1-sulphamoyl-piperidin-4-yl)-piperazin-1-yl]-ethyl 4-(2-oxo-1,2,4,5-tetrahydro-1,3-benzodiazepin-3-yl)-piperidine-1-carboxylate |
| (556) | 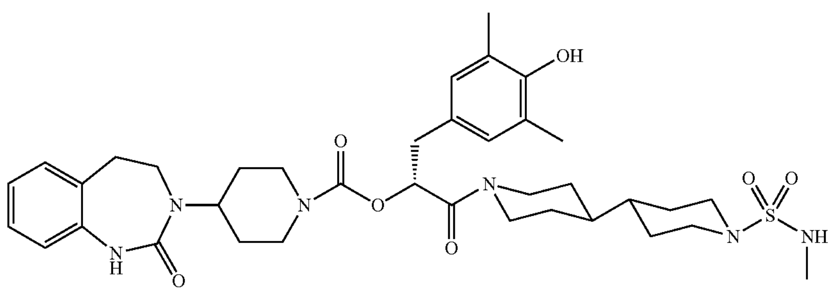 | (R)-1-(4-hydroxy-3,5-dimethyl-benzyl)-2-(1'-methylsulphamoyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Name |
|---|---|
| (557) | (R)-1-(4-hydroxy-3,5-dimethyl-benzyl)-2-[4-(4-methylsulphamoyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (558) | (R)-1-(4-hydroxy-3,5-dimethyl-benzyl)-2-[4-(1-methylsulphamoyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (559) | (R)-2-(1'-dimethylsulphamoyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (560) | 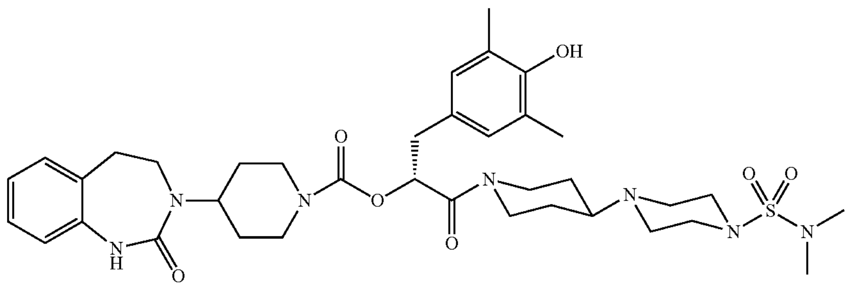 | (R)-2-[4-(4-dimethylsulphamoyl-piperazin-1-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (561) | 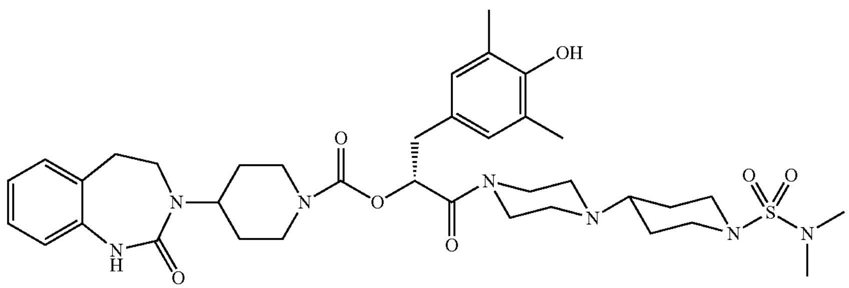 | 4-(2-oxo-1,2,4,5-tetrahydro-1,3-benzodiazepin-(R)-2-[4-(1-dimethyl-sulphamoyl-piperidin-4-yl)-piperazin-1-yl]-1-(4-hydroxy-3,5-dimethyl-benzyl)-2-oxo-ethyl 3-yl)-piperidine-1-carboxylate |
| (562) | 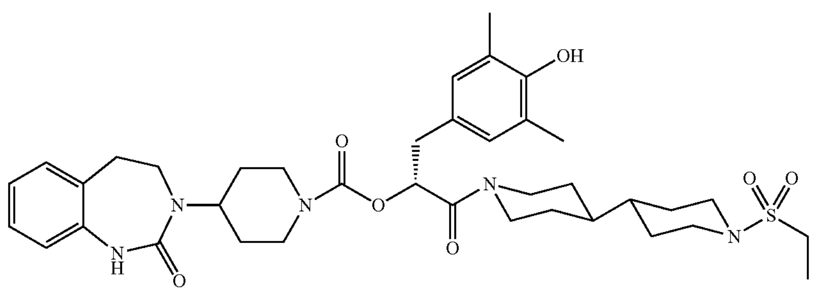 | (R)-2-(1'-ethanesulphonyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (563) | 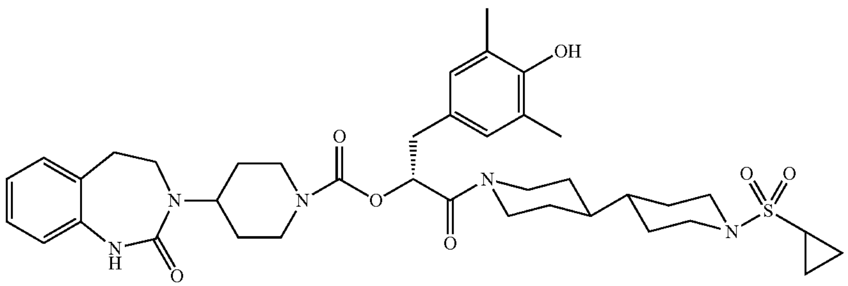 | (R)-2-(1'-cyclopropanesulphonyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (564) | 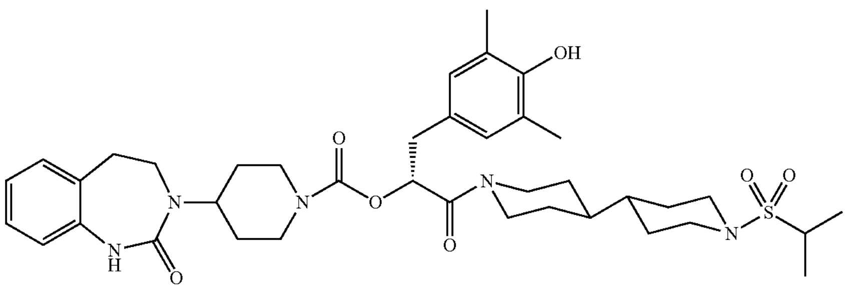 | (R)-1-(4-hydroxy-3,5-dimethyl-benzyl)-2-oxo-2-[1'-(propane-2-sulphonyl)-4,4'-bipiperidinyl-1-yl]-ethyl 4-(2-oxo-1,2,4,5-tetrahydro-1,3-benzodiazepin-3-yl)-piperidine-1-carboxylate |
| (565) | 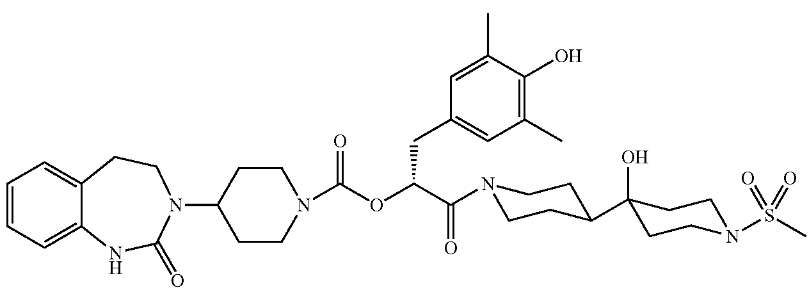 | (R)-1-(4-hydroxy-3,5-dimethyl-benzyl)-2-(4'-hydroxy-1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (566) | 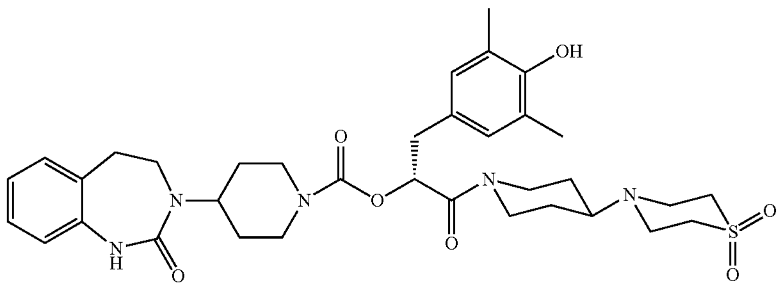 | (R)-2-{4-(1,1-dioxo-1λ⁶-thiomorpholin-4-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (567) | 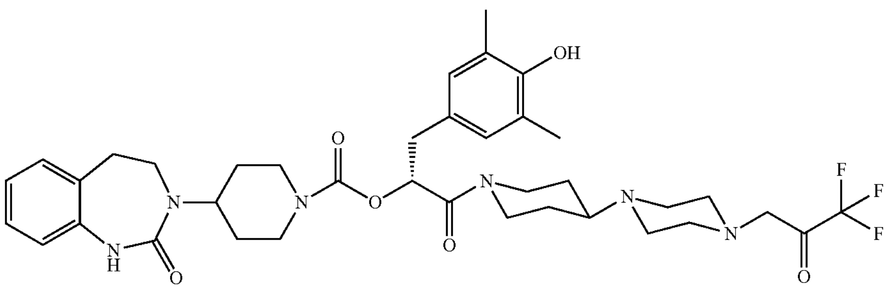 | (R)-1-(4-hydroxy-3,5-dimethyl-benzyl)-2-oxo-2-{4-[4-(3,3,3-trifluoro-2-oxo-propyl)-piperazin-1-yl]-piperidin-1-yl}-ethyl 4-(2-oxo-1,2,4,5-tetrahydro-1,3-benzodiazepin-3-yl)-piperidine-1-carboxylate |
| (568) | 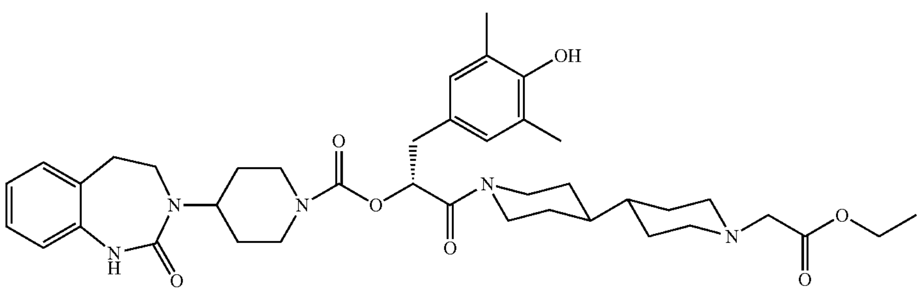 | (R)-2-{1'-ethoxycarbonylmethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (569) | 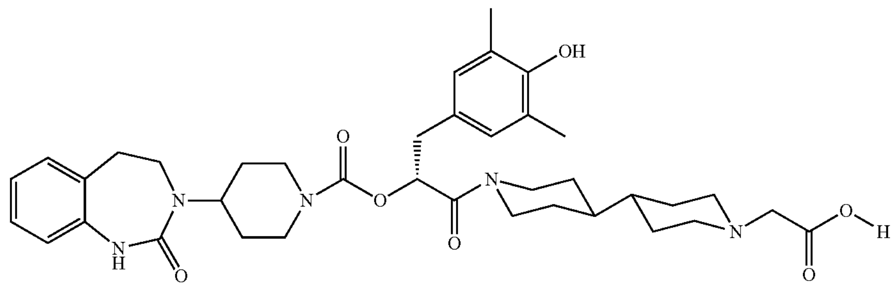 | (R)-2-(1'-carboxymethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (570) | 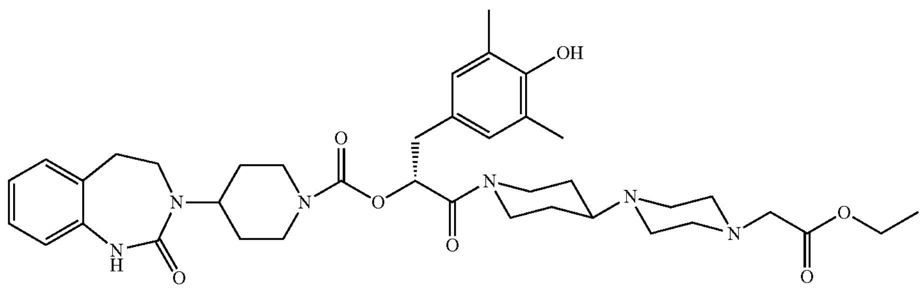 | (R)-2-[4-(4-ethoxycarbonylmethyl-piperazin-1-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (571) | 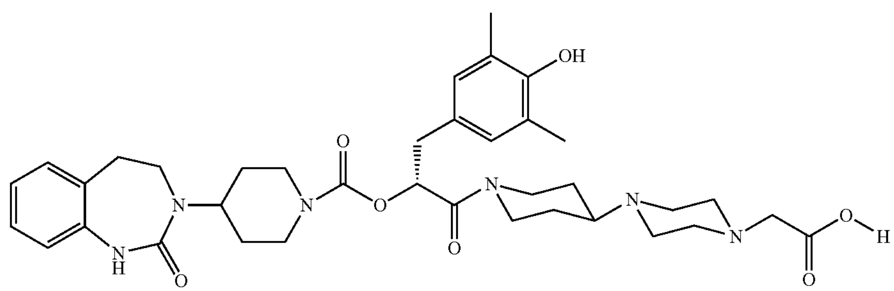 | (R)-2-[4-(4-carboxymethyl-piperazin-1-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (572) | 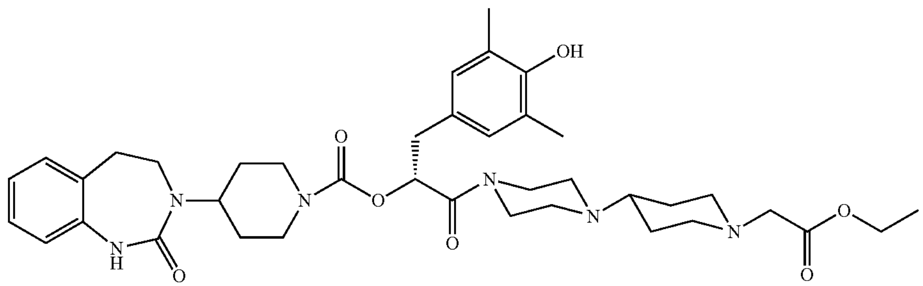 | (R)-2-[4-(1-ethoxycarbonylmethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (573) | 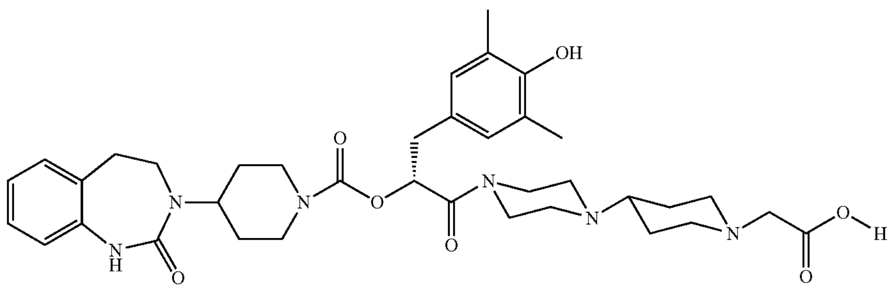 | (R)-2-[4-(1-carboxymethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (574) | 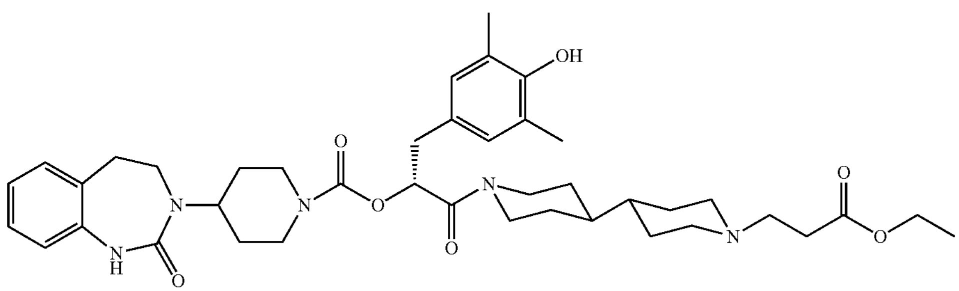 | (R)-2-[1'-(2-ethoxycarbonyl-ethyl)-4,4'-bipiperidinyl-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (575) | 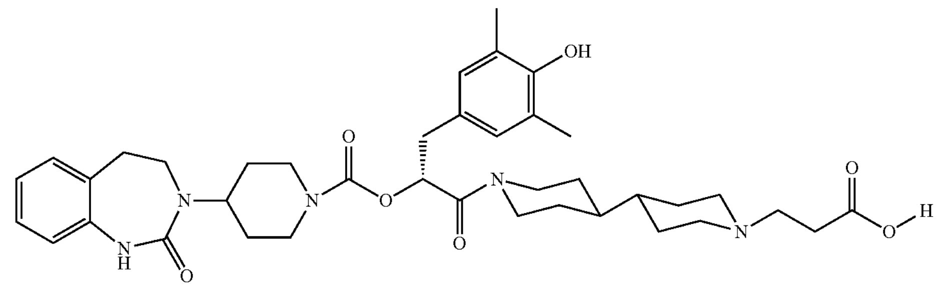 | (R)-2-[1'-(2-carboxy-ethyl)-4,4'-bipiperidinyl-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (576) | 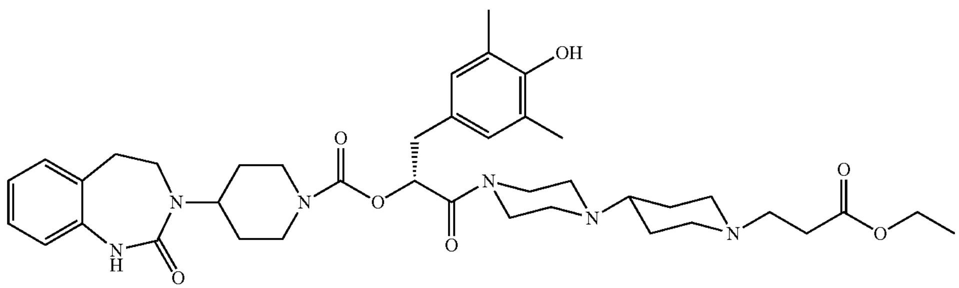 | (R)-2-{4-[1-(2-ethoxycarbonyl-ethyl)-piperidin-4-yl]-piperazin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (577) | 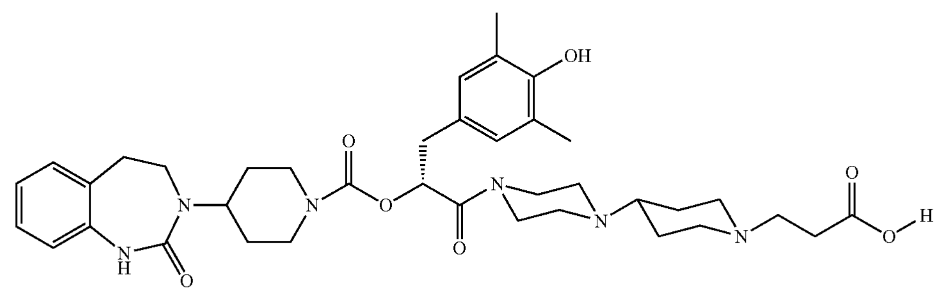 | (R)-2-{4-[1-(2-carboxy-ethyl)-piperidin-4-yl]-piperazin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (578) | 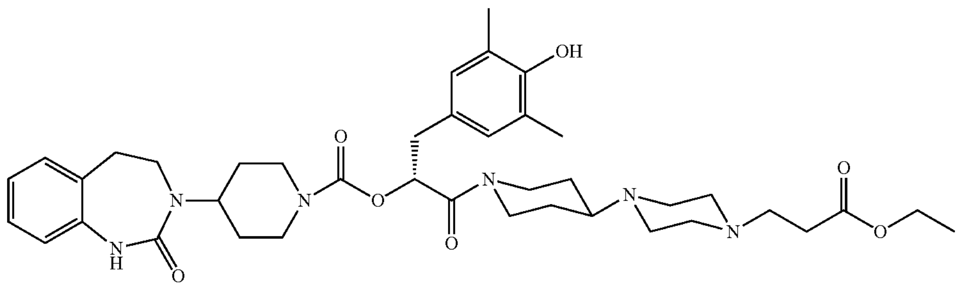 | (R)-2-{4-[4-(2-ethoxycarbonyl-ethyl)-piperazin-1-yl]-piperidin-1-yl}-1-(4-hydroxy-3,5-dimethyl-benzyl) 4-(2-oxo-1,2,4,5-tetrahydro-1,3-benzodiazepin-3-yl)-piperidine-1-carboxylate |
| (579) | 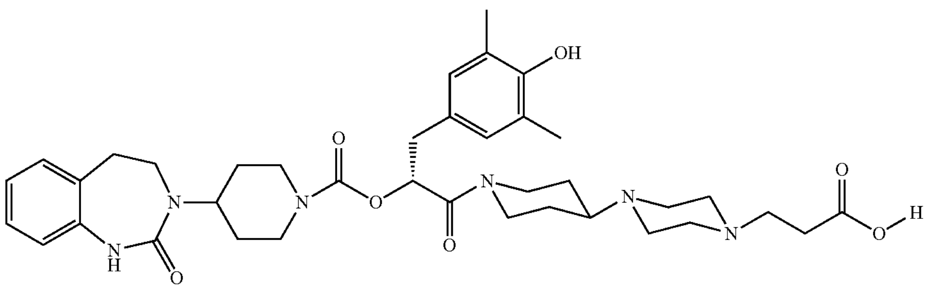 | (R)-2-{4-[4-(2-carboxy-ethyl)-piperazin-1-yl]-piperidin-1-yl}-1-(4-hydroxy-3,5-dimethyl-benzyl) 4-(2-oxo-1,2,4,5-tetrahydro-1,3-benzodiazepin-3-yl)-piperidine-1-carboxylate |
| (580) | 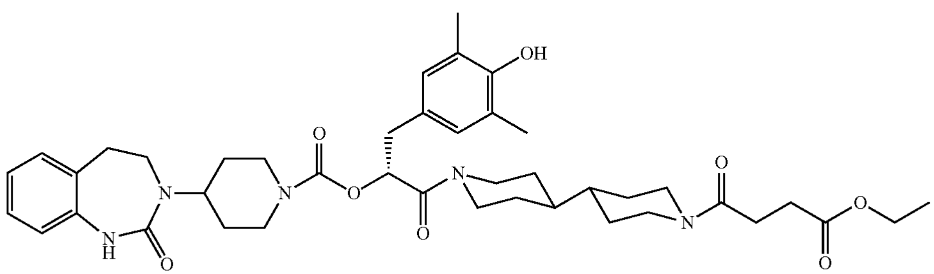 | (R)-2-[1'-(3-ethoxycarbonyl-propionyl)-4,4'-bipiperidinyl-1-yl]-1-(4-hydroxy-3,5-dimethyl-benzyl) 4-(2-oxo-1,2,4,5-tetrahydro-1,3-benzodiazepin-3-yl)-piperidine-1-carboxylate |

| No. | Structure | Name |
|---|---|---|
| (581) | 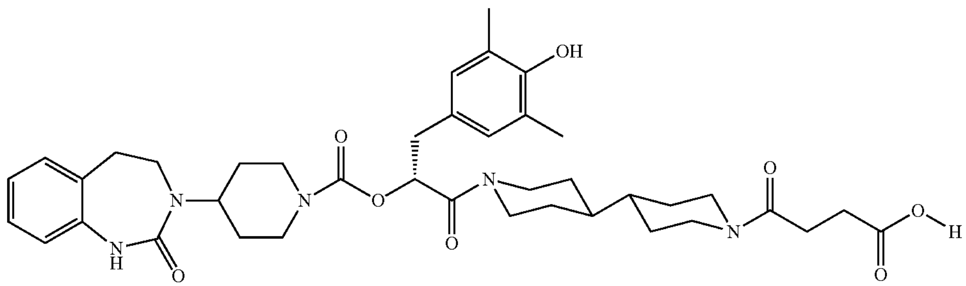 | (R)-2-[1'-(3-carboxy-propionyl)-4,4'-bipiperidinyl-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (582) | 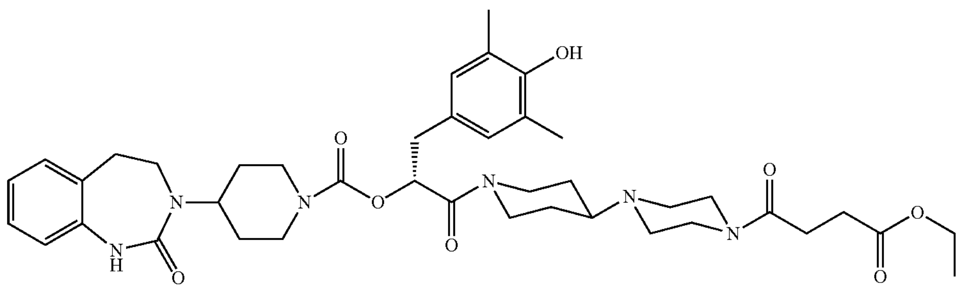 | (R)-2-{4-[4-(3-ethoxycarbonyl-propionyl)-piperazin-1-yl]-piperidin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (583) | 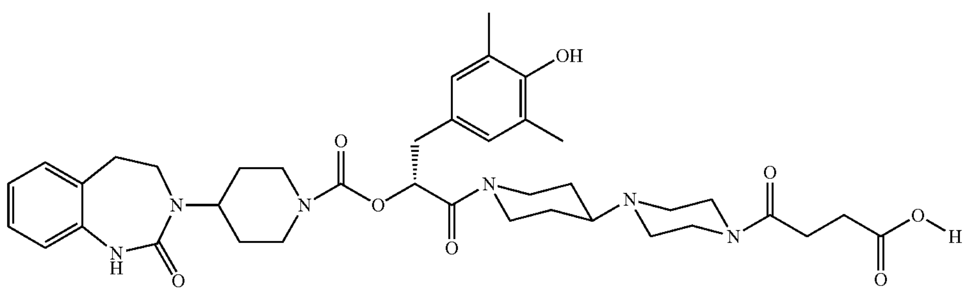 | (R)-2-{4-[4-(3-carboxy-propionyl)-piperazin-1-yl]-piperidin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (584) | 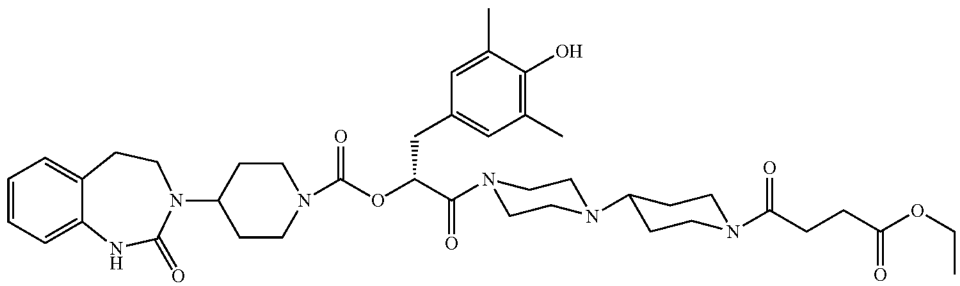 | (R)-2-{4-[1-(3-ethoxycarbonyl-propionyl)-piperidin-4-yl]-piperazin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (585) | 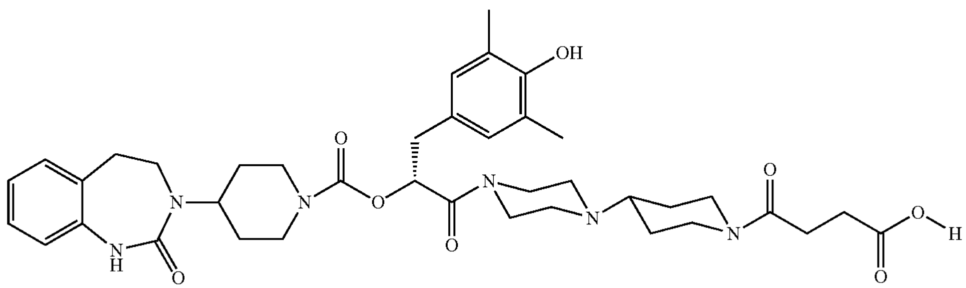 | (R)-2-{4-[1-(3-carboxy-propionyl)-piperidin-4-yl]-piperazin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (586) | 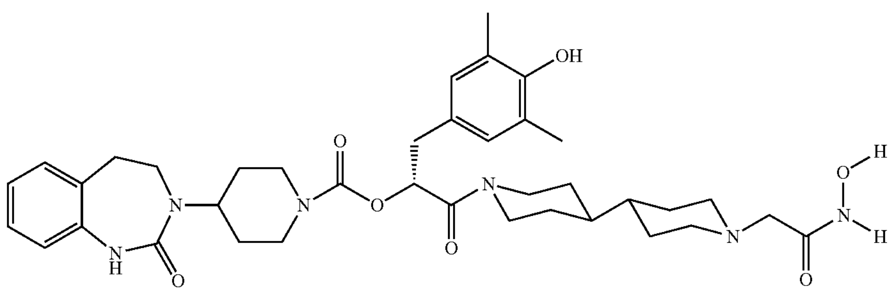 | (R)-2-(1'-hydroxycarbamoylmethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (587) | 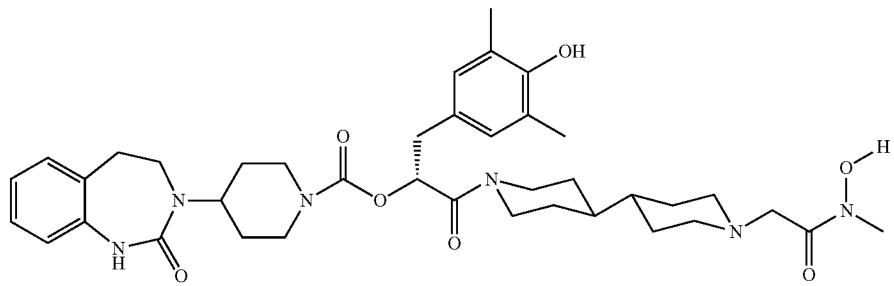 | (R)-1-(4-hydroxy-3,5-dimethyl-benzyl)-2-{1'-[(hydroxy-methyl-carbamoyl)-methyl]-4,4'-bipiperidinyl-1-yl}-2-oxo-ethyl 4-(2-oxo-1,2,4,5-tetrahydro-1,3-benzodiazepin-3-yl)-piperidine-1-carboxylate |
| (588) | 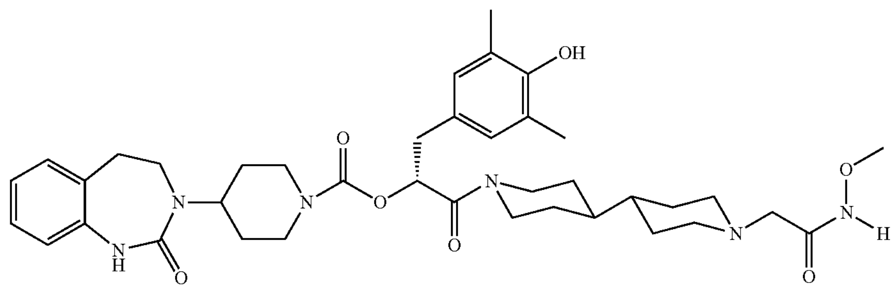 | (R)-1-(4-hydroxy-3,5-dimethyl-benzyl)-2-[1'-(methoxycarbamoyl-methyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |
| (589) | 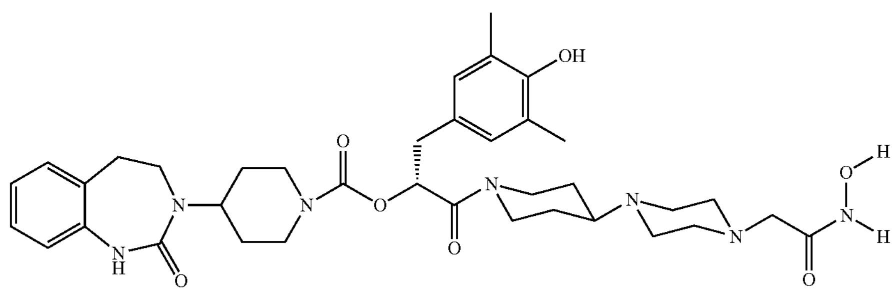 | (R)-2-[4-(4-hydroxycarbamoylmethyl-piperazin-1-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (590) | 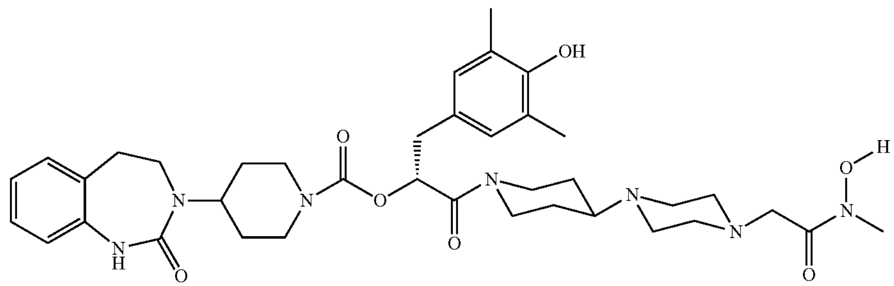 | (R)-1-(4-hydroxy-3,5-dimethyl-benzyl)-2-(4-{4-[(hydroxy-methyl-carbamoyl)-methyl]-piperazin-1-yl}-piperidin-1-yl)-2-oxo-ethyl 4-(2-oxo-1,2,4,5-tetrahydro-1,3-benzodiazepin-3-yl)-piperidine-1-carboxylate |
| (591) | 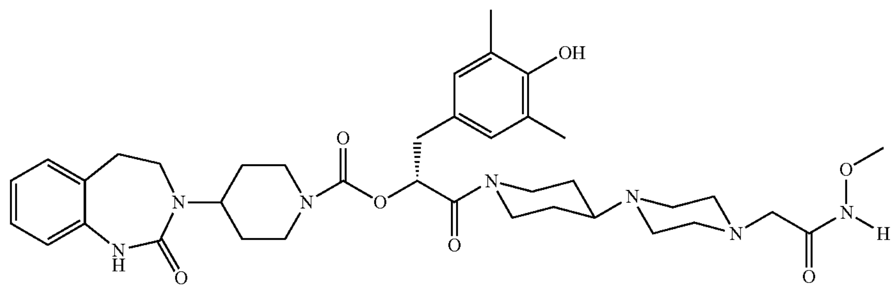 | (R)-1-(4-hydroxy-3,5-dimethyl-benzyl)-2-{4-[4-(methoxycarbamoyl-methyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |
| (592) | 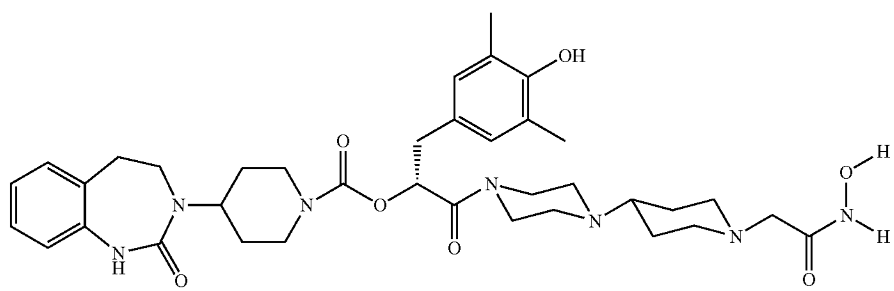 | (R)-2-[4-(1-hydroxycarbamoylmethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (593) | 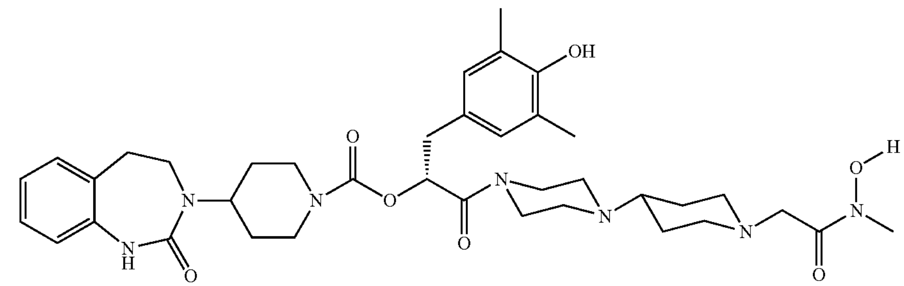 | (R)-1-(4-hydroxy-3,5-dimethyl-benzyl)-2-(4-{1-[(hydroxy-methyl-carbamoyl)-methyl]-piperidin-4-yl}-piperazin-1-yl)-2-oxo-ethyl 4-(2-oxo-1,2,4,5-tetrahydro-1,3-benzodiazepin-3-yl)-piperidine-1-carboxylate |
| (594) | 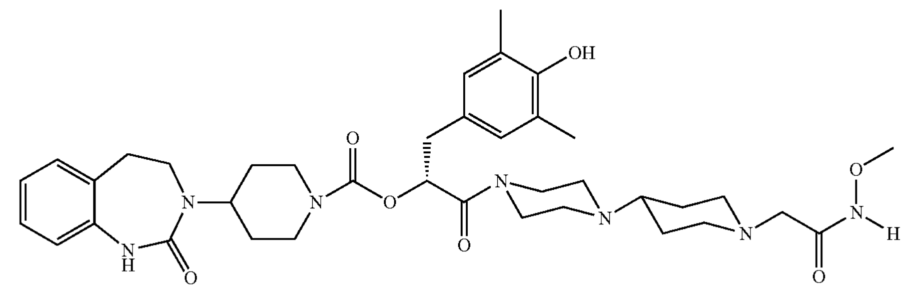 | (R)-1-(4-hydroxy-3,5-dimethyl-benzyl)-2-{4-[1-(methoxycarbamoyl-methyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |
| (595) | 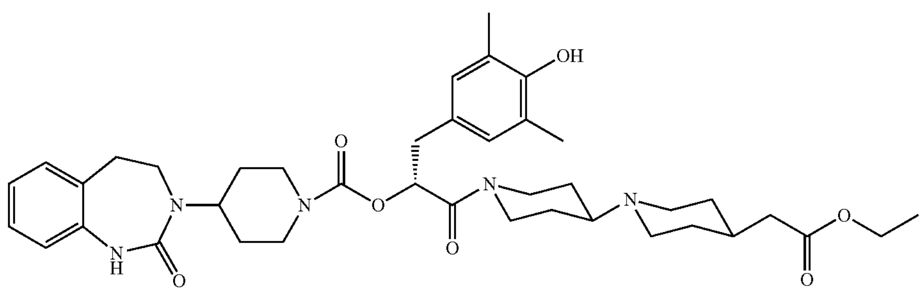 | (R)-2-(4-ethoxycarbonylmethyl-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (596) | 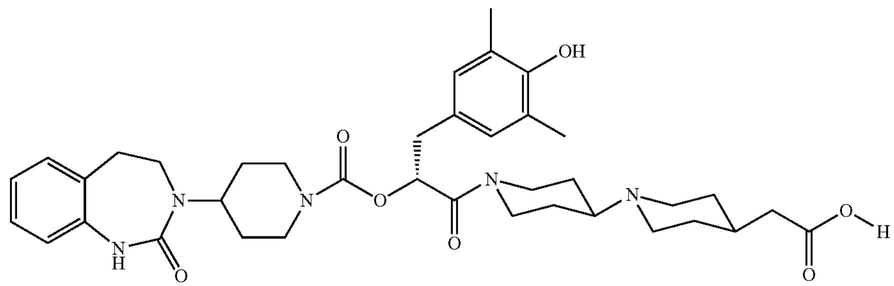 | (R)-2-(4-carboxymethyl-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (597) | 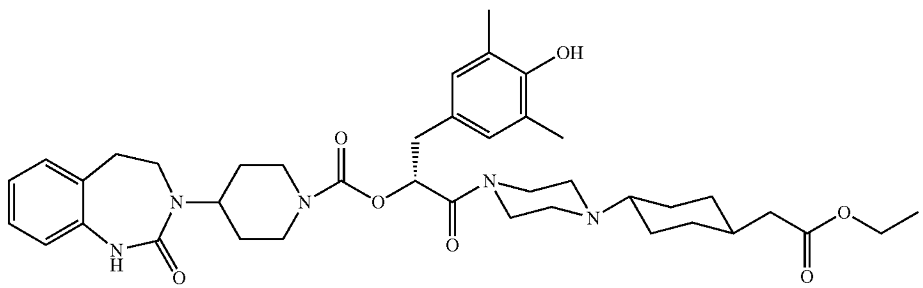 | (R)-2-[4-(4-ethoxycarbonylmethyl-cyclohexyl)-piperazin-1-yl]-1-(4-hydroxy-3,5-dimethyl-benzyl)-2-oxo-ethyl trans-4-(2-oxo-1,2,4,5-tetrahydro-1,3-benzodiazepin-3-yl)-piperidine-1-carboxylate |
| (598) | 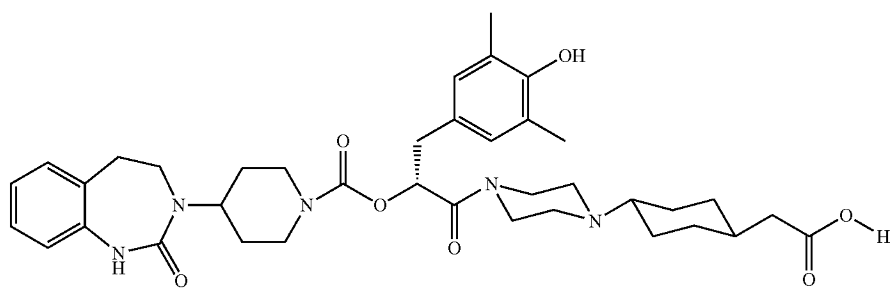 | (R)-2-[4-(4-carboxymethyl-cyclohexyl)-piperazin-1-yl]-1-(4-hydroxy-3,5-dimethyl-benzyl)-2-oxo-ethyl trans-4-(2-oxo-1,2,4,5-tetrahydro-1,3-benzodiazepin-3-yl)-piperidine-1-carboxylate |

-continued

| No. | Structure | Name |
|---|---|---|
| (599) | 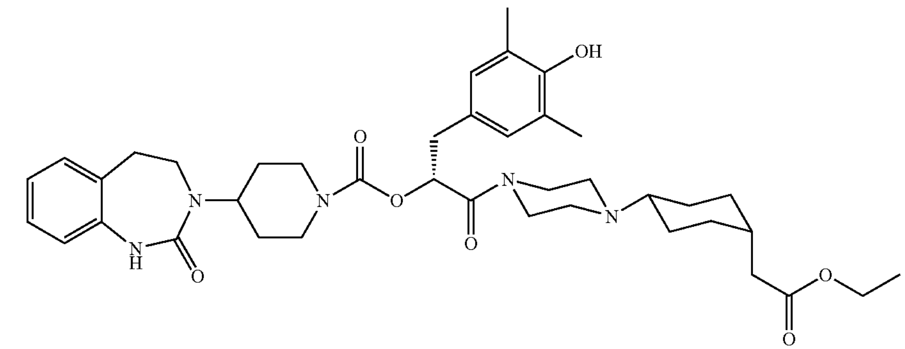 | (R)-2-[4-(4-ethoxycarbonylmethyl-cyclohexyl)-piperazin-1-yl]-1-(4-hydroxy-3,5-dimethyl-benzyl)-2-oxo-ethyl cis-4-(2-oxo-1,2,4,5-tetrahydro-1,3-benzodiazepin-3-yl)-piperidine-1-carboxylate |
| (600) | 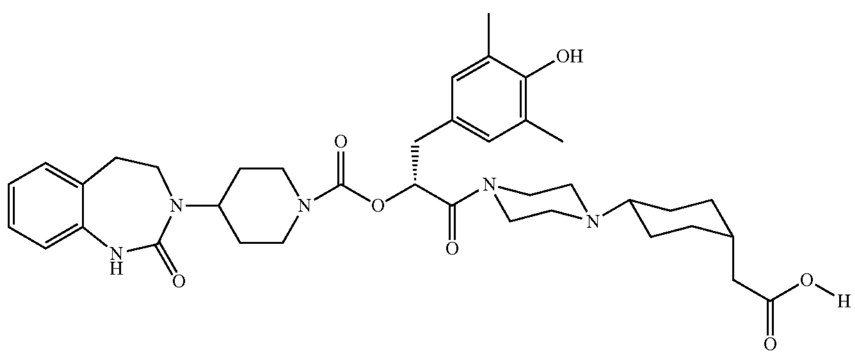 | (R)-2-[4-(4-carboxymethyl-cyclohexyl)-piperazin-1-yl]-1-(4-hydroxy-3,5-dimethyl-benzyl)-2-oxo-ethyl cis-4-(2-oxo-1,2,4,5-tetrahydro-1,3-benzodiazepin-3-yl)-piperidine-1-carboxylate |
| (601) | 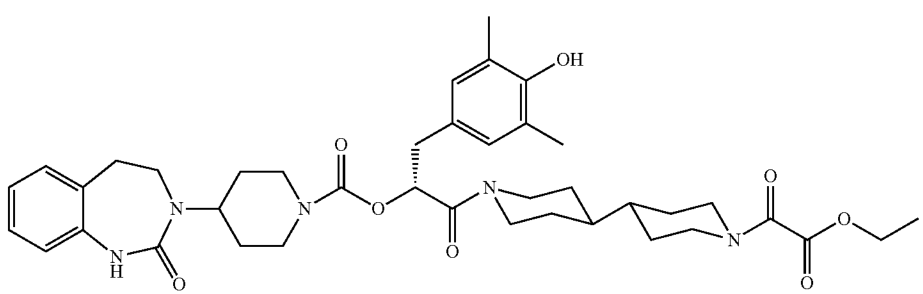 | (R)-2-(1'-ethoxyoxalyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (602) | 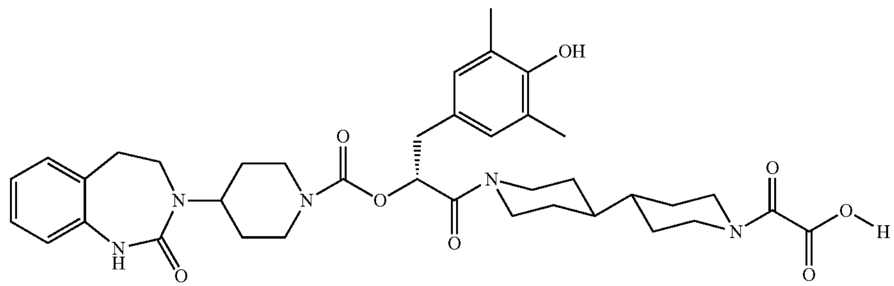 | (R)-1-(4-hydroxy-3,5-dimethyl-benzyl)-2-(1'-oxalyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (603) | 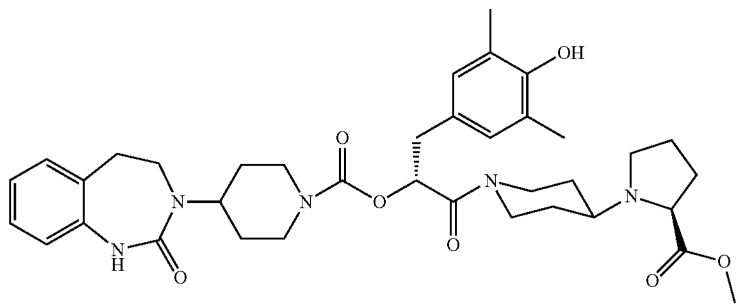 | (R)-1-(4-hydroxy-3,5-dimethyl-benzyl)-2-[4-((S)-2-methoxycarbonyl-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |
| (604) | 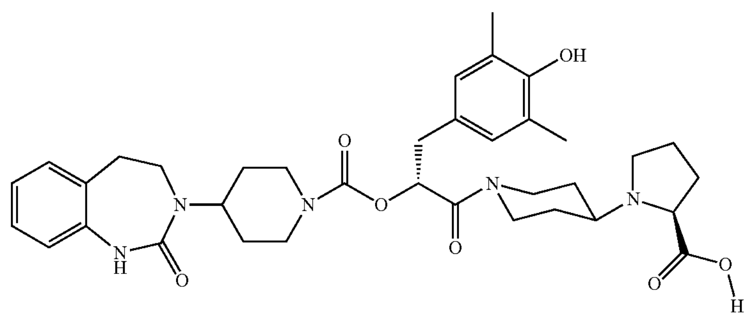 | (R)-2-[4-((S)-2-carboxy-pyrrolidin-1-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |

| No. | Name |
|---|---|
| (605) | (R)-1-(4-hydroxy-3,5-dimethyl-benzyl)-2-[4-((R)-2-methoxycarbonyl-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate |
| (606) | (R)-2-[4-((R)-2-carboxy-pyrrolidin-1-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate |
| (607) | methyl (S)-1'-[(R)-3-(4-hydroxy-3,5-dimethyl-phenyl)-2-[4-(2-oxo-1,2,4,5-tetrahydro-1,3-benzodiazepin-3-yl)-piperidin-1-carbonyloxy]-propionyl]-1,4'-bipiperidinyl-2-carboxylate |

-continued

| No. | Structure | Name |
|---|---|---|
| (608) | 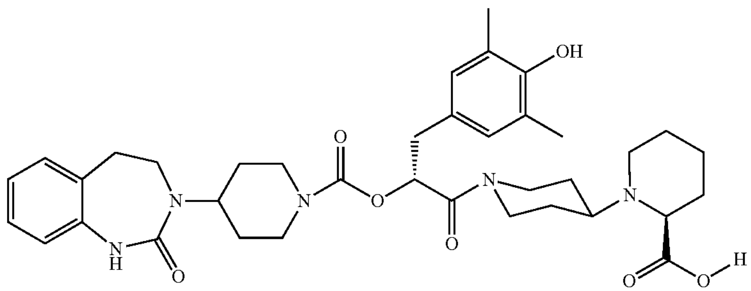 | (S)-1'-[(R)-3-(4-hydroxy-3,5-dimethyl-phenyl)-2-[4-(2-oxo-1,2,4,5-tetrahydro-1,3-benzodiazepin-3-yl)-piperidin-1-carbonyloxy]-propionyl]-1,4'-bipiperidinyl-2-carboxylic acid |
| (609) | 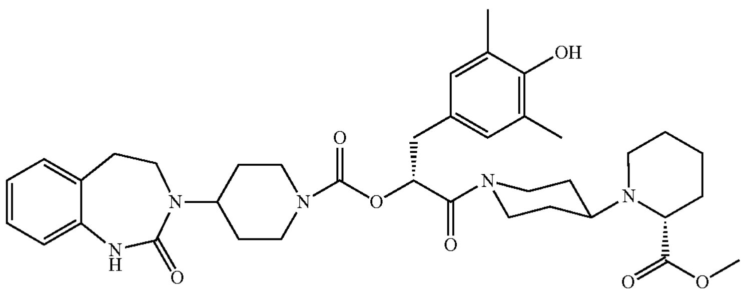 | methyl (R)-1'-[(R)-3-(4-hydroxy-3,5-dimethyl-phenyl)-2-[4-(2-oxo-1,2,4,5-tetrahydro-1,3-benzodiazepin-3-yl)-piperidin-1-carbonyloxy]-propionyl]-1,4'-bipiperidinyl-2-carboxylate |
| (610) | 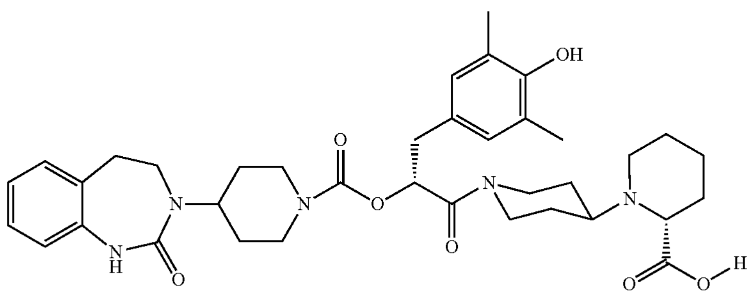 | (R)-1'-[(R)-3-(4-hydroxy-3,5-dimethyl-phenyl)-2-[4-(2-oxo-1,2,4,5-tetrahydro-1,3-benzodiazepin-3-yl)-piperidin-1-carbonyloxy]-propionyl]-1,4'-bipiperidinyl-2-carboxylic acid |

| No. | Structure | Name |
|---|---|---|
| (611) | 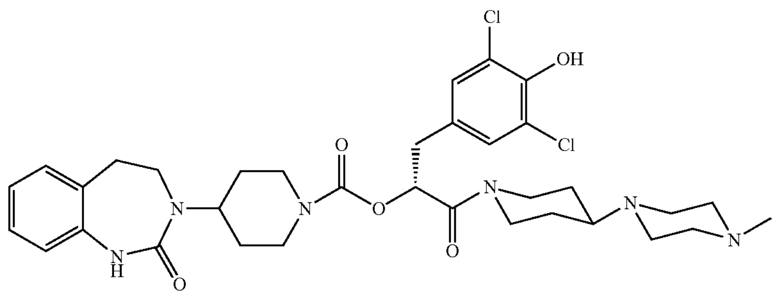 | (R)-1-(3,5-dichloro-4-hydroxy-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (612) | 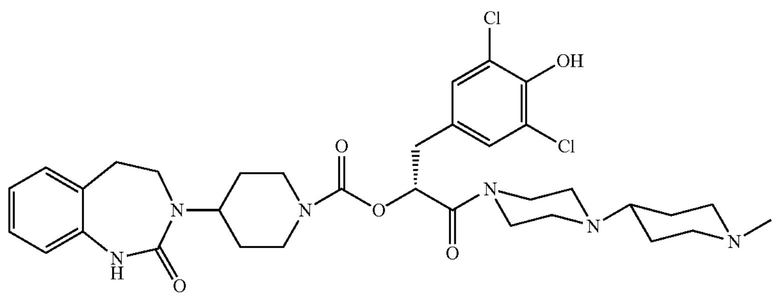 | (R)-1-(3,5-dichloro-4-hydroxy-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (613) | 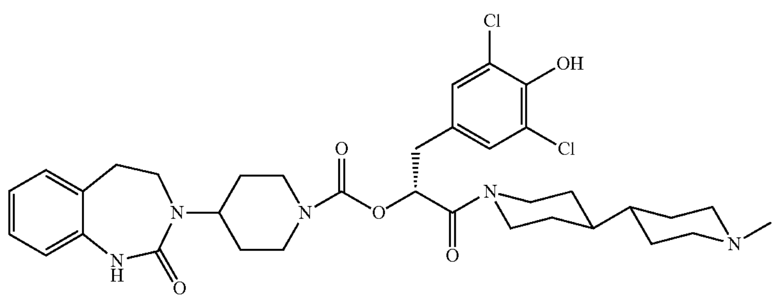 | (R)-1-(3,5-dichloro-4-hydroxy-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (614) | 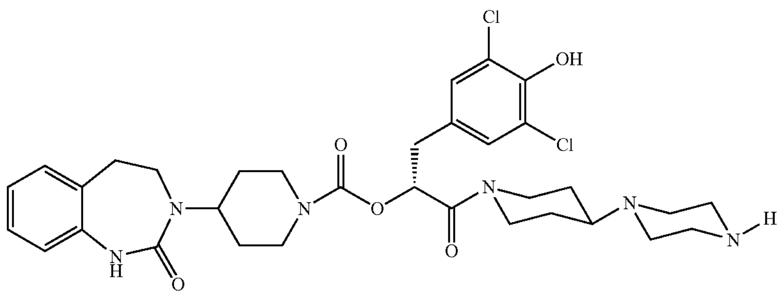 | (R)-1-(3,5-dichloro-4-hydroxy-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (615) | 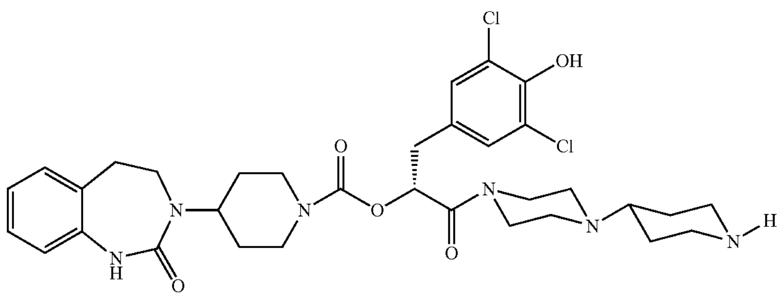 | (R)-1-(3,5-dichloro-4-hydroxy-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (616) | 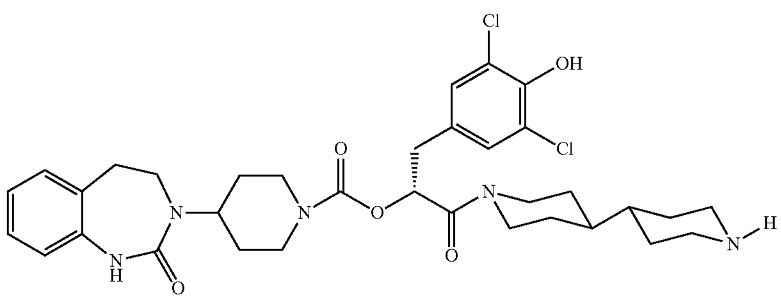 | (R)-2-(4,4'-bipiperidinyl-1-yl)-1-(3,5-dichloro-4-hydroxy-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (617) | 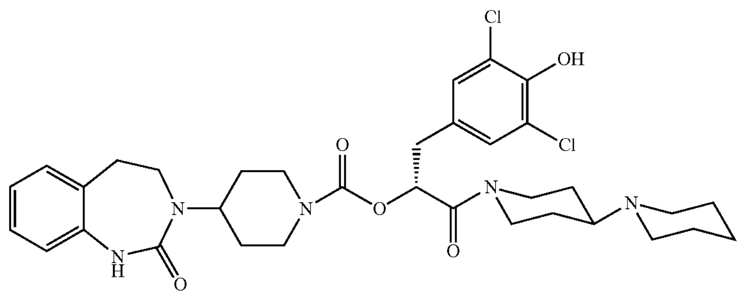 | (R)-2-(1,4'-bipiperidinyl-1'-yl)-1-(3,5-dichloro-4-hydroxy-benzyl)-2-oxo-ethyl 4-(2-oxo-1,2,4,5-tetrahydro-1,3-benzodiazepin-3-yl)-piperidine-1-carboxylate |
| (618) | 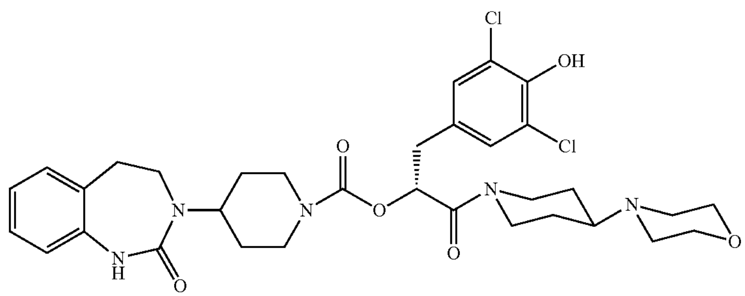 | (R)-1-(3,5-dichloro-4-hydroxy-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (619) | 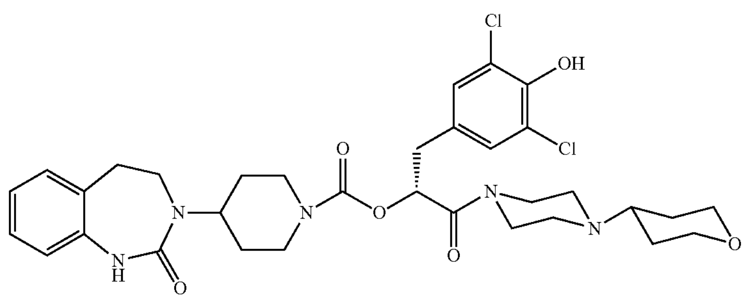 | (R)-1-(3,5-dichloro-4-hydroxy-benzyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |

| No. | Structure | Name |
|---|---|---|
| (620) | 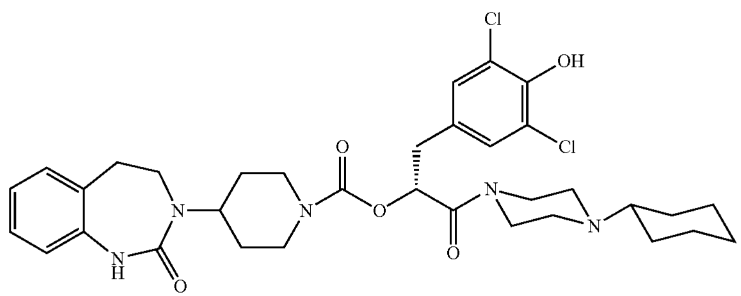 | (R)-2-(4-cyclohexyl-piperazin-1-yl)-1-(3,5-dichloro-4-hydroxy-benzyl)-2-oxo-ethyl 4-(2-oxo-1,2,4,5-tetrahydro-1,3-benzodiazepin-3-yl)-piperidine-1-carboxylate |
| (621) | 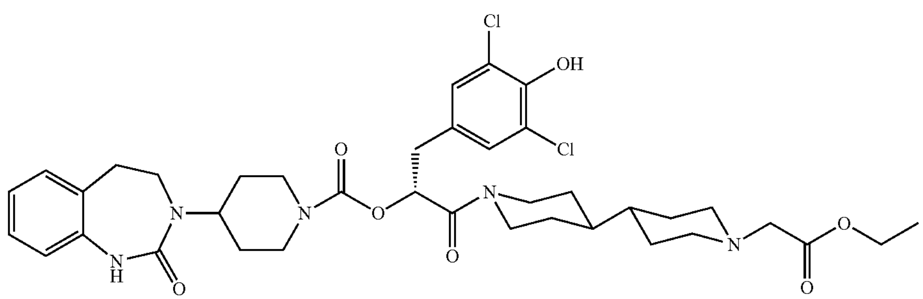 | (R)-1-(3,5-dichloro-4-hydroxy-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (622) | 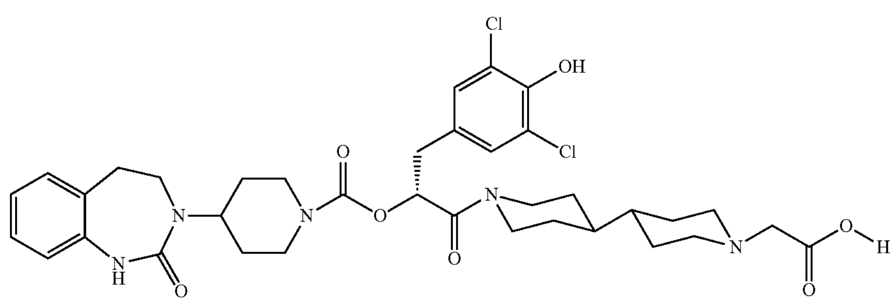 | (R)-2-(1'-carboxymethyl-4,4'-bipiperidinyl-1-yl)-1-(3,5-dichloro-4-hydroxy-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (623) | 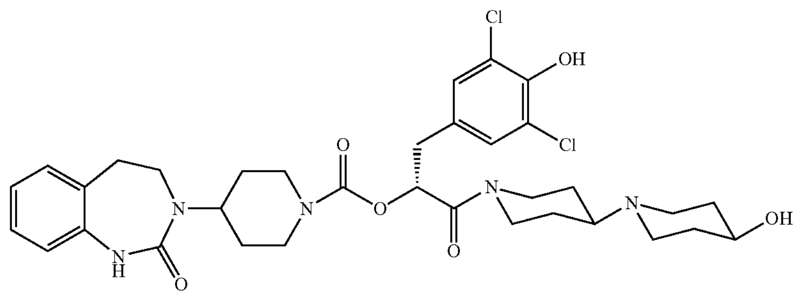 | (R)-1-(3,5-dichloro-4-hydroxy-benzyl)-2-(4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (624) | 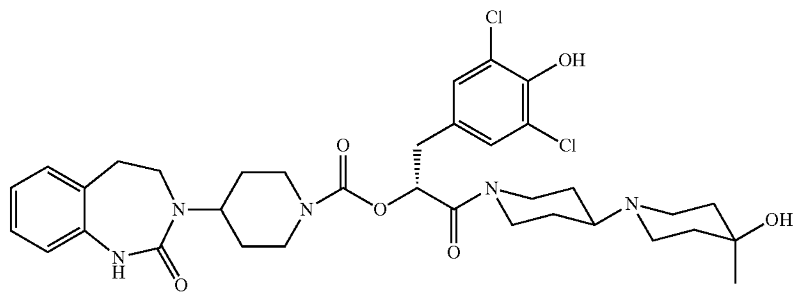 | (R)-1-(3,5-dichloro-4-hydroxy-benzyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (625) | 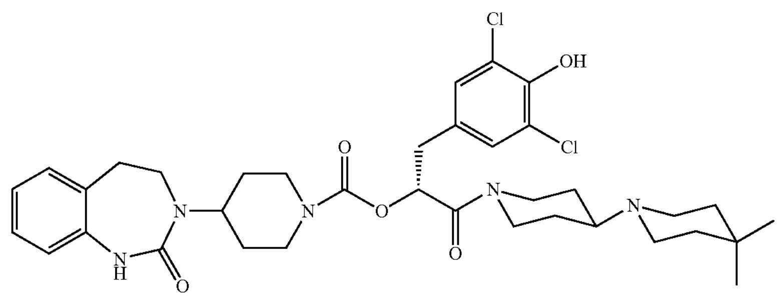 | (R)-1-(3,5-dichloro-4-hydroxy-benzyl)-2-(4,4-dimethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (626) | 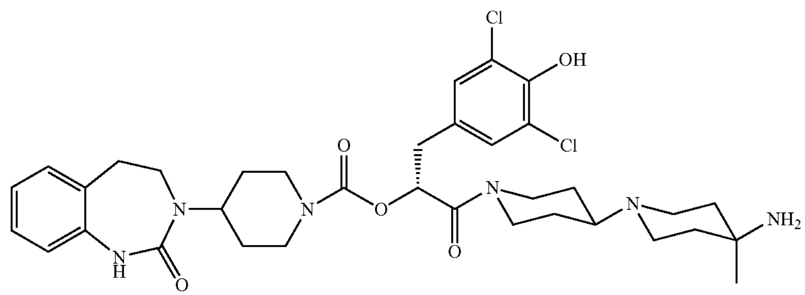 | (R)-2-(4-amino-4-methyl-1,4'-bipiperidinyl-1'-yl)-1-(3,5-dichloro-4-hydroxy-benzyl)-2-oxo-ethyl 4-(2-oxo-1,2,4,5-tetrahydro-1,3-benzodiazepin-3-yl)-piperidine-1-carboxylate |
| (627) | 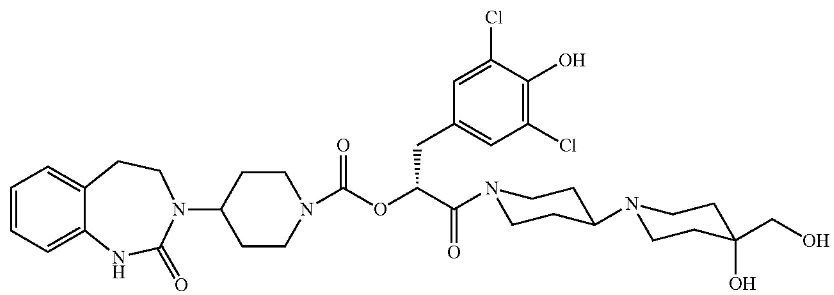 | (R)-1-(3,5-dichloro-4-hydroxy-benzyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (628) | 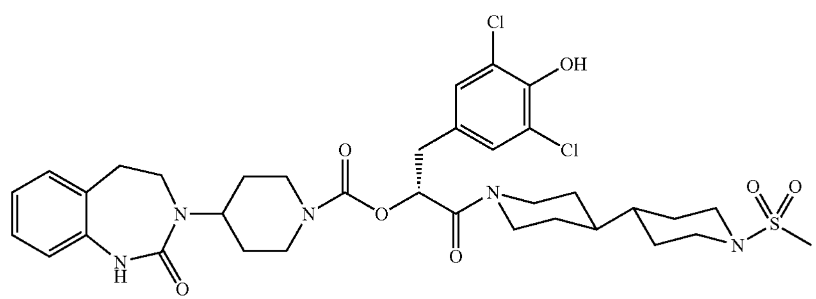 | (R)-1-(3,5-dichloro-4-hydroxy-benzyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (629) | 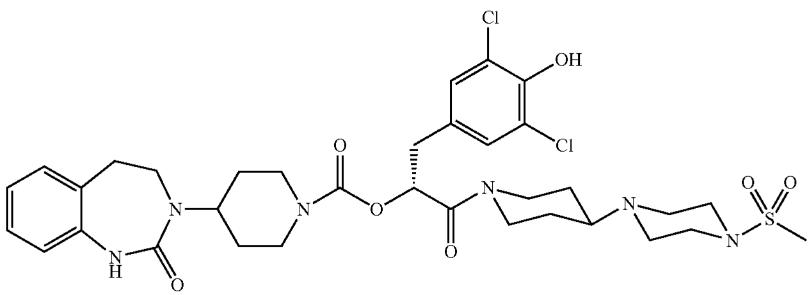 | (R)-1-(3,5-dichloro-4-hydroxy-benzyl)-2-[4-(4-methane-sulphonyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (630) | 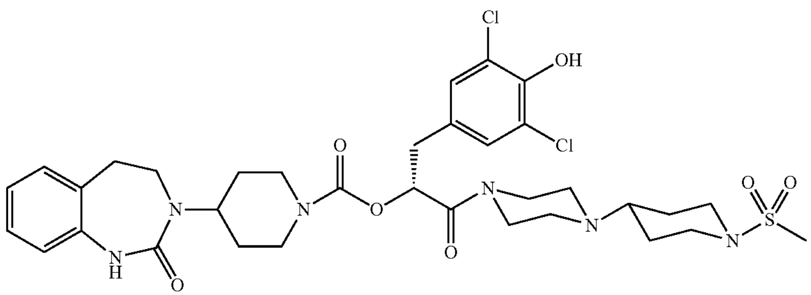 | (R)-1-(3,5-dichloro-4-hydroxy-benzyl)-2-[4-(1-methane-sulphonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (631) | 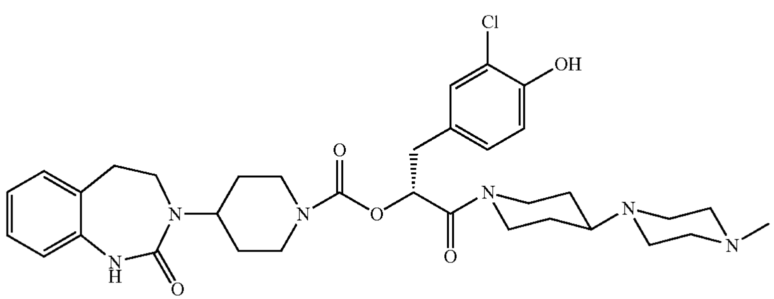 | (R)-1-(3-chloro-4-hydroxy-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (632) | 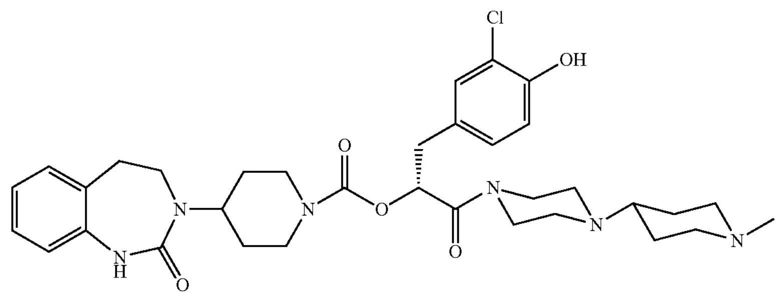 | (R)-1-(3-chloro-4-hydroxy-benzyl)-2-[4-((1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (633) | 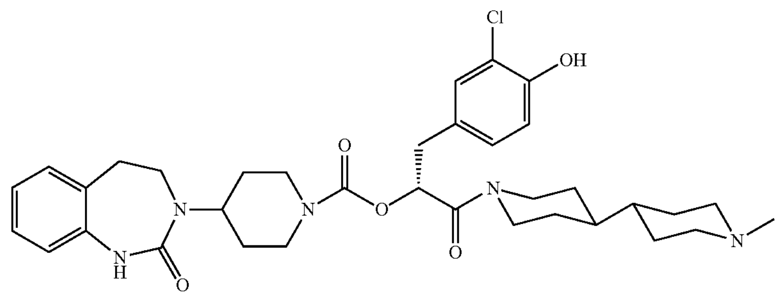 | (R)-1-(3-chloro-4-hydroxy-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (634) | 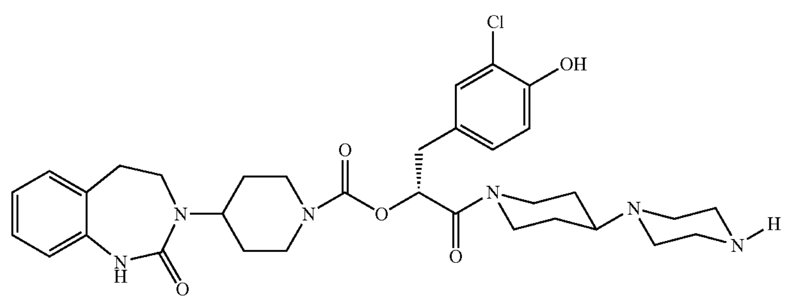 | (R)-1-(3-chloro-4-hydroxy-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

| No. | Structure | Name |
|---|---|---|
| (635) | 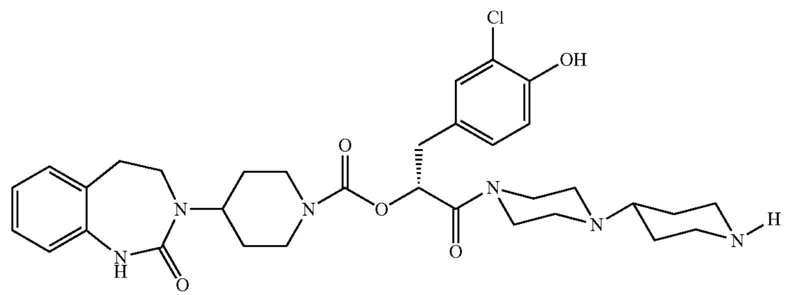 | (R)-1-(3-chloro-4-hydroxy-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (636) | 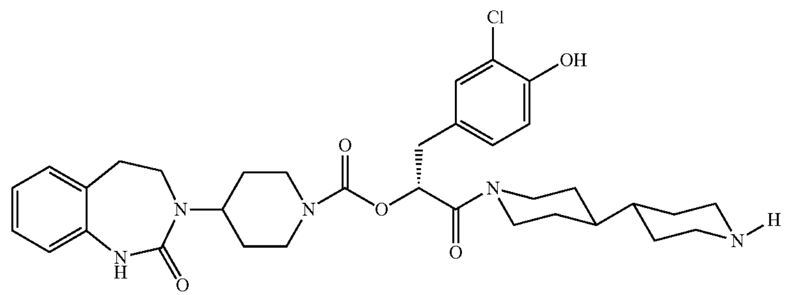 | (R)-2-(4,4'-bipiperidinyl-1-yl)-1-(3-chloro-4-hydroxy-benzyl)-2-oxo-ethyl 4-(2-oxo-1,2,4,5-tetrahydro-1,3-benzodiazepin-3-yl)-piperidine-1-carboxylate |
| (637) | 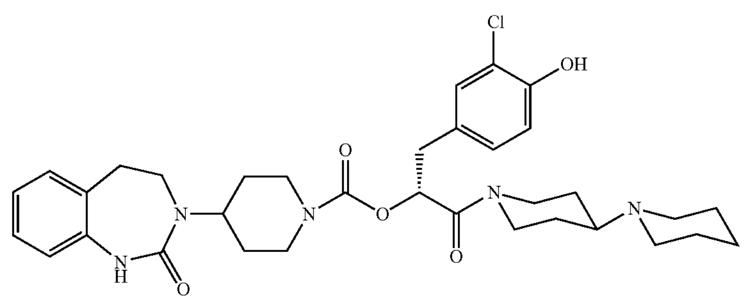 | (R)-2-(1,4'-bipiperidinyl-1'-yl)-1-(3-chloro-4-hydroxy-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (638) | 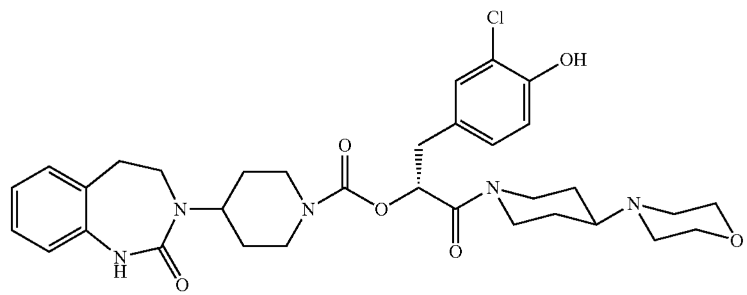 | (R)-1-(3-chloro-4-hydroxy-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (639) | 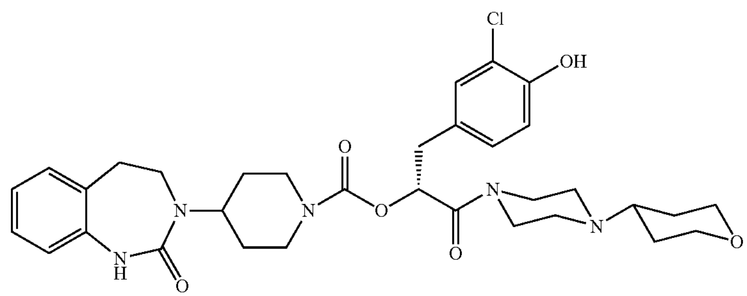 | (R)-1-(3-chloro-4-hydroxy-benzyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (640) | 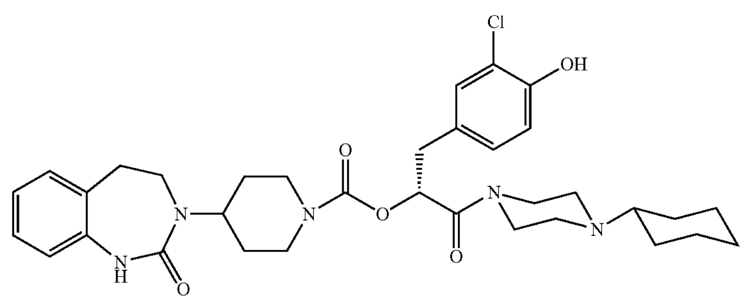 | (R)-1-(3-chloro-4-hydroxy-benzyl)-2-(4-cyclohexyl-piperazin-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (641) | 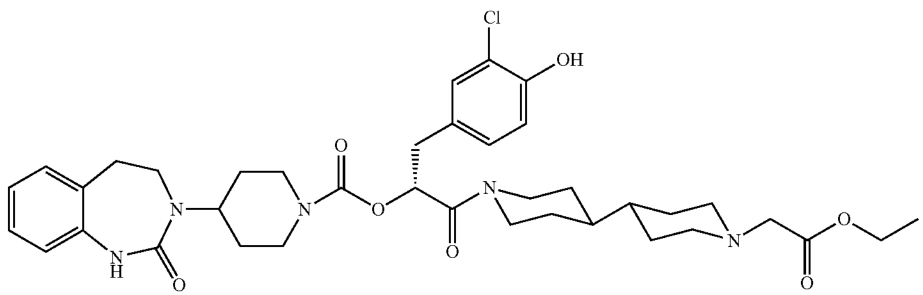 | (R)-1-(3-chloro-4-hydroxy-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (642) | 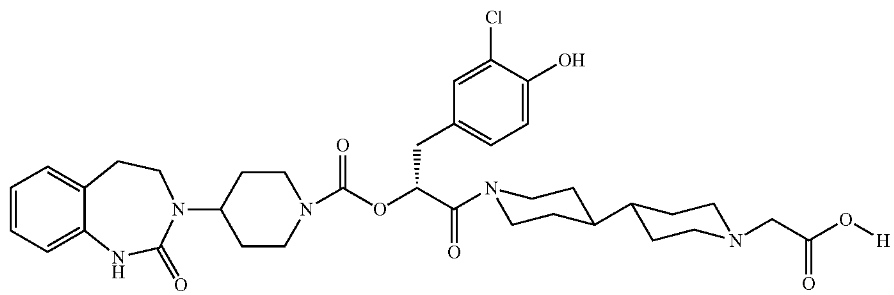 | (R)-2-(1'-carboxymethyl-4,4'-bipiperidinyl-1-yl)-1-(3-chloro-4-hydroxy-benzyl)-2-oxo-ethyl 4-(2-oxo-1,2,4,5-tetrahydro-1,3-benzodiazepin-3-yl)-piperidine-1-carboxylate |
| (643) | 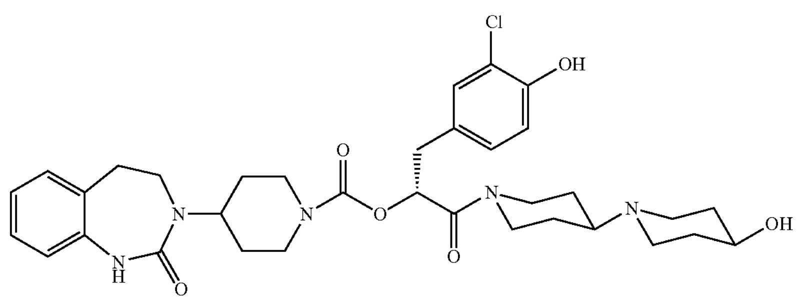 | (R)-1-(3-chloro-4-hydroxy-benzyl)-2-(4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (644) | 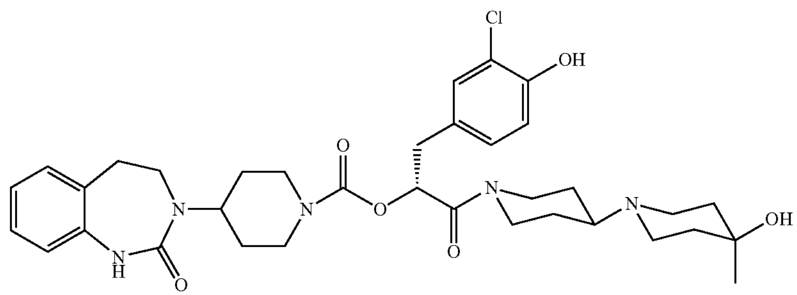 | (R)-1-(3-chloro-4-hydroxy-benzyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (645) | 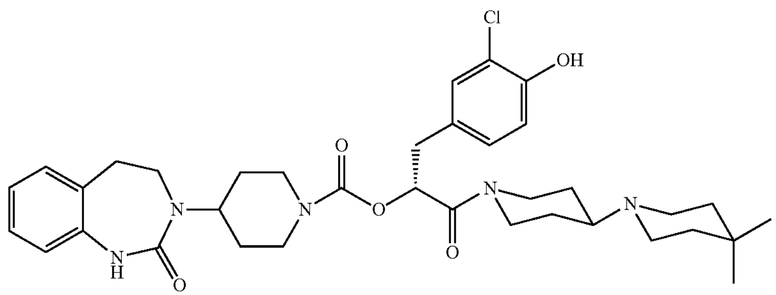 | (R)-1-(3-chloro-4-hydroxy-benzyl)-2-(4,4-dimethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (646) | 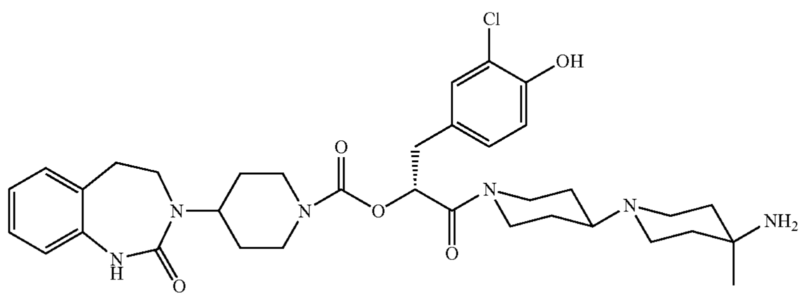 | (R)-2-(4-amino-4-methyl-1,4'-bipiperidinyl-1'-yl)-1-(3-chloro-4-hydroxy-benzyl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (647) | 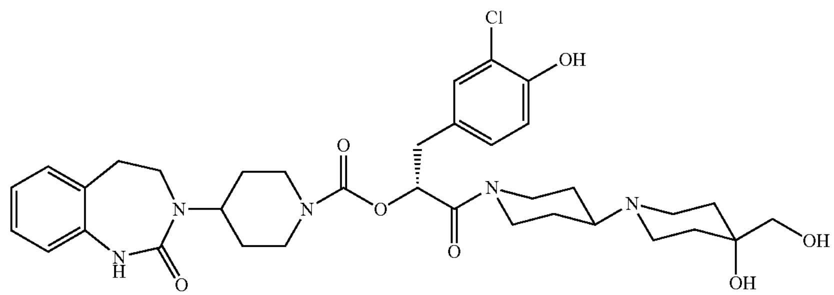 | (R)-1-(3-chloro-4-hydroxy-benzyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (648) | 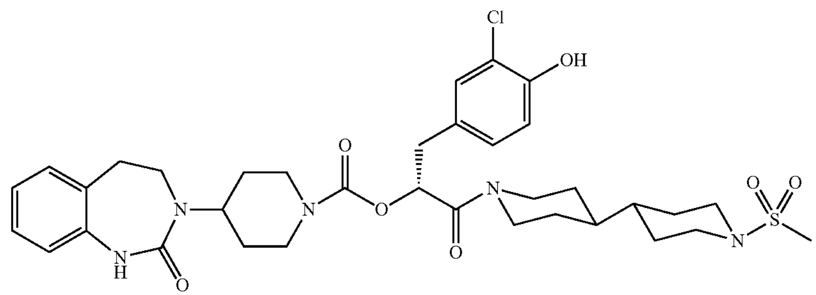 | (R)-1-(3-chloro-4-hydroxy-benzyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (649) | 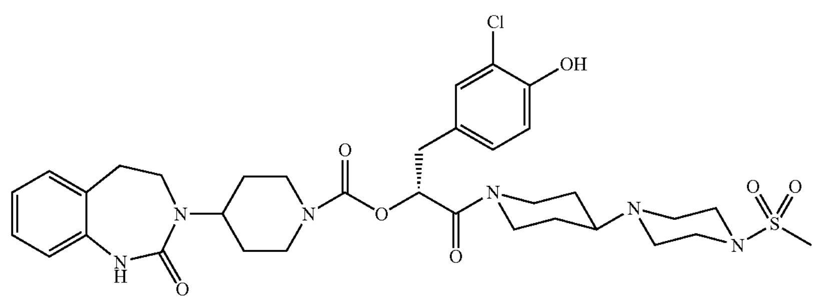 | (R)-1-(3-chloro-4-hydroxy-benzyl)-2-[4-(4-methanesulphonyl-piperazin-1-yl)-piperidin-1-yl]-2-oxo-ethyl 4-(4-methanesulphonyl-piperazin-1-yl)-piperidin-3-yl)-piperidine-1-carboxylate |

| No. | Structure | Name |
|---|---|---|
| (650) | 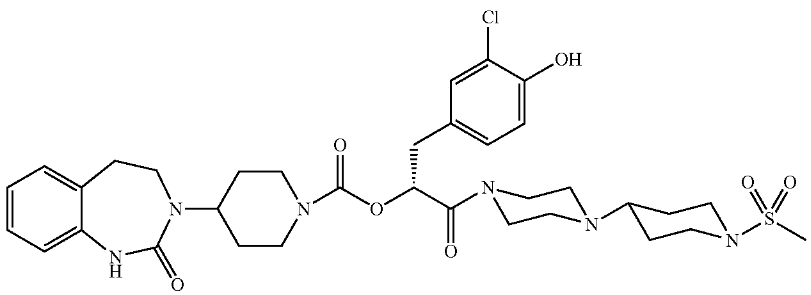 | (R)-1-(3-chloro-4-hydroxy-benzyl)-2-[4-(1-methanesulphonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (651) | 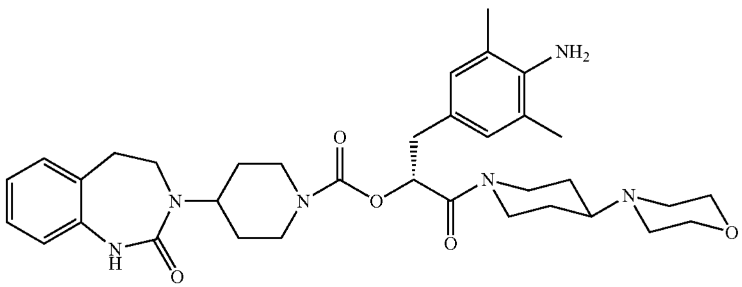 | (R)-1-(4-amino-3,5-dimethyl-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (652) | 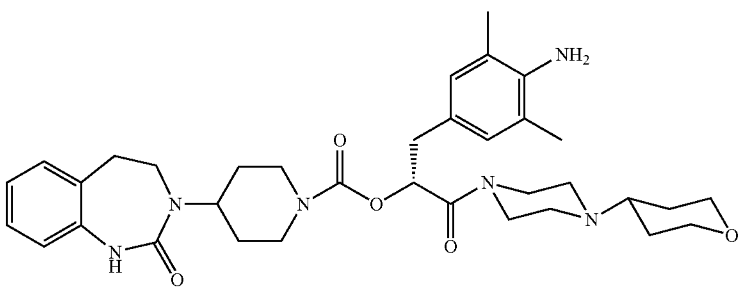 | (R)-1-(4-amino-3,5-dimethyl-benzyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |

-continued

| No. | Structure | Name |
|---|---|---|
| (653) | 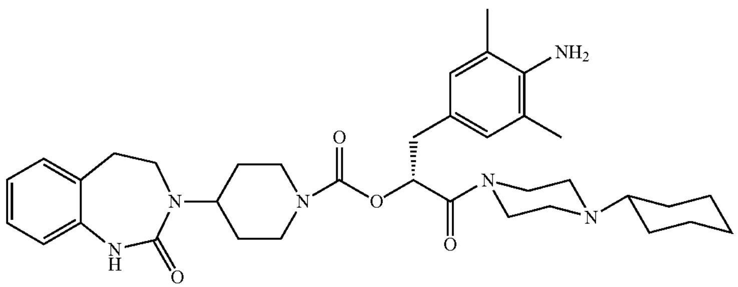 | (R)-1-(4-amino-3,5-dimethyl-benzyl)-2-(4-cyclohexyl-piperazin-1-yl)-2-oxo-ethyl 4-(2-oxo-1,2,4,5-tetrahydro-1,3-benzodiazepin-3-yl)-piperidine-1-carboxylate |
| (654) | 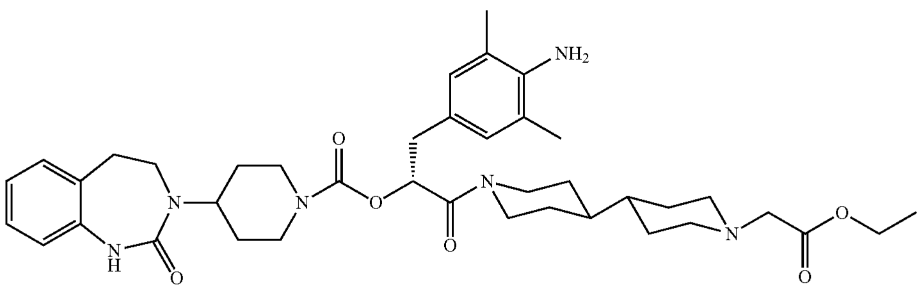 | (R)-1-(4-amino-3,5-dimethyl-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (655) | 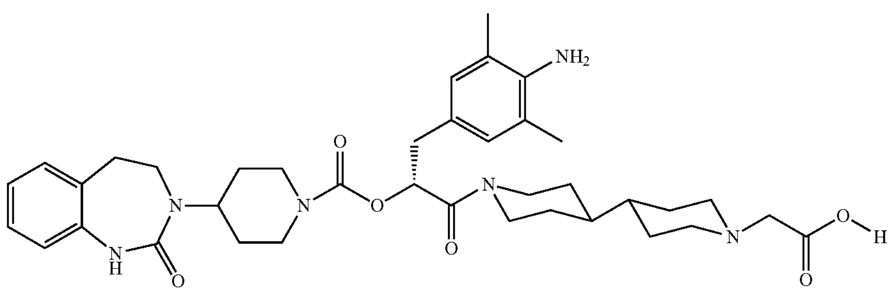 | (R)-1-(4-amino-3,5-dimethyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (656) | 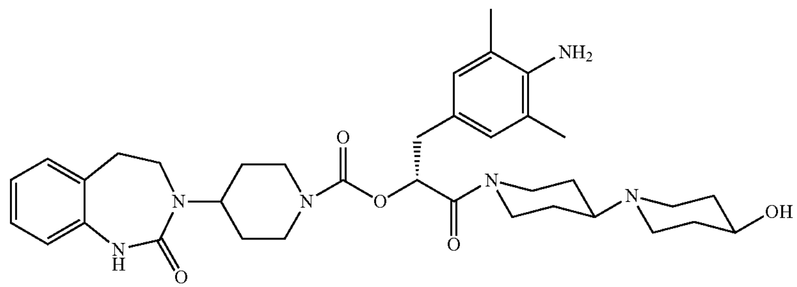 | (R)-1-(4-amino-3,5-dimethyl-benzyl)-2-(4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (657) | 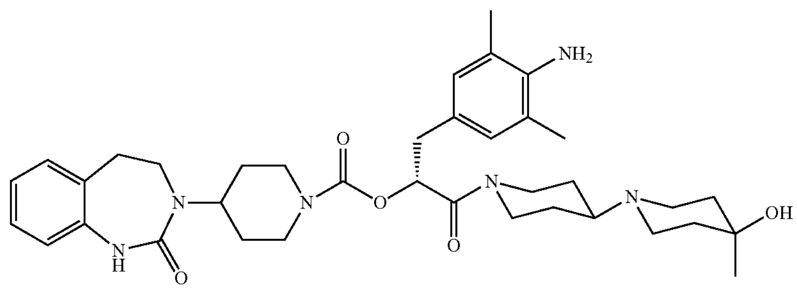 | (R)-1-(4-amino-3,5-dimethyl-benzyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (658) | 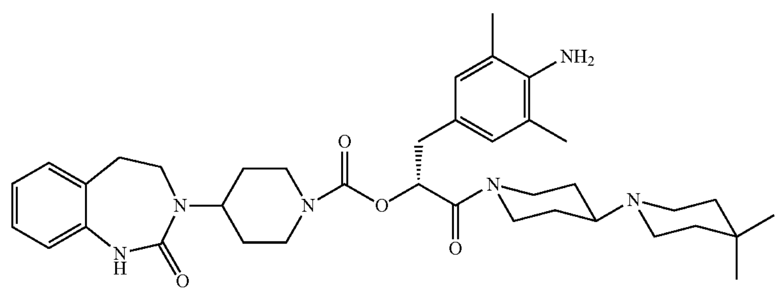 | (R)-1-(4-amino-3,5-dimethyl-benzyl)-2-(4,4-dimethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (659) | 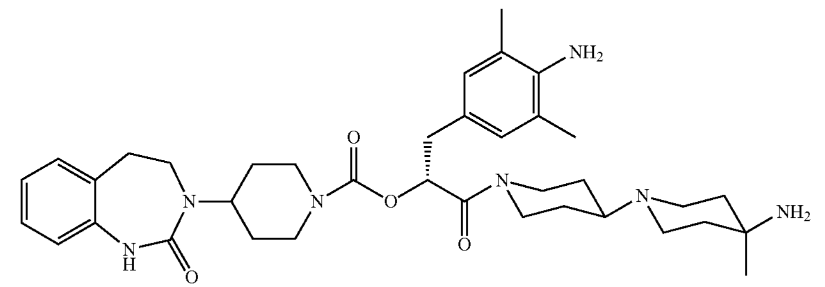 | (R)-1-(4-amino-3,5-dimethyl-benzyl)-2-(4-amino-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (660) | 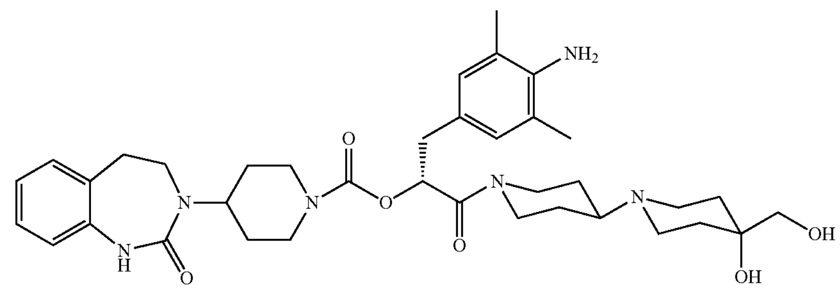 | (R)-1-(4-amino-3,5-dimethyl-benzyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (661) | 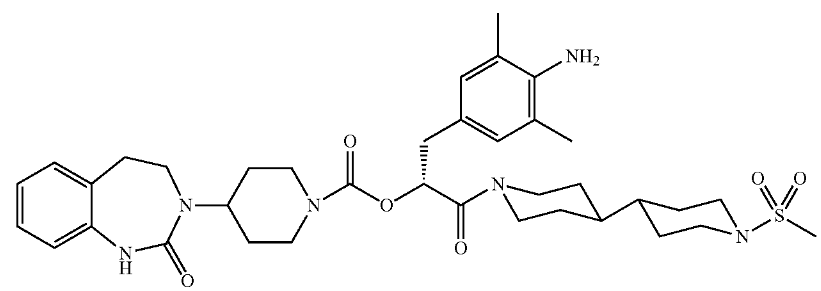 | (R)-1-(4-amino-3,5-dimethyl-benzyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (662) | 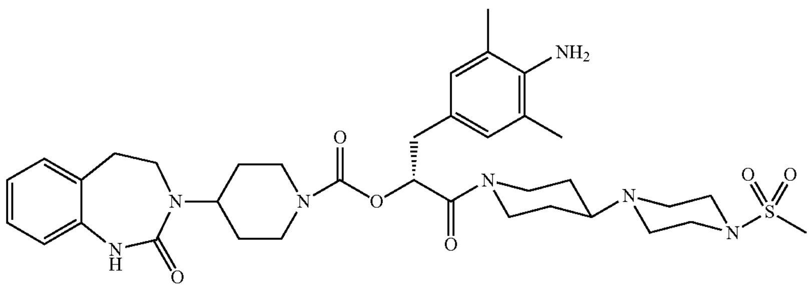 | (R)-1-(4-amino-3,5-dimethyl-benzyl)-2-[4-(4-methanesulphonyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (663) | 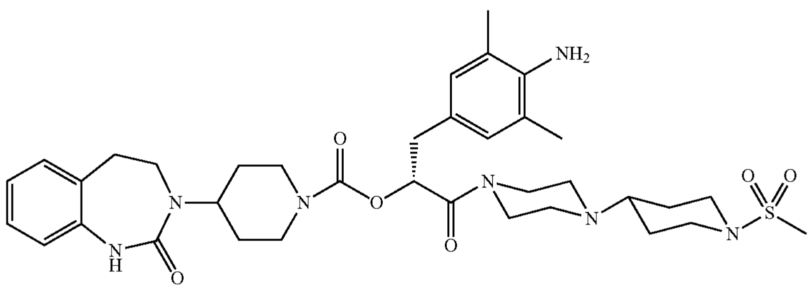 | (R)-1-(4-amino-3,5-dimethyl-benzyl)-2-[4-(1-methanesulphonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (664) | 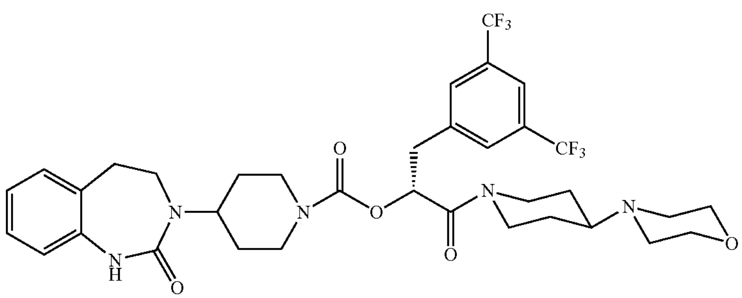 | (R)-1-(3,5-bis-trifluormethyl-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (665) | 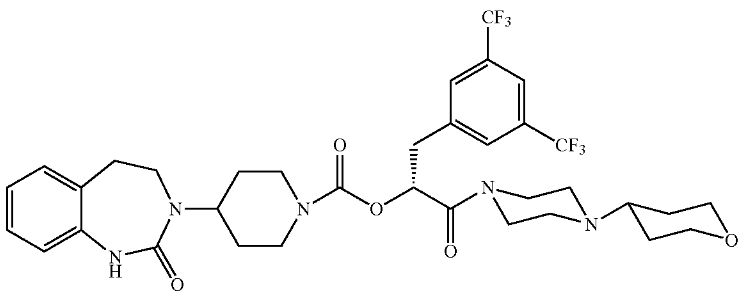 | (R)-1-(3,5-bis-trifluoromethyl-benzyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (666) | 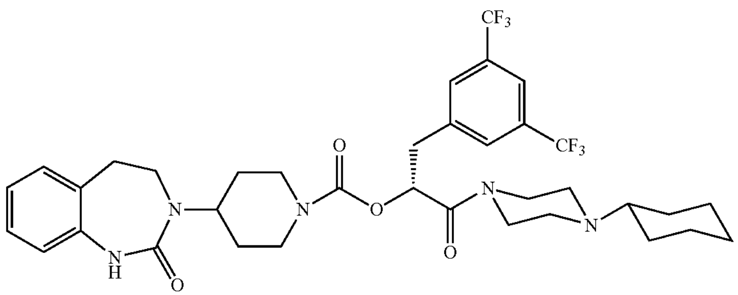 | (R)-1-(3,5-bis-trifluoromethyl-benzyl)-2-(4-cyclohexyl-piperazin-1-yl)-2-oxo-ethyl 4-(2-oxo-1,2,4,5-tetrahydro-1,3-benzodiazepin-3-yl)-piperidine-1-carboxylate |
| (667) | 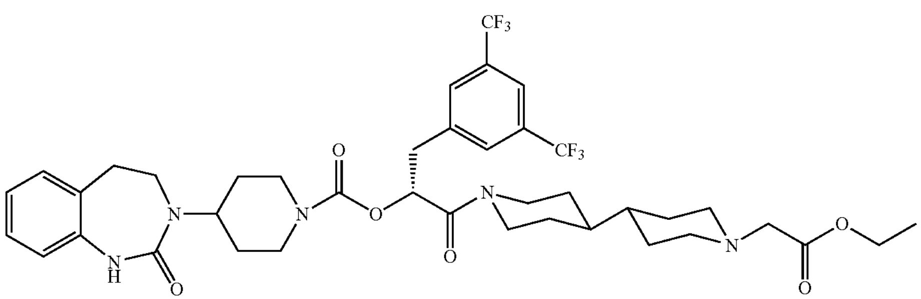 | (R)-1-(3,5-bis-trifluoromethyl-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (668) | 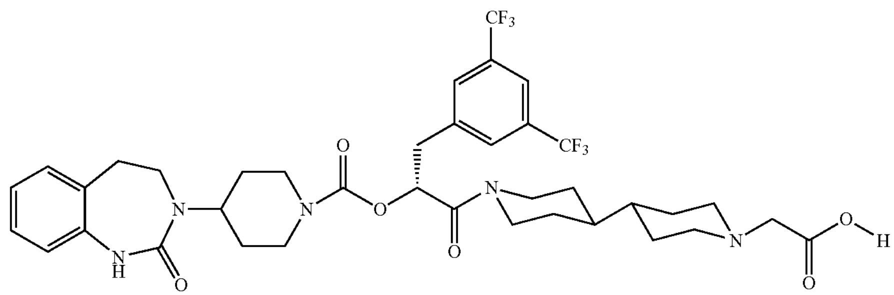 | (R)-1-(3,5-bis-trifluormethyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (669) | 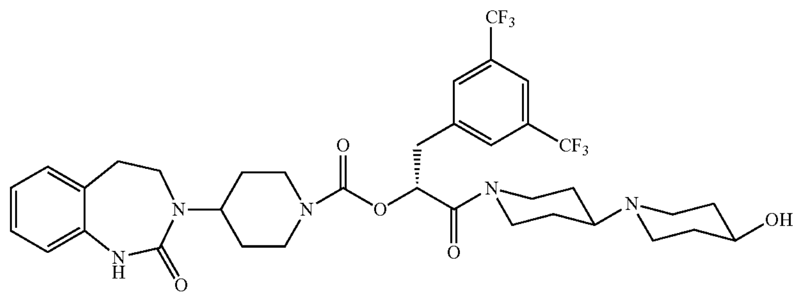 | (R)-1-(3,5-bis-trifluormethyl-benzyl)-2-(4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (670) | 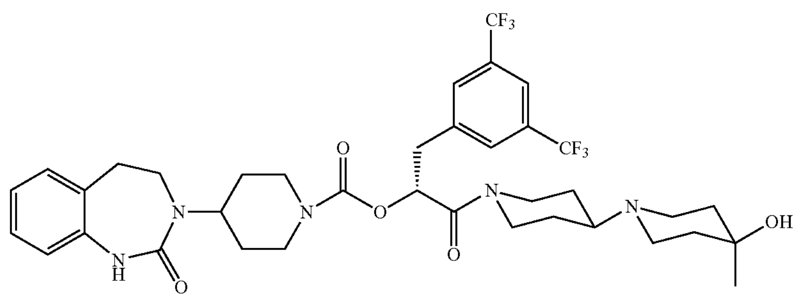 | (R)-1-(3,5-bis-trifluormethyl-benzyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (671) | 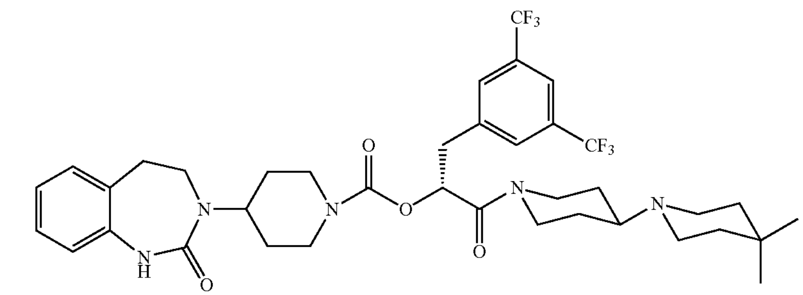 | (R)-1-(3,5-bis-trifluormethyl-benzyl)-2-(4,4-dimethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (672) | 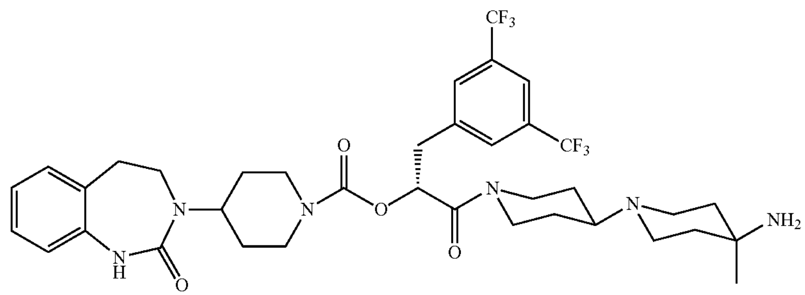 | (R)-2-(4-amino-4-methyl-1,4'-bipiperidinyl-1'-yl)-1-(3,5-bis-trifluormethyl-benzyl)-2-oxo-ethyl 4-(2-oxo-1,2,4,5-tetrahydro-1,3-benzodiazepin-3-yl)-piperidine-1-carboxylate |
| (673) | 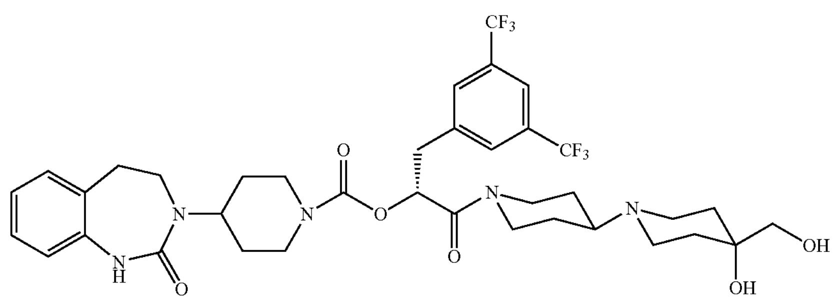 | (R)-1-(3,5-bis-trifluormethyl-benzyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (674) | 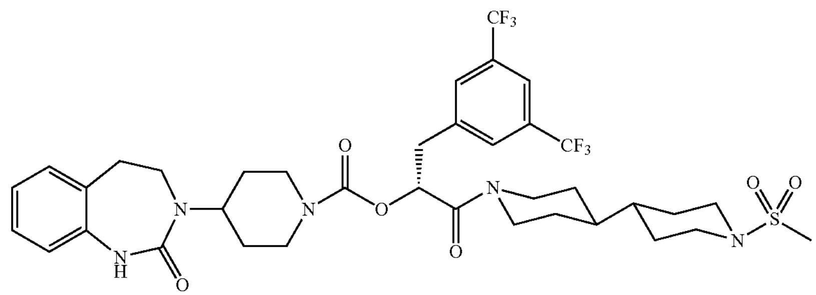 | (R)-1-(3,5-bis-trifluormethyl-benzyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (675) | 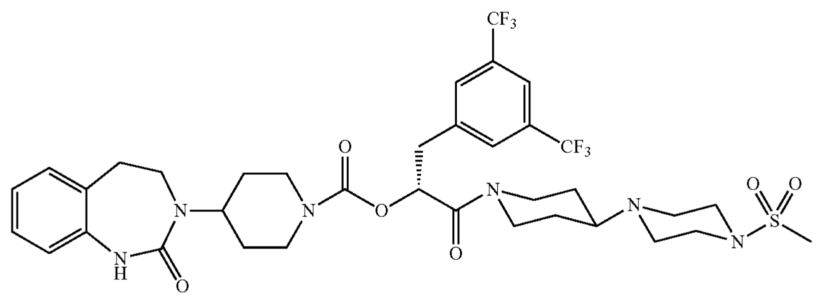 | (R)-1-(3,5-bis-trifluormethyl-benzyl)-2-[4-(4-methanesulphonyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (676) | 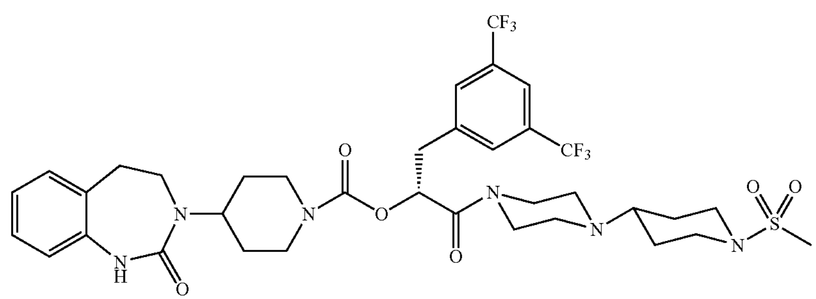 | (R)-1-(3,5-bis-trifluormethyl-benzyl)-2-[4-(1-methanesulphonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (677) | 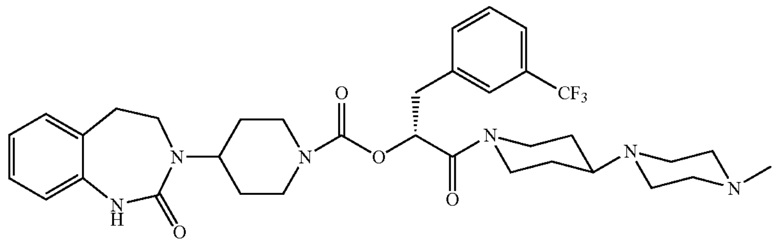 | (R)-2-[4-(4-methyl-piperazin-1-yl)-piperidin-1-yl]-2-oxo-1-(3-trifluormethyl-benzyl)-ethyl 4-(2-oxo-1,2,4,5-tetrahydro-1,3-benzodiazepin-3-yl)-piperidine-1-carboxylate |
| (678) | 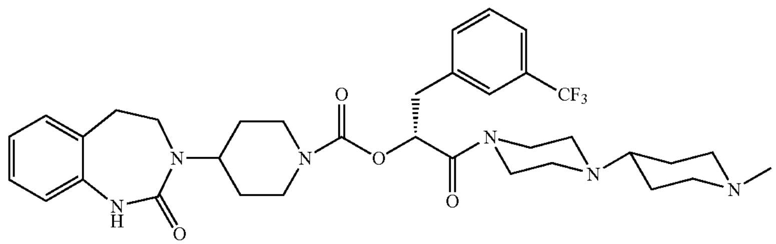 | (R)-2-[4-(1-methyl-piperidin-4-yl)-piperazin-1-yl]-2-oxo-1-(3-trifluormethyl-benzyl)-ethyl 4-(2-oxo-1,2,4,5-tetrahydro-1,3-benzodiazepin-3-yl)-piperidine-1-carboxylate |
| (679) | 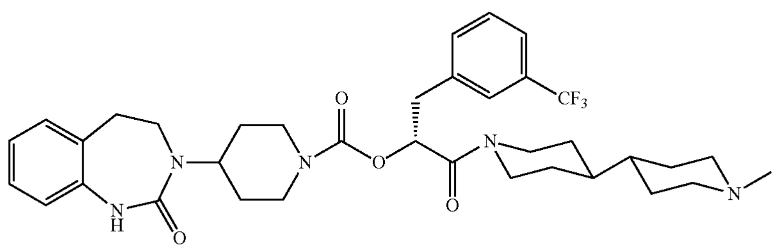 | (R)-2-(1'-methyl-4,4'-bipiperidinyl-1-yl)-2-oxo-1-(3-trifluormethyl-benzyl)-ethyl 4-(2-oxo-1,2,4,5-tetrahydro-1,3-benzodiazepin-3-yl)-piperidine-1-carboxylate |
| (680) | 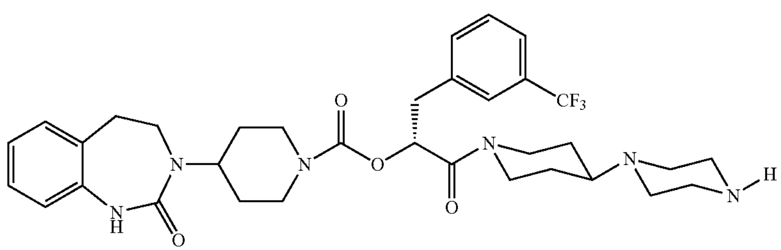 | (R)-2-oxo-2-(4-piperazin-1-yl-piperidin-1-yl)-1-(3-trifluormethyl-benzyl)-ethyl 4-(2-oxo-1,2,4,5-tetrahydro-1,3-benzodiazepin-3-yl)-piperidine-1-carboxylate |

-continued

| No. | Name |
|---|---|
| (681) | (R)-2-oxo-2-(4-piperidin-4-yl-piperazin-1-yl)-1-(3-trifluoromethyl-benzyl)-ethyl 4-(2-oxo-1,2,4,5-tetrahydro-1,3-benzodiazepin-3-yl)-piperidine-1-carboxylate |
| (682) | (R)-2-(4,4'-bipiperidinyl-1-yl)-2-oxo-1-(3-trifluoromethyl-benzyl)-ethyl 4-(2-oxo-1,2,4,5-tetrahydro-1,3-benzodiazepin-3-yl)-piperidine-1-carboxylate |
| (683) | (R)-2-(4-hydroxy-1,4'-bipiperidinyl-1'-yl)-2-oxo-1-(3-trifluoromethyl-benzyl)-ethyl 4-(2-oxo-1,2,4,5-tetrahydro-1,3-benzodiazepin-3-yl)-piperidine-1-carboxylate |
| (684) | (R)-2-(4-hydroxy-4-methyl-1,4'-bipiperidinyl-1'-yl)-2-oxo-1-(3-trifluoromethyl-benzyl)-ethyl 4-(2-oxo-1,2,4,5-tetrahydro-1,3-benzodiazepin-3-yl)-piperidine-1-carboxylate |

| No. | Structure | Name |
|---|---|---|
| (685) | 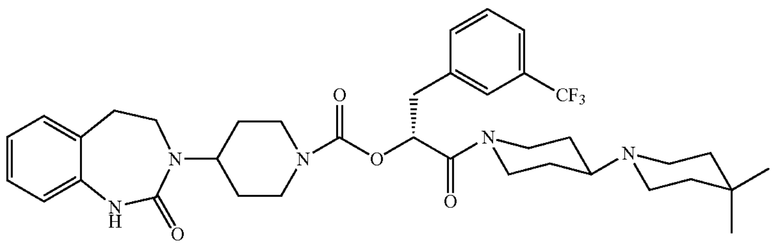 | (R)-2-(4,4-dimethyl-1,4'-bipiperidinyl-1'-yl)-2-oxo-1-(3-trifluormethyl-benzyl)-ethyl 4-(2-oxo-1,2,4,5-tetrahydro-1,3-benzodiazepin-3-yl)-piperidine-1-carboxylate |
| (686) | 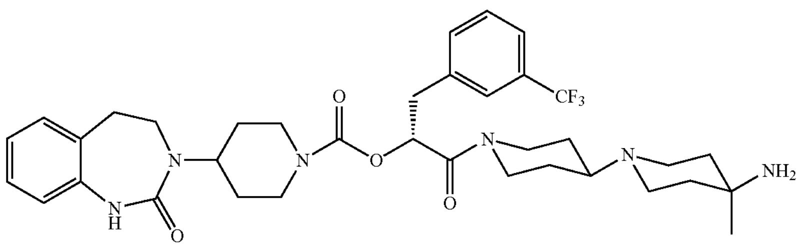 | (R)-2-(4-amino-4-methyl-1,4'-bipiperidinyl-1'-yl)-2-oxo-1-(3-trifluormethyl-benzyl)-ethyl 4-(2-oxo-1,2,4,5-tetrahydro-1,3-benzodiazepin-3-yl)-piperidine-1-carboxylate |
| (687) | 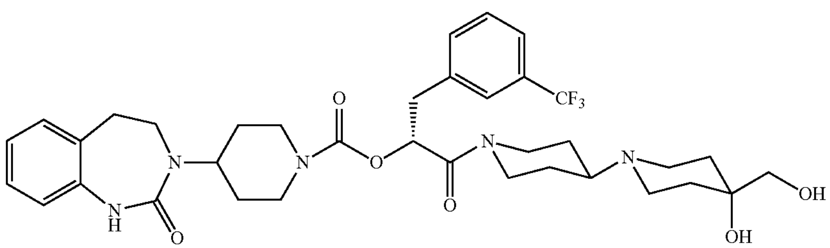 | (R)-2-(4-hydroxy-4-hydroxymethyl-1,4'-bipiperidinyl-1'-yl)-2-oxo-1-(3-trifluormethyl-benzyl)-ethyl 4-(2-oxo-1,2,4,5-tetrahydro-1,3-benzodiazepin-3-yl)-piperidine-1-carboxylate |
| (688) | 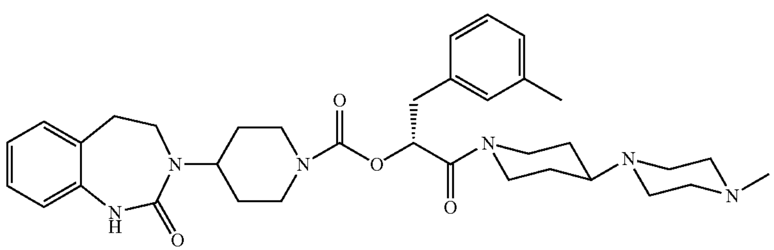 | (R)-1-(3-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

| No. | Structure | Name |
|---|---|---|
| (689) | 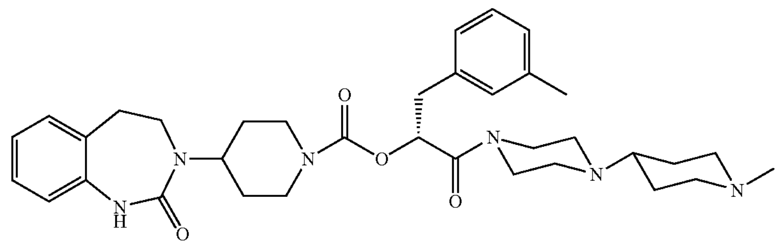 | (R)-1-(3-methyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (690) | 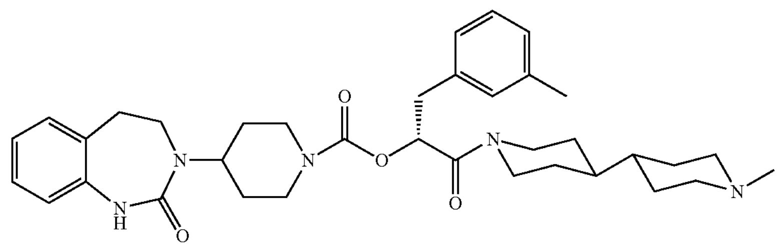 | (R)-1-(3-methyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (691) | 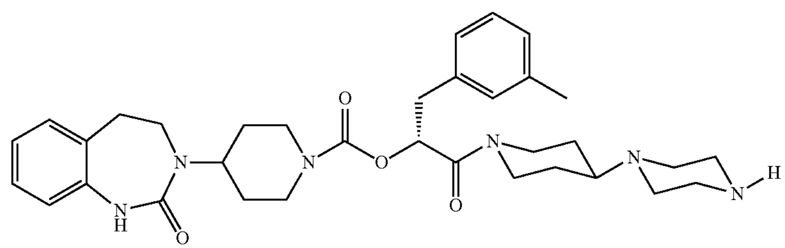 | (R)-1-(3-methyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (692) | 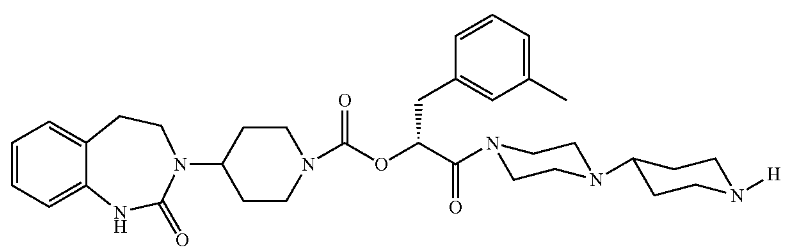 | (R)-1-(3-methyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |

-continued

| No. | Structure | Name |
|---|---|---|
| (693) | 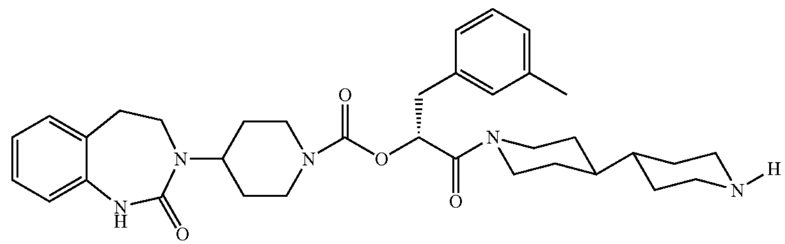 | (R)-2-(4,4'-bipiperidinyl-1-yl)-1-(3-methyl-benzyl)-2-oxo-ethyl 4-(2-oxo-1,2,4,5-tetrahydro-1,3-benzodiazepin-3-yl)-piperidine-1-carboxylate |
| (694) | 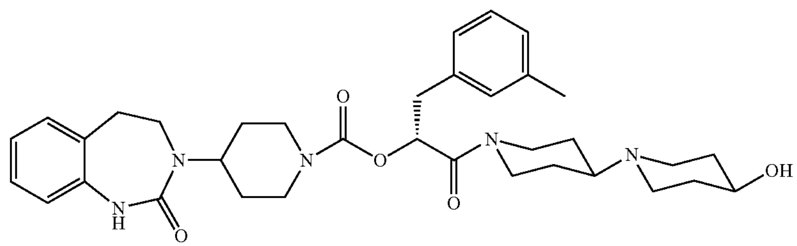 | (R)-2-(4-hydroxy-1,4'-bipiperidinyl-1'-yl)-1-(3-methyl-benzyl)-2-oxo-ethyl 4-(2-oxo-1,2,4,5-tetrahydro-1,3-benzodiazepin-3-yl)-piperidine-1-carboxylate |
| (695) | 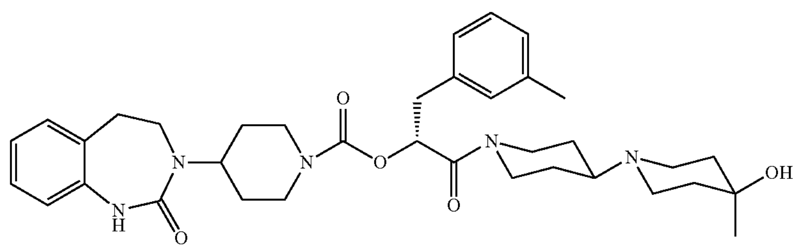 | (R)-2-(4-hydroxy-4-methyl-1,4'-bipiperidinyl-1'-yl)-1-(3-methyl-benzyl)-2-oxo-ethyl 4-(2-oxo-1,2,4,5-tetrahydro-1,3-benzodiazepin-3-yl)-piperidine-1-carboxylate |
| (696) | 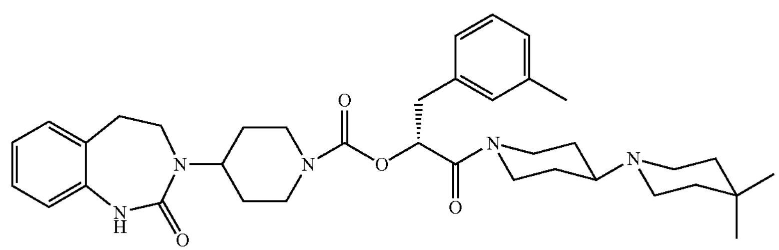 | (R)-2-(4,4-dimethyl-1,4'-bipiperidinyl-1'-yl)-1-(3-methyl-benzyl)-2-oxo-ethyl 4-(2-oxo-1,2,4,5-tetrahydro-1,3-benzodiazepin-3-yl)-piperidine-1-carboxylate |

-continued

| No. | Structure | Name |
|---|---|---|
| (697) | 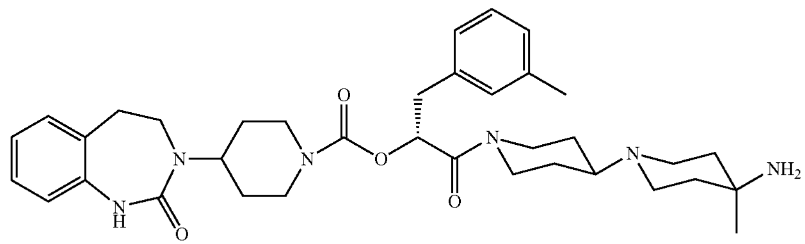 | (R)-2-(4-amino-4-methyl-1,4'-bipiperidinyl-1'-yl)-1-(3-methyl-benzyl)-2-oxo-ethyl 4-(2-oxo-1,2,4,5-tetrahydro-1,3-benzodiazepin-3-yl)-piperidine-1-carboxylate |
| (698) | | (R)-2-(4-hydroxy-4-hydroxymethyl-1,4'-bipiperidinyl-1'-yl)-1-(3-methyl-benzyl)-2-oxo-ethyl 4-(2-oxo-1,2,4,5-tetrahydro-1,3-benzodiazepin-3-yl)-piperidine-1-carboxylate | the enantiomers, the diastereomers and the salts thereof.

The compounds of general formula (I) are prepared by methods known in principle. The following methods have proved particularly useful for preparing the compounds of general formula (I) according to the invention:

(a) In order to prepare compounds of general formula (I) wherein all the groups are as hereinbefore defined:
reacting piperidines of general formula

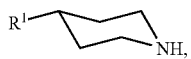

wherein $R^1$ is as hereinbefore defined,
with carbonic acid derivatives of general formula

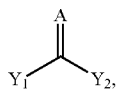

wherein $Y_1$ and $Y_2$ denote nucleofugic groups, which may be identical or different, preferably the chlorine atom, the p-nitrophenoxy or trichloromethoxy group, if A denotes the oxygen atom, or the chlorine atom if A denotes the sulphur atom, and with compounds of general formula

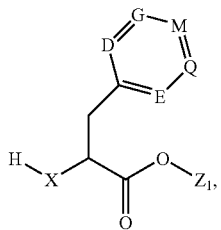

wherein X, D, E, G, M and Q are as hereinbefore defined and $Z_1$ denotes a protective group for a carboxy group, for example a $C_{1-6}$-alkyl or benzyl group, while the alkyl groups may be straight-chain or branched and the benzyl group may be substituted by one or two methoxy groups. Preferably $Z_1$ denotes the methyl, ethyl, tert-butyl or benzyl group. Before the reaction is carried out any carboxylic acid functions, primary or secondary amino functions or hydroxy functions present in the group $R^1$ of a compound of formula (III) and/or in a compound of formula (V) may be protected by conventional protecting groups and any protecting groups used may be cleaved after the reaction is complete using methods familiar to those skilled in the art.

In a first step the compounds of general formula (III) are reacted with the carbonic acid derivatives of general formula (IV) in a solvent, for example in dichloromethane, THF, pyridine or mixtures thereof, at a temperature from −20 to 50° C. in the presence of a base, for example triethylamine, pyridine or ethyldiisopropylamine. The resulting intermediate may be purified or further reacted without purification.

The reaction of these intermediates with compounds of general formula (V) also takes place in one of the above-mentioned solvents and at the temperatures specified above, in the presence of a base, such as triethylamine or pyridine, with or without the addition of an activating reagent, such as e.g. 4-dimethylaminopyridine. To activate them, the compounds of general formula (V) may also be deprotonated using a metal hydride, such as e.g. NaH or KH, while in this case there is no need for the presence of the base of the activating reagent.

(b) In order to prepare compounds of general formula (I) wherein all the groups are as hereinbefore defined:
coupling a carboxylic acid of general formula

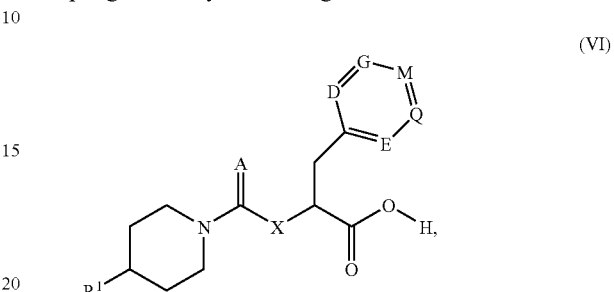

wherein all the groups are as hereinbefore defined, with an amine of general formula $HNR^2R^3$ wherein $R^2$ and $R^3$ are as hereinbefore defined. Before the reaction is carried out any carboxylic acid functions, primary or secondary amino functions or hydroxy functions present in a compound of formula (VI) and/or in the groups $R^2$ and $R^3$ of the amine of formula $HNR^2R^3$ may be protected by conventional protecting groups and any protecting groups used may be cleaved after the reaction is complete using methods familiar to those skilled in the art.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N-N',N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +25° C. If necessary, N-ethyl-diisopropylamine (Hünig base) is preferably used as an additional auxiliary base.

The so-called anhydride process is used as a further coupling method for synthesising compounds of general formula (I) (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the mixed anhydride process is preferred (J. R. Vaughan Jr., J. Amer. Chem. Soc. 73, 3547 (1951)), in which the mixed anhydride of the carboxylic acid of general formula (VIII) which is to be coupled and monoisobutyl carbonate is obtained, using isobutyl chlorocarbonate in the presence of bases such as 4-methylmorpholine or 4-ethylmorpholine. The preparation of this mixed anhydride and the coupling with the amines of general formula $HNR^2R^3$ are carried out in a one-pot process, using the above-mentioned solvents and at temperatures between −20 and +25° C., preferably 0° C. and +25° C.

(c) In order to prepare compounds of general formula (I) wherein all the groups are as hereinbefore defined:

coupling a compound of general formula

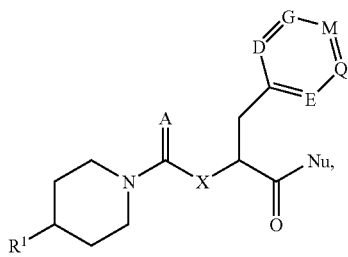

(VII)

with an amine of general formula HNR²R³
wherein all the groups are as hereinbefore defined and Nu denotes a leaving group, for example a halogen atom, such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms or by methyl or nitro groups, while the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxopyrrolidin-1-yloxy, phthalimidyloxy, 1H-benzo-triazol-1-yloxy or azide group. Before the reaction is carried out any carboxylic acid functions, primary or secondary amino functions or hydroxy functions present in a compound of formula (VII) and/or in the groups R² and R³ of the amine of formula HNR²R³ may be protected by conventional protecting groups and any protecting groups used may be cleaved after the reaction is complete using methods familiar to those skilled in the art.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

The new compounds of general formula (I) according to the invention contain one or more chiral centres. If for example there are two chiral centres the compounds may occur in the form of two pairs of diastereomeric antipodes. The invention covers the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula (I) is reacted with one of the above-mentioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

If the group X in compounds of general formula (V) denotes the oxygen atom, the hydroxycarboxylic acids of general formula

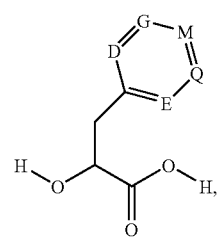

(VIII)

needed for the synthesis may be obtained from compounds of general formula

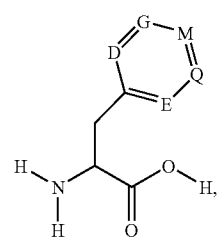

(IX)

wherein D, E, G, M and Q in both formulae are as hereinbefore defined.

By diazotising compounds of general formula (IX) with a suitable diazotising reagent, preferably sodium nitrite in an acid medium, it is possible to obtain the compounds of general formula (VIII). If enantiomerically pure compounds are used the corresponding enantiomerically pure hydroxycarboxylic acid compounds are obtained, the configuration being retained as the reaction proceeds.

An alternative method of obtaining compounds of general formula (VIII) comprises reacting aldehydes of general formula (X) with N-acetylglycine in acetic anhydride as solvent in the presence of alkali metal acetate, preferably sodium or potassium acetate at suitable temperature, preferably at 80-130° C.

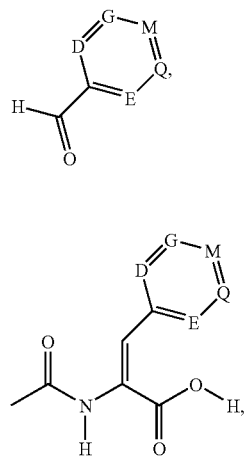

(X)

(XI)

The azlactones formed as primary products are hydrolysed without being isolated to form the compounds of general formula (XI).

By further reaction in the presence of aqueous inorganic acids such as sulphuric, phosphoric or hydrochloric acid, but preferably hydrochloric acid, compounds of general formula (XII) are obtained. These are then converted with suitable reducing agents into the compounds of general formula (VIII).

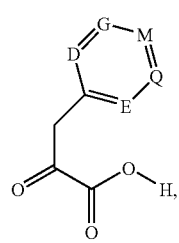

(XII)

The reducing agents used may be alkali metal borohydrides, such as sodium or potassium borohydride. Other reducing agents are chlorodialkylboranes, such as chlorodicyclohexylborane. If chiral chlorodialkylboranes are used, such as e.g. B-chlorodiisopinocampheylborane, the compounds of general formula (VIII) may be isolated in enantiomerically pure form.

Another way of obtaining compounds of general formula (VIII) comprises alkylating the compound (XIII)

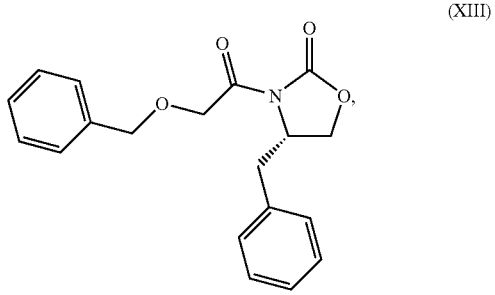

(XIII)

with aryl- or heteroaryl-methylhalides of general formula

(XIV)

wherein Hal denotes a chlorine, bromine or iodine atom, and D, E, G, Q and E are as hereinbefore defined, analogously to methods known from the literature (Michael T. Crimmins, Kyle A. Emmitte and Jason D. Katz, Org. Lett. 2, 2165-2167 [2000]). The diastereomeric products formed may then be separated using physicochemical methods, preferably using chromatographic methods or recrystallisation. The hydrolytic cleaving of the chiral auxiliary and cleaving of the benzyl protecting group also open up a possible method of obtaining enantiomerically pure hydroxycarboxylic acid compounds of general formula (V).

The further reaction of compounds of general formula (VIII) to obtain compounds of general formula (V) is carried out in the alcoholic medium, preferably in methanol or ethanol, in the presence of a suitable acid, such as hydrochloric acid. The reaction may alternatively be carried out by reacting with thionyl chloride in alcoholic solvents, preferably methanol.

If the group X in compounds of general formula (V) denotes the sulphur atom, the thiocarboxylic acids of general formula

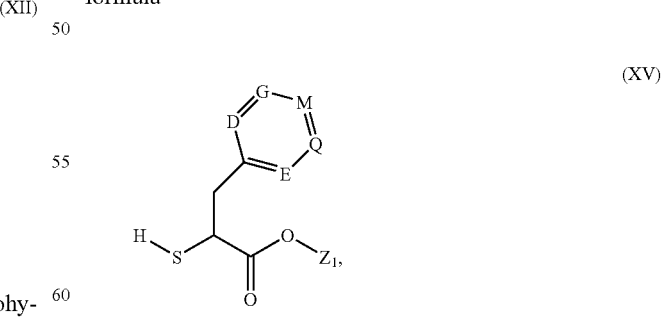

(XV)

needed for the synthesis, wherein D, E, G, M and Q are as hereinbefore defined and $Z_1$ denotes a protective group for a carboxy group as described under process (a), may be obtained from compounds of general formula (V) wherein X denotes the oxygen atom.

By Mitsunobu reaction of the compounds of general formula (V) with $C_{1-6}$-alkylthiocarboxylic acids, where the alkyl chain may be straight or branched but preferably denotes the methyl group, the corresponding alkylthiocarboxylic acid esters of these compounds are obtained. These may be hydrolysed according to known methods to obtain the compounds of general formula (XV) (Bert Strijtveen and Richard M. Kellogg, J. Org. Chem. 51, 3664-3671 [1986]).

All compounds of general formula (I) which contain primary or secondary amino, hydroxy or hydroxycarbonyl functions are preferably obtained from precursors comprising protective groups. Examples of protective groups for amino functions include for example a benzyloxycarbonyl, 2-nitrobenzyloxycarbonyl, 4-nitro-benzyloxycarbonyl, 4-methoxy-benzyloxycarbonyl, 2-chloro-benzyloxycarbonyl, 3-chloro-benzyloxycarbonyl, 4-chloro-benzyloxycarbonyl, 4-biphenylyl-α,α-dimethyl-benzyloxycarbonyl or 3,5-dimethoxy-α,α-dimethyl-benzyloxycarbonyl group, an alkoxycarbonyl group with a total of 1 to 5 carbon atoms in the alkyl moiety, for example the methoxycarbonyl, ethoxycarbonyl, n-propoxycarbonyl, isopropoxycarbonyl, n-butoxycarbonyl, 1-methylpropoxycarbonyl, 2-methylpropoxycarbonyl or tert-butyloxycarbonyl group which allyloxycarbonyl, 2,2,2-trichloro-(1,1-dimethylethoxy)carbonyl or 9-fluorenyl-methoxycarbonyl group or a formyl, acetyl or trifluoroacetyl group.

The protective group for hydroxy functions may be, for example, a trimethylsilyl, triethylsilyl, triisopropyl, tert-butyldimethylsilyl or tert-butyldiphenylsilyl group, a tert-butyl, benzyl, 4-methoxybenzyl or 3,4-dimethoxybenzyl group.

The protective group for hydroxycarbonyl functions may be for example an alkyl group with a total of 1 to 5 carbon atoms, for example the methyl, ethyl, n-propyl, isopropyl, n-butyl, tert-butyl, allyl, 2,2,2-trichloroethyl, benzyl or 4-methoxybenzyl group.

The compounds of general formula I obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, ethanesulphonic acid, benzenesulphonic acid, p-toluenesulphonic acid, acetic acid, fumaric acid, succinic acid, lactic acid, mandelic acid, malic acid, citric acid, tartaric acid or maleic acid.

Moreover, the new compounds of formula (I), if they contain a carboxylic acid function, may be converted into the addition salts thereof with inorganic or organic bases, particularly for pharmaceutical use into the physiologically acceptable addition salts thereof. Suitable bases for this include, for example, sodium hydroxide, potassium hydroxide, ammonia, cyclohexylamine, dicyclohexylamine, ethanolamine, diethanolamine and triethanolamine.

The present invention relates to racemates if the compounds of general formula (I) have only one chiral element. However, the application also includes the individual diastereomeric pairs of antipodes or mixtures thereof which are obtained if there is more than one chiral element in the compounds of general formula (I), as well as the individual optically active enantiomers of which the above-mentioned racemates are made up.

Also included in the subject matter of this invention are the compounds according to the invention, including the salts thereof, in which one or more hydrogen atoms, for example one, two, three, four or five hydrogen atoms, are replaced by deuterium.

The new compounds of general formula (I) and the physiologically acceptable salts thereof have valuable pharmacological properties, based on their selective CGRP-antagonistic properties. The invention further relates to pharmaceutical compositions containing these compounds, their use and the preparation thereof.

The new compounds of general formula I mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, $NaHCO_3$ 16.2, $MgSO_4$ 0.8, $NaHPO_4$ 1.0, $CaCl_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM $MgCl_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM $MgCl_2$, 1 mM EDTA, pH 7.40) and homogenised for 30 seconds with an Ultra-Turrax. 230 μl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 μl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity in the presence of 1 μM human CGRP-alpha during incubation. The concentration binding curves are analysed using computer-aided non-linear curve matching.

The compounds mentioned hereinbefore show $IC_{50}$ values ≦10000 nM in the test described.

B. CGRP Antagonism in SK-N-MC Cells

SK-N-MC cells (1 million cells) are washed twice with 250 μl incubation buffer (Hanks' HEPES, 1 mM 3-isobutyl-1-methylxanthine, 1% BSA, pH 7.4) and pre-incubated at 37° C. for 15 minutes. After the addition of CGRP (10 μl) as agonist in increasing concentrations ($10^{-11}$ to $10^{-6}$ M), or additionally the substance in 3 to 4 different concentrations, the mixture is incubated for another 15 minutes.

Intracellular cAMP is then extracted by the addition of 20 μl of 1M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the $pA_2$ values of antagonistically acting substances are determined graphically.

The compounds of general formula I exhibit CGRP-antagonistic properties in the in vitro test model described, in a dosage range between $10^{-12}$ and $10^{-5}$ M.

In view of their pharmacological properties the compounds of general formula I and the salts thereof with physiologically acceptable acids are thus suitable for the acute and prophylactic treatment of headaches, particularly migraine or cluster headaches. Moreover, the compounds of general formula I also have a positive effect on the following diseases: non-insulin-dependent diabetes mellitus ("NIDDM"), complex regional pain syndrome (CRPS1), cardiovascular diseases, morphine tolerance, diarrhoea caused by clostridium toxin, skin diseases, particularly thermal and radiation-induced skin damage including sunburn, inflammatory diseases, e.g. inflammatory diseases of the joints (arthritis), neurogenic inflammation of the oral mucosa, inflammatory lung diseases, allergic rhinitis, asthma, diseases accompanied by excessive vasodilatation and resultant reduced blood supply to the tissues, e.g. shock and sepsis. In addition, the compounds according to the invention have a general pain-relieving effect.

The symptoms of menopausal hot flushes caused by vasodilatation and increased blood flow in oestrogen-deficient women and hormone-treated patients with prostate carcinoma are favourably affected by the CGRP-antagonists of the present application in a preventive and acute-therapeutic capacity, this therapeutic approach being distinguished from hormone replacement by the absence of side effects.

The dosage required to achieve a corresponding effect is conveniently 0.0001 to 3 mg/kg of body weight, preferably 0.01 to 1 mg/kg of body weight, when administered intravenously or subcutaneously and 0.01 to 10 mg/kg of body weight, preferably 0.1 to 10 mg/kg of body weight when administered orally, nasally or by inhalation, 1 to 3×a day in each case.

If the treatment with CGRP antagonists and/or CGRP release inhibitors is given as a supplement to conventional hormone substitution, it is advisable to reduce the doses specified above, in which case the dosage may be from 1/5 of the lower limits mentioned above up to 1/1 of the upper limits specified.

The compounds prepared according to the invention may be administered either on their own or optionally in combination with other active substances for the treatment of migraine by intravenous, subcutaneous, intramuscular, intrarectal, intranasal route, by inhalation, transdermally or orally, while aerosol formulations are particularly suitable for inhalation. The combinations may be administered either simultaneously or sequentially.

Categories of active substance which may be used in the combination include e.g. antiemetics, prokinetics, neuroleptics, antidepressants, neurokinine antagonists, angiotensin receptor blockers (angiotensin II antagonists), iNOS inhibitors, AMPA antagonists, anticonvulsants, histamine-H1 receptor antagonists, antimuscarinics, β-blockers, α-agonists and α-antagonists, ergot alkaloids, mild analgesics, non-steroidal antiinflammatories, corticosteroids, calcium antagonists, $5\text{-HT}_{1B/1D}$ agonists or other anti-migraine agents, which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, azathioprine, diclofenac, diflunisal, fenbufen, fenoprofen, flurbiprofen, ibuprofen, indometacin, ketoprofen, leflunomide, lomoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib and celecoxib.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, topiramate, riboflavin, montelukast, lisinopril, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, lidocaine or diltiazem and other $5\text{-HT}_{1B/1D}$-agonists such as, for example, almotriptan, avitriptan, eletriptan, frovatriptan, naratriptan, rizatriptan, sumatriptan and zolmitriptan.

The dosage of these active substances is expediently 1/5 of the lowest recommended dose to 1/1 of the normally recommended dose, i.e. for example 20 to 100 mg of sumatriptan.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Experimental Section

As a rule, IR, $^1$H-NMR and/or mass spectra have been obtained for the compounds prepared.

Unless otherwise stated, $R_f$ values are obtained using ready-made silica gel TLC plates 60 F254 (E. Merck, Darmstadt, Item no. 1.05714) without chamber saturation.

The $R_f$ values obtained under the name Polygram are obtained using ready-made Polygram SIL G/UV$_{254}$ TLC films (coated with 0.2 mm silica gel) made by Messrs Macherey-Nagel (Düren, Item no. 805 021).

The $R_f$ values obtained under the name Polygram-Alox are obtained using ready-made Polygram Alox N/UV$_{254}$ TLC plates (coated with 0.2 mm aluminium oxide) made by Messrs Macherey-Nagel (Düren, Item no. 802 021).

The ratios given for the eluants relate to units by volume of the solvent in question. The units by volume specified for NH$_3$ refer to a concentrated solution of NH$_3$ in water.

Unless otherwise stated, the acid, base and salt solutions used for working up the reaction solutions are aqueous systems of the concentrations specified.

For chromatographic purification, silica gel made by Millipore (MATREX™, 35-70 µm) is used.

For chromatographic purification, aluminium oxide made by Messrs ICN Biomedicals (Eschwege, Item no. 02090) is used. The required activity stage is produced before use in accordance with the manufacturer's instructions.

The HPLC data provided are measured using the parameters specified below:

Method A:

| time (min) | percent by volume of water (with 0.1% formic acid) | percent by volume of acetonitrile (with 0.1% formic acid) |
|---|---|---|
| 0 | 95 | 5 |
| 9 | 10 | 90 |
| 10 | 10 | 90 |
| 11 | 95 | 5 |

Analytical column: Zorbax column (Agilent Technologies), SB (Stable Bond) C18; 3.5 µm; 4.6 × 75 mm; column temperature: 30° C.; flow: 0.8 mL/min; injection volume: 5 µL; detection at 254 nm

Method B:

| time (min) | percent by volume of water (with 0.1% formic acid) | percent by volume of acetonitrile (with 0.1% formic acid) |
|---|---|---|
| 0 | 95 | 5 |
| 9 | 10 | 90 |
| 10 | 10 | 90 |
| 11 | 95 | 5 |

Analytical column: Waters Symmetry C18; 3.5 µm; 4.6 × 75 mm; column temperature: 30° C.; flow: 0.8 mL/min; injection volume: 5 µL; detection at 254 nm method C:

| time (min) | percent by volume of water (with 0.1% formic acid) | percent by volume of acetonitrile (with 0.1% formic acid) |
|---|---|---|
| 0 | 95 | 5 |
| 8 | 50 | 50 |
| 9 | 10 | 90 |
| 10 | 10 | 90 |
| 11 | 90 | 10 |

Analytical column: Zorbax column (Agilent Technologies), Bonus-RP C14; 3.5 µm; 4.6 × 75 mm; column temperature: 30° C.; flow: 0.8 mL/min; injection volume: 5 µL; detection at 254 nm

Method D:

| time (min) | percent by volume of water (with 0.1% formic acid) | percent by volume of acetonitrile (with 0.1% formic acid) |
|---|---|---|
| 0 | 95 | 5 |
| 8 | 50 | 50 |
| 9 | 10 | 90 |
| 10 | 10 | 90 |
| 11 | 90 | 10 |

Analytical column: Zorbax-column (Agilent Technologies), SB (Stable Bond) C18; 3.5 µm; 4.6 × 75 mm; column temperature: 30° C.; flow: 0.8 mL/min; injection volume: 5 µL; detection at 254 nm

Method E:

| time (min) | percent by volume of water (with 0.1% formic acid) | percent by volume of acetonitrile (with 0.1% formic acid) |
|---|---|---|
| 0 | 95 | 5 |
| 4.5 | 10 | 90 |
| 5 | 10 | 90 |
| 5.5 | 90 | 10 |

Analytical column: Zorbax column (Agilent Technologies), SB (Stable Bond) C18; 3.5 µm; 4.6 × 75 mm; column temperature: 30° C.; flow: 1.6 mL/min; injection volume: 5 µL; detection at 254 nm method F:

| time (min) | percent by volume of water (with 0.04% trifluoroacetic acid) | percent by volume of acetonitrile (with 0.04% trifluoroacetic acid) |
|---|---|---|
| 0 | 80 | 20 |
| 30 | 20 | 80 |

Analytical column: Waters Symmetry C8; 5 µm; 4.6 × 150 mm; column temperature: 25° C.; flow: 1.3 mL/min; injection volume: 5 µL; detection at 254 nm In preparative HPLC purifications as a rule the same gradients are used as were used to collect the analytical HPLC data.

The products are collected under mass control and the fractions containing the product are combined and freeze-dried.

If no detailed information is given as to the configuration, it is not clear whether it is a pure enantiomer or whether partial or even complete racemisation has occurred.

The following abbreviations are used in the description of the experiments:
Boc tert-butoxycarbonyl
cyc cyclohexane
DCM dichloromethane
DIPE diisopropylether
DMF N,N-dimethylformamide
EtOAc ethyl acetate
EtOH ethanol
Fmoc 9-fluorenylmethoxycarbonyl
semiconc. semi-concentrated
HATU O-(7-azabenzotriazol-1-yl)-N,N,N',N'-tetramethyluronium-hexafluoro-phosphate
HCl hydrochloric acid
HOAc acetic acid
HOBt 1-hydroxybenzotriazole-hydrate
i. vac. in vacuo (under vacuum)
KOH potassium hydroxide
conc. concentrated
LiOH lithium hydroxide
MeOH methanol
NaOAc sodium acetate
NaCl sodium chloride
NaOH sodium hydroxide
n.d. not determined
PE petroleum ether
RT ambient temperature
TBME tert-butylmethylether
TBTU O-(benzotriazol-1-yl)-N,N N',N'-tetramethyluronium-tetrafluoroborate
TFA trifluoroacetic acid
THF tetrahydrofuran

EXAMPLE 1

(R)-1-(3,4-dibromo-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate

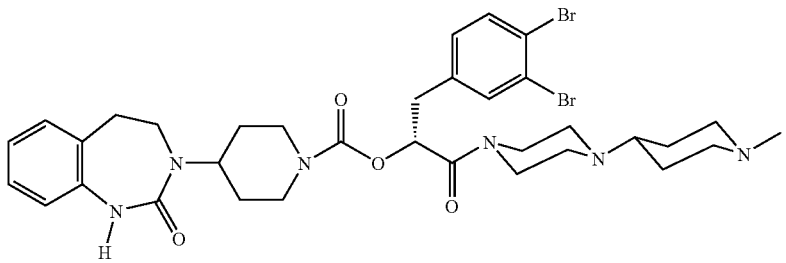

1a (Z,E)-2-acetylamino-3-(3,4-dibromo-phenyl)-acrylic acid

A mixture of 22.1 g (83.7 mmol) of 3,4-dibromobenzaldehyde, 14.7 g (126 mmol) N-acetylglycine and 10.3 g (126 mmol) NaOAc in 100 mL acetic anhydride was heated to 118° C. (internal temperature) for 1.5 h. After the reaction had ended the reaction mixture was cooled to 100° C. and then combined batchwise with 20 g ice (exothermic reaction), while the internal temperature was kept below 120° C. The reaction mixture was heated to 95° C. for a further 2 h, then added to a mixture of 240 mL water and 120 mL toluene and stirred for 1 h at RT. The precipitate was suction filtered, washed with 50 mL each of toluene and water and dried overnight at 40° C. in the circulating air dryer.

Yield: 20.8 g (69% of theory) ESI-MS: (M+H)$^+$=362/364/366 (2 Br) R$_f$=0.19 (silica gel, EtOAc/MeOH/NH$_3$ 90:10:1)

1b 3-(3,4-dibromo-phenyl)-2-oxo-propionic acid 125 mL ice-cooled 4 M HCl were added to a solution of 11.98 g (32.82 mmol) (Z,E)-2-acetylamino-3-(3,4-dibromo-phenyl)-acrylic acid in 90 mL N-methyl-2-pyrrolidinone and the reaction mixture was then refluxed for 2 h. The reaction solution cooled to approx. 40° C. was poured onto 450 mL water, the suspension formed was combined with 300 mL toluene and stirred overnight. The organic phase was extracted with water until a precipitate formed between the phases. This was suction filtered, the phases were separated, the toluene phase was evaporated down by half, mixed with water again and the precipitate formed was suction filtered. It was then combined with the first precipitate and dried at 50° C. in the circulating air dryer.

Yield: 5.73 g (54% of theory) ESI-MS: (M+H)$^+$=319/321/323 (2 Br) R$_f$=0.17 (silica gel, EtOAc/MeOH/NH$_3$ 80:20:2)

1c (R)-3-(3,4-dibromo-phenyl)-2-hydroxy-propionic acid

A solution of 6.1 g (19.0 mmol) (1R)-B-chlorodiisopinocampheylborane in 40 mL THF was added dropwise within 30 min to a solution of 5.1 g (15.8 mmol) 3-(3,4-dibromo-phenyl)-2-oxo-propionic acid and 2.2 mL (15.8 mmol) triethylamine in 20 mL THF which had been cooled to −35° C. and the reaction mixture was kept at this temperature for 1 h.

The reaction solution was carefully combined with 30 mL 1 M NaOH (exothermic) and 30 mL tert-butylmethylether, stirred for 15 min, the organic phase was separated off, then extracted with 25 mL water and 15 mL 1 M NaOH. The combined aqueous phases were acidified with 2 M HCl, extracted three times with in each case 40 mL tert-butylmethylether and the combined organic phases were dried over Na$_2$SO$_4$. After the desiccant and solvent had been eliminated the residue was purified by chromatography (silica gel, EtOAc/MeOH/NH$_3$ 70:30:3).

Yield: 3.2 g (63% of theory) ESI-MS: (M+H)$^+$=321/323/325 (2 Br) retention time (HPLC): 7.0 min (method A)

1d ethyl (R)-3-(3,4-dibromo-phenyl)-2-hydroxy-propionate 0.8 mL (10.9 mmol) thionyl chloride were added dropwise to a solution of 3.2 g (9.9 mmol) of (R)-3-(3,4-dibromo-phenyl)-2-hydroxy-propionic acid in 40 mL dry EtOH cooled to 0° C. and the reaction mixture was stirred for 1 h at RT. The reaction solution was evaporated down i.vac. the residue combined with 30 mL DCM and filtered to remove the insoluble precipitate. After the solvent had been eliminated the product was obtained as a viscous oil, which was further reacted without purification.

Yield: 3.1 g (88% of theory) ESI-MS: (M+H)$^+$=351/353/355 (2 Br) retention time (HPLC): 8.1 min (method A)

1e 4-(2-oxo-1,2,4,5-tetrahydro-1,3-benzodiazepin-3-yl)-piperidine-1-carbonylchloride 6 g (12.1 mmol) phosgene (20 percent by weight in toluene) were added to a solution of 2.5 g (10.2 mmol) 3-piperidin-4-yl-1,3,4,5-tetrahydro-1,3-benzodiazepin-2-one and 2.6 mL (14.9 mmol) ethyldiisopropylamine in 75 mL DCM cooled to 0° C. and the reaction mixture was stirred for 30 min at this temperature. The mixture was allowed to warm up to RT, evaporated down i.vac. to approx. 50 mL and filtered through silica gel, this was washed with 200 mL DCM/EtOAc (1:1) and the combined organic filtrates were again evaporated down i.vac. The residue was stirred with DIPE, suction filtered and dried i.vac.

Yield: 2.42 g (77% of theory) R$_f$=0.43 (silica gel, DCM/EtOAc 1:1)

1f (R)-2-(3,4-dibromo-phenyl)-1-ethoxycarbonyl-ethyl 4-(2-oxo-1,2,4,5-tetrahydro-1,3-benzodiazepin-3-yl)-piperidine-1-carboxylate 362 mg (55% in mineral oil, 9.06 mmol) NaH were added batchwise to a solution of 2.90 g (8.24 mmol) of (R)-3-(3,4-dibromo-phenyl)-2-hydroxy-propionate ethyl in 50 mL dry THF cooled to 0° C. and the mixture was stirred for a further 30 min at this temperature, during which time a dark brown suspension formed. Subsequently 2.15 g (6.99 mmol) 4-(2-oxo-1,2,4,5-tetrahydro-1,3-benzodiazepin-3-yl)-piperidine-1-carbonylchloride were added batchwise while being cooled and the reaction mixture was stirred for 2 h at RT. 50 mL of semisaturated NaHCO$_3$ solution were added, the mixture was extracted twice with in each case 50 mL EtOAc, the combined organic phases were washed with 50 mL saturated NaCl solution and the organic phase was filtered through Na$_2$SO$_4$. After the solvent has been eliminated the residue was purified by chromatography (silica gel, EtOAc/cyc 3:1).

Yield: 3.64 g (84% of theory) ESI-MS: (M+H)$^+$=622/624/626 (2 Br) retention time (HPLC): 10.0 min (method A)

1g (R)-2-(3,4-dibromo-phenyl)-1-hydroxycarbonyl-ethyl 4-(2-oxo-1,2,4,5-tetrahydro-1,3-benzodiazepin-3-yl)-piperidine-1-carboxylate A solution of 210 mg (9 mmol) LiOH.6H$_2$O in 40 mL water was added at RT to a solution of 3.64 g (5.83 mmol) of (R)-2-(3,4-dibromo-phenyl)-1-ethoxycarbonyl-ethyl 4-(2-oxo-1,2,4,5-tetrahydro-1,3-benzodiazepin-3-yl)-piperidine-1-carboxylate in 70 mL THF and the reaction mixture was stirred for 7 h at RT. The mixture was evaporated down i.vac., the residue was taken up in 100 mL water, 1 M HCl was added until an acid reaction was obtained, the precipitate was filtered off and dried in the vacuum drying chamber at 50° C. The product was reacted further without purification.

Yield: 3.36 g (97% of theory) ESI-MS: (M+H)$^+$=594/596/598 (2 Br) retention time (HPLC): 8.5 min (method A)

1h (R)-1-(3,4-dibromo-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate A solution of 80 mg (0.13 mmol) of (R)-2-(3,4-dibromo-phenyl)-1-hydroxycarbonyl-ethyl 4-(2-oxo-1,2,4,5-tetrahydro-1,3-benzodiazepin-3-yl)-piperidine-1-carboxylate, 43.2 mg (0.13 mmol) TBTU and 37 µL (0.27 mmol) triethylamine in 1.5 mL DMF was stirred for 1 h at RT. Then 24.9 mg (0.134 mmol) of 1-(1-methyl-piperidin-4-yl)-piperazine were added and the reaction mixture was then stirred overnight at RT. The reaction solution was filtered through an injection filter and purified directly by HPLC without any further working up. The fractions containing the product were combined and lyophilised.

Yield: 87.6 mg (87% of theory) ESI-MS: (M+H)$^+$=759/761/763 (2 Br) retention time (HPLC): 5.0 min (method A)

The following compounds were prepared analogously from in each case 80 mg of (R)-2-(3,4-dibromo-phenyl)-1-hydroxycarbonyl-ethyl 4-(2-oxo-1,2,4,5-tetrahydro-1,3-benzodiazepin-3-yl)-piperidine-1-carboxylate and the corresponding amount of amine:

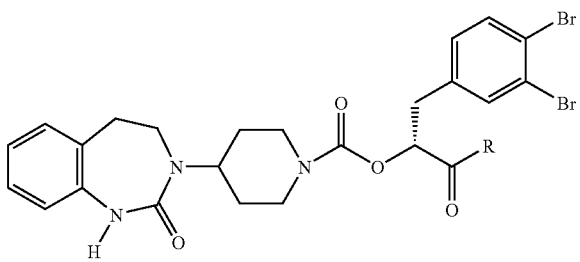

| Example | R | Yield (%) | Mass-spectrum | Retention time HPLC (method) |
|---|---|---|---|---|
| 2 | *-N(piperidine)-N(piperazine)-N-CH$_3$ | 69 | 759/761/763 [M + H]$^+$ | 5.6 min (A) |
| 3 | *-N(piperidine)-CH$_2$-N(piperidine)-CH$_3$ | 72 | 758/760/762 [M + H]$^+$ | 6.0 min (A) |
| 4 | *-N(piperidine)-N(piperidine) | 59 | 744/746/748 [M + H]$^+$ | 6.2 min (A) |
| 5 | *-N(piperidine)-N(CH$_3$)$_2$ | 71 | 704/706/708 [M + H]$^+$ | 5.8 min (A) |
| 6 | *-N(piperidine)-N(homopiperazine)-CH$_3$ | 21 | 773/775/777 [M + H]$^+$ | 5.4 min (A) |

-continued

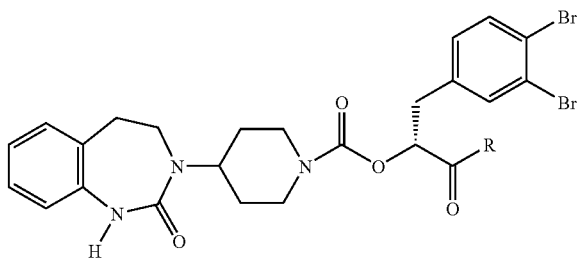

| Example | R | Yield (%) | Mass-spectrum | Retention time HPLC (method) |
|---|---|---|---|---|
| 7 | (N-methylpiperazinyl-diazepane) | 70 | 773/775/777 [M + H]+ | 5.1 min (A) |
| 8 | (piperidinyl-piperazine-Boc) | 69 | 845/847/849 [M + H]+ | 6.6 min (A) |
| 9 | (piperidinyl-piperidine-Boc) | 59 | 845/847/849 [M + H]+ | 6.7 min (A) |

The following compounds may be prepared analogously from 4-(2-oxo-1,2,4,5-tetrahydro-1,3-benzodiazepin-3-yl)-piperidine-1-carboxylate (R)-2-(3,4-dibromo-phenyl)-1-hydroxycarbonyl-ethyl and the corresponding amount of amine:

| Example | R |
|---|---|
| 10 | piperidinyl-azepane |
| 11 | piperidinyl-pyrrolidine |
| 12 | piperidinyl-(4-fluorophenyl) |
| 13 | piperazinyl-(4-fluorophenyl) |
| 14 | piperazinyl-(4-pyridyl) |
| 15 | piperidinyl-(4-pyridyl) |
| 16 | piperidinyl-N-ethylpiperazine |
| 17 | piperidinyl-N-cyclopropylmethyl-piperazine |
| 18 | piperidinyl-N-isopropyl-piperazine |

EXAMPLE 19

(R)-1-(3,4-dibromo-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

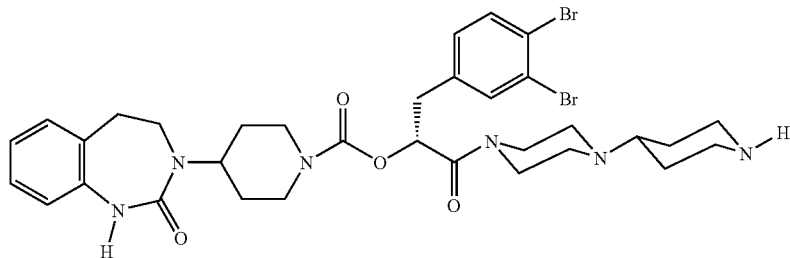

A solution of 125 mg (0.15 mmol) of (R)-1-(3,4-dibromo-benzyl)-2-[4-(1-tert-butoxycarbonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate in 20 mL 2 M HCl was stirred for 16 h at RT. The reaction mixture was lyophilised, and the product was obtained as the bis-hydrochloride salt.

Yield: 110 mg (91% of theory) ESI-MS: $(M+H)^+$=745/747/749 (2 Br) retention time (HPLC): 5.4 min (method A)

EXAMPLE 20

(R)-1-(3,4-dibromo-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

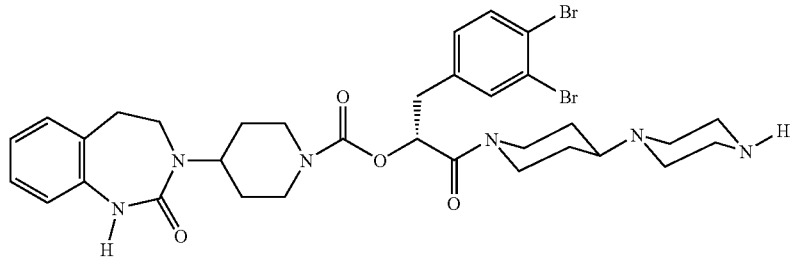

A solution of 79 mg (0.09 mmol) tert-butyl 4-(1-{(R)-3-(3,4-dibromo-phenyl)-2-[4-(2-oxo-1,2,4,5-tetrahydro-1,3-benzodiazepin-3-yl)-piperidine-1-carbonyloxy]-propionyl}-piperidin-4-yl)-piperazine-1-carboxylate in 15 mL 2 M HCl was stirred for 16 h at RT. The reaction mixture was lyophilised, and the product was obtained as the bis-hydrochloride salt.

Yield: 76 mg (100% of theory) ESI-MS: $(M+H)^+$=745/747/749 (2 Br) retention time (HPLC): 5.7 min (method A)

EXAMPLE 21

(R)-1-(3,4-dichloro-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate

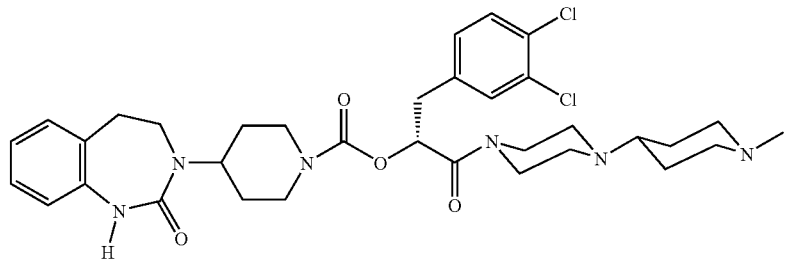

21a 2-acetylamino-3-(3,4-dichloro-phenyl)-acrylic acid

A mixture of 20.0 g (112 mmol) 3,4-dichlorobenzaldehyde, 19.7 g (168 mmol) N-acetylglycine and 13.8 g (168 mmol) NaOAc in 80 mL acetic anhydride were heated to 120° C. (oil bath temperature) for 5 h. After the reaction had ended the reaction mixture was cooled using an ice bath and then combined slowly with 60 mL water (slightly exothermic reaction). The reaction mixture was heated to 80° C. for a further 1.5 h, cooled somewhat, then added to a mixture of 400 mL water and 200 mL toluene and stirred overnight at RT. The precipitate was suction filtered, washed with toluene and water, then combined with diethyl ether and suction filtered.

Yield: 21.0 g (68% of theory) ESI-MS: $(M+H)^+=274/276/278$ (2 Cl) $R_f=0.16$ (silica gel, $DCM/MeOH/NH_3$ 80:20:2)

21b 3-(3,4-dichloro-phenyl)-2-oxo-propionic acid 140 mL 4 M HCl were added to a suspension of 21.0 g (76.6 mmol) 2-acetylamino-3-(3,4-dichloro-phenyl)-acrylic acid in 100 mL N-methyl-2-pyrrolidinone and the reaction mixture was then heated for 4 h at an oil bath temperature of 125° C. The cooled reaction solution was poured onto a cooled mixture of 350 mL water and 120 mL toluene. The phases were separated, the aqueous phase was again extracted with toluene, the combined organic phases were extracted with water, filtered through $Na_2SO_4$ and evaporated down i. vac. The residue was taken up in 1 M NaOH and washed twice with diethyl ether. The aqueous phase was acidified with 2 M HCl and extracted three times with EtOAc. The combined organic phases were filtered through $Na_2SO_4$ and evaporated down i. vac. The residue was combined with diethyl ether, suction filtered and dried in the vacuum drying cupboard.

Yield: 8.20 g (46% of theory) ESI-MS: $(M+H)^+=231/233/235$ (2 Cl) $R_f=0.11$ (silica gel, $DCM/MeOH/cyc/NH_3$ 70:15:15:2)

21c (R)-3-(3,4-dichloro-phenyl)-2-hydroxy-propionic acid

A solution of 12.2 g (38.0 mmol) (1R)-B-chlorodiisopinocampheylborane in 20 mL THF was added dropwise within 30 min to a solution of 8.0 g (34.3 mmol) 3-(3,4-dichloro-phenyl)-2-oxo-propionic acid and 5.2 mL (38.0 mmol) triethylamine in 40 mL THF cooled to −35° C. and the reaction mixture was kept for 1 h at this temperature. The cooling bath was removed and the reaction solution was stirred for 4 h at RT. Then the reaction solution was carefully combined with 50 mL 1 M NaOH (exothermic) and 30 mL TBME at 5-10° C. and stirred for 15 min. The organic phase was separated off and extracted with 25 mL water and 15 mL 1 M NaOH. The combined aqueous phases were acidified with 2 M HCl and extracted three times with in each case 40 mL TBME. The combined organic phases were dried over $Na_2SO_4$ and evaporated down i. vac. The residue was dissolved in 80 mL boiling water and suction filtered through Celite. The filtrate was saturated with NaCl and extracted three times with EtOAc. The combined organic phases were filtered through $Na_2SO_4$ and again evaporated down i. vac. The crude product was further reacted without purification.

Yield: 3.9 g (48% of theory) ESI-MS: $(M+H)^+=233/235/327$ (2 Cl) retention time (HPLC): 6.8 min (method A) $R_f=0.87$ (silica gel, $DCM/MeOH/cyc/NH_3$ 70:15:15:2)

21d ethyl (R)-3-(3,4-dichloro-phenyl)-2-hydroxy-propionate 50 mL ethanolic HCl were added to a solution of 3.5 g (14.9 mmol) of (R)-3-(3,4-dichloro-phenyl)-2-hydroxy-propionic acid in 50 mL EtOH and the reaction mixture was stirred for 4 h at RT. The reaction solution was evaporated down i. vac., the residue was combined with DCM, extracted with 15% $K_2CO_3$ solution and the organic phase was dried over $Na_2SO_4$. After the desiccant and solvent had been eliminated the product was obtained as an oil, which was further reacted without purification.

Yield: 2.6 g (66% of theory) ESI-MS: $(M+H)^+=263/265/267$ (2 Cl) $R_f=0.91$ (silica gel, $DCM/MeOH/cyc/NH_3$ 70:15:15:2)

21e (R)-2-(3,4-dichloro-phenyl)-1-ethoxycarbonyl-ethyl 4-(2-oxo-1,2,4,5-tetrahydro-1,3-benzodiazepin-3-yl)-piperidine-1-carboxylate 450 mg (55% in mineral oil, 10.3 mmol) NaH were added batchwise to a solution of 2.6 g (9.9 mmol) ethyl (R)-3-(3,4-dichloro-phenyl)-2-hydroxy-propionate in 50 mL THF cooled to 0° C. and stirred for a further 30 min at this temperature. Subsequently 3.7 g (11.9 mmol) 4-(2-oxo-1,2,4,5-tetrahydro-1,3-benzodiazepin-3-yl)-piperidine-1-carbonyl-chloride were added batchwise while being cooled and the reaction mixture was stirred overnight at RT. The reaction solution was evaporated down i.vac., the residue combined with DCM, the organic phase was separated off, washed with 10% citric acid solution and 15% $K_2CO_3$ solution and dried over $Na_2SO_4$. After the desiccant and solvent had been eliminated the product was obtained which was reacted without any further purification.

Yield: 5.2 g (98% of theory) ESI-MS: $(M+H)^+=534/536/538$ (2 Cl) $R_f=0.77$ (silica gel, $DCM/MeOH/cyc/NH_3$ 70:15:15:2)

21f 1-carboxy-(R)-2-(3,4-dichloro-phenyl)-ethyl 4-(2-oxo-1,2,4,5-tetrahydro-1,3-benzodiazepin-3-yl)-piperidine-1-carboxylate a solution of 348 mg (14.5 mmol) lithium hydroxide in 10 mL water was added at RT to a solution of 5.2 g (9.7 mmol) 2-(3,4-dichloro-phenyl)-1-ethoxy-carbonyl-ethyl 4-(2-oxo-1,2,4,5-tetrahydro-1,3-benzodiazepin-3-yl)-piperidin-1-(R)-carboxylate in 30 mL THF and the reaction mixture was stirred overnight at RT. It was evaporated down i. vac., the residue was taken up in 15% $K_2CO_3$ solution and the aqueous phase was washed three times with EtOAc. The aqueous phase was mixed with 5 M HCl with stirring until an acid reaction was obtained and extracted exhaustively with DCM. The combined organic phases were filtered through $Na_2SO_4$ and the solvent was eliminated i. vac. The residue was taken up in isopropanol and the precipitate was filtered off. The filtrate was evaporated down i.vac., the residue was purified by chromatography (silica gel, gradient $DCM/MeOH/NH_3$ 10:0:0 to 75:25:5), the corresponding fractions were combined, the solvent was eliminated, the residue was combined with diethyl ether and suction filtered.

Yield: 2.2 g (45% of theory) ESI-MS: $(M+H)^+=506/508/510$ (2 Cl) $R_f=0.51$ (silica gel, $DCM/MeOH/cyc/NH_3$ 70:15:15:2)

21g (R)-1-(3,4-dichloro-benzyl)-2-[4-(1-methyl-piperidin-4-yl)-piperazin-1-yl]-2-oxo-ethyl 4-(2-oxo-1,2,4,5-tetrahydro-benzodiazepin-3-yl)-piperidine-1-carboxylate A solution of 80 mg (0.16 mmol) 1-carboxy-(R)-2-(3,4-dichloro-phenyl)-ethyl 4-(2-oxo-1,2,4,5-tetrahydro-1,3-benzodiazepin-3-yl)-piperidine-1-carboxylate, 58 mg (0.18 mmol) TBTU and 25 μL (0.18 mmol) triethylamine in 2 mL DMF was stirred for 10 min at RT. Then 33 mg (0.18 mmol) of 1-(1-methyl-piperidin-4-yl)-piperazine were added and the reaction mixture was stirred overnight at RT. The reaction solution was filtered through an injection filter and purified directly by HPLC without any further working up. The fractions containing the product were combined and lyophilised.

Yield: 35.0 mg (33% of theory) ESI-MS: (M+H)$^+$=671/673/675 (2 Cl) retention time (HPLC): 5.3 min (method A)

The following compounds were obtained analogously from in each case 80 mg (Examples 22 to 24) or 160 mg (Examples 25 to 27) of 1-carboxy-(R)-2-(3,4-dichloro-phenyl)-ethyl 4-(2-oxo-1,2,4,5-tetra-hydro-1,3-benzodiazepin-3-yl)-piperidine-1-carboxylate and the corresponding amount of amine:

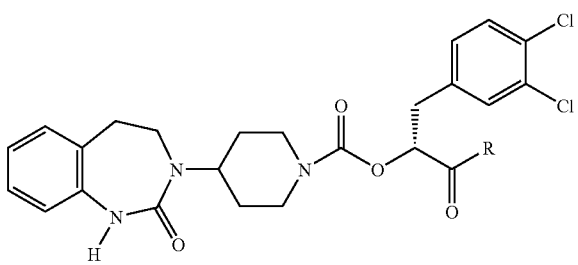

| Example | R | Yield (%) | Mass spectrum | Retention time HPLC (method) |
|---|---|---|---|---|
| 22 | | 33 | 671/673/675 [M + H]$^+$ | 5.8 min (A) |
| 23 | | 29 | 656/658/660 [M + H]$^+$ | 6.5 min (A) |
| 24 | | 38 | 670/672/674 [M + H]$^+$ | 6.2 min (A) |
| 25 | | 13 | 757/759/761 [M + H]$^+$ | 7.0 min (A) |
| 26 | | 15 | 757/759/761 [M + H]$^+$ | 6.9 min (A) |
| 27 | | 13 | n.e. | 5.0 min (A) |

EXAMPLE 28

(R)-1-(3,4-dichloro-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

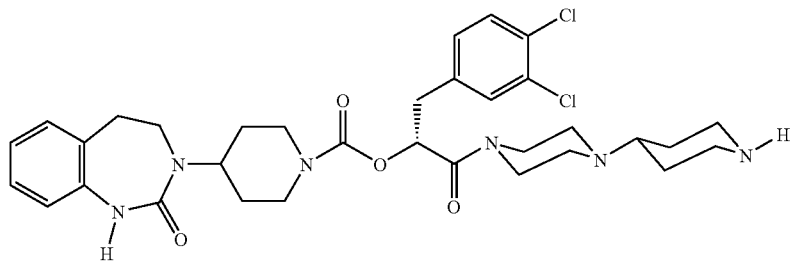

A solution of 30 mg (0.04 mmol) of (R)-1-(3,4-dichloro-benzyl)-2-[4-(1-tert-butoxycarbonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (Example 25) in 5 mL 4 M HCl was stirred overnight at RT. The reaction mixture was lyophilised, and the product was obtained as the HCl salt.

Yield: 18 mg (66% of theory) ESI-MS: $(M+H)^+$=657/659/661 (2 Cl) $R_f$=0.33 (silica gel, DCM/MeOH/cyc/NH$_3$ 70:15:15:2)

EXAMPLE 29

(R)-1-(3,4-dichloro-benzyl)-2-oxo-2-(4-piperazin-1-yl-piperidin-1-yl)-ethyl 4-(2-oxo-1,2,4,5-tetrahydro-benzodiazepin-3-yl)-piperidine-1-carboxylate

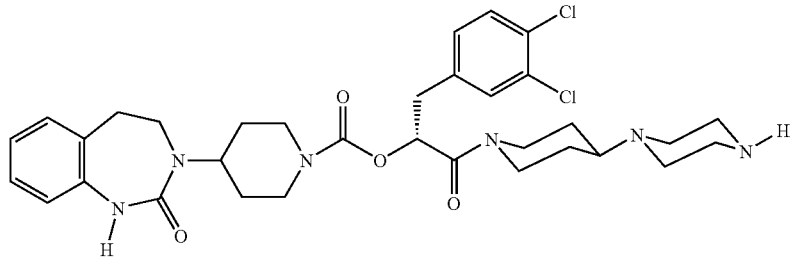

A solution of 35 mg (0.05 mmol) tert-butyl 4-(1-{(R)-3-(3,4-dichloro-phenyl)-2-[4-(2-oxo-1,2,4,5-tetrahydro-1,3-benzodiazepin-3-yl)-piperidine-1-carbonyloxy]-propionyl}-piperidin-4-yl)-piperazine-1-carboxylate (Example 26) in 5 mL 4 M HCl was stirred overnight at RT. The reaction mixture was lyophilised, and the product was obtained as the HCl salt.

Yield: 24 mg (75% of theory) ESI-MS: $(M+H)^+$=657/659/661 (2 Cl) $R_f$=0.30 (silica gel, DCM/MeOH/cyc/NH$_3$ 70:15:15:2)

EXAMPLE 30

(R)-2-4,4'-bipiperidinyl-1-yl-1-(3,4-dichloro-benzyl)-2-oxo-ethyl 4-(2-oxo-1,2,4,5-tetrahydro-benzodiazepin-3-yl)-piperidine-1-carboxylate

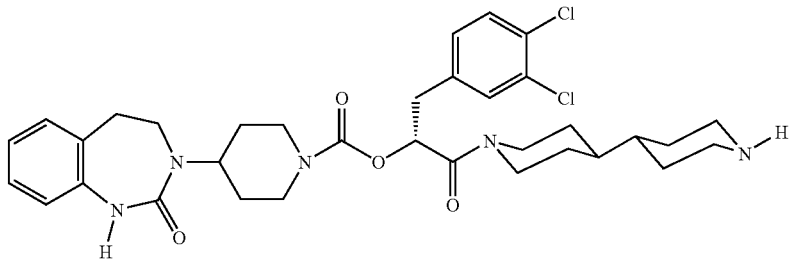

A solution of 30 mg (0.04 mmol) tert-butyl 1'-{(R)-3-(3,4-dichloro-phenyl)-2-[4-(2-oxo-1,2,4,5-tetrahydro-1,3-benzodiazepin-3-yl)-piperidine-1-carbonyloxy]-propionyl}-4,4'-bipiperidinyl-1-carboxylate (Example 27) in 5 mL 4 M HCl was stirred overnight at RT. The reaction mixture was lyophilised, and the product was obtained as the HCl salt.

Yield: 16 mg (58% of theory) ESI-MS: (M+H)⁺=656/658/660 (2 Cl)

EXAMPLE 31

(R)-1-(4-chloro-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

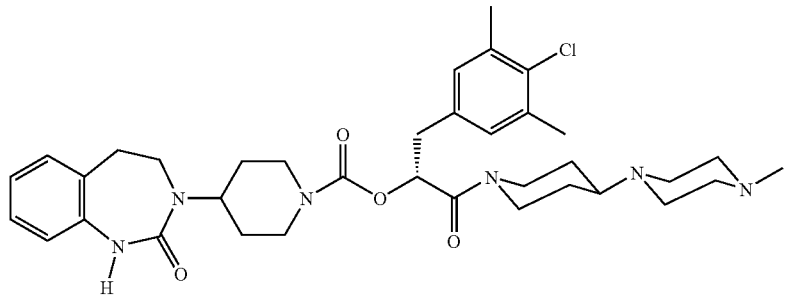

31a 5-bromo-2-chloro-1,3-dimethylbenzene 40.0 g (200 mmol) 4-bromo-2,6-dimethylamine in 100 mL semiconc. HCl were combined at 0° C. with 15.2 g (220 mmol) NaNO₂ in 90 mL water, stirred for 20 min, combined with a solution of 21.7 g (220 mmol) CuCl in 90 mL semiconc. HCl and stirred for 2 h at 70° C. and for 15 h at RT. After the reaction had ended the reaction mixture was poured onto 200 mL water and extracted with TBME. The organic phases were combined, extracted with 2 M NaOH until the organic phase remained colourless and the combined organic phases were then dried over Na₂SO₄. After the desiccant and solvent had been eliminated the residue was purified by chromatography (silica gel, cyc/DCM 1:1).

Yield: 30.7 g (70% of theory) ESI-MS: (M+H)⁺=218/220/222 (Br, Cl) R$_f$=0.84 (silica gel, cyc/DCM 1:1)

31b methyl 2-acetylamino-3-(4-chloro-3,5-dimethyl-phenyl)-acrylate

Under a nitrogen atmosphere 30.0 g (136.7 mmol) 5-bromo-2-chloro-1,3-dimethylbenzene, 24.0 g (164.0 mmol) methyl 2-acetylamino-acrylate in 420 mL triethylamine and 200 mL acetonitrile were combined with 3.4 g (10.9 mmol) tri-o-tolyl-phosphane and 2.4 g (10.9 mmol) Pd(OAc)₂ and stirred for 18 h at 80° C. The precipitate was suction filtered, the filtrate was evaporated down i. vac., combined with 800 mL DCM and 800 mL water, the organic phase was separated off and dried over Na₂SO₄. After the desiccant and solvent had been eliminated the residue was stirred with EtOAc, suction filtered and dried i. vac.

Yield: 29.4 g (76% of theory) ESI-MS: (M+H)⁺=282/284 (Cl) retention time (HPLC-MS): 7.8 min (method A)

31c 3-(4-chloro-3,5-dimethyl-phenyl)-2-oxo-propionic acid 29.4 g (105 mmol) methyl 2-acetylamino-3-(4-chloro-3,5-dimethylphenyl)-acrylate in 330 mL N-methyl-2-pyrrolidinone were combined with 500 mL cooled 4 M HCl, stirred for 6 h at reflux temperature and for 16 h at RT. After the reaction had ended the reaction mixture was poured onto 1650 mL water, stirred for 1 h, suction filtered and the crystals were dried at 50° C. in the vacuum drying cupboard. The product was recrystallised from toluene.

Yield: 12.3 g (52% of theory) ESI-MS: (M+H)⁺=225/227 (Cl) retention time (HPLC-MS): 7.9 min (method A)

31d (R)-3-(4-chloro-3,5-dimethyl-phenyl)-2-hydroxy-propionic acid 12.3 g (54.4 mmol) 3-(4-chloro-3,5-dimethyl-phenyl)-2-oxo-propionic acid in 130 mL THF and 7.6 mL (54.4 mmol) triethylamine were combined at −35° C. with a solution of 21.0 g (65.3 mmol) (1R)-B-chlorodiisopinocampheylborane in 65 mL THF within 30 min and stirred for 2 h at this temperature. After the reaction had ended the reaction mixture was made alkaline at 0° C. with 50 mL 1 M NaOH (exothermic), stirred for 3 h, combined with 30 mL TBME and the phases were separated. The organic phase was washed with 50 mL water and 30 mL 1 M NaOH. The combined aqueous phases were acidified with 2 M HCl and extracted with TBME. The organic phases were dried over Na₂SO₄ and evaporated down i. vac. The product was reacted further without purification.

Yield: 12.5 g (100% of theory) ESI-MS: (M+H)⁺=227/229 (Cl) retention time (HPLC-MS): 7.1 min (method A)

31e methyl (R)-3-(4-chloro-3,5-dimethyl-phenyl)-2-hydroxy-propionate 4.4 mL (59.9 mmol) SOCl₂ were added dropwise to a solution of 12.45 g (54.4 mmol) of (R)-3-(4-chloro-3,5-dimethyl-phenyl)-2-hydroxy-propionic acid in 300 mL MeOH cooled to 0° C. and the reaction mixture was stirred for 1 h at RT. The reaction solution was evaporated down i. vac. and the residue was purified by chromatography (silica gel, cyc/EtOAc 4:1).

Yield: 10.1 g (76% of theory) ESI-MS: (M+NH₄)⁺=260/262 (Cl) retention time (HPLC-MS): 8.1 min (method A)

31f (R)-2-(4-chloro-3,5-dimethyl-phenyl)-1-methoxycarbonyl-ethyl 4-(2-oxo-1,2,4,5-tetrahydro-1,3-benzodiazepin-3-yl)-piperidine-1-carboxylate Under a nitrogen atmosphere 1.0 g (8.2 mmol) 4-dimethylaminopyridine in 30 mL pyridine were combined with 1.7 g (8.2 mmol) 4-nitrophenyl chloroformate, stirred for 40 min at RT, then 2.0 g (8.2 mmol) methyl (R)-3-(4-chloro-3,5-dimethyl-phenyl)-2-hydroxy-propionate were added, the mixture was again stirred for 20 min at RT and then combined with 2.0 g (8.2 mmol) 3-piperidin-4-yl-1,3,4,5-tetrahydro-1,3-benzodiazepin-2-one and the reaction mixture was stirred for 20 h at RT. The mixture was evaporated down i.vac., the residue was taken up in EtOAc, washed with 10% $KHSO_4$ and saturated $NaHCO_3$ solution and the organic phase was dried over. After the desiccant and solvent had been eliminated the residue was purified by chromatography (silica gel, cyc/EtOAc 1:1 to 1:2).

Yield: 2.16 g (51% of theory) ESI-MS: $(M+H)^+$=514/516 (Cl) retention time (HPLC-MS): 10.1 min (method A)

31g (R)-1-carboxy-2-(4-chloro-3,5-dimethyl-phenyl)-ethyl 4-(2-oxo-1,2,4,5-tetrahydro-1,3-benzodiazepin-3-yl)-piperidine-1-carboxylate A solution of 150 mg (0.60 mmol) LiOH in 30 mL water was added to a solution of 2.15 g (4.18 mmol) of (R)-2-(4-chloro-3,5-dimethyl-phenyl)-1-methoxycarbonyl-ethyl 4-(2-oxo-1,2,4,5-tetrahydro-1,3-benzodiazepin-3-yl)-piperidine-1-carboxylate in 60 mL THF and the reaction mixture was stirred for 1 h at RT. The mixture was evaporated down in vacuo, the residue was taken up in 100 mL water, acidified with 1 M HCl, the precipitate was filtered and dried in the vacuum drying cupboard at 40° C.

Yield: 2.05 g (98% of theory) ESI-MS: $(M+H)^+$=500/502 (Cl) retention time (HPLC-MS): 8.8 min (method A)

31h (R)-1-(4-chloro-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate A solution of 80 mg (0.16 mmol) of (R)-2-(4-chloro-3,5-dimethyl-phenyl)-ethyl 4-(2-oxo-1,2,4,5-tetrahydro-benzodiazepin-3-yl)-piperidine-1-carboxylate, 51 mg (0.16 mmol) TBTU and 28 µL (0.20 mmol) triethylamine in 1.5 mL DMF was stirred for 1 h at RT. Then 30 mg (0.16 mmol) 1-methyl-4-(piperidin-4-yl)-piperazine were added and the reaction mixture was stirred for 16 h at RT. The reaction solution was filtered through an injection filter and purified directly by HPLC without any further working up. The fractions containing the product were combined and lyophilised.

Yield: 18 mg (17% of theory) ESI-MS: $(M+H)^+$=665/667 (Cl) retention time (HPLC-MS): 5.6 min (method A)

The following compounds were obtained analogously from in each case 80 mg (Examples 32 to 34) or in each case 140 mg (Examples 35 and 36) of (R)-1-carboxy-2-(4-chloro-3,5-dimethyl-phenyl)-ethyl 4-(2-oxo-1,2,4,5-tetrahydro-1,3-benzodiazepin-3-yl)-piperidine-1-carboxylate and the corresponding amount of amine:

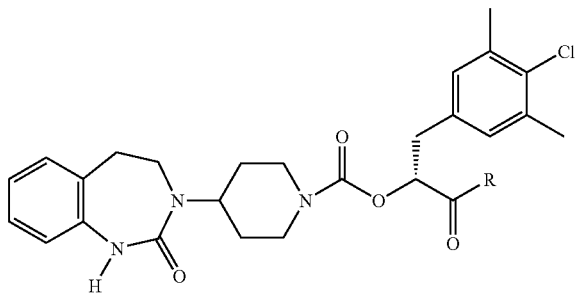

| Example | R | Yield (%) | Mass spectrum | retention time HPLC (method) |
|---|---|---|---|---|
| 32 | | 40 | 665/667 (Cl) $[M+H]^+$ | 5.3 min (A) |
| 33 | | 42 | 664/666 (Cl) $[M+H]^+$ | 6.8 min (A) |
| 34 | | 44 | 610/612 (Cl) $[M+H]^+$ | 6.5 min (A) |
| 35 | | 30 | 751/753 (Cl) $[M+H]+$ | 7.5 min (A) |

-continued

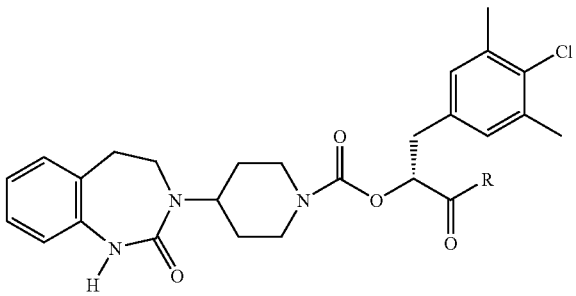

| Example | R | Yield (%) | Mass spectrum | retention time HPLC (method) |
|---|---|---|---|---|
| 36 | *—N(piperazine)—N(piperidine)—N—C(=O)—O—tBu | 28 | 751/753 (Cl) [M + H]+ | 7.7 min (A) |

EXAMPLE 37

(R)-1-(4-chloro-3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

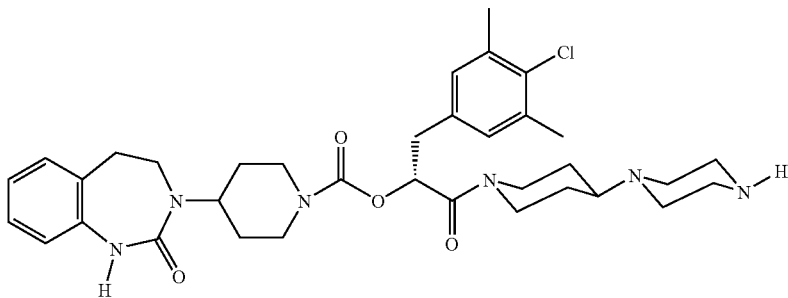

A solution of 64.0 mg (0.09 mmol) tert-butyl 4-(1-{(R)-3-(4-chloro-3,5-dimethyl-phenyl)-2-[4-(2-oxo-1,2,4,5-tetrahydro-1,3-benzodiazepin-3-yl)-piperidine-1-carbonyloxy]-propionyl}-piperidin-4-yl)-piperazine-1-carboxylate (Example 35) in 5 mL 2 M HCl was stirred overnight at RT. The reaction mixture was lyophilised, and the product was obtained as the bis-hydrochloride salt.

Yield: 61.2 mg (99% of theory) ESI-MS: (M+H)⁺=651/653 (Cl) retention time (HPLC-MS): 5.9 min (method A)

EXAMPLE 38

(R)-1-(4-chloro-3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

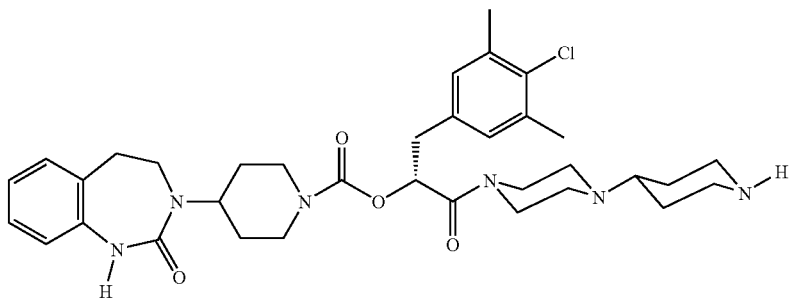

A solution of 59 mg (0.08 mmol) of (R)-1-(4-chloro-3,5-dimethyl-benzyl)-2-[4-(1-tert-butoxy-carbonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (Example 36) in 5 mL of 2 M HCl was stirred overnight at RT. The reaction mixture was lyophilised, and the product was obtained as the bis-hydrochloride salt.

Yield: 55.7 mg (57% of theory) ESI-MS: $(M+H)^+=651/653$ (Cl) retention time (HPLC-MS): 5.5 min (method A)

EXAMPLE 39

(R)-1-(3,5-dimethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate

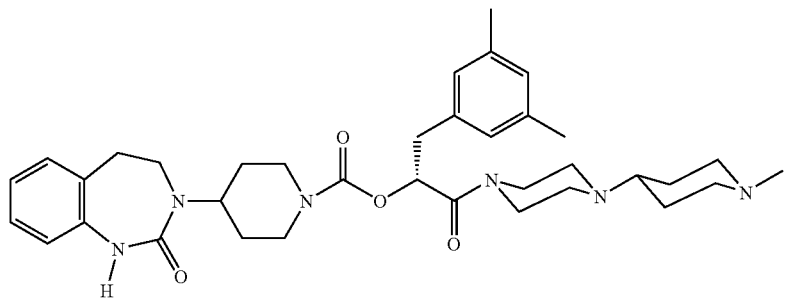

39a (R)-1-carboxy-2-(3,5-dimethyl-phenyl)-ethyl 4-(2-oxo-1,2,4,5-tetrahydro-1,3-benzodiazepin-3-yl)-piperidine-1-carboxylate 500 mg (1.0 mmol) 1-carboxy-(R)-2-(4-chloro-3,5-dimethyl-phenyl)-ethyl 4-(2-oxo-1,2,4,5-tetrahydro-benzodiazepin-3-yl)-piperidine-1-carboxylate (Example 31g) in 20 mL MeOH were combined with 100 mg 10% Pd/C and 2 mL triethylamine and hydrogenated for 10 days at RT and 3 bar. After the reaction had ended the reaction mixture was evaporated down i.vac., the residue was taken up in 25 mL water, acidified with 1 M HCl, the precipitate was suction filtered and dried in the vacuum drying cupboard at 40° C.

Yield: 418 mg (90% of theory) ESI-MS: $(M+H)^+=466$ retention time (HPLC-MS): 8.3 min (method A)

39b (R)-1-(3,5-dimethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate A solution of 50 mg (0.16 mmol) of (R)-1-carboxy-2-(3,5-dimethyl-phenyl)-ethyl 4-(2-oxo-1,2,4,5-tetrahydro-1,3-benzodiazepin-3-yl)-piperidine-1-carboxylate, 35 mg (0.11 mmol) TBTU and 19 μL (0.13 mmol) triethylamine in 1 mL DMF was stirred for 1 h at RT. Then 20 mg (0.11 mmol) 1-(1-methyl-piperidin-4-yl)-piperazine were added and the reaction mixture was stirred for 16 h at RT. The reaction solution was filtered through an injection filter and purified directly by HPLC without any further working up. The fractions containing the product were combined and lyophilised.

Yield: 33 mg (49% of theory) ESI-MS: $(M+H)^+=631$ retention time (HPLC-MS): 5.3 min (method A)

The following compounds were obtained analogously from in each case 50 mg (Examples 40 and 41) or in each case 80 mg (Examples 42 and 43) (R)-1-carboxy-2-(3,5-dimethyl-phenyl)-ethyl 4-(2-oxo-1,2,4,5-tetrahydro-1,3-benzodiazepin-3-yl)-piperidine-1-carboxylate and the corresponding amount of amine:

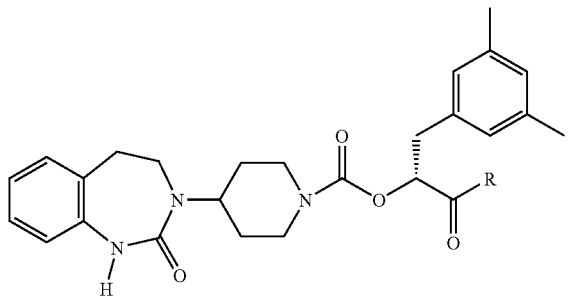

| Example | R | Yield (%) | Mass spectrum | retention time HPLC (method) or $R_f$ (silica gel, eluant) |
|---|---|---|---|---|
| 40 | *⌐N⌐N−N− | 76 | 631 [M + H]⁺ | 5.8 min (A) |

-continued

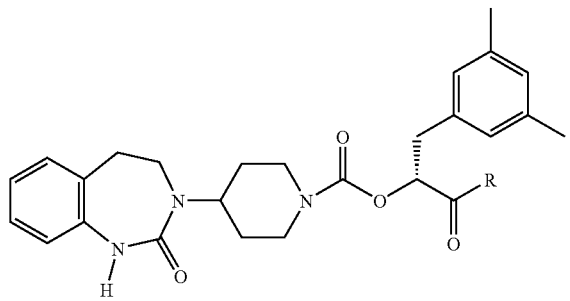

| Example | R | Yield (%) | Mass spectrum | retention time HPLC (method) or $R_f$ (silica gel, eluant) |
|---|---|---|---|---|
| 41 | (4-methylpiperazinyl-piperidinyl) | 55 | 630 [M + H]⁺ | 6.5 min (A) |
| 42 | (Boc-piperazinyl-piperidinyl) | 37 | 717 [M + H]⁺ | 4.7 min (A) |
| 43 | (Boc-piperidinyl-piperidinyl) | 73 | 716 [M + H]⁺ | 0.59 (EtOAc) |

EXAMPLE 44

(R)-1-(3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate A solution of 45 mg (0.06 mmol) of (R)-1-(3,5-dimethyl-benzyl)-2-[4-(1-tert-butoxy-carbonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (Example 42) in 10 mL 2 M HCl was stirred overnight at RT. The reaction mixture was lyophilised. The crude product was taken up in 1 mL DMF, made alkaline with 0.6 mL saturated $K_2CO_3$ solution and purified chromatographically by HPLC.

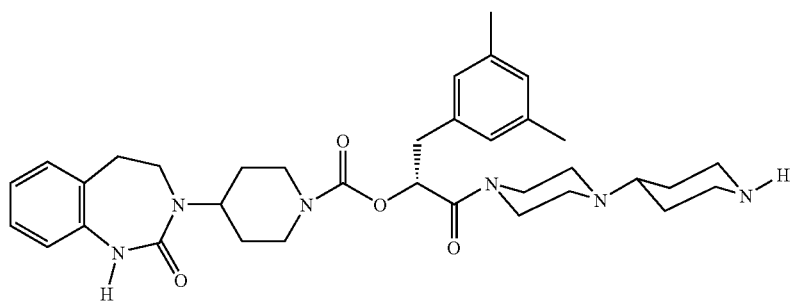

Yield: 26.8 mg (69% of theory) ESI-MS: (M+H)$^+$=617 retention time (HPLC-MS): 5.4 min (method A)

EXAMPLE 45

(R)-2-[4,4']bipiperidinyl-1-yl-1-(3,5-dimethyl-benzyl)-2-oxo-ethyl 4-(2-oxo-1,2,4,5-tetrahydro-1,3-benzodiazepin-3-yl)-piperidine-1-carboxylate

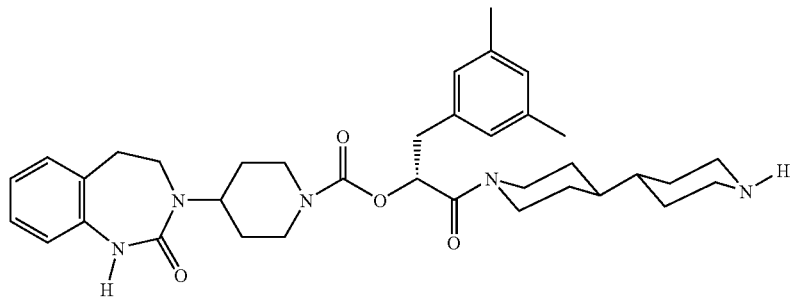

A solution of 101 mg (0.14 mmol) tert-butyl 1'-{(R)-3-(3,5-dimethyl-phenyl)-2-[4-(2-oxo-1,2,4,5-tetrahydro-1,3-benzodiazepin-3-yl)-piperidine-1-carbonyloxy]-propionyl}-4,4'-bipiperidinyl-1-carboxylate (Example 43) in 10 mL 2 M HCl was stirred overnight at RT. The reaction mixture was lyophilised. The crude product was taken up in 1 mL DMF, made alkaline with 0.6 mL saturated K$_2$CO$_3$ solution and purified chromatographically by HPLC.

Yield: 18.7 mg (22% of theory) ESI-MS: (M+H)$^+$=616 retention time (HPLC-MS): 6.5 min (method A)

EXAMPLE 46

(R)-1-(3,5-bis-trifluoromethylbenzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate

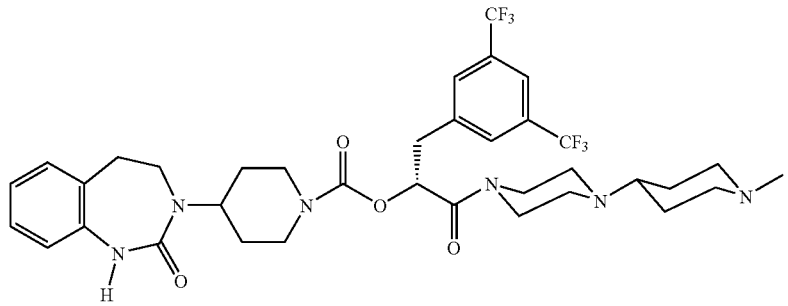

46a methyl 2-acetylamino-3-(3,5-bis-trifluoromethyl-phenyl)acrylate

Under a nitrogen atmosphere 50.0 g (171 mmol) 3,5-bis-(trifluoromethyl)-bromobenzene, 25.0 g (171 mmol) methyl 2-acetylamino-acrylate in 475 mL triethylamine and 250 mL acetonitrile were combined with 3.9 g (12.4 mmol) tri-o-tolyl-phosphane and 2.8 g (12.5 mmol) Pd(OAc)$_2$ and stirred for 18 h at 80° C. After the reaction had ended the reaction mixture was evaporated down i. vac. to approx. 200 mL, combined with 400 mL EtOAc and 400 mL water, the precipitate was suction filtered and the phases were separated. The organic phase was dried over Na$_2$SO$_4$, combined with activated charcoal, filtered and evaporated to dryness. The residue was stirred with DIPE, suction filtered and dried i. vac.

Yield: 19.5 g (32% of theory) ESI-MS: (M+H)$^+$=356 R$_f$=0.76 (silica gel, PE/EtOAc 1:1)

46b 3-(3,5-bis-trifluoromethyl-phenyl)-2-oxo-propionic acid 19.5 g (54.9 mmol) methyl 2-acetylamino-3-(3,5-bis-trifluoromethyl-phenyl)-acrylate in 100 mL 1,4-dioxane were heated to 100° C. bath temperature, combined with 100 mL 4 M HCl and stirred for 8 h at 100° C. bath temperature. The reaction mixture was evaporated down i. vac., the crystals were suction filtered, washed with water and dried in the drying cupboard at 50° C.

Yield: 16.1 g (98% of theory) ESI-MS: (M−H)$^−$=299 R$_f$=0.18 (silica gel, EtOAc)

46c (R)-3-(3,5-bis-trifluoromethyl-phenyl)-2-hydroxy-propionic acid 16.1 g (53.6 mmol) 3-(3,5-bis-trifluoromethyl-phenyl)-2-oxo-propionic acid in 9.5 (70.0 mmol) triethylamine and 100 mL THF were combined at −35° C. with a solution of 26.0 (81.1 mmol) (1R)-B-chlorodiisopinocampheylborane in 40 mL THF within 30 min, stirred for 1 h at this temperature and stirred overnight at RT. After the reaction had ended the reaction mixture was made alkaline at 0° C. with 160 mL 1 M NaOH, stirred for 15 min, combined with 100 mL TBME and the phases were separated. The organic phase was washed with 50 mL water and 50 mL 1 M NaOH. The combined aqueous phases were acidified with 4 M HCl, exhaustively extracted with TBME, the combined organic phases were dried over Na$_2$SO$_4$, suction filtered through activated charcoal and evaporated down i.vac. The product was reacted further without purification.

Yield: 12.5 g (77% of theory) ESI-MS: (M−H)⁻=301
$R_f$=0.45 (silica gel, EtOAc)

46d methyl (R)-3-(3,5-bis-trifluoromethyl-phenyl)-2-hydroxy-propionate 12.5 g (41.4 mmol) of (R)-3-(3,5-bis-trifluoromethyl-phenyl)-2-hydroxy-propionic acid in 150 mL methanolic HCl (1.25 M) were stirred for 4 h at RT and then evaporated down i. vac. The residue was taken up in EtOAc and washed with saturated NaHCO₃ solution, the organic phase was dried over Na₂SO₄, suction filtered through activated charcoal and evaporated down i. vac. The residue was stirred with PE, suction filtered and evaporated down i. vac. The product was reacted further without purification.

Yield: 11.4 g (87% of theory) ESI-MS: (M+H)⁺=316
$R_f$=0.80 (silica gel, PE/EtOAc 1:1)

46e (R)-2-(3,5-bis-trifluoromethyl-phenyl)-1-methoxycarbonyl-ethyl 4-(2-oxo-1,2,4,5-tetrahydro-1,3-benzodiazepin-3-yl)-piperidine-1-carboxylate Analogously to Example 31f the product was obtained from 6.0 g (8.2 mmol) methyl (R)-3-(3,5-bis-trifluoromethyl-phenyl)-2-hydroxy-propionate and 5.13 g (20.9 mmol) 3-piperidin-4-yl-1,3,4,5-tetrahydro-1,3-benzodiazepin-2-one. Purification was carried out by chromatography (silica gel, gradient PE/EtOAc 1:1 to 1:9).

Yield: 5.1 g (46% of theory) ESI-MS: (M+H)⁺=588
$R_f$=0.63 (silica gel, DCM/MeOH/cyc/NH₃ 70:15:15:2)

46f (R)-2-(3,5-bis-trifluoromethyl-phenyl)-1-carboxy-ethyl 4-(2-oxo-1,2,4,5-tetrahydro-1,3-benzodiazepin-3-yl)-piperidine-1-carboxylate A solution of 307 mg (12.8 mmol) LiOH in 5 mL water was added to a solution of 5.0 g (8.5 mmol) of (R)-2-(3,5-bis-trifluoromethyl-phenyl)-1-methoxy-carbonyl-ethyl 4-(2-oxo-1,2,4,5-tetrahydro-1,3-benzodiazepin-3-yl)-piperidine-1-carboxylate in 50 mL THF and the reaction mixture was stirred overnight at RT. The mixture was evaporated down in vacuo, the residue was taken up in water, acidified with 1 M HCl, the precipitate was filtered off and dried in the vacuum drying cupboard at 40° C.

Yield: 4.5 g (92% of theory) ESI-MS: (M+H)⁺=574
$R_f$=0.32 (silica gel, DCM/MeOH/cyc/NH₃ 70:15:15:2)

46g (R)-1-(3,5-bis-trifluoromethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate A solution of 80 mg (0.14 mmol) of (R)-2-(3,5-bis-trifluoromethyl-phenyl)-1-carboxy-ethyl 4-(2-oxo-1,2,4,5-tetrahydro-benzodiazepin-3-yl)-piperidine-1-carboxylate, 51 mg (0.16 mmol) TBTU and 22 μL (0.16 mmol) triethylamine in 1 mL DMF was stirred for 1 h at RT. Then 29 mg (0.16 mmol) 1-(1-methyl-piperidin-4-yl)-piperazine were added and the reaction mixture was stirred overnight at RT. The reaction solution was filtered through an injection filter and purified directly by HPLC without any further working up. The fractions containing the product were combined and lyophilised.

Yield: 56 mg (54% of theory) ESI-MS: (M+H)⁺=739
retention time (HPLC-MS): 5.8 min (method A)

The following compounds were obtained analogously from in each case 80 mg (Examples 47 to 49) or in each case 100 mg (Examples 50 to 53) (R)-2-(3,5-bis-trifluoromethyl-phenyl)-1-carboxy-ethyl 4-(2-oxo-1,2,4,5-tetrahydro-benzodiazepin-3-yl)-piperidine-1-carboxylate and the corresponding amount of amine:

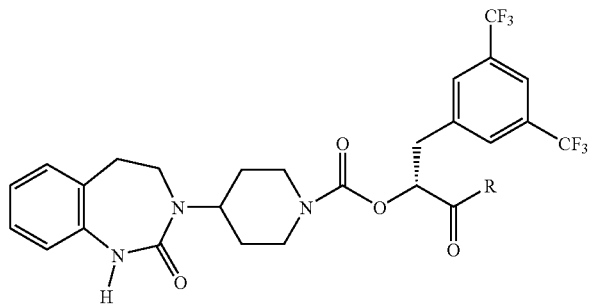

| Example | R | Yield (%) | Mass spectrum | retention time HPLC (method) |
|---------|---|-----------|---------------|------------------------------|
| 47 | *-N⟨⟩-N⟨⟩-N | 49 | 739 [M + H]⁺ | 6.5 min (A) |
| 48 | *-N⟨⟩-⟨⟩-N | 47 | 738 [M + H]⁺ | 7.1 min (A) |

-continued
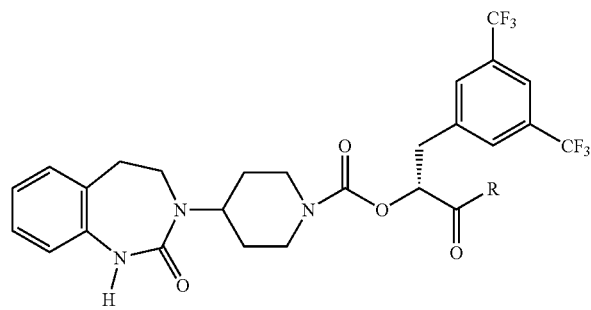
| Example | R | Yield (%) | Mass spectrum | retention time HPLC (method) |
|---|---|---|---|---|
| 49 | *-N piperidine-piperidine | 57 | 724 [M + H]+ | 7.1 min (A) |
| 50 | *-N piperidine-piperidine-CH2C(O)OEt | 39 | 810 [M + H]+ | 7.3 min (A) |
| 51 | *-N piperidine-piperidine-N-benzyl | 53 | 815 [M + H]+ | 6.4 min (A) |
| 52 | *-N piperidine-N-piperidine-benzyl | 46 | 815 [M + H]+ | 6.1 min (A) |
| 53 | *-N piperidine-piperidine-N-benzyl | 65 | 814 [M + H]+ | 7.9 min (A) |

EXAMPLE 54

(R)-1-(3,5-bis-trifluoromethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

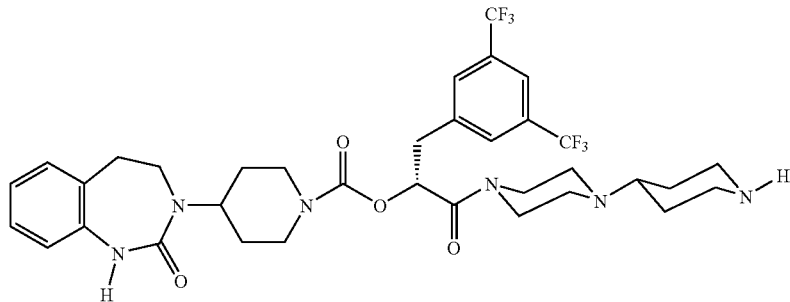

A solution of 77 mg (0.09 mmol) of (R)-2-[4-(1-benzyl-piperidin-4-yl)-piperazin-1-yl]-1-(3,5-bis-trifluoromethyl-benzyl)-2-oxo-ethyl 4-(2-oxo-1,2,4,5-tetrahydro-1,3-benzodiazepin-3-yl)-piperidine-1-carboxylate (Example 51) in 10 mL MeOH was combined with 50 mg 10% Pd/C and shaken for 3 h at RT and 50 psi hydrogen. The catalyst was suction filtered, the solvent was evaporated down i.vac., the residue was combined with acetonitrile and water and lyophilised.

Yield: 46 mg (70% of theory) ESI-MS: (M+H)$^+$=725 retention time (HPLC-MS): 5.7 min (method A)

EXAMPLE 55

(R)-1-(3,5-bis-trifluoromethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

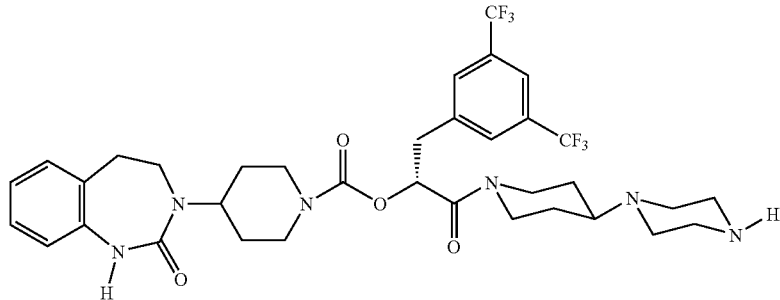

A solution of 64 mg (0.08 mmol) of (R)-2-[4-(4-benzyl-piperazin-1-yl)-piperidin-1-yl]-1-(3,5-bis-trifluoromethyl-benzyl)-2-oxo-ethyl 4-(2-oxo-1,2,4,5-tetrahydro-1,3-benzodiazepin-3-yl)-piperidine-1-carboxylate (Example 52) in 10 mL MeOH was combined with 50 mg 10% Pd/C and shaken for 3 h at RT and 50 psi hydrogen. The catalyst was suction filtered, the solvent was evaporated down i.vac., the residue was combined with acetonitrile and water and lyophilised.

Yield: 43 mg (76% of theory) ESI-MS: (M+H)$^+$=725 retention time (HPLC-MS): 5.7 min (method A)

EXAMPLE 56

(R)-2-(4,4'-bipiperidinyl-1-yl)-1-(3,5-bis-trifluoromethyl-benzyl)-2-oxo-2-ethyl 4-(2-oxo-1,2,4,5-tetrahydro-1,3-benzodiazepin-3-yl)-piperidine-1-carboxylate

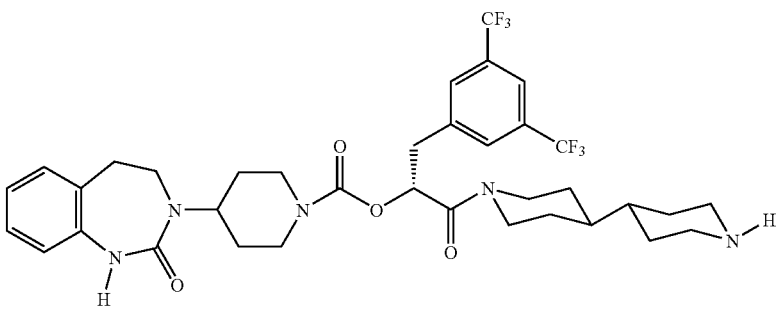

A solution of 92 mg (0.11 mmol) of (R)-2-(1'-benzyl-4,4'-bipiperidinyl-1-yl)-1-(3,5-bis-trifluoro-methyl-benzyl)-2-oxo-ethyl 4-(2-oxo-1,2,4,5-tetrahydro-1,3-benzodiazepin-3-yl)-piperidine-1-carboxylate (Example 53) in 10 mL MeOH was combined with 50 mg 10% Pd/C and shaken for 3 h at RT and 50 psi hydrogen. The catalyst was suction filtered, the solvent was evaporated down i.vac., the residue was combined with acetonitrile and water and lyophilised.

Yield: 55 mg (67% of theory) ESI-MS: (M+H)$^+$=724 retention time (HPLC-MS): 5.6 min (method A)

EXAMPLE 57

(R)-1-(3,5-bis-trifluoromethyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate

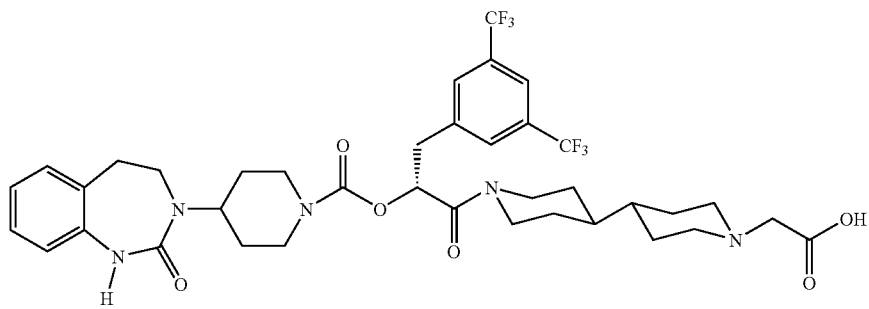

A solution of 1.5 mg (0.06 mmol) LiOH in 1 mL water was added to a solution of 35 mg (0.04 mmol) of (R)-1-(3,5-bis-trifluoromethyl-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate (Example 50) in 5 mL THF and the reaction solution was stirred overnight at RT. The mixture was evaporated down in vacuo, the residue was taken up in water, acidified with 1 N HCl, the precipitate was filtered off and dried in the vacuum drying cupboard.

Yield: 15 mg (44% of theory) ESI-MS: (M+H)$^+$=782 R$_f$=0.41 (silica gel, DCM/MeOH/cyc/NH$_3$ 70:15:15:2)

EXAMPLE 58

(R)-1-(3,5-dibromo-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate

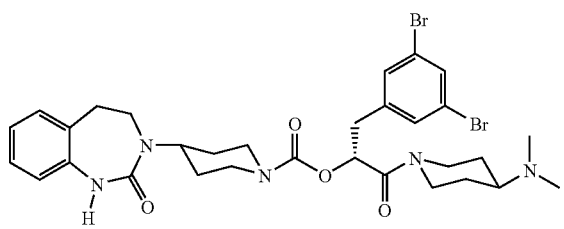

58a (Z,E)-2-acetylamino-3-(3,5-dibromo-phenyl)-acrylic acid

Analogously to Example 1a the product was obtained from 35.0 g (133 mmol) 3,5-dibromo-benzaldehyde and 23.3 g (199 mmol) N-acetyl-glycine.

Yield: 29.2 g (61% of theory) melting point: 248-249° C. ESI-MS (M+H)$^+$=362/364/366 (2 Br) R$_f$=0.1 (silica gel, DCM/MeOH/AcOH 90:10:1)

58b 3-(3,5-dibromo-phenyl)-2-oxo-propionic acid

Analogously to Example 1b the product was obtained from 29.0 g (80.0 mmol) (Z,E)-2-acetylamino-3-(3,5-dibromo-phenyl)-acrylic acid.

Yield: 14.0 g (54% of theory) ESI-MS (M−H)$^-$=318/320/322 (2 Br) R$_f$=0.4 (silica gel, DCM/MeOH/AcOH 90:10:1)

58c (R)-3-(3,5-dibromo-phenyl)-2-hydroxy-propionic acid

Analogously to Example 1c the product was obtained from 12.0 g (37.3 mmol) 3-(3,5-dibromo-phenyl)-2-oxo-propionic acid and 15.1 g (47.1 mmol) (1R)-B-chlorodiisopinocampheylborane.

Yield: 4.1 g (34% of theory) ESI-MS (M−H)$^-$=321/323/325 (2 Br)

58d methyl (R)-3-(3,5-dibromo-phenyl)-2-hydroxy-propionate

Analogously to Example 46d the product was obtained from 4.0 g (12.4 mmol) of (R)-3-(3,5-dibromo-phenyl)-2-hydroxy-propionic acid, using methanolic HCl (6 M) for the esterification.

Yield: 4.0 g (96% of theory) R$_f$=0.9 (silica gel, DCM/MeOH/AcOH 90:10:1)

58e (R)-2-(3,5-dibromo-phenyl)-1-methoxycarbonyl-ethyl 4-(2-oxo-1,2,4,5-tetrahydro-1,3-benzodiazepin-3-yl)-piperidine-1-carboxylate Analogously to Example 31f the product was obtained from 3.40 g (10.06 mmol) methyl (R)-3-(3,5-dibromo-phenyl)-2-hydroxy-propionate and 2.46 g (10.03 mmol) 3-piperidin-4-yl-1,3,4,5-tetrahydro-1,3-benzodiazepin-2-one Yield: 2.0 g (33% of theory) ESI-MS (M+H)$^+$=608/610/612 (2 Br) R$_f$=0.2 (silica gel, n-hexane/EtOAc 3:7) retention time (HPLC): 22.6 min (method F)

58f (R)-1-carboxy-2-(3,5-dibromo-phenyl)-ethyl 4-(2-oxo-1,2,4,5-tetrahydro-1,3-benzodiazepin-3-yl)-piperidine-1-carboxylate A solution of 118 mg (4.9 mmol) LiOH in 5 mL water was added to a solution of 2.0 g (3.3 mmol) of (R)-2-(3,5-dibromo-phenyl)-1-methoxycarbonyl-ethyl 4-(2-oxo-1,2,4,5-tetrahydro-1,3-benzodiazepin-3-yl)-piperidine-1-carboxylate in 12.5 mL THF and the mixture was stirred for 2 h at RT. The reaction mixture was evaporated down i. vac., the residue was combined with water and TBME, the aqueous phase was adjusted to pH 2-3 with conc. HCl and extracted with DCM. The combined organic phases were washed with saturated NaCl solution, dried over $Na_2SO_4$ and evaporated to dryness i. vac.

Yield: 1.9 g (97% of theory) ESI-MS $(M+H)^+$=594/596/598 (2 Br) $R_f$=0.25 (silica gel, DCM/MeOH 9:1) retention time (HPLC): 19.1 min (method F)

58g (R)-1-(3,5-dibromo-benzyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate A solution of 150 mg (0.25 mmol) of (R)-1-carboxy-2-(3,5-dibromo-phenyl)-ethyl 4-(2-oxo-1,2,4,5-tetrahydro-1,3-benzodiazepin-3-yl)-piperidine-1-carboxylate, 90 mg (0.28 mmol) TBTU, 95 μL (0.55 mmol) ethyldiisopropylamine and 38 mg (0.28 mmol) HOBt in 6 mL DMF was stirred for 90 min at RT. Then 42 mg (0.33 mmol) 4-dimethylamino-piperidine were added and the reaction mixture was stirred for 16 h at RT. The reaction solution was combined with water, the organic phase was evaporated down and the residue was purified by chromatography (silica gel, DCM/MeOH/$NH_3$ 95:5:0.5).

Yield: 140 mg (79% of theory) ESI-MS $(M+H)^+$=704/706/708 (2 Br) $R_f$=0.35 (silica gel, DCM/MeOH/$NH_3$ 90:10:1) retention time (HPLC): 12.0 min (method F)

The following compounds were obtained analogously from in each case 150 mg (R)-1-carboxy-2-(3,5-dibromo-phenyl)-ethyl 4-(2-oxo-1,2,4,5-tetrahydro-1,3-benzodiazepin-3-yl)-piperidine-1-carboxylate and the corresponding amount of amine:

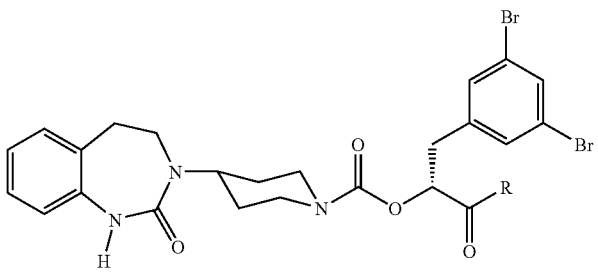

| Example | R | Yield (%) | Mass spectrum | retention time HPLC (method) |
|---|---|---|---|---|
| 59 | | 73 | 759/761/763 $[M + H]^+$ | 10.4 min (F) |
| 60 | | 32 | 744/746/748 $[M + H]^+$ | 12.8 min (F) |
| 61 | | 78 | 758/760/762 $[M + H]^+$ | 12.9 min (F) |
| 62 | | 67 | 759/761/763 $[M + H]^+$ | 9.3 min (F) |

-continued

| Example | R | Yield (%) | Mass spectrum | retention time HPLC (method) |
|---|---|---|---|---|
| 63 | | 91 | 745/747/749 [M + H − Fmox]+ | 17.6 min (F) |
| 64 | | 84 | 845/847/849 [M + H]+ | 14.9 min (F) |
| 65 | | 94 | 844/846/848 [M + H]+ | 27.2 min (F) |

EXAMPLE 66

(R)-1-(3,5-dibromo-benzyl)-2-oxo-2-(4-piperazin-1-yl-piperidin-1-yl-ethyl 4-(2-oxo-1,2,4,5-tetrahydro-1,3-benzodiazepin-3-yl)-piperidine-1-carboxylate

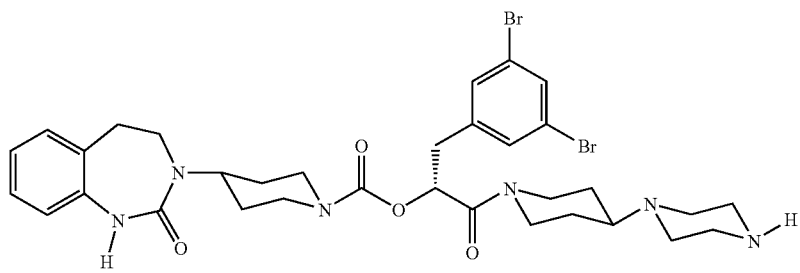

A solution of 300 mg (0.23 mmol) 9H-fluoren-9-ylmethyl 4-(1-{(R)-3-(3,5-dibromo-phenyl)-2-[4-(2-oxo-1,2,4,5-tetrahydro-1,3-benzodiazepin-3-yl)-piperidine-1-carbonyloxy]-propionyl}-piperidin-4-yl)-piperazine-1-carboxylate (Example 63) in 4 mL piperidine was stirred for 1 h at RT. The reaction solution was evaporated to dryness and the residue was purified by chromatography (silica gel, gradient DCM to DCM/MeOH/NH₃ 90:10:1).

Yield: 134 mg (79% of theory) ESI-MS: (M+H)⁺=745/747/749 (2 Br) retention time (HPLC): 9.7 min (method F)

EXAMPLE 67

(R)-1-(3,5-dibromo-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

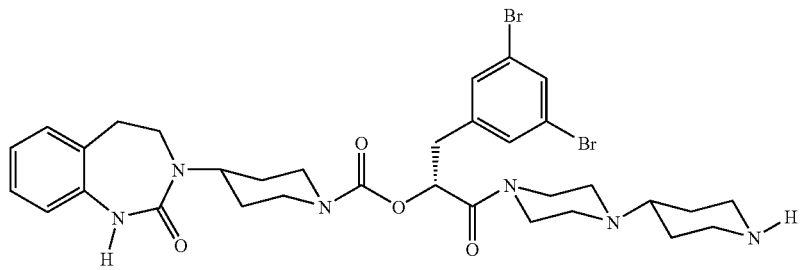

1.8 mL HCl (3.2 M) were added to a solution of 180 mg (0.21 mmol) of (R)-1-(3,5-dibromo-benzyl)-2-[4-(1-tert-butoxy-carbonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (Example 64) in 2 mL water and the reaction mixture was stirred for 3 h at RT. The mixture was combined with 25 mL EtOAc and 20 mL 17% Na₂CO₃ solution, the organic phase was separated off, the aqueous phase was extracted again with 25 mL EtOAc, the combined organic phases were washed with 10 mL saturated NaCl solution and dried over Na₂SO₄. After the desiccant and solvent had been eliminated the residue was suspended in diethyl ether, the organic phase was decanted off and the residue was dried.

Yield: 130 mg (82% of theory) ESI-MS: (M+H)⁺=745/747/749 (2 Br) retention time (HPLC): 9.3 min (method F)

EXAMPLE 68

(R)-2-(4,4'-bipiperidinyl-1-yl)-1-(3,5-dibromo-benzyl)-2-oxo-2-ethyl 4-(2-oxo-1,2,4,5-tetrahydro-1,3-benzodiazepin-3-yl)-piperidine-1-carboxylate

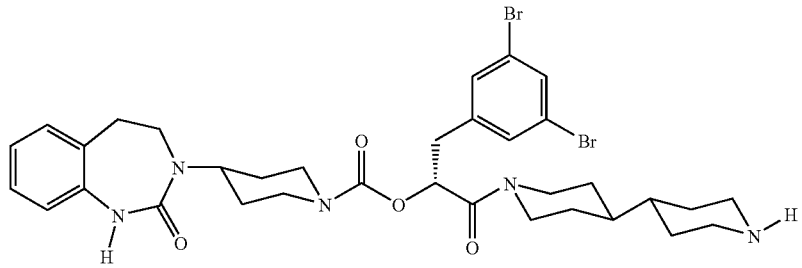

A solution of 160 mg (0.19 mmol) tert. butyl 1'-{(R)-3-(3,5-dibromo-phenyl)-2-[4-(2-oxo-1,2,4,5-tetrahydro-1,3-benzodiazepin-3-yl)-piperidine-1-carbonyloxy]-propionyl}-4,4'-bipiperidinyl-1-carboxylate (Example 65) in 2 mL formic acid was stirred for 1 h at RT. The reaction solution was evaporated down i.vac., the residue was taken up in DCM, the organic phase was washed with 10% Na₂CO₃ solution, filtered and evaporated to dryness. The residue was suspended in 10% NaOH, stirred for 1 h at RT, the precipitate was filtered, washed with a little water and diethyl ether and dried i.vac.

Yield: 86 mg (61% of theory) ESI-MS: (M+H)⁺=744/746/748 (2 Br) retention time (HPLC): 12.6 min (method F)

EXAMPLE 69

(R)-1-(4-hydroxy-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

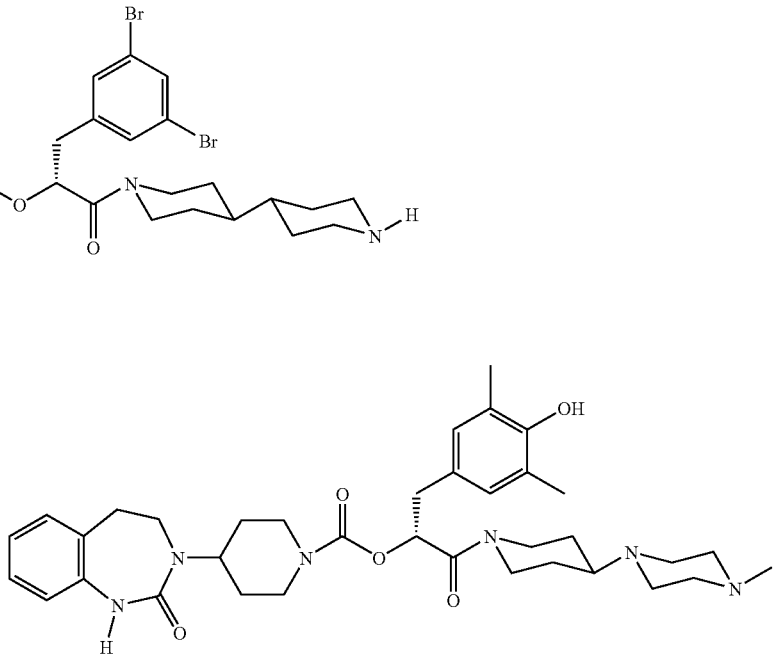

69a 2-benzyloxy-5-bromo-1,3-dimethylbenzene 39.9 g (286 mmol) $K_2CO_3$ were added to a solution of 50.0 g (249 mmol) 2,6-dimethyl-4-bromophenol in 500 mL DMF and stirred for 20 min. Then 34.0 mL (286 mmol) benzyl-chloride were slowly added dropwise and the reaction mixture was stirred for 3 h at 100° C. bath temperature. After the reaction had ended the mixture was poured onto 500 mL water and exhaustively extracted with EtOAc. The organic phases were combined, dried over $Na_2SO_4$ and evaporated down i. vac.

Yield: quantitative GC-MS: $(M^+)$=290/292 (Br) $R_f$=0.87 (silica gel, cyc/EtOAc 3:1)

69b methyl 2-acetylamino-3-(4-benzyloxy-3,5-dimethyl-phenyl)-acrylate

Under a nitrogen atmosphere a mixture of 40.0 g (137 mmol) 2-benzyloxy-5-bromo-1,3-dimethylbenzene and 24.1 g (165 mmol) methyl 2-acetylamino-acrylate in 420 mL tri-ethylamine and 200 mL acetonitrile was combined with 3.5 g (11.2 mmol) tri-o-tolyl-phosphane and 2.5 g (11.1 mmol) $Pd(OAc)_2$ and the mixture was stirred for 18 h at 80° C. The precipitate was suction filtered, the filtrate was evaporated down i. vac. and combined with 800 mL DCM and 800 mL water. The organic phase was separated off, suction filtered through $Na_2SO_4$, the solvent was removed i.vac., the residue was stirred with EtOAc, suction filtered and dried i. vac.

Yield: 31.1 g (64% of theory) ESI-MS: $(M+H)^+$=354 retention time (HPLC-MS): 8.6 min (method A)

69c 3-(4-benzyloxy-3,5-dimethyl-phenyl)-2-oxo-propionic acid 31.1 g (88.1 mmol) methyl 2-acetylamino-3-(4-benzyloxy-3,5-dimethyl-phenyl)-acrylate in 150 mL 1,4-dioxane were combined with 125 mL 4 M HCl, stirred for 7 h at reflux temperature and stirred overnight at RT. The precipitate was suction filtered, washed with water and dried at 45° C. in the vacuum drying cupboard.

Yield: 14.3 g (54% of theory) EI-MS: $(M)^+$=298 retention time (HPLC-MS): 9.0 min (method A)

69d (R)-3-(4-benzoyl-3,5-dimethyl-phenyl)-2-hydroxy-propionic acid

Under a nitrogen atmosphere a solution of 14.3 g (47.8 mmol) 3-(4-benzyloxy-3,5-dimethyl-phenyl)-2-oxo-propionic acid and 8.3 mL (59.8 mmol) triethylamine in 170 mL THF at −35° C. was combined with a solution of 22.1 (69.0 mmol) (1R)-B-chlorodiisopinocampheylborane in 70 mL THF within 30 min. After the addition had ended the cooling bath was removed and the reaction solution was stirred overnight at RT. The reaction mixture was made alkaline at 0° C. with 70 mL 1 M NaOH, combined with 100 mL TBME, stirred for 15 min and the phases were separated. The organic phase was washed with 50 mL water and three times with 50 mL 1 M NaOH. The combined aqueous phases were acidified with semiconc. HCl, exhaustively extracted with EtOAc and the combined organic phases were dried over $Na_2SO_4$. After the desiccant and solvent had been eliminated the residue was reacted further without purification.

Yield: 14.0 g (98% of theory) ESI-MS: $(M-H)^-$=299 retention time (HPLC-MS): 7.9 min (method A)

69e methyl (R)-3-(4-benzyloxy-3,5-dimethyl-phenyl)-2-hydroxy-propionate

To a solution cooled to 0° C. of 14.0 g (23.3 mmol) of (R)-3-(4-benzoyl-3,5-dimethyl-phenyl)-2-hydroxy-propionic acid in 150 mL MeOH, 2.0 mL (27.4 mmol) $SOCl_2$ were added dropwise and the reaction mixture was stirred for 1 h at RT. The reaction solution was evaporated down i. vac. and the residue was purified by chromatography (silica gel, cyc/EtOAc 3:1).

Yield: 5.7 g (78% of theory) ESI-MS: $(M+NH_4)^+$=332 retention time (HPLC-MS): 9.1 min (method A)

69f (R)-2-(4-benzyloxy-3,5-dimethyl-phenyl)-1-methoxycarbonyl-ethyl 4-(2-oxo-1,2,4,5-tetrahydro-1,3-benzodiazepin-3-yl)-piperidine-1-carboxylate Under a nitrogen atmosphere 1.93 g (9.58 mmol) 4-nitro-phenyl chloroformate was added to a solution of 1.17 g (9.58 mmol) 4-dimethylaminopyridine in 50 mL pyridine, stirred for 1.5 h at RT, combined with 3.0 g (9.58 mmol) methyl (R)-3-(4-benzyloxy-3,5-dimethyl-phenyl)-2-hydroxy-propionate and stirred for 20 min at RT. Then 2.35 g (9.58 mmol) 3-piperidin-4-yl-1,3,4,5-tetrahydro-1,3-benzodiazepin-2-one were added and the mixture was stirred for 20 h at RT. The reaction mixture was evaporated down i. vac., the residue was taken up in EtOAc, the organic phase was washed with 10% $KHSO_4$ and saturated $NaHCO_3$ solution and dried over $Na_2SO_4$. After the desiccant and solvent had been eliminated the residue was purified by chromatography (silica gel, gradient cyc/EtOAc 1:1 to 1:2).

Yield: 3.21 g (57% of theory) ESI-MS: $(M+H)^+$=586 retention time (HPLC-MS): 10.4 min (method A)

69q (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate A solution of 3.21 g (5.48 mmol) of (R)-2-(4-benzyloxy-3,5-dimethyl-phenyl)-1-methoxy-carbonyl-ethyl 4-(2-oxo-1,2,4,5-tetrahydro-1,3-benzodiazepin-3-yl)-piperidine-1-carboxylate in 80 mL THF was combined with a solution of 200 mg (8.35 mmol) LiOH in 40 mL water and stirred for 1 h at RT. The reaction mixture was evaporated down i. vac., the residue was taken up in 100 mL water, acidified with 2 M HCl, the precipitate was suction filtered and dried in the vacuum drying cupboard at 40° C.

Yield: quantitative ESI-MS: $(M+H)^+$=572 retention time (HPLC-MS): 9.2 min (method A)

69h (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate 3.72 g (6.51 mmol) of (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate in 50 mL DCM were combined with 300 mg 10% Pd/C and shaken at RT and 3 bar hydrogen until the reaction came to a stop. The catalyst was suction filtered and the solvent was evaporated down i. vac. The residue was triturated with DIPE and suction filtered.

Yield: 2.41 g (77% of theory) ESI-MS: $(M+H)^+$=482 retention time (HPLC-MS): 7.0 min (method A)

69i (R)-1-(4-hydroxy-3,5-dimethyl-benzyl)-2-[4-(4-methyl-piperazin-1-yl)-piperidin-1-yl]-2-oxo-ethyl 4-(2-oxo-1,2,4-tetrahydro-1,3-benzodiazepin-3-yl)-piperidine-1-carboxylate A solution of 70 mg (0.15 mmol) of (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate, 51 mg (0.16 mmol) TBTU and 26 μL (0.18 mmol) triethylamine in 1 mL DMF was stirred for 1 h at RT. Then 27 mg (0.15 mmol) 1-methyl-4-piperidin-4-yl-piperazine were added and the reaction mixture was stirred for 16 h at RT. The reaction solution was filtered through an injection filter and purified directly by HPLC without any further working up. The fractions containing the product were combined and lyophilised.

Yield: 39 mg (42% of theory) ESI-MS: (M+H)$^+$=647 retention time (HPLC-MS): 5.3 min (method A)

The following compounds were obtained analogously from in each case 70 mg (Examples 70 to 76), 100 mg (Examples 77 and 78) or 400 mg (Example 79) of (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate and the corresponding amount of amine:

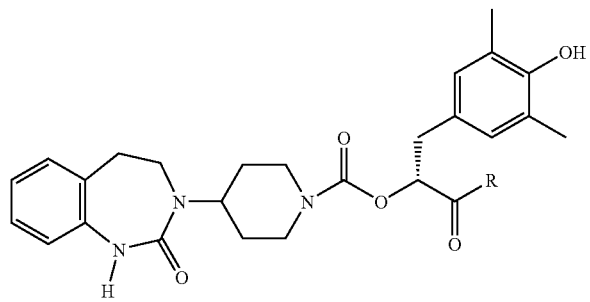

| Example | R | Yield (%) | Mass spectrum | retention time HPLC (method) |
|---|---|---|---|---|
| 70 | | 47 | 647 [M + H]$^+$ | 4.9 min (A) |
| 71 | | 41 | 646 [M + H]$^+$ | 5.8 min (A) |
| 72 | | 32 | 632 [M + H]$^+$ | 5.8 min (A) |
| 73 | | 38 | 634 [M + H]$^+$ | 5.6 min (A) |
| 74 | | 39 | 634 [M + H]$^+$ | 5.7 min (A) |
| 75 | | 37 | 648 [M + H]$^+$ | 5.5 min (A) |

-continued

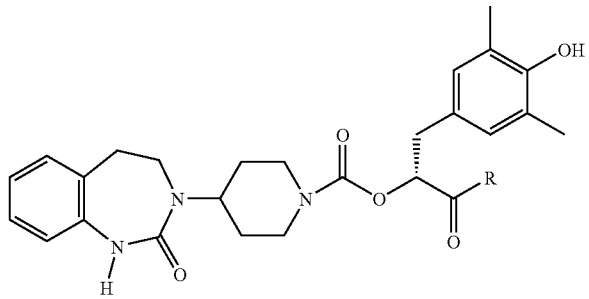

| Example | R | Yield (%) | Mass spectrum | retention time HPLC (method) |
|---|---|---|---|---|
| 76 | (piperidine-N,N-dimethylamino) | 38 | 592 [M + H]$^+$ | 5.6 min (A) |
| 77 | (piperidine-piperazine-Boc) | 21 | 733 [M + H]$^+$ | 6.4 min (A) |
| 78 | (piperidine-piperidine-benzyl) | 36 | 723 [M + H]$^+$ | 5.3 min (A) |
| 79 | (piperidin-4-one) | 71 | 563 [M + H]$^+$ | 6.9 min (A) |

EXAMPLE 80

(R)-1-(4-hydroxy-3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate A solution of 32 mg (0.04 mmol) tert-butyl 4-(1-{(R)-3-(4-hydroxy-3,5-dimethyl-phenyl)-2-[4-(2-oxo-1,2,4,5-tetrahydro-1,3-benzodiazepin-3-yl)-piperidine-1-carbonyloxy]-propionyl}-piperidin-4-yl)-piperazine-1-carboxylate (Example 77) in 5 mL 2 M HCl was stirred for 20 h at RT and then lyophilised, the product being obtained as the bis-hydrochloride.

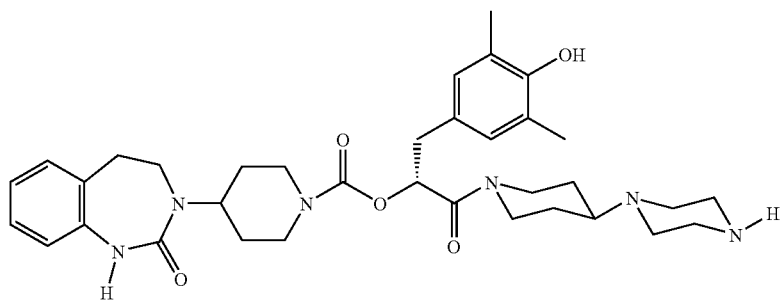

Yield: quantitative ESI-MS: (M+H)$^+$=633 retention time (HPLC-MS): 5.0 min (method A)

EXAMPLE 81

(R)-1-(4hydroxy-3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

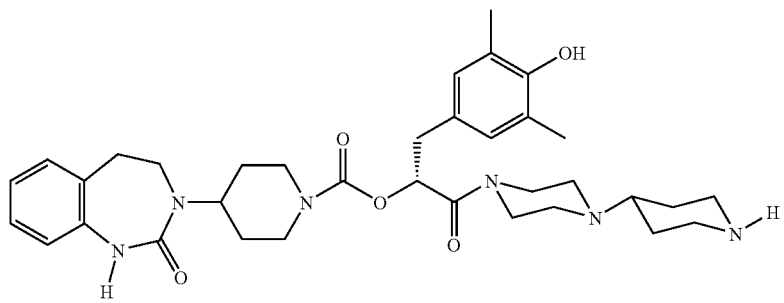

A solution of 54 mg (0.08 mmol) of (R)-2-[4-(1-benzyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate (Example 78) in 5 mL MeOH were combined with 20 mg of 10% Pd/C and shaken at RT and 3 bar hydrogen until the reaction stopped. The catalyst was suction filtered and the solvent evaporated down i.vac. The residue was triturated with DIPE, suction filtered and dried under a high vacuum.

Yield: 35.0 mg (74% of theory) ESI-MS: (M+H)$^+$=633 retention time (HPLC-MS): 4.9 min (method A)

EXAMPLE 82

(R)-1-(4-hydroxy-3,5-dimethyl-benzyl)-2-(4-hydroxy-4-methyl-[1,4']bipiperidinyl-1'-yl)-2-oxo-ethyl 4-(2-oxo-1,2,4,5-tetrahydro-1,3-benzodiazepin-3-yl)-piperidine-1-carboxylate

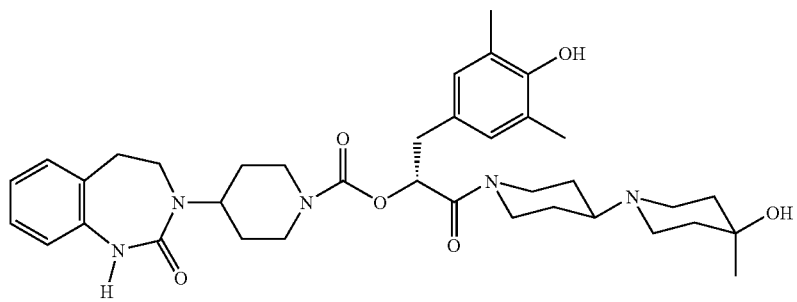

A solution of 50 mg (0.09 mmol) of (R)-1-(4-hydroxy-3,5-dimethyl-benzyl)-2-oxo-2-(4-oxo-piperidin-1-yl)-ethyl 4-(2-oxo-1,2,4,5-tetrahydro-1,3-benzodiazepin-3-yl)-piperidine-1-carboxylate (Example 79) in 1.5 mL DCM was combined with 21 mg (0.18 mmol) 4-methyl-piperidin-4-ol and 10.3 µl (0.19 mmol) AcOH, cooled to 0° C. and stirred for 2 h. Then 28 mg (0.19 mmol) sodium-triacetoxyborohydride were added and the mixture was stirred overnight at 0° C.

After the solvent had been eliminated the residue was combined with 2 mL DMF and purified by HPLC. The fractions containing the product were combined and lyophilised.

Yield: 25 mg (42% of theory) ESI-MS: (M+H)$^+$=662 retention time (HPLC-MS): 2.90 min (method E)

EXAMPLE 83

(R)-2-(4,4-dimethyl-[1,4']bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

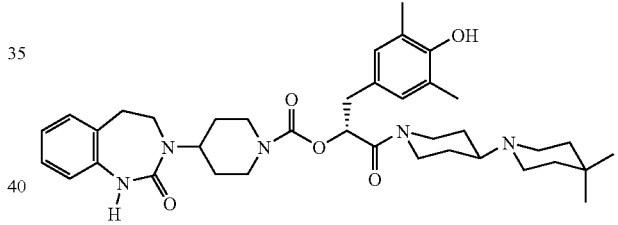

Analogously to Example 82 the product was obtained from 50.0 mg (0.09 mmol) of (R)-1-(4-hydroxy-3,5-dimethyl-benzyl)-2-oxo-2-(4-oxo-piperidin-1-yl)-ethyl 4-(2-oxo-1,2,4,5-tetrahydro-1,3-benzodiazepin-3-yl)-piperidine-1-carboxylate (Example 79) and 31.0 mg (0.18 mmol) 4,4-dimethylpiperidine.

Yield: 18.3 mg (31% of theory) ESI-MS: (M+H)$^+$=660 retention time (HPLC-MS): 3.2 min (method E)

EXAMPLE 84

(R)-2-(4-amino-4-methyl-[1,4']bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

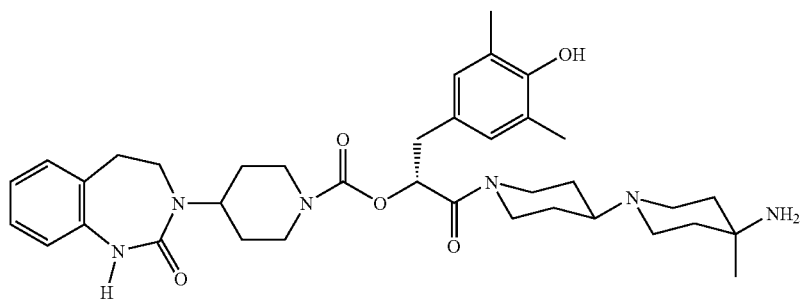

A solution of 150 mg (0.27 mmol) of (R)-1-(4-hydroxy-3,5-dimethyl-benzyl)-2-oxo-2-(4-oxo-piperidin-1-yl)-ethyl 4-(2-oxo-1,2,4,5-tetrahydro-1,3-benzodiazepin-3-yl)-piperidine-1-carboxylate (Example 79) in 4 mL DCM was combined with 120 mg (0.53 mmol) tert-butyl (4-methyl-piperidin-4-yl)-carbamate and 31 µL (0.56 mmol) AcOH, cooled to 0° C. and stirred for 2 h. Then 85 mg (0.56 mmol) sodium-triacetoxyborohydride were added and the mixture was stirred overnight at 0° C. Then the reaction solution was combined with 0.5 mL TFA and again stirred overnight at RT. After elimination of the solvent the residue was dissolved in 2 mL DMF and purified by HPLC. The fractions containing the product were combined and lyophilised, the product being obtained as the TFA salt.

Yield: 94 mg (46% of theory) ESI-MS: $(M+H)^+=661$
retention time (HPLC-MS): 2.50 min (method E)

EXAMPLE 85

(R)-1-(4-amino-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

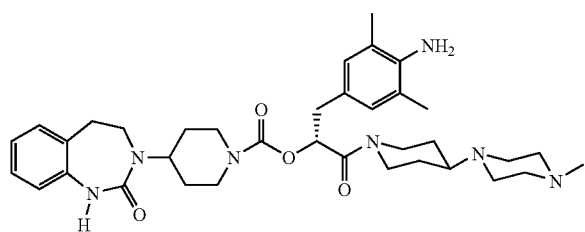

85a methyl (Z,E)-2-acetylamino-3-(4-amino-3,5-dimethyl-phenyl)-acrylate

Under a nitrogen atmosphere first of all a solution of 90.0 g (441 mmol) 4-bromo-2,6-dimethyl-phenylamine in 200 mL acetonitrile was added to a mixture of 7.2 g (32.1 mmol) Pd(OAc)$_2$ and 10.1 g (32.1 mmol) tri-o-tolyl-phosphane in 1.2 L triethylamine and 600 mL acetonitrile and then a solution of 65.0 g (445 mmol) methyl 2-acetylamino-acrylate in 200 mL acetonitrile was added dropwise. After the addition had ended the mixture was stirred for 18 h at 80° C. To complete the reaction the reaction mixture was again combined with 4.0 g (17.8 mmol) Pd(OAc)$_2$ and 5.0 g (16.4 mmol) tri-o-tolyl-phosphane and kept for another 5 h at 80° C. The mixture was evaporated down i.vac to approx. 200 mL, the residue was combined with 400 mL EtOAc, the residue was filtered (A) and the organic phase was dried over Na$_2$SO$_4$. After elimination of the desiccant by filtration over activated charcoal the filtrate was evaporated down to about 100 mL, the precipitated substance was suction filtered, washed with 30 mL EtOAc and dried. The above residue A was combined with 1 L DCM, Na$_2$SO$_4$ and activated charcoal and filtered through Celite. The filtrate was evaporated down, the residue was combined with 350 mL diethyl ether, the precipitate formed was suction filtered, then washed with 100 mL diethyl ether and dried. The two product fractions were combined.

Yield: 74.8 g (65% of theory) ESI-MS: $(M+H)^+=263$
$R_f=0.51$ (silica gel, EtOAc)

85b 3-(4-amino-3,5-dimethyl-phenyl)-2-oxo-propionic acid

A suspension of 74.0 g (282 mmol) methyl (Z,E)-2-acetylamino-3-(4-amino-3,5-dimethyl-phenyl)-acrylate in 500 mL 1,4-dioxane was heated to 100° C. and combined with 460 mL M HCl, whereupon a solution was formed. The mixture was heated for another 8 h at 100° C. and the cooled solution was evaporated down i.vac. to approx. 200 mL, during which time the product crystallised out. It was filtered, the residue was washed with 50 mL water and the product was dried at 50° C.

Yield: 43.6 g (63% of theory) ESI-MS: $(M+H)^+=208$
$R_f=0.68$ (silica gel, PE/EtOAc 1:1)

85c methyl (R)-3-(4-amino-3,5-dimethyl-phenyl)-2-hydroxy-propionate

Under a nitrogen atmosphere a mixture of 20.0 g (82.1 mmol) 3-(4-amino-3,5-dimethyl-phenyl)-2-oxo-propionic acid and 25.7 mL (189 mmol) triethylamine in 400 mL THF was cooled to −35° C. Then a solution of 40.0 g (125 mmol) (1R)-B-chlorodiisopinocampheylborane in 100 mL THF was added dropwise so that the reaction temperature remained between −35° C. and −25° C. The reaction mixture was kept for 1 h at this temperature, the cooling bath was removed and the reaction mixture was stirred overnight at RT. THF was evaporated down i.vac., the residue was combined with methanolic HCl (1.25 M) and stirred for 2 h at RT. It was evaporated down i.vac., the residue was taken up in 2 M HCl and extracted exhaustively with EtOAc. The aqueous phase was made alkaline with semiconc. NaOH and exhaustively extracted with EtOAc. The combined organic phases were dried over Na$_2$SO$_4$, suction filtered through activated charcoal and evaporated down. The product was obtained as a brown oil.

Yield: 8.3 g (45% of theory) ESI-MS: (M+H)$^+$=224 R$_f$=0.46 (silica gel, PE/EtOAc 1:1)

85d (R)-2-(4-amino-3,5-dimethyl-phenyl)-1-methoxycarbonyl-ethyl 4-(2-oxo-1,2,4,5-tetrahydro-1,3-benzodiazepin-3-yl)-piperidine-1-carboxylate Analogously to Example 31f the desired product was obtained from 4.0 g (17.9 mmol) methyl (R)-3-(4-amino-3,5-dimethyl-phenyl)-2-hydroxy-propionate and 4.8 g (19.6 mmol) 3-piperidin-4-yl-1,3,4,5-tetrahydro-1,3-benzodiazepin-2-one.

Yield: 3.2 g (36% of theory) ESI-MS: (M+H)$^+$=495 R$_f$=0.35 (silica gel, DCM/MeOH/NH$_3$ 90:10:1)

85e (R)-2-(4-amino-3,5-dimethyl-phenyl)-1-carboxy-ethyl 4-(2-oxo-1,2,4,5-tetrahydro-1,3-benzodiazepin-3-yl)-piperidine-1-carboxylate A solution of 500 mg (20.9 mmol) LiOH in 10 mL water was added to a solution of 6.7 g (13.6 mmol) of (R)-2-(4-amino-3,5-dimethyl-phenyl)-1-methoxycarbonyl-ethyl 4-(2-oxo-1,2,4,5-tetrahydro-1,3-benzodiazepin-3-yl)-piperidine-1-carboxylate in 50 mL THF and the reaction mixture was stirred overnight at RT. To complete the reaction another 300 mg (12.5 mmol) LiOH were added and the reaction solution was stirred for 3 h at 40° C. It was evaporated down i.vac., the residue was taken up in 15% K$_2$CO$_3$ solution and extracted exhaustively with DCM. The aqueous phase was acidified with 4 M HCl, exhaustively extracted with DCM and the combined organic phases were dried over Na$_2$SO$_4$. After the desiccant and solvent had been eliminated the residue was reacted further without purification.

Yield: 4.2 g (65% of theory) ESI-MS: (M+H)$^+$=481 R$_f$=0.21 (silica gel, DCM/MeOH/cyc/NH$_3$ 70:15:15:2)

85f (R)-1-(4-amino-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate Analogously to Example 1h the product was obtained from 80 mg (0.17 mmol) of (R)-2-(4-amino-3,5-dimethyl-phenyl)-1-carboxy-ethyl 4-(2-oxo-1,2,4,5-tetrahydro-1,3-benzodiazepin-3-yl)-piperidine-1-carboxylate and 35 mg (0.19 mmol) 1-methyl-4-piperidin-4-yl-piperazine.

Yield: 50 mg (47% of theory) ESI-MS: (M+H)$^+$=646 retention time (HPLC): 4.9 min (method B)

The following compounds were obtained analogously from in each case 80 mg (Examples 86 to 89) or 100 mg (Examples 90 to 92) (R)-2-(4-amino-3,5-dimethyl-phenyl)-1-carboxy-ethyl 4-(2-oxo-1,2,4,5-tetrahydro-1,3-benzodiazepin-3-yl)-piperidine-1-carboxylate and the corresponding amount of amine:

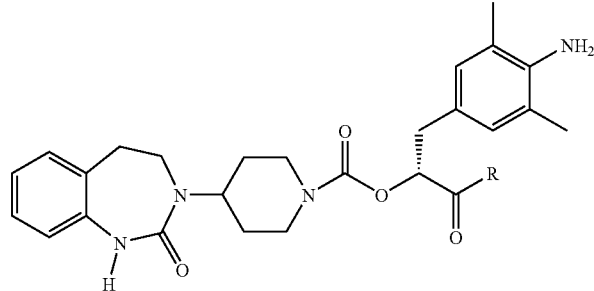

| Example | R | Yield (%) | Mass spectrum | retention time HPLC (method) |
|---|---|---|---|---|
| 86 | 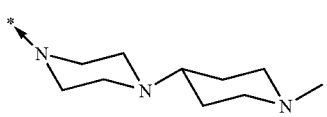 | 55 | 646 [M + H]$^+$ | 3.6 min (B) |
| 87 |  | 48 | 645 [M + H]$^+$ | 4.5 min (B) |
| 88 | 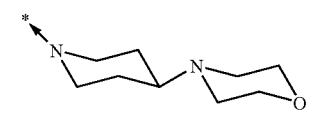 | 49 | 633 [M + H]$^+$ | 4.3 min (B) |

-continued

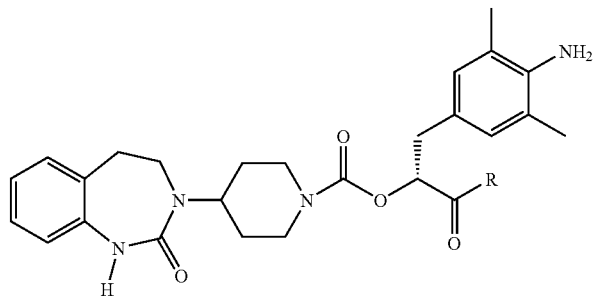

| Example | R | Yield (%) | Mass spectrum | retention time HPLC (method) |
|---|---|---|---|---|
| 89 | [piperidine-piperidine structure] | 42 | 631 [M + H]⁺ | 4.6 min (B) |
| 90 | [piperidine-piperidine-N-CH₂-C(O)OEt structure] | 39 | 717 [M + H]⁺ | 4.7 min (B) |
| 91 | [piperazine-piperidine-N-Boc structure] | 53 | 732 [M + H]⁺ | 5.2 min (B) |
| 92 | [piperidine-piperazine-N-Boc structure] | 44 | 732 [M + H]⁺ | 5.0 min (B) |

EXAMPLE 93

(R)-1-(4-amino-3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate A solution of 80 mg (0.11 mmol) of (R)-1-(4-amino-3,5-dimethyl-benzyl)-2-[4-(1-tert-butoxy-carbonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (Example 91) in 2 mL of 4 M HCl was stirred overnight at RT. The reaction mixture was made alkaline with solid K₂CO₃, exhaustively extracted with DCM and the combined organic phases were evaporated down i.vac. Further purification was carried out by HPLC. The fractions containing the product were combined and lyophilised.

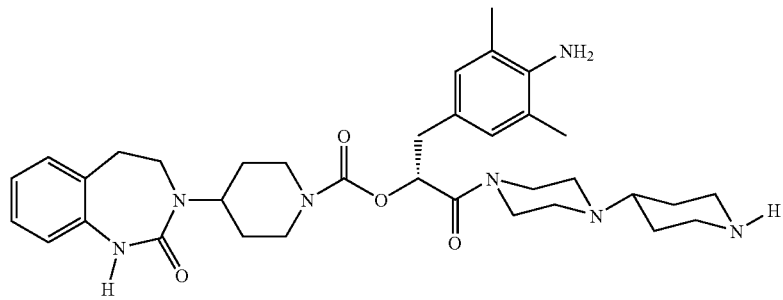

Yield: 4 mg (6% of theory) ESI-MS: (M+H)⁺=632 retention time (HPLC): 3.6 min (method A)

EXAMPLE 94

(R)-1-(4-amino-3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

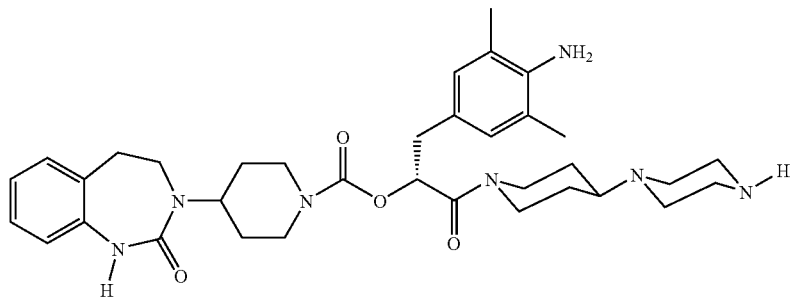

Analogously to Example 93 the product was obtained from 65.0 mg (0.089 mmol) tert-butyl 4-(1-{(R)-3-(4-amino-3,5-dimethyl-phenyl)-2-[4-(2-oxo-1,2,4,5-tetrahydro-1,3-benzodiazepin-3-yl)-piperidine-1-carbonyloxy]-propionyl}-piperidin-4-yl)-piperazine-1-carboxylate (Example 92).

Yield: 7 mg (12% of theory) ESI-MS: (M+H)⁺=632 retention time (HPLC): 3.9 min (method A)

EXAMPLE 95

(R)-1-(4-amino-3,5-dimethyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate A solution of 3.1 mg (0.13 mmol) LiOH in 1 mL water was added to a solution of 55 mg (0.08 mmol) of (R)-1-(4-amino-3,5-dimethyl-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate (Example 90) in 5 mL THF and the reaction mixture was stirred overnight at RT. The mixture was evaporated down i.vac., the residue was taken up in 1 mL DMF and the crude product was purified by HPLC. The fractions containing the product were combined and lyophilised.

Yield: 22 mg (42% of theory) ESI-MS: (M+H)⁺=689 retention time (HPLC): 4.8 min (method A)

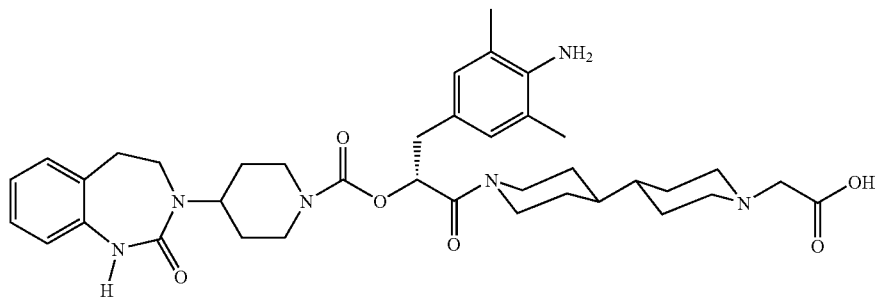

EXAMPLE 96

(R)-1-(3-chloro-4-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

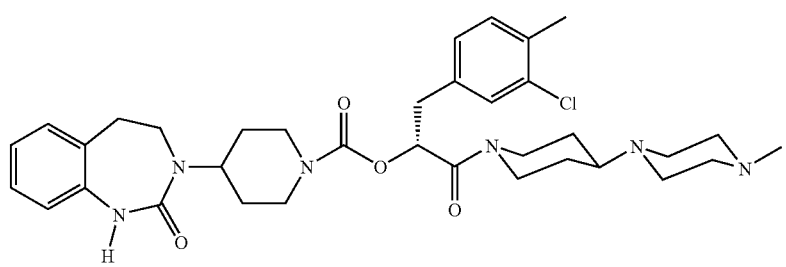

96a methyl (Z,E)-2-acetylamino-3-(3-chloro-4-methyl-phenyl)-acrylate

Under an argon atmosphere 0.65 g (2.9 mmol) Pd(OAc)$_2$ and 0.9 g (2.9 mmol) tri-o-tolyl-phosphane were added to a mixture of 5.2 mL (39.0 mmol) 4-bromo-2-chloro-1-methyl-benzene and 10.0 g (69.9 mmol) methyl 2-acetylamino-acrylate in 100 mL each of acetonitrile and triethylamine and the reaction mixture was heated to 90° C. for 20 h. After cooling the mixture was evaporated down i.vac., the residue was combined with DCM and water, filtered, the organic phase was separated off and dried over Na$_2$SO$_4$. After the desiccant and solvent had been eliminated the residue was purified by chromatography (silica gel, gradient PE/EtOAc 1:1 to EtOAc).

Yield: 7.67 g (73% of theory) ESI-MS: (M+H)$^+$=268/270 (Cl) melting point: 144-145° C. R$_f$=0.65 (Polygram, EtOAc)

96b 3-(3-chloro-4-methyl-phenyl)-2-oxo-propionic acid 100 mL 4 M HCl were added to a solution of 7.67 g (28.7 mmol) methyl (Z,E)-2-acetylamino-3-(3-chloro-4-methyl-phenyl)-acrylate in 150 mL EtOH and the reaction solution was refluxed for 4 h. The EtOH was removed i.vac., the residue was cooled in the ice bath, while the oily residue solidified. The solid was filtered, washed with water, stirred with PE, suction filtered again, washed again with a little PE and dried. The combined filtrates were evaporated down, dissolved in 50 mL MeOH, combined with 50 mL 4 M NaOH and refluxed for 2 h. MeOH was eliminated i.vac., the aqueous residue was acidified with conc. HCl and exhaustively extracted with EtOAc. The combined organic phases were washed with saturated NaCl solution and dried over Na$_2$SO$_4$. After the desiccant and solvent had been eliminated the residue was recrystallised from DCM and combined with the first product fraction.

Yield: 2.02 g (33% of theory) ESI-MS: (M–H)$^-$=211/213 (Cl)

96c (R)-3-(3-chloro-4-methyl-phenyl)-2-hydroxy-propionic acid

Under a nitrogen atmosphere a mixture of 2.6 g (12.23 mmol) 3-(3-chloro-4-methyl-phenyl)-2-oxo-propionic acid and 2.1 mL (15.1 mmol) triethylamine in 40 mL THF was cooled to –35° C. Then a solution of 5.87 g (18.30 mmol) (1R)-B-chlorodiisopinocampheylborane in 20 mL THF was added dropwise so that the reaction temperature remained between –35° C. and –25° C. The cooling bath was removed and the reaction mixture was stirred overnight at RT. While cooling with ice 30 mL 1 M NaOH and 60 mL diethyl ether were added dropwise and the mixture was stirred for 15 min. The aqueous phase was separated off, the organic phase was extracted twice with 20 mL 1 M NaOH and once with 20 mL water. The combined aqueous phases were acidified with semiconc. HCl while cooling with ice, extracted twice with 60 mL EtOAc and the combined organic phases were dried over Na$_2$SO$_4$. After the desiccant and solvent had been eliminated the residue was reacted further without purification.

Yield: 2.8 g (85% of theory)

96d methyl (R)-3-(3-chloro-4-methyl-phenyl)-2-hydroxy-propionate 2.0 mL (27.4 mmol) SOCl$_2$ were slowly added dropwise to a solution of 2.8 g (10.4 mmol) of (R)-3-(3-chloro-4-methyl-phenyl)-2-hydroxy-propionic acid in 100 mL MeOH while cooling with ice and the reaction solution was stirred for 1 h at 0° C. and for 1 h at RT. The reaction mixture was evaporated down i.vac., the residue was taken up in EtOAc, the organic phase was washed with saturated NaHCO$_3$ solution and dried over Na$_2$SO$_4$. After the desiccant and solvent had been eliminated the residue was purified by chromatography (silica gel, gradient DCM to DCM/MeOH 50:1).

Yield: 2.12 g (89% of theory) ESI-MS: (M+H)$^+$=229/231 (Cl) R$_f$=0.34 (Polygram, DCM)

96e (R)-2-(3-chloro-4-methyl-phenyl)-1-methoxycarbonyl-ethyl 4-(2-oxo-1,2,4,5-tetrahydro-1,3-benzodiazepin-3-yl)-piperidine-1-carboxylate Analogously to Example 31f the desired product was obtained from 2.1 g (9.18 mmol) methyl (R)-3-(3-chloro-4-methyl-phenyl)-2-hydroxy-propionate and 2.45 g (9.99 mmol) 3-piperidin-4-yl-1,3,4,5-tetrahydro-1,3-benzodiazepin-2-one.

Yield: 3.4 g (74% of theory) ESI-MS: (M+H)$^+$=500/502 (Cl) R$_f$=0.52 (Polygram, EtOAc)

96f (R)-1-carboxy-2-(3-chloro-4-methyl-phenyl)-ethyl 4-(2-oxo-1,2,4,5-tetrahydro-1,3-benzodiazepin-3-yl)-piperidine-1-carboxylate A solution of 0.34 g (14.2 mmol) LiOH in 20 mL water was added to a solution of 3.38 g (6.76 mmol) of (R)-2-(3-chloro-4-methyl-phenyl)-1-methoxycarbonyl-ethyl 4-(2-oxo-1,2,4,5-tetrahydro-1,3-benzodiazepin-3-yl)-piperidine-1-carboxylate in 30 mL THF and the reaction mixture was stirred for 7 h at RT. The mixture was evaporated down i.vac., diluted with 80 mL water, the aqueous phase was extracted twice with 50 mL diethyl ether, the aqueous phase was acidified with 4 M HCl and stirred for 30 min. The precipitated product was suction filtered, washed with water and dried.

Yield: 3.2 g (97% of theory) ESI-MS: (M+H)$^+$=486/488 (Cl)

96q (R)-1-(3-chloro-4-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate A solution of 100 mg (0.21 mmol) of (R)-1-carboxy-2-(3-chloro-4-methyl-phenyl)-ethyl 4-(2-oxo-1,2,4,5-tetrahydro-1,3-benzodiazepin-3-yl)-piperidine-1-carboxylate, 70.0 mg (0.22 mmol) TBTU and 35 μL (0.27 mmol) triethylamine in 10 mL THF was stirred for 1 h at RT. Then 40 mg (0.22 mmol) 1-methyl-4-piperidin-4-yl-piperazine were added and the reaction mixture was then stirred overnight at RT. The reaction solution was stirred with 20 mL semisaturated NaHCO$_3$ solution, extracted twice with 20 mL EtOAc and the combined organic phases were dried over Na$_2$SO$_4$. After the desiccant and solvent had been eliminated the residue was purified by chromatography (Alox, activity stage II-III DCM/MeOH 40:1).

Yield: 123 mg (83% of theory) ESI-MS: (M+H)$^+$=651/653 (Cl) R$_f$=0.52 (Polygram-Alox, DCM/MeOH 25:1)

The following compounds were obtained analogously from in each case 100 mg (R)-1-carboxy-2-(3-chloro-4-methyl-phenyl)-ethyl 4-(2-oxo-1,2,4,5-tetrahydro-1,3-benzodiazepin-3-yl)-piperidine-1-carboxylate and the corresponding amount of amine:

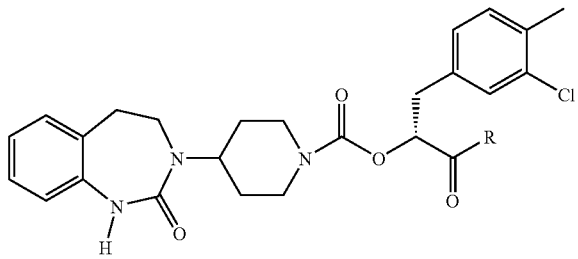

| Example | R | Yield (%) | Mass spectrum | R$_f$ (Polygram-Alox, eluant) |
|---|---|---|---|---|
| 97 | | 74 | 651/653 [M + H]$^+$ | 0.48 DCM/MeOH 25:1 |
| 98 | | 83 | 650/652 [M + H]$^+$ | 0.55 (DCM/MeOH 25:1) |
| 99 | | 74 | 737/739 [M + H]$^+$ | n.d |
| 100 | | 65 | 737/739 [M + H]$^+$ | 0.33 (DCM/MeOH 50:1) |

EXAMPLE 101

(R)-1-(3-chloro-4-methyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate 10 mL 1 M HCl were added to a solution of 130 mg (0.14 mmol) tert-butyl 4-(1-{(R)-3-(3-chloro-4-methyl-phenyl)-2-[4-(2-oxo-1,2,4,5-tetrahydro-1,3-benzodiazepin-3-yl)-piperidine-1-carbonyloxy]-propionyl}-piperidin-4-yl)-piperazine-1-carboxylate (Example 99) in 1 mL MeOH and the reaction mixture was stirred for 24 h at RT. The reaction

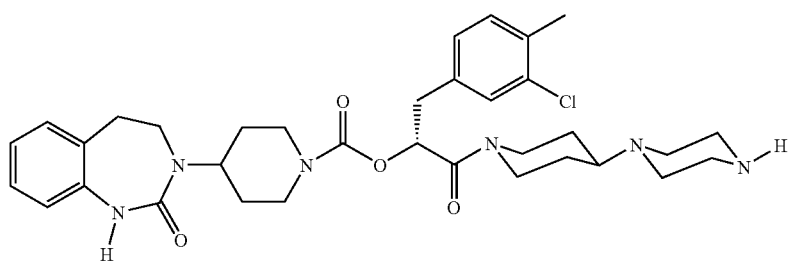

EXAMPLE 102

(R)-1-(3-chloro-4-methyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

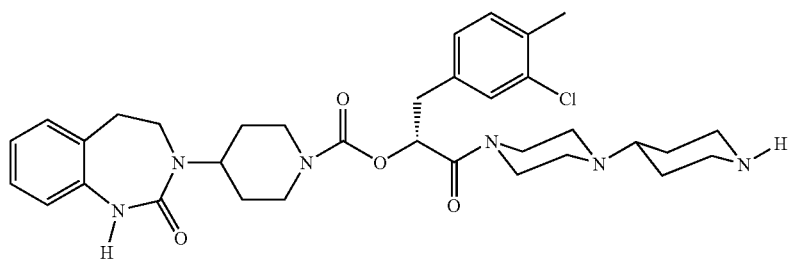

Analogously to Example 101 the product was obtained from 110 mg (0.13 mmol) of (R)-1-(3-chloro-4-methyl-benzyl)-2-[4-(1-tert-butoxy-carbonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (Example 100), in the form of the bis-hydrochloride salt.

Yield: 99 mg (93% of theory) ESI-MS: (M+H)$^+$=637/639 (Cl)

EXAMPLE 103

(R)-1-(3-bromo-4-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

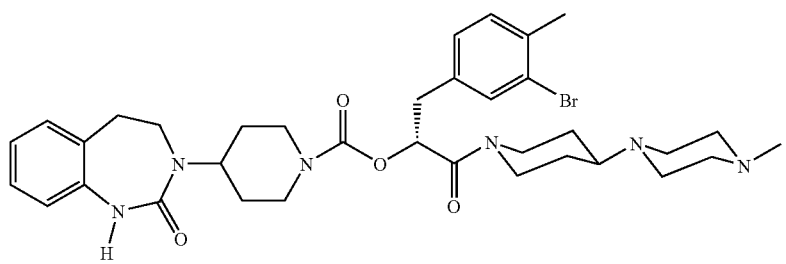

103a (Z,E)-2-acetylamino-3-(3-bromo-4-methyl-phenyl)-acrylic acid

Analogously to Example 1a the product was obtained from 6.0 g (30.1 mmol) 3-bromo-4-methyl-benzaldehyde and 5.3 g (45.3 mmol) N-acetylglycine.

Yield: 4.7 g (52% of theory) ESI-MS: (M+H)$^+$=298/300 (Br) R$_f$=0.12 (silica gel, DCM/MeOH/cyc/NH$_3$ 70:15:15:2)

103b 3-(3-bromo-4-methyl-phenyl)-2-oxo-propionic acid 28 mL 4 M HCl were added to a solution of 4.7 g (15.8 mmol) (Z,E)-2-acetylamino-3-(3-bromo-4-metyl-phenyl)-acrylic acid in 50 mL 1,4-dioxane heated to 105° C. and the reaction mixture was kept for a further 5 h at this temperature. The 1,4-dioxane was eliminated i.vac., the cooled residue was ombined with water, the precipitate formed was filtered off and dried in the circulating air dryer.

Yield: 2.9 g (72% of theory) ESI-MS: (M−H)$^-$=255/257 (Br) R$_f$=0.18 (silica gel, DCM/MeOH/NH$_3$ 80:20:2)

103c (R)-3-(3-bromo-4-methyl-phenyl)-2-hydroxy-propionic acid

Under a nitrogen atmosphere a mixture of 2.9 g (11.3 mmol) 3-(3-bromo-4-methyl-phenyl)-2-oxo-propionic acid and 2.0 mL (15.1 mmol) triethylamine in 40 mL THF was cooled to −35° C. Then a solution of 5.44 g (17.0 mmol) (1R)-B-chlorodiisopinocampheylborane in 20 mL THF was added dropwise so that the reaction temperature remained between −35° C. and −25° C.; the reaction mixture was kept for 1 h at this temperature, then the cooling bath was removed and the mixture was stirred overnight at RT. To complete the reaction another 3.0 g (9.4 mmol) (1R)-B-chlorodiisopinocampheylborane were added and the mixture was stirred for a further 5 h. While cooling with ice 30 mL 1 M NaOH and 30 mL TBME were added dropwise and the mixture was stirred for 15 min. The aqueous phase was separated off, the organic phase was extracted with 15 mL 1 M NaOH and 25 mL water. The combined aqueous phases were acidified with 2 M HCl while cooling with ice, extracted three times with 40 mL TBME and the combined organic phases were dried over Na$_2$SO$_4$. After the desiccant and solvent had been eliminated the residue was reacted further without purification.

Yield: 3.0 g (approx. 70% proportion of product, 72% of theory) ESI-MS: (M−H)$^-$=257/259 (Br) R$_f$=0.12 (silica gel, PE/EtOAc 1:1)

103d methyl (R)-3-(3-bromo-4-methyl-phenyl)-2-hydroxy-propionate

A solution of 2.8 g (approx. 70%; 7.56 mmol) of (R)-3-(3-bromo-4-methyl-phenyl)-2-hydroxy-propionic acid in methanolic HCl (1.25 M) was stirred for 4 h at RT. The mixture was freeze-dried directly without any further working up. The product was obtained as the bis-hydrochloride salt.

Yield: 112 mg (95% of theory) ESI-MS: (M+H)$^+$=637/639 (Cl)

mixture was evaporated down i.vac. and the residue was purified by chromatography (silica gel, gradient PE/EtOAc 9:1 to PE/EtOAc 1:9).

Yield: 1.6 g (77% of theory) ESI-MS: $(M+H)^+$=273/275 (Br) $R_f$=0.72 (silica gel, PE/EtOAc 1:1)

103e (R)-2-(3-bromo-4-methyl-phenyl)-1-methoxy-carbonyl-ethyl 4-(2-oxo-1,2,4,5-tetrahydro-1,3-benzodiazepin-3-yl)-piperidine-1-carboxylate Analogously to Example 1f the crude product was obtained from 1.5 g (5.49 mmol) methyl (R)-3-(3-bromo-4-methyl-phenyl)-2-hydroxy-propionate and 1.7 g (5.52 mmol) 4-(2-oxo-1,2,4,5-tetrahydro-1,3-benzodiazepin-3-yl)-piperidine-1-carbonylchloride. This was purified by chromatography (silica gel, gradient DCM/MeOH/NH$_3$ 100:0:0 to DCM/MeOH/NH$_3$ 0:95:5). The product fractions were combined, evaporated down i.vac., triturated with DIPE, suction filtered and dried.

Yield: 1.1 g (37% of theory) ESI-MS: $(M+H)^+$=544/546 (Br) $R_f$=0.70 (silica gel, DCM/MeOH/cyc/NH$_3$ 70:15:15:2)

103f (R)-2-(3-bromo-4-methyl-phenyl)-1-carboxy-ethyl 4-(2-oxo-1,2,4,5-tetrahydro-1,3-benzodiazepin-3-yl)-piperidine-1-carboxylate A solution of 70 mg (2.92 mmol) LiOH in 5 mL water was added to a solution of 1.0 g (1.84 mmol) of (R)-2-(3-bromo-4-methyl-phenyl)-1-methoxycarbonyl-ethyl 4-(2-oxo-1,2,4,5-tetrahydro-1,3-benzodiazepin-3-yl)-piperidine-1-carboxylate in 20 mL THF and the reaction mixture was stirred for 5 h at RT. The reaction solution was evaporated down i.vac., the residue was combined with DCM, the organic phase was washed with 1 M KHSO$_4$ solution and dried over Na$_2$SO$_4$.

After the desiccant and solvent had been eliminated the residue was triturated with DIPE, suction filtered and dried.

Yield: 0.95 g (98% of theory) ESI-MS: $(M+H)^+$=530/532 (Br) $R_f$=0.29 (silica gel, DCM/MeOH/cyc/NH$_3$ 70:15:15:2)

103q (R)-1-(3-bromo-4-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate Analogously to Example 1h the product was obtained from 100 mg (0.19 mmol) of (R)-2-(3-bromo-4-methyl-phenyl)-1-carboxy-ethyl 4-(2-oxo-1,2,4,5-tetrahydro-1,3-benzodiazepin-3-yl)-piperidine-1-carboxylate and 38 mg (0.21 mmol) 1-methyl-4-piperidin-4-yl-piperazine.

Yield: 90 mg (69% of theory) ESI-MS: $(M+H)^+$=695/697 (Br) $R_f$=0.59 (silica gel, DCM/MeOH/cyc/NH$_3$ 70:15:15:2)

The following compounds were obtained analogously from in each case 100 mg of (R)-2-(3-bromo-4-methyl-phenyl)-1-carboxy-ethyl 4-(2-oxo-1,2,4,5-tetrahydro-1,3-benzodiazepin-3-yl)-piperidine-1-carboxylate and the corresponding amount of amine:

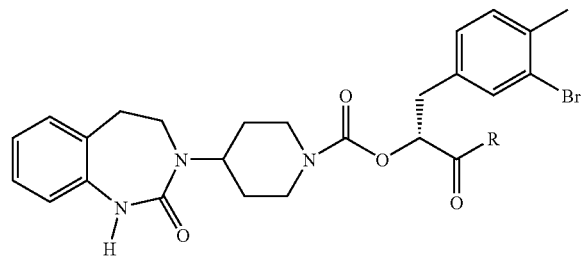

| Example | R | Yield (%) | Mass spectrum | $R_f$ (silica gel, eluant) or retention time HPLC (method) |
|---|---|---|---|---|
| 104 | (piperidinyl-piperidinyl-N-methyl) | 65 | 695/697 $[M+H]^+$ | 0.58 (DCM/MeOH/Cyc/NH$_3$ 70:15:15:2) |
| 105 | (piperidinyl-cyclohexyl-N-methyl) | 61 | 694/696 $[M+H]^+$ | 0.57 (DCM/MeOH/Cyc/NH$_3$ 70:15:15:2) |
| 105 | (piperidinyl-piperidinyl-N-Boc) | 54 | 781/783 $[M+H]^+$ | 7.1 min (A) |
| 106 | (piperidinyl-ethyl-piperazinyl-Boc) | 61 | 781/783 $[M+H]^+$ | 6.9 min (A) |

EXAMPLE 107

(R)-1-(3-bromo-4-methyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

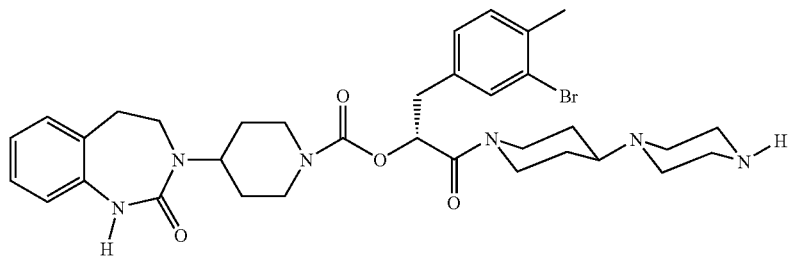

Analogously to Example 93 the product was obtained from 90 mg (0.12 mmol) tert-butyl 4-(1-{(R)-3-(3-bromo-4-methyl-phenyl)-2-[4-(2-oxo-1,2,4,5-tetrahydro-1,3-benzodiazepin-3-yl)-piperidine-1-carbonyl-oxy]-propionyl}-piperidin-4-yl)-piperazine-1-carboxylate (Example 106).

Yield: 15 mg (19% of theory) ESI-MS: (M+H)$^+$=681/683 (Br) retention time (HPLC): 5.7 min (method A)

EXAMPLE 108

(R)-1-(3-bromo-4-methyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

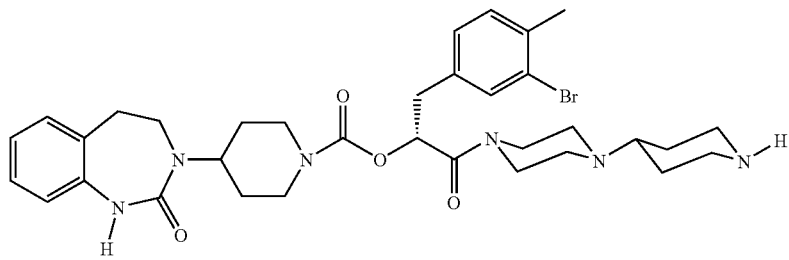

Analogously to Example 93 the product was obtained from 80 mg (0.12 mmol) of (R)-1-(3-bromo-4-methyl-benzyl)-2-[4-(1-tert-butoxy-carbonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (Example 105).

Yield: 44 mg (63% of theory) ESI-MS: (M+H)$^+$=681/683 (Br) retention time (HPLC): 5.5 min (method A)

EXAMPLE 109

(R)-1-(6-amino-5-methyl-pyridin-3-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

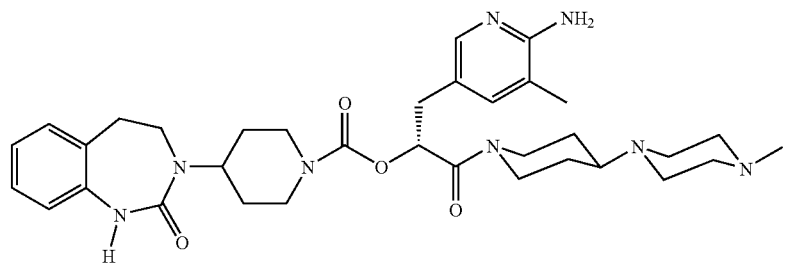

109a methyl (Z,E)-2-acetylamino-3-(6-amino-5-methyl-pyridin-3-yl)-acrylate

Under a nitrogen atmosphere 6.58 g (7.19 mmol) tris-(dibenzylideneacetone)-palladium was added to a mixture of 33.6 g (180 mmol) 5-bromo-3-methyl-pyridin-2-ylamine, 28.9 g (198 mmol) methyl 2-acetylamino-acrylate, 4.42 g (14.4 mmol) tri-o-tolyl-phosphane and 30.9 mL (180 mmol) ethyldiisopropylamine in 500 mL butyronitrile and the reaction mixture was heated to 110° C. for 17 h. The reaction solution was evaporated down i.vac. and the residue was stirred with approx. 500 mL water. The precipitate was filtered, recrystallised from acetonitrile and dried.

The aqueous mother liquor was evaporated down and the residue was purified by chromatography (silica gel, EtOAc/MeOH/NH$_3$ 90:10:1). The fractions containing the product were evaporated down, the residue was triturated with a little acetonitrile, filtered, dried and combined with the above product fraction.

Yield: 16.6 g (37% of theory) ESI-MS: (M+H)$^+$=250 R$_f$=0.46 (silica gel, EtOAc/MeOH/NH$_3$ 90:10:1)

109b 3-(6-amino-5-methyl-Pyridin-3-yl)-2-oxo-propionic acid 230 mL 4 M HCl were added to a solution of 15.57 g (62.46 mmol) methyl (Z,E)-2-acetylamino-3-(6-amino-5-methyl-pyridin-3-yl)-acrylate in 250 mL 1,4-dioxane, the reaction mixture was refluxed for 1.5 h and stirred for a further 16 h at RT. The mixture was evaporated down i.vac., the residue was triturated with EtOAc/DIPE (1:1), filtered and dried in the circulating air dryer. The product was obtained as the hydrochloride salt.

Yield: 14.4 g (100% of theory) ESI-MS: (M+H)$^+$=195 retention time (HPLC): 2.7 min (method A)

109c methyl (R)-3-(6-amino-5-methyl-pyridin-3-yl)-2-hydroxy-propionate

Under an argon atmosphere a mixture of 13.8 g (59.9 mmol) 3-(6-amino-5-methyl-pyridin-3-yl)-2-oxo-propionic acid and 17.5 mL (125.7 mmol) triethylamine in 140 mL THF was cooled to −35° C. Then a solution of 40.3 g (126 mmol) (1R)-B-chlorodiisopinocampheylborane in 210 mL THF was added dropwise so that the reaction temperature remained between −35° C. and −25° C.; the reaction mixture was kept for 3 h at this temperature before adding 150 mL 1 M NaOH at 0-5° C. and stirring the reaction mixture for 2 h at RT. 200 mL TBME were added, the organic phase was separated off and acidified with 200 mL 2 M HCl. The aqueous phase was separated off, evaporated down, the residue was taken up in THF/MeOH (1:1), filtered and the filtrate was then evaporated down. The crude product thus obtained (12.5 g) was dissolved in 300 mL MeOH, 4.3 mL (59.3 mmol) SOCl$_2$ were added dropwise while cooling with ice and the mixture was stirred for a further 2 h at RT. It was evaporated down i.vac and the residue was purified by chromatography (silica gel, EtOAc/MeOH/NH$_3$ 90:10:1).

Yield: 5.62 g (45% of theory) ESI-MS: (M+H)$^+$=211 retention time (HPLC): 2.4 min (method A)

109d (R)-2-(6-amino-5-methyl-pyridin-3-yl)-1-methoxycarbonyl-ethyl 4-(2-oxo-1,2,4,5-tetrahydro-1,3-benzodiazepin-3-yl)-piperidine-1-carboxylate Analogously to Example 31f the desired product was obtained from 2.75 g (13.10 mmol) methyl (R)-3-(6-amino-5-methyl-pyridin-3-yl)-2-hydroxy-propionate and 3.21 g (13.10 mmol) 3-piperidin-4-yl-1,3,4,5-tetrahydro-1,3-benzodiazepin-2-one.

Yield: 1.38 g (22% of theory) ESI-MS: (M+H)$^+$=482 retention time (HPLC): 4.9 min (method C)

109e (R)-2-(6-amino-5-methyl-pyridin-3-yl)-1-carboxy-ethyl 4-(2-oxo-1,2,4,5-tetrahydro-1,3-benzodiazepin-3-yl)-piperidine-1-carboxylate A solution of 100 mg (4.18 mmol) LiOH in 25 mL water was added to a solution of 1.27 g (2.64 mmol) of (R)-2-(6-amino-5-methyl-pyridin-3-yl)-1-methoxycarbonyl-ethyl 4-(2-oxo-1,2,4,5-tetrahydro-1,3-benzodiazepin-3-yl)-piperidine-1-carboxylate in 30 mL THF and the reaction solution was stirred for 1 h at RT. The mixture was evaporated down i.vac., the residue was taken up in water, 2 M KHSO$_4$ solution were added with stirring, the supernatant solution was decanted off, the residue was dried, stirred with THF and the product was filtered.

Yield: 0.92 g (74% of theory) ESI-MS: (M+H)$^+$=468 retention time (HPLC): 4.8 min (method A)

109f (R)-1-(6-amino-5-methyl-pyridin-3-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate Analogously to Example 1h the product was obtained from 50 mg (0.11 mmol) of (R)-2-(6-amino-5-methyl-pyridin-3-yl)-1-carboxy-ethyl 4-(2-oxo-1,2,4,5-tetrahydro-1,3-benzodiazepin-3-yl)-piperidine-1-carboxylate and 20 mg (0.11 mmol) 1-methyl-4-piperidin-4-yl-piperazine.

Yield: 6 mg (9% of theory) ESI-MS: (M+H)$^+$=633 retention time (HPLC): 4.4 min (method A)

The following compounds were obtained analogously from in each case 50 mg (R)-2-(6-amino-5-methyl-pyridin-3-yl)-1-carboxy-ethyl 4-(2-oxo-1,2,4,5-tetrahydro-1,3-benzodiazepin-3-yl)-piperidine-1-carboxylate and the corresponding amount of amine:

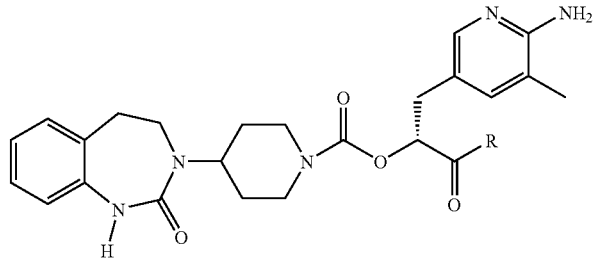

| Example | R | Yield (%) | Mass spectrum | retention time HPLC (method) |
|---|---|---|---|---|
| 110 | ![*-N-piperidine-N-piperidine-N-methyl] | 19 | 633 [M + H]⁺ | 4.4 min (D) |
| 111 | ![*-N-piperidine-piperidine-N-methyl] | 29 | 632 [M + H]⁺ | 5.6 min (D) |
| 112 | ![*-N-piperidine-N-piperidine] | 25 | 618 [M + H]⁺ | 5.4 min (D) |
| 113 | ![*-N-piperidine-N-piperazine-N-Boc] | 54 | 719 [M + H]⁺ | 6.8 min (A) |
| 114 | ![*-N-piperidine-N-piperazine-N-Boc] | 61 | 719 [M + H]⁺ | 6.5 min (D) |

EXAMPLE 115

(R)-1-(6-amino-5-methyl-pyridin-3-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate A solution of 75 mg (0.10 mmol) of tert-butyl 4-(1-{(R)-3-(6-amino-5-methyl-pyridin-3-yl)-2-[4-(2-oxo-1,2,4,5-tetrahydro-1,3-benzodiazepin-3-yl)-piperidine-1-carbonyloxy]-propionyl}-piperidin-4-yl)-piperazine-1-carboxylate (Example 114) in 5 mL 2 M HCl was stirred for 20 h at RT. After lyophilisation of the reaction mixture the residue was dissolved in 1 mL DMF, made alkaline with 0.6 mL saturated

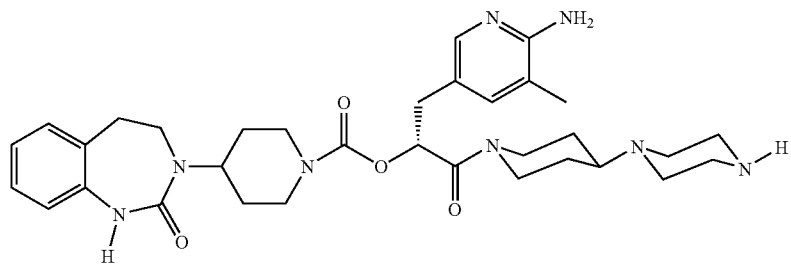

K₂CO₃ solution and purified by HPLC. The fractions containing the product were combined and again lyophilised.
Yield: 28 mg (44% of theory) ESI-MS: (M+H)⁺=619 retention time (HPLC): 3.8 min (method A)

EXAMPLE 116

(R)-1-(6-amino-5-methyl-pyridin-3-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

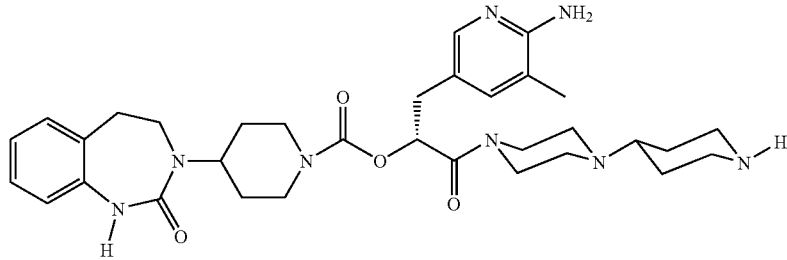

Analogously to Example 115 the product was obtained from 66 mg (0.09 mmol) of (R)-1-(6-amino-5-methyl-pyridin-3-ylmethyl)-2-[4-(1-tert-butoxy-carbonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (Example 113).
Yield: 29 mg (51% of theory) ESI-MS: (M+H)⁺=619 retention time (HPLC): 3.5 min (method A)

EXAMPLE 117

(R)-1-(4-hydroxy-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

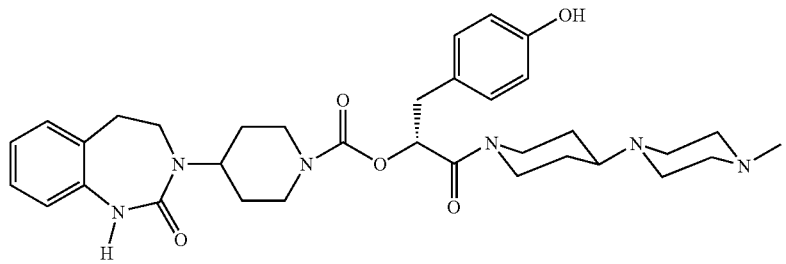

117a (Z,E)-2-acetylamino-3-(4-benzyloxy-phenyl)-acrylic acid

Analogously to Example 1a the product was obtained from 30.0 g (141 mmol) 4-benzyloxy-benzaldehyde and 24.8 g (212 mmol) N-acetyl-glycine.
Yield: 32.0 g (73% of theory) ESI-MS: (M+H)⁺=312 $R_f$=0.35 (silica gel, DCM/MeOH/AcOH 90:10:1)

117b 3-(4-benzyloxy-phenyl)-2-oxo-propionic acid

Analogously to Example 1b the product was obtained from 32.0 g (103 mmol) (Z,E)-2-acetylamino-3-(4-benzyloxy-phenyl)-acrylic acid.

Yield: 12.4 g (45% of theory) ESI-MS: (M–H)⁻=269 $R_f$=0.30 (silica gel, DCM/MeOH/AcOH 80:20:2)

117c (R)-3-(4-benzyloxy-phenyl)-2-hydroxy-propionic acid

Analogously to Example 1c the product was obtained from 11.5 g (42.6 mmol) 3-(4-benzyloxy-phenyl)-2-oxo-propionic acid and 16.7 g (52.1 mmol) (1R)-B-chlorodiisopinocampheylborane.
Yield: 7.43 g (64% of theory) ESI-MS: (M+Na)⁺=294 retention time (HPLC): 13.3 min (method F)

117d methyl (R)-3-(4-benzyloxy-phenyl)-2-hydroxy-propionate

Analogously to Example 46d the product was obtained from 7.3 g (26.8 mmol) of (R)-3-(4-benzyloxy-phenyl)-2-hydroxy-propionic acid.
Yield: 7.6 g (99% of theory) retention time (HPLC): 16.7 min (method F)

117e (R)-2-(4-benzyloxy-phenyl)-1-methoxycarbonyl-ethyl 4-(2-oxo-1,2,4,5-tetrahydro-1,3-benzodiazepin-3-yl)-piperidine-1-carboxylate Analogously to Example 31f the product was obtained from 7.6 g (26.5 mmol) of methyl (R)-3-(4-benzyloxy-phenyl)-2-hydroxy-propionate and 6.5 g (26.5 mmol) 3-piperidin-4-yl-1,3,4,5-tetrahydro-1,3-benzodiazepin-2-one.
Yield: 4.1 g (28% of theory) ESI-MS: (M+H)⁺=558 $R_f$=0.25 (silica gel, n-hexane/EtOAc 3:7) retention time (HPLC): 22.0 min (method F)

117f (R)-1-carboxy-2-(4-benzyloxy-phenyl)-ethyl 4-(2-oxo-1,2,4,5-tetrahydro-1,3-benzodiazepin-3-yl)-piperidine-1-carboxylate Analogously to Example 58f the product was obtained from 4.1 g (7.4 mmol) of (R)-2-(4-benzyloxy-phenyl)-1-methoxycarbonyl-ethyl (4-(2-oxo-1,2,4,5-tetrahydro-1,3-benzodiazepin-3-yl)-piperidine-1-carboxylate and 264 mg (11.0 mmol) LiOH.

Yield: 2.7 g (68% of theory) ESI-MS: (M+H)⁺=544 retention time (HPLC): 18.8 min (method F)

117q (R)-1-carboxy-2-(4-hydroxy-phenyl)-ethyl 4-(2-oxo-1,2,4,5-tetrahydro-1,3-benzodiazepin-3-yl)-piperidine-1-carboxylate 220 mg 10% Pd/C were added to a solution of 2.2 g (4.1 mmol) of (R)-1-carboxy-2-(4-benzyloxy-phenyl)-ethyl 4-(2-oxo-1,2,4,5-tetrahydro-1,3-benzodiazepin-3-yl)-piperidine-1-carboxylate and 450 mg (4.4 mmol) triethylamine in 90 mL MeOH and the reaction mixture was hydrogenated at 3 bar H₂ for 24 h. The catalyst was filtered, washed twice with MeOH and the filtrate was evaporated down i.vac. The residue was taken up in 20 mL water and adjusted to pH 2-3 with 10% HCl. The precipitate formed was filtered, washed with a little water and dried at 50° C.

Yield: 1.4 g (76% of theory) ESI-MS: (M+H)⁺=454 R_f=0.65 (silica gel, DCM/MeOH/AcOH 80:20:2)

117h (R)-1-(4-hydroxy-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate Under a nitrogen atmosphere 74 mg (0.40 mmol) 1-methyl-4-piperidin-4-yl-piperazine was added to a solution of 140 mg (0.31 mmol) of (R)-1-carboxy-2-(4-hydroxy-phenyl)-ethyl 4-(2-oxo-1,2,4,5-tetrahydro-1,3-benzodiazepin-3-yl)-piperidine-1-carboxylate, 150 mg (0.39 mmol) HATU and 80 μL (0.47 mmol) ethyldiisopropylamine in 5 mL DMF and the reaction mixture was stirred for 6 h at RT. The reaction solution was evaporated down i.vac. and the residue was purified by chromatography (silica gel, DCM/MeOH/NH₃ 93:7:0.7).

Yield: 100 mg (52% of theory) ESI-MS: (M+H)⁺=619 R_f=0.6 (silica gel, DCM/MeOH/NH₃ 80:20:2)

The following compounds were obtained analogously from in each case 140 mg (Examples 118 and 119), 150 mg (Examples 120 and 121), 200 mg (Examples 122 and 123) or 230 mg (Example 124) of (R)-1-carboxy-2-(4-hydroxy-phenyl)-ethyl 4-(2-oxo-1,2,4,5-tetrahydro-1,3-benzodiazepin-3-yl)-piperidine-1-carboxylate and the corresponding amount of amine:

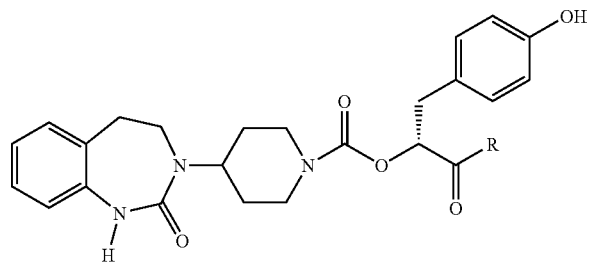

| Example | R | Yield (%) | Mass spectrum | R_f (silica gel, eluant) |
|---|---|---|---|---|
| 118 | | 27 | 604 [M + H]⁺ | 0.70 (DCM/MeOH/NH₃ 80:20:2) |
| 119 | | 47 | 618 [M + H]⁺ | 0.65 (DCM/MeOH/NH₃ 80:20:2) |
| 120 | | 64 | 619 [M + H]⁺ | 0.35 (DCM/MeOH/NH₃ 80:20:2) |
| 121 | | 54 | 564 [M + H]⁺ | 0.40 (DCM/MeOH/NH₃ 80:20:2) |

-continued

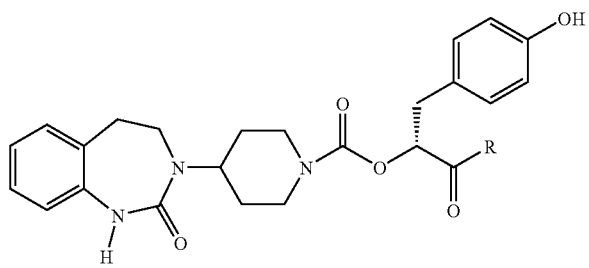

| Example | R | Yield (%) | Mass spectrum | $R_f$ (silica gel, eluant) |
|---------|---|-----------|---------------|----------------------------|
| 122 | | 45 | 704 [M + H]$^+$ | 0.65 (DCM/MeOH/NH$_3$ 80:20:2) |
| 123 | | 43 | 827 [M + H]$^+$ | 0.40 (DCM/MeOH/AcOH 90:10:1) |
| 124 | | 53 | 705 [M + H]$^+$ | 0.65 (DCM/MeOH/NH$_3$ 80:20:2) |

EXAMPLE 125

(R)-1-(4-hydroxy-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

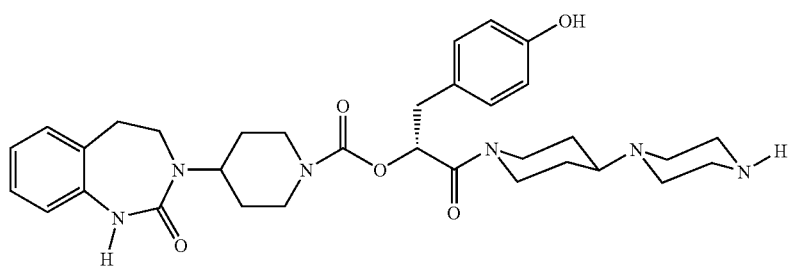

A solution of 250 mg (0.30 mmol) 9H-fluoren-9-ylmethyl 4-(1-{(R)-3-(4-hydroxy-phenyl)-2-[4-(2-oxo-1,2,4,5-tetrahydro-1,3-benzodiazepin-3-yl)-piperidine-1-carbonyloxy]-propionyl}-piperidin-4-yl)-piperazine-1-carboxylate (Example 123) in 4 mL piperidine was stirred for 30 min at RT. The reaction mixture was evaporated down i.vac. and the residue was purified by chromatography (silica gel, DCM/MeOH/NH$_3$ 90:10:1).

Yield: 40 mg (22% of theory) ESI-MS: (M+H)$^+$=605 retention time (HPLC): 4.7 min (method F)

EXAMPLE 126

(R)-1-(4-hydroxy-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

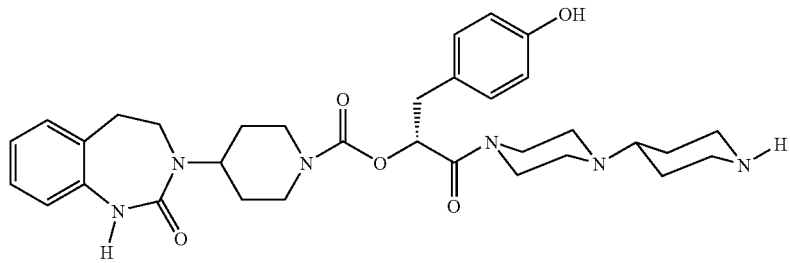

To a solution of 210 mg (0.30 mmol) of (R)-1-(4-hydroxy-benzyl)-2-[4-(1-tert-butoxy-carbonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (Example 124) in 1.5 mL formic acid was stirred for 3 h at RT. The reaction mixture was evaporated down i.vac. and the residue was purified by chromatography (silica gel, DCM/MeOH/NH$_3$ 90:10:1).

Yield: 40 mg (22% of theory) ESI-MS: (M+H)$^+$=605 R$_f$=0.45 (silica gel, DCM/MeOH/NH$_3$ 80:20:2) retention time (HPLC): 4.6 min (method F)

EXAMPLE 127

(R)-2-(4,4'-bipiperidinyl-1-yl)-1-(4-hydroxy-benzyl)-2-oxo-ethyl 4-(2-oxo-1,2,4,5-tetrahydro-1,3-benzodiazepin-3-yl)-piperidine-1-carboxylate Analogously to Example 126 the product was obtained from 130 mg (0.19 mmol) of tert-butyl 1'-{(R)-3-(4-hydroxy-phenyl)-2-[4-(2-oxo-1,2,4,5-tetrahydro-1,3-benzodiazepin-3-yl)-piperidine-1-carbonyloxy]-propionyl}-4,4'-bipiperidinyl-1-carboxylate (Example 122).

Yield: 70 mg (63% of theory) ESI-MS: (M+H)$^+$=604 R$_f$=0.20 (silica gel, DCM/MeOH/NH$_3$ 80:20:2) retention time (HPLC): 6.9 min (method F)

EXAMPLE 128

(R)-1-(3,5-dibromo-4-hydroxy-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

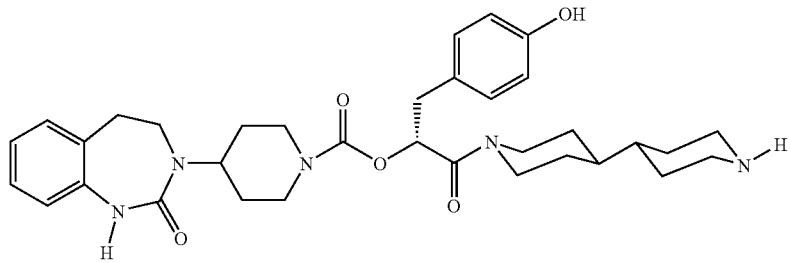

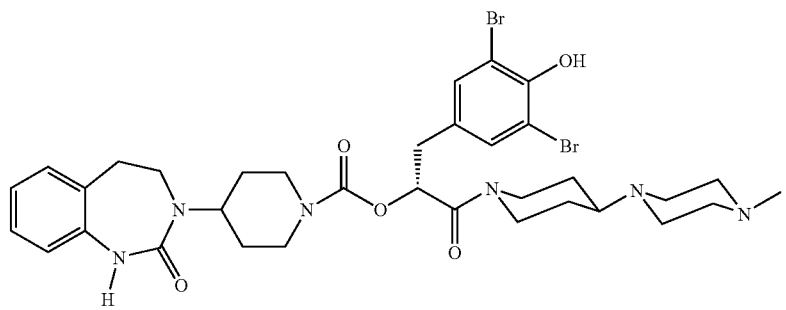

128a (Z,E)-3-(4-acetoxy-3,5-dibromo-phenyl)-2-acetylamino-acrylic acid

Analogously to Example 1a the product was obtained from 30 g (107 mmol) 3,5-dibromo-4-hydroxy-benzaldehyde and 18.8 g (161 mmol) N-acetyl-glycine.

Yield: 35.7 g (79% of theory) ESI-MS: $(M+H)^+=420/422/424$ (2 Br) $R_f=0.20$ (silica gel, DCM/MeOH/AcOH 90:10:1)

128b 3-(3,5-dibromo-4-hydroxy-phenyl)-2-oxo-propionic acid

Analogously to Example 1b the product was obtained from 35.7 g (84.8 mmol) (Z,E)-3-(4-acetoxy-3,5-dibromo-phenyl)-2-acetylamino-acrylic acid.

Yield: 20.5 g (72% of theory) ESI-MS: $(M-H)^-=335/337/339$ (2 Br) $R_f=0.35$ (silica gel, DCM/MeOH/AcOH 80:20:2)

128c (R)-3-(3,5-dibromo-4-hydroxy-phenyl)-2-hydroxy-propionic acid

Analogously to Example 1c the product was obtained from 14.5 g (42.9 mmol) 3-(3,5-dibromo-4-hydroxy-phenyl)-2-oxo-propionic acid and 30.9 g (96.33 mmol) (1R)-B-chloro-diisopinocampheylborane.

Yield: 12.7 g (87% of theory) ESI-MS: $(M-H)^-=337/339/341$ (2 Br) $R_f=0.4$ (silica gel, DCM/MeOH/AcOH 80:20:2) retention time (HPLC): 6.4 min (method F)

128d methyl (R)-3-(3,5-dibromo-4-hydroxy-phenyl)-2-hydroxy-propionate

Analogously to Example 46d the product was obtained from 14.0 g (34.8 mmol) 3(R)-3-(3,5-dibromo-4-hydroxy-phenyl)-2-hydroxy-propionic acid.

Yield: 7.0 g (57% of theory) ESI-MS: $(M-H)^-=351/353/355$ (2 Br) retention time (HPLC): 9.8 min (method F)

128e methyl (R)-3-[3,5-dibromo-4-(2-trimethylsilanyl-ethoxymethoxy)-phenyl]-2-hydroxy-propionate Under a nitrogen atmosphere 11.1 g (76.6 mmol) 40% $KF/Al_2O_3$ were added to a solution of 6.78 g (19.2 mmol) methyl (R)-3-(3,5-dibromo-4-hydroxy-phenyl)-2-hydroxy-propionate in 100 mL acetonitrile and the resulting suspension was stirred for a few minutes at RT. Subsequently a solution of 4.07 mL (23.0 mmol) (2-chloromethoxy-ethyl)-trimethyl-silane in 20 mL acetonitrile was added and the reaction mixture was stirred for 20 h at RT. The mixture was filtered through Celite, the solvent was evaporated down i.vac. and the residue was purified by chromatography (silica gel, n-hexane/EtOAc 7:3).

Yield: 5.49 g (59% of theory) $R_f=0.45$ (silica gel, n-hexane/EtOAc 1:1)

128f (R)-2-[3,5-dibromo-4-(2-trimethylsilanyl-ethoxymethoxy)-phenyl]-1-methoxy-carbonyl-ethyl 4-(2-oxo-1,2,4,5-tetrahydro-1,3-benzodiazepin-3-yl)-piperidine-1-carboxylate Analogously to Example 31f the product was obtained from 4.63 g (9.56 mmol) methyl (R)-3-[3,5-dibromo-4-(2-trimethylsilanyl-ethoxymethoxy)-phenyl]-2-hydroxy-propionate and 2.35 g (9.56 mmol) 3-piperidin-4-yl-1,3,4,5-tetrahydro-1,3-benzodiazepin-2-one.

Yield: 4.35 g (69% of theory) ESI-MS: $(M+H)^+=754/756/758$ (2 Br) retention time (HPLC): 29.2 min (method F)

128q (R)-2-(3,5-dibromo-4-hydroxy-phenyl)-1-methoxycarbonyl-ethyl 4-(2-oxo-1,2,4,5-tetrahydro-1,3-benzodiazepin-3-yl)-piperidine-1-carboxylate Under a nitrogen atmosphere 5.46 mL methanolic $H_2SO_4$ (0.5 M) were added to a solution of 4.30 g (5.69 mmol) of (R)-2-[3,5-dibromo-4-(2-trimethylsilanyl-ethoxymethoxy)-phenyl]-1-methoxy-carbonyl-ethyl 4-(2-oxo-1,2,4,5-tetrahydro-1,3-benzodiazepin-3-yl)-piperidine-1-carboxylate in 40 mL THF and 40 mL MeOH and the reaction solution was stirred for 6 h at RT. The reaction mixture was evaporated down i.vac and the residue was reacted further without purification.

Yield: quantitative ESI-MS: $(M+H)^+=624/626/628$ (2 Br) retention time (HPLC): 17.3 min (method F)

128h (R)-1-carboxy-2-(3,5-dibromo-4-hydroxy-phenyl)-ethyl 4-(2-oxo-1,2,4,5-tetrahydro-1,3-benzodiazepin-3-yl)-piperidine-1-carboxylate A solution of 0.51 g (21.3 mmol) LiOH was added to a solution of (R)-2-(3,5-dibromo-4-hydroxy-phenyl)-1-methoxycarbonyl-ethyl 4-(2-oxo-1,2,4,5-tetrahydro-1,3-benzodiazepin-3-yl)-piperidine-1-carboxylate (crude product from Example 128g) in 80 mL THF and the reaction mixture was stirred for 3 h at RT. The THF was eliminated i. vac., the aqueous phase was washed with EtOAc, acidified with 10% HCl and the aqueous phase was extracted exhaustively with EtOAc. The combined organic phases were evaporated down i.vac., suspended in diethyl ether, filtered, the residue was dried and then purified by chromatography (silica gel, DCM/MeOH/AcOH 90:10:1).

Yield: 3.5 g (100% of theory) ESI-MS: $(M+H)^+=610/612/614$ (2 Br) retention time (HPLC): 14.1 min (method F)

128i (R)-1-(3,5-dibromo-4-hydroxy-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate Under a nitrogen atmosphere 55 mg (0.30 mmol) 1-methyl-4-piperidin-4-yl-piperazine was added to a solution of 151 mg (0.25 mmol) of (R)-1-carboxy-2-(3,5-dibromo-4-hydroxy-phenyl)-ethyl 4-(2-oxo-1,2,4,5-tetrahydro-1,3-benzodiazepin-3-yl)-piperidine-1-carboxylate, 104 mg (0.27 mmol) HATU and 47 µL (0.27 mmol) ethyldiisopropylamine in 5 mL DMF and the reaction mixture was stirred for 3 h at RT. The reaction solution was evaporated down i.vac. and the residue was purified by chromatography (silica gel, DCM/MeOH/NH₃ 80:20:2).

Yield: 190 mg (99% of theory) ESI-MS: $(M+H)^+=775/777/779$ (2 Br) $R_f=0.3$ (silica gel, DCM/MeOH/AcOH 80:20:2) retention time (HPLC): 7.2 min (method F)

The following compounds were obtained analogously from in each case 151 mg (R)-1-carboxy-2-(3,5-dibromo-4-hydroxy-phenyl)-ethyl 4-(2-oxo-1,2,4,5-tetrahydro-1,3-benzodiazepin-3-yl)-piperidine-1-carboxylate and the corresponding amount of amine:

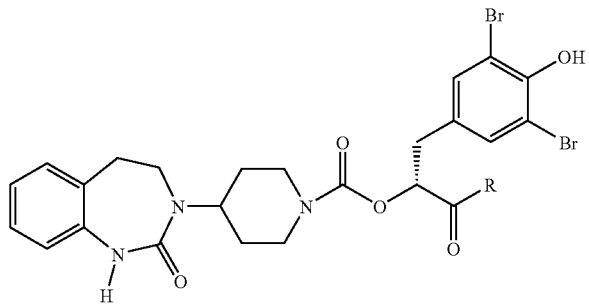

| Example | R | Yield (%) | Mass spectrum | retention time HPLC (method) |
|---|---|---|---|---|
| 129 | ![piperidinyl-piperidine] | 95 | 760/762/764 [M + H]+ | 9.5 min (F) |
| 130 | ![piperazinyl-N-methylpiperidine] | 89 | 775/777/779 [M + H]+ | 6.7 min (F) |
| 131 | ![piperidinyl-N-methylpiperidine] | 93 | 774/776/778 [M + H]+ | 9.6 min (F) |
| 132 | ![piperidinyl-dimethylamine] | 82 | 720/722/724 [M + H]+ | 8.7 min (F) |
| 133 | ![piperazinyl-piperidine-Fmoc] | 91 | 761/763/765 [M + H − Fmoc]+ | 15.0 min (F) |

EXAMPLE 134

(R)-1-(3,5-dibromo-4-hydroxy-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

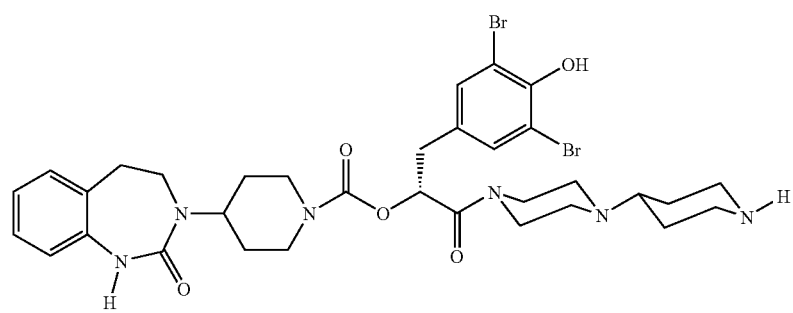

Analogously to Example 128i the crude product was obtained from 200 mg (0.33 mmol) of (R)-1-carboxy-2-(3,5-dibromo-4-hydroxy-phenyl)-ethyl 4-(2-oxo-1,2,4,5-tetrahydro-1,3-benzodiazepin-3-yl)-piperidine-1-carboxylate, 140 μL (0.82 mmol) ethyldiisopropylamine and 135 mg (0.44 mmol) tert-butyl 4-piperazin-1-yl-piperidine-1-carboxylate (used as the hydrochloride salt). This product was dissolved in 2 mL formic acid and stirred for 2 h at RT. The reaction mixture was evaporated down i.vac. and the residue was purified by chromatography (silica gel, eluting first with DCM/MeOH/NH$_3$ 80:20:2 then with DCM/MeOH/NH$_3$ 50:50:5).

Yield: 20 mg (8% of theory) ESI-MS: (M+H)$^+$=761/763/765 (2 Br) R$_f$=0.35 (silica gel, DCM/MeOH/NH$_3$ 80:20:2) retention time (HPLC): 6.5 min (method F)

EXAMPLE 135

(R)-1-(3,5-dibromo-4-hydroxy-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

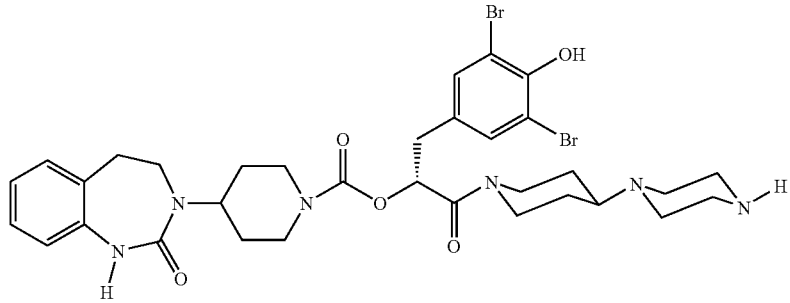

A solution of 200 mg (0.20 mmol) 9H-fluoren-9-ylmethyl 4-(1-{(R)-3-(3,5-dibromo-4-hydroxy-phenyl)-2-[4-(2-oxo-1,2,4,5-tetrahydro-1,3-benzodiazepin-3-yl)-piperidine-1-carbonyloxy]-propionyl}-piperidin-4-yl)-piperazine-1-carboxylate (Example 133) in 4 mL piperidine was stirred for 30 min at RT. The reaction mixture was evaporated down i.vac. and the residue was purified by chromatography (silica gel, DCM/MeOH/NH$_3$ 80:20:2).

Yield: 20 mg (8% of theory) ESI-MS: (M+H)$^+$=761/763/765 (2 Br) retention time (HPLC): 6.8 min (method F)

EXAMPLE 136

(R)-1-(3,5-dibromo-4-hydroxy-benzyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate A solution of 130 mg (0.21 mmol) of (R)-1-carboxy-2-(3,5-dibromo-4-hydroxy-phenyl)-ethyl 4-(2-oxo-1,2,4,5-tetrahydro-1,3-benzodiazepin-3-yl)-piperidine-1-carboxylate, 80 mg (0.25 mmol) TBTU and 50 μL (0.27 mmol) ethyldiisopropylamine in 10 mL THF was stirred for 50 min at RT. Then 60 mg (0.24 mmol) 1-methanesulphonyl-[4,4']bipiperidinyl were added and the reaction mixture was stirred overnight at RT. The reaction solution was diluted with 50 mL EtOAc, extracted twice with 30 mL 15% K$_2$CO$_3$ solution, the organic phase was separated off and dried over MgSO$_4$. After the desiccant and solvent had been eliminated the residue was triturated with water and filtered. The solid was combined with 5 mL 1 M HCl and stirred overnight. Further purification of the crude product was carried out by chromatography (silica gel, gradient DCM to DCM/MeOH/NH$_3$ 50:45:5). The fractions containing the product were combined, evaporated down i.vac., triturated with DIPE, suction filtered and dried at 40° C.

Yield: 80 mg (45% of theory) ESI-MS: (M+H)$^+$=838/840/842 (2 Br) R$_f$=0.42 (silica gel, DCM/MeOH/cyc/NH$_3$ 70:15:15:2)

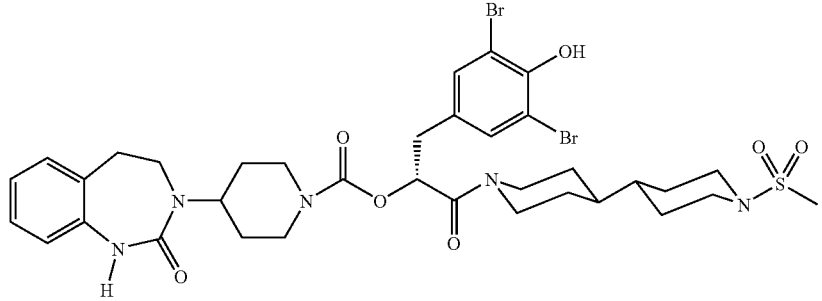

EXAMPLE 137

(R)-2-(4-amino-4-methyl-1,4'-bipiperidinyl-1'-yl)-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate

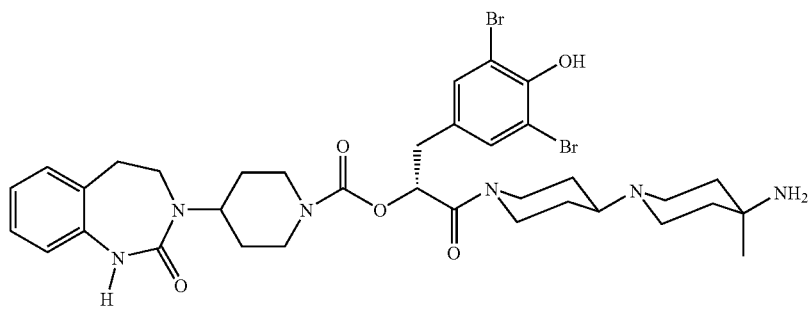

Analogously to Example 1h the product was obtained from 80 mg (0.13 mmol) of (R)-1-carboxy-2-(3,5-dibromo-4-hydroxy-phenyl)-ethyl 4-(2-oxo-1,2,4,5-tetrahydro-1,3-benzodiazepin-3-yl)-piperidine-1-carboxylate and 36 mg (0.14 mmol) 4-methyl-[1,4']bipiperidinyl-4-ylamine (used as the bis-hydrochloride salt), being obtained as the formate salt.

Yield: 6 mg (6% of theory) ESI-MS: (M+H)$^+$=789/791/793 (2 Br) retention time (HPLC): 4.9 min (method A)

EXAMPLE 138

(R)-1-(3,5-dibromo-4-hydroxy-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate 208 mg (0.82 mmol) ethyl [4,4']bipiperidinyl-1-yl-acetate were added to a solution of 500 mg (0.82 mmol) of (R)-1-carboxy-2-(3,5-dibromo-4-hydroxy-phenyl)-ethyl 4-(2-oxo-1,2,4,5-tetrahydro-1,3-benzodiazepin-3-yl)-piperidine-1-carboxylate, 315 mg (0.98 mmol) TBTU and 150 µL (1.06 mmol) triethylamine in 5 mL DMF and the reaction mixture was stirred overnight at RT. To complete the reaction a further 315 mg (0.98 mmol) TBTU, 150 µL (1.06 mmol) triethylamine and 208 mg (0.82 mmol) ethyl [4,4']bipiperidinyl-1-yl-acetate were added and the mixture was again stirred overnight at RT. The reaction mixture was purified directly by HPLC without any further working up. The fractions containing the product were combined, evaporated down i.vac., neutralised with saturated NaHCO$_3$ solution, the aqueous phase was extracted twice with 100 mL DCM and the combined organic phases were dried over Na$_2$SO$_4$. After the desiccant and solvent had been eliminated the residue was triturated with DIPE, suction filtered and dried in the air.

Yield: 204 mg (29% of theory) ESI-MS: (M+H)$^+$=846/848/850 (2 Br) retention time (HPLC): 6.5 min (method A)

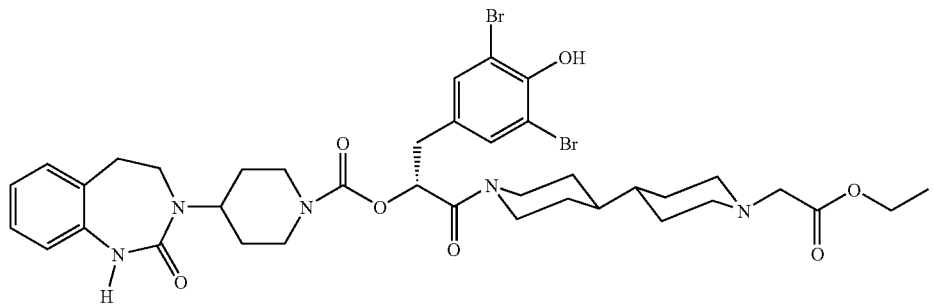

EXAMPLE 139

(R)-2-(1'-carboxymethyl-4,4'-bipiperidinyl-1-yl)-1-(3,5-dibromo-4-hydroxy-benzyl)-2-oxo-ethyl 4-(2-oxo-1,2,4,5-tetrahydro-1,3-benzodiazepin-3-yl)-piperidine-1-carboxylate

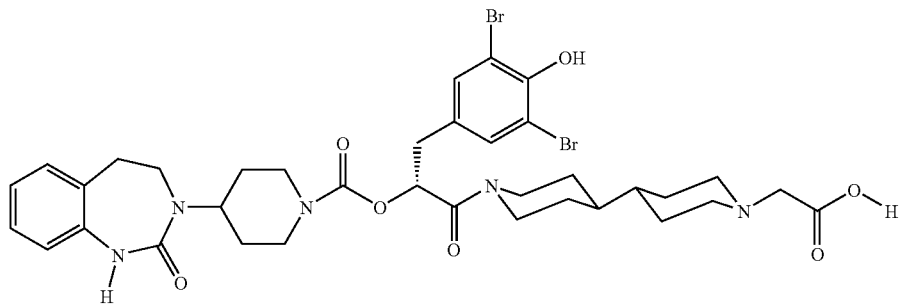

A solution of 1.4 mg (0.06 mmol) LiOH in 1 mL water was added to a solution of 30 mg (0.04 mmol) of (R)-1-(3,5-dibromo-4-hydroxy-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate (Example 138) in 3 mL THF and the reaction solution was stirred overnight at RT. The solvent was eliminated in the nitrogen current, the residue was taken up in 1 mL water, acidified with formic acid, the precipitate formed was removed by suction filtering and dried in vacuo.

Yield: 20 mg (69% of theory) ESI-MS: $(M+H)^+=818/820/822$ (2 Br) retention time (HPLC): 6.5 min (method A)

EXAMPLE 140

(R)-2-(4-amino-4-methyl-1,4'-bipiperidinyl-1'-yl)-1-(3,5-bis-trifluoromethyl-benzyl)-2-oxo-ethyl 4-(2-oxo-1,2,4,5-tetrahydro-1,3-benzodiazepin-3-yl)-piperidine-1-carboxylate Analogously to Example 1h the product was obtained from 80 mg (0.14 mmol) of (R)-2-(3,5-bis-trifluoromethyl-phenyl)-1-carboxy-ethyl 4-(2-oxo-1,2,4,5-tetrahydro-1,3-benzodiazepin-3-yl)-piperidine-1-carboxylate (Example 46f) and 38 mg (0.14 mmol) 4-methyl-[1,4']bipiperidinyl-4-ylamine (used as the bis-hydrochloride salt), in the form of the formate salt.

Yield: 47 mg (42% of theory) ESI-MS: $(M+H)^+=753$ retention time (HPLC): 5.4 min (method A)

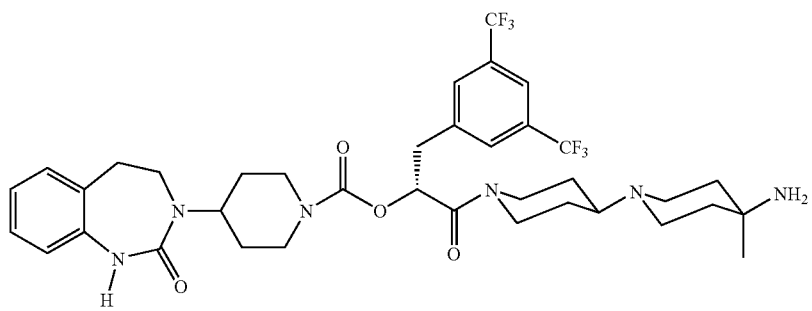

EXAMPLE 141

(R)-2-(1'-ethoxycarbonylmethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

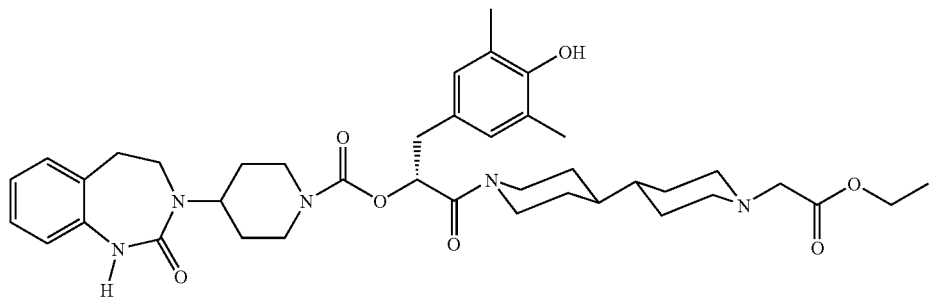

Analogously to Example 46g the product was obtained from 200 mg (0.42 mmol) of (R)-1-carboxy-2-(4-hydroxy-3,5-dimethyl-phenyl)-ethyl 4-(2-oxo-1,2,4,5-tetrahydro-1,3-benzodiazepin-3-yl)-piperidine-1-carboxylate (Example 69h) and 117 mg (0.46 mmol) ethyl [4,4']bipiperidinyl-1-yl-acetate.

Yield: 222 mg (74% of theory) ESI-MS: $(M+H)^+=718$
retention time (HPLC): 3.1 min (method E)

Analogously to Example 139 the product was obtained from 100 mg (0.14 mmol) of (R)-2-(1'-ethoxycarbonylmethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate (Example 141) and 3.8 mg (0.16 mmol) LiOH.

Yield: 56 mg (58% of theory) ESI-MS: $(M-H)^-=688$
retention time (HPLC): 3.0 min (method E)

EXAMPLE 142

(R)-2-(1'-carboxymethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

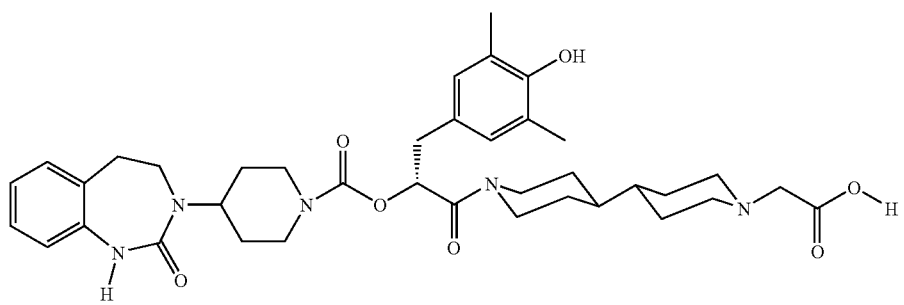

EXAMPLE 143

(R)-2-(4-cyclohexyl-piperazin-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

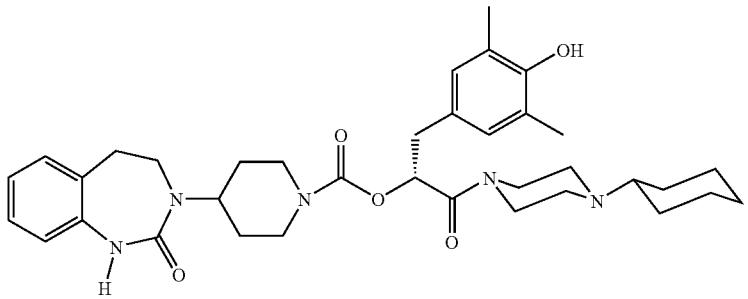

Analogously to Example 1h the product was obtained from 69 mg (0.14 mmol) of (R)-1-carboxy-2-(4-hydroxy-3,5-dimethyl-phenyl)-ethyl 4-(2-oxo-1,2,4,5-tetrahydro-1,3-benzodiazepin-3-yl)-piperidine-1-carboxylate (Example 69h) and 24 mg (0.14 mmol) 1-cyclohexyl-piperazine.

Yield: 51 mg (91% of theory) ESI-MS: $(M+H)^+=632$
retention time (HPLC): 3.1 min (method E)

EXAMPLE 144

(R)-2-[4-(4-methyl-piperazin-1-yl)-piperidin-1-yl]-2-oxo-1-(3-trifluoromethyl-benzyl)-ethyl 4-(2-oxo-1,2,4,5-tetrahydro-1,3-benzodiazepin-3-yl)-piperidine-1-carboxylate

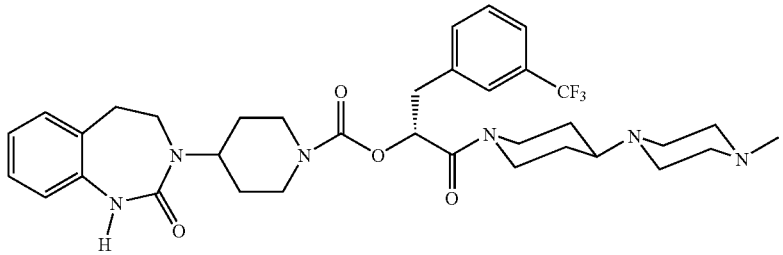

144a (Z,E)-2-acetylamino-3-(3-trifluoromethyl-phenyl)-acrylic acid

Analogously to Example 1a the product was obtained from 15.8 g (115 mmol) 3-trifluoromethyl-benzaldehyde and 21.3 g (182 mmol) N-acetyl-glycine.

Yield: 16.7 g (53% of theory) ESI-MS: $(M+H)^+=274$
$R_f=0.4$ (silica gel, DCM/MeOH/AcOH 90:10:1)

144b 2-oxo-3-(3-trifluoromethyl-phenyl)-propionic acid

Analogously to Example 46b the product was obtained from 16.6 g (60.8 mmol) (Z,E)-2-acetylamino-3-(3-trifluoromethyl-phenyl)-acrylic acid.

Yield: 5.7 g (40% of theory) ESI-MS: $(M-H)^-=231$
$R_f=0.19$ (silica gel, DCM/MeOH/cyc/NH$_3$ 70:15:15:2)

144c (R)-2-hydroxy-3-(3-trifluoromethyl-phenyl)-propionic acid

Analogously to Example 1c the product was obtained from 5.70 g (24.6 mmol) 2-oxo-3-(3-trifluoromethyl-phenyl)-propionic acid and 11.8 g (36.8 mmol) (1R)-B-chlorodiisopinocampheylborane.

Yield: 4.25 g (74% of theory) ESI-MS: $(M-H)^-=233$
$R_f=0.35$ (silica gel, DCM/MeOH/cyc/NH$_3$ 70:15:15:2)

144d methyl (R)-2-hydroxy-3-(3-trifluoromethyl-phenyl)-propionate

Analogously to Example 46d the product was obtained from 4.20 g (17.9 mmol) of (R)-2-hydroxy-3-(3-trifluoromethyl-phenyl)-propionic acid.

Yield: 2.47 g (55% of theory) ESI-MS: $(M+H)^+=249$
$R_f=0.73$ (silica gel, DCM/MeOH/cyc/NH$_3$ 70:15:15:2)

144e (R)-1-methoxycarbonyl-2-(3-trifluoromethyl-phenyl)-ethyl 4-(2-oxo-1,2,4,5-tetrahydro-1,3-benzodiazepin-3-yl)-piperidine-1-carboxylate Analogously to Example 31f the product was obtained from 2.47 g (9.95 mmol) methyl (R)-2-hydroxy-3-(3-trifluoromethyl-phenyl)-propionate and 4.10 g (65% purity, 10.9 mmol) 3-piperidin-4-yl-1,3,4,5-tetrahydro-1,3-benzodiazepin-2-one.

Yield: 3.16 g (61% of theory) ESI-MS: $(M+H)^+=520$
$R_f=0.93$ (silica gel, EtOAc/MeOH/NH$_3$ 80:20:2)

144f (R)-1-carboxy-2-(3-trifluoromethyl-phenyl)-ethyl 4-(2-oxo-1,2,4,5-tetrahydro-1,3-benzodiazepin-3-yl)-piperidine-1-carboxylate Analogously to Example 46f the product was obtained from 3.10 g (5.97 mmol) of (R)-1-methoxycarbonyl-2-(3- trifluoro-methyl-phenyl)-ethyl 4-(2-oxo-1,2,4,5-tetrahydro-1,3-benzodiazepin-3-yl)-piperidine-1-carboxylate and 0.22 g (9.00 mmol) LiOH.

Yield: 2.80 g (93% of theory) ESI-MS: (M+H)⁺=506
R_f=0.58 (silica gel, EtOAc/MeOH/NH₃ 70:30:3)

144q (R)-2-[4-(4-methyl-piperazin-1-yl)-piperidin-1-yl]-2-oxo-1-(3-trifluoromethyl-benzyl)-ethyl 4-(2-oxo-1,2,4,5-tetrahydro-1,3-benzodiazepin-3-yl)-piperidine-1-carboxylate Analogously to Example 1h the product was obtained from 80.0 mg (0.16 mmol) of (R)-1-carboxy-2-(3-trifluoromethyl-phenyl)-ethyl 4-(2-oxo-1,2,4,5-tetrahydro-1,3-benzodiazepin-3-yl)-piperidine-1-carboxylate and 29.6 mg (0.16 mmol) 1-methyl-4-piperidin-4-yl-piperazine.

Yield: 67 mg (63% of theory) ESI-MS: (M+H)⁺=671
R_f=0.4 (silica gel, DCM/MeOH/cyc/NH₃ 70:15:15:2)

The following compounds were obtained analogously from in each case 80 mg (Examples 145 to 148) or 140 mg (Examples 149 and 150) of (R)-1-carboxy-2-(3-trifluoro-methyl-phenyl)-ethyl 4-(2-oxo-1,2,4,5-tetrahydro-1,3-benzodiazepin-3-yl)-piperidine-1-carboxylate and the corresponding amount of amine:

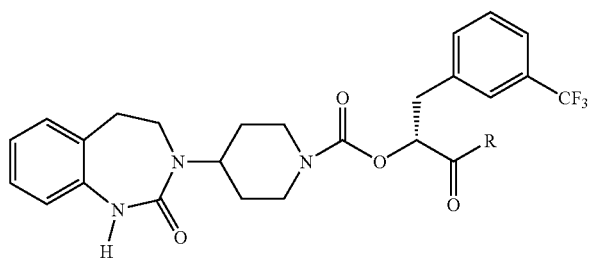

| Example | R | Yield (%) | Mass spectrum | R_f (silica gel, DCM/MeOH/cyc/NH₃ 70:15:15:2) or retention time HPLC (method) |
|---|---|---|---|---|
| 145 | | 93 | 656 [M + H]⁺ | 0.68 |
| 146 | | 64 | 671 [M + H]⁺ | 0.35 |
| 147 | | 74 | 670 [M + H]⁺ | 0.53 |
| 148 | | 48 | 685 [M + H]⁺ | 5.1 min (A) |
| 149 | | 62 | 757 [M + H]⁺ | 0.51 |
| 150 | | 71 | 757 [M + H]⁺ | 0.50 |

EXAMPLE 151

(R)-1-(3-methyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

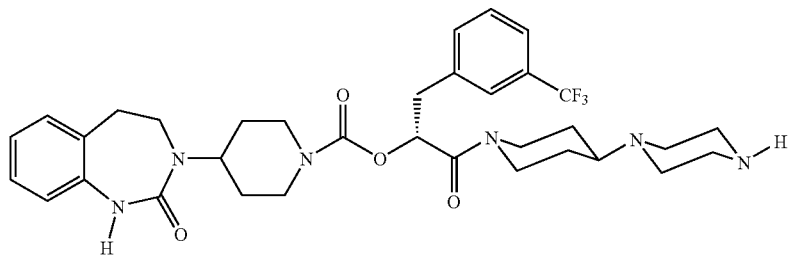

A solution of 131 mg (0.17 mmol) tert-butyl 4-{1-[(R)-2-[4-(2-oxo-1,2,4,5-tetrahydro-1,3-benzodiazepin-3-yl)-piperidine-1-carbonyloxy]-3-(3-trifluoromethyl-phenyl)-propionyl]-piperidin-4-yl}-piperazine-1-carboxylate (Example 149) in 1.5 mL of 4 M HCl was stirred overnight at RT. The reaction solution was purified by HPLC without any further working up. The fractions containing the product were combined and lyophilised.

Yield: 75 mg (67% of theory) ESI-MS: $(M+H)^+=657$
$R_f=0.38$ (silica gel, DCM/MeOH/cyc/NH$_3$ 70:15:15:2)

EXAMPLE 152

(R)-2-oxo-2-(4-piperidin-4-yl-piperazin-1-yl)-1-(3-trifluoromethyl-benzyl)-ethyl 4-(2-oxo-1,2,4,5-tetrahydro-1,3-benzodiazepin-3-yl)-piperidine-1-carboxylate

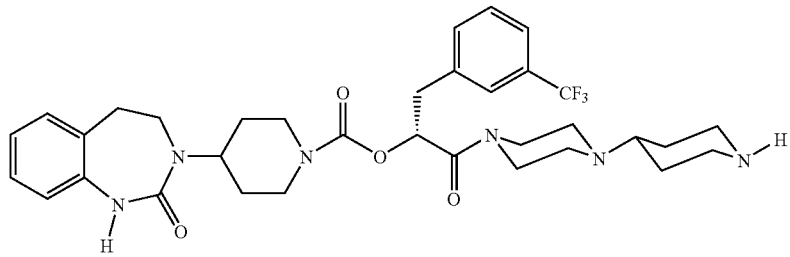

Analogously to Example 151 the product was obtained from 149 mg (0.20 mmol) of (R)-1-(3-trifluoromethyl-benzyl)-2-[4-(1-tert-butoxy-carbonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (Example 150).

Yield: 66 mg (51% of theory) ESI-MS: $(M+H)^+=657$
$R_f=0.18$ (silica gel, DCM/MeOH/cyc/NH$_3$ 70:15:15:2)

EXAMPLE 153

(R)-2-[4-(4-methyl-piperazin-1-yl)-piperidin-1-yl]-2-oxo-1-(3-methyl-benzyl)-ethyl 4-(2-oxo-1,2,4,5-tetrahydro-1,3-benzodiazepin-3-yl)-piperidine-1-carboxylate

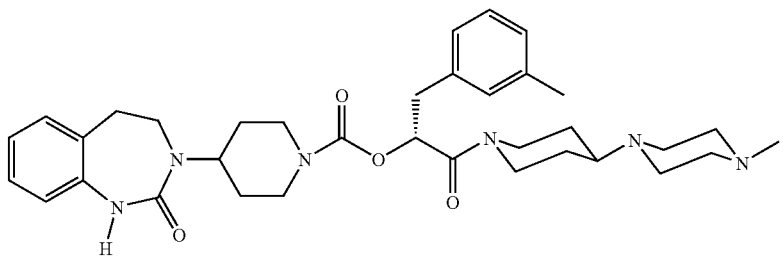

153a (Z,E)-2-acetylamino-3-m-tolyl-acrylic acid

Analogously to Example 1a the product was obtained from 25.0 g (212 mmol) 3-methyl-benzaldehyde and 24.9 g (212 mmol) N-acetyl-glycine.
Yield: 26.0 g (56% of theory) ESI-MS: (M+H)$^+$=220 retention time (HPLC): 5.4 min (method A)

153b 2-oxo-3-m-tolyl-propionic acid

Analogously to Example 46b the product was obtained from 13.0 g (59.3 mmol) (Z,E)-2-acetylamino-3-m-tolyl-acrylic acid.
Yield: 9.2 g (88% of theory) ESI-MS: (M−H)$^-$=177 retention time (HPLC): 7.3 min (method A)

153c (R)-2-hydroxy-3-m-tolyl-propionic acid

Analogously to Example 1c the product was obtained from 9.24 g (51.9 mmol) of 2-oxo-3-m-tolyl-propionic acid and 24.0 g (74.8 mmol) (1R)-B-chlorodiisopino-campheylborane.
Yield: 8.4 g (90% of theory) ESI-MS: (M−H)$^-$=179 retention time (HPLC): 7.2 min (method A)

153d methyl (R)-2-hydroxy-3-m-tolyl-propionate

Analogously to Example 31e the product was obtained from 8.40 g (46.6 mmol) of (R)-2-hydroxy-3-m-tolyl-propionic acid and 3.74 mL (51.28 mmol) SOCl$_2$.
Yield: 6.28 g (69% of theory) ESI-MS: (M+H)$^+$=195 retention time (HPLC): 6.9 min (method A)

153e (R)-1-methoxycarbonyl-2-m-tolyl-ethyl 4-(2-oxo-1,2,4,5-tetrahydro-1,3-benzodiazepin-3-yl)-piperidine-1-carboxylate Analogously to Example 31f the product was obtained from 1.12 g (5.76 mmol) methyl (R)-2-hydroxy-3-m-tolyl-propionate and 1.41 g (5.76 mmol) 3-piperidin-4-yl-1,3,4,5-tetrahydro-1,3-benzodiazepin-2-one.
Yield: 2.07 g (77% of theory) ESI-MS: (M+H)$^+$=466 retention time (HPLC): 9.0 min (method A)

153f (R)-1-carboxy-2-m-tolyl-ethyl 4-(2-oxo-1,2,4,5-tetrahydro-1,3-benzodiazepin-3-yl)-piperidine-1-carboxylate Analogously to Example 46f the product was obtained from 2.07 g (4.45 mmol) of (R)-1-methoxycarbonyl-2-m-tolyl-ethyl 4-(2-oxo-1,2,4,5-tetrahydro-1,3-benzodiazepin-3-yl)-piperidine-1-carboxylate and 0.16 g (6.72 mmol) LiOH.
Yield: 1.86 g (93% of theory) ESI-MS: (M+H)$^+$=452 retention time (HPLC): 8.0 min (method A)

153q (R)-2-[4-(4-methyl-piperazin-1-yl)-piperidin-1-yl]-2-oxo-1-(3-methyl-benzyl)-ethyl 4-(2-oxo-1,2,4,5-tetrahydro-1,3-benzodiazepin-3-yl)-piperidine-1-carboxylate Analogously to Example 1h the product was obtained from 80.0 mg (0.18 mmol) of (R)-1-carboxy-2-m-tolyl-ethyl 4-(2-oxo-1,2,4,5-tetrahydro-1,3-benzodiazepin-3-yl)-piperidine-1-carboxylate and 33.1 mg (0.18 mmol) 1-methyl-4-piperidin-4-yl-piperazine.
Yield: 46.7 mg (43% of theory) ESI-MS: (M+H)$^+$=617 retention time (HPLC): 5.5 min (method A)

The following compounds were obtained analogously from in each case 80 mg of (R)-1-carboxy-2-m-tolyl-ethyl 4-(2-oxo-1,2,4,5-tetrahydro-1,3-benzodiazepin-3-yl)-piperidine-1-carboxylate and the corresponding amount of amine:

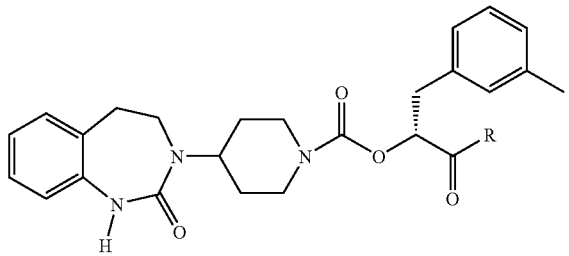

| Example | R | Yield (%) | Mass spectrum | retention time HPLC (method) |
|---|---|---|---|---|
| 154 | ![structure] | 80 | 617 [M + H]$^+$ | 5.0 min (A) |
| 155 | ![structure] | 75 | 616 [M + H]$^+$ | 6.2 min (A) |

The following Examples describe the preparation of pharmaceutical formulations which contain as active substance any desired compound of general formula (I):

EXAMPLE I

Capsules for Powder Inhalation Containing 1 mg of Active Ingredient

| Composition: 1 capsule for powder inhalation contains: | |
| --- | --- |
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

EXAMPLE II

Inhalable Solution for Respimat® Containing 1 mg of Active Ingredient

| Composition: 1 puff contains: | |
| --- | --- |
| active ingredient | 1.0 mg |
| benzalkonium chloride | 0.002 mg |
| disodium edetate | 0.0075 mg |
| purified water ad | 15.0 µl |

Method of Preparation:

The active ingredient and benzalkonium chloride are dissolved in water and transferred into Respimat® cartridges.

EXAMPLE III

Inhalable Solution for Nebulisers Containing 1 mg of Active Ingredient

| Composition: 1 vial contains: | |
| --- | --- |
| active ingredient | 0.1 g |
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

EXAMPLE IV

Propellant Gas-Operated Metering Aerosol Containing 1 mg of Active Ingredient

| Composition: 1 puff contains: | |
| --- | --- |
| active ingredient | 1.0 mg |
| lecithin | 0.1% |
| propellant gas ad | 50.0 µl |

Method of Preparation:

The micronised active ingredient is homogeneously suspended in the mixture of lecithin and propellant gas. The suspension is transferred into a pressurised container with a metering valve.

EXAMPLE V

Nasal Spray Containing 1 mg of Active Ingredient

| Composition: | |
| --- | --- |
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

EXAMPLE VI

Injectable Solution Containing 5 mg of Active Substance Per 5 ml

| Composition: | |
| --- | --- |
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (WfI); human serum albumin is added; active ingredient is dissolved with heating; made up to specified volume with WfI; transferred into ampoules under nitrogen gas.

EXAMPLE VII

Injectable Solution Containing 100 mg of Active Substance Per 20 ml

| Composition: | |
|---|---|
| active substance | 100 mg |
| monopotassium dihydrogen phosphate = KH$_2$PO$_4$ | 12 mg |
| disodium hydrogen phosphate = Na$_2$HPO$_4$·2H$_2$O | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (WfI); human serum albumin is added; active ingredient is dissolved with heating; made up to specified volume with WfI; transferred into ampoules.

EXAMPLE VIII

Lyophilisate Containing 10 mg of Active Substance

| Composition: | |
|---|---|
| Active substance | 10 mg |
| Mannitol | 300 mg |
| human serum albumin | 20 mg |
| water for injections ad | 2 ml |

Preparation:

Mannitol is dissolved in water for injections (WfI); human serum albumin is added; active ingredient is dissolved with heating; made up to specified volume with WfI; transferred into vials; freeze-dried.

| Solvent for lyophilisate: | |
|---|---|
| Polysorbate 80 = Tween 80 | 20 mg |
| mannitol | 200 mg |
| water for injections ad | 10 ml |

Preparation:

Polysorbate 80 and mannitol are dissolved in water for injections (WfI); transferred into ampoules.

EXAMPLE IX

Tablets Containing 20 mg of Active Substance

| Composition: | |
|---|---|
| active substance | 20 mg |
| lactose | 120 mg |
| maize starch | 40 mg |
| magnesium stearate | 2 mg |
| Povidone K 25 | 18 mg |

Preparation:

Active substance, lactose and maize starch are homogeneously mixed; granulated with an aqueous solution of Povidone; mixed with magnesium stearate; compressed in a tablet press; weight of tablet 200 mg.

EXAMPLE X

Capsules Containing 20 mg Active Substance

| Composition: | |
|---|---|
| active substance | 20 mg |
| maize starch | 80 mg |
| highly dispersed silica | 5 mg |
| magnesium stearate | 2.5 mg |

Preparation:

Active substance, maize starch and silica are homogeneously mixed; mixed with magnesium stearate; the mixture is packed into size for 3 hard gelatine capsules in a capsule filling machine.

EXAMPLE XI

Suppositories Containing 50 mg of Active Substance

| Composition: | |
|---|---|
| active substance | 50 mg |
| hard fat (Adeps solidus) q.s. ad | 1700 mg |

Preparation:

Hard fat is melted at about 38° C.; ground active substance is homogeneously dispersed in the molten hard fat; after cooling to about 35° C. it is poured into chilled moulds.

EXAMPLE XII

Injectable Solution Containing 10 mg of Active Substance Per 1 ml

| Composition: | |
|---|---|
| active substance | 10 mg |
| mannitol | 50 mg |
| human serum albumin | 10 mg |
| water for injections ad | 1 ml |

Preparation:

Mannitol is dissolved in water for injections (WfI); human serum albumin is added; active ingredient is dissolved with heating; made up to specified volume with WfI; transferred into ampoules under nitrogen gas.

What is claimed is:

1. A compound selected from the group consisting of:

| Compound No. | Structure |
|---|---|
| (572) | (structure shown) and |
| (573) | (structure shown) | or a tautomer or salt thereof.

2. The compound, in accordance with claim 1, having the following structure:

| No. | Structure |
|---|---|
| (572) | (structure shown), | or a tautomer or salt thereof.

3. The compound, in accordance with claim 1, having the following structure:

| No. | Structure |
|---|---|
| (573) | (structure shown), | or a tautomer or salt thereof.

4. A physiologically acceptable salt of a compound according to claim 1, 2, or 3.

5. A pharmaceutical composition containing a compound according to claim 1, 2, or 3 or a physiologically acceptable salt thereof together with one or more inert carriers and/or diluents.

6. A method for treating migraine or cluster headaches which comprises administering to a host suffering from the same a therapeutically effective amount of a compound of the formula I in accordance with claim 1, 2 or 3, or a tautomer or physiologically acceptable salt thereof.

* * * * *